US012697400B2

(12) United States Patent
Smith et al.

(10) Patent No.: US 12,697,400 B2
(45) Date of Patent: Aug. 4, 2026

(54) GENE EDITING METHODS FOR TREATING ALPHA-1 ANTITRYPSIN (AAT) DEFICIENCY

(71) Applicant: Precision BioSciences, Inc., Durham, NC (US)

(72) Inventors: James Jefferson Smith, Morrisville, NC (US); John Morris, Raleigh, NC (US); Janel Lape, Wake Forest, NC (US); Cassandra Gorsuch, Hillsborough, NC (US); Paige Scarlett Nemec, Durham, NC (US); Jason Richard Harris, Durham, NC (US); Wendy Shoop, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 50 days.

(21) Appl. No.: 18/702,749

(22) PCT Filed: Oct. 19, 2022

(86) PCT No.: PCT/US2022/078387
§ 371 (c)(1),
(2) Date: Apr. 18, 2024

(87) PCT Pub. No.: WO2023/070002
PCT Pub. Date: Apr. 27, 2023

(65) Prior Publication Data
US 2025/0228973 A1     Jul. 17, 2025

Related U.S. Application Data

(60) Provisional application No. 63/257,506, filed on Oct. 19, 2021, provisional application No. 63/257,513, filed on Oct. 19, 2021, provisional application No. 63/257,502, filed on Oct. 19, 2021, provisional application No. 63/257,528, filed on Oct. 19, 2021, provisional application No. 63/257,518, filed on Oct. 19, 2021.

(51) Int. Cl.
| | |
|---|---|
| *A61P 5/00* | (2006.01) |
| *A61K 9/127* | (2006.01) |
| *A61K 9/51* | (2006.01) |
| *A61K 38/57* | (2006.01) |
| *A61K 48/00* | (2006.01) |
| *C12N 9/22* | (2006.01) |
| *C12N 15/86* | (2006.01) |
| *C12N 15/88* | (2006.01) |
| *C12N 15/90* | (2006.01) |

(52) U.S. Cl.
CPC .......... *A61K 48/0058* (2013.01); *A61K 9/127* (2013.01); *A61K 9/5123* (2013.01); *A61K 38/57* (2013.01); *A61P 5/00* (2018.01); *C12N 9/22* (2013.01); *C12N 15/86* (2013.01); *C12N 15/88* (2013.01); *C12N 15/907* (2013.01); *C12N 2750/14143* (2013.01); *C12N 2830/008* (2013.01); *C12N 2830/50* (2013.01)

(58) Field of Classification Search
None
See application file for complete search history.

(56) References Cited

U.S. PATENT DOCUMENTS

2020/0216843 A1 * 7/2020 Shen ...................... C12N 15/86

FOREIGN PATENT DOCUMENTS

| | | |
|---|---|---|
| WO | WO 2007/047859 A2 | 4/2007 |
| WO | WO 2016/179112 A1 | 11/2016 |
| WO | WO 2017/044649 A1 | 3/2017 |
| WO | WO 2017/093804 A2 | 6/2017 |
| WO | WO 2017/112859 A1 | 6/2017 |
| WO | WO-2017192741 A1 * 11/2017 ............. C12N 15/00 |
| WO | WO 2019/005957 A1 | 1/2019 |
| WO | WO 2020/132659 A1 | 6/2020 |

OTHER PUBLICATIONS

Smith Julianne et al., (2006) "A combinatorial approach to create artificial homing endonucleases cleaving chosen sequences", Nucleic Acids Research, Oxford University Press, GB, vol. 34, No. 22, pp. e149-1, XP002457876.

* cited by examiner

*Primary Examiner* — Brian Whiteman
*Assistant Examiner* — Khaleda B Hasan
(74) *Attorney, Agent, or Firm* — Womble Bond Dickinson (US) LLP

(57) ABSTRACT

Disclosed are engineered meganucleases that bind and cleave a recognition sequence within a serine peptidase inhibitor, Clade A, Member 1 (SERPINA1) gene, which encodes alpha-1 antitrypsin (AAT). Further disclosed are donor polynucleotides that encode functional AAT proteins. The present disclosure also encompasses methods of using such engineered meganucleases and donor polynucleotides to make genetically-modified cells and use of such compositions for treatment of AAT deficiency.

4 Claims, 76 Drawing Sheets
Specification includes a Sequence Listing.

AAT 9              AAT 10
                            Half-Site          Half-Site AAT 9-10                    TGCCCGGTCACAACAGACCCTG          SEQ ID NO: 3
Recognition Sequence        ACGGGCGATGTGGTCTGGGAC           SEQ ID NO: 4

AAT 33             AAT 34
                            Half-Site          Half-Site AAT 33-34                   TTCAGACAGTTGCTCAACCTCT          SEQ ID NO :7
Recognition Sequence        AAGTCTGTCAACGAGTTGGAGA          SEQ ID NO: 8

AAT 35             AAT 36
                            Half-Site          Half-Site AAT 35-36                   GGCCTGGTCACATTGGGTTTA           SEQ ID NO: 9
Recognition Sequence        CCGGACCAGTGTGAACCCAAAT          SEQ ID NO: 10

AAT 37             AAT 38
                            Half-Site          Half-Site AAT 37-38                   CCCCACTTTGCAAACTGGGGA           SEQ ID NO: 11
Recognition Sequence        GGGGTGAACGTGTTGACCCCT           SEQ ID NO: 12

AAT 41             AAT 42
                            Half-Site          Half-Site AAT 41-42                   TGAGGATCCTTGGAGTGTTGG           SEQ ID NO: 13
Recognition Sequence        ACTCCTAGCAACACTCACAACC          SEQ ID NO: 14

AAT 43             AAT 44
                            Half-Site          Half-Site AAT 43-44                   AGGACCTAGATGTAGGATTCTG          SEQ ID NO: 15
Recognition Sequence        TCCTGGATCTACATCCTAAGAC          SEQ ID NO: 16

FIG. 1

```
AAT35-36x.70(SEQIDNO: 17)   MNTKYNKEFLLYLAGFVDADGSIYACIRPRQSSKFKHTLELGFQVSQKTCRRWFLDKLVD 60
AAT35-36x.49(SEQIDNO: 18)   MNTKYNKEFLLYLAGFVDSDGSIYACIRPRQARKFKHTLELGFQVTQATCRRWFLDKLVD 60
AAT35-36L.79(SEQIDNO: 19)   MNTKYNKEFLLYLAGFVDADGSIYACIRPRQRRKFKHMLELGFQVSQKTCRRWFLDKLVD 60
AAT35-36L.141(SEQIDNO: 20)  MNTKYNKEFLLYLAGFVDADGSIYASIRPRQRRKFKHMLILGFQVSQKTCRRWFLDKLVD 60
AAT35-36L.210(SEQIDNO: 21)  MNTKYNKEFLLYLAGFVDSDGSIYATIRPRQRRKFKHMLELFFQVSQKTCRRWFLDKLVD 60
AAT35-36L.290(SEQIDNO: 22)  MNTKYNKEFLLYLAGFVDADGSIYARIRPRQRRKFKHMLEFGFQVSQKTRRRWFLDKLVD 60
                            ****************** ****** ****** **** *   *** * * *********

AAT35-36x.70(SEQIDNO: 17)   EIGVGYVRDRGRASDYRLSQIKPLHNFLTQLQPFLKLKQKQANLVLKIIEQLPSAKESPD 120
AAT35-36x.49(SEQIDNO: 18)   EIGVGYVRDRGRASDYRLSEIKPLHNFLTQLQPFLKLKQKQANLVLKIIEQLPSAKESPD 120
AAT35-36L.79(SEQIDNO: 19)   EIGVGYVRDRGRASDYRLSEIKPLHNFLTQLQPFLKLKQKQANLVLKIIEQLPSAKESPD 120
AAT35-36L.141(SEQIDNO: 20)  EIGVGYVRDRGRASDYRLSEIKPLHNFLTQLQPFLKLKQKQANLVLKIIEQLPSAKESPD 120
AAT35-36L.210(SEQIDNO: 21)  EIGVGYVRDRGRASDYRLSEIKPLHNFLTQLQPFLKLKQKQANLVLKIIEQLPSAKESPD 120
AAT35-36L.290(SEQIDNO: 22)  EIGVGYVRDRGRASDYRLSEIKPLHNFLTQLQPFLKLKQKQANLVLKIIEQLPSAKESPD 120
                            ****************** *****************************************

AAT35-36x.70(SEQIDNO: 17)   KFLEVCTWVDQIAALNDSKTRKTTSETVRAVLDSLPGSVGGLSPSQASSAASSASSSPGS 180
AAT35-36x.49(SEQIDNO: 18)   KFLEVCTWVDQIAALNDSKTRKTTSETVRAVLDSLPGSVGGLSPSQASSAASSASSSPGS 180
AAT35-36L.79(SEQIDNO: 19)   KFLEVCTWVDQIAALNDSKTRKTTSETVRAVLDSLPGSVGGLSPSQASSAASSASSSPGS 180
AAT35-36L.141(SEQIDNO: 20)  KFLEVCTWVDQIAALNDSKTRKTTSETVRAVLDSLPGSVGGLSPSQASSAASSASSSPGS 180
AAT35-36L.210(SEQIDNO: 21)  KFLEVCTWVDQIAALNDSKTRKTTSETVRAVLDSLPGSVGGLSPSQASSAASSASSSPGS 180
AAT35-36L.290(SEQIDNO: 22)  KFLEVCTWVDQIAALNDSKTRKTTSETVRAVLDSLPGSVGGLSPSQASSAASSASSSPGS 180
                            **************** ******************************************

AAT35-36x.70(SEQIDNO: 17)   GISEALRAGAGSGTGYNKEFLLYLAGFVDGDGSIYAKITPHQKYKFKHQLTLRFAVSQKT 240
AAT35-36x.49(SEQIDNO: 18)   GISEALRAGAGSGTGYNKEFLLYLAGFVDGDGSIYAMIKPNQRYKFKHQLNLRFNVSQKT 240
AAT35-36L.79(SEQIDNO: 19)   GISEALRAGAGSGTGYNKEFLLYLAGFVDGDGSIYAKITPHQKYKFKHQLTLRFVVSQKT 240
AAT35-36L.141(SEQIDNO: 20)  GISEALRAGAGSGTGYNKEFLLYLAGFVDGDGSIYAKITPHQKYKFKHQLVLRFVVSQKT 240
AAT35-36L.210(SEQIDNO: 21)  GISEALRAGAGSGTGYNKEFLLYLAGFVDGDGSIYAKITPHQKYKFKHQLHLRFVVSQKT 240
AAT35-36L.290(SEQIDNO: 22)  GISEALRAGAGSGTGYNKEFLLYLAGFVDGDGSIYAKITPHQKYKFKHQLHLRFVVSQKT 240
                            ***************************************** * * * ****** *** *****

AAT35-36x.70(SEQIDNO: 17)   QRRWFLDKLVDEIGVGYVSDNGSVSSYTLSQIKPLHNFLTQLQPFLKLKQKQANLVLKII 300
AAT35-36x.49(SEQIDNO: 18)   QRRWFLDKLVDEIGVGYVSDNGSVSSYTLSQIKPLHNFLTQLQPFLKLKQKQANLVLKII 300
AAT35-36L.79(SEQIDNO: 19)   QRRWFLDKLVDEIGVGYVSDNGSVSSYTLSEIKPLHNFLTQLQPFLKLKQKQANLVLKII 300
AAT35-36L.141(SEQIDNO: 20)  QRRWFLDKLVDEIGVGYVSDNGSVSSYTLSQIKPLHNFLTQLQPFLKLKQKQANLVLKII 300
AAT35-36L.210(SEQIDNO: 21)  QRRWFLDKLVDEIGVGYVSDNGSMSAYTLSEIKPLHNFLTQLQPFLKLKQKQANLVLKII 300
AAT35-36L.290(SEQIDNO: 22)  QRRWFLDKLVDEIGVGYVSDNGSMSAYTLSQIKPLHNFLTQLQPFLKLKQKQANLVLKII 300
                            ********************** * **** ****************************

AAT35-36x.70(SEQIDNO: 17)   EQLPSAKESPDKFLEVCTWVDQIAALNDSHTRKTTSETVPAVLDSLSEKKKSSP 354
AAT35-36x.49(SEQIDNO: 18)   EQLPSAKESPDKFLEVCTWVDQIAALNDSRTRKTTSETVPAVLDSLSEKKKSSP 354
AAT35-36L.79(SEQIDNO: 19)   EQLPSAKESPDKFLEVCTWVDQIAALNDSKTRKTTSETVPAVLDSLSEKKKSSP 354
AAT35-36L.141(SEQIDNO: 20)  EQLPSAKESPDKFLEVCTWVDQIAALNDSHTRKTTSETVPAVLDSLSEKKKSSP 354
AAT35-36L.210(SEQIDNO: 21)  EQLPSAKESPDKFLEVCTWVDQIAALNDSHTRKTTSETVPAVLDSLSEKKKSSP 354
AAT35-36L.290(SEQIDNO: 22)  EQLPSAKESPDKFLEVCTWVDQIAALNDSHTRKTTSETVPAVLDSLSEKKKSSP 354
                            ***************************** ***********************
```

FIG. 3A

```
AAT37-38x.50(SEQ ID NO: 41)   MNTKYNKEFLLYLAGFVDADGSIHAIIRPKQSYKFKHELMLRFTVTQKTKRRWFLDKLVD  60
AAT37-38x.61(SEQ ID NO: 42)   MNTKYNKEFLLYLAGFVDSDGSIFACIRPSQASKFKHRLELRFTVTQKTRRRWFLDKLVD  60
AAT37-38L.158(SEQ ID NO: 43)  MNTKYNKEFLLYLAGFVDADGSIHAIIRPKQDYKFKHELMLRFVVSQKTKRRWFLDKLVD  60
AAT37-38L.167(SEQ ID NO: 44)  MNTKYNKEFLLYLAGFVDSDGSIHAIIRPKQDYKFKHELMLRFVVSQKTKRRWFLDKLVD  60
AAT37-38L.175(SEQ ID NO: 45)  MNTKYNKEFLLYLAGFVDADGSIHAIIRPKQDYKFKHELMLRFIVSQKTKRRWFLDKLVD  60
AAT37-38L.262(SEQ ID NO: 46)  MNTKYNKEFLLYLAGFVDADGSIHAIIRPKQDYKFKHELMLRFVVSQKTKRRWFLDKLVD  60
                              ****************** **** * *** *   **** * *** * *** *********

AAT37-38x.50(SEQ ID NO: 41)   EIGVGYVFDAGMTSHYCLSQIKPLHNFLTQLQPFLKLKQKQANLVLKIIEQLPSAKESPD  120
AAT37-38x.61(SEQ ID NO: 42)   EIGVGYVFDGGSVSHYCLSEIKPLHNFLTQLQPFLKLKQKQANLVLKIIEQLPSAKESPD  120
AAT37-38L.158(SEQ ID NO: 43)  EIGVGYVFDAGMTSHYCLSEIKPLHNFLTQLQPFLKLKQKQANLVLKIIEQLPSAKESPD  120
AAT37-38L.167(SEQ ID NO: 44)  EIGVGYVFDGGMTSHYCLSEIKPLHNFLTQLQPFLKLKQKQANLVLKIIEQLPSAKESPD  120
AAT37-38L.175(SEQ ID NO: 45)  EIGVGYVFDGGMTSHYCLSEIKPLHNFLTQLQPFLKLKQKQANLVLKIIEQLPSAKESPD  120
AAT37-38L.262(SEQ ID NO: 46)  EIGVGYVFDGRGTSHYCLSEIKPLHNFLTQLQPFLKLKQKQANLVLKIIEQLPSAKESPD  120
                              ********   *****  ******************************************

AAT37-38x.50(SEQ ID NO: 41)   KFLEVCTWVDQIAALNDSKTRKTTSETVRAVLDSLPGSVGGLSPSQASSAASSASSSPGS  180
AAT37-38x.61(SEQ ID NO: 42)   KFLEVCTWADQIAALNDSKTRKTTSETVRAVLDSLPGSVGGLSPSQASSAASSASSSPGS  180
AAT37-38L.158(SEQ ID NO: 43)  KFLEVCTWVDQIAALNDSKTRKTTSETVRAVLDSLPGSVGGLSPSQASSAASSASSSPGS  180
AAT37-38L.167(SEQ ID NO: 44)  KFLEVCTWVDQIAALNDSKTRKTTSETVRAVLDSLPGSVGGLSPSQASSAASSASSSPGS  180
AAT37-38L.175(SEQ ID NO: 45)  KFLEVCTWVDQIAALNDSKTRKTTSETVRAVLDSLPGSVGGLSPSQASSAASSASSSPGS  180
AAT37-38L.262(SEQ ID NO: 46)  KFLEVCTWVDQIAALNDSKARKTTSETVRAVLDSLPGSVGGLSPSQASSAASSASSSPGS  180
                              ******* *******  *******************************************

AAT37-38x.50(SEQ ID NO: 41)   GISEALRAGAGSGTGYNKEFLLYLAGFVDGDGSIFAAIHPCQRSKFKHELRLLFTVTQKT  240
AAT37-38x.61(SEQ ID NO: 42)   GISEALRAGAGSGTGYNKEFLLYLAGFVDGDGSIFAAIHPCQRSKFKHELRLLFTVTQKT  240
AAT37-38L.158(SEQ ID NO: 43)  GISEALRAGAGSGTGYNKEFLLYLAGFVDGDGSIFAAIHPCQRSKFKHELRLLFTVTQKT  240
AAT37-38L.167(SEQ ID NO: 44)  GISEALRAGAGSGTGYNKEFLLYLAGFVDGDGSIFAAIHPCQRSKFKHELRLLFTVTQKT  240
AAT37-38L.175(SEQ ID NO: 45)  GISEALRAGAGSGTGYNKEFLLYLAGFVDGDGSIFAAIHPCQRSKFKHELRLLFTVTQKT  240
AAT37-38L.262(SEQ ID NO: 46)  GISEALRAGAGSGTGYNKEFLLYLAGFVDGDGSIFAAIHPCQRSKFKHELRLLFTVTQKT  240
                              ************************************************************

AAT37-38x.50(SEQ ID NO: 41)   QRRWFLDKLVDEIGVGYVRDTGSVSEYTLSQIKPLHNFLTQLQPFLKLKQKQANLVLKII  300
AAT37-38x.61(SEQ ID NO: 42)   QRRWFLDKLVDEIGVGYVRDTGSVSEYTLSQIKPLHNFLTQLQPFLKLKQKQANLVLKII  300
AAT37-38L.158(SEQ ID NO: 43)  QRRWFLDKLVDEIGVGYVRDTGSVSHYTLSQIKPLHNFLTQLQPFLKLKQKQANLVLKII  300
AAT37-38L.167(SEQ ID NO: 44)  QRRWFLDKLVDEIGVGYVRDAGSVSHYTLSQIKPLHNFLTQLQPFLKLKQKQANLVLKII  300
AAT37-38L.175(SEQ ID NO: 45)  QRRWFLDKLVDEIGVGYVRDAGSVSHYTLSQIKPLHNFLTQLQPFLKLKQKQANLVLKII  300
AAT37-38L.262(SEQ ID NO: 46)  QRRWFLDKLVDEIGVGYVRDAGSVSHYTLSEIKPLHNFLTQLQPFLKLKQKQANLVLKII  300
                              ********************** **** **** ***************************

AAT37-38x.50(SEQ ID NO: 41)   EQLPSAKESPDKFLEVCTWVDQIAALNDSKTRKTTSETVRAVLDSLSEKKKSSP  354
AAT37-38x.61(SEQ ID NO: 42)   EQLPSAKESPDKFLEVCTWVDQIAALNDSKTRKTTSETVRAVLDSLSEKKKSSP  354
AAT37-38L.158(SEQ ID NO: 43)  EQLPSAKESPDKFLEVCTWVDQIAALNDSKTRKTTSETVRAVLDSLSEKKKSSP  354
AAT37-38L.167(SEQ ID NO: 44)  EQLPSAKESPDKFLEVCTWVDQIAALNDSKTRKTTSETVRAVLDSLSEKKKSSP  354
AAT37-38L.175(SEQ ID NO: 45)  EQLPSAKESPDKFLEVCTWVDQIAALNDSKTRKTTSETVRAVLDSLSEKKKSSP  354
AAT37-38L.262(SEQ ID NO: 46)  EQLPSAKESPDKFLEVCTWVDQIAALNDSKTRKTTSETVRAVLDSLSEKKKSSP  354
                              ************************************* ********************
```

FIG. 3B

```
AAT41-42x.1(SEQIDNO:65)    MNTKYNKEFLLYLAGFVDADGSIYASITPDQARKFKHQLRLYFNVRQATKRRWFLDKLVD  60
AAT41-42x.32(SEQIDNO:66    MNTKYNKEFLLYLAGFVDADGSIYASITPSQGRKFKHQLRLYFNVRQSTKRRWFLDKLVD  60
AAT41-42L.42(SEQIDNO:67)   MNTKYNKEFLLYLAGFVDADGSIYASIEPSQARKFKHQLRLRFNVRQATKRRWFLDKLVD  60
AAT41-42L.104(SEQIDNO:68)  MNTKYNKEFLLYLAGFVDADGSIYASIEPSQARKFKHQLRLRFNVRQATKRRWFLDKLVD  60
AAT41-42L.153(SEQIDNO:69)  MNTKYNKEFLLYLAGFVDSDGSIYASIEPSQARKFKHQLRLRFNVRQATKRRWFLDKLVD  60
AAT41-42L.185(SEQIDNO:70)  MNTKYNKEFLLYLAGFVDADGSIYASIEPSQARKFKHQLRLRFNVRQATKRRWFLDKLVD  60
AAT41-42L.294(SEQIDNO:71)  MNTKYNKEFLLYLAGFVDADGSIYASIEPSQARKFKHQLRLRFNVRQATKRRWFLDKLVD  60
                           ******************* ******* * * ********* ***** ***********

AAT41-42x.1(SEQIDNO:65)    EIGVGYVTDGGTVSTYILSQIKPLHNFLTQLQPFLKLKQKQANLVLKIIEQLPSAKESPD  120
AAT41-42x.32(SEQIDNO:66)   EIGVGYVTDKGSVSTYLLSQIKPLHNFLTQLQPFLKLKQKQANLVLKIIEQLPSAKESPD  120
AAT41-42L.42(SEQIDNO:67)   EIGVGYVIDEGTVSTYILSQIKPLHNFLTQLQPFLKLKQKQANLVLKIIEQLPSAKESPD  120
AAT41-42L.104(SEQIDNO:68)  EIGVGYVVDDGTVSTYLLSQIKPLHNFLTQLQPFLKLKQKQANLVLKIIEQLPSAKESPD  120
AAT41-42L.153(SEQIDNO:69)  EIGVGYVVDDGTVSTYMLSQIKPLHNFLTQLQPFLKLKQKQANLVLKIIEQLPSAKESPD  120
AAT41-42L.185(SEQIDNO:70)  EIGVGYVVDDGTVSTYMLSQIKPLHNFLTQLQPFLKLKQKQANLVLKIIEQLPSAKESPD  120
AAT41-42L.294(SEQIDNO:71)  EIGVGYVVATGTVSTYMLSQIKPLHNFLTQLQPFLKLKQKQANLVLKIIEQLPSAKESPD  120
                           ******   * **** ******************************************

AAT41-42x.1(SEQIDNO:65)    KFLEVCTWVDQIAALNDSKTRKTTSETVRAVLDSLPGSVGGLSPSQASSAASSASSSPGS  180
AAT41-42x.32(SEQIDNO:66)   KFLEVCTWVDQIAALNDSKTRKTTSETVRAVLDSLPGSVGGLSPSQASSAASSASSSPGS  180
AAT41-42L.42(SEQIDNO:67)   KFLEVCTWVDQIAALNDSKTRKTTSETVRAVLDSLPGSVGGLSPSQASSAASSASSSPGS  180
AAT41-42L.104(SEQIDNO:68)  KFLEVCTWVDQIAALNDSKTRKTTSETVRAVLDSLPGSVGGLSPSQAPSAASSASSSPGS  180
AAT41-42L.153(SEQIDNO:69)  KFLEVCTWVDQIAALNDSKTRKTTSETVRAVLDSLPGSVGGLSPSQASSAASSASSSPGS  180
AAT41-42L.185(SEQIDNO:70)  KFLEVCTWVDQIAALNDSKTRKTTSETVRAVLDSLPGSVGGLSPSQAPSAASSASSSPGS  180
AAT41-42L.294(SEQIDNO:71)  KFLEVCTWVDQIAALNDSKTRKTTSETVRAVLDSLPGSVGGLSPSQAFSAASSASSSPGS  180
                           *********************************************** **********
```

FIG. 3C-1

```
AAT41-42x.1(SEQ|DNO: 65)    GISEALRAGAGSGTGYNKEFLLYLAGFVDGDGSIFAAITPDQTCKFKHTLRLRFQVTQHT  240
AAT41-42x.32(SEQ|DNO: 66)   GISEALRAGAGSGTGYNKEFLLYLAGFVDGDGSIFAAITPDQTCKFKHTLRLRFQVTQKT  240
AAT41-42L.42(SEQ|DNO: 67)   GISEALRAGAGSGTGYNKEFLLYLAGFVDGDGSIFAAITPDQTCKFKHTLRLRFQVTQHT  240
AAT41-42L.104(SEQ|DNO: 68)  GISEALRAGAGSGTGYNKEFLLYLAGFVDGDGSIFAAITPDQTCKFKHWLRLRFQVTQHT  240
AAT41-42L.153(SEQ|DNO: 69)  GISEALRAGAGSGTGYNKEFLLYLAGFVDGDGSIFAAITPDQTCKFKHTLRLRFRVTQHT  240
AAT41-42L.185(SEQ|DNO: 70)  GISEALRAGAGSGTGYNKEFLLYLAGFVDGDGSIFAAITPDQTCKFKHWLRLRFRVTQHT  240
AAT41-42L.294(SEQ|DNO: 71)  GISEALRAGAGSGTGYNKEFLLYLAGFVDGDGSIFAAIRPDQTCKFKHWLQLYFRVTQHT  240
                            ********************************** ********* * * * *** *

AAT41-42x.1(SEQ|DNO: 65)    CRRWFLDKLVDEIGVGYVSDRGRASDYTLSQIKPLHNFLTQLQPFLKLKQKQANLVLKII  300
AAT41-42x.32(SEQ|DNO: 66)   CRRWFLDKLVDEIGVGYVSDRGRASDYTLSQIKPLHNFLTQLQPFLKLKQKQANLVLKII  300
AAT41-42L.42(SEQ|DNO: 67)   CRRWFLDKLVDEIGVGYVSDRGRASDYTLSQIKPLHNFLTQLQPFLKLKQKQANLVLKII  300
AAT41-42L.104(SEQ|DNO: 68)  CRRWFLDKLVDEIGVGYVTDRGRASDYTLSEIKPLHNFLTQLQPFLKLKQKQANLVLKII  300
AAT41-42L.153(SEQ|DNO: 69)  CRRWFLDKLVDEIGVGYVSDRGRASDYTLSQIKPLHNFLTQLQPFLKLKQKQANLVLKII  300
AAT41-42L.185(SEQ|DNO: 70)  CRRWFLDKLVDEIGVGYVSDRGRASDYTLSQIKPLHNFLTQLQPFLKLKQKQANLVLKII  300
AAT41-42L.294(SEQ|DNO: 71)  CRRWFLDKLVDEIGVGYVSDRGRASDYTLSQIKPLHNFLTQLQPFLKLKQKQANLVLKII  300
                            ****************** *********** ***************************

AAT41-42x.1(SEQ|DNO: 65)    EQLPSAKESPDKFLEVCTWVDQIAALNDSRTRKTTSETVRAVLDSLSEKKKSSP  354
AAT41-42x.32(SEQ|DNO: 66)   EQLPSAKESPDKFLEVCTWVDQIAALNDSRTRKTTSETVRAVLDSLSEKKKSSP  354
AAT41-42L.42(SEQ|DNO: 67)   EQLPSAKESPDKFLEVCTWVDQIAALNDSKTRKTTSETVRAVLDSLSEKKKSSP  354
AAT41-42L.104(SEQ|DNO: 68)  EQLPSAKESPDKFLEVCTWVDQIAALNDSKTRKTTSETVRAVLDSLSEKKKSSP  354
AAT41-42L.153(SEQ|DNO: 69)  EQLPSAKESPDKFLEVCTWVDQIAALNDSKTRKTTSETVRAVLDSLSEKKKSSP  354
AAT41-42L.185(SEQ|DNO: 70)  EQLPSAKESPDKFLEVCTWVDQIAALNDSKTRKTTSETVRAVLDSLSEKKKSSP  354
AAT41-42L.294(SEQ|DNO: 71)  EQLPSAKESPDKFLEVCTWVDQIAALNDSHTRKTTSETVRAVLDSLSEKKKSSP  354
                            ***************************** **********************
```

FIG. 3C-2

```
AAT43-44x.34(SEQIDNO: 93)    MNTKYNKEFLLYLAGFVDSDGSIYARIVPSQTSKFKHKLRLVFAVAQSTCRRWFLDKLVD  60
AAT43-44x.58(SEQIDNO: 94)    MNTKYNKEFLLYLAGFVDSDGSIYARIVPSQTSKFKHKLRLTFAVTQKTCRRWFLDKLVD  60
AAT43-44L.47(SEQIDNO: 95)    MNTKYNKEFLLYLAGFVDSDGSIYARIVPSQGSKFKHKLRLTFAVTQKTCRRWFLDKLVD  60
AAT43-44L.105(SEQIDNO: 96)   MNTKYNKEFLLYLAGFVDADGSIFARIVPSQTRKFKHKLNLTFAVTQKTCRRWFLDKLVD  60
AAT43-44L.132(SEQIDNO: 97)   MNTKYNKEFLLYLAGFVDSDGSIYARIVPSQHRKFKHKLQLTFAVTQKTCRRWFLDKLVD  60
AAT43-44L.157(SEQIDNO: 98)   MNTKYNKEFLLYLAGFVDADGSIFARIVPSQSRKFKHKLNLTFAVTQKTCRRWFLDKLVD  60
AAT43-44L.276(SEQIDNO: 99)   MNTKYNKEFLLYLAGFVDADGSIFARIVPEQGRKFKHKLQLTFAVTQKTCRRWFLDKLVD  60
AAT43-44L.384(SEQIDNO: 100)  MNTKYNKEFLLYLAGFVDADGSIFARIVPEQGRKFKHKLQLTFAVTQKTCRRWFLDKLVD  60
                             *****************  ****  *****  *   ****** *  *** *  **********

AAT43-44x.34(SEQIDNO: 93)    EIGVGYVRDHGRASYYTLSEIKPLHNFLTQLQPFLKLKQKQANLVLKIIEQLPSAKESPD  120
AAT43-44x.58(SEQIDNO: 94)    EIGVGYVTDNGRASNYFLSQIKPLHNFLTQLQPFLKLKQKQANLVLKIIEQLPSAKESPD  120
AAT43-44L.47(SEQIDNO: 95)    EIGVGYVIDNGRASNYFLSEIKPLHNFLTQLQPFLKLKQKQANLVLKIIEQLPSAKESPD  120
AAT43-44L.105(SEQIDNO: 96)   EIGVGYVIDNGRASNYFLSEIKPLHNFLTQLQPFLKLKQKQANLVLKIIEQLPSAKESPD  120
AAT43-44L.132(SEQIDNO: 97)   EIGVGYVIDNGRASNYFLSEIKPLHNFLTQLQPFLKLKQKQADLVLKIIEQLPSAKESPD  120
AAT43-44L.157(SEQIDNO: 98)   EIGVGYVIDNGRASNYFLSQIKPLHNFLTQLQPFLKLKQKQANLVLKIIEQLPSAKESPD  120
AAT43-44L.276(SEQIDNO: 99)   EIGVGYVIDGGRASNYWLSEIKPLHNFLTQLQPFLKLKQKQANLVLKIIEQLPSAKESPD  120
AAT43-44L.384(SEQIDNO: 100)  EIGVGYVIDNGRASNYVLSQIKPLHNFLTQLQPFLKLKQKQANLVLKIIEQLPSAKESPD  120
                             *******  *  ****  *  **  ***********************  ****************

AAT43-44x.34(SEQIDNO: 93)    KFLEVCTWVDQIAALNDSKTRKTTSETVRAVLDSLPGSVGGLSPSQASSAASSASSSPGS  180
AAT43-44x.58(SEQIDNO: 94)    KFLEVCTWVDQIAALNDSKTRKTTSETVRAVLDSLPGSVGGLSPSQASSAASSASSSPGS  180
AAT43-44L.47(SEQIDNO: 95)    KFLEVCTWVDQIAALNDSKTRKTTSETVRAVLDSLPGSVGGLSPSQASSAASSASSSPGS  180
AAT43-44L.105 SEQIDNO: 96)   KFLEVCTWVDQIAALNDSKTRKTTSETVRAVLDSLPGSVGGLSPSQASGAASSASSSPGS  180
AAT43-44L.132(SEQIDNO: 97)   KFLEVCTWVDQIAALNDSKTRKTTSETVRAVLDSLPGSVGGLSPSQASSAASSASSSPGS  180
AAT43-44L.157(SEQIDNO: 98)   KFLEVCTWVDQIAALNDSKTRKTTSETVRAVLDSLPGSVGGLSPSQASSAASSASSSPGS  180
AAT43-44L.276(SEQIDNO: 99)   KFLEVCTWVDQIAALNDSKTRKTTSETVRAVLDSLPGSVGGLSPSQASGAASSASSSPGS  180
AAT43-44L.384(SEQIDNO: 100)  KFLEVCTWVDQIAALNDSNTRKTTSETVRAVLDSLPGSVGGLSPSQASGAASSASSSPGS  180
                             *******************  *****************************  **********
```

FIG. 3D-1

```
AAT43-44x.34(SEQIDNO:93)    GISEALRAGAGSGTGYNKEFLLYLAGFVDGDGSIFATIVPQQDRKFKHALRLQFRVHQKT  240
AAT43-44x.58(SEQIDNO:94)    GISEALRAGAGSGTGYNKEFLLYLAGFVDGDGSIFATIVPQQDRKFKHALRLQFRVHQHT  240
AAT43-44L.47(SEQIDNO:95)    GISEALRAGAGSGTGYNKEFLLYLAGFVDGDGSIFATIVPQQDRKFKHALRLNFRVHQHT  240
AAT43-44L.105(SEQIDNO:96)   GISEALRAGAGSGTGYNKEFLLYLAGFVDGDGSIFATIVPQQDRKFKHALRLNFRVHQHT  240
AAT43-44L.132(SEQIDNO:97)   GISEALRAGAGSGTGYNKEFLLYLAGFVDGDGSIFATIVPQQDRKFKHALRLNFRVHQHT  240
AAT43-44L.157(SEQIDNO:98)   GISEALRAGAGSGTGYNKEFLLYLAGFVDGDGSIFATIVPQQDRKFKHALRLNFRVHQHT  240
AAT43-44L.276(SEQIDNO:99)   GISEALRAGAGSGTGYNKEFLLYLAGFVDGDGSIFATIVPQQDRKFKHALRLNFRLHQHT  240
AAT43-44L.384(SEQIDNO:100)  GTSEALRAGAGSGTGYNKEFLLYLAGFVDGDGSIFAQIVPQQDRKFKHALRLKFRLHQHT  240
                            * ****************************** ************** ** ** *

AAT43-44x.34(SEQIDNO:93)    CRRWFLDKLVDEIGVGYVYDFGRASHYCLSEIKPLHNFLTQLQPFLKLKQKQANLVLKII  300
AAT43-44x.58(SEQIDNO:94)    RRRWFLDKLVDEIGMGYVSDRGRASFYSLSQIKPLHNFLTQLQPFLKLKQKQANLVLKII  300
AAT43-44L.47(SEQIDNO:95)    RRRWFLDKLVDEIGMGYVSDRGRASFYHLSEIKPLHNFLTQLQPFLKLKQKQANLVLKII  300
AAT43-44L.105(SEQIDNO:96)   RRRWFLDKLVDEIGVGYVSDGGRASFYHLSEIKPLHNFLTQLQPFLKLKQKQANLVLKII  300
AAT43-44L.132(SEQIDNO:97)   RRRWFLDKLVDEIGVGYVSDTGRASFYHLSQIKPLHNFLTQLQPFLKLKQKQANLVLKII  300
AAT43-44L.157(SEQIDNO:98)   RRRWFLDKLVDEIGVGYVSDKGRASFYHLSQIKPLHNFLTQLQPFLKLKQKQANLVLKII  300
AAT43-44L.276(SEQIDNO:99)   RRRWFLDKLVDEIGVGYVSDGGRASFYHLSEIKPLHNFLTQLQPFLKLKQKQANLVLKII  300
AAT43-44L.384(SEQIDNO:100)  RRRWFLDKLVDEIGVGYVSDGGRASFYNLSQIKPLHNFLTQLQPFLKLKQKQANLVLKII  300
                            ************ *** * **** * ** *****************************

AAT43-44x.34(SEQIDNO:93)    EQLPSAKESPDKFLEVCTWVDQIAALNDSKTRKTTSETVRAVLDSLSEKKKSSP  354
AAT43-44x.58(SEQIDNO:94)    EQLPSAKESPDKFLEVCTWVDQIAALNDSRTRKTTSETVRAVLDSLSEKKKSSP  354
AAT43-44L.47(SEQIDNO:95)    EQLPSAKESPDKFLEVCTWVDQIAALNDSRTRKTTSETVRAVLDSLSEKKKSSP  354
AAT43-44L.105(SEQIDNO:96)   EQLPSAKESPDKFLEVCTWVDQIAALNDSKTRKTTSETVRAVLDSLSEKKKSSP  354
AAT43-44L.132(SEQIDNO:97)   EQLPSAKESPDKFLEVCTWVDQIAALNDSKTRKTTSETVRAVLDSLSEKKKSSP  354
AAT43-44L.157(SEQIDNO:98)   EQLPSAKESPDKFLEVCTWVDQIAALNDSRTRKTTSETVRAVLDSLSEKKKSSP  354
AAT43-44L.276(SEQIDNO:99)   EQLPSAKESPDKFLEVCTWVDQIAALNDSRTRKTTSETVRAVLDSLSEKKKSSP  354
AAT43-44L.384(SEQIDNO:100)  EQLPSAKESPDKFLEVCTWVDQIAALNDSKTRKTTSETVRAVLDSLSEKKKSSP  354
```

FIG. 3D-2

Group 1

Group 2

Design 1: ssAAV8

Design 2: scAAV8

FIG. 14

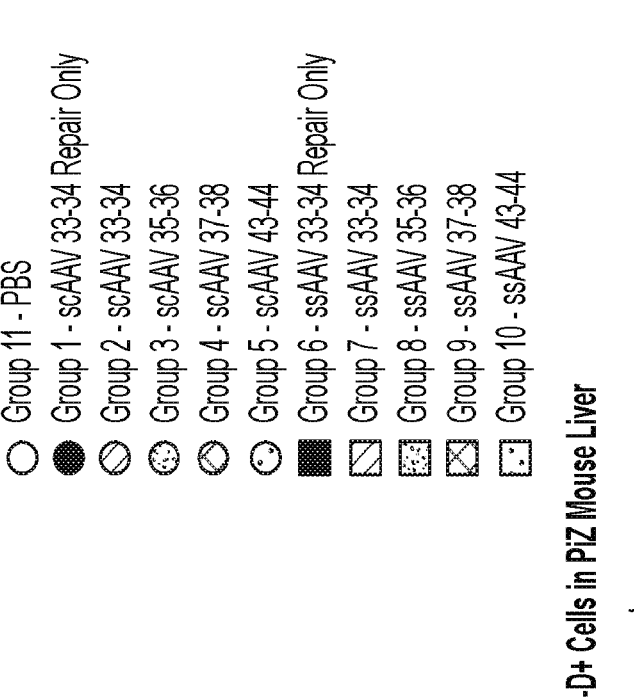
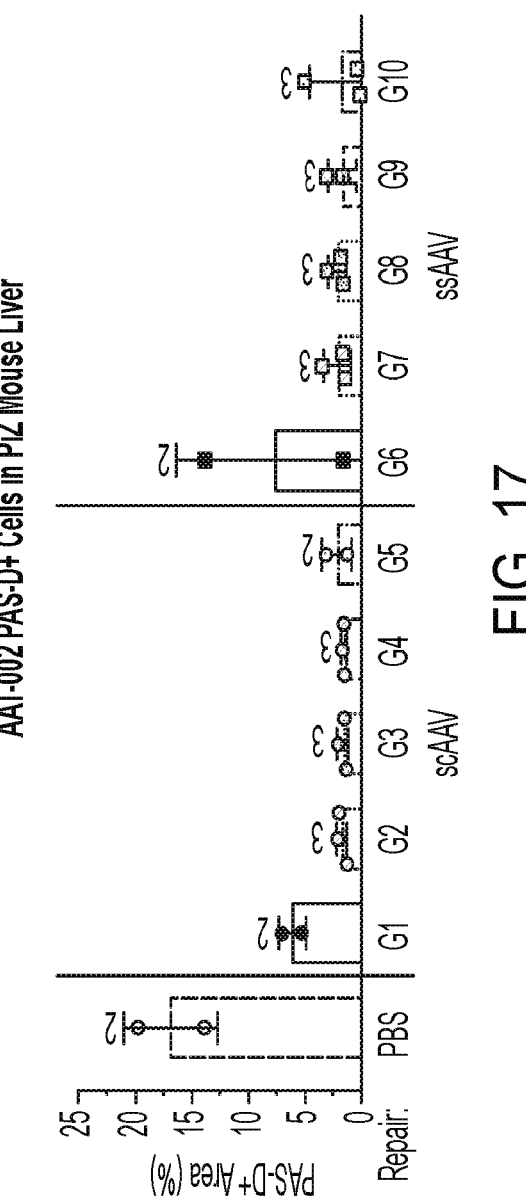
FIG. 17

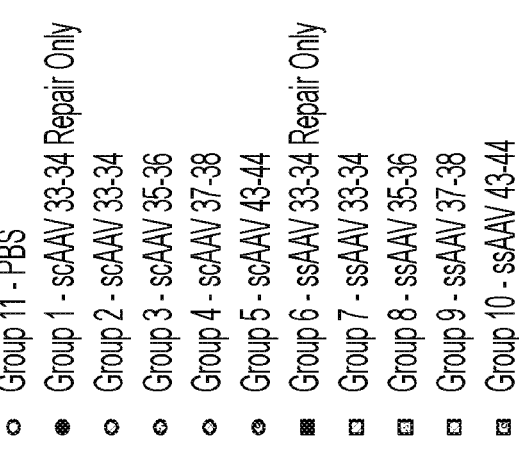
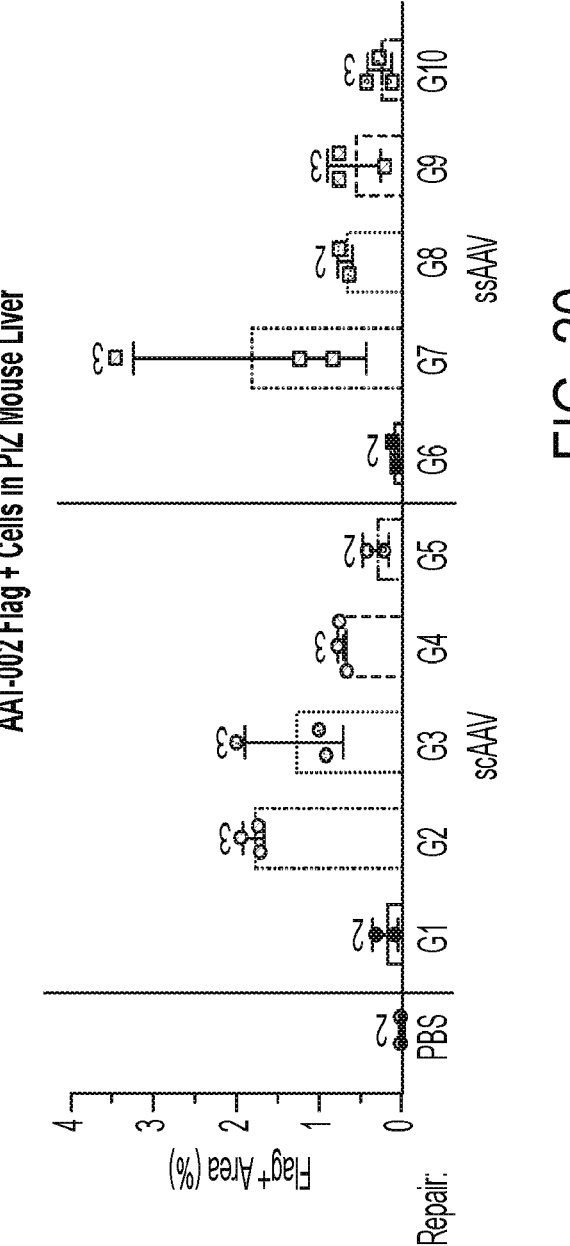
FIG. 20

Body Weights

-o- Group 1 - PBS, PBS

-□- Group 2 - AAV repair + LNP, PBS

-△- Group 3 - AAV repair + PBS, LNP

-◇- Group 4 - AAV repair + LNP, LNP

-●- Group 5 - AAV repair + LNP, PBS

-□- Group 6 - AAV repair + LNP, LNP

-△- Group 7 - PBS + LNP, PBS

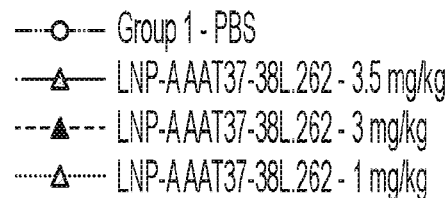
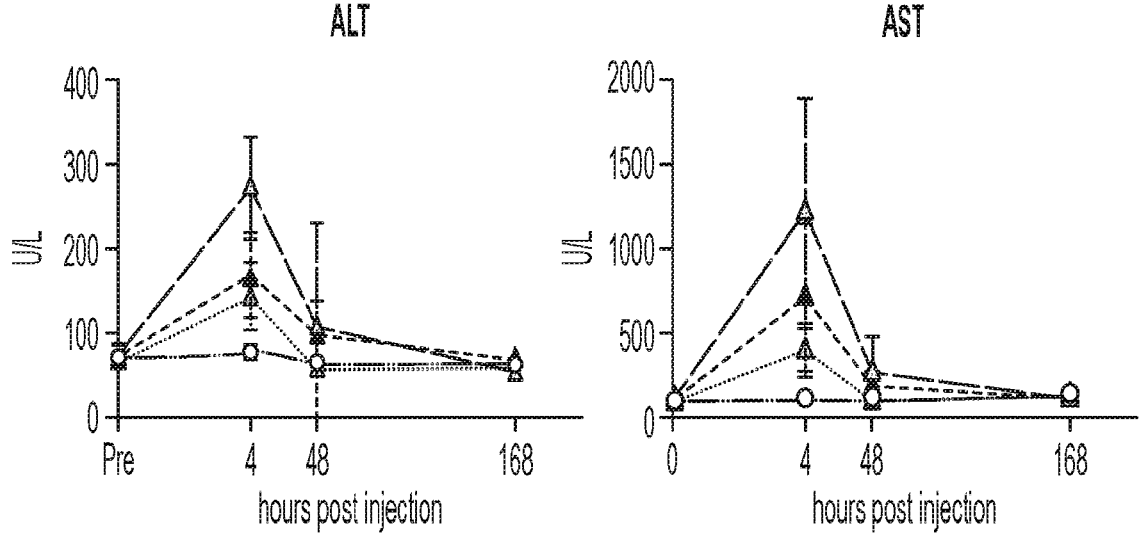
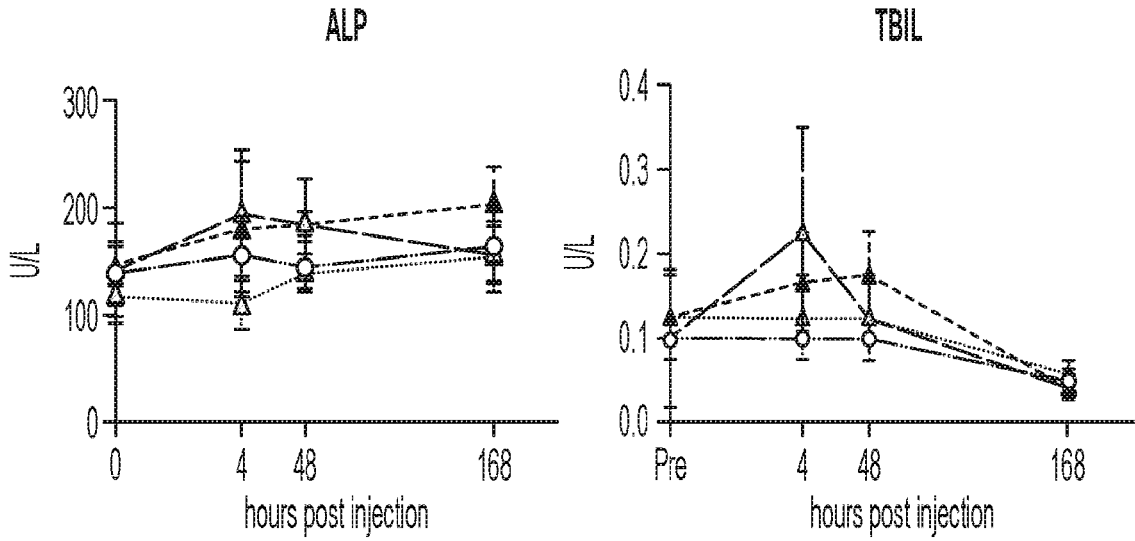
FIG. 54

SEQUENCE LISTING

Sequence total quantity: 265
SEQ ID NO: 1          moltype = AA  length = 163
FEATURE               Location/Qualifiers
source                1..163
                      mol_type = protein
                      organism = Chlamydomonas reinhardtii
SEQUENCE: 1
MNTKYNKEFL LYLAGFVDGD GSIIAQIKPN QSYKFKHQLS LAFQVTQKTQ RRWFLDKLVD   60

```
EIGVGYVRDR GSVSDYILSE IKPLHNFLTQ LQPFLKLKQK QANLVLKIIW RLPSAKESPD   120
KFLEVCTWVD QIAALNDSKT RKTTSETVRA VLDSLSEKKK SSP                    163

SEQ ID NO: 2          moltype = AA  length = 9
FEATURE               Location/Qualifiers
source                1..9
                      mol_type = protein
                      organism = synthetic construct
SEQUENCE: 2
LAGLIDADG                                                             9

SEQ ID NO: 3          moltype = DNA  length = 22
FEATURE               Location/Qualifiers
source                1..22
                      mol_type = other DNA
                      organism = synthetic construct
SEQUENCE: 3
tgcccgctca caccagaccc tg                                              22

SEQ ID NO: 4          moltype = DNA  length = 22
FEATURE               Location/Qualifiers
source                1..22
                      mol_type = other DNA
                      organism = synthetic construct
SEQUENCE: 4
acgggcgagt gtggtctggg ac                                              22

SEQ ID NO: 5          moltype = DNA  length = 22
FEATURE               Location/Qualifiers
source                1..22
                      mol_type = other DNA
                      organism = synthetic construct
SEQUENCE: 5
gctgctcagg catctgcatt tc                                              22

SEQ ID NO: 6          moltype = DNA  length = 22
FEATURE               Location/Qualifiers
source                1..22
                      mol_type = other DNA
                      organism = synthetic construct
SEQUENCE: 6
cgacgagtcc gtagacgtaa ag                                              22

SEQ ID NO: 7          moltype = DNA  length = 22
FEATURE               Location/Qualifiers
source                1..22
                      mol_type = other DNA
                      organism = synthetic construct
SEQUENCE: 7
ttcagacagt tgctcaacct ct                                              22

SEQ ID NO: 8          moltype = DNA  length = 22
FEATURE               Location/Qualifiers
source                1..22
                      mol_type = other DNA
                      organism = synthetic construct
SEQUENCE: 8
aagtctgtca acgagttgga ga                                              22

SEQ ID NO: 9          moltype = DNA  length = 22
FEATURE               Location/Qualifiers
source                1..22
                      mol_type = other DNA
                      organism = synthetic construct
SEQUENCE: 9
ggcctggtca cacttgggtt ta                                              22

SEQ ID NO: 10         moltype = DNA  length = 22
FEATURE               Location/Qualifiers
source                1..22
                      mol_type = other DNA
                      organism = synthetic construct
SEQUENCE: 10
ccggaccagt gtgaacccaa at                                              22

SEQ ID NO: 11         moltype = DNA  length = 22
FEATURE               Location/Qualifiers
source                1..22
                      mol_type = other DNA
```

-continued

```
                            organism = synthetic construct
SEQUENCE: 11
ccccactttg cacaactggg ga                                          22

SEQ ID NO: 12       moltype = DNA   length = 22
FEATURE             Location/Qualifiers
source              1..22
                    mol_type = other DNA
                    organism = synthetic construct
SEQUENCE: 12
gggggtgaaac gtgttgaccc ct                                         22

SEQ ID NO: 13       moltype = DNA   length = 22
FEATURE             Location/Qualifiers
source              1..22
                    mol_type = other DNA
                    organism = synthetic construct
SEQUENCE: 13
tgaggatcct tgtgagtgtt gg                                          22

SEQ ID NO: 14       moltype = DNA   length = 22
FEATURE             Location/Qualifiers
source              1..22
                    mol_type = other DNA
                    organism = synthetic construct
SEQUENCE: 14
actcctagga acactcacaa cc                                          22

SEQ ID NO: 15       moltype = DNA   length = 22
FEATURE             Location/Qualifiers
source              1..22
                    mol_type = other DNA
                    organism = synthetic construct
SEQUENCE: 15
aggacctaga tgtaggattc tg                                          22

SEQ ID NO: 16       moltype = DNA   length = 22
FEATURE             Location/Qualifiers
source              1..22
                    mol_type = other DNA
                    organism = synthetic construct
SEQUENCE: 16
tcctggatct acatcctaag ac                                          22

SEQ ID NO: 17       moltype = AA   length = 354
FEATURE             Location/Qualifiers
source              1..354
                    mol_type = protein
                    organism = synthetic construct
SEQUENCE: 17
MNTKYNKEFL LYLAGFVDAD GSIYACIRPR QSSKFKHTLE LGFQVSQKTC RRWFLDKLVD   60
EIGVGYVRDR GRASDYRLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIYAKITP HQKYKFKHQL TLRFAVSQKT  240
QRRWFLDKLV DEIGVGYVSD NGSVSSYTLS QIKPLHNFLT QLQPFLKLKQ KQANLVLKII  300
EQLPSAKESP DKFLEVCTWV DQIAALNDSH TRKTTSETVR AVLDSLSEKK KSSP        354

SEQ ID NO: 18       moltype = AA   length = 354
FEATURE             Location/Qualifiers
source              1..354
                    mol_type = protein
                    organism = synthetic construct
SEQUENCE: 18
MNTKYNKEFL LYLAGFVDSD GSIYACIRPR QARKFKHTLE LGFQVTQATC RRWFLDKLVD   60
EIGVGYVRDR GRASDYRLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIYAMIKP NQRYKFKHQL NLRFNVSQKT  240
QRRWFLDKLV DEIGVGYVSD NGSVSSYTLS QIKPLHNFLT QLQPFLKLKQ KQANLVLKII  300
EQLPSAKESP DKFLEVCTWV DQIAALNDSR TRKTTSETVR AVLDSLSEKK KSSP        354

SEQ ID NO: 19       moltype = AA   length = 354
FEATURE             Location/Qualifiers
source              1..354
                    mol_type = protein
                    organism = synthetic construct
SEQUENCE: 19
MNTKYNKEFL LYLAGFVDAD GSIYACIRPR QRRKFKHMLE LGFQVSQKTC RRWFLDKLVD   60
EIGVGYVRDR GRASDYRLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
```

-continued

```
GISEALRAGA GSGTGYNKEF LLYLAGFVDG DGSIYAKITP HQKYKFKHQL TLRFVVSQKT  240
QRRWFLDKLV DEIGVGYVSD NGSVSSYTLS EIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 20              moltype = AA   length = 354
FEATURE                    Location/Qualifiers
source                     1..354
                           mol_type = protein
                           organism = synthetic construct
SEQUENCE: 20
MNTKYNKEFL LYLAGFVDAD GSIYASIRPR QRRKFKHMLI LGFQVSQKTC RRWFLDKLVD  60
EIGVGYVRDR GRASDYRLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIYAKITP HQKYKFKHQL VLRFVVSQKT  240
QRRWFLDKLV DEIGVGYVSD NGSVSSYTLS QIKPLHNFLT QLQPFLKLKQ KQANLVLKII  300
EQLPSAKESP DKFLEVCTWV DQIAALNDSH TRKTTSETVR AVLDSLSEKK KSSP        354

SEQ ID NO: 21              moltype = AA   length = 354
FEATURE                    Location/Qualifiers
source                     1..354
                           mol_type = protein
                           organism = synthetic construct
SEQUENCE: 21
MNTKYNKEFL LYLAGFVDSD GSIYATIRPR QRRKFKHMLE LFFQVSQKTC RRWFLDKLVD  60
EIGVGYVRDR GRASDYRLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIYAKITP HQKYKFKHQL HLRFVVSQKT  240
QRRWFLDKLV DEIGVGYVSD NGSMSAYTLS EIKPLHNFLT QLQPFLKLKQ KQANLVLKII  300
EQLPSAKESP DKFLEVCTWV DQIAALNDSH TRKTTSETVR AVLDSLSEKK KSSP        354

SEQ ID NO: 22              moltype = AA   length = 354
FEATURE                    Location/Qualifiers
source                     1..354
                           mol_type = protein
                           organism = synthetic construct
SEQUENCE: 22
MNTKYNKEFL LYLAGFVDAD GSIYARIRPR QRRKFKHMLE FGFQVSQKTR RRWFLDKLVD  60
EIGVGYVRDR GRASDYRLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIYAKITP HQKYKFKHQL HLRFVVSQKT  240
QRRWFLDKLV DEIGVGYVSD NGSMSAYTLS QIKPLHNFLT QLQPFLKLKQ KQANLVLKII  300
EQLPSAKESP DKFLEVCTWV DQIAALNDSH TRKTTSETVR AVLDSLSEKK KSSP        354

SEQ ID NO: 23              moltype = AA   length = 147
FEATURE                    Location/Qualifiers
source                     1..147
                           mol_type = protein
                           organism = synthetic construct
SEQUENCE: 23
KEFLLYLAGF VDADGSIYAC IRPRQSSKFK HTLELGFQVS QKTCRRWFLD KLVDEIGVGY  60
VRDRGRASDY RLSQIKPLHN FLTQLQPFLK LKQKQANLVL KIIEQLPSAK ESPDKFLEVC  120
TWVDQIAALN DSKTRKTTSE TVRAVLD                                     147

SEQ ID NO: 24              moltype = AA   length = 147
FEATURE                    Location/Qualifiers
source                     1..147
                           mol_type = protein
                           organism = synthetic construct
SEQUENCE: 24
KEFLLYLAGF VDSDGSIYAC IRPRQARKFK HTLELGFQVT QATCRRWFLD KLVDEIGVGY  60
VRDRGRASDY RLSEIKPLHN FLTQLQPFLK LKQKQANLVL KIIEQLPSAK ESPDKFLEVC  120
TWVDQIAALN DSKTRKTTSE TVRAVLD                                     147

SEQ ID NO: 25              moltype = AA   length = 147
FEATURE                    Location/Qualifiers
source                     1..147
                           mol_type = protein
                           organism = synthetic construct
SEQUENCE: 25
KEFLLYLAGF VDADGSIYAC IRPRQRRKFK HMLELGFQVS QKTCRRWFLD KLVDEIGVGY  60
VRDRGRASDY RLSEIKPLHN FLTQLQPFLK LKQKQANLVL KIIEQLPSAK ESPDKFLEVC  120
TWVDQIAALN DSKTRKTTSE TVRAVLD                                     147

SEQ ID NO: 26              moltype = AA   length = 147
FEATURE                    Location/Qualifiers
source                     1..147
                           mol_type = protein
                           organism = synthetic construct
SEQUENCE: 26
```

```
KEFLLYLAGF VDADGSIYAS IRPRQRRKFK HMLILGFQVS QKTCRRWFLD KLVDEIGVGY    60
VRDRGRASDY RLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 27              moltype = AA   length = 147
FEATURE                    Location/Qualifiers
source                     1..147
                           mol_type = protein
                           organism = synthetic construct
SEQUENCE: 27
KEFLLYLAGF VDSDGSIYAT IRPRQRRKFK HMLELFFQVS QKTCRRWFLD KLVDEIGVGY    60
VRDRGRASDY RLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 28              moltype = AA   length = 147
FEATURE                    Location/Qualifiers
source                     1..147
                           mol_type = protein
                           organism = synthetic construct
SEQUENCE: 28
KEFLLYLAGF VDADGSIYAR IRPRQRRKFK HMLEFGFQVS QKTRRRWFLD KLVDEIGVGY    60
VRDRGRASDY RLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 29              moltype = AA   length = 147
FEATURE                    Location/Qualifiers
source                     1..147
                           mol_type = protein
                           organism = synthetic construct
SEQUENCE: 29
KEFLLYLAGF VDGDGSIYAK ITPHQKYKFK HQLTLRFAVS QKTQRRWFLD KLVDEIGVGY    60
VSDNGSVSSY TLSQIKPLHN FLTQLQPFLK LKQKQANLVL KIIEQLPSAK ESPDKFLEVC   120
TWVDQIAALN DSHTRKTTSE TVRAVLD                                       147

SEQ ID NO: 30              moltype = AA   length = 147
FEATURE                    Location/Qualifiers
source                     1..147
                           mol_type = protein
                           organism = synthetic construct
SEQUENCE: 30
KEFLLYLAGF VDGDGSIYAM IKPNQRYKFK HQLNLRFNVS QKTQRRWFLD KLVDEIGVGY    60
VSDNGSVSSY TLSQIKPLHN FLTQLQPFLK LKQKQANLVL KIIEQLPSAK ESPDKFLEVC   120
TWVDQIAALN DSRTRKTTSE TVRAVLD                                       147

SEQ ID NO: 31              moltype = AA   length = 147
FEATURE                    Location/Qualifiers
source                     1..147
                           mol_type = protein
                           organism = synthetic construct
SEQUENCE: 31
KEFLLYLAGF VDGDGSIYAK ITPHQKYKFK HQLTLRFVVS QKTQRRWFLD KLVDEIGVGY    60
VSDNGSVSSY TLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 32              moltype = AA   length = 147
FEATURE                    Location/Qualifiers
source                     1..147
                           mol_type = protein
                           organism = synthetic construct
SEQUENCE: 32
KEFLLYLAGF VDGDGSIYAK ITPHQKYKFK HQLVLRFVVS QKTQRRWFLD KLVDEIGVGY    60
VSDNGSVSSY TLSQIKPLHN FLTQLQPFLK LKQKQANLVL KIIEQLPSAK ESPDKFLEVC   120
TWVDQIAALN DSHTRKTTSE TVRAVLD                                       147

SEQ ID NO: 33              moltype = AA   length = 147
FEATURE                    Location/Qualifiers
source                     1..147
                           mol_type = protein
                           organism = synthetic construct
SEQUENCE: 33
KEFLLYLAGF VDGDGSIYAK ITPHQKYKFK HQLHLRFVVS QKTQRRWFLD KLVDEIGVGY    60
VSDNGSMSAY TLSEIKPLHN FLTQLQPFLK LKQKQANLVL KIIEQLPSAK ESPDKFLEVC   120
TWVDQIAALN DSHTRKTTSE TVRAVLD                                       147

SEQ ID NO: 34              moltype = AA   length = 147
FEATURE                    Location/Qualifiers
source                     1..147
                           mol_type = protein
                           organism = synthetic construct
```

```
SEQUENCE: 34
KEFLLYLAGF VDGDGSIYAK ITPHQKYKFK HQLHLRFVVS QKTQRRWFLD KLVDEIGVGY  60
VSDNGSMSAY TLSQIKPLHN FLTQLQPFLK LKQKQANLVL KIIEQLPSAK ESPDKFLEVC 120
TWVDQIAALN DSHTRKTTSE TVRAVLD                                    147

SEQ ID NO: 35         moltype = DNA  length = 1062
FEATURE               Location/Qualifiers
source                1..1062
                      mol_type = other DNA
                      organism = synthetic construct
SEQUENCE: 35
atgaatacaa aatataataa agagttctta ctctacttag cagggtttgt agactctgac   60
ggttccatct atgcctgtat caggccgagg caggcgcgga agttcaagca cacgctggag  120
ctcgggttcc aggtcaccca ggctacatgc cgccgttcat tcctcgacaa gctggtggac  180
gagatcggtg tgggttacgt gagggaccgg ggccgcgcgt ccgactaccg gctgtccagg  240
atcaagcctt tgcataattt tttaacacag ctacaacctt ttctaaaact aaaacaaaaa  300
caagcaaatt tagtttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctatgccat gatcaagcct  660
aatcaaaggt ataagttcaa gcaccagctg aatctcaggt tcaatgtcag tcagaagaca  720
cagcgccgtt ggtcctcga caagctggtg gacgagatcg gtgtgggtta cgtgtcggac  780
aatggcagcg tctcctcgta cacgctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                   1062

SEQ ID NO: 36         moltype = DNA  length = 1062
FEATURE               Location/Qualifiers
source                1..1062
                      mol_type = other DNA
                      organism = synthetic construct
SEQUENCE: 36
atgaatacaa aatataataa agagttctta ctctacttag cagggtttgt agacgctgac   60
ggttccatct atgcctgtat ccggccgcgg cagagtagta agttcaagca cacgctggag  120
ctcgggttcc aggtcagcca gaagacatgc cgccgttggt tcctcgacaa gctggtggac  180
gagatcggtg tgggttacgt gagggaccgg ggccgcgcgt ccgactaccg gctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctatgccaa gatcacgcct  660
catcaaaagt ataagttcaa gcaccagctg acgctccgtt tcgcggtctc tcagaagaca  720
cagcgccgtt ggtcctcga caagctggtg gacgagatcg gtgtgggtta cgtgagtgac  780
aatggcagcg tctcctcgta cactctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactcccac acccgcaaga ccacttccga aaccgtccgc 1020
gccgttctag acagtctctc cgagaagaag aagtcgtccc cc                   1062

SEQ ID NO: 37         moltype = DNA  length = 1062
FEATURE               Location/Qualifiers
source                1..1062
                      mol_type = other DNA
                      organism = synthetic construct
SEQUENCE: 37
atgaatacaa aatataataa agagttctta ctctacttag cagggtttgt agacgctgac   60
ggttccatct atgcctgtat ccggccgcgg cagaggcgga agttcaagca catgctggag  120
ctcgggttcc aggtcagcca gaagacatgc cgccgttggt tcctcgacaa gctggtggac  180
gagatcggtg tgggttacgt gagggaccgg ggccgcgcgt ccgactaccg gctgtccag   240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctatgccaa gatcacgcct  660
catcaaaagt ataagttcaa gcaccagctg acgctccgtt tcgttgtctc tcagaagaca  720
cagcgccgtt ggtcctcga caagctggtg gacgagatcg gtgtgggtta cgtgagtgac  780
aatggcagcg tctcctcgta cactctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccaag acccgcaaga ccacttccga aaccgtccgc 1020
gccgttctag acagtctctc cgagaagaag aagtcgtccc cc                   1062
```

-continued

```
SEQ ID NO: 38            moltype = DNA  length = 1062
FEATURE                  Location/Qualifiers
source                   1..1062
                         mol_type = other DNA
                         organism = synthetic construct
SEQUENCE: 38
atgaatacaa aatataataa agagttctta ctctacttag cagggtttgt agacgctgac    60
ggttccatct atgcctctat ccggccgcgg cagaggcgga agttcaagca catgctgatt   120
ctcggtttcc aggtcagcca gaagacatgc cgccgttggt tcctcgacaa gctggtggac   180
gagatcggtg tgggttacgt gagggaccgg ggccgcgcgt ccgactaccg gctgtccgag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctatgccaa gatcacgcct   660
catcaaaagt ataagttcaa gcaccagctg gttctccgtt tcgttgtctc tcagaagaca   720
cagcgccgtt ggttcctcga caagctggtg gacgagatcg gtgtgtggtta cgtgagtgac   780
aatggcagca tctccagtta cactctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactcccac acccgcaaga ccacttccga aaccgtccgc  1020
gccgttctag acagtctctc cgagaagaag aagtcgtccc cc                     1062

SEQ ID NO: 39            moltype = DNA  length = 1062
FEATURE                  Location/Qualifiers
source                   1..1062
                         mol_type = other DNA
                         organism = synthetic construct
SEQUENCE: 39
atgaatacaa aatataataa agagttctta ctctacttag cagggtttgt agactctgac    60
ggttccatct atgccaccat ccggccgcgg cagaggcgga agttcaagca catgctggag   120
ctcttttttcc aggtcagcca gaagacatgc cgccgttggt tcctcgacaa gctggtggac   180
gagatcggtg tgggttacgt gagggaccgg ggccgcgcgt ccgactaccg gctgtccgag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctatgccaa gatcacgcct   660
catcagaagt acaagttcaa gcaccagctg catctccgtt tcgttgtcag tcagaagaca   720
cagcgccgtt ggttcctcga caagctggtg gacgagatcg gtgtgtggtta cgtgagtgac   780
aatggcagca tgtccgctta cactctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactcccac acccgcaaga ccacttccga aaccgtccgc  1020
gccgttctag acagtctctc cgagaagaag aagtcgtccc cc                     1062

SEQ ID NO: 40            moltype = DNA  length = 1062
FEATURE                  Location/Qualifiers
source                   1..1062
                         mol_type = other DNA
                         organism = synthetic construct
SEQUENCE: 40
atgaatacaa aatataataa agagttctta ctctacttag cagggtttgt agacgctgac    60
ggttccatct atgcgaggat tcggccgcgg cagaggcgga agttcaagca catgctggag   120
tttgggtttc aggtcagcca gaagacccgc cgccgttggt tcctcgacaa gctggtggac   180
gagatcggtg tgggttacgt gagggaccgg ggccgcgcgt ccgactaccg gctgtccgag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agccggagca ggttccggca ctggatacaa caaggaattc   600
ctgctctacc tggcgggctt cgtcgacggg gacggctcca tctatgccaa gatcacgcct   660
catcagaagt acaagttcaa gcaccagctg catctccgtt tcgttgtcag tcagaagaca   720
cagcgccgtt ggttcctcga caagctggtg gacgagatcg gtgtgtggtta cgtgagtgac   780
aatggcagca tgtccgctta cactctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactcccac acccgcaaga ccacttccga aaccgtccgc  1020
gccgttctag acagtctctc cgagaagaag aagtcgtccc cc                     1062

SEQ ID NO: 41            moltype = AA  length = 354
FEATURE                  Location/Qualifiers
source                   1..354
```

```
                              mol_type = protein
                              organism = synthetic construct
SEQUENCE: 41
MNTKYNKEFL LYLAGFVDAD GSIHAIIRPK QSYKFKHELM LRFTVTQKTK RRWFLDKLVD    60
EIGVGYVFDA GMTSHYCLSQ IKPLHNFLTQ LQPFLKLQK QANLVLKIIE QLPSAKESPD     120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAIHP CQRSKFKHEL RLLFTVTQKT    240
QRRWFLDKLV DEIGVGYVRD TGSVSEYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 42              moltype = AA   length = 354
FEATURE                    Location/Qualifiers
source                     1..354
                           mol_type = protein
                           organism = synthetic construct
SEQUENCE: 42
MNTKYNKEFL LYLAGFVDSD GSIFACIRPS QASKFKHRLE LRFTVTQKTR RRWFLDKLVD    60
EIGVGYVFDG GSVSHYCLSE IKPLHNFLTQ LQPFLKLQK QANLVLKIIE QLPSAKESPD     120
KFLEVCTWAD QIAALNDSKT RKTTSETVRA VLDSLPGSVG GLSPSQASSA ASSASSSPGS    180
GISEALRAGA GSGTGYNKEF LLYLAGFVDG DGSIFAAIHP CQRSKFKHEL RLLFTVTQKT    240
QRRWFLDKLV DEIGVGYVRD TGSVSEYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 43              moltype = AA   length = 354
FEATURE                    Location/Qualifiers
source                     1..354
                           mol_type = protein
                           organism = synthetic construct
SEQUENCE: 43
MNTKYNKEFL LYLAGFVDAD GSIHAIIRPK QDYKFKHELM LRFVVSQKTK RRWFLDKLVD    60
EIGVGYVFDA GMTSHYCLSE IKPLHNFLTQ LQPFLKLQK QANLVLKIIE QLPSAKESPD     120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAIHP CQRSKFKHEL RLLFTVTQKT    240
QRRWFLDKLV DEIGVGYVRD TGSVSHYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 44              moltype = AA   length = 354
FEATURE                    Location/Qualifiers
source                     1..354
                           mol_type = protein
                           organism = synthetic construct
SEQUENCE: 44
MNTKYNKEFL LYLAGFVDSD GSIHAIIRPK QDYKFKHELM LRFVVSQKTK RRWFLDKLVD    60
EIGVGYVFDG GMTSHYCLSE IKPLHNFLTQ LQPFLKLQK QANLVLKIIE QLPSAKESPD     120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAIHP CQRSKFKHEL RLLFTVTQKT    240
QRRWFLDKLV DEIGVGYVRD AGSVSHYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 45              moltype = AA   length = 354
FEATURE                    Location/Qualifiers
source                     1..354
                           mol_type = protein
                           organism = synthetic construct
SEQUENCE: 45
MNTKYNKEFL LYLAGFVDAD GSIHAIIRPK QDYKFKHELM LRFIVSQKTK RRWFLDKLVD    60
EIGVGYVFDG GMTSHYCLSE IKPLHNFLTQ LQPFLKLQK QANLVLKIIE QLPSAKESPD     120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAIHP CQRSKFKHEL RLLFTVTQKT    240
QRRWFLDKLV DEIGVGYVRD AGSVSHYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 46              moltype = AA   length = 354
FEATURE                    Location/Qualifiers
source                     1..354
                           mol_type = protein
                           organism = synthetic construct
SEQUENCE: 46
MNTKYNKEFL LYLAGFVDAD GSIHAIIRPK QDYKFKHELM LRFVVSQKTK RRWFLDKLVD    60
EIGVGYVFDG RGTSHYCLSE IKPLHNFLTQ LQPFLKLQK QANLVLKIIE QLPSAKESPD     120
KFLEVCTWVD QIAALNDSKA RKTTSETVRA VLDSLPGSVG GLSPSQASSA ASSASSSPGS    180
GISEALRAGA GSGTGYNKEF LLYLAGFVDG DGSIFAAIHP CQRSKFKHEL RLLFTVTQKT    240
QRRWFLDKLV DEIGVGYVRD AGSVSHYTLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 47              moltype = AA   length = 147
FEATURE                    Location/Qualifiers
source                     1..147
                           mol_type = protein
```

-continued

```
                          organism = synthetic construct
SEQUENCE: 47
KEFLLYLAGF VDADGSIHAI IRPKQSYKFK HELMLRFTVT QKTKRRWFLD KLVDEIGVGY   60
VFDAGMTSHY CLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 48           moltype = AA   length = 147
FEATURE                 Location/Qualifiers
source                  1..147
                        mol_type = protein
                        organism = synthetic construct
SEQUENCE: 48
KEFLLYLAGF VDSDGSIFAC IRPSQASKFK HRLELRFTVT QKTRRRWFLD KLVDEIGVGY   60
VFDGGSVSHY CLSEIKPLHN FLTQLQPFLK LKQKQANLVL KIIEQLPSAK ESPDKFLEVC   120
TWADQIAALN DSKTRKTTSE TVRAVLD                                      147

SEQ ID NO: 49           moltype = AA   length = 147
FEATURE                 Location/Qualifiers
source                  1..147
                        mol_type = protein
                        organism = synthetic construct
SEQUENCE: 49
KEFLLYLAGF VDADGSIHAI IRPKQDYKFK HELMLRFVVS QKTKRRWFLD KLVDEIGVGY   60
VFDAGMTSHY CLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 50           moltype = AA   length = 147
FEATURE                 Location/Qualifiers
source                  1..147
                        mol_type = protein
                        organism = synthetic construct
SEQUENCE: 50
KEFLLYLAGF VDSDGSIHAI IRPKQDYKFK HELMLRFVVS QKTKRRWFLD KLVDEIGVGY   60
VFDGGMTSHY CLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 51           moltype = AA   length = 147
FEATURE                 Location/Qualifiers
source                  1..147
                        mol_type = protein
                        organism = synthetic construct
SEQUENCE: 51
KEFLLYLAGF VDADGSIHAI IRPKQDYKFK HELMLRFIVS QKTKRRWFLD KLVDEIGVGY   60
VFDGGMTSHY CLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 52           moltype = AA   length = 147
FEATURE                 Location/Qualifiers
source                  1..147
                        mol_type = protein
                        organism = synthetic construct
SEQUENCE: 52
KEFLLYLAGF VDADGSIHAI IRPKQDYKFK HELMLRFVVS QKTKRRWFLD KLVDEIGVGY   60
VFDGRGTSHY CLSEIKPLHN FLTQLQPFLK LKQKQANLVL KIIEQLPSAK ESPDKFLEVC   120
TWVDQIAALN DSKARKTTSE TVRAVLD                                      147

SEQ ID NO: 53           moltype = AA   length = 147
FEATURE                 Location/Qualifiers
source                  1..147
                        mol_type = protein
                        organism = synthetic construct
SEQUENCE: 53
KEFLLYLAGF VDGDGSIFAA IHPCQRSKFK HELRLLFTVT QKTQRRWFLD KLVDEIGVGY   60
VRDTGSVSEY TLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 54           moltype = AA   length = 147
FEATURE                 Location/Qualifiers
source                  1..147
                        mol_type = protein
                        organism = synthetic construct
SEQUENCE: 54
KEFLLYLAGF VDGDGSIFAA IHPCQRSKFK HELRLLFTVT QKTQRRWFLD KLVDEIGVGY   60
VRDTGSVSEY TLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 55           moltype = AA   length = 147
FEATURE                 Location/Qualifiers
source                  1..147
```

-continued

```
                          mol_type = protein
                          organism = synthetic construct
SEQUENCE: 55
KEFLLYLAGF VDGDGSIFAA IHPCQRSKFK HELRLLFTVT QKTQRRWFLD KLVDEIGVGY   60
VRDTGSVSHY TLSQIKPLHN FLTQLQPFLK LKQKQANLVL KIIEQLPSAK ESPDKFLEVC  120
TWVDQIAALN DSKTRKTTSE TVRAVLD                                      147

SEQ ID NO: 56           moltype = AA   length = 147
FEATURE                 Location/Qualifiers
source                  1..147
                          mol_type = protein
                          organism = synthetic construct
SEQUENCE: 56
KEFLLYLAGF VDGDGSIFAA IHPCQRSKFK HELRLLFTVT QKTQRRWFLD KLVDEIGVGY   60
VRDAGSVSHY TLSQIKPLHN FLTQLQPFLK LKQKQANLVL KIIEQLPSAK ESPDKFLEVC  120
TWVDQIAALN DSKTRKTTSE TVRAVLD                                      147

SEQ ID NO: 57           moltype = AA   length = 147
FEATURE                 Location/Qualifiers
source                  1..147
                          mol_type = protein
                          organism = synthetic construct
SEQUENCE: 57
KEFLLYLAGF VDGDGSIFAA IHPCQRSKFK HELRLLFTVT QKTQRRWFLD KLVDEIGVGY   60
VRDAGSVSHY TLSQIKPLHN FLTQLQPFLK LKQKQANLVL KIIEQLPSAK ESPDKFLEVC  120
TWVDQIAALN DSKTRKTTSE TVRAVLD                                      147

SEQ ID NO: 58           moltype = AA   length = 147
FEATURE                 Location/Qualifiers
source                  1..147
                          mol_type = protein
                          organism = synthetic construct
SEQUENCE: 58
KEFLLYLAGF VDGDGSIFAA IHPCQRSKFK HELRLLFTVT QKTQRRWFLD KLVDEIGVGY   60
VRDAGSVSHY TLSEIKPLHN FLTQLQPFLK LKQKQANLVL KIIEQLPSAK ESPDKFLEVC  120
TWVDQIAALN DSRTRKTTSE TVRAVLD                                      147

SEQ ID NO: 59           moltype = DNA   length = 1062
FEATURE                 Location/Qualifiers
source                  1..1062
                          mol_type = other DNA
                          organism = synthetic construct
SEQUENCE: 59
atgaatacaa aatataataa agagttctta ctctacttag cagggtttgt agacgctgac   60
ggttccatcc atgccattat ccggcctaag caaagttata agttcaagca cgagctgatg  120
ctccgtttca ccgtcaccca gaagacaaag cgccgttggt tcctcgacaa gctggtggac  180
gagatcggtg tgggttacgt gttcgacgcg ggcatgacct cccactactg cctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatccatcct  660
tgtcaacgta gtaagttcaa gcacgagctg cgtctcttgt tcactgtcac gcagaagaca  720
cagcgccgtt ggttcctcga caagctggtg gacgagatcg gtgtgggtta cgtgcgggac  780
actggcagcg tctccgagta cacgctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccaag acccgcaaga ccacttccga aaccgtccgc 1020
gccgttctag acagtctctc cgagaagaag aagtcgtccc cc                    1062

SEQ ID NO: 60           moltype = DNA   length = 1062
FEATURE                 Location/Qualifiers
source                  1..1062
                          mol_type = other DNA
                          organism = synthetic construct
SEQUENCE: 60
atgaatacaa aatataataa agagttctta ctctacttag cagggtttgt agactctgac   60
ggttccatct ttgcctgtat ccgtccttcg caagctagta agttcaagca ccggctggag  120
ctccggttca cggtcaccca gaagacaagg cgccgttggt tcctcgacaa gctggtggac  180
gagatcggtg tgggttacgt gtttgacggt ggcagcgtct cccattactg cctgtccgag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggcggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cctcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatccatcct  660
```

```
tgtcaacgta gtaagttcaa gcacgagctg cgtctcttgt tcactgtcac gcagaagaca  720
cagcgccgtt ggttcctcga caagctggtg gacgagatcg gtgtgggtta cgtgcgggac  780
actggcagcg tctccgagta cacgctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccaag acccgcaaga ccacttccga aaccgtccgc 1020
gccgttctag acagtctctc cgagaagaag aagtcgtccc cc                    1062
```

SEQ ID NO: 61          moltype = DNA  length = 1062
FEATURE                Location/Qualifiers
source                 1..1062
                       mol_type = other DNA
                       organism = synthetic construct
SEQUENCE: 61

```
atgaatacaa aatataataa agagttctta ctctacttag cagggtttgt agacgctgac   60
ggttccatcc atgccattat ccggcctaag caggactaca agttcaagca cgagctgatg  120
ctccgtttcg ttgtctctca gaagacaaag cgccgttggt tcctcgacaa gctggtggac  180
gagatcggtg tgggttacgt gttcgacgct ggcatgacct cccattactg cctgtccgag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatccatcct  660
tgtcaacgta gtaagttcaa gcacgagctg cgtctctttgt tcactgtcac gcagaagaca  720
cagcgccgtt ggttcctcga caagctggtg gacgagatcg gtgtgggtta cgtgcgggac  780
actggcagcg tctcccatta cacgctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccaag acccgcaaga ccacttccga aaccgtccgc 1020
gccgttctag acagtctctc cgagaagaag aagtcgtccc cc                    1062
```

SEQ ID NO: 62          moltype = DNA  length = 1062
FEATURE                Location/Qualifiers
source                 1..1062
                       mol_type = other DNA
                       organism = synthetic construct
SEQUENCE: 62

```
atgaatacaa aatataataa agagttctta ctctacttag cagggtttgt agactctgac   60
ggttccatcc atgccattat ccggcctaag caggactaca agttcaagca cgagctgatg  120
ctccgtttcg ttgtcagtca gaagacaaag cgccgttggt tcctcgacaa gctggtggac  180
gagatcggtg tgggttacgt gttcgacggg ggcatgacct cccattactg cctgtccgag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatccatcct  660
tgtcaacgta gtaagttcaa gcacgagctg cgtctcttgt tcacggtcac gcagaagaca  720
cagcgccgtt ggttcctcga caagctggtg gacgagatcg gtgtgggtta cgtgcgggac  780
gctggcagcg tctcccatta cacgctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccaag acccgcaaga ccacttccga aaccgtccgc 1020
gccgttctag acagtctctc cgagaagaag aagtcgtccc cc                    1062
```

SEQ ID NO: 63          moltype = DNA  length = 1062
FEATURE                Location/Qualifiers
source                 1..1062
                       mol_type = other DNA
                       organism = synthetic construct
SEQUENCE: 63

```
atgaatacaa aatataataa agagttctta ctctacttag cagggtttgt agacgctgac   60
ggttccatcc atgccattat ccggcctaag caggactaca agttcaagca cgagctgatg  120
ctccgtttca ttgtctctca gaagacaaag cgccgttggt tcctcgacaa gctggtggac  180
gagatcggtg tgggttacgt gttcgacggg ggcatgacct cccattactg cctgtccgag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatccatcct  660
tgtcaacgta gtaagttcaa gcacgagctg cgtctcttgt tcacggtcac gcagaagaca  720
cagcgccgtt ggttcctcga caagctggtg gacgagatcg gtgtgggtta cgtgcgggac  780
gctggcagcg tctcccatta cacgctgtcc cagatcaagc ctctgcacaa cttcctgacc  840
cagctccagc ccttcctgaa gctcaagcag aagcaggcca acctcgtgct gaagatcatc  900
```

-continued

```
gagcagctgc cctccgccaa ggaatccccg gacaagttcc tggaggtgtg cacctgggtg    960
gaccagatcg ccgctctgaa cgactccaag acccgcaaga ccacttccga aaccgtccgc   1020
gccgttctag acagtctctc cgagaagaag aagtcgtccc cc                       1062

SEQ ID NO: 64         moltype = DNA   length = 1062
FEATURE               Location/Qualifiers
source                1..1062
                      mol_type = other DNA
                      organism = synthetic construct
SEQUENCE: 64
atgaatacaa atataataa agagttctta ctctacttag cagggtttgt agacgctgac     60
ggttccatcc atgccattat ccggcctaag caggactata agttcaagca cgagctgatg    120
ctccgtttcg tggtcagtca gaagacaaag cgccgttggt tcctcgacaa gctggttggac  180
gagatcggtg tgggttacgt gttcgacggg aggggacgt cccattactg cctgtccgag    240
atcaagcctt tgcataattt tttaacacaa ctacaacctt ttctaaaact aaaacaaaaa    300
caagcaaatt tagttttaaa aattattgaa caacttccgt cagcaaaaga tccccggac     360
aaattcttag aagtttgtac atgggtggat caaattgcag ctctgaatga ttcgaaggcg    420
cgtaaaacaa cttctgaaac cgttcgtgct gtgctagaca gtttaccagg atccgtggga    480
ggtctatcgc catctcaggc atccagcgcc gcatcctcgg cttcctcaag cccaggttca    540
gggatctccg aagcactcag agctggagca ggttccggca ctggatacaa caaggaattc    600
ctgctctacc tggcgggctt cgtcgacggg gacggctcca tctttgccgc tatccatcct    660
tgtcaacgta gtaagttcaa gcacgaactg cgtctctttg tcacggtcag gcagaagaca    720
cagcgccgtt ggttcctcga caagctggtg gacgagatcg gtgtgggtta cgtgcgggac    780
gctggcagcg tctcccatta cacgctgtcc gagatcaagc tctctcacaa cttcctgacc    840
cagtccagc ccttcctgaa gctcaagcag aagcaggcca acctcgtgct gaagatcatc     900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cc                       1062

SEQ ID NO: 65         moltype = AA   length = 354
FEATURE               Location/Qualifiers
source                1..354
                      mol_type = protein
                      organism = synthetic construct
SEQUENCE: 65
MNTKYNKEFL LYLAGFVDAD GSIYASITPD QARKFKHQLR LYFNVRQATK RRWFLDKLVD     60
EIGVGYVTDG GTVSTYILSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAITP DQTCKFKHTL RLRFQVTQHT    240
CRRWFLDKLV DEIGVGYVSD RGRASDYTLS QIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 66         moltype = AA   length = 354
FEATURE               Location/Qualifiers
source                1..354
                      mol_type = protein
                      organism = synthetic construct
SEQUENCE: 66
MNTKYNKEFL LYLAGFVDAD GSIYASITPS QGRKFKHQLR LYFNVRQSTK RRWFLDKLVD     60
EIGVGYVTDK GSVSTYLLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAITP DQTCKFKHTL RLRFQVTQKT    240
CRRWFLDKLV DEIGVGYVSD RGRASDYTLS QIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 67         moltype = AA   length = 354
FEATURE               Location/Qualifiers
source                1..354
                      mol_type = protein
                      organism = synthetic construct
SEQUENCE: 67
MNTKYNKEFL LYLAGFVDAD GSIYASIEPS QARKFKHQLR LRFNVRQATK RRWFLDKLVD     60
EIGVGYVIDE GTVSTYILSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAITP DQTCKFKHTL RLRFQVTQHT    240
CRRWFLDKLV DEIGVGYVSD RGRASDYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 68         moltype = AA   length = 354
FEATURE               Location/Qualifiers
source                1..354
                      mol_type = protein
                      organism = synthetic construct
SEQUENCE: 68
MNTKYNKEFL LYLAGFVDAD GSIYASIEPS QARKFKHQLR LRFNVRQATK RRWFLDKLVD     60
EIGVGYVVDD GTVSTYLLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQAPSA ASSASSSPGS    180
GISEALRAGA GSGTGYNKEF LLYLAGFVDG DGSIFAAITP DQTCKFKHWL RLRFQVTQHT    240
CRRWFLDKLV DEIGVGYVTD RGRASDYTLS EIKPLHNFLT QLQPFLKLKQ KQANLVLKII    300
```

```
EQLPSAKESP DKFLEVCTWV DQIAALNDSK TRKTTSETVR AVLDSLSEKK KSSP          354

SEQ ID NO: 69              moltype = AA  length = 354
FEATURE                    Location/Qualifiers
source                     1..354
                           mol_type = protein
                           organism = synthetic construct
SEQUENCE: 69
MNTKYNKEFL LYLAGFVDSD GSIYASIEPS QARKFKHQLR LRFNVRQATK RRWFLDKLVD    60
EIGVGYVVDD GTVSTYMLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFAAITP DQTCKFKHTL RLRFRVTQHT    240
CRRWFLDKLV DEIGVGYVSD RGRASDYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 70              moltype = AA  length = 354
FEATURE                    Location/Qualifiers
source                     1..354
                           mol_type = protein
                           organism = synthetic construct
SEQUENCE: 70
MNTKYNKEFL LYLAGFVDAD GSIYASIEPS QARKFKHQLR LRFNVRQATK RRWFLDKLVD    60
EIGVGYVVDD GTVSTYMLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQAPSA ASSASSSPGS    180
GISEALRAGA GSGTGYNKEF LLYLAGFVDG DGSIFAAITP DQTCKFKHWL RLRFRVTQHT    240
CRRWFLDKLV DEIGVGYVSD RGRASDYTLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 71              moltype = AA  length = 354
FEATURE                    Location/Qualifiers
source                     1..354
                           mol_type = protein
                           organism = synthetic construct
SEQUENCE: 71
MNTKYNKEFL LYLAGFVDAD GSIYASIEPS QARKFKHQLR LRFNVRQATK RRWFLDKLVD    60
EIGVGYVAT GTVSTYMLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQAFSA ASSASSSPGS    180
GISEALRAGA GSGTGYNKEF LLYLAGFVDG DGSIFAAIRP DQTCKFKHWL QLYFRVTQHT    240
CRRWFLDKLV DEIGVGYVSD RGRASDYTLS QIKPLHNFLT QLQPFLKLKQ KQANLVLKII    300
EQLPSAKESP DKFLEVCTWV DQIAALNDSH TRKTTSETVR AVLDSLSEKK KSSP          354

SEQ ID NO: 72              moltype = AA  length = 147
FEATURE                    Location/Qualifiers
source                     1..147
                           mol_type = protein
                           organism = synthetic construct
SEQUENCE: 72
KEFLLYLAGF VDADGSIYAS ITPDQARKFK HQLRLYFNVR QATKRRWFLD KLVDEIGVGY    60
VTDGGTVSTY ILSQIKPLHN FLTQLQPFLK LKQKQANLVL KIIEQLPSAK ESPDKFLEVC    120
TWVDQIAALN DSKTRKTTSE TVRAVLD                                        147

SEQ ID NO: 73              moltype = AA  length = 147
FEATURE                    Location/Qualifiers
source                     1..147
                           mol_type = protein
                           organism = synthetic construct
SEQUENCE: 73
KEFLLYLAGF VDADGSIYAS ITPSQGRKFK HQLRLYFNVR QSTKRRWFLD KLVDEIGVGY    60
VTDKGSVSTY LLSQIKPLHN FLTQLQPFLK LKQKQANLVL KIIEQLPSAK ESPDKFLEVC    120
TWVDQIAALN DSKTRKTTSE TVRAVLD                                        147

SEQ ID NO: 74              moltype = AA  length = 147
FEATURE                    Location/Qualifiers
source                     1..147
                           mol_type = protein
                           organism = synthetic construct
SEQUENCE: 74
KEFLLYLAGF VDADGSIYAS IEPSQARKFK HQLRLRFNVR QATKRRWFLD KLVDEIGVGY    60
VIDEGTVSTY ILSQIKPLHN FLTQLQPFLK LKQKQANLVL KIIEQLPSAK ESPDKFLEVC    120
TWVDQIAALN DSKTRKTTSE TVRAVLD                                        147

SEQ ID NO: 75              moltype = AA  length = 147
FEATURE                    Location/Qualifiers
source                     1..147
                           mol_type = protein
                           organism = synthetic construct
SEQUENCE: 75
KEFLLYLAGF VDADGSIYAS IEPSQARKFK HQLRLRFNVR QATKRRWFLD KLVDEIGVGY    60
VVDDGTVSTY LLSQIKPLHN FLTQLQPFLK LKQKQANLVL KIIEQLPSAK ESPDKFLEVC    120
```

```
TWVDQIAALN DSKTRKTTSE TVRAVLD                                              147

SEQ ID NO: 76              moltype = AA   length = 147
FEATURE                    Location/Qualifiers
source                     1..147
                           mol_type = protein
                           organism = synthetic construct
SEQUENCE: 76
KEFLLYLAGF VDSDGSIYAS IEPSQARKFK HQLRLRFNVR QATKRRWFLD KLVDEIGVGY         60
VVDDGTVSTY MLSQIKPLHN FLTQLQPFLK LKQKQANLVL KIIEQLPSAK ESPDKFLEVC         120
TWVDQIAALN DSKTRKTTSE TVRAVLD                                             147

SEQ ID NO: 77              moltype = AA   length = 147
FEATURE                    Location/Qualifiers
source                     1..147
                           mol_type = protein
                           organism = synthetic construct
SEQUENCE: 77
KEFLLYLAGF VDADGSIYAS IEPSQARKFK HQLRLRFNVR QATKRRWFLD KLVDEIGVGY         60
VVDDGTVSTY MLSQIKPLHN FLTQLQPFLK LKQKQANLVL KIIEQLPSAK ESPDKFLEVC         120
TWVDQIAALN DSKTRKTTSE TVRAVLD                                             147

SEQ ID NO: 78              moltype = AA   length = 147
FEATURE                    Location/Qualifiers
source                     1..147
                           mol_type = protein
                           organism = synthetic construct
SEQUENCE: 78
KEFLLYLAGF VDADGSIYAS IEPSQARKFK HQLRLRFNVR QATKRRWFLD KLVDEIGVGY         60
VVATGTVSTY MLSQIKPLHN FLTQLQPFLK LKQKQANLVL KIIEQLPSAK ESPDKFLEVC         120
TWVDQIAALN DSKTRKTTSE TVRAVLD                                             147

SEQ ID NO: 79              moltype = AA   length = 147
FEATURE                    Location/Qualifiers
source                     1..147
                           mol_type = protein
                           organism = synthetic construct
SEQUENCE: 79
KEFLLYLAGF VDGDGSIFAA ITPDQTCKFK HTLRLRFQVT QHTCRRWFLD KLVDEIGVGY         60
VSDRGRASDY TLSQIKPLHN FLTQLQPFLK LKQKQANLVL KIIEQLPSAK ESPDKFLEVC         120
TWVDQIAALN DSRTRKTTSE TVRAVLD                                             147

SEQ ID NO: 80              moltype = AA   length = 147
FEATURE                    Location/Qualifiers
source                     1..147
                           mol_type = protein
                           organism = synthetic construct
SEQUENCE: 80
KEFLLYLAGF VDGDGSIFAA ITPDQTCKFK HTLRLRFQVT QKTCRRWFLD KLVDEIGVGY         60
VSDRGRASDY TLSQIKPLHN FLTQLQPFLK LKQKQANLVL KIIEQLPSAK ESPDKFLEVC         120
TWVDQIAALN DSRTRKTTSE TVRAVLD                                             147

SEQ ID NO: 81              moltype = AA   length = 147
FEATURE                    Location/Qualifiers
source                     1..147
                           mol_type = protein
                           organism = synthetic construct
SEQUENCE: 81
KEFLLYLAGF VDGDGSIFAA ITPDQTCKFK HTLRLRFQVT QHTCRRWFLD KLVDEIGVGY         60
VSDRGRASDY TLSQIKPLHN FLTQLQPFLK LKQKQANLVL KIIEQLPSAK ESPDKFLEVC         120
TWVDQIAALN DSKTRKTTSE TVRAVLD                                             147

SEQ ID NO: 82              moltype = AA   length = 147
FEATURE                    Location/Qualifiers
source                     1..147
                           mol_type = protein
                           organism = synthetic construct
SEQUENCE: 82
KEFLLYLAGF VDGDGSIFAA ITPDQTCKFK HWLRLRFQVT QHTCRRWFLD KLVDEIGVGY         60
VTDRGRASDY TLSEIKPLHN FLTQLQPFLK LKQKQANLVL KIIEQLPSAK ESPDKFLEVC         120
TWVDQIAALN DSKTRKTTSE TVRAVLD                                             147

SEQ ID NO: 83              moltype = AA   length = 147
FEATURE                    Location/Qualifiers
source                     1..147
                           mol_type = protein
                           organism = synthetic construct
SEQUENCE: 83
KEFLLYLAGF VDGDGSIFAA ITPDQTCKFK HTLRLRFRVT QHTCRRWFLD KLVDEIGVGY         60
```

-continued

```
VSDRGRASDY TLSQIKPLHN FLTQLQPFLK LKQKQANLVL KIIEQLPSAK ESPDKFLEVC    120
TWVDQIAALN DSKTRKTTSE TVRAVLD                                        147

SEQ ID NO: 84           moltype = AA  length = 147
FEATURE                 Location/Qualifiers
source                  1..147
                        mol_type = protein
                        organism = synthetic construct
SEQUENCE: 84
KEFLLYLAGF VDGDGSIFAA ITPDQTCKFK HWLRLRFRVT QHTCRRWFLD KLVDEIGVGY     60
VSDRGRASDY TLSQIKPLHN FLTQLQPFLK LKQKQANLVL KIIEQLPSAK ESPDKFLEVC    120
TWVDQIAALN DSKTRKTTSE TVRAVLD                                        147

SEQ ID NO: 85           moltype = AA  length = 147
FEATURE                 Location/Qualifiers
source                  1..147
                        mol_type = protein
                        organism = synthetic construct
SEQUENCE: 85
KEFLLYLAGF VDGDGSIFAA IRPDQTCKFK HWLQLYFRVT QHTCRRWFLD KLVDEIGVGY     60
VSDRGRASDY TLSQIKPLHN FLTQLQPFLK LKQKQANLVL KIIEQLPSAK ESPDKFLEVC    120
TWVDQIAALN DSHTRKTTSE TVRAVLD                                        147

SEQ ID NO: 86           moltype = DNA  length = 1062
FEATURE                 Location/Qualifiers
source                  1..1062
                        mol_type = other DNA
                        organism = synthetic construct
SEQUENCE: 86
atgaatacaa aatataataa agagttctta ctctacttag cagggtttgt agacgctgac     60
ggttccatct atgccagtat cactcctgat caagcgcgga agttcaagca ccagctgcgt    120
ctctatttca acgtcaggca ggcgacaaag cgccgttggt tcctcgacaa gctggtggac    180
gagatcggtg tgggttacgt gacggacggc ggcaccgtct ccacctacat cctgtcccag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctggaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgccgc tatcacgccg    660
gatcagacgt gtaagttcaa gcacacgctg aggctccggt tccaggtcac gcagcacaca    720
tgccgccgtt ggttcctcga caagctggtg gacgagatcg tgtgtgggtta cgtgtccgac    780
aggggccgcg cgtccgacta caccctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctggggtg   960
gaccagatcg ccgctctgaa cgactccagg acccgcaaga ccacttccga aaccgtccgc   1020
gccgttctag acagtctctc cgagaagaag aagtcgtccc cc                      1062

SEQ ID NO: 87           moltype = DNA  length = 1062
FEATURE                 Location/Qualifiers
source                  1..1062
                        mol_type = other DNA
                        organism = synthetic construct
SEQUENCE: 87
atgaatacaa aatataataa agagttctta ctctacttag cagggtttgt agacgctgac     60
ggttccatct atgccagtat cacgccttct caagggcgta agttcaagca ccagctgcgg    120
ctctatttca acgtcaggca gtcgacaaag cgccgttggt tcctcgacaa gctggtggac    180
gagatcggtg tgggttacgt gacggacaag ggcagcgtct ccacctacct cctgtcccag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgccgc tatcacgccg    660
gatcagacgt gtaagttcaa gcacacgctg aggctccggt tccaggtcac tcagaagaca    720
tgtcgccgtt ggttcctcga caagctggtg gacgagatcg tgtgtgggtta cgtgtccgac    780
aggggccgcg cgtccgacta caccctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctggggtg   960
gaccagatcg ccgctctgaa cgactccagg acccgcaaga ccacttccga aaccgtccgc   1020
gccgttctag acagtctctc cgagaagaag aagtcgtccc cc                      1062

SEQ ID NO: 88           moltype = DNA  length = 1062
FEATURE                 Location/Qualifiers
source                  1..1062
                        mol_type = other DNA
                        organism = synthetic construct
SEQUENCE: 88
```

-continued

```
atgaatacaa aatataataa agagttctta ctctacttag cagggtttgt agacgctgac   60
ggttccatct atgccagtat cgagccttcc caagcgcgga agttcaagca ccagctgcgt  120
ctccgtttca acgtcaggca ggcgacaaag cgccgttggt tcctcgacaa gctggtggac  180
gagatcggtg tgggttacgt gattgacgag ggcaccgtct ccacctacat cctgtcccag  240
atcaagcctt tgcataattt tttaaacacaa ctacaacctt ttctaaaact aaaacaaaaa  300
caagcaaatt tagttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctggaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatcacgccg  660
gatcagacgt gtaagttcaa gcacacgctg aggctccggt tccaggtcac gcagcacaca  720
tgccgccgtt ggttcctcga caagctggtg gacgagatcg tgtgtgggtta cgtgtcggac  780
aggggccgcg cgtccgacta caccctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctggggtg  960
gaccagatcg ccgctctgaa cgactccaag acccgcaaga ccacttccga aaccgtccgc 1020
gccgttctag acagtctctc cgagaagaag aagtcgtccc cc                     1062
```

SEQ ID NO: 89              moltype = DNA   length = 1062
FEATURE                    Location/Qualifiers
source                     1..1062
                           mol_type = other DNA
                           organism = synthetic construct
SEQUENCE: 89

```
atgaatacaa aatataataa agagttctta ctctacttag cagggtttgt agacgctgac   60
ggttccatct atgccagtat cgagccttcg caagcgcgga agttcaagca ccagctgcgt  120
ctccgtttca acgtcaggca ggcgacaaag cgccgttggt tcctcgacaa gctggtggac  180
gagatcggtg tgggttacgt ggttgacgat ggcaccgtct ccacctactt gctgtcccag  240
atcaagcctt tgcataattt tttaaacacaa ctacaacctt ttctaaaact aaaacaaaaa  300
caagcaaatt tagttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctggaca gtttaccagg atccgtggga  480
ggtctatcgc catctcaggc acccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatcacgccg  660
gatcagacgt gtaagttcaa gcactggctg aggctccggt tccaggtcac gcagcacaca  720
tgccgccgtt ggttcctcga caagctggtg gacgagatcg tgtgtgggtta cgtgacggac  780
aggggccgcg cgtccgacta caccctgtcc gagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctggggtg  960
gaccagatcg ccgctctgaa cgactccaag acccgcaaga ccacttccga aaccgtccgc 1020
gccgttctag acagtctctc cgagaagaag aagtcgtccc cc                     1062
```

SEQ ID NO: 90              moltype = DNA   length = 1062
FEATURE                    Location/Qualifiers
source                     1..1062
                           mol_type = other DNA
                           organism = synthetic construct
SEQUENCE: 90

```
atgaatacaa aatataataa agagttctta ctctacttag cagggtttgt agactctgac   60
ggttccatct atgccagtat cgagccttcg caagcgcgga agttcaagca ccagctgcgt  120
ctccgtttca acgtcaggca ggcgacaaag cgccgttggt tcctcgacaa gctggtggac  180
gagatcggtg tgggttacgt ggtggacgat ggcaccgtct ccacctacat gctgtcccag  240
atcaagcctt tgcataattt tttaaacacaa ctacaacctt ttctaaaact aaaacaaaaa  300
caagcaaatt tagttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctggaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgccgc tatcacgccg  660
gatcagacgt gtaagttcaa gcacacgctg aggctccggt tccgggtcac gcagcacaca  720
tgccgccgtt ggttcctcga caagctggtg gacgagatcg tgtgtgggtta cgtgtcggac  780
aggggccgcg cgtccgacta caccctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctggggtg  960
gaccagatcg ccgctctgaa cgactccaag acccgcaaga ccacttccga aaccgtccgc 1020
gccgttctag acagtctctc cgagaagaag aagtcgtccc cc                     1062
```

SEQ ID NO: 91              moltype = DNA   length = 1062
FEATURE                    Location/Qualifiers
source                     1..1062
                           mol_type = other DNA
                           organism = synthetic construct
SEQUENCE: 91

```
atgaatacaa aatataataa agagttctta ctctacttag cagggtttgt agacgctgac   60
ggttccatct atgccagtat cgagccttcg caagcgcgga agttcaagca ccagctgcgt  120
ctccgtttca atgtccgtca ggcgacaaag cgccgttggt tcctcgacaa gctggtggac  180
gagatcggtg tgggttacgt ggttgacgat ggcaccgtct ccacctacat gctgtcccag  240
```

-continued

```
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctggaca gtttaccagg atccgtggga    480
ggtctatcgc catctcaggc acccagcgcc gcatcctcag cttcctcaag cccgggttca    540
gggatctccg aagcactcag agctggagca ggttccggca ctggatacaa caaggaattc    600
ctgctctacc tggcgggctt cgtcgacggg gacggctcca tctttgccgc tatcacgccg    660
gatcagacgt gtaagttcaa gcactggctg aggctccggt tccgcgtcac gcagcacaca    720
tgccgccgtt ggttcctcga caagctggtg gacgagatcg gtgtgggtta cgtgagcgac    780
aggggccgcg cgtccgacta caccctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctggggtg    960
gaccagatcg ccgctctgaa cgactccaag acccgcaaga ccacttccga aaccgtccgc   1020
gccgttctag acagtctctc cgagaagaag aagtcgtccc cc                       1062
```

SEQ ID NO: 92          moltype = DNA   length = 1062
FEATURE                Location/Qualifiers
source                 1..1062
                       mol_type = other DNA
                       organism = synthetic construct
SEQUENCE: 92

```
atgaatacaa aatataataa agagttctta ctctacttag cagggtttgt agacgctgac    60
ggttccatct atgccagtat cgagccttcg caagcgcgga agttcaagca ccagctgcgt   120
ctccgtttca atgtccgtca ggcgacaaag cgccgttggt tcctcgacaa gctggtggac   180
gagatcggtg tgggttacgt ggttgcgact ggcaccgtct ccacctacat gctgtcccag   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctggaca gtttaccagg atccgtggga   480
ggtctatcgc catctcaggc attcagcgcc gcatcctcag cttcctcaag cccgggttca   540
gggatctccg aagcactcag agctggagca ggttccggca ctggatacaa caaggaattc   600
ctgctctacc tggcgggctt cgtcgacggg gacggctcca tctttgccgc tatcaggccg   660
gatcagacgt gtaagttcaa gcactggctg cagctctatt tccgggtcac gcagcacaca   720
tgccgccgtt ggttcctcga caagctggtg gacgagatcg gtgtgggtta cgtgagcgac   780
aggggccgcg cgtccgacta caccctgtcc cagatcaagc ctctgcacaa cttcctgacc   840
cagctccagc ccttcctgaa gctcaagcag aagcaggcca acctcgtgct gaagatcatc    900
gagcagctgc cctccgccaa ggaatccccg gacaagttcc tggaggtgtg cacctggggtg   960
gaccagatcg ccgctctgaa cgactccac acccgcaaga ccacttccga aaccgtccgc   1020
gccgttctag acagtctctc cgagaagaag aagtcgtccc cc                       1062
```

SEQ ID NO: 93          moltype = AA   length = 354
FEATURE                Location/Qualifiers
source                 1..354
                       mol_type = protein
                       organism = synthetic construct
SEQUENCE: 93

```
MNTKYNKEFL LYLAGFVDSD GSIYARIVPS QTSKFKHKLR LVFAVAQSTC RRWFLDKLVD    60
EIGVGYVRDH GRASYYTLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFATIVP QQDRKFKHAL RLQFRVHQKT   240
CRRWFLDKLV DEIGVGYVYD FGRASHYCLS EIKPLHNFLT QLQPFLKLKQ KQANLVLKII   300
EQLPSAKESP DKFLEVCTWV DQIAALNDSK TRKTTSETVR AVLDSLSEKK KSSP           354
```

SEQ ID NO: 94          moltype = AA   length = 354
FEATURE                Location/Qualifiers
source                 1..354
                       mol_type = protein
                       organism = synthetic construct
SEQUENCE: 94

```
MNTKYNKEFL LYLAGFVDSD GSIYARIVPS QTSKFKHKLR LTFAVTQKTC RRWFLDKLVD    60
EIGVGYVTDN GRASNYFLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFATIVP QQDRKFKHAL RLQFRVHQHT   240
RRRWFLDKLV DEIGMGYVSD RGRASFYSLS QIKPLHNFLT QLQPFLKLKQ KQANLVLKII   300
EQLPSAKESP DKFLEVCTWV DQIAALNDSR TRKTTSETVR AVLDSLSEKK KSSP           354
```

SEQ ID NO: 95          moltype = AA   length = 354
FEATURE                Location/Qualifiers
source                 1..354
                       mol_type = protein
                       organism = synthetic construct
SEQUENCE: 95

```
MNTKYNKEFL LYLAGFVDSD GSIYARIVPS QGSKFKHKLR LTFAVTQKTC RRWFLDKLVD    60
EIGVGYVIDN GRASNYFLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFATIVP QQDRKFKHAL RLNFRVHQHT   240
RRRWFLDKLV DEIGMGYVSD RGRASFYHLS EIKPLHNFLT QLQPFLKLKQ KQANLVLKII   300
EQLPSAKESP DKFLEVCTWV DQIAALNDSR TRKTTSETVR AVLDSLSEKK KSSP           354
```

-continued

```
SEQ ID NO: 96               moltype = AA   length = 354
FEATURE                     Location/Qualifiers
source                      1..354
                            mol_type = protein
                            organism = synthetic construct
SEQUENCE: 96
MNTKYNKEFL LYLAGFVDAD GSIFARIVPS QTRKFKHKLN LTFAVTQKTC RRWFLDKLVD   60
EIGVGYVIDN GRASNYFLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASGA ASSASSSPGS  180
GISEALRAGA GSGTGYNKEF LLYLAGFVDG DGSIFATIVP QQDRKFKHAL RLNFRVHQHT  240
RRRWFLDKLV DEIGVGYVSD GGRASFYHLS EIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 97               moltype = AA   length = 354
FEATURE                     Location/Qualifiers
source                      1..354
                            mol_type = protein
                            organism = synthetic construct
SEQUENCE: 97
MNTKYNKEFL LYLAGFVDSD GSIYARIVPS QHRKFKHKLQ LTFAVTQKTC RRWFLDKLVD   60
EIGVGYVIDN GRASNYFLSE IKPLHNFLTQ LQPFLKLKQK QADLVLKIIE QLPSAKESPD  120
KFLEVCTWVD QIAALNDSKT RKTTSETVRA VLDSLPGSVG GLSPSQASGA ASSASSSPGS  180
GISEALRAGA GSGTGYNKEF LLYLAGFVDG DGSIFATIVP QQDRKFKHAL RLNFRVHQHT  240
RRRWFLDKLV DEIGVGYVSD TGRASFYHLS QIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 98               moltype = AA   length = 354
FEATURE                     Location/Qualifiers
source                      1..354
                            mol_type = protein
                            organism = synthetic construct
SEQUENCE: 98
MNTKYNKEFL LYLAGFVDAD GSIFARIVPS QSRKFKHKLN LTFAVTQKTC RRWFLDKLVD   60
EIGVGYVIDN GRASNYFLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIFATIVP QQDRKFKHAL RLNFRVHQHT  240
RRRWFLDKLV DEIGVGYVSD KGRASFYHLS QIKPLHNFLT QLQPFLKLKQ KQANLVLKII  300
EQLPSAKESP DKFLEVCTWV DQIAALNDSR TRKTTSETVR AVLDSLSEKK KSSP        354

SEQ ID NO: 99               moltype = AA   length = 354
FEATURE                     Location/Qualifiers
source                      1..354
                            mol_type = protein
                            organism = synthetic construct
SEQUENCE: 99
MNTKYNKEFL LYLAGFVDAD GSIFARIVPE QGRKFKHKLQ LTFAVTQKTC RRWFLDKLVD   60
EIGVGYVIDG GRASNYWLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASGA ASSASSSPGS  180
GISEALRAGA GSGTGYNKEF LLYLAGFVDG DGSIFATIVP QQDRKFKHAL RLNFRLHQHT  240
RRRWFLDKLV DEIGVGYVSD GGRASFYHLS EIKPLHNFLT QLQPFLKLKQ KQANLVLKII  300
EQLPSAKESP DKFLEVCTWV DQIAALNDSR TRKTTSETVR AVLDSLSEKK KSSP        354

SEQ ID NO: 100              moltype = AA   length = 354
FEATURE                     Location/Qualifiers
source                      1..354
                            mol_type = protein
                            organism = synthetic construct
SEQUENCE: 100
MNTKYNKEFL LYLAGFVDAD GSIFARIVPE QGRKFKHKLQ LTFAVTQKTC RRWFLDKLVD   60
EIGVGYVIDN GRASNYVLSQ IKPLHNFLTQ LQPFLKLKQK QANLVLKIIE QLPSAKESPD  120
KFLEVCTWVD QIAALNDSNT RKTTSETVRA VLDSLPGSVG GLSPSQASGA ASSASSSPGS  180
GTSEALRAGA GSGTGYNKEF LLYLAGFVDG DGSIFAQIVP QQDRKFKHAL RLKFRLHQHT  240
RRRWFLDKLV DEIGVGYVSD GGRASFYNLS QIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 101              moltype = AA   length = 147
FEATURE                     Location/Qualifiers
source                      1..147
                            mol_type = protein
                            organism = synthetic construct
SEQUENCE: 101
KEFLLYLAGF VDSDGSIYAR IVPSQTSKFK HKLRLVFAVA QSTCRRWFLD KLVDEIGVGY   60
VRDHGRASYY TLSEIKPLHN FLTQLQPFLK LKQKQANLVL KIIEQLPSAK ESPDKFLEVC  120
TWVDQIAALN DSKTRKTTSE TVRAVLD                                     147

SEQ ID NO: 102              moltype = AA   length = 147
FEATURE                     Location/Qualifiers
source                      1..147
                            mol_type = protein
```

```
                              organism = synthetic construct
SEQUENCE: 102
KEFLLYLAGF VDSDGSIYAR IVPSQTSKFK HKLRLTFAVT QKTCRRWFLD KLVDEIGVGY      60
VTDNGRASNY FLSQIKPLHN FLTQLQPFLK LKQKQANLVL KIIEQLPSAK ESPDKFLEVC     120
TWVDQIAALN DSKTRKTTSE TVRAVLD                                        147

SEQ ID NO: 103         moltype = AA  length = 147
FEATURE                Location/Qualifiers
source                 1..147
                       mol_type = protein
                       organism = synthetic construct
SEQUENCE: 103
KEFLLYLAGF VDSDGSIYAR IVPSQGSKFK HKLRLTFAVT QKTCRRWFLD KLVDEIGVGY      60
VIDNGRASNY FLSEIKPLHN FLTQLQPFLK LKQKQANLVL KIIEQLPSAK ESPDKFLEVC     120
TWVDQIAALN DSKTRKTTSE TVRAVLD                                        147

SEQ ID NO: 104         moltype = AA  length = 147
FEATURE                Location/Qualifiers
source                 1..147
                       mol_type = protein
                       organism = synthetic construct
SEQUENCE: 104
KEFLLYLAGF VDADGSIFAR IVPSQTRKFK HKLNLTFAVT QKTCRRWFLD KLVDEIGVGY      60
VIDNGRASNY FLSEIKPLHN FLTQLQPFLK LKQKQANLVL KIIEQLPSAK ESPDKFLEVC     120
TWVDQIAALN DSKTRKTTSE TVRAVLD                                        147

SEQ ID NO: 105         moltype = AA  length = 147
FEATURE                Location/Qualifiers
source                 1..147
                       mol_type = protein
                       organism = synthetic construct
SEQUENCE: 105
KEFLLYLAGF VDSDGSIYAR IVPSQHRKFK HKLQLTFAVT QKTCRRWFLD KLVDEIGVGY      60
VIDNGRASNY FLSEIKPLHN FLTQLQPFLK LKQKQADLVL KIIEQLPSAK ESPDKFLEVC     120
TWVDQIAALN DSKTRKTTSE TVRAVLD                                        147

SEQ ID NO: 106         moltype = AA  length = 147
FEATURE                Location/Qualifiers
source                 1..147
                       mol_type = protein
                       organism = synthetic construct
SEQUENCE: 106
KEFLLYLAGF VDADGSIFAR IVPSQSRKFK HKLNLTFAVT QKTCRRWFLD KLVDEIGVGY      60
VIDNGRASNY FLSQIKPLHN FLTQLQPFLK LKQKQANLVL KIIEQLPSAK ESPDKFLEVC     120
TWVDQIAALN DSKTRKTTSE TVRAVLD                                        147

SEQ ID NO: 107         moltype = AA  length = 147
FEATURE                Location/Qualifiers
source                 1..147
                       mol_type = protein
                       organism = synthetic construct
SEQUENCE: 107
KEFLLYLAGF VDADGSIFAR IVPEQGRKFK HKLQLTFAVT QKTCRRWFLD KLVDEIGVGY      60
VIDGGRASNY WLSEIKPLHN FLTQLQPFLK LKQKQANLVL KIIEQLPSAK ESPDKFLEVC     120
TWVDQIAALN DSKTRKTTSE TVRAVLD                                        147

SEQ ID NO: 108         moltype = AA  length = 147
FEATURE                Location/Qualifiers
source                 1..147
                       mol_type = protein
                       organism = synthetic construct
SEQUENCE: 108
KEFLLYLAGF VDADGSIFAR IVPEQGRKFK HKLQLTFAVT QKTCRRWFLD KLVDEIGVGY      60
VIDNGRASNY VLSQIKPLHN FLTQLQPFLK LKQKQANLVL KIIEQLPSAK ESPDKFLEVC     120
TWVDQIAALN DSNTRKTTSE TVRAVLD                                        147

SEQ ID NO: 109         moltype = AA  length = 147
FEATURE                Location/Qualifiers
source                 1..147
                       mol_type = protein
                       organism = synthetic construct
SEQUENCE: 109
KEFLLYLAGF VDGDGSIFAT IVPQQDRKFK HALRLQFRVH QKTCRRWFLD KLVDEIGVGY      60
VYDFGRASHY CLSEIKPLHN FLTQLQPFLK LKQKQANLVL KIIEQLPSAK ESPDKFLEVC     120
TWVDQIAALN DSKTRKTTSE TVRAVLD                                        147

SEQ ID NO: 110         moltype = AA  length = 147
FEATURE                Location/Qualifiers
source                 1..147
```

```
                        mol_type = protein
                        organism = synthetic construct
SEQUENCE: 110
KEFLLYLAGF VDGDGSIFAT IVPQQDRKFK HALRLQFRVH QHTRRRWFLD KLVDEIGMGY  60
VSDRGRASFY SLSQIKPLHN FLTQLQPFLK LKQKQANLVL KIIEQLPSAK ESPDKFLEVC  120
TWVDQIAALN DSRTRKTTSE TVRAVLD                                      147

SEQ ID NO: 111          moltype = AA  length = 147
FEATURE                 Location/Qualifiers
source                  1..147
                        mol_type = protein
                        organism = synthetic construct
SEQUENCE: 111
KEFLLYLAGF VDGDGSIFAT IVPQQDRKFK HALRLNFRVH QHTRRRWFLD KLVDEIGMGY  60
VSDRGRASFY HLSEIKPLHN FLTQLQPFLK LKQKQANLVL KIIEQLPSAK ESPDKFLEVC  120
TWVDQIAALN DSRTRKTTSE TVRAVLD                                      147

SEQ ID NO: 112          moltype = AA  length = 147
FEATURE                 Location/Qualifiers
source                  1..147
                        mol_type = protein
                        organism = synthetic construct
SEQUENCE: 112
KEFLLYLAGF VDGDGSIFAT IVPQQDRKFK HALRLNFRVH QHTRRRWFLD KLVDEIGVGY  60
VSDGGRASFY HLSEIKPLHN FLTQLQPFLK LKQKQANLVL KIIEQLPSAK ESPDKFLEVC  120
TWVDQIAALN DSKTRKTTSE TVRAVLD                                      147

SEQ ID NO: 113          moltype = AA  length = 147
FEATURE                 Location/Qualifiers
source                  1..147
                        mol_type = protein
                        organism = synthetic construct
SEQUENCE: 113
KEFLLYLAGF VDGDGSIFAT IVPQQDRKFK HALRLNFRVH QHTRRRWFLD KLVDEIGVGY  60
VSDTGRASFY HLSQIKPLHN FLTQLQPFLK LKQKQANLVL KIIEQLPSAK ESPDKFLEVC  120
TWVDQIAALN DSKTRKTTSE TVRAVLD                                      147

SEQ ID NO: 114          moltype = AA  length = 147
FEATURE                 Location/Qualifiers
source                  1..147
                        mol_type = protein
                        organism = synthetic construct
SEQUENCE: 114
KEFLLYLAGF VDGDGSIFAT IVPQQDRKFK HALRLNFRVH QHTRRRWFLD KLVDEIGVGY  60
VSDKGRASFY HLSQIKPLHN FLTQLQPFLK LKQKQANLVL KIIEQLPSAK ESPDKFLEVC  120
TWVDQIAALN DSRTRKTTSE TVRAVLD                                      147

SEQ ID NO: 115          moltype = AA  length = 147
FEATURE                 Location/Qualifiers
source                  1..147
                        mol_type = protein
                        organism = synthetic construct
SEQUENCE: 115
KEFLLYLAGF VDGDGSIFAT IVPQQDRKFK HALRLNFRLH QHTRRRWFLD KLVDEIGVGY  60
VSDGGRASFY HLSEIKPLHN FLTQLQPFLK LKQKQANLVL KIIEQLPSAK ESPDKFLEVC  120
TWVDQIAALN DSRTRKTTSE TVRAVLD                                      147

SEQ ID NO: 116          moltype = AA  length = 147
FEATURE                 Location/Qualifiers
source                  1..147
                        mol_type = protein
                        organism = synthetic construct
SEQUENCE: 116
KEFLLYLAGF VDGDGSIFAQ IVPQQDRKFK HALRLKFRLH QHTRRRWFLD KLVDEIGVGY  60
VSDGGRASFY NLSQIKPLHN FLTQLQPFLK LKQKQANLVL KIIEQLPSAK ESPDKFLEVC  120
TWVDQIAALN DSKTRKTTSE TVRAVLD                                      147

SEQ ID NO: 117          moltype = DNA  length = 1062
FEATURE                 Location/Qualifiers
source                  1..1062
                        mol_type = other DNA
                        organism = synthetic construct
SEQUENCE: 117
atgaatacaa aatataataa agagttctta ctctacttag cagggtttgt agactctgac  60
ggttccatct atgcccggat cgttccgtcg cagactagta agttcaagca caagctgagg  120
ctcgtgttcg ccgtcgccca gtctacatgt cgccgttggt tcctgacaa gctggtggac   180
gagatcggtg tgggttacgt gcgggaccac ggccgcgcgt cctactacac cctgtccgag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
```

```
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag ggctggagca ggttccggca ctggatacaa caaggaattc   600
ctgctctacc tggcgggctt cgtcgacggg gacggctcca tctttgccac tatcgttccg   660
cagcaggatc ggaagttcaa gcacgctctg cgtctccagt tcagggtcca ccagaagaca   720
tgccgccgtt ggttcctcga caagctggtg gacgagatcg gtgtgggtta cgtgtacgac   780
ttcggccgcg cgtcccacta ctgcctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccaag acccgcaaga ccacttccga aaccgtccgc  1020
gccgttctag acagtctctc cgagaagaag aagtcgtccc cc                     1062

SEQ ID NO: 118          moltype = DNA  length = 1062
FEATURE                 Location/Qualifiers
source                  1..1062
                        mol_type = other DNA
                        organism = synthetic construct
SEQUENCE: 118
atgaatacaa aatataataa agagttctta ctctacttag cagggtttgt agactctgac    60
ggttccatct atgcccggat cgttccgtcg cagactagta agttcaagca caagctgcgc   120
ctcaccttcg ccgtcaccca gaagacatgc cgccgttggt tcctcgacaa gctggtggac   180
gagatcggtg tgggttacgt gaccgacaac ggccgcgcgt ccaactactt cctgtcccag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgccac tatcgttccg   660
cagcaggatc ggaagttcaa gcacgctctg cgtctccagt tcagggtcca ccagcacaca   720
aggcgccgtt ggttcctcga caagctggtg gacgagatcg gtatgggtta cgtgtccgac   780
cgcggccgcg cgtccttcta cagcctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                     1062

SEQ ID NO: 119          moltype = DNA  length = 1062
FEATURE                 Location/Qualifiers
source                  1..1062
                        mol_type = other DNA
                        organism = synthetic construct
SEQUENCE: 119
atgaatacaa aatataataa agagttctta ctctacttag cagggtttgt agactctgac    60
ggttccatct atgcccggat cgttccgtcg cagggtagta agttcaagca caagctgcgc   120
ctcaccttcg ccgtcaccca gaagacatgc cgccgttggt tcctcgacaa gctggtggac   180
gagatcggtg tgggttacgt gattgacaac ggccgcgcgt ccaactactt tctgtccag    240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgccac tatcgttccg   660
cagcaggatc ggaagttcaa gcacgctctg cgtctcaatt tcagggtcca ccagcacaca   720
aggcgccgtt ggttcctcga caagctggtg gacgagatcg gtatgggtta cgtgtccgac   780
cgcggccgcg cgtccttcta ccatctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                     1062

SEQ ID NO: 120          moltype = DNA  length = 1062
FEATURE                 Location/Qualifiers
source                  1..1062
                        mol_type = other DNA
                        organism = synthetic construct
SEQUENCE: 120
atgaatacaa aatataataa agagttctta ctctacttag cagggtttgt agacgctgac    60
ggttccatct tgcccggat cgttccgtcg cagactcgga agttcaagca caagctgaat   120
ctcaccttcg ccgtcaccca gaagacatgc cgccgttggt tcctcgacaa gctggtggac   180
gagatcggtg tgggttacgt gattgacaac ggccgcgcgt ccaactactt tctgtccgag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccggcgcc gcatcctcgg cttcctcaag cccgggttca   540
gggatctccg aagcactcag agctggagca ggttccggca ctggatacaa caaggaattc   600
```

-continued

```
ctgctctacc tggcgggctt cgtcgacggg gacggctcca tctttgccac tatcgttccg   660
cagcaggatc ggaagttcaa gcacgctctg cgtctcaatt tcagggtcca ccagcacaca   720
aggcgccgtt ggtcctcga caagctggtg gacgagatcg gtgtgggtta cgtgtccgac    780
ggtggccgcg cgtcctttta ccatctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccaag acccgcaaga ccacttccga aaccgtccgc  1020
gccgttctag acagtctctc cgagaagaag aagtcgtccc cc                     1062

SEQ ID NO: 121          moltype = DNA  length = 1062
FEATURE                 Location/Qualifiers
source                  1..1062
                        mol_type = other DNA
                        organism = synthetic construct
SEQUENCE: 121
atgaatacaa aatataataa agagttctta ctctacttag cagggtttgt agactctgac    60
ggttccatct atgcccggat cgttccgtcg cagcatcgga agttcaagca caagctgcag   120
ctcaccttcg ccgtcaccca gaagacatgc cgccgttggt tcctcgacaa gctggtggac   180
gagatcggtg tgggttacgt gattgacaac ggccgcgcgt ccaactactt tctgtccgaa   240
atcaagcctt tgcataattt tttaacacaa ctacaacctt ttctaaaact aaaacaaaaa   300
caagcagatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgccac tatcgttccg   660
cagcaggatc ggaagttcaa gcacgctctg cgtctcaatt tcagggtcca ccagcacaca   720
aggcgccgtt ggtcctcga caagctggtg gacgagatcg gtgtgggtta cgtgtccgac    780
actggccgcg cgtcctttta ccatctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccaag acccgcaaga ccacttccga aaccgtccgc  1020
gccgttctag acagtctctc cgagaagaag aagtcgtccc cc                     1062

SEQ ID NO: 122          moltype = DNA  length = 1062
FEATURE                 Location/Qualifiers
source                  1..1062
                        mol_type = other DNA
                        organism = synthetic construct
SEQUENCE: 122
atgaatacaa aatataataa agagttctta ctctacttag cagggtttgt agacgctgac    60
ggttccatct ttgcccggat cgttccgtcg cagagtcgga agttcaagca caagctgaat   120
ctcaccttcg ccgtcaccca gaagacatgc cgccgttggt tcctcgacaa gctggtggac   180
gagatcggtg tgggttacgt gattgacaac ggccgcgcgt ccaactactt tctgtccgaa   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgccac tatcgttccg   660
cagcaggatc ggaagttcaa gcacgctctg cgtctcaatt tcagggtcca ccagcacaca   720
aggcgccgtt ggtcctcga caagctggtg gacgagatcg gtgtgggtta cgtgtccgac    780
aagggccgcg cgtcctttta ccatctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                     1062

SEQ ID NO: 123          moltype = DNA  length = 1062
FEATURE                 Location/Qualifiers
source                  1..1062
                        mol_type = other DNA
                        organism = synthetic construct
SEQUENCE: 123
atgaatacaa aatataataa agagttctta ctctacttag cagggtttgt agacgctgac    60
ggttccatct ttgcccggat cgttccggag cagggtagga agttcaagca caagctgcag   120
ctcaccttcg ccgtcaccca gaagacatgc cgccgttggt tcctcgacaa gctggtggac   180
gagatcggtg tgggttacgt gattgacggg ggccgcgcgt ccaactactg gctgtccgaa   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccggcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgccac tatcgttccg   660
cagcaggatc ggaagttcaa gcacgctctg cgtctcaatt tcaggctcca ccagcacaca   720
aggcgccgtt ggtcctcga caagctggtg gacgagatcg gtgtgggtta cgtgtccgac    780
ggtggccgcg cgtcctttta ccatctgtcc gagatcaagc ctctgcacaa cttcctgacc   840
```

```
cagctccagc ccttcctgaa gctcaagcag aagcaggcca acctcgtgct gaagatcatc      900
gagcagctgc cctccgccaa ggaatccccg gacaagttcc tggaggtgtg cacctgggtg      960
gaccagatcg ccgctctgaa cgactccagg acccgcaaga ccacttccga aaccgtccgc      1020
gccgttctag acagtctctc cgagaagaag aagtcgtccc cc                         1062

SEQ ID NO: 124            moltype = DNA   length = 1062
FEATURE                   Location/Qualifiers
source                    1..1062
                          mol_type = other DNA
                          organism = synthetic construct
SEQUENCE: 124
atgaatacaa aatataataa agagttctta ctctacttag cagggtttgt agacgctgac      60
ggttccatct ttgcccggat cgttccggag cagggtagga agttcaagca caagctgcag      120
ctcaccttcg ccgtcaccca gaagacatgc cgccgttggt tcctcgacaa gctggtggac      180
gagatcggtg tgggttacgt gattgacaat ggccgcgcgt ccaactacgt gctgtcccag      240
atcaagcctt tgcataattt tttaacacaa ctacaacctt ttctaaaact aaaacaaaaa      300
caagcaaatt tagtttttaaa aattattgaa caacttccgt cagcaaaaga atccccggac      360
aaattcttag aagtttgtac atgggtggat caaattgcag ctctgaatga ttcgaatacg      420
cgtaaaacaa cttctgaaac cgttcgtgct gtgctagaca gtttaccagg atccgtggga      480
ggtctatcgc catctcaggc atccggcgcc gcatcctcgg cttcctcaag cccgggttca      540
gggacctccg aagcactcag agctggagca ggttccggca ctggatacaa caaggaattc      600
ctgctctacc tggcgggctt cgtcgacggg gacggctcca tcttgcccca gatcgttccg      660
cagcaggatc ggaagttcaa gcacgctctg cgtctcaagt tcaggctcca ccagcacaca      720
aggcgccgtt ggttcctcga caagctggtg gacgagatcg gtgtgggtta cgtgtccgac      780
ggtggccgcg cgtccttttta caatctgtcc cagatcaagc ctctgcacaa cttcctgacc      840
cagctccagc ccttcctgaa gctcaagcag aagcaggcca acctcgtgct gaagatcatc      900
gagcagctgc cctccgccaa ggaatccccg gacaagttcc tggaggtgtg cacctgggtg      960
gaccagatcg ccgctctgaa cgactccagg acccgcaaga ccacttccga aaccgtccgc      1020
gccgttctag acagtctctc cgagaagaag aagtcgtccc cc                         1062

SEQ ID NO: 125            moltype = DNA   length = 1257
FEATURE                   Location/Qualifiers
source                    1..1257
                          mol_type = other DNA
                          organism = synthetic construct
SEQUENCE: 125
atgccgtctt ctgtctcgtg gggcatcctc ctgctggcag cctgtgctg cctggtccct       60
gtctccctgg ctgaggatcc ccagggagat gctgcccaga agacagatac atcccaccat      120
gatcaggatc acccaacctt caacaagatc accccaacc tggctgagtt cgccttcagc       180
ctataccgcc agctggcaca ccagtccaac agcaccaata tcttcttctc cccagtgagc      240
atcgctacag cctttgcaat gctctccctg gggaccaagc tgacactca cgatgaaatc       300
ctggagggcc tgaatttcaa cctcacggag attccggagg ctcagatcca tgaaggcttc      360
caggaactcc tccgtaccct caaccagcca gacagccagc tccagctgac caccggcaat      420
ggcctgttcc tcagcgaggg cctgaagcta gtggataagt ttttggagga tgttaaaaag      480
ttgtaccact cagaagcctt cactgtcaac ttcgggggaca ccgaagaggc caagaaacag      540
atcaacgatt acgtggagaa gggtactcaa gggaaaattg tggatttggt caaggagctt      600
gacagagaca cagttttgct tctggtgaat tacatcttct ttaaaggcaa atgggagaga      660
cccctttgaag tcaaggacac cgaggaagag gacttccacg tggaccaggt gaccaccgtg      720
aaggtgccta tgatgaagcg tttaggcatg tttaacatcc agcactgtaa gaagctgtcc      780
agctgggtgc tgctgatgaa atacctgggc aatgccaccg ccatcttctt cctgcctgat      840
gagggaaac tacagcacct ggaaaatgaa ctcacccacg atatcatcac caagttcctg      900
gaaaatgaag acagaaggtc tgccagctta catttaccca aactgtccat tactggaacc      960
tatgatctga gagcgtcct gggtcaactg ggcatcacta aggtcttcag caatggggct      1020
gacctctccg gggtcacaga ggaggcaccc ctgaagctct ccaaggccgt gcataaggct      1080
gtgctgacca tcgacgagaa agggactgaa gctgctgggg ccatgttttt agaggccata      1140
cccatgtcta tccccccga ggtcaagttc aacaaaccct ttgtcttctt aatgattgaa      1200
caaaataccaa agtctccct cttcatggga aaagtggtga atcccacca aaaataa         1257

SEQ ID NO: 126            moltype = DNA   length = 4789
FEATURE                   Location/Qualifiers
source                    1..4789
                          mol_type = other DNA
                          organism = synthetic construct
SEQUENCE: 126
atgccgtctt ctgtctcgtg gggcatcctc ctgctggcag cctgtgctg cctggtccct       60
gtctccctgg ctgaggatcc ccagggagat gctgcccaga agacagatac atcccaccat      120
gatcaggatc acccaacctt caacaagatc accccaacc tggctgagtt cgccttcagc       180
ctataccgcc agctggcaca ccagtccaac agcaccaata tcttcttctc cccagtgagc      240
atcgctacag cctttgcaat gctctccctg gggaccaagc tgacactca cgatgaaatc       300
ctggagggcc tgaatttcaa cctcacggag attccggagg ctcagatcca tgaaggcttc      360
caggaactcc tccgtaccct caaccagcca gacagccagc tccagctgac caccggcaat      420
ggcctgttcc tcagcgaggg cctgaagcta gtggataagt ttttggagga tgttaaaaag      480
ttgtaccact cagaagcctt cactgtcaac ttcgggggaca ccgaagaggc caagaaacag      540
atcaacgatt acgtggagaa gggtactcaa gggaaaattg tggatttggt caaggagctt      600
gacagagaca cagttttgct tctggtgaat tacatcttct ttaaaggtaa ggttgctcaa      660
ccagcctgag ctgttcccat agaaacaagc aaaaatattc tcaaaccatc agttcttgaa      720
ctctccttgg caatgcatta tgggccatag caatgctttt cagcgtggat tcttcagttt      780
tctacacaca aacactaaaa tgttttccat cattgagtaa tttgaggaaa taatagatta      840
aactgtcaaa actactgaca gctctgcaga acttttcaga gcctttaatg tccttgtgta      900
```

-continued

```
tactgtatat gtagaatata taatgcttag aactatagaa caaattgtaa tacactgcat    960
aaagggatag tttcatggaa catactttac acgactctag tgtcccagaa tcagtatcag   1020
ttttgcaatc tgaaagacct gggttcaaat cctgcctcta acacaattag cttttgacaa   1080
aaacaatgca ttctacctct ttgaggtgct aatttctcat cttagcatgg acaaaatacc   1140
attcttgctg tcaggttttt ttaggattaa acaaatgaca aagactgtgg ggatggtgtg   1200
tggcatacag caggtgatgg actcttctgt atctcaggct gccttcctgc ccctgagggg   1260
ttaaaatgcc agggtcctgg gggcccagg gcattctaag ccagctccca ctgtcccagg    1320
aaaacagcat aggggagggg aggtgggagg caaggccagg ggctgcttcc tccactctga   1380
ggctcccttg ctcttgaggc aaaggagggc agtggagagc agccaggctg cagtcagcac   1440
agctaaagtc ctggctctgc tgtggcctta gtgggggccc aggtccctct ccagccccag   1500
tctcctcctt ctgtccaatg agaaagctgg gatcaggggt ccctgaggcc cctgtccact   1560
ctgcatgcct cgatggtgaa gctctgttgg tatggcagag gggaggctgc tcaggcatct   1620
gcatttcccc tgccaatcta gaggatgagg aaagctctca ggaatagtaa gcagaatgtt   1680
tgccctggat gaataactga gctgccaatt aacaaggggc aggagcctt agacagaagg     1740
taccaaatat gcctgatgct ccaacatttt atttgtaata tccaagacac cctcaaataa   1800
acatatgatt ccaataaaaa tgcacagcca cgatggcatc tcttagcctg acatcgccac   1860
gatgtagaaa ttctgcatct tcctctagtt ttgaattatc cccacacaat cttttttcggc   1920
agcttggatg gtcagtttca gcacctttta cagatgatga agctgagcct cgagggatgt   1980
gtgtcgtcaa gggggctcag ggcttctcag ggaggggact catggtttct ttattctgct   2040
acactcttcc aaaccttcac tcacccctgg tgatgcccac cttcccctct ctccaggcaa   2100
atgggagaga ccctttgaag tcaaggacac cgaggaagag gacttccacg tggaccaggt   2160
gaccaccgtg aaggtgccta tgatgaagcg tttaggcatg tttaacatcc agcactgtaa   2220
gaagctgtcc agctgggtgc tgctgatgaa atacctgggc aatgccaccg ccatcttctt   2280
cctgcctgat gaggggaaac tacagcacct ggaaaatgaa ctcacccacg atatcatcac   2340
caagttcctg gaaaatgaag acagaaggtg attcccaac ctgagggtga ccaagaagct    2400
gcccacacct cttagccatg ttgggactga ggcccatcag gacttggccag agggctgagg   2460
agggtgaacc ccacatccct gggtcactgc tactctgtat aaacttggct tccagaatga   2520
ggccaccact gagttcaggc agcgccatcc atgctccatg aggaggacag tacccagggg   2580
tgaggaggta aaggtctcgt ccctggggac ttcccactcc agtgtggaca ctgtcccttc   2640
ccaatatcca gtgcccaggg cagggacagc agcaccaaca cacgttctgg cagaaccaaa   2700
aaggaacaga tgggcttcct ggcaaaggca gcagtggagt gtggagttca agggtagaat   2760
gtccctgggg ggacgggga agagcctgtg tggcaaggcc cagaaaagca aggttcggaa    2820
ttggaacagc caggccatgt tcgcagaagg cttgcgtttc tctgtcactt tatcggtgct   2880
gttagattgg gtgtcctgta gtaagtgata cttaaacatg agccacacat tagtgtatgt   2940
gtgtgcattc gtgattatgc ccatgccctg ctgatctagt tcgtttttgta cactgtaaaa   3000
ccaagatgaa aatacaaaag gtgtcgggtt cataatagga atcgaggctg gaattttctct   3060
gttccatgcc agcacctcct gaggtctctg ctccaggggt tgagaaagaa caaagaggct   3120
gagagggtaa cggatcagag agcccagagc caagctgccc gctcacacca gacctgctc    3180
agggtggcat tgtctcccca tggaaaacca gagaggagca ctcagcctgg tgtggtcact   3240
cttctcttat ccactaaacg gttgtcactg ggcactgcca ccagcccgt gtttctctgg     3300
gtgtagggcc ctgggatgt tacaggctgg gggccaggtg acccaacact acagggcaag     3360
atgagacagg cttccaggac acctagaata tcagaggagg tggcatttca agctttttgtg   3420
attcattcga tgttaacatt ctttgactca atgtagaaga gctaaaagta gaacaaacca   3480
aagccgagtt cccatcttag tgtgggtgga ggacacagga gtaagtggca gaaataatca   3540
gaaaagaaaa cacttgcact gtggtgggtc ccagaagaac aagaggaatg ctgtgccatg    3600
ccttgaattt cttttctgca cgacaggtct gccagcttac atttacccaa actgtccatt    3660
actggaacct atgatctgaa gagcgtcctg ggtcaactgg gcatcactaa ggtcttcagc    3720
aatgggggctg acctctccgg ggtcacagag gaggcacccc tgaagctctc caaggtgaga   3780
tcaccctgac gaccttgttg caccctggta tctgtaggga agaatgtgtg ggggctgcag    3840
ctctgtcctg aggctgagga aggggccgag ggaaacaaat gaagacccag gctgagctcc    3900
tgaagatgcc cgtgattcac tgacacggga cgtggtcaaa cagcaaagcc aggcagggga    3960
ctgctgtgca gctggcactt tcggggcctc ccttgaggtt gtgtcactga ccctgaatt    4020
caactttgcc caagaccttc tagacattgg gccttgattt atccatactg acacagaaag    4080
gtttgggcta agttgtttca aaggaatttc tgactccttc gatctgtgag atttggtgtc    4140
tgaattaatg aatgatttca gctaaagatg acacttattt tggaaaacta aaggcgacca   4200
atgaacaact gcagttccat gaatggctgc attatcttgg ggtctgggca ctgtgaaggt   4260
cactgccagg gtccgtgtcc tcaaggagct tcaagccgtg tactagaaag gagagagccc    4320
tggaggcaga cgtggagtga cgatgctctt ccctgttctg agttgtgggt gcacctgagc   4380
aggggggagag gcgcttgtca ggaagatgga cagaggggag ccagccccat cagccaaagc   4440
cttgaggagg agcaaggcct atgtgacagg gagggagagg atgtgcaggg ccagggccgt   4500
ccaggggggag tgagcgcttc ctgggaggtg tccacgtgag ccttgctcga ggcctgggat   4560
cagccttaca acgtgtctct gcttctctcc cctccaggcc gtgcataagg ctgtgctgac   4620
catcgacgag aaagggactg aagctgctgg ggccatgttt ttagaggcca tacccatgtc   4680
tatccccccc gaggtcaagt tcaacaaacc ctttgtcttc ttaatgattg aacaaaatac   4740
caagtctccc ctcttcatgg gaaaagtggt gaatcccacc caaaaataa               4789
```

SEQ ID NO: 127          moltype = DNA  length = 8712
FEATURE                 Location/Qualifiers
source                  1..8712
                        mol_type = other DNA
                        organism = synthetic construct
SEQUENCE: 127

```
tgggcaggaa ctgggcactg tgcccagggc atgcactgcc tccacgcagc aaccctcaga    60
gtcctgagct gaaccaagaa ggaggagggg gtcgggcctc cgaggaaggc ctagccgctg    120
ctgctgccag gaattccagg ttggagggc ggcaacctcc tgccagcctt caggccactc     180
tcctgtgcct gccagaagag acagagcttg aggagagctt gaggagagca ggaaaggtgg   240
gacattgctg ctgctgctca ctcagttcca caggtgggag ggacagcagg cttagagtg    300
ggggtcattg tgcagatggg aaaacaaagg cccagagagg ggaagaaatg cccaggagct   360
accgagggca ggcgacctca accacagccc agtgctggag ctgtgagtgg atgtagagca   420
```

-continued

```
gcggaatatc cattcagcca gctcagggga aggacagggg ccctgaagcc aggggatgga    480
gctgcaggga agggagctca gagagaaggg gaggggagtc tgagctcagt ttcccgctgc    540
ctgaaaggag ggtggtacct actcccttca cagggtaact gaatgagaga ctgcctggag    600
gaaagctctt caagtgtggc ccaccccacc ccagtgacac cagcccctga cacggggggag   660
ggagggcagc atcaggaggg gctttctggg cacacccagt acccgtctct gagctttcct    720
tgaactgttg cattttaatc ctcacagcag ctcaacaagg tacataccgt caccatcccc    780
attttacaga tagggaaatt gaggctcgga gcggttaaac aactcacctg aggcctcaca    840
gccagtaagt gggttccctg gtctgaatgt gtgtgctgga ggatcctgtg ggtcactcgc    900
ctggtagagc cccaaggtgg aggcataaat gggactggtg aatgacagaa ggggcaaaaa    960
tgcactcatc cattcactct gcaagtatct acggcacgta cgccagctcc caagcaggtt   1020
tgcgggttgc acagcgggcg atgcaatctg atttaggctt ttaaagggat tgcaatcaag   1080
tggggccca ctagcctcaa ccctgtacct cccctcccct ccaccccag cagtctccaa     1140
aggcctccaa caaccccaga gtggggggcca tgtatccaaa gaaactccaa gctgtatacg   1200
gatcacactg gtttccagg agcaaaaaca gaaacaggcc tgaggctggt caaaattgaa    1260
cctcctcctg ctctgagcag cctggggggc agactaagca gagggctgtg cagacccaca   1320
taaagagcct actgtgtgcc aggcacttca cccgaggcac ttcacaagca tgcttgggaa   1380
tgaaacttcc aactctttgg gatgcaggtg aaacagttcc tggttcagag aggtgaagcg   1440
gcctgcctga ggcagcacag ctcttcttta cagatgtgct tccccacctc taccctgtct   1500
cacggcccc catgccagcc tgacggttgt gtctgcctca gtcatgctcc atttttccat    1560
cgggaccatc aagagggtgt ttgtgtctaa ggctgactgg gtaactttgg atgagcggtc   1620
tctccgctct gagcctgttt cctcatctgt caaatgggct ctaacccact ctgatctccc   1680
agggcggcag taagtcttca gcatcaggca ttttggggtg actcagtaaa tggtagatct   1740
tgctaccagt ggaacagcca ctaaggattc tgcagtgaga gcagagggcc agctaagtgg   1800
tactctccca gagactgtct gactcacgcc accccctcca ccttggacac aggacgctgt   1860
ggtttctgag ccaggtacaa tgactccttt cggtaagtgc agtggaagct gtacactgcc   1920
caggcaaagc gtccgggcag cgtaggcggg cgactcagat cccagccagt ggacttagcc   1980
cctgtttgct cctccgataa ctgggtgac cttggttaat attcaccagc agcctccccc    2040
gttgcccctc tggatccact gcttaaatac ggacgaggac agggccctgt ctcctcagct   2100
tcaggcacca ccactgacct gggacagtga atcgtaagta tgcctttcac tgcgagaggt   2160
tctggagagg cttctgagct ccccatggcc caggcaggca gcaggtctgg ggcaggaggg   2220
gggttgtgga gtgggtatcc gcctgctgag gtgcagggca gatggagagg ctgcagctga   2280
gctcctattt tcataataac agcagccatg agggttgtgt cctgtttccc agtcctgccc   2340
ggtcccccct cggtacctcc tggtggatac actggttcct gtaagcagaa gtggatgagg   2400
gtgtctaggt ctgcagtcct ggcaccccag gatgggggac accagccaag atacagcaac   2460
agcaacaaag cgcagccatt tctttctgtt tgcacagctc ctctgtctgt cgggggctcc   2520
tgtctgttgt ctcctataag cctcaccacc tctcctactg cttgggcatg catctttctc   2580
cccttctata gatgaggagg ttaaggtcca gagaggggtg gggaggaacg ccggctcaca   2640
ttctccatcc cctccagata tgaccaggaa cagacctgtg ccaggcctca gccttacatc   2700
aaaatgggcc tccccatgca ccgtggacct ctgggccctc ctgtcccagt ggaggacagg   2760
aagctgtgag gggcactgtc acccagggct caagctggca ttcctgaata atcgctctgc   2820
accaggccac ggctaagctc agtgcgtgat taagcctcat aaccctccaa ggcagttact   2880
agtgtgattc ccattttaca gatgaggaag atggggacag agaggtgaat aactggcccc   2940
aaatcacaca ccatccataa ttcgggctca ggcacctggc tccagtcccc aaactcttga   3000
acctggcccct agtgtcactg tttctcttgg gtctcaggcg ctggatgggg aacaggaaac   3060
ctgggctgga cttgaggcct ctctgatgct cggtgacttc agacagttgc tcaacctctc   3120
tgttctcttg ggcaaaacat gataaccttt gacttctgtc ccctcccctc accccacccg   3180
accttgatct ctgaagtgtt ggaaggattt aattttcct gcactgagtt ttggagacag    3240
gtcaaaaaga tgaccaaggc caaggtggcc agtttcctat agaacgcctc taaaagacct   3300
gcagcaaatag cagcaagaac tggtattctc gagaacttgc tgcgcagcag gcacttcttg   3360
gcattttatg tgtatttaat ttcacaatag ctctatgaca aagtccacct ttctcatctc   3420
caggaaactg aggttcagag aggttaagta acttgtccaa ggtcacacag ctaatagcaa   3480
gttgacgtgg agcaatctgg cctcagagcc tttaatttta gccacagact gatgctcccc   3540
tcttcattta gccaggctgc ctctgaagtt ttctgattca agacttctgg cttcagcttt   3600
gtacacagag atgattcaat gtcaggtttt ggagtgaaat ctgtttaatc ccagacaaaa   3660
catttaggat tacatctcag ttttgtaagc aagtagctct gtgattttta gtgagttatt   3720
taatgctctt tggggctcaa tttttctatc tataaaatag ggctaataat ttgcacctta   3780
tagggtaagc tttgaggaca gattagatga tacggtgcct gtaaaacacc aggtgttagt   3840
aagtgtggca atgatggtga cgctgaggct gatgtttgct tagcataggg ttaggcagct   3900
ggcaggcagt aaacagttgg ataatttaat ggaaaatttg ccaaactcag atgctgttca   3960
ctgctgagca ggagcccctt cctgctgaaa tggtcctggg gagtgcagca ggctctccgg   4020
gaagaaatct accatctctc gggcaggagc tcaacctgtg tgcaggtaca gggaggggctt   4080
cctcacctgg tgcccactca tgcattacgt cagttattcc tcatccctgt ccaaaggatt   4140
ctttttctcca ttgtacagct atgaagctag tgctcaaaga agtgaagtca tttaccccag   4200
gcccccctgcc agtaagtgac agggcctggt cacacttggg tttatttatt gcccagttca   4260
acaggttgtt tgaccatagg cgagattctc ttccctgcac cctgccgggt tgctcttggt   4320
cccttatttt atgctcccgg gtagaaatgg tgtgagatta ggcagggagt ggctcgcttc   4380
cctgtccctg gccccgcaaa gagtgctccc acctgccccg atcccagaaa tgtcaccatg   4440
aagccttcat tctttttggtt taaagcttgg cctcagtgtc cgtacaccat ggggtacttg   4500
gccagatggc gactttctcc tctccagtcg ccctcccagg cactagcttt taggagtgca   4560
gggtgctgcc tctgatagaa gggccaggag agagcaggtt ttggagtcct gatgttataa   4620
ggaacagctt gggaggcata atgaacccaa catgatgctt gagaccaatg tcacagccca   4680
attctgacat tcatcatctg agatctgagg acacagctgt ctcagttcat gatctgagtg   4740
ctgggaaagc caagacttgt tccagctttg tcactgactt gctgtatagc ctcaacaagg   4800
ccctgaccct ctctgggctt caaactcttc actgtgaaag gaggaaacca gagtaggtga   4860
tgtgacacca ggaaagatgg atgggtgtgg gggaatgtgc tcctcccagc tgtcacccc    4920
tcgccaccct ccctgcacca gcctctccac ctccttgag cccagaattc ccctgtctag    4980
gagggcacct gtctcatgcc tagccatggg aattctccat ctgttttgct acattgaacc   5040
cagatgccat tctaaccaag aatcctggct gggtgcaggg gctctcgcct gtaacccag    5100
cactttggga ggccaaggca ggcggatcaa gaggtcagga gttcaagacc tgcctggcca   5160
```

-continued

```
acacggtgaa acctcagctc tactaaaaat acaaaaatta gccaggcgtg gtggcacacg 5220
cctgtaatcc cagctatttg ggaagctgag acagaagaat ttcttgaacc cgggaggtgg 5280
aggtttcagt gagccgagat cacgccactg cactccaccc tggcagataa agcgagactc 5340
tgtctcaaaa aaaacccaaa aacctatgtt agtgtacaga gggccccagt gaagtcttct 5400
cccagcccca ctttgcacaa ctggggagag tgaggcccca ggaccagagg attcttgcta 5460
aaggccaagt ggatagtgat ggccctgcca gggctagaag ccacaacctc tggccctgag 5520
gccactcagc atatttagtg tccccaccct gcagaggccc aactccctcc tgaccactga 5580
gccctgtaat gatgggggaa tttccataag ccatgaagga ctgcacaaag ttcagttggg 5640
aagtgaaaga gaaattaaag ggagatgaaa atatacagca ctaattttag caccgtcttt 5700
agttctaaca acactagcta gctgaagaaa aatacaaaca tgtattatgt aatgtgtggt 5760
ctgttccatt tggattactt agaggcacga gggccaggag aaaggtggtg gagagaaacc 5820
agctttgcac ttcatttgtt gctttattgg aaggaaactt ttaaaagtcc aaggggggttg 5880
aagaatctca atatttgtta tttccagctt ttttctcca gttttcatt tcccaaattc 5940
aaggacacct tttctttgt attttgttaa gatgatggtt ttggttttgt gactagtagt 6000
taacaatgtg gctgccgggc atattctcct cagctaggac ctcagttttc ccatctgtga 6060
agacggcagg ttctacctag ggggctgcag gctggtggtc cgaagcctgg gcatatctgg 6120
agtagaagga tcactgtggg gcagggcagg ttctgtgttg ctgtggatga cgttgacttt 6180
gaccattgct cggcagagcc tgctctcgct ggttcagcca caggccccac cactccctat 6240
tgtctcagcc ccgggtatga aacatgtatt cctcactggc ctatcacctg aagcctttga 6300
atttgcaaca cctgccaacc cctccctcaa aagagttgcc ctctcagatc cttttgatgt 6360
aaggtttggt gttgagactt atttcactaa attctcatac ataaacatca ctttatgtat 6420
gaggcaaaat gaggaccagg gagatgaatg acttgtcctg actcatacac ctggaaagtg 6480
acagagtcag attagatccc aggtctatct gaagttaaaa gaggtgtctt ttcacttccc 6540
acctcctcca tctactttaa agcagcacaa acccctgctt tcaaggagag atgagcgtct 6600
ctaaagcccc tgacagcaag agcccagaac tgggacacca ttagtgaccc agacggcagg 6660
taagctgact gcaggagcat cagcctattc ttgtgtctgg gaccacagag cattgtgggg 6720
acagccccgt ctcttgggaa aaaaacccta agggctgagg atccttgtga gtgttgggtg 6780
ggaacagctc ccaggaggtt taatcacagc ccctccatgc tctctagctg ttgccattgt 6840
gcaagatgca tttcccttct gtgcagcagt ttccctggcc actaaatagt gggattagat 6900
agaagccctc caagggcttc cagcttgaca tgattcttga ttctgatctg gcccgattcc 6960
tggataatcg tgggcaggcc cattcctctt cttgtgcctc attttcttct tttgtaaaac 7020
aatggctgta ccatttgcat cttagggtca ttgcagatgt aagtgttgct gtccagagcc 7080
tgggtgcagg acctagatgt aggattctgg ttctgctact tcctcagtga cattgaatag 7140
ctgacctaat ctctctggct ttggtttctt catctgtaaa agaaggatat tagcattagc 7200
acctcacggg attgttacaa gaaagcaatg aattaacaca tgtgagcacg gagaacagtg 7260
cttggcatat ggtaagcact acgtacattt tgctattctt ctgattcttt cagtgttact 7320
gatgtcggca agtacttggc acaggctggt ttaataatcc ctaggcactt ccacgtggtg 7380
tcaatccctg atcactggga gtcatcatgt gccttgactc ggggcctggc cccccatct 7440
ctgtcttgca ggacaatgcc gtcttctgtc tcgtggggca tcctcctgct ggcaggcctg 7500
tgctgcctgg tccctgtctc cctggctgag gatccccagg gagatgctgc cagaagaca 7560
gatacatccc accatgatca ggatcaccca accttcaaca agatcacccc caacctggct 7620
gagttcgcct tcagcctata ccgccagctg gcacaccagt ccaacagcac caatatcttc 7680
ttctccccag tgagcatcgc tacagccttt gcaatgctct caagctgggt caaggctgac 7740
actcacgatg aaatcctgga gggcctgaat ttcaacctca cggagattcc ggaggctcag 7800
atccatgaag gcttccagga actcctccgt accctcaacc agccagacag ccagctccag 7860
ctgaccaccg gcaatggcct gttcctcagc gagggcctga agctagtgga taagttttg 7920
gaggatgtta aaaagttgta ccactcagaa gccttcactg tcaacttcgg ggacaccgaa 7980
gaggccaaga aacagatcaa cgattacgtg gagaagggta ctcaagggaa aattgtggat 8040
ttggtcaagg agcttgacag agacacagtt tttgctctgg tgaattacat cttctttaaa 8100
ggcaaatggg agagacccct tgaagtcaag gacaccgagg aagaggactt ccacgtggac 8160
caggtaccca ccgtgaaggt gcctatgatg aagcgtttag gcatgtttaa catccagcac 8220
tgtaagaagc tgtccagctg ggtgctgctg atgaaatacc tgggcaatgc caccgccatc 8280
ttcttcctgc ctgatgaggg gaaactacag cacctggaaa atgaactcac ccacgatatc 8340
atcaccaagt tcctggaaaa tgaagacaga aggtctgcca gcttacattt acccaaactg 8400
tccattactg gaacctatga tctgaagagc gtcctgggtc aactgggcat cactaaggtc 8460
ttcagcaatg gggctgacct ctccggggtc acagaggagg cacccctgaa gctctccaag 8520
gccgtgcata aggctgtgct gaccatcgac gagaaaggga ctgaagctgc tggggccatg 8580
tttttagagg ccatacccat gtctatcccc cccgaggtca agttcaacaa acccttgtc 8640
ttcttaatga ttgaacaaaa taccaagtct cccctcttca tgggaaaagt ggtgaatccc 8700
acccaaaaat aa 8712
```

```
SEQ ID NO: 128        moltype = AA  length = 10
FEATURE               Location/Qualifiers
source                1..10
                      mol_type = protein
                      organism = synthetic construct
SEQUENCE: 128
MAPKKKRKVH                                                          10

SEQ ID NO: 129        moltype = DNA  length = 22
FEATURE               Location/Qualifiers
source                1..22
                      mol_type = other DNA
                      organism = synthetic construct
SEQUENCE: 129
gctggactgg tatttgtgtc tg                                            22

SEQ ID NO: 130        moltype = DNA  length = 22
FEATURE               Location/Qualifiers
```

-continued

```
source                   1..22
                         mol_type = other DNA
                         organism = synthetic construct
SEQUENCE: 130
cgacctgacc ataaacacag ac                                             22

SEQ ID NO: 131           moltype = DNA  length = 32
FEATURE                  Location/Qualifiers
source                   1..32
                         mol_type = other DNA
                         organism = synthetic construct
SEQUENCE: 131
tatccagtcc aagctgtata cggatcacac tg                                  32

SEQ ID NO: 132           moltype = DNA  length = 32
FEATURE                  Location/Qualifiers
source                   1..32
                         mol_type = other DNA
                         organism = synthetic construct
SEQUENCE: 132
atgcacctcc aagctgtata cggatcacac tg                                  32

SEQ ID NO: 133           moltype = DNA  length = 32
FEATURE                  Location/Qualifiers
source                   1..32
                         mol_type = other DNA
                         organism = synthetic construct
SEQUENCE: 133
cagttccacc aagctgtata cggatcacac tg                                  32

SEQ ID NO: 134           moltype = DNA  length = 32
FEATURE                  Location/Qualifiers
source                   1..32
                         mol_type = other DNA
                         organism = synthetic construct
SEQUENCE: 134
tctcgcctcc aagctgtata cggatcacac tg                                  32

SEQ ID NO: 135           moltype = DNA  length = 35
FEATURE                  Location/Qualifiers
source                   1..35
                         mol_type = other DNA
                         organism = synthetic construct
SEQUENCE: 135
gtggttcctg aaccaggaac tgtttcacct gcatc                               35

SEQ ID NO: 136           moltype = DNA  length = 35
FEATURE                  Location/Qualifiers
source                   1..35
                         mol_type = other DNA
                         organism = synthetic construct
SEQUENCE: 136
cgaacttctg aaccaggaac tgtttcacct gcatc                               35

SEQ ID NO: 137           moltype = DNA  length = 35
FEATURE                  Location/Qualifiers
source                   1..35
                         mol_type = other DNA
                         organism = synthetic construct
SEQUENCE: 137
aggaatggtg aaccaggaac tgtttcacct gcatc                               35

SEQ ID NO: 138           moltype = DNA  length = 35
FEATURE                  Location/Qualifiers
source                   1..35
                         mol_type = other DNA
                         organism = synthetic construct
SEQUENCE: 138
gttaggaatg aaccaggaac tgtttcacct gcatc                               35

SEQ ID NO: 139           moltype = DNA  length = 35
FEATURE                  Location/Qualifiers
source                   1..35
                         mol_type = other DNA
                         organism = synthetic construct
SEQUENCE: 139
cgttgaggtg aaccaggaac tgtttcacct gcatc                               35

SEQ ID NO: 140           moltype = DNA  length = 35
```

-continued

```
FEATURE                 Location/Qualifiers
source                  1..35
                        mol_type = other DNA
                        organism = synthetic construct
SEQUENCE: 140
ctcccaaatg aaccaggaac tgtttcacct gcatc                                  35

SEQ ID NO: 141          moltype = DNA  length = 35
FEATURE                 Location/Qualifiers
source                  1..35
                        mol_type = other DNA
                        organism = synthetic construct
SEQUENCE: 141
gacatttctg aaccaggaac tgtttcacct gcatc                                  35

SEQ ID NO: 142          moltype = DNA  length = 35
FEATURE                 Location/Qualifiers
source                  1..35
                        mol_type = other DNA
                        organism = synthetic construct
SEQUENCE: 142
tgagagattg aaccaggaac tgtttcacct gcatc                                  35

SEQ ID NO: 143          moltype = DNA  length = 31
FEATURE                 Location/Qualifiers
source                  1..31
                        mol_type = other DNA
                        organism = synthetic construct
SEQUENCE: 143
tatccagtct cttgaacctg gccctagtgt c                                      31

SEQ ID NO: 144          moltype = DNA  length = 31
FEATURE                 Location/Qualifiers
source                  1..31
                        mol_type = other DNA
                        organism = synthetic construct
SEQUENCE: 144
atgcacctct cttgaacctg gccctagtgt c                                      31

SEQ ID NO: 145          moltype = DNA  length = 31
FEATURE                 Location/Qualifiers
source                  1..31
                        mol_type = other DNA
                        organism = synthetic construct
SEQUENCE: 145
cagttccact cttgaacctg gccctagtgt c                                      31

SEQ ID NO: 146          moltype = DNA  length = 31
FEATURE                 Location/Qualifiers
source                  1..31
                        mol_type = other DNA
                        organism = synthetic construct
SEQUENCE: 146
tctcgcctct cttgaacctg gccctagtgt c                                      31

SEQ ID NO: 147          moltype = DNA  length = 44
FEATURE                 Location/Qualifiers
source                  1..44
                        mol_type = other DNA
                        organism = synthetic construct
SEQUENCE: 147
gtggttccaa attaaatcct tccaacactt cagagatcaa ggtc                        44

SEQ ID NO: 148          moltype = DNA  length = 44
FEATURE                 Location/Qualifiers
source                  1..44
                        mol_type = other DNA
                        organism = synthetic construct
SEQUENCE: 148
cgaacttcaa attaaatcct tccaacactt cagagatcaa ggtc                        44

SEQ ID NO: 149          moltype = DNA  length = 44
FEATURE                 Location/Qualifiers
source                  1..44
                        mol_type = other DNA
                        organism = synthetic construct
SEQUENCE: 149
aggaatggaa attaaatcct tccaacactt cagagatcaa ggtc                        44
```

-continued

```
SEQ ID NO: 150          moltype = DNA   length = 44
FEATURE                 Location/Qualifiers
source                  1..44
                        mol_type = other DNA
                        organism = synthetic construct
SEQUENCE: 150
gttaggaaaa attaaatcct tccaacactt cagagatcaa ggtc                    44

SEQ ID NO: 151          moltype = DNA   length = 44
FEATURE                 Location/Qualifiers
source                  1..44
                        mol_type = other DNA
                        organism = synthetic construct
SEQUENCE: 151
cgttgaggaa attaaatcct tccaacactt cagagatcaa ggtc                    44

SEQ ID NO: 152          moltype = DNA   length = 44
FEATURE                 Location/Qualifiers
source                  1..44
                        mol_type = other DNA
                        organism = synthetic construct
SEQUENCE: 152
ctcccaaaaa attaaatcct tccaacactt cagagatcaa ggtc                    44

SEQ ID NO: 153          moltype = DNA   length = 44
FEATURE                 Location/Qualifiers
source                  1..44
                        mol_type = other DNA
                        organism = synthetic construct
SEQUENCE: 153
gacatttcaa attaaatcct tccaacactt cagagatcaa ggtc                    44

SEQ ID NO: 154          moltype = DNA   length = 44
FEATURE                 Location/Qualifiers
source                  1..44
                        mol_type = other DNA
                        organism = synthetic construct
SEQUENCE: 154
tgagagataa attaaatcct tccaacactt cagagatcaa ggtc                    44

SEQ ID NO: 155          moltype = DNA   length = 35
FEATURE                 Location/Qualifiers
source                  1..35
                        mol_type = other DNA
                        organism = synthetic construct
SEQUENCE: 155
tatccagtct ccattgtaca gctatgaagc tagtg                              35

SEQ ID NO: 156          moltype = DNA   length = 35
FEATURE                 Location/Qualifiers
source                  1..35
                        mol_type = other DNA
                        organism = synthetic construct
SEQUENCE: 156
atgcacctct ccattgtaca gctatgaagc tagtg                              35

SEQ ID NO: 157          moltype = DNA   length = 35
FEATURE                 Location/Qualifiers
source                  1..35
                        mol_type = other DNA
                        organism = synthetic construct
SEQUENCE: 157
cagttccact ccattgtaca gctatgaagc tagtg                              35

SEQ ID NO: 158          moltype = DNA   length = 35
FEATURE                 Location/Qualifiers
source                  1..35
                        mol_type = other DNA
                        organism = synthetic construct
SEQUENCE: 158
tctcgcctct ccattgtaca gctatgaagc tagtg                              35

SEQ ID NO: 159          moltype = DNA   length = 35
FEATURE                 Location/Qualifiers
source                  1..35
                        mol_type = other DNA
                        organism = synthetic construct
SEQUENCE: 159
gtggttccgg gagcataaaa taagggacca agagc                              35
```

-continued

```
SEQ ID NO: 160            moltype = DNA   length = 35
FEATURE                   Location/Qualifiers
source                    1..35
                          mol_type = other DNA
                          organism = synthetic construct
SEQUENCE: 160
cgaacttcgg gagcataaaa taagggacca agagc                          35

SEQ ID NO: 161            moltype = DNA   length = 35
FEATURE                   Location/Qualifiers
source                    1..35
                          mol_type = other DNA
                          organism = synthetic construct
SEQUENCE: 161
aggaatgggg gagcataaaa taagggacca agagc                          35

SEQ ID NO: 162            moltype = DNA   length = 35
FEATURE                   Location/Qualifiers
source                    1..35
                          mol_type = other DNA
                          organism = synthetic construct
SEQUENCE: 162
gttaggaagg gagcataaaa taagggacca agagc                          35

SEQ ID NO: 163            moltype = DNA   length = 35
FEATURE                   Location/Qualifiers
source                    1..35
                          mol_type = other DNA
                          organism = synthetic construct
SEQUENCE: 163
cgttgagggg gagcataaaa taagggacca agagc                          35

SEQ ID NO: 164            moltype = DNA   length = 35
FEATURE                   Location/Qualifiers
source                    1..35
                          mol_type = other DNA
                          organism = synthetic construct
SEQUENCE: 164
ctcccaaagg gagcataaaa taagggacca agagc                          35

SEQ ID NO: 165            moltype = DNA   length = 35
FEATURE                   Location/Qualifiers
source                    1..35
                          mol_type = other DNA
                          organism = synthetic construct
SEQUENCE: 165
gacatttcgg gagcataaaa taagggacca agagc                          35

SEQ ID NO: 166            moltype = DNA   length = 35
FEATURE                   Location/Qualifiers
source                    1..35
                          mol_type = other DNA
                          organism = synthetic construct
SEQUENCE: 166
tgagagatgg gagcataaaa taagggacca agagc                          35

SEQ ID NO: 167            moltype = DNA   length = 32
FEATURE                   Location/Qualifiers
source                    1..32
                          mol_type = other DNA
                          organism = synthetic construct
SEQUENCE: 167
tatccagttg gcagataaag cgagactctg tc                             32

SEQ ID NO: 168            moltype = DNA   length = 32
FEATURE                   Location/Qualifiers
source                    1..32
                          mol_type = other DNA
                          organism = synthetic construct
SEQUENCE: 168
atgcaccttg gcagataaag cgagactctg tc                             32

SEQ ID NO: 169            moltype = DNA   length = 32
FEATURE                   Location/Qualifiers
source                    1..32
                          mol_type = other DNA
                          organism = synthetic construct
SEQUENCE: 169
```

-continued

```
cagttccatg gcagataaag cgagactctg tc                           32

SEQ ID NO: 170            moltype = DNA   length = 32
FEATURE                   Location/Qualifiers
source                    1..32
                          mol_type = other DNA
                          organism = synthetic construct
SEQUENCE: 170
tctcgccttg gcagataaag cgagactctg tc                           32

SEQ ID NO: 171            moltype = DNA   length = 32
FEATURE                   Location/Qualifiers
source                    1..32
                          mol_type = other DNA
                          organism = synthetic construct
SEQUENCE: 171
gccgaatgtg gcagataaag cgagactctg tc                           32

SEQ ID NO: 172            moltype = DNA   length = 32
FEATURE                   Location/Qualifiers
source                    1..32
                          mol_type = other DNA
                          organism = synthetic construct
SEQUENCE: 172
tactgcagtg gcagataaag cgagactctg tc                           32

SEQ ID NO: 173            moltype = DNA   length = 32
FEATURE                   Location/Qualifiers
source                    1..32
                          mol_type = other DNA
                          organism = synthetic construct
SEQUENCE: 173
catgttgatg gcagataaag cgagactctg tc                           32

SEQ ID NO: 174            moltype = DNA   length = 32
FEATURE                   Location/Qualifiers
source                    1..32
                          mol_type = other DNA
                          organism = synthetic construct
SEQUENCE: 174
atagagtctg gcagataaag cgagactctg tc                           32

SEQ ID NO: 175            moltype = DNA   length = 32
FEATURE                   Location/Qualifiers
source                    1..32
                          mol_type = other DNA
                          organism = synthetic construct
SEQUENCE: 175
tcacgctctg gcagataaag cgagactctg tc                           32

SEQ ID NO: 176            moltype = DNA   length = 31
FEATURE                   Location/Qualifiers
source                    1..31
                          mol_type = other DNA
                          organism = synthetic construct
SEQUENCE: 176
gtggttccgg gccagaggtt gtggcttcta g                            31

SEQ ID NO: 177            moltype = DNA   length = 31
FEATURE                   Location/Qualifiers
source                    1..31
                          mol_type = other DNA
                          organism = synthetic construct
SEQUENCE: 177
cgaacttcgg gccagaggtt gtggcttcta g                            31

SEQ ID NO: 178            moltype = DNA   length = 31
FEATURE                   Location/Qualifiers
source                    1..31
                          mol_type = other DNA
                          organism = synthetic construct
SEQUENCE: 178
aggaatgggg gccagaggtt gtggcttcta g                            31

SEQ ID NO: 179            moltype = DNA   length = 31
FEATURE                   Location/Qualifiers
source                    1..31
                          mol_type = other DNA
                          organism = synthetic construct
```

-continued

```
SEQUENCE: 179
gttaggaagg gccagaggtt gtggcttcta g                                      31

SEQ ID NO: 180           moltype = DNA   length = 31
FEATURE                  Location/Qualifiers
source                   1..31
                         mol_type = other DNA
                         organism = synthetic construct
SEQUENCE: 180
cgttgagggg gccagaggtt gtggcttcta g                                      31

SEQ ID NO: 181           moltype = DNA   length = 31
FEATURE                  Location/Qualifiers
source                   1..31
                         mol_type = other DNA
                         organism = synthetic construct
SEQUENCE: 181
ctcccaaagg gccagaggtt gtggcttcta g                                      31

SEQ ID NO: 182           moltype = DNA   length = 31
FEATURE                  Location/Qualifiers
source                   1..31
                         mol_type = other DNA
                         organism = synthetic construct
SEQUENCE: 182
gacatttcgg gccagaggtt gtggcttcta g                                      31

SEQ ID NO: 183           moltype = DNA   length = 31
FEATURE                  Location/Qualifiers
source                   1..31
                         mol_type = other DNA
                         organism = synthetic construct
SEQUENCE: 183
tgagagatgg gccagaggtt gtggcttcta g                                      31

SEQ ID NO: 184           moltype = DNA   length = 29
FEATURE                  Location/Qualifiers
source                   1..29
                         mol_type = other DNA
                         organism = synthetic construct
SEQUENCE: 184
tatccagtgc tgactgcagg agcatcagc                                         29

SEQ ID NO: 185           moltype = DNA   length = 32
FEATURE                  Location/Qualifiers
source                   1..32
                         mol_type = other DNA
                         organism = synthetic construct
SEQUENCE: 185
gtggttccac agaagggaaa tgcatcttgc ac                                     32

SEQ ID NO: 186           moltype = DNA   length = 31
FEATURE                  Location/Qualifiers
source                   1..31
                         mol_type = other DNA
                         organism = synthetic construct
SEQUENCE: 186
cgaacttaca gaagggaaat gcatcttgca c                                      31

SEQ ID NO: 187           moltype = DNA   length = 32
FEATURE                  Location/Qualifiers
source                   1..32
                         mol_type = other DNA
                         organism = synthetic construct
SEQUENCE: 187
aggaatggac agaagggaaa tgcatcttgc ac                                     32

SEQ ID NO: 188           moltype = DNA   length = 32
FEATURE                  Location/Qualifiers
source                   1..32
                         mol_type = other DNA
                         organism = synthetic construct
SEQUENCE: 188
gttaggaaac agaagggaaa tgcatcttgc ac                                     32

SEQ ID NO: 189           moltype = DNA   length = 32
FEATURE                  Location/Qualifiers
source                   1..32
                         mol_type = other DNA
```

```
                             organism = synthetic construct
SEQUENCE: 189
cgttgaggac agaagggaaa tgcatcttgc ac                                      32

SEQ ID NO: 190            moltype = DNA   length = 32
FEATURE                   Location/Qualifiers
source                    1..32
                          mol_type = other DNA
                          organism = synthetic construct
SEQUENCE: 190
ctcccaaaac agaagggaaa tgcatcttgc ac                                      32

SEQ ID NO: 191            moltype = DNA   length = 32
FEATURE                   Location/Qualifiers
source                    1..32
                          mol_type = other DNA
                          organism = synthetic construct
SEQUENCE: 191
gacatttcac agaagggaaa tgcatcttgc ac                                      32

SEQ ID NO: 192            moltype = DNA   length = 32
FEATURE                   Location/Qualifiers
source                    1..32
                          mol_type = other DNA
                          organism = synthetic construct
SEQUENCE: 192
tgagagatac agaagggaaa tgcatcttgc ac                                      32

SEQ ID NO: 193            moltype = DNA   length = 30
FEATURE                   Location/Qualifiers
source                    1..30
                          mol_type = other DNA
                          organism = synthetic construct
SEQUENCE: 193
tatccagtag gcccattcct cttcttgtgc                                         30

SEQ ID NO: 194            moltype = DNA   length = 30
FEATURE                   Location/Qualifiers
source                    1..30
                          mol_type = other DNA
                          organism = synthetic construct
SEQUENCE: 194
atgcacctag gcccattcct cttcttgtgc                                         30

SEQ ID NO: 195            moltype = DNA   length = 30
FEATURE                   Location/Qualifiers
source                    1..30
                          mol_type = other DNA
                          organism = synthetic construct
SEQUENCE: 195
cagttccaag gcccattcct cttcttgtgc                                         30

SEQ ID NO: 196            moltype = DNA   length = 30
FEATURE                   Location/Qualifiers
source                    1..30
                          mol_type = other DNA
                          organism = synthetic construct
SEQUENCE: 196
tctcgcctag gcccattcct cttcttgtgc                                         30

SEQ ID NO: 197            moltype = DNA   length = 30
FEATURE                   Location/Qualifiers
source                    1..30
                          mol_type = other DNA
                          organism = synthetic construct
SEQUENCE: 197
gtggttccca atcccgtgag gtgctaatgc                                         30

SEQ ID NO: 198            moltype = DNA   length = 29
FEATURE                   Location/Qualifiers
source                    1..29
                          mol_type = other DNA
                          organism = synthetic construct
SEQUENCE: 198
cgaacttcaa tcccgtgagg tgctaatgc                                          29

SEQ ID NO: 199            moltype = DNA   length = 30
FEATURE                   Location/Qualifiers
source                    1..30
```

-continued

```
                        mol_type = other DNA
                        organism = synthetic construct
SEQUENCE: 199
aggaatggca atcccgtgag gtgctaatgc                                      30

SEQ ID NO: 200          moltype = DNA   length = 30
FEATURE                 Location/Qualifiers
source                  1..30
                        mol_type = other DNA
                        organism = synthetic construct
SEQUENCE: 200
gttaggaaca atcccgtgag gtgctaatgc                                      30

SEQ ID NO: 201          moltype = DNA   length = 30
FEATURE                 Location/Qualifiers
source                  1..30
                        mol_type = other DNA
                        organism = synthetic construct
SEQUENCE: 201
cgttgaggca atcccgtgag gtgctaatgc                                      30

SEQ ID NO: 202          moltype = DNA   length = 30
FEATURE                 Location/Qualifiers
source                  1..30
                        mol_type = other DNA
                        organism = synthetic construct
SEQUENCE: 202
ctcccaaaca atcccgtgag gtgctaatgc                                      30

SEQ ID NO: 203          moltype = DNA   length = 30
FEATURE                 Location/Qualifiers
source                  1..30
                        mol_type = other DNA
                        organism = synthetic construct
SEQUENCE: 203
gacatttcca atcccgtgag gtgctaatgc                                      30

SEQ ID NO: 204          moltype = DNA   length = 30
FEATURE                 Location/Qualifiers
source                  1..30
                        mol_type = other DNA
                        organism = synthetic construct
SEQUENCE: 204
tgagagatca atcccgtgag gtgctaatgc                                      30

SEQ ID NO: 205          moltype = DNA   length = 23
FEATURE                 Location/Qualifiers
source                  1..23
                        mol_type = other DNA
                        organism = synthetic construct
SEQUENCE: 205
ctgctcaggc atctgcattt ccc                                             23

SEQ ID NO: 206          moltype = DNA   length = 17
FEATURE                 Location/Qualifiers
source                  1..17
                        mol_type = other DNA
                        organism = synthetic construct
SEQUENCE: 206
atgcctcgat ggtgaag                                                    17

SEQ ID NO: 207          moltype = DNA   length = 22
FEATURE                 Location/Qualifiers
source                  1..22
                        mol_type = other DNA
                        organism = synthetic construct
SEQUENCE: 207
ggcaaacatt ctgcttacta tt                                              22

SEQ ID NO: 208          moltype = DNA   length = 25
FEATURE                 Location/Qualifiers
source                  1..25
                        mol_type = other DNA
                        organism = synthetic construct
SEQUENCE: 208
cctcgctgga ctggtatttg tgtct                                           25

SEQ ID NO: 209          moltype = DNA   length = 19
FEATURE                 Location/Qualifiers
```

-continued

```
source                  1..19
                        mol_type = other DNA
                        organism = synthetic construct
SEQUENCE: 209
gacaggatgg cttcccttc                                              19

SEQ ID NO: 210          moltype = DNA   length = 21
FEATURE                 Location/Qualifiers
source                  1..21
                        mol_type = other DNA
                        organism = synthetic construct
SEQUENCE: 210
gtctaactgc catgtctgga t                                          21

SEQ ID NO: 211          moltype = DNA   length = 24
FEATURE                 Location/Qualifiers
source                  1..24
                        mol_type = other DNA
                        organism = synthetic construct
SEQUENCE: 211
accttagtga tgcccagttg accc                                       24

SEQ ID NO: 212          moltype = DNA   length = 21
FEATURE                 Location/Qualifiers
source                  1..21
                        mol_type = other DNA
                        organism = synthetic construct
SEQUENCE: 212
ccacaactag aatgcagtga a                                          21

SEQ ID NO: 213          moltype = DNA   length = 19
FEATURE                 Location/Qualifiers
source                  1..19
                        mol_type = other DNA
                        organism = synthetic construct
SEQUENCE: 213
gaatcacggg catcttcag                                             19

SEQ ID NO: 214          moltype = DNA   length = 19
FEATURE                 Location/Qualifiers
source                  1..19
                        mol_type = other DNA
                        organism = synthetic construct
SEQUENCE: 214
ctgcccgctc acaccagac                                             19

SEQ ID NO: 215          moltype = DNA   length = 16
FEATURE                 Location/Qualifiers
source                  1..16
                        mol_type = other DNA
                        organism = synthetic construct
SEQUENCE: 215
agcacctcct gaggtc                                                16

SEQ ID NO: 216          moltype = DNA   length = 16
FEATURE                 Location/Qualifiers
source                  1..16
                        mol_type = other DNA
                        organism = synthetic construct
SEQUENCE: 216
cacaccaggc tgagtg                                                16

SEQ ID NO: 217          moltype = DNA   length = 20
FEATURE                 Location/Qualifiers
source                  1..20
                        mol_type = other DNA
                        organism = synthetic construct
SEQUENCE: 217
tggacaaacc acaactagaa                                            20

SEQ ID NO: 218          moltype = DNA   length = 19
FEATURE                 Location/Qualifiers
source                  1..19
                        mol_type = other DNA
                        organism = synthetic construct
SEQUENCE: 218
agcctggcta aatgaagag                                             19

SEQ ID NO: 219          moltype = DNA   length = 24
```

-continued

```
FEATURE                 Location/Qualifiers
source                  1..24
                        mol_type = other DNA
                        organism = synthetic construct
SEQUENCE: 219
agcaagttga cgtggagcaa tctg                                              24

SEQ ID NO: 220          moltype = DNA   length = 20
FEATURE                 Location/Qualifiers
source                  1..20
                        mol_type = other DNA
                        organism = synthetic construct
SEQUENCE: 220
tggacaaacc acaactagaa                                                   20

SEQ ID NO: 221          moltype = DNA   length = 19
FEATURE                 Location/Qualifiers
source                  1..19
                        mol_type = other DNA
                        organism = synthetic construct
SEQUENCE: 221
ctcccaagct gttccttat                                                    19

SEQ ID NO: 222          moltype = DNA   length = 23
FEATURE                 Location/Qualifiers
source                  1..23
                        mol_type = other DNA
                        organism = synthetic construct
SEQUENCE: 222
agggtgctgc ctctgataga agg                                               23

SEQ ID NO: 223          moltype = DNA   length = 20
FEATURE                 Location/Qualifiers
source                  1..20
                        mol_type = other DNA
                        organism = synthetic construct
SEQUENCE: 223
tggacaaacc acaactagaa                                                   20

SEQ ID NO: 224          moltype = DNA   length = 20
FEATURE                 Location/Qualifiers
source                  1..20
                        mol_type = other DNA
                        organism = synthetic construct
SEQUENCE: 224
ccacagtgat ccttctactc                                                   20

SEQ ID NO: 225          moltype = DNA   length = 24
FEATURE                 Location/Qualifiers
source                  1..24
                        mol_type = other DNA
                        organism = synthetic construct
SEQUENCE: 225
tctgtgaaga cggcaggttc tacc                                              24

SEQ ID NO: 226          moltype = DNA   length = 20
FEATURE                 Location/Qualifiers
source                  1..20
                        mol_type = other DNA
                        organism = synthetic construct
SEQUENCE: 226
tggacaaacc acaactagaa                                                   20

SEQ ID NO: 227          moltype = DNA   length = 21
FEATURE                 Location/Qualifiers
source                  1..21
                        mol_type = other DNA
                        organism = synthetic construct
SEQUENCE: 227
cgtgaggtgc taatgctaat a                                                 21

SEQ ID NO: 228          moltype = DNA   length = 26
FEATURE                 Location/Qualifiers
source                  1..26
                        mol_type = other DNA
                        organism = synthetic construct
SEQUENCE: 228
agctgaccta atctctctgg ctttgg                                            26
```

-continued

```
SEQ ID NO: 229          moltype = DNA   length = 20
FEATURE                 Location/Qualifiers
source                  1..20
                        mol_type = other DNA
                        organism = synthetic construct
SEQUENCE: 229
tggacaaacc acaactagaa                                                    20

SEQ ID NO: 230          moltype = DNA   length = 18
FEATURE                 Location/Qualifiers
source                  1..18
                        mol_type = other DNA
                        organism = synthetic construct
SEQUENCE: 230
ctgcaagaca gagatggg                                                      18

SEQ ID NO: 231          moltype = DNA   length = 23
FEATURE                 Location/Qualifiers
source                  1..23
                        mol_type = other DNA
                        organism = synthetic construct
SEQUENCE: 231
agtcatcatg tgccttgact cgg                                                23

SEQ ID NO: 232          moltype = DNA   length = 20
FEATURE                 Location/Qualifiers
source                  1..20
                        mol_type = other DNA
                        organism = synthetic construct
SEQUENCE: 232
gagagaacgc accactttac                                                    20

SEQ ID NO: 233          moltype = DNA   length = 19
FEATURE                 Location/Qualifiers
source                  1..19
                        mol_type = other DNA
                        organism = synthetic construct
SEQUENCE: 233
agcctggcta aatgaagag                                                     19

SEQ ID NO: 234          moltype = DNA   length = 24
FEATURE                 Location/Qualifiers
source                  1..24
                        mol_type = other DNA
                        organism = synthetic construct
SEQUENCE: 234
agcaagttga cgtggagcaa tctg                                               24

SEQ ID NO: 235          moltype = DNA   length = 20
FEATURE                 Location/Qualifiers
source                  1..20
                        mol_type = other DNA
                        organism = synthetic construct
SEQUENCE: 235
gagagaacgc accactttac                                                    20

SEQ ID NO: 236          moltype = DNA   length = 19
FEATURE                 Location/Qualifiers
source                  1..19
                        mol_type = other DNA
                        organism = synthetic construct
SEQUENCE: 236
ctcccaagct gttccttat                                                     19

SEQ ID NO: 237          moltype = DNA   length = 23
FEATURE                 Location/Qualifiers
source                  1..23
                        mol_type = other DNA
                        organism = synthetic construct
SEQUENCE: 237
agggtgctgc ctctgataga agg                                                23

SEQ ID NO: 238          moltype = DNA   length = 20
FEATURE                 Location/Qualifiers
source                  1..20
                        mol_type = other DNA
                        organism = synthetic construct
SEQUENCE: 238
gagagaacgc accactttac                                                    20
```

-continued

```
SEQ ID NO: 239          moltype = DNA   length = 20
FEATURE                 Location/Qualifiers
source                  1..20
                        mol_type = other DNA
                        organism = synthetic construct
SEQUENCE: 239
ccacagtgat ccttctactc                                               20

SEQ ID NO: 240          moltype = DNA   length = 24
FEATURE                 Location/Qualifiers
source                  1..24
                        mol_type = other DNA
                        organism = synthetic construct
SEQUENCE: 240
tctgtgaaga cggcaggttc tacc                                          24

SEQ ID NO: 241          moltype = DNA   length = 20
FEATURE                 Location/Qualifiers
source                  1..20
                        mol_type = other DNA
                        organism = synthetic construct
SEQUENCE: 241
gagagaacgc accactttac                                               20

SEQ ID NO: 242          moltype = DNA   length = 21
FEATURE                 Location/Qualifiers
source                  1..21
                        mol_type = other DNA
                        organism = synthetic construct
SEQUENCE: 242
cgtgaggtgc taatgctaat a                                             21

SEQ ID NO: 243          moltype = DNA   length = 26
FEATURE                 Location/Qualifiers
source                  1..26
                        mol_type = other DNA
                        organism = synthetic construct
SEQUENCE: 243
agctgaccta atctctctgg ctttgg                                        26

SEQ ID NO: 244          moltype = DNA   length = 20
FEATURE                 Location/Qualifiers
source                  1..20
                        mol_type = other DNA
                        organism = synthetic construct
SEQUENCE: 244
gagagaacgc accactttac                                               20

SEQ ID NO: 245          moltype = DNA   length = 18
FEATURE                 Location/Qualifiers
source                  1..18
                        mol_type = other DNA
                        organism = synthetic construct
SEQUENCE: 245
ctgcaagaca gagatggg                                                 18

SEQ ID NO: 246          moltype = DNA   length = 23
FEATURE                 Location/Qualifiers
source                  1..23
                        mol_type = other DNA
                        organism = synthetic construct
SEQUENCE: 246
agtcatcatg tgccttgact cgg                                           23

SEQ ID NO: 247          moltype = DNA   length = 20
FEATURE                 Location/Qualifiers
source                  1..20
                        mol_type = other DNA
                        organism = synthetic construct
SEQUENCE: 247
ctgtttctct tgggtctcag                                               20

SEQ ID NO: 248          moltype = DNA   length = 21
FEATURE                 Location/Qualifiers
source                  1..21
                        mol_type = other DNA
                        organism = synthetic construct
SEQUENCE: 248
```

-continued

```
gggacagaag tcaaaggtta t                                               21

SEQ ID NO: 249           moltype = DNA   length = 22
FEATURE                  Location/Qualifiers
source                   1..22
                         mol_type = other DNA
                         organism = synthetic construct
SEQUENCE: 249
aacagagagg ttgagcaact gt                                              22

SEQ ID NO: 250           moltype = DNA   length = 20
FEATURE                  Location/Qualifiers
source                   1..20
                         mol_type = other DNA
                         organism = synthetic construct
SEQUENCE: 250
tgaagtcatt taccccaggc                                                 20

SEQ ID NO: 251           moltype = DNA   length = 20
FEATURE                  Location/Qualifiers
source                   1..20
                         mol_type = other DNA
                         organism = synthetic construct
SEQUENCE: 251
ctcacaccat ttctacccgg                                                 20

SEQ ID NO: 252           moltype = DNA   length = 24
FEATURE                  Location/Qualifiers
source                   1..24
                         mol_type = other DNA
                         organism = synthetic construct
SEQUENCE: 252
aataaaccca agtgtgacca ggcc                                            24

SEQ ID NO: 253           moltype = DNA   length = 18
FEATURE                  Location/Qualifiers
source                   1..18
                         mol_type = other DNA
                         organism = synthetic construct
SEQUENCE: 253
gcgagactct gtctcaaa                                                   18

SEQ ID NO: 254           moltype = DNA   length = 18
FEATURE                  Location/Qualifiers
source                   1..18
                         mol_type = other DNA
                         organism = synthetic construct
SEQUENCE: 254
ggccatcact atccactt                                                   18

SEQ ID NO: 255           moltype = DNA   length = 17
FEATURE                  Location/Qualifiers
source                   1..17
                         mol_type = other DNA
                         organism = synthetic construct
SEQUENCE: 255
tccccagttg tgcaaag                                                    17

SEQ ID NO: 256           moltype = DNA   length = 17
FEATURE                  Location/Qualifiers
source                   1..17
                         mol_type = other DNA
                         organism = synthetic construct
SEQUENCE: 256
caggagcatc agcctat                                                    17

SEQ ID NO: 257           moltype = DNA   length = 18
FEATURE                  Location/Qualifiers
source                   1..18
                         mol_type = other DNA
                         organism = synthetic construct
SEQUENCE: 257
atggcaacag ctagagag                                                   18

SEQ ID NO: 258           moltype = DNA   length = 24
FEATURE                  Location/Qualifiers
source                   1..24
                         mol_type = other DNA
                         organism = synthetic construct
```

-continued

```
SEQUENCE: 258
atccttgtga gtgttgggtg ggaa                                               24

SEQ ID NO: 259        moltype = DNA   length = 20
FEATURE               Location/Qualifiers
source                1..20
                      mol_type = other DNA
                      organism = synthetic construct
SEQUENCE: 259
ggcccgattc ctggataatc                                                    20

SEQ ID NO: 260        moltype = DNA   length = 20
FEATURE               Location/Qualifiers
source                1..20
                      mol_type = other DNA
                      organism = synthetic construct
SEQUENCE: 260
gccagagaga ttaggtcagc                                                    20

SEQ ID NO: 261        moltype = DNA   length = 27
FEATURE               Location/Qualifiers
source                1..27
                      mol_type = other DNA
                      organism = synthetic construct
SEQUENCE: 261
ccagaatcct acatctaggt cctgcac                                            27

SEQ ID NO: 262        moltype = DNA   length = 18
FEATURE               Location/Qualifiers
source                1..18
                      mol_type = other DNA
                      organism = synthetic construct
SEQUENCE: 262
ctccaaggcc gtgcataa                                                      18

SEQ ID NO: 263        moltype = DNA   length = 20
FEATURE               Location/Qualifiers
source                1..20
                      mol_type = other DNA
                      organism = synthetic construct
SEQUENCE: 263
agacatgggt atggcctcta                                                    20

SEQ ID NO: 264        moltype = DNA   length = 20
FEATURE               Location/Qualifiers
source                1..20
                      mol_type = other DNA
                      organism = synthetic construct
SEQUENCE: 264
ctgaccatcg acgagaaagg                                                    20

SEQ ID NO: 265        moltype = DNA   length = 20
FEATURE               Location/Qualifiers
source                1..20
                      mol_type = other DNA
                      organism = synthetic construct
SEQUENCE: 265
ctgaccatcg acaagaaagg                                                    20
```

GENE EDITING METHODS FOR TREATING ALPHA-1 ANTITRYPSIN (AAT) DEFICIENCY

CROSS-REFERENCE TO RELATED APPLICATIONS

This application is a national stage filing under 35 U.S.C. 371 of International Application No. PCT/US2022/078387, filed Oct. 19, 2022, which was published by the International Bureau in English on Apr. 27, 2023, and which claims the benefit under 35 U.S.C. § 119(e) of the earlier filing dates of U.S. Provisional Application No. 63/257,528, filed Oct. 19, 2021; U.S. Provisional Application No. 63/257,506, filed Oct. 19, 2021; U.S. Provisional Application No. 63/257,518, filed Oct. 19, 2021; U.S. Provisional Application No. 63/257,513, filed Oct. 19, 2021; and U.S. Provisional Application No. 63/257,502, filed Oct. 19, 2021, the contents of which are incorporated by reference herein in their entirety.

REFERENCE TO AN ELECTRONIC SEQUENCE LISTING

The contents of the electronic sequence listing (P109070070WO00-SEQ-NTJ.xml; Size: 294,341 bytes; and Date of Creation: Oct. 19, 2022) are herein incorporated by reference in their entirety.

FIELD OF THE INVENTION

The invention relates to the field of molecular biology and recombinant nucleic acid technology. In particular, the embodiments of the present disclosure described herein relate to engineered meganucleases having specificity for a recognition sequence within a serpin family A member 1 (SERPINA1) gene encoding alpha-1 antitrypsin (AAT). Such engineered meganucleases are useful in methods for treating AAT deficiency by gene editing to restore AAT function.

BACKGROUND OF THE INVENTION

AAT deficiency is an autosomal codominant disorder caused by a mutation in the SERPINA1 gene, which encodes the AAT protein. Mutations in the coding sequence of the SERPINA1 gene result in expression of a mutant AAT protein with reduced or abrogated function. AAT is produced in the liver, and transported to the lungs, where it inhibits the activities of serine proteases (serpins), such as neutrophil elastase. Uncontrolled neutrophil elastase activity degrades connective tissue in the lungs. Additionally, mutated AAT is less able to be exported from the liver, causing buildup of AAT aggregates in the liver and subsequent liver toxicity. Current therapies for AAT deficiency are limited to liver transplant and/or regular injections of a plasma containing elevated amounts of functional AAT.

AAT deficiency may be caused by one of multiple mutations in the SERPINA1 gene. The most common mutation in severe disease is the Pi*Z mutation, a single nucleotide polymorphism that results in the substitution of glutamate with lysine at residue 342 (Glu342Lys or E342K). A second common mutation is the Pi*S mutation, which results in the substitution of valine with glutamic acid at residue 264 (V264E).

SUMMARY OF THE INVENTION

The present disclosure involves the use of site-specific, rare-cutting nucleases that are engineered to recognize DNA sequences within the SERPINA1 genetic sequence. In a particular embodiment of the disclosure, the DNA break-inducing agent is an engineered homing endonuclease (also called a "meganuclease"). Homing endonucleases are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38:49-95). Homing endonucleases are commonly grouped into four families: (1) the LAGLIDADG (SEQ ID NO: 2) family, (2) the GIY-YIG family, (3) the His-Cys box family and (4) the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001), *Nucleic Acids Res.* 29 (18): 3757-3774). The LAGLIDADG homing endonucleases with a single copy of the LAGLIDADG motif form homodimers, whereas members with two copies of the LAGLIDADG motif are found as monomers.

I-CreI (SEQ ID NO: 1) is a member of the LAGLIDADG family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342:31-41; Chames et al. (2005), *Nucleic Acids Res.* 33: e178; Seligman et al. (2002), *Nucleic Acids Res.* 30:3870-9, Arnould et al. (2006), *J. Mol. Biol.* 355:443-58). Methods for rationally-designing mono-LAGLIDADG homing endonucleases were described which are capable of comprehensively redesigning I-CreI and other homing endonucleases to target widely-divergent DNA sites, including sites in mammalian, yeast, plant, bacterial, and viral genomes (WO 2007/047859).

As first described in International Publication No. WO 2009/059195, I-CreI and its engineered derivatives are normally dimeric but can be fused into a single polypeptide using a short peptide linker that joins the C-terminus of a first subunit to the N-terminus of a second subunit (Li, et al. (2009) *Nucleic Acids Res.* 37:1650-62; Grizot, et al. (2009) *Nucleic Acids Res.* 37:5405-19). Thus, a functional "single-chain" meganuclease can be expressed from a single transcript. This, coupled with the extremely low frequency of off-target cutting observed with engineered meganucleases makes them the preferred endonuclease for the present disclosure.

The present disclosure provides novel engineered meganucleases that bind and cleave a recognition sequence within the SERPINA1 gene, specifically the AAT 35-36 recognition sequence set forth in SEQ ID NO: 9, the AAT 37-38 recognition sequence set forth in SEQ ID NO: 11, the AAT 41-42 recognition sequence set forth in SEQ ID NO: 13, or the AAT 43-44 recognition sequence set forth in SEQ ID NO: 15, generating a modified SERPINA1 gene that no longer encodes a full-length mutant AAT protein. Further, the disclosed engineered meganucleases are effective at generating a modified SERPINA1 gene by enabling the introduction of a donor sequence into the cleavage site, for example by homologous recombination. Transcription of the modified SERPINA1 gene which includes the donor sequence results in a pre-mRNA that is spliced during processing to form an mRNA encoding a full-length, functional (e.g., wild-type) AAT protein, while excluding mutations such as the Pi*Z and Pi*S mutations. By reducing expression of the mutant, dysfunctional AAT protein and promoting the expression of a functional (e.g., wild-type) AAT protein, this gene editing approach alleviates the progression of AAT deficiency. Furthermore, the approach described herein allows for a one-step knockout of endogenous mutant AAT protein expression and knock-in of a donor template that allows for expression of a functional (e.g., wild-type) AAT protein. Accordingly, the present disclosure fulfills a need in the art for gene therapy approaches to treat AAT deficiency.

Accordingly, in one aspect, the present disclosure provides an engineered meganuclease that binds and cleaves a recognition sequence within a SERPINA1 gene. In some embodiments, the engineered meganuclease binds and cleaves a recognition sequence comprising SEQ ID NO: 9 (i.e., AAT 35-36) within a SERPINA1 gene. In some embodiments, the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 17-22. In some embodiments, the HVR1 region comprises residues corresponding to residues 24, 26, 28, 30, 32, 33, 38, 40, 42, 44, 46, 68, 70, 75, and 77 of any one of SEQ ID NOs: 17-22. In some embodiments, the HVR1 region comprises a residue corresponding to residue 41 of SEQ ID NO: 22. In some embodiments, the HVR1 region comprises a residue corresponding to residue 48 of SEQ ID NO: 17. In some embodiments, the HVR1 region comprises a residue corresponding to residue 50 of any one of SEQ ID NOs: 17-22. In some embodiments, the HVR1 region comprises a residue corresponding to residue 72 of any one of SEQ ID NOs: 17-22. In some embodiments, the HVR1 region comprises a residue corresponding to residue 73 of any one of SEQ ID NOs: 17-22. In some embodiments, the HVR1 region comprises Y, R. K, or D at a residue corresponding to residue 66 of any one of SEQ ID NOs: 17-22. In some embodiments, the HVR1 region comprises residues 24-79 of any one of SEQ ID NOs: 17-22.

In some embodiments, the first subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 7-153 of any one of SEQ ID NOs: 17-22. In some embodiments, the first subunit comprises a residue corresponding to residue 19 of any one of SEQ ID NOs: 17-22 In some embodiments, the first subunit comprises a residue corresponding to residue 80 of SEQ ID NO: 18. In some embodiments, the first subunit comprises G, S, or A at a residue corresponding to residue 19 of any one of SEQ ID NOs: 17-22. In some embodiments, the first subunit comprises E, Q, or K at a residue corresponding to residue 80 of any one of SEQ ID NOs: 17-22. In some embodiments, the first subunit comprises residues 7-153 of any one of SEQ ID NOs: 17-22.

In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 17-22. In some embodiments, the HVR2 region comprises residues corresponding to residues 215, 217, 219, 221, 223, 224, 229, 231, 233, 235, 237, 259, 261, 266, and 268 of any one of SEQ ID NOs: 17-22. In some embodiments, the HVR2 region comprises a residue corresponding to residue 264 of SEQ ID NO: 21 or 22. In some embodiments, the HVR2 region comprises Y, R, K, or D at a residue corresponding to residue 257 of any one of SEQ ID NOs: 17-22. In some embodiments, the HVR2 region comprises residues 215-270 of any one of SEQ ID NOs: 17-22.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 198-344 of any one of SEQ ID NOs: 17-22. In some embodiments, the second subunit comprises a residue corresponding to residue 271 of SEQ ID NOs: 17, 18, 20, or 22. In some embodiments, the second subunit comprises a residue corresponding to residue 330 of SEQ ID NOs: 17, 18, 20, 21, or 22. In some embodiments, the second subunit comprises G, S, or A at a residue corresponding to residue 210 of any one of SEQ ID NOs: 17-22. In some embodiments, the second subunit comprises E, Q, or K at a residue corresponding to residue 271 of any one of SEQ ID NOs: 17-22. In some embodiments, the second subunit comprises residues 198-344 of any one of SEQ ID NOs: 17-22.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to any one of SEQ ID NOs: 17-22. In some embodiments, the engineered meganuclease comprises an amino acid sequence of any one of SEQ ID NOs: 17-22.

In some embodiments, the engineered meganuclease is encoded by a nucleic sequence having at least at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of any one of SEQ ID NOs: 35-40. In some embodiments, the engineered meganuclease is encoded by a nucleic acid sequence of any one of SEQ ID NOs: 35-40. In each of the embodiments above, the engineered meganuclease can comprise a nuclear localization signal.

In some embodiments, the nuclear localization signal is at the N-terminus of the engineered meganuclease. In some embodiments, the nuclear localization signal comprises an amino acid sequence having at least 80% or at least 90% sequence identity to SEQ ID NO: 128. In some embodiments, the nuclear localization signal comprises SEQ ID NO: 128.

In another aspect, the disclosure provides an engineered meganuclease that binds and cleaves a recognition sequence comprising SEQ ID NO: 11 (i.e., AAT 37-38) within a SERPINA1 gene, wherein the engineered meganuclease comprises a first subunit and a second subunit, wherein the first subunit binds to a first recognition half-site of the recognition sequence and comprises an HVR1 region, and wherein the second subunit binds to a second recognition half-site of the recognition sequence and comprises an HVR2 region.

In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 41-46. In some embodiments, the HVR1 region comprises residues corresponding to residues 24, 26, 28, 30, 32, 33, 38, 40, 42, 44, 46, 68, 70, 75, and 77 of any one of SEQ ID NOs: 41-46. In some embodiments, wherein the HVR1 region comprises a residue corresponding to residue 50 of any one of SEQ ID NOs: 41-46. In some embodiments, the HVR1 region comprises a residue corresponding to residue 71 of SEQ ID NO: 46. In some embodiments, the HVR1 region comprises a residue corresponding to residue 72 of any one of SEQ ID NOs: 41 and 43-46. In some embodiments, the HVR1 region comprises a residue corresponding to residue 73 of any one of SEQ ID NOs: 41 and 43-46. In some embodiments, the HVR1 region comprises Y, R, K, or D at a residue corresponding to residue 66 of any one of SEQ ID NOs: 41-46. In some embodiments, the HVR1 region comprises residues 24-79 of any one of SEQ ID NOs: 41-46.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of any one of SEQ ID NOs: 41-46. In some embodiments, the first subunit comprises a residue corresponding to residue 19 of any one of SEQ ID NOs: 41-46. In some embodiments, the first subunit comprises a residue corresponding to residue 80 of SEQ ID NO: 41. In some embodiments, the first subunit comprises a residue corresponding to residue 129 of SEQ ID NO: 42. In some embodiments, the first subunit comprises a residue corresponding to residue 140 of SEQ ID NO: 46. In some embodiments, the first subunit comprises G, S, or A at a residue corresponding to residue 19 of any one of SEQ ID NOs: 41-46. In some embodiments, the first subunit comprises E, Q, or K at a residue corresponding to residue 80 of any one of SEQ ID NOs: 41-46. In some embodiments, the first subunit comprises residues 7-153 of any one of SEQ ID NOs: 41-46.

In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 41-46. In some embodiments, the HVR2 region comprises residues corresponding to residues 215, 217, 219, 221, 223, 224, 229, 231, 233, 235, 237, 259, 261, 266, and 268 of any one of SEQ ID NOs: 41-46. In some embodiments, the HVR2 region comprises Y, R. K, or D at a residue corresponding to residue 257 of any one of SEQ ID NOs: 41-46. In some embodiments, the HVR2 region comprises residues 215-270 of any one of SEQ ID NOs: 41-46.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of any one of SEQ ID NOs: 41-46. In some embodiments, the second subunit comprises a residue corresponding to residue 271 of SEQ ID NOs: 41-45. In some embodiments, the second subunit comprises a residue corresponding to residue 330 of SEQ ID NO: 46. In some embodiments, the second subunit comprises G, S, or A at a residue corresponding to residue 210 of any one of SEQ ID NOs: 41-46. In some embodiments, the second subunit comprises E, Q, or K at a residue corresponding to residue 271 of any one of SEQ ID NOs: 41-46. In some embodiments, the second subunit comprises residues 198-344 of any one of SEQ ID NOs: 41-46.

In some embodiments, the engineered meganuclease is a single-chain meganuclease comprising a linker and wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to any one of SEQ ID NOs: 41-46. In some embodiments, the engineered meganuclease comprises an amino acid sequence of any one of SEQ ID NOs: 41-46.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of any one of SEQ ID NOs: 59-64. In some embodiments, the engineered meganuclease is encoded by a nucleic acid sequence of any one of SEQ ID NOs: 59-64.

In each of the embodiments above, the engineered meganuclease can comprise a nuclear localization signal. In some embodiments, the nuclear localization signal is at the N-terminus of the engineered meganuclease. In some embodiments, the nuclear localization signal comprises an amino acid sequence having at least 80% or at least 90% sequence identity to SEQ ID NO: 128. In some embodiments, the nuclear localization signal comprises SEQ ID NO: 128.

In another aspect, the disclosure provides an engineered meganuclease that binds and cleaves a recognition sequence comprising SEQ ID NO: 13 (i.e., AAT 41-42) within a SERPINA1 gene, wherein the engineered meganuclease comprises a first subunit and a second subunit, wherein the first subunit binds to a first recognition half-site of the recognition sequence and comprises an HVR1 region, and wherein the second subunit binds to a second recognition half-site of the recognition sequence and comprises an HVR2 region.

In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 65-71. In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 65-71. In some embodiments, the HVR1 region comprises a residue corresponding to residue 48 of any one of SEQ ID NOs: 65-71. In some embodiments, the HVR1 region comprises a residue corresponding to residue 50 of any one of SEQ ID NOs: 65-71. In some embodiments, the HVR1 region comprises a residue corresponding to residue 69 of SEQ ID NO: 71. In some embodiments, the HVR1 region comprises a residue corresponding to residue 72 of any one of SEQ ID NOs: 65 and 67-71. In some embodiments, the HVR1 region comprises Y, R, K, or D at a residue corresponding to residue 66 of any one of SEQ ID NOs: 65-71. In some embodiments, the HVR1 region comprises residues 24-79 of any one of SEQ ID NOs: 65-71.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of any one of SEQ ID NOs: 65-71. In some embodiments, the first subunit comprises a residue corresponding to residue 19 of any one of SEQ ID NOs: 65-71. In some embodiments, the first subunit comprises a residue corresponding to residue 80 of any one of SEQ ID NOs: 65-71. In some embodiments, the first subunit comprises G, S, or A at a residue corresponding to residue 19 of any one of SEQ ID NOs: 65-71. In some embodiments, the first subunit comprises E, Q, or K at a residue corresponding to residue 80 of any one of SEQ ID NOs: 65-71. In some embodiments, the first subunit comprises residues 7-153 of any one of SEQ ID NOs: 65-71.

In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 65-71. In some embodiments, the HVR2 region comprises residues corresponding to residues 215, 217, 219, 221, 223, 224, 229, 231, 233, 235, 237, 259, 261, 266, and 268 of any one of SEQ ID NOs: 65-71. In some embodiments, the HVR2 region comprises a residue corresponding to residue 239 of any one of SEQ ID NOs: 65 or 67-71. In some embodiments, the HVR2 region comprises a residue corresponding to residue 241 of any one of SEQ ID NOs: 65-71. In some embodiments, the HVR2 region comprises a residue corresponding to residue 263 of any one of SEQ ID NOS: 65-71. In some embodiments, the HVR2 region comprises a residue corresponding to residue 264 of any one of SEQ ID NOs: 65-71. In some embodiments, the HVR2 region comprises Y, R, K, or D at a residue corresponding to residue 257 of any one of SEQ ID NOs: 65-71. In some embodiments, the HVR2 region comprises residues 215-270 of any one of SEQ ID NOs: 65-71.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of any one of SEQ ID NOs: 65-71. In some embodiments, the second subunit comprises a residue corresponding to residue 271 of any one of SEQ ID NOs: 65-67 or 69-71. In some embodiments, the second subunit comprises a residue corresponding to residue 330 of SEQ ID NOs: 65, 66, or 71. In some embodiments, the second subunit comprises G, S, or A at a residue corresponding to residue 210 of any one of SEQ ID NOs: 65-71. In some embodiments, the second subunit comprises E, Q, or K at a residue corresponding to residue 271 of any one of SEQ ID NOs: 65-71. In some embodiments, the second subunit comprises residues 198-344 of any one of SEQ ID NOs: 65-71.

In some embodiments, the engineered meganuclease is a single-chain meganuclease comprising a linker and wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to any one of SEQ ID NOs: 65-71. In some embodiments, the engineered meganuclease comprises an amino acid sequence of any one of SEQ ID NOs: 65-71.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of any one of SEQ ID NOs: 86-92. In some embodiments, the engineered meganuclease is encoded by a nucleic acid sequence of any one of SEQ ID NOs: 86-92.

In each of the embodiments above, the engineered meganuclease can comprise a nuclear localization signal. In some embodiments, the nuclear localization signal is at the N-terminus of the engineered meganuclease. In some embodiments, the nuclear localization signal comprises an amino acid sequence having at least 80% or at least 90% sequence identity to SEQ ID NO: 128. In some embodiments, the nuclear localization signal comprises SEQ ID NO: 128.

In another aspect, the disclosure provides an engineered meganuclease that binds and cleaves a recognition sequence comprising SEQ ID NO: 15 (i.e., AAT 43-44) within a SERPINA1 gene, wherein the engineered meganuclease comprises a first subunit and a second subunit, wherein the first subunit binds to a first recognition half-site of the recognition sequence and comprises an HVR1 region, and wherein the second subunit binds to a second recognition half-site of the recognition sequence and comprises an HVR2 region.

In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 93-100. In some embodiments, the HVR1 region comprises residues corresponding to residues 24, 26, 28, 30, 32, 33, 38, 40, 42, 44, 46, 68, 70, 75, and 77 of any one of SEQ ID NOs: 93-100. In some embodiments, the HVR1 region comprises a residue corresponding to residue 48 of SEQ ID NO: 93. In some embodiments, the HVR1 region comprises a residue corresponding to residue 50 of any one of SEQ ID NOs: 93-100. In some embodiments, the HVR1 region comprises a residue corresponding to residue 72 of any one of SEQ ID NOs: 93-100. In some embodiments, the HVR1 region comprises a residue corresponding to residue 73 of any one of SEQ ID NOs: 93-100. In some embodiments, the HVR1 region comprises Y, R, K, or D at a residue corresponding to residue 66 of any one of SEQ ID NOs: 93-100. In some embodiments, the HVR1 region comprises residues 24-79 of any one of SEQ ID NOs: 93-100.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of any one of SEQ ID NOs: 93-100. In some embodiments, the first subunit comprises a residue corresponding to residue 19 of any one of SEQ ID NOs: 93-100. In some embodiments, the first subunit comprises a residue corresponding to residue 80 of any one of SEQ ID NOs: 94, 98, and 100. In some embodiments, the first subunit comprises a residue corresponding to residue 103 of SEQ ID NO: 97. In some embodiments, the first subunit comprises a residue corresponding to residue 139 of SEQ ID NO: 100. In some embodiments, the first subunit comprises G, S, or A at a residue corresponding to residue 19 of any one of SEQ ID NOs: 93-100. In some embodiments, the first subunit comprises E, Q. or K at a residue corresponding to residue 80 of any one of SEQ ID NOs: 93-100. In some embodiments, the first subunit comprises residues 7-153 of any one of SEQ ID NOs: 93-100.

In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 93-100. In some embodiments, the HVR2 region comprises residues corresponding to residues 215, 217, 219, 221, 223, 224, 229, 231, 233, 235, 237, 259, 261, 266, and 268 of any one of SEQ ID NOs: 93-100. In some embodiments, the HVR2 region comprises a residue corresponding to residue 236 of SEQ ID NO: 99 or 100. In some embodiments, the HVR2 region comprises a residue corresponding to residue 239 of any one of SEQ ID NOs: 94-100. In some embodiments, the HVR2 region comprises a residue corresponding to residue 241 of any one of SEQ ID NOs: 93-100. In some embodiments, the HVR2 region comprises a residue corresponding to residue 255 of SEQ ID NO: 94 or 95. In some embodiments, the HVR2 region comprises a residue corresponding to residue 263 of any one of SEQ ID NOs: 93-100. In some embodiments, the HVR2 region comprises a residue corresponding to residue 264 of any one of SEQ ID NOs: 93-100. In some embodiments, the HVR2 region comprises Y, R, K, or D at a residue corresponding to residue 257 of any one of SEQ ID NOs: 93-100. In some embodiments, the HVR2 region comprises residues 215-270 of any one of SEQ ID NOs: 93-100.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of any one of SEQ ID NOs: 93-100. In some embodiments, the second subunit comprises a residue corresponding to residue 271 of any one of SEQ ID NOs: 94, 97, 98, and 100. In some embodiments, the second subunit comprises a residue corresponding to residue 330 of any one of SEQ ID NOs: 94, 95, 98, and 99. In some embodiments, the second subunit comprises G, S, or A at a residue corresponding to residue 210 of any one of SEQ ID NOs: 93-100. In some embodiments, the second subunit comprises E, Q, or K at a residue corresponding to residue 271 of any one of SEQ ID NOs: 93-100. In some embodiments, the second subunit comprises residues 198-344 of any one of SEQ ID NOs: 93-100.

In some embodiments, the engineered meganuclease is a single-chain meganuclease comprising a linker and wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to any one of SEQ ID NOs: 93-100. In some embodiments, the engineered meganuclease comprises an amino acid sequence of any one of SEQ ID NOs: 93-100.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of any one of SEQ ID NOs: 117-124. In some embodiments, the engineered meganuclease is encoded by a nucleic acid sequence of any one of SEQ ID NOs: 117-124.

In each of the embodiments above, the engineered meganuclease can comprise a nuclear localization signal. In some embodiments, the nuclear localization signal is at the N-terminus of the engineered meganuclease. In some embodiments, the nuclear localization signal comprises an amino acid sequence having at least 80% or at least 90% sequence identity to SEQ ID NO: 128. In some embodiments, the nuclear localization signal comprises SEQ ID NO: 128.

In another aspect, the present disclosure provides a polynucleotide comprising a nucleic acid sequence encoding an engineered meganuclease described herein. In some embodiments, the polynucleotide is an mRNA.

In another aspect, the present disclosure provides a recombinant DNA construct comprising a polynucleotide comprising a nucleic acid sequence encoding an engineered meganuclease described herein. In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV. In some embodiments, the recombinant AAV has an AAV8 capsid. In some embodiments, the polynucleotide comprises a promoter operably linked to the nucleic acid sequence encoding the engineered meganuclease. In some embodiments, the promoter is a liver-specific promoter. In some embodiments, the liver-specific promoter is a TBG promoter, alpha-1 antitrypsin promoter, hybrid liver-specific promoter comprising a hepatic locus control region from an ApoE gene and an alpha-1 antitrypsin promoter, or apolipoprotein A-II promoter.

In another aspect, the present disclosure provides a recombinant virus comprising a polynucleotide comprising a nucleic acid sequence encoding an engineered meganuclease described herein. In some embodiments, the recombinant virus is a recombinant adenovirus, a recombinant lentivirus, a recombinant retrovirus, or a recombinant AAV. In some embodiments, the recombinant virus is a recombinant AAV. In some embodiments, the recombinant AAV has an AAV8 capsid. In some embodiments, the polynucleotide comprises a promoter operably linked to the nucleic acid sequence encoding the engineered meganuclease. In some embodiments, the promoter is a liver-specific promoter. In some embodiments, the liver-specific promoter is a TBG promoter, alpha-1 antitrypsin promoter, hybrid liver-specific promoter comprising a hepatic locus control region from an ApoE gene and an alpha-1 antitrypsin promoter, or apolipoprotein A-II promoter.

In another aspect, the present disclosure provides a lipid nanoparticle composition comprising lipid nanoparticles comprising a polynucleotide described herein (i.e., that encodes an engineered meganuclease described herein). In particular embodiments, the polynucleotide is an mRNA.

In another aspect, the present disclosure provides a pharmaceutical composition comprising a pharmaceutically acceptable carrier and an engineered meganuclease described herein.

In another aspect, the present disclosure provides a pharmaceutical composition comprising a pharmaceutically acceptable carrier and a polynucleotide described herein (i.e., that encodes an engineered meganuclease described herein).

In another aspect, the present disclosure provides a pharmaceutical composition comprising a pharmaceutically acceptable carrier and a recombinant DNA construct described herein (i.e., comprising a polynucleotide comprising a nucleic acid sequence that encodes an engineered meganuclease described herein).

In another aspect, the present disclosure provides a pharmaceutical composition comprising a pharmaceutically acceptable carrier and a recombinant virus described herein (i.e., comprising a polynucleotide comprising a nucleic acid sequence that encodes an engineered meganuclease described herein).

In another aspect, the present disclosure provides a pharmaceutical composition comprising a pharmaceutically acceptable carrier and a lipid nanoparticle composition described herein (i.e., comprising lipid nanoparticles comprising a polynucleotide comprising a nucleic acid sequence that encodes an engineered meganuclease described herein).

In another aspect, the present disclosure provides a method for producing a genetically-modified eukaryotic cell having a modified target sequence in a SERPINA1 gene of the genetically-modified eukaryotic cell, the method comprising: introducing into a eukaryotic cell a polynucleotide comprising a nucleic acid sequence encoding an engineered meganuclease described herein, wherein the engineered meganuclease is expressed in the eukaryotic cell, wherein the engineered meganuclease produces a cleavage site in the SERPINA1 gene at a recognition sequence comprising SEQ ID NO: 9, 11, 13, or 15 (by AAT 35-36, AAT 37-38, AAT 41-42, and AAT 43-44 meganucleases, respectively), and wherein the cleavage site is repaired by non-homologous end joining.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In some embodiments, the polynucleotide is an mRNA. In some embodiments, the polynucleotide is introduced into the eukaryotic cell by a lipid nanoparticle or by a recombinant virus. In some embodiments, the recombinant virus is a recombinant AAV.

In another aspect, the present disclosure provides a method for producing a genetically-modified eukaryotic cell having a modified target sequence in an SERPINA1 gene of the genetically-modified eukaryotic cell, the method comprising: introducing into a eukaryotic cell an engineered meganuclease described herein, wherein the engineered meganuclease produces a cleavage site in the SERPINA1 gene at a recognition sequence comprising SEQ ID NO: 9, 11, 13, or 15 (by AAT 35-36, AAT 37-38, AAT 41-42, and AAT 43-44 meganucleases, respectively), and wherein the cleavage site is repaired by non-homologous end joining.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In another aspect, the present disclosure provides a method for producing a genetically-modified eukaryotic cell comprising an exogenous sequence of interest inserted into a SERPINA1 gene of the genetically-modified eukaryotic cell, the method comprising introducing into a eukaryotic cell a first polynucleotide comprising a nucleic acid sequence encoding an engineered meganuclease described herein and a second polynucleotide comprising the sequence of interest, wherein the engineered meganuclease is expressed in the eukaryotic cell and produces a cleavage site in the SERPINA1 gene at a recognition sequence comprising SEQ ID NO: 9, 11, 13, or 15 (by AAT 35-36, AAT 37-38, AAT 41-42, and AAT 43-44 meganucleases, respectively), and wherein the sequence of interest is inserted into the SERPINA1 gene at the cleavage site.

In some embodiments, the first polynucleotide is introduced into the eukaryotic cell as an mRNA. In some embodiments, the second polynucleotide is introduced into the eukaryotic cell as a double-stranded DNA (dsDNA). In some embodiments, the first polynucleotide is introduced into the eukaryotic cell by a recombinant virus. In some embodiments, the second polynucleotide is introduced into the eukaryotic cell by a recombinant virus. In some embodiments, the recombinant virus is a recombinant AAV.

In some embodiments, the second polynucleotide further comprises nucleic acid sequences homologous to nucleic acid sequences flanking the cleavage site, and the sequence of interest is inserted at the cleavage site by homologous recombination.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In another aspect, the present disclosure provides a method for producing a genetically-modified eukaryotic cell comprising an exogenous sequence of interest inserted into a SERPINA1 gene of the genetically-modified eukaryotic cell, the method comprising introducing into a eukaryotic cell an engineered meganuclease described herein and a polynucleotide comprising the sequence of interest, wherein the engineered meganuclease produces a cleavage site in the SERPINA1 gene at a recognition sequence comprising SEQ ID NO: 9, 11, 13, or 15 (by AAT 35-36, AAT 37-38, AAT 41-42, and AAT 43-44 meganucleases, respectively), and wherein the sequence of interest is inserted into the SER-PINA1 gene at the cleavage site.

In some embodiments, the polynucleotide comprising the sequence of interest further comprises nucleic acid sequences homologous to nucleic acid sequences flanking the cleavage site, and the sequence of interest is inserted at the cleavage site by homologous recombination.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In some embodiments, the polynucleotide is introduced into the eukaryotic cell as a double-stranded DNA (dsDNA). In some embodiments, the polynucleotide is introduced into the eukaryotic cell by a recombinant virus. In some embodiments, the recombinant virus is a recombinant AAV.

In another aspect, the present disclosure provides a polynucleotide comprising a template nucleic acid, wherein the template nucleic acid comprises, from 5' to 3': (a) a splicing sequence comprising a splice acceptor sequence capable of pairing with an endogenous splice donor sequence that is positioned 3' downstream and adjacent to exon 1c in a SERPINA1 gene; (b) a donor nucleic acid sequence encoding an AAT protein encoded by exons 2, 3, 4, and 5 of a SERPINA1 gene; and (c) a termination sequence.

In some embodiments, the polynucleotide comprises a 5' homology arm and a 3' homology arm flanking the template nucleic acid, wherein the 5' homology arm and the 3' homology arm share homology to sequences flanking SEQ ID NO: 9, 11, 13, or 15.

In some embodiments, the polynucleotide does not comprise a promoter.

In some embodiments, the splicing sequence comprises a branch point. In some embodiments, the splicing sequence is a naturally-occurring splicing sequence (e.g., a naturally occurring intron). In some embodiments, the splicing sequence comprises an SV40 splicing sequence (e.g., intron), a CMV splicing sequence (e.g., intron), or a transferrin gene splicing sequence (e.g., intron). In some embodiments, the splicing sequence is a synthetic splicing sequence (e.g., a synthetic intron).

In some embodiments, the termination sequence comprises a stop codon. In some embodiments, the termination sequence comprises a poly A sequence. In some embodiments, the termination sequence comprises a stop codon and a poly A sequence.

In some embodiments, the AAT protein encoded by the donor nucleic acid is a wild-type AAT protein.

In some embodiments, the donor nucleic acid sequence comprises one or more exons of a wild-type SERPINA1 gene. In some embodiments, the donor nucleic acid sequence comprises exons of a wild-type SERPINA1 gene. In some embodiments, the donor nucleic acid sequence comprises one or more exons of a SERPINA1 gene that have been codon-modified but encodes a wild-type AAT protein.

In some embodiments, the donor nucleic acid sequence comprises exons 2, 3, 4, and 5 of a SERPINA1 gene, or codon-modified variants of one or more of exons 2, 3, 4, and 5 of a SERPINA1 gene.

In some embodiments, the donor nucleic acid sequence does not comprise one or more of introns 2, 3, and 4 of a SERPINA1 gene. In some embodiments, the donor nucleic acid sequence comprises one or more of introns 2, 3, and 4 of a SERPINA1 gene. In some embodiments, the donor nucleic acid sequence comprises introns 2, 3, and 4 of a SERPINA1 gene.

In some embodiments, the donor nucleic acid sequence comprises a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a sequence set forth in SEQ ID NO: 125. In some embodiments, the donor nucleic acid sequence comprises a nucleic acid sequence set forth in SEQ ID NO: 125. In some embodiments, the donor nucleic acid sequence comprises a nucleic acid sequence having at least 80% at least 85%, at least 90%, at least 91%, at least 92%, at least 93%, at least 94%, at least 95%, at least 96%, at least 97%, at least 98%, at least 99%, or more, sequence identity to a sequence set forth in SEQ ID NO: 126. In some embodiments, the donor nucleic acid sequence comprises a nucleic acid sequence set forth in SEQ ID NO: 126.

In some embodiments, the template nucleic acid is a bidirectional template nucleic acid. In some such embodiments, the donor nucleic acid sequence further comprises a reverse segment that is 3' downstream of the termination sequence, wherein the reverse segment comprises, from 5' to 3': (a) a reverse complement of a second termination sequence; (b) a reverse complement of a second donor nucleic acid sequence encoding an AAT protein encoded by exons 2, 3, 4, and 5 of a SERPINA1 gene; and (c) a reverse complement of a second splicing sequence comprising a splice acceptor sequence capable of pairing with an endogenous splice donor sequence that is positioned 3' downstream and adjacent to exon 1c in a SERPINA1 gene.

In some embodiments, the second termination sequence is identical to the first termination sequence. In some embodiments, the second termination sequence differs from the first termination sequence.

In some embodiments, the second donor nucleic acid sequence is identical to the first donor nucleic acid sequence. In some embodiments, the second donor nucleic acid sequence differs from the first donor nucleic acid sequence, but encodes the same AAT protein.

In some embodiments, the second splicing sequence is identical to the first splicing sequence. In some embodiments, the second splicing sequence differs from the first splicing sequence, but is still capable of pairing with the same endogenous splice donor sequence in a SERPINA1 gene.

In another aspect, the present disclosure provides a recombinant DNA construct comprising a polynucleotide described herein (i.e., comprising a template nucleic acid described herein). In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant AAV. In some embodiments, the recombinant virus is a recombinant AAV. In some embodiments, the recombinant AAV has an AAV8 capsid.

In another aspect, the present disclosure provides a recombinant virus comprising a polynucleotide described herein (i.e., comprising a template nucleic acid described herein). In some embodiments, the recombinant virus is a recombinant adenovirus, a recombinant lentivirus, a recombinant retrovirus, or a recombinant AAV. In some embodiments, the recombinant virus is a recombinant AAV. In some embodiments, the recombinant AAV has an AAV8 capsid. In some embodiments, the polynucleotide is flanked by inverted terminal repeat (ITR) sequences.

In another aspect, the present disclosure provides a lipid nanoparticle composition comprising lipid nanoparticles comprising a polynucleotide described herein (i.e., comprising a template nucleic acid described herein).

In another aspect, the present disclosure provides a lipid nanoparticle composition comprising lipid nanoparticles comprising a recombinant DNA construct described herein (i.e., comprising a polynucleotide comprising a template nucleic acid described herein).

In another aspect, the present disclosure provides a pharmaceutical composition comprising a pharmaceutically acceptable carrier and a polynucleotide described herein (i.e., comprising a template nucleic acid described herein).

In another aspect, the present disclosure provides a pharmaceutical composition comprising a pharmaceutically acceptable carrier and a recombinant DNA construct described herein (i.e., comprising a polynucleotide comprising a template nucleic acid described herein).

In another aspect, the present disclosure provides a pharmaceutical composition comprising a pharmaceutically acceptable carrier and a recombinant virus described herein (i.e., comprising a polynucleotide comprising a template nucleic acid described herein).

In another aspect, the present disclosure provides a pharmaceutical composition comprising a pharmaceutically acceptable carrier and a lipid nanoparticle composition described herein (i.e., comprising a polynucleotide comprising a template nucleic acid described herein).

In another aspect, the present disclosure provides a method for producing a genetically-modified eukaryotic cell comprising a modified SERPINA1 gene, the method comprising introducing into a eukaryotic cell: (a) a polynucleotide comprising a template nucleic acid described herein; and (b) an engineered meganuclease described herein, or a second polynucleotide comprising a nucleic acid sequence encoding an engineered meganuclease described herein that is expressed in the eukaryotic cell; wherein the engineered meganuclease is an engineered meganuclease described herein that binds and cleaves a recognition sequence comprising SEQ ID NO: 9 within an endogenous SERPINA1 gene, and wherein such engineered meganuclease binds and cleaves the recognition sequence comprising SEQ ID NO: 9 to generate a cleavage site; or wherein the engineered meganuclease is an engineered meganuclease described herein that binds and cleaves a recognition sequence comprising SEQ ID NO: 11 within an endogenous SERPINA1 gene, and wherein such engineered meganuclease binds and cleaves the recognition sequence comprising SEQ ID NO: 11 to generate a cleavage site; or wherein the engineered meganuclease is an engineered meganuclease described herein that binds and cleaves a recognition sequence comprising SEQ ID NO: 13 within an endogenous SERPINA1 gene, and wherein such engineered meganuclease binds and cleaves the recognition sequence comprising SEQ ID NO: 13 to generate a cleavage site; or wherein the engineered meganuclease is an engineered meganuclease described herein that binds and cleaves a recognition sequence comprising SEQ ID NO: 15 within an endogenous SERPINA1 gene, and wherein such engineered meganuclease binds and cleaves the recognition sequence comprising SEQ ID NO: 15 to generate a cleavage site; and wherein the template nucleic acid is inserted into the cleavage site to generate the modified SERPINA1 gene.

In some embodiments, the endogenous SERPINA1 gene comprises at least one mutation relative to a wild-type SERPINA1 gene and encodes a mutant AAT protein. In some embodiments, the endogenous SERPINA1 gene comprises a Z allele mutation in exon 5. In some embodiments, some embodiments, the endogenous SERPINA1 gene comprises an S allele mutation in exon 3.

In some embodiments, the genetically-modified cell expresses less of a mutant AAT protein, relative to an unmodified cell.

In some embodiments, the template nucleic acid is inserted in-frame in the SERPINA1 gene.

In some embodiments, the donor nucleic acid sequence of the template nucleic acid is operably linked to an endogenous SERPINA/promoter following insertion of the template nucleic acid into the cleavage site.

In some embodiments, the template nucleic acid does not comprise an exogenous promoter.

In some embodiments, the modified SERPINA1 gene encodes a full-length AAT protein that does not comprise a Z allele mutation or an S allele mutation. In some embodiments, the modified SERPINA1 gene encodes a full-length wild-type AAT protein. In some embodiments, the modified SERPINA1 gene comprises a nucleic acid sequence of a wild-type SERPINA1 gene. In some embodiments, the modified SERPINA1 gene comprises a nucleic acid sequence of a wild-type SERPINA1 gene but lacking one or more of introns 2, 3, and 4, and optionally lacking each of introns 2, 3, and 4. In some embodiments, the modified SERPINA1 gene comprises one or more codon-modified exons and/or introns and encodes a wild-type AAT protein. In some embodiments, the modified SERPINA1 gene comprises a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a sequence set forth in SEQ ID NO: 127. In some embodiments, the modified SERPINA1 gene comprises a nucleic acid sequence set forth in SEQ ID NO: 127.

In some embodiments, the second polynucleotide comprises a promoter that is operably linked to the nucleic acid sequence encoding the engineered meganuclease. In some embodiments, the promoter is a liver-specific promoter. In some embodiments, the liver-specific promoter is a TBG promoter, alpha-1 antitrypsin promoter, hybrid liver-specific promoter comprising a hepatic locus control region from an ApoE gene and an alpha-1 antitrypsin promoter, or apolipoprotein A-II promoter. In some embodiments, the liver-specific promoter is a TBG promoter.

In some embodiments, the polynucleotide comprising a template nucleic acid is introduced into the eukaryotic cell by a first recombinant virus and the second polynucleotide is introduced into the eukaryotic cell by a second recombinant virus. In some such embodiments, the first recombinant virus and/or the second recombinant virus is a recombinant AAV. In some such embodiments, the first recombinant AAV and/or the second recombinant AAV has a capsid of serotype AAV8. In some such embodiments, the polynucleotide comprising a template nucleic acid and the second polynucleotide are flanked by ITR sequences. In some such embodiments, the second polynucleotide comprises a promoter that is operably linked to the nucleic acid sequence encoding the engineered meganuclease. In some such embodiments, the promoter is a liver-specific promoter. In some such embodiments, the liver-specific promoter is a TBG promoter.

In some embodiments, the polynucleotide comprising a template nucleic acid is introduced into the eukaryotic cell by a recombinant virus, and the engineered meganuclease or the second polynucleotide is introduced into the eukaryotic cell by a lipid nanoparticle. In some such embodiments, the recombinant virus is a recombinant AAV. In some such embodiments, the recombinant AAV has a capsid of serotype AAV8. In some such embodiments, the polynucleotide comprising a template nucleic acid is flanked by ITR sequences. In some such embodiments, the second polynucleotide is an mRNA encapsulated by a lipid nanoparticle. In some embodiments, the second polynucleotide is a double-stranded DNA encapsulated by a lipid nanoparticle.

In some embodiments, the polynucleotide comprising a template nucleic acid is introduced into the eukaryotic cell by a lipid nanoparticle, and the second polynucleotide is introduced into the eukaryotic cell by a recombinant virus. In some such embodiments, the polynucleotide comprising a template nucleic acid is a double-stranded DNA encapsulated by a lipid nanoparticle. In some such embodiments, the recombinant virus is a recombinant AAV. In some such embodiments, the recombinant AAV has a capsid of serotype AAV8. In some such embodiments, the second polynucleotide is flanked by ITR sequences. In some such embodiments, the second polynucleotide comprises a promoter that is operably linked to the nucleic acid sequence encoding the engineered nuclease. In some such embodiments, the promoter is a liver-specific promoter. In some such embodiments, the liver-specific promoter is a TBG promoter.

In some embodiments, the polynucleotide comprising a template nucleic acid is introduced into the eukaryotic cell by a first lipid nanoparticle, and the engineered meganuclease or the second polynucleotide is introduced into the eukaryotic cell by a second lipid nanoparticle. In some embodiments, the polynucleotide comprising a template nucleic acid is a double-stranded DNA encapsulated by the first lipid nanoparticle. In some embodiments, the second polynucleotide is an mRNA encapsulated by the second lipid nanoparticle. In some embodiments, the second polynucleotide is a double-stranded DNA encapsulated by the second lipid nanoparticle.

In some embodiments, the eukaryotic cell is a mammalian cell. In some embodiments, the mammalian cell is a human cell. In some embodiments, the mammalian cell is a liver cell. In some embodiments, the mammalian cell is a liver progenitor cell or stem cell.

In another aspect, the present disclosure provides a method for modifying a SERPINA1 gene in a target cell in a subject, the method comprising delivering to the target cell: (a) a polynucleotide comprising a template nucleic acid described herein; and (b) an engineered meganuclease described herein, or a second polynucleotide comprising a nucleic acid sequence encoding an engineered meganuclease described herein that is expressed in the target cell; wherein the engineered meganuclease is an engineered meganuclease described herein that binds and cleaves a recognition sequence comprising SEQ ID NO: 9 within an endogenous SERPINA1 gene, and wherein such engineered meganuclease binds and cleaves the recognition sequence comprising SEQ ID NO: 9 to generate a cleavage site; or wherein the engineered meganuclease is an engineered meganuclease described herein that binds and cleaves a recognition sequence comprising SEQ ID NO: 11 within an endogenous SERPINA1 gene, and wherein such engineered meganuclease binds and cleaves the recognition sequence comprising SEQ ID NO: 11 to generate a cleavage site; or wherein the engineered meganuclease is an engineered meganuclease described herein that binds and cleaves a recognition sequence comprising SEQ ID NO: 13 within an endogenous SERPINA1 gene, and wherein such engineered meganuclease binds and cleaves the recognition sequence comprising SEQ ID NO: 13 to generate a cleavage site; or wherein the engineered meganuclease is an engineered meganuclease described herein that binds and cleaves a recognition sequence comprising SEQ ID NO: 15 within an endogenous SERPINA1 gene, and wherein such engineered meganuclease binds and cleaves the recognition sequence comprising SEQ ID NO: 15 to generate a cleavage site; and wherein the template nucleic acid is inserted into the cleavage site to generate the modified SERPINA1 gene.

In some embodiments, the endogenous SERPINA1 gene comprises at least one mutation relative to a wild-type SERPINA1 gene and encodes a mutant AAT protein. In some embodiments, the endogenous SERPINA1 gene comprises a Z allele mutation in exon 5. In some embodiments, the endogenous SERPINA1 gene comprises an S allele mutation in exon 3.

In some embodiments, the target cell expresses less of a mutant AAT protein after insertion of the template nucleic acid, relative to before insertion.

In some embodiments, the template nucleic acid is inserted in-frame in the SERPINA1 gene.

In some embodiments, the donor nucleic acid sequence of the template nucleic acid is operably linked to an endogenous SERPINA/promoter following insertion of the template nucleic acid into the cleavage site.

In some embodiments, the template nucleic acid does not comprise an exogenous promoter.

In some embodiments, the modified SERPINA1 gene encodes a full-length AAT protein that does not comprise a Z allele mutation or an S allele mutation. In some embodiments, the modified SERPINA1 gene encodes a full-length wild-type AAT protein. In some embodiments, the modified SERPINA1 gene comprises a nucleic acid sequence of a wild-type SERPINA1 gene. In some embodiments, the modified SERPINA1 gene comprises a nucleic acid sequence of a wild-type SERPINA1 gene but lacking one or more of introns 2, 3, and 4, and optionally lacking each of introns 2, 3, and 4. In some embodiments, the modified SERPINA1 gene comprises one or more codon-modified exons and/or introns and encodes a wild-type AAT protein. In some embodiments, the modified SERPINA1 gene comprises a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a sequence set forth in SEQ ID NO: 127. In some embodiments, the modified SERPINA1 gene comprises a nucleic acid sequence set forth in SEQ ID NO: 127.

In some embodiments, the second polynucleotide comprises a promoter that is operably linked to the nucleic acid sequence encoding the engineered meganuclease. In some embodiments, the promoter is a liver-specific promoter. In some embodiments, the liver-specific promoter is a TBG promoter, alpha-1 antitrypsin promoter, hybrid liver-specific promoter comprising a hepatic locus control region from an ApoE gene and an alpha-1 antitrypsin promoter, or apolipoprotein A-II promoter. In some embodiments, the liver-specific promoter is a TBG promoter.

In some embodiments, the polynucleotide comprising a template nucleic acid is delivered to the target cell by a first recombinant virus and the second polynucleotide is delivered to the eukaryotic cell by a second recombinant virus. In some such embodiments, the first recombinant virus and/or the second recombinant virus is a recombinant AAV. In some such embodiments, the first recombinant AAV and/or the second recombinant AAV has a capsid of serotype AAV8. In some such embodiments, the polynucleotide comprising a template nucleic acid and the second polynucleotide are flanked by ITR sequences. In some such embodiments, the second polynucleotide comprises a promoter that is operably linked to the nucleic acid sequence encoding the engineered meganuclease. In some such embodiments, the promoter is a liver-specific promoter. In some such embodiments, the liver-specific promoter is a TBG promoter.

In some embodiments, the polynucleotide comprising a template nucleic acid is delivered to the target cell by a recombinant virus, and the engineered meganuclease or the second polynucleotide is delivered to the target cell by a lipid nanoparticle. In some such embodiments, the recombinant virus is a recombinant AAV. In some such embodiments, the recombinant AAV has a capsid of serotype AAV8. In some such embodiments, the polynucleotide comprising a template nucleic acid is flanked by ITR sequences. In some embodiments, the second polynucleotide is an mRNA encapsulated by the lipid nanoparticle. In some such embodiments, the second polynucleotide is a double-stranded DNA encapsulated by the lipid nanoparticle.

In some embodiments, the polynucleotide comprising a template nucleic acid is delivered to the target cell by a lipid nanoparticle, and the second polynucleotide is delivered to the target cell by a recombinant virus. In some such embodiments, the polynucleotide comprising a template nucleic acid is a double-stranded DNA encapsulated by the lipid nanoparticle. In some embodiments, the recombinant virus is a recombinant AAV. In some such embodiments, the recombinant AAV has a capsid of serotype AAV8. In some such embodiments, the second polynucleotide is flanked by ITR sequences. In some such embodiments, the second polynucleotide comprises a promoter that is operably linked to the nucleic acid sequence encoding the engineered meganuclease. In some such embodiments, the promoter is a liver-specific promoter. In some such embodiments, the liver-specific promoter is a TBG promoter.

In some embodiments, the polynucleotide comprising a template nucleic acid is delivered to the target cell by a first lipid nanoparticle, and the engineered meganuclease or the second polynucleotide is delivered to the target cell by a second lipid nanoparticle. In some such embodiments, the polynucleotide comprising a template nucleic acid is a double-stranded DNA encapsulated by the first lipid nanoparticle. In some such embodiments, the second polynucleotide is an mRNA encapsulated by the second lipid nanoparticle. In some such embodiments, the second polynucleotide is a double-stranded DNA encapsulated by the second lipid nanoparticle.

In some embodiments, the target cell is a mammalian cell. In some embodiments, the mammalian cell is a human cell. In some embodiments, the mammalian cell is a liver cell. In some embodiments, the mammalian cell is a liver progenitor cell or stem cell.

In another aspect, the present disclosure herein provides a method for treating AAT deficiency in a subject in need thereof, the method comprising administering to the subject: (a) a pharmaceutical composition comprising an effective amount of a polynucleotide comprising a template nucleic described herein; and (b) a pharmaceutical composition comprising an effective amount of an engineered meganuclease described herein, or a second polynucleotide comprising a nucleic acid sequence encoding an engineered meganuclease described herein; wherein the polynucleotide comprising the template nucleic acid, and the engineered meganuclease or second polynucleotide, are delivered to a target cell in the subject, wherein the engineered meganuclease is expressed in the target cell if encoded by the second polynucleotide, wherein the engineered meganuclease is an engineered meganuclease described herein that binds and cleaves a recognition sequence comprising SEQ ID NO: 9 within an endogenous SERPINA1 gene, and wherein such engineered meganuclease binds and cleaves the recognition sequence comprising SEQ ID NO: 9 to generate a cleavage site; or wherein the engineered meganuclease is an engineered meganuclease described herein that binds and cleaves a recognition sequence comprising SEQ ID NO: 11 within an endogenous SERPINA1 gene, and wherein such engineered meganuclease binds and cleaves the recognition sequence comprising SEQ ID NO: 11 to generate a cleavage site; or wherein the engineered meganuclease is an engineered meganuclease described herein that binds and cleaves a recognition sequence comprising SEQ ID NO: 13 within an endogenous SERPINA1 gene, and wherein such engineered meganuclease binds and cleaves the recognition sequence comprising SEQ ID NO: 13 to generate a cleavage site; or wherein the engineered meganuclease is an engineered meganuclease described herein that binds and cleaves a recognition sequence comprising SEQ ID NO: 15 within an endogenous SERPINA1 gene, and wherein such engineered meganuclease binds and cleaves the recognition sequence comprising SEQ ID NO: 15 to generate a cleavage site; and wherein the template nucleic acid is inserted into the cleavage site to generate the modified SERPINA1 gene.

In some embodiments, the endogenous SERPINA1 gene comprises at least one mutation relative to a wild-type SERPINA1 gene and encodes a mutant AAT protein. In some embodiments, the endogenous SERPINA1 gene comprises a Z allele mutation in exon 5. In some embodiments, the endogenous SERPINA1 gene comprises an S allele mutation in exon 3. In some embodiments, the target cell expresses less of the mutant AAT protein after insertion of the template nucleic acid, relative to before insertion.

In some embodiments, the target cell expresses less of a mutant AAT protein after insertion of the template nucleic acid, relative to before insertion. In some embodiments, the template nucleic acid is inserted in-frame in the SERPINA1 gene. In some embodiments, the donor nucleic acid sequence of the template nucleic acid is operably linked to an endogenous SERPINA1 promoter following insertion of the template nucleic acid into the cleavage site. In some embodiments, the template nucleic acid does not comprise an exogenous promoter.

In some embodiments, the modified SERPINA1 gene encodes a full-length AAT protein that does not comprise a Z allele mutation or an S allele mutation. In some embodiments, the modified SERPINA1 gene encodes a full-length wild-type AAT protein. In some embodiments, the modified SERPINA1 gene comprises a nucleic acid sequence of a wild-type SERPINA1 gene. In some embodiments, the modified SERPINA1 gene comprises a nucleic acid sequence of a wild-type SERPINA1 gene but lacking one or more of introns 2, 3, and 4, and optionally lacking each of introns 2, 3, and 4. In some embodiments, the modified SERPINA1 gene comprises one or more codon-modified exons and/or introns and encodes a wild-type AAT protein. In some embodiments, the modified SERPINA1 gene comprises a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a sequence set forth in SEQ ID NO: 127. In some embodiments, the modified SERPINA1 gene comprises a nucleic acid sequence set forth in SEQ ID NO: 127.

In some embodiments, the second polynucleotide comprises a promoter that is operably linked to the nucleic acid sequence encoding the engineered meganuclease. In some embodiments, the promoter is a liver-specific promoter. In some embodiments, the liver-specific promoter is a TBG promoter, alpha-1 antitrypsin promoter, hybrid liver-specific promoter comprising a hepatic locus control region from an ApoE gene and an alpha-1 antitrypsin promoter, or apolipoprotein A-II promoter. In some embodiments, the liver-specific promoter is a TBG promoter.

In some embodiments, the polynucleotide comprising a template nucleic acid is administered to the subject in a first recombinant virus and the second polynucleotide is administered to the subject in a second recombinant virus. In some such embodiments, the first recombinant virus and/or the second recombinant virus is a recombinant AAV. In some such embodiments, the first recombinant AAV and/or the second recombinant AAV has a capsid of serotype AAV8. In some such embodiments, the polynucleotide comprising a template nucleic acid and the second polynucleotide are flanked by ITR sequences. In some such embodiments, the second polynucleotide comprises a promoter that is operably linked to the nucleic acid sequence encoding the engineered meganuclease. In some such embodiments, the promoter is a liver-specific promoter. In some such embodiments, the liver-specific promoter is a TBG promoter.

In some embodiments, the polynucleotide comprising a template nucleic acid is administered to the subject in a recombinant virus, and the engineered meganuclease or the second polynucleotide is administered to the subject in a lipid nanoparticle. In some such embodiments, the recombinant virus is a recombinant AAV. In some such embodiments, the recombinant AAV has a capsid of serotype AAV8. In some such embodiments, the polynucleotide comprising a template nucleic acid is flanked by ITR sequences. In some such embodiments, the second polynucleotide is an mRNA encapsulated by the lipid nanoparticle. In some such embodiments, the second polynucleotide is a double-stranded DNA encapsulated by the lipid nanoparticle.

In some embodiments, the polynucleotide comprising a template nucleic acid is administered to the subject using a lipid nanoparticle, and wherein the second polynucleotide is administered to the subject using a recombinant virus. In some such embodiments, the polynucleotide comprising a template nucleic acid is a double-stranded DNA encapsulated by the lipid nanoparticle. In some such embodiments, the recombinant virus is a recombinant AAV. In some such embodiments, the recombinant AAV has a capsid of serotype AAV8. In some such embodiments, the second polynucleotide is flanked by ITR sequences. In some such embodiments, the second polynucleotide comprises a promoter that is operably linked to the nucleic acid sequence encoding the engineered meganuclease. In some such embodiments, the promoter is a liver-specific promoter. In some such embodiments, the liver-specific promoter is a TBG promoter.

In some embodiments, the polynucleotide comprising a template nucleic acid is administered to the subject using a first lipid nanoparticle, and the engineered meganuclease or the second polynucleotide is administered to the subject using a second lipid nanoparticle. In some such embodiments, the polynucleotide comprising a template nucleic acid is a double-stranded DNA encapsulated by the first lipid nanoparticle. In some such embodiments, the second polynucleotide is an mRNA encapsulated by the second lipid nanoparticle. In some such embodiments, the second polynucleotide is a double-stranded DNA encapsulated by the second lipid nanoparticle.

In some embodiments, the subject is a human. In some embodiments, the target cell is a liver cell. In some embodiments, the target cell is a liver progenitor cell or stem cell.

BRIEF DESCRIPTION OF THE FIGURES

FIG. 1 illustrates engineered meganuclease recognition sequences in the human AAT gene. Each AAT recognition sequence targeted by engineered meganucleases disclosed herein comprises two recognition half-sites. Each recognition half-site comprises 9 base pairs, separated by a 4 base pair central sequence.

FIGS. 3A-3D provide a pairwise alignment of the amino acid sequences of the AAT 35-36, AAT 37-38, AAT 41-42, and AAT 43-44 meganucleases described herein. Asterisks indicate conserved residues amongst all aligned nucleases, and a space indicates that at least one amino acid differed amongst the meganucleases.

FIG. 5A shows results of the indicated engineered meganucleases for cleaving the AAT 33-34 recognition sequence. FIG. 5B shows results of the indicated engineered meganucleases for cleaving the AAT 35-36 recognition sequence. FIG. 5C shows results of the indicated engineered meganucleases for cleaving the AAT 37-38 recognition sequence. FIG. 5D shows results of the indicated engineered meganucleases for cleaving the AAT 41-42 recognition sequence. FIG. 5E shows results of the indicated engineered meganucleases for cleaving the AAT 43-44 recognition sequence.

FIG. 6A-FIG. 6C shows results of the indicated engineered meganucleases for cleaving the AAT 35-36 recognition sequence. FIG. 6D and FIG. 6E shows results of the indicated engineered meganucleases for cleaving the AAT 37-38 recognition sequence. FIGS. 6F-FIG. 6H shows results of the indicated engineered meganucleases for cleaving the AAT 41-42 recognition sequence. FIG. 6I-FIG. 6K shows results of the indicated engineered meganucleases for cleaving the AAT 43-44 recognition sequence.

FIG. 14 provides schematics for two AAT donor polynucleotide constructs that will be used in the in the PiZ AAT murine model of Example 4.

FIG. 16A provides the percentage of productive insertions (transgene inserted in the correct orientation). FIG. 16B provides the total insertion for each site and the mechanism of action for that insertion as being homology directed repair (HDR) or non-homologous end joining (NHEJ).

FIG. 17. Provides a bar graph quantifying the percentage of PAS-D positive cells in the PiZ mouse liver of the indicated treatment groups of Example 4.

FIG. 20. Provides a bar graph indicating the amount of Flag tagged AAT detected in the liver of PiZ mice from the indicated treatment groups of Example 4.

FIG. 54. Provides graphs showing the levels of liver enzymes ALT, AST, ALP, and TBIL from the livers of rats treated with an LNP-A containing the AAT 37-38L.262 meganuclease at 3.5 mg/kg, 3 mg/kg, and 1 mg/kg.

BRIEF DESCRIPTION OF THE SEQUENCES

Figure 2:
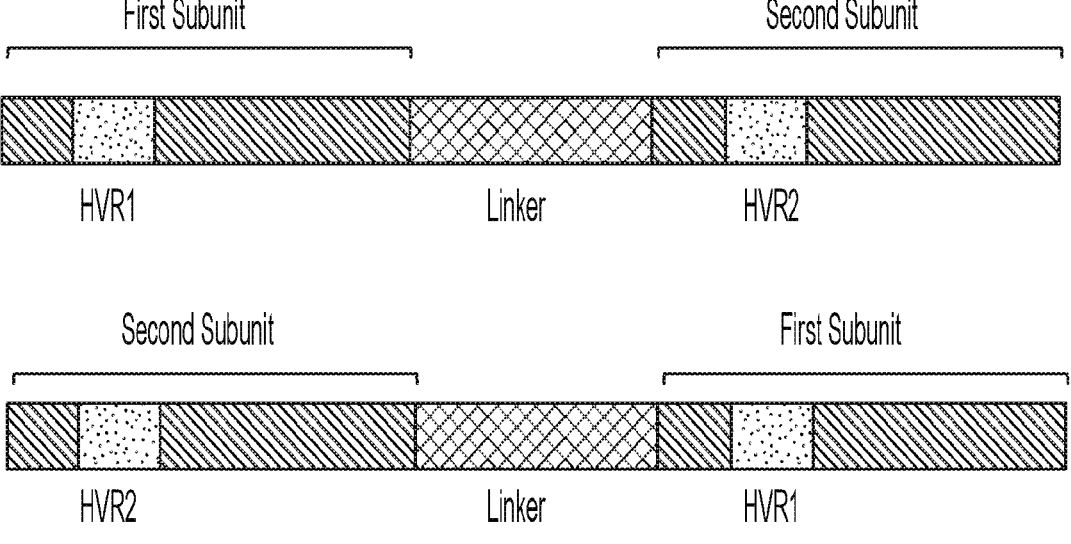
FIG. 2 illustrates orientations of engineered meganucleases described herein. The engineered meganucleases described herein comprise two subunits, wherein the first subunit comprising the HVR1 region binds to a first recognition half-site and the second subunit comprising the HVR2 region binds to a second recognition half-site. In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.
Figure 4:
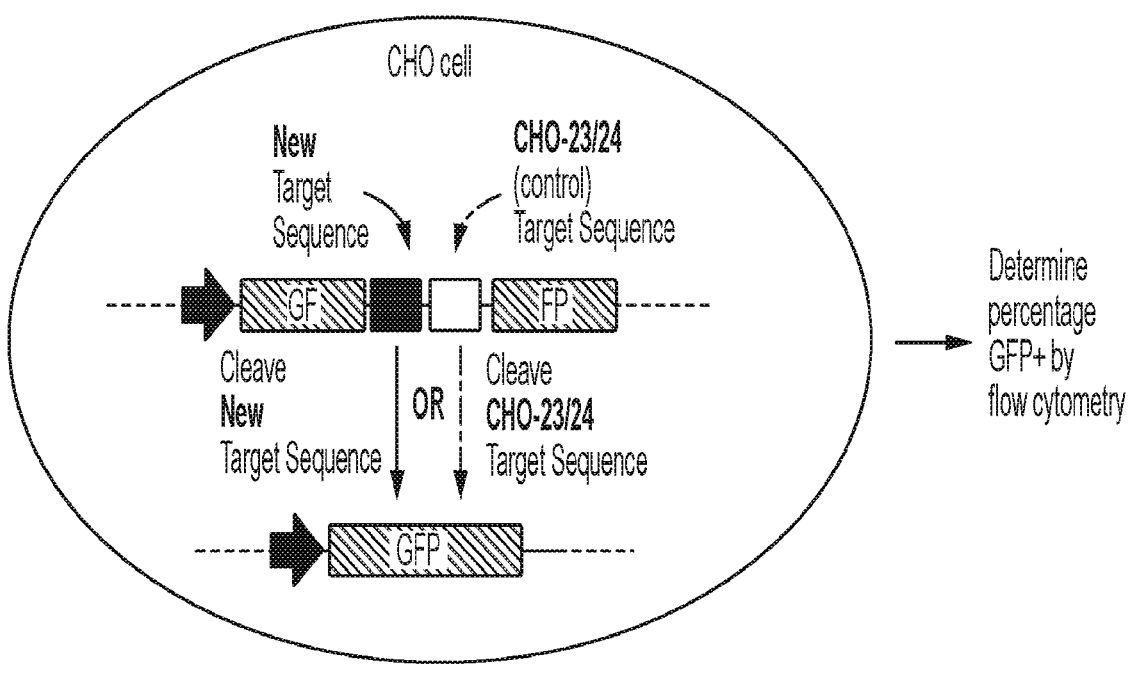
FIG. 4 provides a schematic of a reporter assay in CHO cells for evaluating engineered meganucleases targeting recognition sequences found in the AAT gene. For the engineered meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease described herein (e.g., the AAT 35-36 sequence; SEQ ID NO: 9); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of an mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

SEQ ID NO: 1 sets forth the amino acid sequence of a wild-type I-CreI meganuclease.

SEQ ID NO: 2 sets forth the amino acid sequence of a LAGLIDADG motif.

SEQ ID NO: 3 sets forth the nucleic acid sequence of an AAT 9-10 recognition sequence (sense).

SEQ ID NO: 4 sets forth the nucleic acid sequence of an AAT 9-10 recognition sequence (antisense).

SEQ ID NO: 5 sets forth the nucleic acid sequence of an AAT 13-14 recognition sequence (sense).

SEQ ID NO: 6 sets forth the nucleic acid sequence of an AAT 13-14 recognition sequence (antisense).

SEQ ID NO: 7 sets forth the nucleic acid sequence of an AAT 33-34 recognition sequence (sense).

SEQ ID NO: 8 sets forth the nucleic acid sequence of an AAT 33-34 recognition sequence (antisense).

SEQ ID NO: 9 sets forth the nucleic acid sequence of an AAT 35-36 recognition sequence (sense).

SEQ ID NO: 10 sets forth the nucleic acid sequence of an AAT 35-36 recognition sequence (antisense).

SEQ ID NO: 11 sets forth the nucleic acid sequence of an AAT 37-38 recognition sequence (sense).

SEQ ID NO: 12 sets forth the nucleic acid sequence of an AAT 37-38 recognition sequence (antisense).

SEQ ID NO: 13 sets forth the nucleic acid sequence of an AAT 41-42 recognition sequence (sense).

SEQ ID NO: 14 sets forth the nucleic acid sequence of an AAT 41-42 recognition sequence (antisense).

SEQ ID NO: 15 sets forth the nucleic acid sequence of an AAT 43-44 recognition sequence (sense).

SEQ ID NO: 16 sets forth the nucleic acid sequence of an AAT 43-44 recognition sequence (antisense).

SEQ ID NO: 17 sets forth the amino acid sequence of an AAT 35-36x.70 meganuclease.

SEQ ID NO: 18 sets forth the amino acid sequence of an AAT 35-36x.49 meganuclease.

SEQ ID NO: 19 sets forth the amino acid sequence of an AAT 35-36L.79 meganuclease.

SEQ ID NO: 20 sets forth the amino acid sequence of an AAT 35-36L.141 meganuclease.

SEQ ID NO: 21 sets forth the amino acid sequence of an AAT 35-36L.210 meganuclease.

SEQ ID NO: 22 sets forth the amino acid sequence of an AAT 35-36L.290 meganuclease.

SEQ ID NO: 23 sets forth the amino acid sequence of a first subunit of an AAT 35-36x.70 meganuclease.

SEQ ID NO: 24 sets forth the amino acid sequence of a first subunit of an AAT 35-36x.49 meganuclease.

SEQ ID NO: 25 sets forth the amino acid sequence of a first subunit of an AAT 35-36L.79 meganuclease.

SEQ ID NO: 26 sets forth the amino acid sequence of a first subunit of an AAT 35-36L.141 meganuclease.

SEQ ID NO: 27 sets forth the amino acid sequence of a first subunit of an AAT 35-36L.210 meganuclease.

SEQ ID NO: 28 sets forth the amino acid sequence of a first subunit of an AAT 35-36L.290 meganuclease.

SEQ ID NO: 29 sets forth the amino acid sequence of a second subunit of an AAT 35-36x.70 meganuclease.

SEQ ID NO: 30 sets forth the amino acid sequence of a second subunit of an AAT 35-36x.49 meganuclease.

SEQ ID NO: 31 sets forth the amino acid sequence of a second subunit of an AAT 35-36L.79 meganuclease.

SEQ ID NO: 32 sets forth the amino acid sequence of a second subunit of an AAT 35-36L.141 meganuclease.

SEQ ID NO: 33 sets forth the amino acid sequence of a second subunit of an AAT 35-36L.210 meganuclease.

SEQ ID NO: 34 sets forth the amino acid sequence of a second subunit of an AAT 35-36L.290 meganuclease.

SEQ ID NO: 35 sets forth the nucleic acid sequence of an AAT 35-36x.70 meganuclease.

SEQ ID NO: 36 sets forth the nucleic acid sequence of an AAT 35-36x.49 meganuclease.

SEQ ID NO: 37 sets forth the nucleic acid sequence of an AAT 35-36L.79 meganuclease.

SEQ ID NO: 38 sets forth the nucleic acid sequence of an AAT 35-36L.141 meganuclease.

SEQ ID NO: 39 sets forth the nucleic acid sequence of an AAT 35-36L.210 meganuclease.

SEQ ID NO: 40 sets forth the nucleic acid sequence of an AAT 35-36L.290 meganuclease.

SEQ ID NO: 41 sets forth the amino acid sequence of an AAT 37-38x.50 meganuclease.

SEQ ID NO: 42 sets forth the amino acid sequence of an AAT 37-38x.61 meganuclease.

SEQ ID NO: 43 sets forth the amino acid sequence of an AAT 37-38L.158 meganuclease.

SEQ ID NO: 44 sets forth the amino acid sequence of an AAT 37-38L.167 meganuclease.

SEQ ID NO: 45 sets forth the amino acid sequence of an AAT 37-38L.175 meganuclease.

SEQ ID NO: 46 sets forth the amino acid sequence of an AAT 37-38L.262 meganuclease.

SEQ ID NO: 47 sets forth the amino acid sequence of a first subunit of an AAT 37-38x.50 meganuclease.

SEQ ID NO: 48 sets forth the amino acid sequence of a first subunit of an AAT 37-38x.61 meganuclease.

SEQ ID NO: 49 sets forth the amino acid sequence of a first subunit of an AAT 37-38L.158 meganuclease.

SEQ ID NO: 50 sets forth the amino acid sequence of a first subunit of an AAT 37-38L.167 meganuclease.

SEQ ID NO: 51 sets forth the amino acid sequence of a first subunit of an AAT 37-38L.175 meganuclease.

SEQ ID NO: 52 sets forth the amino acid sequence of a first subunit of an AAT 37-38L.262 meganuclease.

SEQ ID NO: 53 sets forth the amino acid sequence of a second subunit of an AAT 37-38x.50 meganuclease.

SEQ ID NO: 54 sets forth the amino acid sequence of a second subunit of an AAT 37-38x.61 meganuclease.

SEQ ID NO: 55 sets forth the amino acid sequence of a second subunit of an AAT 37-38L.158 meganuclease.

SEQ ID NO: 56 sets forth the amino acid sequence of a second subunit of an AAT 37-38L.167 meganuclease.

SEQ ID NO: 57 sets forth the amino acid sequence of a second subunit of an AAT 37-38L.175 meganuclease.

SEQ ID NO: 58 sets forth the amino acid sequence of a second subunit of an AAT 37-38L.262 meganuclease.

SEQ ID NO: 59 sets forth the nucleic acid sequence of an AAT 37-38x.50 meganuclease.

SEQ ID NO: 60 sets forth the nucleic acid sequence of an AAT 37-38x.61 meganuclease.

SEQ ID NO: 61 sets forth the nucleic acid sequence of an AAT 37-38L.158 meganuclease.

SEQ ID NO: 62 sets forth the nucleic acid sequence of an AAT 37-38L.167 meganuclease.

SEQ ID NO: 63 sets forth the nucleic acid sequence of an AAT 37-38L.175 meganuclease.

SEQ ID NO: 64 sets forth the nucleic acid sequence of an AAT 37-38L.262 meganuclease.

SEQ ID NO: 65 sets forth the amino acid sequence of an AAT 41-42x.1 meganuclease.

SEQ ID NO: 66 sets forth the amino acid sequence of an AAT 41-42x.32 meganuclease.

SEQ ID NO: 67 sets forth the amino acid sequence of an AAT 41-42L.42 meganuclease.

SEQ ID NO: 68 sets forth the amino acid sequence of an AAT 41-42L.104 meganuclease.

SEQ ID NO: 69 sets forth the amino acid sequence of an AAT 41-42L.153 meganuclease.

SEQ ID NO: 70 sets forth the amino acid sequence of an AAT 41-42L.185 meganuclease.

SEQ ID NO: 71 sets forth the amino acid sequence of an AAT 41-42L.294 meganuclease.

SEQ ID NO: 72 sets forth the amino acid sequence of a first subunit of an AAT 41-42x.1 meganuclease.

SEQ ID NO: 73 sets forth the amino acid sequence of a first subunit of an AAT 41-42x.32 meganuclease.

SEQ ID NO: 74 sets forth the amino acid sequence of a first subunit of an AAT 41-42L.42 meganuclease.

SEQ ID NO: 75 sets forth the amino acid sequence of a first subunit of an AAT 41-42L.104 meganuclease.

SEQ ID NO: 76 sets forth the amino acid sequence of a first subunit of an AAT 41-42L.153 meganuclease.

SEQ ID NO: 77 sets forth the amino acid sequence of a first subunit of an AAT 41-42L.185 meganuclease.

SEQ ID NO: 78 sets forth the amino acid sequence of a first subunit of an AAT 41-42L.294 meganuclease.

SEQ ID NO: 79 sets forth the amino acid sequence of a second subunit of an AAT 41-42x.1 meganuclease.

SEQ ID NO: 80 sets forth the amino acid sequence of a second subunit of an AAT 41-42x.32 meganuclease.

SEQ ID NO: 81 sets forth the amino acid sequence of a second subunit of an AAT 41-42L.42 meganuclease.

SEQ ID NO: 82 sets forth the amino acid sequence of a second subunit of an AAT 41-42L.104 meganuclease.

SEQ ID NO: 83 sets forth the amino acid sequence of a second subunit of an AAT 41-42L.153 meganuclease.

SEQ ID NO: 84 sets forth the amino acid sequence of a second subunit of an AAT 41-42L.185 meganuclease.

SEQ ID NO: 85 sets forth the amino acid sequence of a second subunit of an AAT 41-42L.294 meganuclease.

SEQ ID NO: 86 sets forth the nucleic acid sequence of an AAT 41-42x.1 meganuclease.

SEQ ID NO: 87 sets forth the nucleic acid sequence of an AAT 41-42x.32 meganuclease.

SEQ ID NO: 88 sets forth the nucleic acid sequence of an AAT 41-42L.42 meganuclease.

SEQ ID NO: 89 sets forth the nucleic acid sequence of an AAT 41-42L.104 meganuclease.

SEQ ID NO: 90 sets forth the nucleic acid sequence of an AAT 41-42L.153 meganuclease.

SEQ ID NO: 91 sets forth the nucleic acid sequence of an AAT 41-42L.185 meganuclease.

SEQ ID NO: 92 sets forth the nucleic acid sequence of an AAT 41-42L.294 meganuclease.

SEQ ID NO: 93 sets forth the amino acid sequence of an AAT 43-44x.58 meganuclease.

SEQ ID NO: 94 sets forth the amino acid sequence of an AAT 43-44x.34 meganuclease.

SEQ ID NO: 95 sets forth the amino acid sequence of an AAT 43-44L.47 meganuclease.

SEQ ID NO: 96 sets forth the amino acid sequence of an AAT 43-44L.105 meganuclease.

SEQ ID NO: 97 sets forth the amino acid sequence of an AAT 43-44L.132 meganuclease.

SEQ ID NO: 98 sets forth the amino acid sequence of an AAT 43-44L.157 meganuclease.

SEQ ID NO: 99 sets forth the amino acid sequence of an AAT 43-44L.276 meganuclease.

SEQ ID NO: 100 sets forth the amino acid sequence of an AAT 43-44L.384 meganuclease.

SEQ ID NO: 101 sets forth the amino acid sequence of a first subunit of an AAT 43-44x.58 meganuclease.

SEQ ID NO: 102 sets forth the amino acid sequence of a first subunit of an AAT 43-44x.34 meganuclease.

SEQ ID NO: 103 sets forth the amino acid sequence of a first subunit of an AAT 43-44L.47 meganuclease.

SEQ ID NO: 104 sets forth the amino acid sequence of a first subunit of an AAT 43-44L.105 meganuclease.

SEQ ID NO: 105 sets forth the amino acid sequence of a first subunit of an AAT 43-44L.132 meganuclease.

SEQ ID NO: 106 sets forth the amino acid sequence of a first subunit of an AAT 43-44L.157 meganuclease.

SEQ ID NO: 107 sets forth the amino acid sequence of a first subunit of an AAT 43-44L.276 meganuclease.

SEQ ID NO: 108 sets forth the amino acid sequence of a first subunit of an AAT 43-44L.384 meganuclease.

SEQ ID NO: 109 sets forth the amino acid sequence of a second subunit of an AAT 43-44x.58 meganuclease.

SEQ ID NO: 110 sets forth the amino acid sequence of a second subunit of an AAT 43-44x.34 meganuclease.

SEQ ID NO: 111 sets forth the amino acid sequence of a second subunit of an AAT 43-44L.47 meganuclease.

SEQ ID NO: 112 sets forth the amino acid sequence of a second subunit of an AAT 43-44L.105 meganuclease.

SEQ ID NO: 113 sets forth the amino acid sequence of a second subunit of an AAT 43-44L.132 meganuclease.

SEQ ID NO: 114 sets forth the amino acid sequence of a second subunit of an AAT 43-44L.157 meganuclease.

SEQ ID NO: 115 sets forth the amino acid sequence of a second subunit of an AAT 43-44L.276 meganuclease.

SEQ ID NO: 116 sets forth the amino acid sequence of a second subunit of an AAT 43-44L.384 meganuclease.

SEQ ID NO: 117 sets forth the nucleic acid sequence of an AAT 43-44x.58 meganuclease.

SEQ ID NO: 118 sets forth the nucleic acid sequence of an AAT 43-44x.34 meganuclease.

SEQ ID NO: 119 sets forth the nucleic acid sequence of an AAT 43-44L.47 meganuclease.

SEQ ID NO: 120 sets forth the nucleic acid sequence of an AAT 43-44L.105 meganuclease.

SEQ ID NO: 121 sets forth the nucleic acid sequence of an AAT 43-44L.132 meganuclease.

SEQ ID NO: 122 sets forth the nucleic acid sequence of an AAT 43-44L.157 meganuclease.

SEQ ID NO: 123 sets forth the nucleic acid sequence of an AAT 43-44L.276 meganuclease.

SEQ ID NO: 124 sets forth the nucleic acid sequence of an AAT 43-44L.384 meganuclease.

SEQ ID NO: 125 sets forth the nucleic acid sequence of a donor nucleic acid sequence, WT SERPINA1 exons 2-5.

SEQ ID NO: 126 sets forth the nucleic acid sequence of a donor nucleic acid sequence, WT SERPINA1 exons 2-5.

SEQ ID NO: 127 sets forth the nucleic acid sequence of a modified SERPINA1 gene from exon 1a through end of exon 5 in template.

SEQ ID NO: 128 sets forth the amino acid sequence of a SV40 nuclear localization sequence.

SEQ ID NO: 129 sets forth the nucleic acid sequence of a TTR 5-6 recognition sequence (sense).

SEQ ID NO: 130 sets forth the nucleic acid sequence of a TTR 5-6 recognition sequence (antisense).

SEQ ID NO: 131 sets forth the nucleic acid sequence of an AAT 31-32 Fwd primer.

SEQ ID NO: 132 sets forth the nucleic acid sequence of an AAT 31-32 Fwd primer.

SEQ ID NO: 133 sets forth the nucleic acid sequence of an AAT 31-32 Fwd primer.

SEQ ID NO: 134 sets forth the nucleic acid sequence of an AAT 31-32 Fwd primer.

SEQ ID NO: 135 sets forth the nucleic acid sequence of an AAT 31-32 Rvs primer.

SEQ ID NO: 136 sets forth the nucleic acid sequence of an AAT 31-32 Rvs primer.

SEQ ID NO: 137 sets forth the nucleic acid sequence of an AAT 31-32 Rvs primer.

SEQ ID NO: 138 sets forth the nucleic acid sequence of an AAT 31-32 Rvs primer.

SEQ ID NO: 139 sets forth the nucleic acid sequence of an AAT 31-32 Rvs primer.

SEQ ID NO: 140 sets forth the nucleic acid sequence of an AAT 31-32 Rvs primer.

SEQ ID NO: 141 sets forth the nucleic acid sequence of an AAT 31-32 Rvs primer.

SEQ ID NO: 142 sets forth the nucleic acid sequence of an AAT 31-32 Rvs primer.

SEQ ID NO: 143 sets forth the nucleic acid sequence of an AAT 33-34 Fwd primer.

SEQ ID NO: 144 sets forth the nucleic acid sequence of an AAT 33-34 Fwd primer.

SEQ ID NO: 145 sets forth the nucleic acid sequence of an AAT 33-34 Fwd primer.

SEQ ID NO: 146 sets forth the nucleic acid sequence of an AAT 33-34 Fwd primer.

SEQ ID NO: 147 sets forth the nucleic acid sequence of an AAT 33-34 Rvs primer.

SEQ ID NO: 148 sets forth the nucleic acid sequence of an AAT 33-34 Rvs primer.

SEQ ID NO: 149 sets forth the nucleic acid sequence of an AAT 33-34 Rvs primer.

SEQ ID NO: 150 sets forth the nucleic acid sequence of an AAT 33-34 Rvs primer.

SEQ ID NO: 151 sets forth the nucleic acid sequence of an AAT 33-34 Rvs primer.

SEQ ID NO: 152 sets forth the nucleic acid sequence of an AAT 33-34 Rvs primer.

SEQ ID NO: 153 sets forth the nucleic acid sequence of an AAT 33-34 Rvs primer.

SEQ ID NO: 154 sets forth the nucleic acid sequence of an AAT 33-34 Rvs primer.

SEQ ID NO: 155 sets forth the nucleic acid sequence of an AAT 35-36 Fwd primer.

SEQ ID NO: 156 sets forth the nucleic acid sequence of an AAT 35-36 Fwd primer.

SEQ ID NO: 157 sets forth the nucleic acid sequence of an AAT 35-36 Fwd primer.

SEQ ID NO: 158 sets forth the nucleic acid sequence of an AAT 35-36 Fwd primer.

SEQ ID NO: 159 sets forth the nucleic acid sequence of an AAT 35-36 Rvs primer.

SEQ ID NO: 160 sets forth the nucleic acid sequence of an AAT 35-36 Rvs primer.

SEQ ID NO: 161 sets forth the nucleic acid sequence of an AAT 35-36 Rvs primer.

SEQ ID NO: 162 sets forth the nucleic acid sequence of an AAT 35-36 Rvs primer.

SEQ ID NO: 163 sets forth the nucleic acid sequence of an AAT 35-36 Rvs primer.

SEQ ID NO: 164 sets forth the nucleic acid sequence of an AAT 35-36 Rvs primer.

SEQ ID NO: 165 sets forth the nucleic acid sequence of an AAT 35-36 Rvs primer.

SEQ ID NO: 166 sets forth the nucleic acid sequence of an AAT 35-36 Rvs primer.

SEQ ID NO: 167 sets forth the nucleic acid sequence of an AAT 37-38 Fwd primer.

SEQ ID NO: 168 sets forth the nucleic acid sequence of an AAT 37-38 Fwd primer.

SEQ ID NO: 169 sets forth the nucleic acid sequence of an AAT 37-38 Fwd primer.

SEQ ID NO: 170 sets forth the nucleic acid sequence of an AAT 37-38 Fwd primer.

SEQ ID NO: 171 sets forth the nucleic acid sequence of an AAT 37-38 Fwd primer.

SEQ ID NO: 172 sets forth the nucleic acid sequence of an AAT 37-38 Fwd primer.

SEQ ID NO: 173 sets forth the nucleic acid sequence of an AAT 37-38 Fwd primer.

SEQ ID NO: 174 sets forth the nucleic acid sequence of an AAT 37-38 Fwd primer.

SEQ ID NO: 175 sets forth the nucleic acid sequence of an AAT 37-38 Fwd primer.

SEQ ID NO: 176 sets forth the nucleic acid sequence of an AAT 37-38 Rvs primer.

SEQ ID NO: 177 sets forth the nucleic acid sequence of an AAT 37-38 Rvs primer.

SEQ ID NO: 178 sets forth the nucleic acid sequence of an AAT 37-38 Rvs primer.

SEQ ID NO: 179 sets forth the nucleic acid sequence of an AAT 37-38 Rvs primer.

SEQ ID NO: 180 sets forth the nucleic acid sequence of an AAT 37-38 Rvs primer.

SEQ ID NO: 181 sets forth the nucleic acid sequence of an AAT 37-38 Rvs primer.

SEQ ID NO: 182 sets forth the nucleic acid sequence of an AAT 37-38 Rvs primer.

SEQ ID NO: 183 sets forth the nucleic acid sequence of an AAT 37-38 Rvs primer.

SEQ ID NO: 184 sets forth the nucleic acid sequence of an AAT 41-42 Fwd primer.

SEQ ID NO: 185 sets forth the nucleic acid sequence of an AAT 41-42 Rvs primer.

SEQ ID NO: 186 sets forth the nucleic acid sequence of an AAT 41-42 Rvs primer.

SEQ ID NO: 187 sets forth the nucleic acid sequence of an AAT 41-42 Rvs primer.

SEQ ID NO: 188 sets forth the nucleic acid sequence of an AAT 41-42 Rvs primer.

SEQ ID NO: 189 sets forth the nucleic acid sequence of an AAT 41-42 Rvs primer.

SEQ ID NO: 190 sets forth the nucleic acid sequence of an AAT 41-42 Rvs primer.

SEQ ID NO: 191 sets forth the nucleic acid sequence of an AAT 41-42 Rvs primer.

SEQ ID NO: 192 sets forth the nucleic acid sequence of an AAT 41-42 Rvs primer.

SEQ ID NO: 193 sets forth the nucleic acid sequence of an AAT 43-44 Fwd primer.

SEQ ID NO: 194 sets forth the nucleic acid sequence of an AAT 43-44 Fwd primer.

SEQ ID NO: 195 sets forth the nucleic acid sequence of an AAT 43-44 Fwd primer.

SEQ ID NO: 196 sets forth the nucleic acid sequence of an AAT 43-44 Fwd primer.

SEQ ID NO: 197 sets forth the nucleic acid sequence of an AAT 43-44 Rvs primer.

SEQ ID NO: 198 sets forth the nucleic acid sequence of an AAT 43-44 Rvs primer.

SEQ ID NO: 199 sets forth the nucleic acid sequence of an AAT 43-44 Rvs primer.

SEQ ID NO: 200 sets forth the nucleic acid sequence of an AAT 43-44 Rvs primer.

SEQ ID NO: 201 sets forth the nucleic acid sequence of an AAT 43-44 Rvs primer.

SEQ ID NO: 202 sets forth the nucleic acid sequence of an AAT 43-44 Rvs primer.

SEQ ID NO: 203 sets forth the nucleic acid sequence of an AAT 43-44 Rvs primer.

SEQ ID NO: 204 sets forth the nucleic acid sequence of an AAT 43-44 Rvs primer.

SEQ ID NO: 205 sets forth the nucleic acid sequence of a P1 probe.

SEQ ID NO: 206 sets forth the nucleic acid sequence of a F1 primer.

SEQ ID NO: 207 sets forth the nucleic acid sequence of a R1 primer.

SEQ ID NO: 208 sets forth the nucleic acid sequence of a P2 probe.

SEQ ID NO: 209 sets forth the nucleic acid sequence of a F2 primer.

SEQ ID NO: 210 sets forth the nucleic acid sequence of a R2 primer.

SEQ ID NO: 211 sets forth the nucleic acid sequence of a P3 probe.

SEQ ID NO: 212 sets forth the nucleic acid sequence of a F3 primer.

SEQ ID NO: 213 sets forth the nucleic acid sequence of a R3 primer.

SEQ ID NO: 214 sets forth the nucleic acid sequence of a P4 probe.

SEQ ID NO: 215 sets forth the nucleic acid sequence of a F4 primer,

SEQ ID NO: 216 sets forth the nucleic acid sequence of a R4 primer.

SEQ ID NO: 217 sets forth the nucleic acid sequence of an AAT33-34 Fwd primer.

SEQ ID NO: 218 sets forth the nucleic acid sequence of an AAT33-34 Rvs primer.

SEQ ID NO: 219 sets forth the nucleic acid sequence of an AAT33-34 Probe.

SEQ ID NO: 220 sets forth the nucleic acid sequence of an AAT35-36 Fwd primer.

SEQ ID NO: 221 sets forth the nucleic acid sequence of an AAT35-36 Rvs primer.

SEQ ID NO: 222 sets forth the nucleic acid sequence of an AAT35-36 Probe.

SEQ ID NO: 223 sets forth the nucleic acid sequence of an AAT37-38 Fwd primer.

SEQ ID NO: 224 sets forth the nucleic acid sequence of an AAT37-38 Rvs primer.

SEQ ID NO: 225 sets forth the nucleic acid sequence of an AAT37-38 Probe.

SEQ ID NO: 226 sets forth the nucleic acid sequence of an AAT41-42 Fwd primer.

SEQ ID NO: 227 sets forth the nucleic acid sequence of an AAT41-42 Rvs primer.

SEQ ID NO: 228 sets forth the nucleic acid sequence of an AAT41-42 Probe.

SEQ ID NO: 229 sets forth the nucleic acid sequence of an AAT43-44 Fwd primer

SEQ ID NO: 230 sets forth the nucleic acid sequence of an AAT43-44 Rvs primer.

SEQ ID NO: 231 sets forth the nucleic acid sequence of an AAT43-44 Probe.

SEQ ID NO: 232 sets forth the nucleic acid sequence of an AAT33-34 Fwd primer.

SEQ ID NO: 233 sets forth the nucleic acid sequence of an AAT33-34 Rvs primer.

SEQ ID NO: 234 sets forth the nucleic acid sequence of an AAT33-34 Probe.

SEQ ID NO: 235 sets forth the nucleic acid sequence of an AAT35-36 Fwd primer.

SEQ ID NO: 236 sets forth the nucleic acid sequence of an AAT35-36 Rvs primer.

SEQ ID NO: 237 sets forth the nucleic acid sequence of an AAT35-36 Probe.

SEQ ID NO: 238 sets forth the nucleic acid sequence of an AAT37-38 Fwd primer.

SEQ ID NO: 239 sets forth the nucleic acid sequence of an AAT37-38 Rvs primer.

SEQ ID NO: 240 sets forth the nucleic acid sequence of an AAT37-38 Probe.

SEQ ID NO: 241 sets forth the nucleic acid sequence of an AAT41-42 Fwd primer.

SEQ ID NO: 242 sets forth the nucleic acid sequence of an AAT41-42 Rvs primer

SEQ ID NO: 243 sets forth the nucleic acid sequence of an AAT41-42 Probe.

SEQ ID NO: 244 sets forth the nucleic acid sequence of an AAT43-44 Fwd primer.

SEQ ID NO: 245 sets forth the nucleic acid sequence of an AAT43-44 Rvs primer.

SEQ ID NO: 246 sets forth the nucleic acid sequence of an AAT43-44 Probe.

SEQ ID NO: 247 sets forth the nucleic acid sequence of an AAT33-34 Fwd primer for the indel assay of Example 6.

SEQ ID NO: 248 sets forth the nucleic acid sequence of an AAT33-34 Rev primer for the indel assay of example 6.

SEQ ID NO: 249 sets forth the nucleic acid sequence of an AAT33-34 Probe for the indel assay of Example 6.

SEQ ID NO: 250 sets forth the nucleic acid sequence of an AAT35-36 Fwd primer for the indel assay of example 6.

SEQ ID NO: 251 sets forth the nucleic acid sequence of an AAT35-36 Rev primer for the indel assay of example 6.

SEQ ID NO: 252 sets forth the nucleic acid sequence of an AAT35-36 Probe for the indel assay of Example 6.

SEQ ID NO: 253 sets forth the nucleic acid sequence of an AAT37-38 Fwd primer for the indel assay of example 6.

SEQ ID NO: 254 sets forth the nucleic acid sequence of an AAT37-38 Rev primer for the indel assay of example 6.

SEQ ID NO: 255 sets forth the nucleic acid sequence of an AAT37-38 Probe for the indel assay of Example 6.

SEQ ID NO: 256 sets forth the nucleic acid sequence of an AAT41-42 Fwd primer for the indel assay of example 6.

SEQ ID NO: 257 sets forth the nucleic acid sequence of an AAT41-42 Rev primer for the indel assay of example 6.

SEQ ID NO: 258 sets forth the nucleic acid sequence of an AAT41-42 Probe for the indel assay of Example 6.

SEQ ID NO: 259 sets forth the nucleic acid sequence of an AAT43-44 Fwd primer for the indel assay of example 6.

SEQ ID NO: 260 sets forth the nucleic acid sequence of an AAT43-44 Rev primer for the indel assay of example 6.

SEQ ID NO: 261 sets forth the nucleic acid sequence of an AAT43-44 Probe for the indel assay of Example 6, SEQ ID NO: 262 sets forth the nucleic acid sequence of an AAT Transcript fwd primer for the AAT transcript assay of Example 7.

SEQ ID NO: 263 sets forth the nucleic acid sequence of an AAT Transcript rev primer for the AAT transcript assay of Example 7.

SEQ ID NO: 264 sets forth the nucleic acid sequence of an WT AAT Transcript Probe for the AAT transcript assay of Example 7.

SEQ ID NO: 265 sets forth the nucleic acid sequence of an Z AAT Transcript Probe for the AAT transcript assay of Example 7.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally occurring or engineered enzymes, which cleave a phosphodiester bond within a polynucleotide chain. Engineered nucleases can include, without limitation, engineered meganucleases such as those described herein.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 1), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or 100% sequence identity to residues 154-197 of any one of SEQ ID NOs: 17-22, 41-46, 65-71, and 93-100.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered. Exemplary transfection techniques of the disclosure include, but are not limited to, electroporation and lipofection using Lipofectamine (e.g., Lipofectamine® MessengerMax (ThermoFisher)).

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term with respect to recombinant proteins, the term "modification" means any insertion, deletion, or substitution of an amino acid residue in the recombinant sequence relative to a reference sequence (e.g., a wild-type or a native sequence).

As used herein, the term "disrupted" or "disrupts" or "disrupts expression" or "disrupting a target sequence" refers to the introduction of a mutation (e.g., frameshift mutation) that interferes with the gene function and prevents expression and/or function of the polypeptide/expression product encoded thereby. For example, nuclease-mediated disruption of a gene can result in the expression of a truncated protein and/or expression of a protein that does not retain its wild-type function. Additionally, introduction of a donor template into a gene can result in no expression of an encoded protein, expression of a truncated protein, and/or expression of a protein that does not retain its wild-type function.

As used herein, the term "intron" refers to a nucleotide sequence within a gene that is removed from an RNA by RNA splicing prior to translation of the RNA. An intron in a DNA sequence refers to a nucleotide sequence that is transcribed during transcription and thus present in pre-mRNA, but removed from the pre-mRNA by splicing in the production of mature mRNA.

As used herein, the terms "recognition sequence" or "recognition site" refers to a DNA sequence that is bound and cleaved by a nuclease. In the case of a meganuclease, a recognition sequence comprises a pair of inverted, 9 base-pair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the term "target site" or "target sequence" refers to a region of the chromosomal DNA of a cell comprising a recognition sequence for a nuclease. This term embraces chromosomal DNA duplexes as well as single-stranded chromosomal DNA.

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" refers to the ability of a nuclease to bind and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art, such as unbiased identification of DSBs enabled by sequencing (GUIDE-seq), oligonucleotide (oligo) capture assay, whole genome sequencing, and long-range next generation sequencing of the recognition sequence. In some embodiments, specificity is measured using GUIDE-seq. As used herein, "specificity" is synonymous with a low incidence of cleavage of sequences different from the target sequences (non-target sequences), i.e., off-target cutting. A low incidence of off-target cutting may comprise an incidence of cleavage of non-target sequences of less than 25%, less than 20%, less than 18%, less than 15%, less than 12.5%, less than 10%, less than 9%, less than 8%, less than 7%, less than 6%, less than 5%, less than 4%, less than 3%, less than 2.5%, less than 2%, less than 1.5%, less than 1%, less than 0.75%, less than 0.5%, or less than 0.25%. Off-target cleavage by a meganuclease can be measured using any method known in the art, including for example, oligo capture analysis as described here, a T7 endonuclease (T7E) assay as described herein, digital PCR as described herein, targeted sequencing of particular off-target sites, exome sequencing, whole genome sequencing, direct in situ breaks labeling enrichment on streptavidin and next-generation sequencing (BLESS), genome-wide, GUIDE-seq, and linear amplification-mediated high-throughput genome-wide translocation sequencing (LAM-HTGTS) (see, e.g., Zischewski et al. (2017), Biotechnology Advances 35 (1): 95-104, which is incorporated by reference in its entirety).

As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2x, or 2x-10x) relative to a reference meganuclease.

As used herein, the term "efficiency of cleavage" refers to the incidence by which a meganuclease cleaves a recognition sequence in a double-stranded DNA molecule relative to the incidence of all cleavage events by the meganuclease on the DNA molecule. "Efficiency of cleavage" is synonymous with DNA editing efficiency or on-target editing. Efficiency of cleavage and/or indel formation by a meganuclease can be measured using any method known in the art, including T7E assay, digital PCR (ddPCR), mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35 (1): 95-104, which is incorporated by reference in its entirety). In some embodiments, efficiency of cleavage is measured by ddPCR. In some embodiments, the disclosed meganucleases generate efficiencies of cleavage of at least about 35%, 40%, 50%, 60%, 70%, 80%, 85%, 90%, 95%, 98%, or 99% at the recognition sequence.

As used herein, "SERPINA1 gene" refers to a gene encoding a polypeptide having antitrypsin activity, or a variant thereof, particularly the AAT polypeptide, which is also referred to as the serpin peptidase inhibitor, member 1. A SERPINA1 gene can include a human SERPINA1 gene (NCBI Accession No.: NM_000295, 5; Gene ID: 5265); cynomolgus monkey (*Macaca fascicularis*) SERPINA1 (NCBI Accession No.: XM 005562106. 2); and mouse (*Mus musculus*) SERPINA1, (NM_009243. 4). Additional examples of SERPINA1 mRNA sequences are readily available using publicly available databases, e.g., GenBank, UniProt, OMIM, and the *Macaca* genome project web site. The term SERPINA1 also refers to naturally occurring DNA sequence variations of the SERPINA1 gene, such as a single nucleotide polymorphism (SNP) in the SERPINA1 gene. Exemplary SNPs may be found through the publicly accessible National Center for Biotechnology Information dbSNP Short Genetic Variations database.

As used herein, the term "AAT polypeptide" refers to a polypeptide encoded by a SERPINA1 gene. The AAT polypeptide is also known as alpha-1-antitrypsin.

As used herein, the term "AAT deficiency" refers to an autosomal codominant disorder caused by a mutation in the SERPINA1 gene encoding AAT, a serine protease inhibitor, in which the mutation results in the expression of a mutant AAT protein with reduced ability to inhibit serine protease activity, and consequently results in increased serine protease activity.

An "indel", as used herein, refers to the insertion or deletion of a nucleobase within a nucleic acid, such as DNA. In some embodiments, it is desirable to generate one or more insertions or deletions (i.e., indels) in the nucleic acid, e.g., in a foreign nucleic acid such as viral DNA. Accordingly, as used herein, "efficiency of indel formation" refers to the incidence by which a meganuclease generates one or more indels through cleavage of a recognition sequence relative to the incidence of all cleavage events by the meganuclease on the DNA molecule. In some embodiments, efficiency of indel formation is measured by ddPCR. In some embodiments, the disclosed meganucleases generate efficiencies of indel formation of at least about 35%, 40%, 50%, 60%, 70%, 80%, 85%, 90%, 95%, 98%, or 99% at the recognition sequence. The disclosed meganucleases may generate efficiencies of cleavage and/or efficiencies of indel formation of at least about 60%, 61%, 62%, 63%, 64%, 65%, 66%, 67%, 68%, 69%, 70%, 71%, 72%, 73%, 74%, or 75% at the recognition sequence.

As used herein, the term "homologous recombination" or "HR" refers to the natural, cellular process in which a double-stranded DNA-break is repaired using a homologous DNA sequence as the repair template (see, e.g., Cahill et al. (2006), *Front. Biosci.* 11:1958-1976). The homologous DNA sequence may be an endogenous chromosomal sequence or an exogenous nucleic acid that was delivered to the cell.

As used herein, a "template nucleic acid," "donor nucleic acid," "donor template," or "donor polynucleotide" refers to a nucleic acid that is desired to be inserted into a cleavage site within a cell's genome. Such template nucleic acids or donor templates can comprise, for example, a transgene, such as an exogenous transgene, which encodes a protein of interest. The template nucleic acid or donor template can comprise 5' and 3' homology arms having homology to 5' and 3' sequences, respectively, that flank a cleavage site in the genome where insertion of the template is desired. Insertion can be accomplished, for example, by homology-directed repair (HDR).

As used herein, the term "non-homologous end-joining" or "NHEJ" refers to the natural, cellular process in which a double-stranded DNA-break is repaired by the direct joining of two non-homologous DNA segments (see, e.g., Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knockout a gene in a population of cells.

As used herein, the term "homology arms" or "sequences homologous to sequences flanking a nuclease cleavage site" refer to sequences flanking the 5' and 3' ends of a nucleic acid molecule, which promote insertion of the nucleic acid molecule into a cleavage site generated by a nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (World Wide Web at ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7 (1-2): 203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 17-22, 41-46, 65-71, and 93-100. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the disclosure, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 17-22, 41-46, 65-71, and 93-100. In certain embodiments, variable residues within a hypervariable region can further correspond to residues 48, 50, 59, or 72 of any one of any one of SEQ ID NOs: 17-22, 41-46, 65-71, and 93-100. In other embodiments, variable residues within a hypervariable region correspond to one or more of positions 215, 217, 219, 221, 223, 224, 229, 231, 233, 235, 237, 259, 261, 266, and 268 of any one of any one of SEQ ID NOs: 17-22, 41-46, 65-71, and 93-100. In certain embodiments, variable residues within a hypervariable region can further correspond to residues 41, 48, 50, 69, 71, 72, 73, 236, 239, 241, 255, 263, or 264 of any one of SEQ ID NOs: 17-22, 41-46, 65-71, and 93-100.

As used herein, the term "reference level" in the context of AAT protein or mRNA levels refers to a level of AAT protein or mRNA as measured in, for example, a control cell, control cell population or a control subject, at a previous time point in the control cell, the control cell population or the subject undergoing treatment (e.g., a pre-dose baseline level obtained from the control cell, control cell population or subject), or a pre-defined threshold level of AAT protein or mRNA (e.g., a threshold level identified through previous experimentation).

As used herein, the term "a control" or "a control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype. A control subject may comprise, for example: a wild-type subject, i.e., of the same genotype as the starting subject for the genetic alteration which resulted in the genetically-modified subject (e.g., a subject having the same mutation in a SERPINA1 gene), which is not exposed to conditions or stimuli or further genetic modifications that would induce expression of altered genotype or phenotype in the subject.

As used herein, the term "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the disclosure.

As used herein, a "vector" can also refer to a viral vector. Viral vectors can include, without limitation, retroviral vectors, lentiviral vectors, adenoviral vectors, and adeno-associated viral vectors (AAV).

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, the terms "treatment" or "treating a subject" refers to the administration of an engineered meganuclease described herein, or a polynucleotide encoding an engineered meganuclease described herein, or a pair of such engineered meganucleases or polynucleotides, to a subject having AAT deficiency for the purpose of increasing levels of wild-type AAT in the blood of the subject. In some embodiments, expression of a full-length and/or functional version of the AAT protein results from cleavage by one or more of the disclosed meganucleases, followed by homology-directed repair to insert a polynucleotide encoding functional AAT or a portion thereof into the SERPINA1 locus. In some embodiments, cleavage by one or more of the disclosed meganucleases generates a nonsense mutation (e.g., introduction of a stop codon) upstream from the nucleic acid sequence encoding the non-functional portion of AAT, such that translation of the non-functional portion of AAT is prevented.

As used herein, the term "gc/kg" or "gene copies/kilogram" refers to the number of copies of a nucleic acid sequence encoding an engineered meganuclease described herein, or the number of copies of a template nucleic acid described herein, per weight in kilograms of a subject that is administered a polynucleotide comprising the nucleic acid sequence or a polynucleotide comprising a template nucleic acid.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of an engineered meganuclease or pair of engineered meganucleases described herein, or polynucleotide or pair of polynucleotides encoding the same, or pharmaceutical compositions disclosed herein, in combination with a polynucleotide encoding functional AAT or a portion thereof, increases the level of expression of a functional AAT protein (e.g., a full-length AAT protein) and ameliorates at least one symptom associated with AAT deficiency.

As used herein, the term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values 20 and ≤2 if the variable is inherently continuous.

2.1 Principle of the Invention

The present invention is based, in part, on the hypothesis that engineered meganucleases can be designed to bind and cleave recognition sequences found within a SERPINA1 gene (e.g., the human SERPINA1 gene). In particular, the meganucleases described herein bind and cleave a target sequence within intron 1c of a SERPINA1 gene (i.e., the AAT 35-36, AAT 37-38, AAT 41-42, or AAT 43-44 recognition sequences). Once cleaved, a polynucleotide comprising homology arms at its 5' and 3' ends, with one homology arm having homology to a DNA sequence upstream from the cleavage site and the other homology arm having homology to a DNA sequence downstream from the cleavage site, is inserted into the SERPINA1 locus to generate a modified SERPINA1 gene that encodes a functional, full-length (e.g., wild-type) AAT protein. This process of DNA cleavage followed by insertion of a polynucleotide with homology to sequences flanking the cleavage site, known as homology-directed repair (HDR), can be used to introduce a DNA sequence encoding the functional protein, thereby correcting one or more mutations that result in expression of a non-functional AAT protein. As a result, it is expected that trypsin protease activity in the liver and lungs will be reduced due to inhibition by the encoded functional AAT protein, relative to protease activity prior to editing by meganuclease-mediated cleavage and HDR. Effectiveness of treatment may be evaluated by measurement of lung and liver function inflammation, which may be measured by changes in levels of inflammatory cytokines, such as IL-1β and TNF-α, levels of fluid and swelling in the lungs, and signs of cirrhosis in the liver, all of which are characteristic of AAT deficiency.

Thus, the present disclosure encompasses engineered meganucleases that bind and cleave a recognition sequence within the SERPINA1 gene. The present disclosure further provides methods comprising the delivery of an engineered protein, or nucleic acids encoding an engineered meganuclease, to a eukaryotic cell in order to produce a genetically-modified eukaryotic cell. Further, the present disclosure provides pharmaceutical compositions, methods for treatment of AAT deficiency, and methods for increasing levels of wild-type AAT in the liver, blood, and lungs of a subject, which utilize an engineered meganuclease having specificity for a recognition sequence positioned within the SERPINA1 gene and a DNA repair polynucleotide encoding a functional AAT protein or portion thereof, such that meganuclease-mediated cleavage and HDR by the DNA repair polynucleotide produces a SERPINA1 gene encoding a functional AAT protein. In addition, optimized generations of meganucleases that underwent significant protein engineering are disclosed herein, which demonstrate improved functional AAT protein insertion and reduced off target effects compared to first generation AAT meganucleases.

2.2 Meganucleases that Bind and Cleave Recognition Sequences within a SERPINA1 Gene

Recognition Sequences

It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-strand break in a target locus is known to stimulate homologous recombination, particularly of transgenic DNA sequences flanked by sequences that are homologous to the genomic target. In this manner, exogenous polynucleotides can be inserted into a target locus. Such exogenous polynucleotides can encode any sequence or polypeptide of interest.

In some particular embodiments, engineered meganucleases of the disclosure have been designed to bind and cleave an AAT 35-36 recognition sequence (SEQ ID NO: 9). Exemplary meganucleases that bind and cleave the AAT 35-36 recognition sequence are provided in SEQ ID NOs: 17-22. In other particular embodiments, engineered meganucleases of the disclosure have been designed to bind and cleave an AAT 37-38 recognition sequence (SEQ ID NO: 11). Exemplary meganucleases that bind and cleave the AAT 37-38 recognition sequence are provided in SEQ ID NOs: 41-46. In other particular embodiments, engineered meganucleases of the disclosure have been designed to bind and cleave an AAT 41-42 recognition sequence (SEQ ID NO: 13). Exemplary meganucleases that bind and cleave the AAT 41-42 recognition sequence are provided in SEQ ID NOs: 65-71. In other particular embodiments, engineered meganucleases of the disclosure have been designed to bind and cleave an AAT 43-44 recognition sequence (SEQ ID NO:

15). Exemplary meganucleases that bind and cleave the AAT 43-44 recognition sequence are provided in SEQ ID NOs: 93-100.

Exemplary Engineered Meganucleases

Engineered meganucleases of the disclosure comprise a first subunit, comprising a first hypervariable (HVR1) region, and a second subunit, comprising a second hypervariable (HVR2) region. Further, the first subunit binds to a first recognition half-site in the recognition sequence (e.g., the AAT35, AAT37, AAT41, or AAT43 half-site), and the second subunit binds to a second recognition half-site in the recognition sequence (e.g., the AAT36, AAT38, AAT42, or AAT44 half-site).

In particular embodiments, the meganucleases used to practice the disclosure are single-chain meganucleases. A single-chain meganuclease comprises an N-terminal subunit and a C-terminal subunit joined by a linker peptide. Each of the two subunits recognizes and binds to half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

As discussed, the meganucleases of the disclosure have been engineered to bind and cleave the AAT 35-36 recognition sequence (SEQ ID NO: 9), the AAT 37-38 recognition sequence (SEQ ID NO: 11), the AAT 41-42 recognition sequence (SEQ ID NO: 13), or the AAT 43-44 recognition sequence (SEQ ID NO: 15). The AAT 35-36, 37-38, 41-42, and 43-44 recognition sequences are each positioned within intron 1c of the human SERPINA1 gene. Such engineered meganucleases are collectively referred to herein as "AAT 35-36 meganucleases.", "AAT 37-38 meganucleases", "AAT 41-42 meganucleases", or "AAT 43-44 meganucleases", respectively.

In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit.

Exemplary AAT 35-36 meganucleases of the disclosure are provided in Table 1 and are further described below.

AAT 35-36x.70 (SEQ ID NO: 17)

In some embodiments, the HVR1 region comprises one or more residues corresponding to residues 24, 26, 28, 30, 32, 33, 38, 40, 42, 44, 46, 68, 70, 75, and 77 of SEQ ID NO: 17. In some embodiments, the HVR1 region comprises residues corresponding to residues 24, 26, 28, 30, 32, 33, 38, 40, 42, 44, 46, 68, 70, 75, and 77 of SEQ ID NO: 17. In some embodiments, the HVR1 region comprises a residue corresponding to residue 48 of SEQ ID NO: 17. In some embodiments, the HVR1 region comprises a residue corresponding to residue 50 of SEQ ID NO: 17. In some embodiments, the HVR1 region comprises a residue corresponding to residue 72 of SEQ ID NO: 17. In some embodiments, the HVR1 region comprises a residue corresponding to residue 73 of SEQ ID NO: 17. In some embodiments, the HVR1 region comprises Y, R, K, or D at a residue corresponding to residue 66 of SEQ ID NO: 17. In some embodiments, the HVR1 region comprises residues 24-79 of SEQ ID NO: 17.

In some embodiments, the first subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 17. In some embodiments, the first subunit comprises a residue corresponding to residue 19 of SEQ ID NO: 17. In some embodiments, the first subunit comprises G, S, or A at a residue corresponding to residue 19 of SEQ ID NO: 17. In some embodiments, the first subunit comprises E, Q, or K at a residue corresponding to residue 80 of SEQ ID NO: 17. In some embodiments, the first subunit comprises residues 7-153 of SEQ ID NO: 5.

In some embodiments, the HVR2 region comprises one or more residues corresponding to residues 215, 217, 219, 221, 223, 224, 229, 231, 233, 235, 237, 259, 261, 266, and 268 of SEQ ID NO: 17. In some embodiments, the HVR2 region comprises residues corresponding to residues 215, 217, 219, 221, 223, 224, 229, 231, 233, 235, 237, 259, 261, 266, and 268 of SEQ ID NO: 17. In some embodiments, the HVR2 region comprises Y, R, K, or D at a residue corresponding to residue 257 of SEQ ID NO: 17. In some embodiments, the HVR2 region comprises residues 215-270 of SEQ ID NO: 17.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 17. In some embodiments, the second subunit comprises a residue corresponding to residue 271 of SEQ ID NO: 17. In some embodiments, the second

TABLE 1

| Meganuclease | AA SEQ ID | *% ID | AAT35 Subunit Residues | AAT35 Subunit SEQ ID | *AAT35 Subunit % | AAT36 Subunit Residues | AAT36 Subunit SEQ ID | *AAT36 Subunit % |
|---|---|---|---|---|---|---|---|---|
| AAT 35-36x.70 | 17 | 100 | 7-153 | 23 | 100 | 198-344 | 29 | 100 |
| AAT 35-36x.49 | 18 | 96.33 | 7-153 | 24 | 95.92 | 198-344 | 30 | 95.24 |
| AAT 35-36x.79 | 19 | 98.02 | 7-153 | 25 | 97.28 | 198-344 | 31 | 97.96 |
| AAT 35-36L.141 | 20 | 97.74 | 7-153 | 26 | 95.92 | 198-344 | 32 | 98.64 |
| AAT 35-36L.210 | 21 | 96.61 | 7-153 | 27 | 95.24 | 198-344 | 33 | 96.6 |
| AAT 35-36L.290 | 22 | 96.89 | 7-153 | 28 | 95.24 | 198-344 | 34 | 97.28 |

*"% ID" represents the amino acid sequence identity between the full-length sequence of each meganuclease and the AAT 35-36x.70 meganuclease. "AAT35 Subunit %" and "AAT36 Subunit %" represent the amino acid sequence identity between the AAT35-binding and AAT36-binding subunit regions of each meganuclease and the AAT35-binding and AAT36-binding subunit regions, respectively, of the AAT 35-36x.70 meganuclease.

subunit comprises a residue corresponding to residue 330 of SEQ ID NO: 17. In some embodiments, the second subunit comprises G, S, or A at a residue corresponding to residue 210 of SEQ ID NO: 17. In some embodiments, the second subunit comprises E, Q, or K at a residue corresponding to residue 271 of SEQ ID NO: 17. In some embodiments, the second subunit comprises residues 198-344 of SEQ ID NO: 17.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 17. In some embodiments, the engineered meganuclease comprises an amino acid sequence of SEQ ID NO: 17.

In some embodiments, the engineered meganuclease is encoded by a nucleic sequence having at least at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 35. In some embodiments, the engineered meganuclease is encoded by a nucleic acid sequence of SEQ ID NO: 35.

AAT 35-36x.49 (SEQ ID NO: 18)

In some embodiments, the HVR1 region comprises one or more residues corresponding to residues 24, 26, 28, 30, 32, 33, 38, 40, 42, 44, 46, 68, 70, 75, and 77 of SEQ ID NO: 18. In some embodiments, the HVR1 region comprises residues corresponding to residues 24, 26, 28, 30, 32, 33, 38, 40, 42, 44, 46, 68, 70, 75, and 77 of SEQ ID NO: 18. In some embodiments, the HVR1 region comprises a residue corresponding to residue 50 of SEQ ID NO: 18. In some embodiments, the HVR1 region comprises a residue corresponding to residue 72 of SEQ ID NO: 18. In some embodiments, the HVR1 region comprises a residue corresponding to residue 73 of SEQ ID NO: 18. In some embodiments, the HVR1 region comprises Y, R. K, or D at a residue corresponding to residue 66 of SEQ ID NO: 18. In some embodiments, the HVR1 region comprises residues 24-79 of SEQ ID NO: 18.

In some embodiments, the first subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 18. In some embodiments, the first subunit comprises a residue corresponding to residue 19 of SEQ ID NO: 18. In some embodiments, the first subunit comprises E, Q, or K at a residue corresponding to residue 80 of SEQ ID NO: 18. In some embodiments, the first subunit comprises a residue corresponding to residue 80 of SEQ ID NO: 18. In some embodiments, the first subunit comprises G, S, or A at a residue corresponding to residue 19 of SEQ ID NO: 18. In some embodiments, the first subunit comprises residues 7-153 of SEQ ID NO: 18.

In some embodiments, the HVR2 region comprises one or more residues corresponding to residues 215, 217, 219, 221, 223, 224, 229, 231, 233, 235, 237, 259, 261, 266, and 268 of SEQ ID NO: 18. In some embodiments, the HVR2 region comprises residues corresponding to residues 215, 217, 219, 221, 223, 224, 229, 231, 233, 235, 237, 259, 261, 266, and 268 of SEQ ID NO: 18. In some embodiments, the HVR2 region comprises Y, R, K, or D at a residue corresponding to residue 257 of SEQ ID NO: 18. In some embodiments, the HVR2 region comprises residues 215-270 of SEQ ID NO: 18.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 18. In some embodiments, the second subunit comprises a residue corresponding to residue 271 of SEQ ID NO: 18. In some embodiments, the second subunit comprises a residue corresponding to residue 330 of SEQ ID NO: 18. In some embodiments, the second subunit comprises G, S, or A at a residue corresponding to residue 210 of SEQ ID NO: 18. In some embodiments, the second subunit comprises E, Q, or K at a residue corresponding to residue 271 of SEQ ID NO: 18. In some embodiments, the second subunit comprises residues 198-344 of SEQ ID NO: 18.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 18. In some embodiments, the engineered meganuclease comprises an amino acid sequence of SEQ ID NO: 18.

In some embodiments, the engineered meganuclease is encoded by a nucleic sequence having at least at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 36. In some embodiments, the engineered meganuclease is encoded by a nucleic acid sequence of SEQ ID NO: 36.

AAT 35-36L.79 (SEQ ID NO: 19)

In some embodiments, the HVR1 region comprises one or more residues corresponding to residues 24, 26, 28, 30, 32, 33, 38, 40, 42, 44, 46, 68, 70, 75, and 77 of SEQ ID NO: 19. In some embodiments, the HVR1 region comprises residues corresponding to residues 24, 26, 28, 30, 32, 33, 38, 40, 42, 44, 46, 68, 70, 75, and 77 of SEQ ID NO: 19. In some embodiments, the HVR1 region comprises a residue corresponding to residue 50 of SEQ ID NO: 19. In some embodiments, the HVR1 region comprises a residue corresponding to residue 72 of SEQ ID NO: 19. In some embodiments, the HVR1 region comprises a residue corresponding to residue 73 of SEQ ID NO: 19. In some embodiments, the HVR1 region comprises Y, R, K, or D at a residue corresponding to residue 66 of SEQ ID NO: 19. In some embodiments, the HVR1 region comprises residues 24-79 of SEQ ID NO: 19.

In some embodiments, the first subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 19. In some embodiments, the first subunit comprises a residue corresponding to residue 19 of SEQ ID NO: 19. In some embodiments, the first subunit comprises G, S, or A at a residue corresponding to residue 19 of SEQ ID NO: 19. In some embodiments, the first subunit comprises E, Q, or K at a residue corresponding to residue 80 of SEQ ID NO: 19. In some embodiments, the first subunit comprises residues 7-153 of SEQ ID NO: 5.

In some embodiments, the HVR2 region comprises one or more residues corresponding to residues 215, 217, 219, 221, 223, 224, 229, 231, 233, 235, 237, 259, 261, 266, and 268 of SEQ ID NO: 19. In some embodiments, the HVR2 region comprises residues corresponding to residues 215, 217, 219, 221, 223, 224, 229, 231, 233, 235, 237, 259, 261, 266, and 268 of SEQ ID NO: 19. In some embodiments, the HVR2 region comprises Y, R, K, or D at a residue corresponding to residue 257 of SEQ ID NO: 19. In some embodiments, the HVR2 region comprises residues 215-270 of SEQ ID NO: 19.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 19. In some embodiments, the second subunit comprises G, S, or A at a residue corresponding to residue 210 of SEQ ID NO: 19. In some embodiments, the second subunit comprises E, Q, or K at a residue corresponding to residue 271 of SEQ ID NO: 19. In some embodiments, the second subunit comprises residues 198-344 of SEQ ID NO: 19.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 19. In some embodiments, the engineered meganuclease comprises an amino acid sequence of SEQ ID NO: 19.

In some embodiments, the engineered meganuclease is encoded by a nucleic sequence having at least at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 37. In some embodiments, the engineered meganuclease is encoded by a nucleic acid sequence of SEQ ID NO: 37.

AAT 35-36L.141 (SEQ ID NO: 20)

In some embodiments, the HVR1 region comprises one or more residues corresponding to residues 24, 26, 28, 30, 32, 33, 38, 40, 42, 44, 46, 68, 70, 75, and 77 of SEQ ID NO: 20. In some embodiments, the HVR1 region comprises residues corresponding to residues 24, 26, 28, 30, 32, 33, 38, 40, 42, 44, 46, 68, 70, 75, and 77 of SEQ ID NO: 20. In some embodiments, the HVR1 region comprises a residue corresponding to residue 50 of SEQ ID NO: 20. In some embodiments, the HVR1 region comprises a residue corresponding to residue 72 of SEQ ID NO: 20. In some embodiments, the HVR1 region comprises a residue corresponding to residue 73 of SEQ ID NO: 20. In some embodiments, the HVR1 region comprises Y, R. K, or D at a residue corresponding to residue 66 of SEQ ID NO: 20. In some embodiments, the HVR1 region comprises residues 24-79 of SEQ ID NO: 20.

In some embodiments, the first subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 20. In some embodiments, the first subunit comprises a residue corresponding to residue 19 of SEQ ID NO: 20. In some embodiments, the first subunit comprises G, S, or A at a residue corresponding to residue 19 of SEQ ID NO: 20. In some embodiments, the first subunit comprises E, Q, or K at a residue corresponding to residue 80 of SEQ ID NO: 20. In some embodiments, the first subunit comprises residues 7-153 of SEQ ID NO: 5.

In some embodiments, the HVR2 region comprises one or more residues corresponding to residues 215, 217, 219, 221, 223, 224, 229, 231, 233, 235, 237, 259, 261, 266, and 268 of SEQ ID NO: 20. In some embodiments, the HVR2 region comprises residues corresponding to residues 215, 217, 219, 221, 223, 224, 229, 231, 233, 235, 237, 259, 261, 266, and 268 of SEQ ID NO: 20. In some embodiments, the HVR2 region comprises Y, R, K, or D at a residue corresponding to residue 257 of SEQ ID NO: 20. In some embodiments, the HVR2 region comprises residues 215-270 of SEQ ID NO: 20.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 20. In some embodiments, the second subunit comprises a residue corresponding to residue 271 of SEQ ID NO: 20. In some embodiments, the second subunit comprises a residue corresponding to residue 330 of SEQ ID NO: 20. In some embodiments, the second subunit comprises G, S, or A at a residue corresponding to residue 210 of SEQ ID NO: 20. In some embodiments, the second subunit comprises E, Q, or K at a residue corresponding to residue 271 of SEQ ID NO: 20. In some embodiments, the second subunit comprises residues 198-344 of SEQ ID NO: 20.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 20. In some embodiments, the engineered meganuclease comprises an amino acid sequence of SEQ ID NO: 20.

In some embodiments, the engineered meganuclease is encoded by a nucleic sequence having at least at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 38. In some embodiments, the engineered meganuclease is encoded by a nucleic acid sequence of SEQ ID NO: 38.

AAT 35-36L.210 (SEQ ID NO: 21)

In some embodiments, the HVR1 region comprises one or more residues corresponding to residues 24, 26, 28, 30, 32, 33, 38, 40, 42, 44, 46, 68, 70, 75, and 77 of SEQ ID NO: 21. In some embodiments, the HVR1 region comprises residues corresponding to residues 24, 26, 28, 30, 32, 33, 38, 40, 42, 44, 46, 68, 70, 75, and 77 of SEQ ID NO: 21. In some embodiments, the HVR1 region comprises a residue corresponding to residue 50 of SEQ ID NO: 21. In some embodiments, the HVR1 region comprises a residue corresponding to residue 72 of SEQ ID NO: 21. In some embodiments, the HVR1 region comprises a residue corresponding to residue 73 of SEQ ID NO: 21. In some embodiments, the HVR1 region comprises Y, R, K, or D at a residue corresponding to residue 66 of SEQ ID NO: 21. In some embodiments, the HVR1 region comprises residues 24-79 of SEQ ID NO: 21.

In some embodiments, the first subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 21. In some embodiments, the first subunit comprises a residue corresponding to residue 19 of SEQ ID NO: 21. In some embodiments, the first subunit comprises G, S, or A at a residue corresponding to residue 19 of SEQ ID NO: 21. In some embodiments, the first subunit comprises E, Q, or K at a residue corresponding to residue 80 of SEQ ID NO: 21. In some embodiments, the first subunit comprises residues 7-153 of SEQ ID NO: 5.

In some embodiments, the HVR2 region comprises one or more residues corresponding to residues 215, 217, 219, 221, 223, 224, 229, 231, 233, 235, 237, 259, 261, 266, and 268 of SEQ ID NO: 21. In some embodiments, the HVR2 region comprises residues corresponding to residues 215, 217, 219, 221, 223, 224, 229, 231, 233, 235, 237, 259, 261, 266, and 268 of SEQ ID NO: 21. In some embodiments, the HVR2 region comprises Y, R, K, or D at a residue corresponding to residue 257 of SEQ ID NO: 21. In some embodiments, the HVR2 region comprises a residue corresponding to residue 264 of SEQ ID NO: 21. In some embodiments, the HVR2 region comprises residues 215-270 of SEQ ID NO: 21.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 21. In some embodiments, the second subunit comprises a residue corresponding to residue 330 of SEQ ID NO: 21. In some embodiments, the second subunit comprises G, S, or A at a residue corresponding to residue 210 of SEQ ID NO: 21. In some embodiments, the second subunit comprises E, Q, or K at a residue corresponding to residue 271 of SEQ ID NO: 21. In some embodiments, the second subunit comprises residues 198-344 of SEQ ID NO: 21.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 21. In some embodiments, the engineered meganuclease comprises an amino acid sequence of SEQ ID NO: 21.

In some embodiments, the engineered meganuclease is encoded by a nucleic sequence having at least at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 39. In some embodiments, the engineered meganuclease is encoded by a nucleic acid sequence of SEQ ID NO: 39.

AAT 35-36L.290 (SEQ ID NO: 22)

In some embodiments, the HVR1 region comprises one or more residues corresponding to residues 24, 26, 28, 30, 32, 33, 38, 40, 42, 44, 46, 68, 70, 75, and 77 of SEQ ID NO: 22. In some embodiments, the HVR1 region comprises residues corresponding to residues 24, 26, 28, 30, 32, 33, 38, 40, 42, 44, 46, 68, 70, 75, and 77 of SEQ ID NO: 22. In some embodiments, the HVR1 region comprises a residue corresponding to residue 41 of SEQ ID NO: 22. In some embodiments, the HVR1 region comprises a residue corresponding to residue 50 of SEQ ID NO: 22. In some embodiments, the HVR1 region comprises a residue corresponding to residue 72 of SEQ ID NO: 22. In some embodiments, the HVR1 region comprises a residue corresponding to residue 73 of SEQ ID NO: 22. In some embodiments, the HVR1 region comprises Y, R, K, or D at a residue corresponding to residue 66 of SEQ ID NO: 22. In some embodiments, the HVR1 region comprises residues 24-79 of SEQ ID NO: 22.

In some embodiments, the first subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 22. In some embodiments, the first subunit comprises a residue corresponding to residue 19 of SEQ ID NO: 22. In some embodiments, the first subunit comprises G, S, or A at a residue corresponding to residue 19 of SEQ ID NO: 22. In some embodiments, the first subunit comprises E, Q, or K at a residue corresponding to residue 80 of SEQ ID NO: 22. In some embodiments, the first subunit comprises residues 7-153 of SEQ ID NO: 5.

In some embodiments, the HVR2 region comprises one or more residues corresponding to residues 215, 217, 219, 221, 223, 224, 229, 231, 233, 235, 237, 259, 261, 266, and 268 of SEQ ID NO: 22. In some embodiments, the HVR2 region comprises residues corresponding to residues 215, 217, 219, 221, 223, 224, 229, 231, 233, 235, 237, 259, 261, 266, and 268 of SEQ ID NO: 22. In some embodiments, the HVR2 region comprises Y, R, K, or D at a residue corresponding to residue 257 of SEQ ID NO: 22. In some embodiments, the HVR2 region comprises a residue corresponding to residue 264 of SEQ ID NO: 22. In some embodiments, the HVR2 region comprises residues 215-270 of SEQ ID NO: 22.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 22. In some embodiments, the second subunit comprises a residue corresponding to residue 271 of SEQ ID NO: 22. In some embodiments, the second subunit comprises a residue corresponding to residue 330 of SEQ ID NO: 22. In some embodiments, the second subunit comprises G, S, or A at a residue corresponding to residue 210 of SEQ ID NO: 22. In some embodiments, the second subunit comprises E, Q, or K at a residue corresponding to residue 271 of SEQ ID NO: 22. In some embodiments, the second subunit comprises residues 198-344 of SEQ ID NO: 22.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 22. In some embodiments, the engineered meganuclease comprises an amino acid sequence of SEQ ID NO: 22.

In some embodiments, the engineered meganuclease is encoded by a nucleic sequence having at least at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 40. In some embodiments, the engineered meganuclease is encoded by a nucleic acid sequence of SEQ ID NO: 40.

Exemplary AAT 37-38 meganucleases of the disclosure are provided in Table 2 and are further described below.

221, 223, 224, 229, 231, 233, 235, 237, 259, 261, 266, and 268 of SEQ ID NO: 41. In some embodiments, the HVR2 region comprises Y, R, K, or D at a residue corresponding to residue 257 of SEQ ID NO: 41. In some embodiments, the HVR2 region comprises residues 215-270 of SEQ ID NO: 41.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 41. In some embodiments, the second subunit comprises a residue corresponding to residue 271 of SEQ ID NO: 41. In some embodiments, the second subunit

TABLE 2

| Meganuclease | AA SEQ ID | *% ID | AAT37 Subunit Residues | AAT37 Subunit SEQ ID | *AAT37 Subunit % | AAT38 Subunit Residues | AAT38 Subunit SEQ ID | *AAT38 Subunit % |
|---|---|---|---|---|---|---|---|---|
| AAT 37-38x.50 | 41 | 100 | 7-153 | 47 | 100 | 198-344 | 53 | 100 |
| AAT 37-38x.61 | 42 | 96.05 | 7-153 | 48 | 90.48 | 198-344 | 54 | 100 |
| AAT 37-38L.158 | 43 | 98.59 | 7-153 | 49 | 97.28 | 198-344 | 55 | 99.32 |
| AAT 37-38L.167 | 44 | 97.74 | 7-153 | 50 | 95.92 | 198-344 | 56 | 98.64 |
| AAT 37-38L.175 | 45 | 98.02 | 7-153 | 51 | 96.6 | 198-344 | 57 | 98.64 |
| AAT 37-38L.262 | 46 | 96.61 | 7-153 | 52 | 94.56 | 198-344 | 58 | 97.28 |

*"% ID" represents the amino acid sequence identity between the full-length sequence of each meganuclease and the AAT 37-38x.50 meganuclease. "AAT37 Subunit %" and "AAT38 Subunit %" represent the amino acid sequence identity between the AAT37-binding and AAT38-binding subunit regions of each meganuclease and the AAT37-binding and AAT38-binding subunit regions, respectively, of the AAT 37-38x.50 meganuclease.

AAT 37-38x.50 (SEQ ID NO: 41)

In some embodiments, the HVR1 region comprises one or more residues corresponding to residues 24, 26, 28, 30, 32, 33, 38, 40, 42, 44, 46, 68, 70, 75, and 77 of SEQ ID NO: 41. In some embodiments, the HVR1 region comprises residues corresponding to residues 24, 26, 28, 30, 32, 33, 38, 40, 42, 44, 46, 68, 70, 75, and 77 of SEQ ID NO: 41. In some embodiments, the HVR1 region comprises a residue corresponding to residue 50 of SEQ ID NO: 41. In some embodiments, the HVR1 region comprises a residue corresponding to residue 72 of SEQ ID NO: 41. In some embodiments, the HVR1 region comprises a residue corresponding to residue 73 of SEQ ID NO: 41. In some embodiments, the HVR1 region comprises Y, R, K, or D at a residue corresponding to residue 66 of SEQ ID NO: 41. In some embodiments, the HVR1 region comprises residues 24-79 of SEQ ID NO: 41.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 41. In some embodiments, the first subunit comprises a residue corresponding to residue 19 of SEQ ID NO: 41. In some embodiments, the first subunit comprises a residue corresponding to residue 80 of SEQ ID NO: 41. In some embodiments, the first subunit comprises G, S, or A at a residue corresponding to residue 19 of SEQ ID NO: 41. In some embodiments, the first subunit comprises E, Q, or K at a residue corresponding to residue 80 of SEQ ID NO: 41. In some embodiments, the first subunit comprises residues 7-153 of SEQ ID NO: 41.

In some embodiments, the HVR2 region comprises one or more residues corresponding to residues 215, 217, 219, 221, 223, 224, 229, 231, 233, 235, 237, 259, 261, 266, and 268 of SEQ ID NO: 41. In some embodiments, the HVR2 region comprises residues corresponding to residues 215, 217, 219, comprises G, S, or A at a residue corresponding to residue 210 of SEQ ID NO: 41. In some embodiments, the second subunit comprises E, Q, or K at a residue corresponding to residue 271 of SEQ ID NO: 41. In some embodiments, the second subunit comprises residues 198-344 of SEQ ID NO: 41.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 41. In some embodiments, the engineered meganuclease comprises an amino acid sequence of SEQ ID NO: 41.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 59. In some embodiments, the engineered meganuclease is encoded by a nucleic acid sequence of SEQ ID NO: 59.

AAT 37-38x.61 (SEQ ID NO: 42)

In some embodiments, the HVR1 region comprises one or more residues corresponding to residues 24, 26, 28, 30, 32, 33, 38, 40, 42, 44, 46, 68, 70, 75, and 77 of SEQ ID NO: 42. In some embodiments, the HVR1 region comprises residues corresponding to residues 24, 26, 28, 30, 32, 33, 38, 40, 42, 44, 46, 68, 70, 75, and 77 of SEQ ID NO: 42. In some embodiments, the HVR1 region comprises a residue corresponding to residue 50 of SEQ ID NO: 42. In some embodiments, the HVR1 region comprises Y, R. K, or D at a residue corresponding to residue 66 of SEQ ID NO: 42. In some embodiments, the HVR1 region comprises residues 24-79 of SEQ ID NO: 42.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 42. In some embodiments, the first subunit comprises a residue corresponding to residue 19 of SEQ ID NO: 42. In some embodiments, the first subunit comprises a residue corresponding to residue 129 of SEQ ID NO: 42. In some embodiments, the first subunit comprises G, S, or A at a residue corresponding to residue 19 of SEQ ID NO: 42. In some embodiments, the first subunit comprises E, Q, or K at a residue corresponding to residue 80 of SEQ ID NO: 42. In some embodiments, the first subunit comprises residues 7-153 of SEQ ID NO: 42.

In some embodiments, the HVR2 region comprises one or more residues corresponding to residues 215, 217, 219, 221, 223, 224, 229, 231, 233, 235, 237, 259, 261, 266, and 268 of SEQ ID NO: 42. In some embodiments, the HVR2 region comprises residues corresponding to residues 215, 217, 219, 221, 223, 224, 229, 231, 233, 235, 237, 259, 261, 266, and 268 of SEQ ID NO: 42. In some embodiments, the HVR2 region comprises Y, R, K, or D at a residue corresponding to residue 257 of SEQ ID NO: 42. In some embodiments, the HVR2 region comprises residues 215-270 of SEQ ID NO: 42.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 42. In some embodiments, the second subunit comprises a residue corresponding to residue 271 of SEQ ID NO: 42. In some embodiments, the second subunit comprises G, S, or A at a residue corresponding to residue 210 of SEQ ID NO: 42. In some embodiments, the second subunit comprises E, Q, or K at a residue corresponding to residue 271 of SEQ ID NO: 42. In some embodiments, the second subunit comprises residues 198-344 of SEQ ID NO: 42.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 42. In some embodiments, the engineered meganuclease comprises an amino acid sequence of SEQ ID NO: 42.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 60. In some embodiments, the engineered meganuclease is encoded by a nucleic acid sequence of SEQ ID NO: 60.

AAT 37-38L.158 (SEQ ID NO: 43)

In some embodiments, the HVR1 region comprises one or more residues corresponding to residues 24, 26, 28, 30, 32, 33, 38, 40, 42, 44, 46, 68, 70, 75, and 77 of SEQ ID NO: 43. In some embodiments, the HVR1 region comprises residues corresponding to residues 24, 26, 28, 30, 32, 33, 38, 40, 42, 44, 46, 68, 70, 75, and 77 of SEQ ID NO: 43. In some embodiments, the HVR1 region comprises a residue corresponding to residue 50 of SEQ ID NO: 43. In some embodiments, the HVR1 region comprises a residue corresponding to residue 72 of SEQ ID NO: 43. In some embodiments, the HVR1 region comprises a residue corresponding to residue 73 of SEQ ID NO: 43. In some embodiments, the HVR1 region comprises Y, R, K, or D at a residue corresponding to residue 66 of SEQ ID NO: 43. In some embodiments, the HVR1 region comprises residues 24-79 of SEQ ID NO: 43.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 43. In some embodiments, the first subunit comprises a residue corresponding to residue 19 of SEQ ID NO: 43. In some embodiments, the first subunit comprises G, S, or A at a residue corresponding to residue 19 of SEQ ID NO: 43. In some embodiments, the first subunit comprises E, Q, or K at a residue corresponding to residue 80 of SEQ ID NO: 43. In some embodiments, the first subunit comprises residues 7-153 of SEQ ID NO: 43.

In some embodiments, the HVR2 region comprises one or more residues corresponding to residues 215, 217, 219, 221, 223, 224, 229, 231, 233, 235, 237, 259, 261, 266, and 268 of SEQ ID NO: 43. In some embodiments, the HVR2 region comprises residues corresponding to residues 215, 217, 219, 221, 223, 224, 229, 231, 233, 235, 237, 259, 261, 266, and 268 of SEQ ID NO: 43. In some embodiments, the HVR2 region comprises Y, R, K, or D at a residue corresponding to residue 257 of SEQ ID NO: 43. In some embodiments, the HVR2 region comprises residues 215-270 of SEQ ID NO: 43.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 43. In some embodiments, the second subunit comprises a residue corresponding to residue 271 of SEQ ID NO: 43. In some embodiments, the second subunit comprises G, S, or A at a residue corresponding to residue 210 of SEQ ID NO: 43. In some embodiments, the second subunit comprises E, Q, or K at a residue corresponding to residue 271 of SEQ ID NO: 43. In some embodiments, the second subunit comprises residues 198-344 of SEQ ID NO: 43.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 43. In some embodiments, the engineered meganuclease comprises an amino acid sequence of SEQ ID NO: 43.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 61. In some embodiments, the engineered meganuclease is encoded by a nucleic acid sequence of SEQ ID NO: 61.

AAT 37-38L.167 (SEQ ID NO: 44)

In some embodiments, the HVR1 region comprises one or more residues corresponding to residues 24, 26, 28, 30, 32, 33, 38, 40, 42, 44, 46, 68, 70, 75, and 77 of SEQ ID NO: 44. In some embodiments, the HVR1 region comprises residues corresponding to residues 24, 26, 28, 30, 32, 33, 38, 40, 42, 44, 46, 68, 70, 75, and 77 of SEQ ID NO: 44. In some embodiments, the HVR1 region comprises a residue corresponding to residue 50 of SEQ ID NO: 44. In some embodiments, the HVR1 region comprises a residue corresponding to residue 72 of SEQ ID NO: 44. In some embodiments, the HVR1 region comprises a residue corresponding to residue 73 of SEQ ID NO: 44. In some embodiments, the HVR1 region comprises Y, R. K, or D at a residue corresponding to residue 66 of SEQ ID NO: 44. In some embodiments, the HVR1 region comprises residues 24-79 of SEQ ID NO: 44.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 44. In some embodiments, the first subunit comprises a residue corresponding to residue 19 of SEQ ID NO: 44. In some embodiments, the first subunit comprises G, S, or A at a residue corresponding to residue 19 of SEQ ID NO: 44. In some embodiments, the first subunit comprises E, Q, or K at a residue corresponding to residue 80 of SEQ ID NO: 44. In some embodiments, the first subunit comprises residues 7-153 of SEQ ID NO: 44.

In some embodiments, the HVR2 region comprises one or more residues corresponding to residues 215, 217, 219, 221, 223, 224, 229, 231, 233, 235, 237, 259, 261, 266, and 268 of SEQ ID NO: 44. In some embodiments, the HVR2 region comprises residues corresponding to residues 215, 217, 219, 221, 223, 224, 229, 231, 233, 235, 237, 259, 261, 266, and 268 of SEQ ID NO: 44. In some embodiments, the HVR2 region comprises Y, R, K, or D at a residue corresponding to residue 257 of SEQ ID NO: 44. In some embodiments, the HVR2 region comprises residues 215-270 of SEQ ID NO: 44.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 44. In some embodiments, the second subunit comprises a residue corresponding to residue 271 of SEQ ID NO: 44. In some embodiments, the second subunit comprises G, S, or A at a residue corresponding to residue 210 of SEQ ID NO: 44. In some embodiments, the second subunit comprises E, Q, or K at a residue corresponding to residue 271 of SEQ ID NO: 44. In some embodiments, the second subunit comprises residues 198-344 of SEQ ID NO: 44.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 44. In some embodiments, the engineered meganuclease comprises an amino acid sequence of SEQ ID NO: 44.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 62. In some embodiments, the engineered meganuclease is encoded by a nucleic acid sequence of SEQ ID NO: 62.

AAT 37-38L.175 (SEQ ID NO: 45)

In some embodiments, the HVR1 region comprises one or more residues corresponding to residues 24, 26, 28, 30, 32, 33, 38, 40, 42, 44, 46, 68, 70, 75, and 77 of SEQ ID NO: 45. In some embodiments, the HVR1 region comprises residues corresponding to residues 24, 26, 28, 30, 32, 33, 38, 40, 42, 44, 46, 68, 70, 75, and 77 of SEQ ID NO: 45. In some embodiments, the HVR1 region comprises a residue corresponding to residue 50 of SEQ ID NO: 45. In some embodiments, the HVR1 region comprises a residue corresponding to residue 72 of SEQ ID NO: 45. In some embodiments, the HVR1 region comprises a residue corresponding to residue 73 of SEQ ID NO: 45. In some embodiments, the HVR1 region comprises Y, R, K, or D at a residue corresponding to residue 66 of SEQ ID NO: 45 In some embodiments, the HVR1 region comprises residues 24-79 of SEQ ID NO: 45.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 45. In some embodiments, the first subunit comprises a residue corresponding to residue 19 of SEQ ID NO: 45. In some embodiments, the first subunit comprises G, S, or A at a residue corresponding to residue 19 of SEQ ID NO: 45. In some embodiments, the first subunit comprises E, Q, or K at a residue corresponding to residue 80 of SEQ ID NO: 45. In some embodiments, the first subunit comprises residues 7-153 of SEQ ID NO: 45.

In some embodiments, the HVR2 region comprises one or more residues corresponding to residues 215, 217, 219, 221, 223, 224, 229, 231, 233, 235, 237, 259, 261, 266, and 268 of SEQ ID NO: 45. In some embodiments, the HVR2 region comprises residues corresponding to residues 215, 217, 219, 221, 223, 224, 229, 231, 233, 235, 237, 259, 261, 266, and 268 of SEQ ID NO: 45. In some embodiments, the HVR2 region comprises Y, R, K, or D at a residue corresponding to residue 257 of SEQ ID NO: 45. In some embodiments, the HVR2 region comprises residues 215-270 of SEQ ID NO: 45.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 45. In some embodiments, the second subunit comprises a residue corresponding to residue 271 of SEQ ID NO: 45. In some embodiments, the second subunit comprises G, S, or A at a residue corresponding to residue 210 of SEQ ID NO: 45. In some embodiments, the second subunit comprises E, Q, or K at a residue corresponding to residue 271 of SEQ ID NO: 45. In some embodiments, the second subunit comprises residues 198-344 of SEQ ID NO: 45.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 45. In some embodiments, the engineered meganuclease comprises an amino acid sequence of SEQ ID NO: 45.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 63. In some embodiments, the engineered meganuclease is encoded by a nucleic acid sequence of SEQ ID NO: 63.

AAT 37-38L.262 (SEQ ID NO: 46)

In some embodiments, the HVR1 region comprises one or more residues corresponding to residues 24, 26, 28, 30, 32, 33, 38, 40, 42, 44, 46, 68, 70, 75, and 77 of SEQ ID NO: 46. In some embodiments, the HVR1 region comprises residues corresponding to residues 24, 26, 28, 30, 32, 33, 38, 40, 42, 44, 46, 68, 70, 75, and 77 of SEQ ID NO: 46. In some embodiments, the HVR1 region comprises a residue corresponding to residue 50 of SEQ ID NO: 46. In some embodiments, the HVR1 region comprises a residue corresponding to residue 71 of SEQ ID NO: 46. In some embodiments, the HVR1 region comprises a residue corresponding to residue 72 of SEQ ID NO: 46. In some embodiments, the HVR1 region comprises a residue corresponding to residue 73 of SEQ ID NO: 46. In some embodiments, the HVR1 region comprises Y, R. K, or D at a residue corresponding to residue 66 of SEQ ID NO: 46. In some embodiments, the HVR1 region comprises residues 24-79 of SEQ ID NO: 46.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 46. In some embodiments, the first subunit comprises a residue corresponding to residue 19 of SEQ ID NO: 46. In some embodiments, the first subunit comprises a residue corresponding to residue 140 of SEQ ID NO: 46. In some embodiments, the first subunit comprises G, S, or A at a residue corresponding to residue 19 of SEQ ID NO: 46. In some embodiments, the first subunit comprises E, Q, or K at a residue corresponding to residue 80 of SEQ ID NO: 46. In some embodiments, the first subunit comprises residues 7-153 of SEQ ID NO: 46.

In some embodiments, the HVR2 region comprises one or more residues corresponding to residues 215, 217, 219, 221, 223, 224, 229, 231, 233, 235, 237, 259, 261, 266, and 268 of SEQ ID NO: 46. In some embodiments, the HVR2 region comprises residues corresponding to residues 215, 217, 219, 221, 223, 224, 229, 231, 233, 235, 237, 259, 261, 266, and 268 of SEQ ID NO: 46. In some embodiments, the HVR2 region comprises Y, R, K, or D at a residue corresponding to residue 257 of SEQ ID NO: 46. In some embodiments, the HVR2 region comprises residues 215-270 of SEQ ID NO: 46.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 46. In some embodiments, the second subunit comprises a residue corresponding to residue 330 of SEQ ID NO: 46. In some embodiments, the second subunit comprises G, S, or A at a residue corresponding to residue 210 of SEQ ID NO: 46. In some embodiments, the second subunit comprises E, Q, or K at a residue corresponding to residue 271 of SEQ ID NO: 46. In some embodiments, the second subunit comprises residues 198-344 of SEQ ID NO: 46.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 46. In some embodiments, the engineered meganuclease comprises an amino acid sequence of SEQ ID NO: 46.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 64. In some embodiments, the engineered meganuclease is encoded by a nucleic acid sequence of SEQ ID NO: 64.

Exemplary AAT 41-42 meganucleases of the disclosure are provided in Table 3 and are further described below.

TABLE 3

| Meganuclease | AA SEQ ID | *% ID | AAT41 Subunit Residues | AAT41 Subunit SEQ ID | *AAT41 Subunit % | AAT42 Subunit Residues | AAT42 Subunit SEQ ID | *AAT42 Subunit % |
|---|---|---|---|---|---|---|---|---|
| AAT 41-42x.1 | 65 | 100 | 7-153 | 72 | 100 | 198-344 | 79 | 100 |
| AAT 41-42x.32 | 66 | 98.02 | 7-153 | 73 | 95.92 | 198-344 | 80 | 99.32 |
| AAT 41-42L.42 | 67 | 98.31 | 7-153 | 74 | 96.6 | 198-344 | 81 | 99.32 |
| AAT 41-42L.104 | 68 | 96.89 | 7-153 | 75 | 95.92 | 198-344 | 82 | 97.28 |
| AAT 41-42L.153 | 69 | 97.46 | 7-153 | 76 | 95.24 | 198-344 | 83 | 98.64 |
| AAT 41-42L.185 | 70 | 97.18 | 7-153 | 77 | 95.92 | 198-344 | 84 | 97.96 |
| AAT 41-42L.294 | 71 | 96.05 | 7-153 | 78 | 95.24 | 198-344 | 85 | 95.92 |

*"% ID" represents the amino acid sequence identity between the full-length sequence of each meganuclease and the AAT 41-42x.1 meganuclease. "AAT41 Subunit %" and "AAT42 Subunit %" represent the amino acid sequence identity between the AAT41-binding and AAT42-binding subunit regions of each meganuclease and the AAT41-binding and AAT42-binding subunit regions, respectively, of the AAT 41-42x.1 meganuclease.

AAT 41-42x.1 (SEQ ID NO: 65)

In some embodiments, the HVR1 region comprises one or more residues corresponding to residues 24, 26, 28, 30, 32, 33, 38, 40, 42, 44, 46, 68, 70, 75, and 77 of SEQ ID NO: 65. In some embodiments, the HVR1 region comprises residues corresponding to residues 24, 26, 28, 30, 32, 33, 38, 40, 42, 44, 46, 68, 70, 75, and 77 of SEQ ID NO: 65. In some embodiments, the HVR1 region comprises a residue corresponding to residue 48 of SEQ ID NO: 65. In some embodiments, the HVR1 region comprises a residue corresponding to residue 50 of SEQ ID NO: 65. In some embodiments, the HVR1 region comprises a residue corresponding to residue 72 of SEQ ID NO: 65. In some embodiments, the HVR1 region comprises Y, R, K, or D at a residue corresponding to residue 66 of SEQ ID NO: 65. In some embodiments, the HVR1 region comprises residues 24-79 of SEQ ID NO: 65.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 65. In some embodiments, the first subunit comprises a residue corresponding to residue 19 of SEQ ID NO: 65. In some embodiments, the first subunit comprises a residue corresponding to residue 80 of SEQ ID NO: 65. In some embodiments, the first subunit comprises G, S, or A at a residue corresponding to residue 19 of SEQ ID NO: 65. In some embodiments, the first subunit comprises E, Q, or K at a residue corresponding to residue 80 of SEQ ID NO: 65. In some embodiments, the first subunit comprises residues 7-153 of SEQ ID NO: 65.

In some embodiments, the HVR2 region comprises one or more residues corresponding to residues 215, 217, 219, 221, 223, 224, 229, 231, 233, 235, 237, 259, 261, 266, and 268 of SEQ ID NO: 65. In some embodiments, the HVR2 region comprises residues corresponding to residues 215, 217, 219, 221, 223, 224, 229, 231, 233, 235, 237, 259, 261, 266, and 268 of SEQ ID NO: 65. In some embodiments, the HVR2 region comprises a residue corresponding to residue 239 of SEQ ID NO: 65. In some embodiments, the HVR2 region comprises a residue corresponding to residue 241 of SEQ ID NO: 65. In some embodiments, the HVR2 region comprises a residue corresponding to residue 263 of SEQ ID NO: 65. In some embodiments, the HVR2 region comprises a residue corresponding to residue 264 of SEQ ID NO: 65. In some embodiments, the HVR2 region comprises Y, R, K, or D at a residue corresponding to residue 257 of SEQ ID NO: 65. In some embodiments, the HVR2 region comprises residues 215-270 of SEQ ID NO: 65.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 65. In some embodiments, the second subunit comprises a residue corresponding to residue 271 of SEQ ID NO: 65. In some embodiments, the second subunit comprises a residue corresponding to residue 330 of SEQ ID NO: 65. In some embodiments, the second subunit comprises G, S, or A at a residue corresponding to residue 210 of SEQ ID NO: 65. In some embodiments, the second subunit comprises E, Q, or K at a residue corresponding to residue 271 of SEQ ID NO: 65. In some embodiments, the second subunit comprises residues 198-344 of SEQ ID NO: 65.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 65. In some embodiments, the engineered meganuclease comprises an amino acid sequence of SEQ ID NO: 65.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 86. In some embodiments, the engineered meganuclease is encoded by a nucleic acid sequence of SEQ ID NO: 86.

AAT 41-42x.32 (SEQ ID NO: 66)

In some embodiments, the HVR1 region comprises one or more residues corresponding to residues 24, 26, 28, 30, 32, 33, 38, 40, 42, 44, 46, 68, 70, 75, and 77 of SEQ ID NO: 66. In some embodiments, the HVR1 region comprises residues corresponding to residues 24, 26, 28, 30, 32, 33, 38, 40, 42, 44, 46, 68, 70, 75, and 77 of SEQ ID NO: 66. In some embodiments, the HVR1 region comprises a residue corresponding to residue 48 of SEQ ID NO: 66. In some embodiments, the HVR1 region comprises a residue corresponding to residue 50 of SEQ ID NO: 66. In some embodiments, the HVR1 region comprises Y, R, K, or D at a residue corresponding to residue 66 of SEQ ID NO: 66. In some embodiments, the HVR1 region comprises residues 24-79 of SEQ ID NO: 66.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 66. In some embodiments, the first subunit comprises a residue corresponding to residue 19 of SEQ ID NO: 66. In some embodiments, the first subunit comprises a residue corresponding to residue 80 of SEQ ID NO: 66. In some embodiments, the first subunit comprises G, S, or A at a residue corresponding to residue 19 of SEQ ID NO: 66. In some embodiments, the first subunit comprises E, Q, or K at a residue corresponding to residue 80 of SEQ ID NO: 66. In some embodiments, the first subunit comprises residues 7-153 of SEQ ID NO: 66.

In some embodiments, the HVR2 region comprises one or more residues corresponding to residues 215, 217, 219, 221, 223, 224, 229, 231, 233, 235, 237, 259, 261, 266, and 268 of SEQ ID NO: 66. In some embodiments, the HVR2 region comprises residues corresponding to residues 215, 217, 219, 221, 223, 224, 229, 231, 233, 235, 237, 259, 261, 266, and 268 of SEQ ID NO: 66. In some embodiments, the HVR2 region comprises a residue corresponding to residue 241 of SEQ ID NO: 66. In some embodiments, the HVR2 region comprises a residue corresponding to residue 263 of SEQ ID NO: 66. In some embodiments, the HVR2 region comprises a residue corresponding to residue 264 of SEQ ID NO: 66. In some embodiments, the HVR2 region comprises Y, R, K, or D at a residue corresponding to residue 257 of SEQ ID NO: 66. In some embodiments, the HVR2 region comprises residues 215-270 of SEQ ID NO: 66.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 66. In some embodiments, the second subunit comprises a residue corresponding to residue 271 of SEQ ID NO: 66. In some embodiments, the second subunit comprises a residue corresponding to residue 330 of SEQ ID NO: 66. In some embodiments, the second subunit comprises G, S, or A at a residue corresponding to residue 210 of SEQ ID NO: 66. In some embodiments, the second subunit comprises E, Q, or K at a residue corresponding to residue 271 of SEQ ID NO: 66. In some embodiments, the second subunit comprises residues 198-344 of SEQ ID NO: 66.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 66. In some embodiments, the engineered meganuclease comprises an amino acid sequence of SEQ ID NO: 66.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 87. In some embodiments, the engineered meganuclease is encoded by a nucleic acid sequence of SEQ ID NO: 87.

AAT 41-42L.42 (SEQ ID NO: 67)

In some embodiments, the HVR1 region comprises one or more residues corresponding to residues 24, 26, 28, 30, 32, 33, 38, 40, 42, 44, 46, 68, 70, 75, and 77 of SEQ ID NO: 67. In some embodiments, the HVR1 region comprises residues corresponding to residues 24, 26, 28, 30, 32, 33, 38, 40, 42, 44, 46, 68, 70, 75, and 77 of SEQ ID NO: 67. In some embodiments, the HVR1 region comprises a residue corresponding to residue 48 of SEQ ID NO: 67. In some embodiments, the HVR1 region comprises a residue corresponding to residue 50 of SEQ ID NO: 67. In some embodiments, the HVR1 region comprises a residue corresponding to residue 72 of SEQ ID NO: 67. In some embodiments, the HVR1 region comprises Y, R, K, or D at a residue corresponding to residue 66 of SEQ ID NO: 67. In some embodiments, the HVR1 region comprises residues 24-79 of SEQ ID NO: 67.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 67. In some embodiments, the first subunit comprises a residue corresponding to residue 19 of SEQ ID NO: 67. In some embodiments, the first subunit comprises a residue corresponding to residue 80 of SEQ ID NO: 67. In some embodiments, the first subunit comprises G, S, or A at a residue corresponding to residue 19 of SEQ ID NO: 67. In some embodiments, the first subunit comprises E, Q, or K at a residue corresponding to residue 80 of SEQ ID NO: 67. In some embodiments, the first subunit comprises residues 7-153 of SEQ ID NO: 67.

In some embodiments, the HVR2 region comprises one or more residues corresponding to residues 215, 217, 219, 221, 223, 224, 229, 231, 233, 235, 237, 259, 261, 266, and 268 of SEQ ID NO: 67. In some embodiments, the HVR2 region comprises residues corresponding to residues 215, 217, 219, 221, 223, 224, 229, 231, 233, 235, 237, 259, 261, 266, and 268 of SEQ ID NO: 67. In some embodiments, the HVR2 region comprises a residue corresponding to residue 239 of SEQ ID NO: 67. In some embodiments, the HVR2 region comprises a residue corresponding to residue 241 of SEQ ID NO: 67. In some embodiments, the HVR2 region comprises a residue corresponding to residue 263 of SEQ ID NO: 67. In some embodiments, the HVR2 region comprises a residue corresponding to residue 264 of SEQ ID NO: 67. In some embodiments, the HVR2 region comprises Y, R, K, or D at a residue corresponding to residue 257 of SEQ ID NO: 67. In some embodiments, the HVR2 region comprises residues 215-270 of SEQ ID NO: 67.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 67. In some embodiments, the second subunit comprises a residue corresponding to residue 271 of SEQ ID NO: 67. In some embodiments, the second subunit comprises G, S, or A at a residue corresponding to residue 210 of SEQ ID NO: 67. In some embodiments, the second subunit comprises E, Q, or K at a residue corresponding to residue 271 of SEQ ID NO: 67. In some embodiments, the second subunit comprises residues 198-344 of SEQ ID NO: 67.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 67. In some embodiments, the engineered meganuclease comprises an amino acid sequence of SEQ ID NO: 67.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 88. In some embodiments, the engineered meganuclease is encoded by a nucleic acid sequence of SEQ ID NO: 88.

AAT 41-42L.104 (SEQ ID NO: 68)

In some embodiments, the HVR1 region comprises one or more residues corresponding to residues 24, 26, 28, 30, 32, 33, 38, 40, 42, 44, 46, 68, 70, 75, and 77 of SEQ ID NO: 68. In some embodiments, the HVR1 region comprises residues corresponding to residues 24, 26, 28, 30, 32, 33, 38, 40, 42, 44, 46, 68, 70, 75, and 77 of SEQ ID NO: 68. In some embodiments, the HVR1 region comprises a residue corresponding to residue 48 of SEQ ID NO: 68. In some embodiments, the HVR1 region comprises a residue corresponding to residue 50 of SEQ ID NO: 68. In some embodiments, the HVR1 region comprises a residue corresponding to residue 72 of SEQ ID NO: 68. In some embodiments, the HVR1 region comprises Y, R. K, or D at a residue corresponding to residue 66 of SEQ ID NO: 68. In some embodiments, the HVR1 region comprises residues 24-79 of SEQ ID NO: 68.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 68. In some embodiments, the first subunit comprises a residue corresponding to residue 19 of SEQ ID NO: 68. In some embodiments, the first subunit comprises a residue corresponding to residue 80 of SEQ ID NO: 68. In some embodiments, the first subunit comprises G, S, or A at a residue corresponding to residue 19 of SEQ ID NO: 68. In some embodiments, the first subunit comprises E, Q, or K at a residue corresponding to residue 80 of SEQ ID NO: 68. In some embodiments, the first subunit comprises residues 7-153 of SEQ ID NO: 68.

In some embodiments, the HVR2 region comprises one or more residues corresponding to residues 215, 217, 219, 221, 223, 224, 229, 231, 233, 235, 237, 259, 261, 266, and 268 of SEQ ID NO: 68. In some embodiments, the HVR2 region comprises residues corresponding to residues 215, 217, 219, 221, 223, 224, 229, 231, 233, 235, 237, 259, 261, 266, and 268 of SEQ ID NO: 68. In some embodiments, the HVR2 region comprises a residue corresponding to residue 239 of SEQ ID NO: 68. In some embodiments, the HVR2 region comprises a residue corresponding to residue 241 of SEQ ID NO: 68. In some embodiments, the HVR2 region comprises a residue corresponding to residue 263 of SEQ ID NO: 68. In some embodiments, the HVR2 region comprises a residue corresponding to residue 264 of SEQ ID NO: 68. In some embodiments, the HVR2 region comprises Y, R. K, or D at a residue corresponding to residue 257 of SEQ ID NO: 68. In some embodiments, the HVR2 region comprises residues 215-270 of SEQ ID NO: 68.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 68. In some embodiments, the second subunit comprises G, S, or A at a residue corresponding to residue 210 of SEQ ID NO: 68. In some embodiments, the second subunit comprises E, Q, or K at a residue corresponding to residue 271 of SEQ ID NO: 68. In some embodiments, the second subunit comprises residues 198-344 of SEQ ID NO: 68.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 68. In some embodiments, the engineered mega-nuclease comprises an amino acid sequence of SEQ ID NO: 68.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 89. In some embodiments, the engineered meganuclease is encoded by a nucleic acid sequence of SEQ ID NO: 89.

AAT 41-42L.153 (SEQ ID NO: 69)

In some embodiments, the HVR1 region comprises one or more residues corresponding to residues 24, 26, 28, 30, 32, 33, 38, 40, 42, 44, 46, 68, 70, 75, and 77 of SEQ ID NO: 69. In some embodiments, the HVR1 region comprises residues corresponding to residues 24, 26, 28, 30, 32, 33, 38, 40, 42, 44, 46, 68, 70, 75, and 77 of SEQ ID NO: 69. In some embodiments, the HVR1 region comprises a residue corresponding to residue 48 of SEQ ID NO: 69. In some embodiments, the HVR1 region comprises a residue corresponding to residue 50 of SEQ ID NO: 69. In some embodiments, the HVR1 region comprises a residue corresponding to residue 72 of SEQ ID NO: 69. In some embodiments, the HVR1 region comprises Y, R. K, or D at a residue corresponding to residue 66 of SEQ ID NO: 69. In some embodiments, the HVR1 region comprises residues 24-79 of SEQ ID NO: 69.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 69. In some embodiments, the first subunit comprises a residue corresponding to residue 19 of SEQ ID NO: 69. In some embodiments, the first subunit comprises a residue corresponding to residue 80 of SEQ ID NO: 69. In some embodiments, the first subunit comprises G, S, or A at a residue corresponding to residue 19 of SEQ ID NO: 69. In some embodiments, the first subunit comprises E, Q, or K at a residue corresponding to residue 80 of SEQ ID NO: 69. In some embodiments, the first subunit comprises residues 7-153 of SEQ ID NO: 69.

In some embodiments, the HVR2 region comprises one or more residues corresponding to residues 215, 217, 219, 221, 223, 224, 229, 231, 233, 235, 237, 259, 261, 266, and 268 of SEQ ID NO: 69. In some embodiments, the HVR2 region comprises residues corresponding to residues 215, 217, 219, 221, 223, 224, 229, 231, 233, 235, 237, 259, 261, 266, and 268 of SEQ ID NO: 69. In some embodiments, the HVR2 region comprises a residue corresponding to residue 239 of SEQ ID NO: 69. In some embodiments, the HVR2 region comprises a residue corresponding to residue 241 of SEQ ID NO: 69. In some embodiments, the HVR2 region comprises a residue corresponding to residue 263 of SEQ ID NO: 69. In some embodiments, the HVR2 region comprises a residue corresponding to residue 264 of SEQ ID NO: 69. In some embodiments, the HVR2 region comprises Y, R, K, or D at a residue corresponding to residue 257 of SEQ ID NO: 69. In some embodiments, the HVR2 region comprises residues 215-270 of SEQ ID NO: 69.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 69. In some embodiments, the second subunit comprises a residue corresponding to residue 271 of SEQ ID NO: 69. In some embodiments, the second subunit comprises G, S, or A at a residue corresponding to residue 210 of SEQ ID NO: 69. In some embodiments, the second subunit comprises E, Q, or K at a residue corresponding to residue 271 of SEQ ID NO: 69. In some embodiments, the second subunit comprises residues 198-344 of SEQ ID NO: 69.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 69. In some embodiments, the engineered meganuclease comprises an amino acid sequence of SEQ ID NO: 69.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 90. In some embodiments, the engineered meganuclease is encoded by a nucleic acid sequence of SEQ ID NO: 90.

AAT 41-42L.185 (SEQ ID NO: 70)

In some embodiments, the HVR1 region comprises one or more residues corresponding to residues 24, 26, 28, 30, 32, 33, 38, 40, 42, 44, 46, 68, 70, 75, and 77 of SEQ ID NO: 70. In some embodiments, the HVR1 region comprises residues corresponding to residues 24, 26, 28, 30, 32, 33, 38, 40, 42, 44, 46, 68, 70, 75, and 77 of SEQ ID NO: 70. In some embodiments, the HVR1 region comprises a residue corresponding to residue 48 of SEQ ID NO: 70. In some embodiments, the HVR1 region comprises a residue corresponding to residue 50 of SEQ ID NO: 70. In some embodiments, the HVR1 region comprises a residue corresponding to residue 72 of SEQ ID NO: 70. In some embodiments, the HVR1 region comprises Y, R, K, or D at a residue corresponding to residue 66 of SEQ ID NO: 70. In some embodiments, the HVR1 region comprises residues 24-79 of SEQ ID NO: 70.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 70. In some embodiments, the first subunit comprises a residue corresponding to residue 19 of SEQ ID NO: 70. In some embodiments, the first subunit comprises a residue corresponding to residue 80 of SEQ ID NO: 70. In some embodiments, the first subunit comprises G, S, or A at a residue corresponding to residue 19 of SEQ ID NO: 70. In some embodiments, the first subunit comprises E, Q, or K at a residue corresponding to residue 80 of SEQ ID NO: 70. In some embodiments, the first subunit comprises residues 7-153 of SEQ ID NO: 70.

In some embodiments, the HVR2 region comprises one or more residues corresponding to residues 215, 217, 219, 221, 223, 224, 229, 231, 233, 235, 237, 259, 261, 266, and 268 of SEQ ID NO: 70. In some embodiments, the HVR2 region comprises residues corresponding to residues 215, 217, 219, 221, 223, 224, 229, 231, 233, 235, 237, 259, 261, 266, and 268 of SEQ ID NO: 70. In some embodiments, the HVR2 region comprises a residue corresponding to residue 239 of SEQ ID NO: 70. In some embodiments, the HVR2 region comprises a residue corresponding to residue 241 of SEQ ID NO: 70. In some embodiments, the HVR2 region comprises a residue corresponding to residue 263 of SEQ ID NO: 70. In some embodiments, the HVR2 region comprises a residue corresponding to residue 264 of SEQ ID NO: 70. In some embodiments, the HVR2 region comprises Y, R, K, or D at a residue corresponding to residue 257 of SEQ ID NO: 70. In some embodiments, the HVR2 region comprises residues 215-270 of SEQ ID NO: 70.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 70. In some embodiments, the second subunit comprises a residue corresponding to residue 271 of SEQ ID NO: 70. In some embodiments, the second subunit comprises G, S, or A at a residue corresponding to residue 210 of SEQ ID NO: 70. In some embodiments, the second subunit comprises E, Q, or K at a residue corresponding to residue 271 of SEQ ID NO: 70. In some embodiments, the second subunit comprises residues 198-344 of SEQ ID NO: 70.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 70. In some embodiments, the engineered meganuclease comprises an amino acid sequence of SEQ ID NO: 70.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 91. In some embodiments, the engineered meganuclease is encoded by a nucleic acid sequence of SEQ ID NO: 91.

AAT 41-42L.294 (SEQ ID NO: 71)

In some embodiments, the HVR1 region comprises one or more residues corresponding to residues 24, 26, 28, 30, 32, 33, 38, 40, 42, 44, 46, 68, 70, 75, and 77 of SEQ ID NO: 71. In some embodiments, the HVR1 region comprises residues corresponding to residues 24, 26, 28, 30, 32, 33, 38, 40, 42, 44, 46, 68, 70, 75, and 77 of SEQ ID NO: 71. In some embodiments, the HVR1 region comprises a residue corresponding to residue 48 of SEQ ID NO: 71. In some embodiments, the HVR1 region comprises a residue corresponding to residue 50 of SEQ ID NO: 71. In some embodiments, the HVR1 region comprises a residue corresponding to residue 69 of SEQ ID NO: 71. In some embodiments, the HVR1 region comprises a residue corresponding to residue 72 of SEQ ID NO: 71. In some embodiments, the HVR1 region comprises Y, R, K, or D at a residue corresponding to residue 66 of SEQ ID NO: 71. In some embodiments, the HVR1 region comprises residues 24-79 of SEQ ID NO: 71.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 71. In some embodiments, the first subunit comprises a residue corresponding to residue 19 of SEQ ID NO: 71. In some embodiments, the first subunit comprises a residue corresponding to residue 80 of SEQ ID NO: 71. In some embodiments, the first subunit comprises G, S, or A at a residue corresponding to residue 19 of SEQ ID NO: 71. In some embodiments, the first subunit comprises E, Q, or K at a residue corresponding to residue 80 of SEQ ID NO: 71. In some embodiments, the first subunit comprises residues 7-153 of SEQ ID NO: 71.

In some embodiments, the HVR2 region comprises one or more residues corresponding to residues 215, 217, 219, 221, 223, 224, 229, 231, 233, 235, 237, 259, 261, 266, and 268 of SEQ ID NO: 71. In some embodiments, the HVR2 region comprises residues corresponding to residues 215, 217, 219, 221, 223, 224, 229, 231, 233, 235, 237, 259, 261, 266, and 268 of SEQ ID NO: 71. In some embodiments, the HVR2

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 92. In some embodiments, the engineered meganuclease is encoded by a nucleic acid sequence of SEQ ID NO: 92.

Exemplary AAT 43-44 meganucleases of the disclosure are provided in Table 4 and are further described below.

TABLE 4

| Meganuclease | AA SEQ ID | *% ID | AAT43 Subunit Residues | AAT43 Subunit SEQ ID | *AAT43 Subunit % | AAT44 Subunit Residues | AAT44 Subunit SEQ ID | *AAT44 Subunit % |
|---|---|---|---|---|---|---|---|---|
| AAT 43-44x.58 | 93 | 100 | 7-153 | 101 | 100 | 198-344 | 109 | 100 |
| AAT 43-44x.34 | 94 | 95.2 | 7-153 | 102 | 94.56 | 198-344 | 110 | 93.88 |
| AAT 43-44L.47 | 95 | 98.31 | 7-153 | 103 | 97.96 | 198-344 | 111 | 97.96 |
| AAT 43-44L.105 | 96 | 96.33 | 7-153 | 104 | 95.92 | 198-344 | 112 | 95.92 |
| AAT 43-44L.132 | 97 | 96.89 | 7-153 | 105 | 95.92 | 198-344 | 113 | 96.6 |
| AAT 43-44L.157 | 98 | 97.18 | 7-153 | 106 | 95.92 | 198-344 | 114 | 97.28 |
| AAT 43-44L.276 | 99 | 95.2 | 7-153 | 107 | 93.2 | 198-344 | 115 | 95.92 |
| AAT 43-44L.384 | 100 | 94.92 | 7-153 | 108 | 93.88 | 198-344 | 116 | 95.24 |

*""% ID" represents the amino acid sequence identity between the full-length sequence of each meganuclease and the AAT 43-44x.58 meganuclease. "AAT43 Subunit %" and "AAT44 Subunit %" represent the amino acid sequence identity between the AAT43-binding and AAT44-binding subunit regions of each meganuclease and the AAT43-binding and AAT44-binding subunit regions, respectively, of the AAT 43-44x.58 meganuclease.

region comprises a residue corresponding to residue 239 of SEQ ID NO: 71. In some embodiments, the HVR2 region comprises a residue corresponding to residue 241 of SEQ ID NO: 71. In some embodiments, the HVR2 region comprises a residue corresponding to residue 263 of SEQ ID NO: 71. In some embodiments, the HVR2 region comprises a residue corresponding to residue 264 of SEQ ID NO: 71. In some embodiments, the HVR2 region comprises Y, R, K, or D at a residue corresponding to residue 257 of SEQ ID NO: 71. In some embodiments, the HVR2 region comprises residues 215-270 of SEQ ID NO: 71.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 71. In some embodiments, the second subunit comprises a residue corresponding to residue 271 of SEQ ID NO: 71. In some embodiments, the second subunit comprises a residue corresponding to residue 330 of SEQ ID NO: 71. In some embodiments, the second subunit comprises G, S, or A at a residue corresponding to residue 210 of SEQ ID NO: 71. In some embodiments, the second subunit comprises E, Q, or K at a residue corresponding to residue 271 of SEQ ID NO: 71. In some embodiments, the second subunit comprises residues 198-344 of SEQ ID NO: 71.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 71. In some embodiments, the engineered meganuclease comprises an amino acid sequence of SEQ ID NO: 71.

AAT 43-44x.34 (SEQ ID NO: 93)

In some embodiments, the HVR1 region comprises one or more residues corresponding to residues 24, 26, 28, 30, 32, 33, 38, 40, 42, 44, 46, 68, 70, 75, and 77 of SEQ ID NO: 93. In some embodiments, the HVR1 region comprises residues corresponding to residues 24, 26, 28, 30, 32, 33, 38, 40, 42, 44, 46, 68, 70, 75, and 77 of SEQ ID NO: 93. In some embodiments, the HVR1 region comprises a residue corresponding to residue 48 of SEQ ID NO: 93. In some embodiments, the HVR1 region comprises a residue corresponding to residue 50 of SEQ ID NO: 93. In some embodiments, the HVR1 region comprises a residue corresponding to residue 72 of SEQ ID NO: 93. In some embodiments, the HVR1 region comprises a residue corresponding to residue 73 of SEQ ID NO: 93. In some embodiments, the HVR1 region comprises Y, R. K, or D at a residue corresponding to residue 66 of SEQ ID NO: 93. In some embodiments, the HVR1 region comprises residues 24-79 of SEQ ID NO: 93.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 93. In some embodiments, the first subunit comprises a residue corresponding to residue 19 of SEQ ID NO: 93. In some embodiments, the first subunit comprises G, S, or A at a residue corresponding to residue 19 of SEQ ID NO: 93. In some embodiments, the first subunit comprises E, Q, or K at a residue corresponding to residue 80 of SEQ ID NO: 93. In some embodiments, the first subunit comprises residues 7-153 of SEQ ID NO: 93.

In some embodiments, the HVR2 region comprises one or more residues corresponding to residues 215, 217, 219, 221, 223, 224, 229, 231, 233, 235, 237, 259, 261, 266, and 268 of SEQ ID NO: 93. In some embodiments, the HVR2 region comprises residues corresponding to residues 215, 217, 219, 221, 223, 224, 229, 231, 233, 235, 237, 259, 261, 266, and 268 of SEQ ID NO: 93. In some embodiments, the HVR2 region comprises a residue corresponding to residue 241 of SEQ ID NO: 93. In some embodiments, the HVR2 region comprises a residue corresponding to residue 263 of SEQ ID NO: 93. In some embodiments, the HVR2 region comprises a residue corresponding to residue 264 of SEQ ID NO: 93. In some embodiments, the HVR2 region comprises Y, R, K, or D at a residue corresponding to residue 257 of SEQ ID NO: 93. In some embodiments, the HVR2 region comprises residues 215-270 of SEQ ID NO: 93.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 93. In some embodiments, the second subunit comprises G, S, or A at a residue corresponding to residue 210 of SEQ ID NO: 93. In some embodiments, the second subunit comprises E, Q, or K at a residue corresponding to residue 271 of SEQ ID NO: 93. In some embodiments, the second subunit comprises residues 198-344 of SEQ ID NO: 93.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 93. In some embodiments, the engineered meganuclease comprises an amino acid sequence of SEQ ID NO: 93.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 117. In some embodiments, the engineered meganuclease is encoded by a nucleic acid sequence of SEQ ID NO: 117.

AAT 43-44x.58 (SEQ ID NO: 94)

In some embodiments, the HVR1 region comprises one or more residues corresponding to residues 24, 26, 28, 30, 32, 33, 38, 40, 42, 44, 46, 68, 70, 75, and 77 of SEQ ID NO: 94. In some embodiments, the HVR1 region comprises residues corresponding to residues 24, 26, 28, 30, 32, 33, 38, 40, 42, 44, 46, 68, 70, 75, and 77 of SEQ ID NO: 94. In some embodiments, the HVR1 region comprises a residue corresponding to residue 50 of SEQ ID NO: 94. In some embodiments, the HVR1 region comprises a residue corresponding to residue 72 of SEQ ID NO: 94. In some embodiments, the HVR1 region comprises a residue corresponding to residue 73 of SEQ ID NO: 94. In some embodiments, the HVR1 region comprises Y, R. K, or D at a residue corresponding to residue 66 of SEQ ID NO: 94. In some embodiments, the HVR1 region comprises residues 24-79 of SEQ ID NO: 94.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 94. In some embodiments, the first subunit comprises a residue corresponding to residue 19 of SEQ ID NO: 94. In some embodiments, the first subunit comprises a residue corresponding to residue 80 of SEQ ID NO: 94. In some embodiments, the first subunit comprises G, S, or A at a residue corresponding to residue 19 of SEQ ID NO: 94. In some embodiments, the first subunit comprises E, Q, or K at a residue corresponding to residue 80 of SEQ ID NO: 94. In some embodiments, the first subunit comprises residues 7-153 of SEQ ID NO: 94.

In some embodiments, the HVR2 region comprises one or more residues corresponding to residues 215, 217, 219, 221, 223, 224, 229, 231, 233, 235, 237, 259, 261, 266, and 268 of SEQ ID NO: 94. In some embodiments, the HVR2 region comprises residues corresponding to residues 215, 217, 219, 221, 223, 224, 229, 231, 233, 235, 237, 259, 261, 266, and 268 of SEQ ID NO: 94. In some embodiments, the HVR2 region comprises a residue corresponding to residue 239 of SEQ ID NO: 94. In some embodiments, the HVR2 region comprises a residue corresponding to residue 241 of SEQ ID NO: 94. In some embodiments, the HVR2 region comprises a residue corresponding to residue 255 of SEQ ID NO: 94. In some embodiments, the HVR2 region comprises a residue corresponding to residue 263 of SEQ ID NO: 94. In some embodiments, the HVR2 region comprises a residue corresponding to residue 264 of SEQ ID NO: 94. In some embodiments, the HVR2 region comprises Y, R. K, or D at a residue corresponding to residue 257 of SEQ ID NO: 94. In some embodiments, the HVR2 region comprises residues 215-270 of SEQ ID NO: 94.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 94. In some embodiments, the second subunit comprises a residue corresponding to residue 271 of SEQ ID NO: 94. In some embodiments, the second subunit comprises a residue corresponding to residue 330 of SEQ ID NO: 94. In some embodiments, the second subunit comprises G, S, or A at a residue corresponding to residue 210 of SEQ ID NO: 94. In some embodiments, the second subunit comprises E, Q, or K at a residue corresponding to residue 271 of SEQ ID NO: 94. In some embodiments, the second subunit comprises residues 198-344 of SEQ ID NO: 94.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 94. In some embodiments, the engineered meganuclease comprises an amino acid sequence of SEQ ID NO: 94.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 118. In some embodiments, the engineered meganuclease is encoded by a nucleic acid sequence of SEQ ID NO: 118.

AAT 43-44L.47 (SEQ ID NO: 95)

In some embodiments, the HVR1 region comprises one or more residues corresponding to residues 24, 26, 28, 30, 32, 33, 38, 40, 42, 44, 46, 68, 70, 75, and 77 of SEQ ID NO: 95. In some embodiments, the HVR1 region comprises residues corresponding to residues 24, 26, 28, 30, 32, 33, 38, 40, 42, 44, 46, 68, 70, 75, and 77 of SEQ ID NO: 95. In some embodiments, the HVR1 region comprises a residue corresponding to residue 50 of SEQ ID NO: 95. In some embodiments, the HVR1 region comprises a residue corresponding to residue 72 of SEQ ID NO: 95. In some embodiments, the HVR1 region comprises a residue corresponding to residue 73 of SEQ ID NO: 95. In some embodiments, the HVR1 region comprises Y, R, K, or D at a residue corresponding to residue 66 of SEQ ID NO: 95. In some embodiments, the HVR1 region comprises residues 24-79 of SEQ ID NO: 95.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 95. In some embodiments, the first subunit comprises a residue corresponding to residue 19 of SEQ ID NO: 95. In some embodiments, the first subunit comprises G, S, or A at a residue corresponding to residue 19 of SEQ ID NO: 95. In some embodiments, the first subunit comprises E, Q, or K at a residue corresponding to residue 80 of SEQ ID NO: 95. In some embodiments, the first subunit comprises residues 7-153 of SEQ ID NO: 95.

In some embodiments, the HVR2 region comprises one or more residues corresponding to residues 215, 217, 219, 221, 223, 224, 229, 231, 233, 235, 237, 259, 261, 266, and 268 of SEQ ID NO: 95. In some embodiments, the HVR2 region comprises residues corresponding to residues 215, 217, 219, 221, 223, 224, 229, 231, 233, 235, 237, 259, 261, 266, and 268 of SEQ ID NO: 95. In some embodiments, the HVR2 region comprises a residue corresponding to residue 239 of SEQ ID NO: 95. In some embodiments, the HVR2 region comprises a residue corresponding to residue 241 of SEQ ID NO: 95. In some embodiments, the HVR2 region comprises a residue corresponding to residue 255 of SEQ ID NO: 95. In some embodiments, the HVR2 region comprises a residue corresponding to residue 263 of SEQ ID NO: 95. In some embodiments, the HVR2 region comprises a residue corresponding to residue 264 of SEQ ID NO: 95. In some embodiments, the HVR2 region comprises Y, R, K, or D at a residue corresponding to residue 257 of SEQ ID NO: 95. In some embodiments, the HVR2 region comprises residues 215-270 of SEQ ID NO: 95.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 95. In some embodiments, the second subunit comprises a residue corresponding to residue 330 of SEQ ID NO: 95. In some embodiments, the second subunit comprises G, S, or A at a residue corresponding to residue 210 of SEQ ID NO: 95. In some embodiments, the second subunit comprises E, Q, or K at a residue corresponding to residue 271 of SEQ ID NO: 95. In some embodiments, the second subunit comprises residues 198-344 of SEQ ID NO: 95.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 95. In some embodiments, the engineered meganuclease comprises an amino acid sequence of SEQ ID NO: 95.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 119. In some embodiments, the engineered meganuclease is encoded by a nucleic acid sequence of SEQ ID NO: 119.

AAT 43-44L.105 (SEQ ID NO: 96)

In some embodiments, the HVR1 region comprises one or more residues corresponding to residues 24, 26, 28, 30, 32, 33, 38, 40, 42, 44, 46, 68, 70, 75, and 77 of SEQ ID NO: 96. In some embodiments, the HVR1 region comprises residues corresponding to residues 24, 26, 28, 30, 32, 33, 38, 40, 42, 44, 46, 68, 70, 75, and 77 of SEQ ID NO: 96. In some embodiments, the HVR1 region comprises a residue corresponding to residue 50 of SEQ ID NO: 96. In some embodiments, the HVR1 region comprises a residue corresponding to residue 72 of SEQ ID NO: 96. In some embodiments, the HVR1 region comprises a residue corresponding to residue 73 of SEQ ID NO: 96. In some embodiments, the HVR1 region comprises Y, R. K, or D at a residue corresponding to residue 66 of SEQ ID NO: 96. In some embodiments, the HVR1 region comprises residues 24-79 of SEQ ID NO: 96.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 96. In some embodiments, the first subunit comprises a residue corresponding to residue 19 of SEQ ID NO: 96. In some embodiments, the first subunit comprises G, S, or A at a residue corresponding to residue 19 of SEQ ID NO: 96. In some embodiments, the first subunit comprises E, Q, or K at a residue corresponding to residue 80 of SEQ ID NO: 96. In some embodiments, the first subunit comprises residues 7-153 of SEQ ID NO: 96.

In some embodiments, the HVR2 region comprises one or more residues corresponding to residues 215, 217, 219, 221, 223, 224, 229, 231, 233, 235, 237, 259, 261, 266, and 268 of SEQ ID NO: 96. In some embodiments, the HVR2 region comprises residues corresponding to residues 215, 217, 219, 221, 223, 224, 229, 231, 233, 235, 237, 259, 261, 266, and 268 of SEQ ID NO: 96. In some embodiments, the HVR2 region comprises a residue corresponding to residue 239 of SEQ ID NO: 96. In some embodiments, the HVR2 region comprises a residue corresponding to residue 241 of SEQ ID NO: 96. In some embodiments, the HVR2 region comprises a residue corresponding to residue 263 of SEQ ID NO: 96. In some embodiments, the HVR2 region comprises a residue corresponding to residue 264 of SEQ ID NO: 96. In some embodiments, the HVR2 region comprises Y, R, K, or D at a residue corresponding to residue 257 of SEQ ID NO: 96. In some embodiments, the HVR2 region comprises residues 215-270 of SEQ ID NO: 96.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 96. In some embodiments, the second subunit comprises G, S, or A at a residue corresponding to residue 210 of SEQ ID NO: 96. In some embodiments, the second subunit comprises E, Q, or K at a residue corresponding to residue 271 of SEQ ID NO: 96. In some embodiments, the second subunit comprises residues 198-344 of SEQ ID NO: 96.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 96. In some embodiments, the engineered meganuclease comprises an amino acid sequence of SEQ ID NO: 96.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 120. In some embodiments, the engineered meganuclease is encoded by a nucleic acid sequence of SEQ ID NO: 120.

AAT 43-44L.132 (SEQ ID NO: 97)

In some embodiments, the HVR1 region comprises one or more residues corresponding to residues 24, 26, 28, 30, 32, 33, 38, 40, 42, 44, 46, 68, 70, 75, and 77 of SEQ ID NO: 97. In some embodiments, the HVR1 region comprises residues corresponding to residues 24, 26, 28, 30, 32, 33, 38, 40, 42, 44, 46, 68, 70, 75, and 77 of SEQ ID NO: 97. In some embodiments, the HVR1 region comprises a residue corresponding to residue 50 of SEQ ID NO: 97. In some embodiments, the HVR1 region comprises a residue corresponding to residue 72 of SEQ ID NO: 97. In some embodiments, the HVR1 region comprises a residue corresponding to residue 73 of SEQ ID NO: 97. In some embodiments, the HVR1 region comprises Y, R. K, or D at a residue corresponding to residue 66 of SEQ ID NO: 97. In some embodiments, the HVR1 region comprises residues 24-79 of SEQ ID NO: 97.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 97. In some embodiments, the first subunit comprises a residue corresponding to residue 19 of SEQ ID NO: 97. In some embodiments, the first subunit comprises a residue corresponding to residue 103 of SEQ ID NO: 97. In some embodiments, the first subunit comprises G, S, or A at a residue corresponding to residue 19 of SEQ ID NO: 97. In some embodiments, the first subunit comprises E, Q, or K at a residue corresponding to residue 80 of SEQ ID NO: 97. In some embodiments, the first subunit comprises residues 7-153 of SEQ ID NO: 97.

In some embodiments, the HVR2 region comprises one or more residues corresponding to residues 215, 217, 219, 221, 223, 224, 229, 231, 233, 235, 237, 259, 261, 266, and 268 of SEQ ID NO: 97. In some embodiments, the HVR2 region comprises residues corresponding to residues 215, 217, 219, 221, 223, 224, 229, 231, 233, 235, 237, 259, 261, 266, and 268 of SEQ ID NO: 97. In some embodiments, the HVR2 region comprises a residue corresponding to residue 239 of SEQ ID NO: 97. In some embodiments, the HVR2 region comprises a residue corresponding to residue 241 of SEQ ID NO: 97. In some embodiments, the HVR2 region comprises a residue corresponding to residue 263 of SEQ ID NO: 97. In some embodiments, the HVR2 region comprises a residue corresponding to residue 264 of SEQ ID NO: 97. In some embodiments, the HVR2 region comprises Y, R, K, or D at a residue corresponding to residue 257 of SEQ ID NO: 97. In some embodiments, the HVR2 region comprises residues 215-270 of SEQ ID NO: 97.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 97. In some embodiments, the second subunit comprises a residue corresponding to residue 271 of SEQ ID NO: 97. In some embodiments, the second subunit comprises G, S, or A at a residue corresponding to residue 210 of SEQ ID NO: 97. In some embodiments, the second subunit comprises E, Q, or K at a residue corresponding to residue 271 of SEQ ID NO: 97. In some embodiments, the second subunit comprises residues 198-344 of SEQ ID NO: 97.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 97. In some embodiments, the engineered meganuclease comprises an amino acid sequence of SEQ ID NO: 97.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 121. In some embodiments, the engineered meganuclease is encoded by a nucleic acid sequence of SEQ ID NO: 121.

AAT 43-44L.157 (SEQ ID NO: 98)

In some embodiments, the HVR1 region comprises one or more residues corresponding to residues 24, 26, 28, 30, 32, 33, 38, 40, 42, 44, 46, 68, 70, 75, and 77 of SEQ ID NO: 98. In some embodiments, the HVR1 region comprises residues corresponding to residues 24, 26, 28, 30, 32, 33, 38, 40, 42, 44, 46, 68, 70, 75, and 77 of SEQ ID NO: 98. In some embodiments, the HVR1 region comprises a residue corresponding to residue 50 of SEQ ID NO: 98. In some embodiments, the HVR1 region comprises a residue corresponding to residue 72 of SEQ ID NO: 98. In some embodiments, the HVR1 region comprises a residue corresponding to residue 73 of SEQ ID NO: 98. In some embodiments, the HVR1 region comprises Y, R, K, or D at a residue corresponding to residue 66 of SEQ ID NO: 98. In some embodiments, the HVR1 region comprises residues 24-79 of SEQ ID NO: 98.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 98. In some embodiments, the first subunit comprises a residue corresponding to residue 19 of SEQ ID NO: 98. In some embodiments, the first subunit comprises a residue corresponding to residue 80 of SEQ ID NO: 98. In some embodiments, the first subunit comprises G, S, or A at a residue corresponding to residue 19 of SEQ ID NO: 98. In some embodiments, the first subunit comprises E, Q, or K at a residue corresponding to residue 80 of SEQ ID NO: 98. In some embodiments, the first subunit comprises residues 7-153 of SEQ ID NO: 98.

In some embodiments, the HVR2 region comprises one or more residues corresponding to residues 215, 217, 219, 221, 223, 224, 229, 231, 233, 235, 237, 259, 261, 266, and 268 of SEQ ID NO: 98. In some embodiments, the HVR2 region comprises residues corresponding to residues 215, 217, 219, 221, 223, 224, 229, 231, 233, 235, 237, 259, 261, 266, and 268 of SEQ ID NO: 98. In some embodiments, the HVR2 region comprises a residue corresponding to residue 239 of SEQ ID NO: 98. In some embodiments, the HVR2 region comprises a residue corresponding to residue 241 of SEQ ID NO: 98. In some embodiments, the HVR2 region comprises a residue corresponding to residue 263 of SEQ ID NO: 98. In some embodiments, the HVR2 region comprises a residue corresponding to residue 264 of SEQ ID NO: 98. In some embodiments, the HVR2 region comprises Y, R, K, or D at a residue corresponding to residue 257 of SEQ ID NO: 98. In some embodiments, the HVR2 region comprises residues 215-270 of SEQ ID NO: 98.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 98. In some embodiments, the second subunit comprises a residue corresponding to residue 271 of SEQ ID NO: 98. In some embodiments, the second subunit comprises a residue corresponding to residue 330 of SEQ ID NO: 98. In some embodiments, the second subunit comprises G, S, or A at a residue corresponding to residue 210 of SEQ ID NO: 98. In some embodiments, the second subunit comprises E, Q, or K at a residue corresponding to residue 271 of SEQ ID NO: 98. In some embodiments, the second subunit comprises residues 198-344 of SEQ ID NO: 98.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 98. In some embodiments, the engineered meganuclease comprises an amino acid sequence of SEQ ID NO: 98.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 122. In some embodiments, the engineered meganuclease is encoded by a nucleic acid sequence of SEQ ID NO: 122.

AAT 43-44L.276 (SEQ ID NO: 99)

In some embodiments, the HVR1 region comprises one or more residues corresponding to residues 24, 26, 28, 30, 32, 33, 38, 40, 42, 44, 46, 68, 70, 75, and 77 of SEQ ID NO: 99. In some embodiments, the HVR1 region comprises residues corresponding to residues 24, 26, 28, 30, 32, 33, 38, 40, 42, 44, 46, 68, 70, 75, and 77 of SEQ ID NO: 99. In some embodiments, the HVR1 region comprises a residue corresponding to residue 50 of SEQ ID NO: 99. In some embodiments, the HVR1 region comprises a residue corresponding to residue 72 of SEQ ID NO: 99. In some embodiments, the HVR1 region comprises a residue corresponding to residue 73 of SEQ ID NO: 99. In some embodiments, the HVR1 region comprises Y, R. K, or D at a residue corresponding to residue 66 of SEQ ID NO: 99. In some embodiments, the HVR1 region comprises residues 24-79 of SEQ ID NO: 99.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 99. In some embodiments, the first subunit comprises a residue corresponding to residue 19 of SEQ ID NO: 99. In some embodiments, the first subunit comprises G, S, or A at a residue corresponding to residue 19 of SEQ ID NO: 99. In some embodiments, the first subunit comprises E, Q, or K at a residue corresponding to residue 80 of SEQ ID NO: 99. In some embodiments, the first subunit comprises residues 7-153 of SEQ ID NO: 99.

In some embodiments, the HVR2 region comprises one or more residues corresponding to residues 215, 217, 219, 221, 223, 224, 229, 231, 233, 235, 237, 259, 261, 266, and 268 of SEQ ID NO: 99. In some embodiments, the HVR2 region comprises residues corresponding to residues 215, 217, 219, 221, 223, 224, 229, 231, 233, 235, 237, 259, 261, 266, and 268 of SEQ ID NO: 99. In some embodiments, the HVR2 region comprises a residue corresponding to residue 236 of SEQ ID NO: 99. In some embodiments, the HVR2 region comprises a residue corresponding to residue 239 of SEQ ID NO: 99. In some embodiments, the HVR2 region comprises a residue corresponding to residue 241 of SEQ ID NO: 99. In some embodiments, the HVR2 region comprises a residue corresponding to residue 263 of SEQ ID NO: 99. In some embodiments, the HVR2 region comprises a residue corresponding to residue 264 of SEQ ID NO: 99. In some embodiments, the HVR2 region comprises Y, R, K, or D at a residue corresponding to residue 257 of SEQ ID NO: 99. In some embodiments, the HVR2 region comprises residues 215-270 of SEQ ID NO: 99.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 99. In some embodiments, the second subunit comprises a residue corresponding to residue 330 of SEQ ID NO: 99. In some embodiments, the second subunit comprises G, S, or A at a residue corresponding to residue 210 of SEQ ID NO: 99. In some embodiments, the second subunit comprises E, Q, or K at a residue corresponding to residue 271 of SEQ ID NO: 99. In some embodiments, the second subunit comprises residues 198-344 of SEQ ID NO: 99.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 99. In some embodiments, the engineered meganuclease comprises an amino acid sequence of SEQ ID NO: 99.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 123. In some embodiments, the engineered meganuclease is encoded by a nucleic acid sequence of SEQ ID NO: 123.

AAT 43-44L.384 (SEQ ID NO: 100)

In some embodiments, the HVR1 region comprises one or more residues corresponding to residues 24, 26, 28, 30, 32, 33, 38, 40, 42, 44, 46, 68, 70, 75, and 77 of SEQ ID NO: 100. In some embodiments, the HVR1 region comprises residues corresponding to residues 24, 26, 28, 30, 32, 33, 38, 40, 42, 44, 46, 68, 70, 75, and 77 of SEQ ID NO: 100. In some embodiments, the HVR1 region comprises a residue corresponding to residue 50 of SEQ ID NO: 100. In some embodiments, the HVR1 region comprises a residue corresponding to residue 72 of SEQ ID NO: 100. In some embodiments, the HVR1 region comprises a residue corresponding to residue 73 of SEQ ID NO: 100. In some embodiments, the HVR1 region comprises Y, R, K, or D at a residue corresponding to residue 66 of SEQ ID NO: 100. In some embodiments, the HVR1 region comprises residues 24-79 of SEQ ID NO: 100.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of SEQ ID NO: 100. In some embodiments, the first subunit comprises a residue corresponding to residue 19 of SEQ ID NO: 100. In some embodiments, the first subunit comprises a residue corresponding to residue 80 of SEQ ID NO: 100. In some embodiments, the first subunit comprises a residue corresponding to residue 139 of SEQ ID NO: 100. In some embodiments, the first subunit comprises G, S, or A at a residue corresponding to residue 19 of SEQ ID NO: 100. In some embodiments, the first subunit comprises E. Q, or K at a residue corresponding to residue 80 of SEQ ID NO: 100. In some embodiments, the first subunit comprises residues 7-153 of SEQ ID NO: 100.

In some embodiments, the HVR2 region comprises one or more residues corresponding to residues 215, 217, 219, 221, 223, 224, 229, 231, 233, 235, 237, 259, 261, 266, and 268 of SEQ ID NO: 100. In some embodiments, the HVR2 region comprises residues corresponding to residues 215, 217, 219, 221, 223, 224, 229, 231, 233, 235, 237, 259, 261, 266, and 268 of SEQ ID NO: 100. In some embodiments, the HVR2 region comprises a residue corresponding to residue 236 of SEQ ID NO: 100. In some embodiments, the HVR2 region comprises a residue corresponding to residue 239 of SEQ ID NO: 100. In some embodiments, the HVR2 region comprises a residue corresponding to residue 241 of SEQ ID NO: 100. In some embodiments, the HVR2 region comprises a residue corresponding to residue 263 of SEQ ID NO: 100. In some embodiments, the HVR2 region comprises a residue corresponding to residue 264 of SEQ ID NO: 100. In some embodiments, the HVR2 region comprises Y, R. K, or D at a residue corresponding to residue 257 of SEQ ID NO: 100. In some embodiments, the HVR2 region comprises residues 215-270 of SEQ ID NO: 100.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of SEQ ID NO: 100. In some embodiments, the second subunit comprises a residue corresponding to residue 271 of SEQ ID NO: 100. In some embodiments, the second subunit comprises G, S, or A at a residue corresponding to residue 210 of SEQ ID NO: 100. In some embodiments, the second subunit comprises E, Q, or K at a residue corresponding to residue 271 of SEQ ID NO: 100. In some embodiments, the second subunit comprises residues 198-344 of SEQ ID NO: 100.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 100. In some embodiments, the engineered meganuclease comprises an amino acid sequence of SEQ ID NO: 100.

In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 124. In some embodiments, the engineered meganuclease is encoded by a nucleic acid sequence of SEQ ID NO: 124.

In some embodiments, the presently disclosed engineered meganucleases exhibit at least one optimized characteristic in comparison to previously described engineered nucleases (e.g., meganucleases) which target the SERPINA1 gene. Such optimized characteristics include improved (i.e., increased) specificity resulting in reduced off-target cutting, and enhanced (i.e., increased) efficiency of cleavage and insertion of a donor template into the SERPINA1 gene. Thus, in particular embodiments, the presently disclosed engineered meganucleases, when delivered to a population of cells, is able to generate a greater percentage of cells with a cleavage in and/or donor template insertion into the SERPINA1 gene. In some of these embodiments, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% of cells are target cells that comprise a cleavage in and/or donor template insertion into the SERPINA1 gene. Cleavage and/or indel formation by a meganuclease can be measured using any method known in the art, including for example the T7E assay, digital PCR, mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) *Biotechnology Advances* 35 (1): 95-104, which is incorporated by reference in its entirety).

In some embodiments, the target cell is a hepatocyte (e.g., a human hepatocyte in vivo). In some embodiments, the target cell is a primary human hepatocyte (PHH). In some embodiments, the target cell is a non-human, mammalian hepatocyte.

2.3 Methods for Delivering and Expressing Engineered Meganucleases and Donor Polynucleotides In different aspects, the disclosure provides engineered meganucleases described herein that are useful for binding and cleaving recognition sequences within a SERPINA1 gene of a cell (e.g., the human SERPINA1 gene). The disclosure further provides donor polynucleotides comprising a template nucleic acid that encodes a functional (e.g., wild-type) AAT protein, which are meant to be inserted into the cleavage site generated by the engineered meganuclease in the SERPINA1 gene. The disclosure provides various methods for modifying a SERPINA1 gene in cells using the engineered meganucleases and donor polynucleotides described herein, methods for making genetically-modified cells comprising a modified SERPINA1 gene, and methods of modifying a SERPINA1 gene in a target cell in a subject. In further aspects, the disclosure provides methods for treating AAT deficiency in a subject by administering the engineered meganucleases (or polynucleotides encoding the same) and donor polynucleotides described herein to a subject, in some cases as part of a pharmaceutical composition. In each case, it is envisioned that the engineered meganucleases (or polynucleotides encoding the same) and the donor polynucleotides are introduced into cells, such as liver cells (e.g., hepatocytes), liver progenitor cells, or stem cells that express an AAT protein.

Disruption of mutant AAT protein expression, either by gene knockout or by insertion of a template nucleic acid provided by a donor polynucleotide, can reduce the accumulation of mutant AAT proteins in the blood. Such reductions can be determined, for example, by measuring the amount of mutant AAT protein produced by the genetically-modified cell or the amount of mutant AAT protein present in a subject relative to a control (e.g., a control cell, a control subject, or a sample taken prior to treatment with the engineered meganuclease cell), using well-known protein measurement techniques known in the art including immunofluorescence, western blotting, and enzyme-linked immunosorbent assays (ELISA), which use antibodies that specifically bind mutant, but not functional, AAT protein. In specific embodiments, the expression or presence of a mutant AAT protein can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or up to 100% relative to the control. In some embodiments, the expression or presence of a mutant AAT protein can be reduced by 1%-5%, 5%-10%, 10%-20%, 20%-30%, 30%-40%, 40%-50%, 50%-60%, 70%-80%, 90%-95%, 95%-98%, or up 100% relative to the control.

Modification of the SERPINA1 gene to introduce a coding sequence encoding a functional (e.g., wild-type) AAT protein can be determined, for example, by sequencing the SERPINA1 gene in a genetically-modified cell, by measuring the abundance of the RNA encoding functional AAT, or by measuring the protein level of the functional AAT protein by protein measurement techniques (immunofluorescence, western blotting, and ELISA) using antibodies that specifically bind functional, but not mutant, AAT protein.

Levels of functional AAT (e.g., wild-type AAT) can be increased in a genetically-modified eukaryotic cell relative to a control (e.g., a control cell, such as a eukaryotic cell treated with a meganuclease that does not target the SERPINA1 gene), and can be increased in the blood or serum of a subject relative to a control (e.g., a sample taken prior to treatment with the engineered meganuclease). In some embodiments, the production of functional AAT, or functional AAT level, can be increased by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or up to 100% relative to the control. In some embodiments, the production of functional AAT can be increased by 1%-5%, 5%-10%, 10%-20%, 20%-30%, 30%-40%, 40%-50%, 50%-60%, 70%-80%, 90%-95%, 95%-98%, or up to 100% relative to the control. In various aspects, the methods described herein can increase protein levels of a functional (e.g., wild-type) AAT protein in a genetically-modified cell, target cell, or subject (e.g., as measured in a cell, a tissue, an organ, or a biological sample obtained from the subject), to at least 1%, 2%, 3%, 4%, 5%, 10%, 15%, 20%, 25%, 30%, 40%, 50%, 60%, 70%, 80%, 90%, 95%, 100%, 200%, 300%, 400%, 500%, or more, of a reference level (i.e., expression level of AAT in a wild-type cell or subject). Functional and/or wild-type AAT levels can be measured in a cell, tissue, organ, or blood, as described elsewhere herein.

The methods disclosed herein can be effective to decrease the risk of lung disease in the subject relative to a control subject having AAT deficiency. The control subject may be a subject having AAT deficiency treated with a meganuclease that does not target the SERPINA1 gene or treated with a meganuclease targeting the SERPINA1 gene but not a donor polynucleotide comprising a template nucleic acid encoding a functional AAT protein.

In some embodiments, the risk of lung disease can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 98%, or 100% relative to the reference level. In some embodiments, the risk of lung disease can be reduced by 1%-5%, 5%-10%, 10%-20%, 20%-30%, 30%-40%, 40%-50%, 50%-60%, 70%-80%, 90%-95%, 95%-98%, or up to 100% relative to the reference level.

In some embodiments, the risk of liver disease can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or 100% relative to the reference level. In some embodiments, the risk of liver disease can be reduced by 1%-5%, 5%-10%, 10%-20%, 20%-30%, 30%-40%, 40%-50%, 50%-60%, 70%-80%, 90%-95%, 95%-98%, or up to 100% relative to the reference level.

Detection and Expression

Expression of a functional AAT protein (e.g., a wild-type AAT protein) in a genetically-modified cell or subject can be detected using standard methods in the art. For example, levels of functional AAT protein may be assessed based on the level of any variable associated with AAT gene expression, e.g., SERPINA1 mRNA levels or AAT protein levels. Increased levels or expression of functional AAT protein may be assessed by an increase in an absolute or relative level of one or more of these variables compared with a reference level. Such functional AAT protein levels may be measured in a biological sample isolated from a subject, such as a tissue biopsy or a bodily fluid including blood, serum, plasma, cerebrospinal fluid, or urine. Optionally, such functional AAT protein levels are normalized to a standard protein or substance in the sample. Further, such functional AAT protein levels can be assessed any time before, during, or after treatment in accordance with the methods herein.

Introduction of Engineered Meganucleases and Donor Polynucleotides into Cells

Engineered meganuclease proteins disclosed herein, polynucleotides encoding engineered meganucleases described herein, and donor polynucleotides comprising a template nucleic acid described herein, can be delivered into cells by a variety of different mechanisms known in the art, including those further detailed herein below.

Engineered meganucleases disclosed herein can be delivered into a cell in the form of protein or, preferably, as a polynucleotide comprising a nucleic acid sequence encoding the engineered meganuclease. Such polynucleotides can be, for example, DNA (e.g., circular or linearized plasmid DNA, PCR products, or viral genomes) or RNA (e.g., mRNA).

For embodiments in which the engineered meganuclease coding sequence is delivered in DNA form, it should be operably linked to a promoter to facilitate transcription of the meganuclease gene. Mammalian promoters suitable for the invention include constitutive promoters such as the cytomegalovirus early (CMV) promoter (Thomsen et al. (1984), *Proc Natl Acad Sci USA*. 81 (3): 659-63) or the SV40 early promoter (Benoist and Chambon (1981), *Nature*. 290 (5804): 304-10) as well as inducible promoters such as the tetracycline-inducible promoter (Dingermann et al. (1992), *Mol Cell Biol*. 12 (9): 4038-45). An engineered meganuclease of the disclosure can also be operably linked to a synthetic promoter. Synthetic promoters can include, without limitation, the JeT promoter (WO 2002/012514).

In specific embodiments, a nucleic acid sequence encoding an engineered meganuclease described herein is operably linked to a tissue-specific promoter, such as a liver-specific promoter. Examples of liver-specific promoters include, without limitation, a human thyroxine binding globulin (TBG) promoter, human alpha-1 antitrypsin promoter, hybrid liver-specific promoter (hepatic locus control region from ApoE gene (ApoE-HCR) and a liver-specific alpha1-antitrypsin promoter), and apolipoprotein A-II promoter. In particular embodiments, the liver-specific promoter is a TBG promoter.

In specific embodiments, a polynucleotide comprising a nucleic acid sequence encoding an engineered meganuclease described herein is delivered on a recombinant DNA construct or expression cassette. For example, the recombinant DNA construct can comprise an expression cassette (i.e., "cassette") comprising a promoter and a nucleic acid sequence encoding an engineered meganuclease described herein.

In another particular embodiment, a polynucleotide comprising a nucleic acid sequence encoding an engineered meganuclease described herein is introduced into the cell using a single-stranded DNA template. The single-stranded DNA can further comprise a 5' and/or a 3' AAV ITR upstream and/or downstream of the sequence encoding the engineered meganuclease. The single-stranded DNA can further comprise a 5' and/or a 3' homology arm upstream and/or downstream of the sequence encoding the engineered meganuclease.

In another particular embodiment, a polynucleotide comprising a nucleic acid sequence encoding an engineered meganuclease described herein can be introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

In some embodiments, mRNA encoding an engineered meganuclease described herein is delivered to a cell because this reduces the likelihood that the gene encoding the engineered meganuclease will integrate into the genome of the cell. Such mRNA can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. Such elements can include, for example, posttranslational regulatory elements such as a woodchuck hepatitis virus posttranslational regulatory element (WPRE). The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

In some embodiments, the meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisam, et al. (2008) *Mol Ther*. 16:1624-9), TAT peptide from the HIV virus (Hudecz et al. (2005), *Med. Res. Rev*. 25:679-736), MPG (Simeoni, et al. (2003) *Nucleic Acids Res*. 31:2717-2724), Pep-1 (Deshayes et al. (2004) *Biochemistry* 43:7698-7706, and HSV-1 VP-22 (Deshayes et al. (2005) *Cell Mol Life Sci*. 62:1839-49. In an alternative embodiment, engineered nucleases, or DNA/mRNA encoding nucleases, are coupled covalently or non-covalently to an antibody that recognizes a specific cell-surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell-surface receptor. (McCall, et al. (2014) *Tissue Barriers*. 2 (4): e944449; Dinda, et al. (2013) *Curr Pharm Biotechnol*. 14:1264-74; Kang, et al. (2014) *Curr Pharm Biotechnol*. 15 (3): 220-30; Qian et al. (2014) *Expert Opin Drug Metab Toxicol*. 10 (11): 1491-508).

In some embodiments, meganuclease proteins, or DNA/mRNA encoding meganucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, meganuclease proteins, or DNA/mRNA encoding meganucleases, are coupled covalently or, preferably, non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 μm, preferably <100 nm. Such nanoparticles may be designed using a core composed of metal, lipid, polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33 (30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins, or DNA/mRNA encoding meganucleases, are encapsulated within liposomes or complexed using cationic lipids (see, e.g., LIPOFECTAMINE™, Life Technologies Corp., Carlsbad, CA; Zuris et al. (2015) Nat Biotechnol. 33:73-80; Mishra et al. (2011) J Drug Deliv. 2011:863734). In some embodiments, the meganuclease proteins, or DNA/mRNA encoding meganucleases, are encapsulated within Lipofectamine® MessengerMax cationic lipid. The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) *Ther Deliv.* 2 (4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding meganucleases, are combined with amphiphilic molecules that self-assemble into micelles (Tong et al. (2007) *J Gene Med.* 9 (11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015, 832, 6,506,803, 6,635,676, 6,559,189, and 7,767,216, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) *Nanoscale.* 7 (9): 3845-56; Cheng et al. (2008) *J Pharm Sci.* 97 (1): 123-43). The dendrimer generation can control the payload capacity and size and can provide a high payload capacity. Moreover, display of multiple surface groups can be leveraged to improve stability, reduce nonspecific interactions, and enhance cell-specific targeting and drug release.

In some embodiments, polynucleotides comprising a nucleic acid sequence encoding an engineered meganuclease described herein are introduced into a cell using a recombinant virus (i.e., a recombinant viral vector). Such recombinant viruses are known in the art and include recombinant retroviruses, recombinant lentiviruses, recombinant adenoviruses, and recombinant AAVs (reviewed in Vannucci, et al. (2013 *New Microbiol.* 36:1-22). Recombinant AAVs useful in the invention can have any serotype that allows for transduction of the virus into a target cell type and expression of the meganuclease gene in the target cell. For example, in some embodiments, recombinant AAVs have a serotype (i.e., a capsid) of AAV1, AAV2, AAV5 AAV6, AAV7, AAV8, AAV9, or AAV12. It is known in the art that different AAVs tend to localize to different tissues (Wang et al., *Expert Opin Drug Deliv* 11 (3). 2014). In some particular embodiments, the AAV serotype is AAV8. AAVs can also be self-complementary such that they do not require second-strand DNA synthesis in the host cell (McCarty, et al. (2001) Gene Ther. 8:1248-54). Polynucleotides delivered by recombinant AAVs can include left (5') and right (3') ITRs as part of the viral genome. In some embodiments, the recombinant viruses are injected directly into target tissues. In alternative embodiments, the recombinant viruses are delivered systemically via the circulatory system.

The AAV vectors and viral particles of the disclosure may exhibit transduction and/or activity in a multitude of tissue types, including but not limited to liver tissue, spleen tissue, adrenal tissue, lung tissue and heart tissue. In certain embodiments, the AAV vectors and viral particles of the disclosure may exhibit high, efficient transduction and/or activity in liver tissues. In some embodiments, the AAV8 capsid is used in combination with the TBG liver-specific promoter. The AAV8 serotype exhibits preferential tropism for liver tissues, and the specificity of the liver TBG promoter may control, mediate or limit editing to liver tissues to the exclusion of non-liver tissues.

In one embodiment, a recombinant virus used for meganuclease gene delivery is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide a coding sequence for a promoter, an engineered meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome, and cut the recombinant viral genome at this target site. Once cut, the 5' and 3' ends of the viral genome will be exposed and degraded by exonucleases, thus killing the virus and ceasing production of the meganuclease.

If a polynucleotide comprising a nucleic acid sequence encoding an engineered meganuclease described herein is delivered to a cell by a recombinant virus (e.g., an AAV), the nucleic acid sequence encoding the engineered meganuclease can be operably linked to a promoter. In some embodiments, this can be a viral promoter such as endogenous promoters from the recombinant virus (e.g., the LTR of a lentivirus) or the well-known cytomegalovirus- or SV40 virus-early promoters. In particular embodiments, nucleic acid sequences encoding the engineered meganucleases are operably linked to a promoter that drives gene expression preferentially in the target cells (e.g., liver cells). Examples of liver-specific tissue promoters include but are not limited to those liver-specific promoters previously described, including the TBG promoter.

In some embodiments, the methods include delivering an engineered meganuclease described herein, or a polynucleotide encoding the same, to a cell in combination with a donor polynucleotide comprising a template nucleic acid encoding a sequence of interest (i.e., a sequence encoding a functional AAT protein), wherein the engineered meganuclease is expressed in the cells, recognizes and cleaves a recognition sequence described herein (e.g., SEQ ID NO: 9, 11, 13, or 15) within a SERPINA1 gene of the cell, and generates a cleavage site, wherein the template nucleic acid and sequence of interest are inserted into the genome at the cleavage site (e.g., by homologous recombination).

Such donor polynucleotides comprising a template nucleic acid can be introduced into a cell and/or delivered to a target cell in a subject by any of the means previously discussed for delivery of a polynucleotide. In particular embodiments, such donor polynucleotides comprising a template nucleic acid molecule are introduced by way of a recombinant virus (i.e., a viral vector), such as a recombinant lentivirus, recombinant retrovirus, recombinant adenovirus, or a recombinant AAV. Recombinant AAVs useful for introducing a donor polynucleotide comprising a template nucleic acid can have any serotype (i.e., capsid) that allows for transduction of the virus into the cell and insertion of the template nucleic acid molecule sequence into the cell genome. In some embodiments, recombinant AAVs have a serotype of AAV1, AAV2, AAV5 AAV6, AAV7, AAV8, AAV9, or AAV12. In some particular embodiments, the AAV serotype is AAV8. The recombinant AAV can also be self-complementary such that it does not require second-strand DNA synthesis in the host cell. Template nucleic acids introduced using a recombinant AAV can be flanked by a 5' (left) and 3' (right) ITR in the viral genome.

In another particular embodiment, a donor polynucleotide comprising a template nucleic acid can be introduced into a cell and/or delivered to a target cell in a subject by way of a lipid nanoparticle. Examples of lipid nanoparticles useful for delivery of a donor polynucleotide are known in the art, and certain examples are described herein. When a template nucleic acid molecule is introduced or delivered by a lipid nanoparticle, the template nucleic acid molecule can be, for example, in the form of a double-stranded DNA template. In other embodiments, the donor polynucleotide can be in the form of a single-stranded DNA template. The single-stranded DNA can comprise, for example, the template nucleic acid molecule and, in particular embodiments, 5' and 3' homology arms to promote insertion of the template nucleic acid sequence into the meganuclease cleavage site by homologous recombination. The single-stranded DNA can, in some cases, further comprise a 5' AAV ITR sequence 5' upstream of the 5' homology arm, and a 3' AAV ITR sequence 3' downstream of the 3' homology arm. In yet further examples, a donor polynucleotide of the disclosure can be in the form of a linearized DNA template. In some such examples, a plasmid DNA comprising an exogenous nucleic acid sequence can be digested by one or more restriction enzymes such that the circular plasmid DNA is linearized.

In particular examples, the donor polynucleotide does not comprise an exogenous promoter that is operably linked to the template nucleic acid. In such examples, the template nucleic acid is operably linked to an endogenous promoter (e.g., the endogenous SERPINA1 promoter) following insertion into the engineered meganuclease cleavage site in the SERPINA1 gene.

In some examples, the donor polynucleotide does comprise an exogenous promoter, and the template nucleic acid described herein is operably linked to the exogenous promoter suitable which is suitable for expression of the encoded AAT protein in the cell. Such promoters can include, for example, those mammalian, inducible, and tissue-specific promoters previously discussed.

Administration

The target tissue(s) or target cell(s) include, without limitation, liver cells (e.g., hepatocytes), such as human liver cells. In some embodiments, the target cell is a liver progenitor cell.

In some embodiments, engineered meganucleases described herein, polynucleotides encoding the same, and/or donor polynucleotides comprising a template nucleic acid described herein are delivered to a cell in vitro. In some embodiments, engineered meganucleases described herein, polynucleotides encoding the same, and/or donor polynucleotides comprising a template nucleic acid described herein are delivered to a target cell in a subject in vivo. In some embodiments, engineered meganucleases described herein, polynucleotides encoding the same, and/or donor polynucleotides comprising a template nucleic acid described herein are supplied to target cells (e.g., a liver cell or liver progenitor cell) via injection directly to the target tissue. Alternatively, engineered meganucleases described herein, polynucleotides encoding the same, and/or donor polynucleotides comprising a template nucleic acid described herein can be delivered systemically via the circulatory system.

In various embodiments of the methods, the compositions described herein can be administered via any suitable route of administration known in the art. Such routes of administration can include, for example, intravenous, intramuscular, intraperitoneal, subcutaneous, intrahepatic, transmucosal, transdermal, intraarterial, and sublingual. In some embodiments, the compositions described herein are supplied to target cells (e.g., liver cells or liver precursor cells) via injection directly to the target tissue (e.g., liver tissue). Other suitable routes of administration can be readily determined by the treating physician as necessary.

In some embodiments, a therapeutically effective amount of an engineered meganuclease described herein, a polynucleotide encoding the same, is administered in combination with a donor polynucleotide comprising a template nucleic acid described herein to a subject in need thereof for the treatment of a disease, such as AAT deficiency. As appropriate, the dosage or dosing frequency of the engineered meganuclease, the polynucleotide encoding the same, and/or the donor polynucleotide may be adjusted over the course of the treatment, based on the judgment of the administering physician. Appropriate doses will depend, among other factors, on the specifics of any AAV chosen (e.g., serotype), any lipid nanoparticle chosen, on the route of administration, on the subject being treated (i.e., age, weight, sex, and general condition of the subject), and the mode of administration. Thus, the appropriate dosage may vary from patient to patient. An appropriate effective amount can be readily determined by one of skill in the art or treating physician. Dosage treatment may be a single dose schedule or, if multiple doses are required, a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

In some embodiments, the methods further include administration of a polynucleotide comprising a nucleic acid sequence encoding a secretion-impaired hepatotoxin, or encoding tPA, which stimulates hepatocyte regeneration without acting as a hepatotoxin.

In some embodiments, a subject is administered a pharmaceutical composition comprising a polynucleotide comprising a nucleic acid sequence encoding an engineered meganuclease described herein, wherein the encoding nucleic acid sequence is administered at a dose of about $1 \times 10^{10}$ gc/kg to about $1 \times 10^{14}$ gc/kg (e.g., about $1 \times 10^{10}$ gc/kg, about $1 \times 10^{11}$ gc/kg, about $1 \times 10^{12}$ gc/kg, about $1 \times 10^{13}$ gc/kg, or about $1 \times 10^{14}$ gc/kg). In some embodiments, a subject is administered a pharmaceutical composition comprising a polynucleotide comprising a nucleic acid sequence encoding an engineered meganuclease described herein, wherein the encoding nucleic acid sequence is administered at a dose of about $1 \times 10^{10}$ gc/kg, about $1 \times 10^{11}$ gc/kg, about $1 \times 10^{12}$ gc/kg, about $1 \times 10^{13}$ gc/kg, or about $1 \times 10^{14}$ gc/kg. In some embodiments, a subject is administered a pharmaceutical composition comprising a polynucleotide comprising a nucleic acid sequence encoding an engineered meganuclease described herein, wherein the encoding nucleic acid sequence is administered at a dose of about $1 \times 10^{10}$ gc/kg to about $1 \times 10^{11}$ gc/kg, about $1 \times 10^{11}$ gc/kg to about $1 \times 10^{12}$ gc/kg, about $1 \times 10^{12}$ gc/kg to about $1 \times 10^{13}$ gc/kg, or about $1 \times 10^{13}$ gc/kg to about $1 \times 10^{14}$ gc/kg.

In some embodiments, a subject is administered a pharmaceutical composition comprising a donor polynucleotide comprising a template nucleic acid described herein, wherein the template nucleic acid is administered at a dose of about $1 \times 10^{10}$ g/kg to about $1 \times 10^{14}$ gc/kg (e.g., about $1 \times 10^{10}$ gc/kg, about $1 \times 10^{11}$ gc/kg, about $1 \times 10^{12}$ gc/kg, about $1 \times 10^{13}$ gc/kg, or about $1 \times 10^{14}$ gc/kg). In some embodiments, a subject is administered a pharmaceutical composition comprising a donor polynucleotide comprising a template nucleic acid described herein, wherein the template nucleic acid is administered at a dose of about $1 \times 10^{10}$ gc/kg, about $1 \times 10^{11}$ gc/kg, about $1 \times 10^{12}$ gc/kg, about $1 \times 10^{13}$ gc/kg, or about $1 \times 10^{14}$ gc/kg. In some embodiments, a subject is administered a pharmaceutical composition comprising a donor polynucleotide comprising a template nucleic acid described herein, wherein the template nucleic acid is administered at a dose of about $1 \times 10^{10}$ gc/kg to about $1 \times 10^{11}$ gc/kg, about $1 \times 10^{11}$ gc/kg to about $1 \times 10^{12}$ gc/kg, about $1 \times 10^{12}$ gc/kg to about $1 \times 10^{13}$ gc/kg, or about $1 \times 10^{13}$ gc/kg to about $1 \times 10^{14}$ gc/kg.

In some embodiments, a subject is administered a lipid nanoparticle formulation comprising a polynucleotide (e.g., mRNA) comprising a nucleic acid sequence encoding an engineered meganuclease described herein, wherein the dose of the polynucleotide (e.g., mRNA) is about 0.1 mg/kg to about 3 mg/kg. In some embodiments, a subject is administered a lipid nanoparticle formulation comprising a polynucleotide (e.g., mRNA) comprising a nucleic acid sequence encoding an engineered meganuclease described herein, wherein the dose of the polynucleotide (e.g., mRNA) is about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg. In some embodiments, a subject is administered a lipid nanoparticle formulation comprising a polynucleotide (e.g., mRNA) comprising a nucleic acid sequence encoding an engineered meganuclease described herein, wherein the dose of the polynucleotide (e.g., mRNA) is about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg.

In some embodiments, a subject is administered a lipid nanoparticle formulation comprising a donor polynucleotide comprising a template nucleic acid described herein, wherein the dose of the donor polynucleotide is about 0.1 mg/kg to about 3 mg/kg. In some embodiments, a subject is administered a lipid nanoparticle formulation comprising a donor polynucleotide comprising a template nucleic acid described herein, wherein the dose of the donor polynucleotide is about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg. In some embodiments, a subject is administered a lipid nanoparticle formulation comprising a donor polynucleotide comprising a template nucleic acid described herein, wherein the dose of the donor polynucleotide is about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg.

2.4 Donor Polynucleotides and Template Nucleic Acids Encoding Functional AAT Proteins In different aspects, the disclosure provides a polynucleotide, also referred to herein as a donor polynucleotide, that comprises a template nucleic acid encoding a functional AAT protein. Insertion of such a template nucleic acid into the SERPINA1 gene, such that RNA encoding a functional AAT protein is transcribed and translated, allows for the restoration of AAT activity in a cell or subject having one or more mutations that prevent expression of functional AAT from an endogenous SERPINA1 gene.

In some embodiments, the template nucleic acid comprises, in 5' to 3' order: (a) a splicing sequence comprising a splice acceptor sequence capable of pairing with an endogenous splice donor sequence that is positioned 3' downstream and adjacent to exon 1c in a SERPINA1 gene; (b) a donor nucleic acid sequence encoding an AAT protein encoded by exons 2, 3, 4, and 5 of a SERPINA1 gene; and (c) a termination sequence.

In some embodiments, the polynucleotide comprising the template nucleic acid further comprises a 5' homology arm and a 3' homology arm flanking the template nucleic acid, wherein the 5' homology arm and the 3' homology arm share homology to sequences flanking SEQ ID NO: 9, 11, 13, or 15 (i.e., the AAT 35-36, AAT 37-38, AAT 41-42, or AAT 43-44 recognition sequences, respectively). Inclusion of the homology arms is meant to promote insertion of the template nucleic acid by HDR.

Insertion of the template nucleic acid into the endogenous SERPINA1 gene produces a modified SERPINA1 gene. Transcription of this modified SERPINA1 gene produces an RNA with multiple exons separated by introns, which must be removed by splicing to produce messenger RNA (mRNA) containing an open reading frame encoding the AAT protein. Splicing occurs through interactions between a splice donor sequence at the 5' end of an intron, and a splice acceptor sequence at the 3' end of the intron. Pairing of the splice donor and splice acceptor results in the formation of a covalent bond between the nucleotide immediately 5' to splice donor sequence (last nucleotide of a first exon) and the nucleotide immediately 3' to the splice acceptor sequence (first nucleotide of a second exon), resulting in the excision of the intron from the RNA sequence, and joining of two exons into one nucleic acid sequence. Following transcription, the inserted splice acceptor sequence of (a) in the modified SERPINA1 gene allows the inserted AAT coding sequence of (b) to be joined to the upstream exon in the modified SERPINA1 gene (i.e., exon 1c), thereby forming an open reading frame encoding a functional AAT protein (e.g., a wild-type AAT protein). The termination sequence downstream of the AAT coding sequence causes translation to stop, preventing the addition of any additional amino acids to a polypeptide beyond those encoded by the AAT coding sequence of (b). Thus, the AAT protein expressed from the modified SERPINA1 gene does not comprise amino acids encoded by nucleic acid sequences downstream of the template nucleic acid in the modified SERPINA1 gene. Thus, the termination sequence prevents translation of mutant AAT proteins, even if such exons containing missense or frameshift mutations are incorporated into mRNA produced by transcription of the modified SERPINA1 gene.

In some embodiments of the template nucleic acid described herein, the termination sequence comprises a stop codon. In some embodiments, the stop codon comprises the nucleotide sequence TAG. In some embodiments, the stop codon comprises the nucleotide sequence TAA. In some embodiments, the stop codon comprises the nucleotide sequence TGA. In some embodiments, the termination sequence comprises a poly A sequence. In some embodiments, the termination sequence comprises a stop codon and a poly A sequence. Transcription of a DNA polynucleotide comprising a poly A sequence produces an RNA comprising a poly A tail. A "poly A tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a poly A tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a poly A tail contains 50 to 250 adenosine monophosphates. In a relevant biological setting (e.g., in cells, in vivo, etc.) the poly(A) tail functions to protect mRNA from enzymatic degradation, e.g., in the cytoplasm, and aids in transcription termination, export of the mRNA from the nucleus, and translation.

In some embodiments, the donor polynucleotide and the template nucleic acid do not comprise a promoter (i.e., an exogenous promoter). Rather, the donor nucleic acid sequence encoding the AAT protein becomes operably linked to the endogenous SERPINA1 promoter after insertion into the meganuclease cleavage site.

In some embodiments of the template nucleic acid described herein, the splicing sequence comprises a branch point. A branch point refers to a site in an intron that forms an intermediate structure during splicing. Typically, a branch point nucleotide forms a covalent bond with the first nucleotide of an intron via nucleophilic attack, forming a lariat intermediate. Then, the 3' OH of the released first exon forms a covalent bond with the first nucleotide downstream from the intron, which is the first nucleotide of the following exon, resulting in the formation of a nucleic acid sequence containing the two exons. In some embodiments, the splicing sequence is a naturally-occurring splicing sequence. In some embodiments, the splicing sequence comprises an SV40 splicing sequence (e.g., intron), a CMV splicing sequence (e.g., intron), or a transferrin gene splicing sequence (e.g., intron). In some embodiments, the splicing sequence is a synthetic splicing sequence (e.g., intron).

In some embodiments, the AAT protein encoded by the donor nucleic acid sequence is a wild-type AAT protein. A wild-type AAT protein refers to an AAT protein comprising the amino acid sequence of the common form of human AAT, defined by UniProt Accession No. P01009.

In some embodiments, the donor nucleic acid sequence comprises one or more exons of a wild-type SERPINA1 gene. In some embodiments, the donor nucleic acid sequence comprises only wild-type exons of a SERPINA1 gene. In some embodiments, the donor nucleic acid sequence comprises one or more exons of a SERPINA1 gene that have been codon-modified but still encode a wild-type AAT protein. Codon modification, or codon optimization, refers to modifications in a DNA or RNA sequence that do not affect the amino acids encoded by the DNA or RNA sequence. Codon optimization may, however, improve expression of an encoded protein due to changes in the relative number and frequency of tRNAs used in translation. Replacing codons for a given amino acid with codons corresponding to tRNAs that are more abundant in human cells, for example, allows for faster translation of an RNA sequence into the same amino acid sequence.

In some embodiments, the donor nucleic acid sequence encodes an AAT protein encoded by exons 2, 3, 4, and 5 of a SERPINA1 gene. The endogenous SERPINA1 gene comprises seven exons, referred to as exons 1a, 1b, 1c, 2, 3, 4, and 5, and six introns, referred to as introns 1a, 1b, 1c, 2, 3, and 4. The endogenous SERPINA1 gene comprises, in 5' to 3' order: exon 1a, intron 1a, exon 1b, intron 1b, exon 1c, intron 1b, exon 2, intron 2, exon 3, intron 3, exon 4, intron 4, and exon 5. The open reading frame encoding AAT comprises exons 2, 3, 4, and 5, while exons 1a, 1b, and 1c are comprised in the 5' UTR of the RNA produced by transcription of the SERPINA1 gene. Thus, exons 1a, 1b, and 1c do not encode amino acids of AAT. Accordingly, the same coding sequence encoding functional AAT, comprising exons 2, 3, 4, and 5 of a wild-type SERPINA1 gene, may be inserted downstream of exon 1c in intron 1c, where the AAT 35-36, AAT 37-38, AAT 41-42, or AAT 43-44 recognition sequences of SEQ ID NOs: 9, 11, 13, and 15, respectively, are positioned, and still encode wild-type AAT.

Insertion into Intron 1c

As described herein, the donor nucleic acid sequence of the template nucleic acid encodes an AAT protein encoded by exons 2, 3, 4, and 5 of a SERPINA1 gene, and the splice acceptor sequence is capable of pairing with an endogenous splice donor sequence that is positioned 3' downstream and adjacent to exon 1c in a SERPINA1 gene. Accordingly, the elements of the template nucleic acids described herein are designed for insertion into intron 1c of the SERPINA1 gene. Splicing of RNA transcribed from the modified SERPINA1 gene formed by insertion of the template nucleic acid into intron 1c thus produces an open reading frame comprising in 5' to 3' order: exons 1a, 1b, and 1c of the endogenous SERPINA1 gene, and exons 2, 3, 4, and 5 of the donor nucleic acid sequence. In some embodiments, the donor nucleic acid sequence comprises exons 2, 3, 4, and 5 of a SERPINA1 gene, or codon-modified variants of one or more of exons 2, 3, 4, and 5 of a SERPINA1 gene.

In some embodiments, the donor nucleic acid sequence does not comprise one or more of introns 2, 3, and 4 of a SERPINA1 gene. In some embodiments, the donor nucleic acid sequence comprises a nucleic acid sequence having at least 80%, at least 85%, at least 90%, at least 95%, at least 96%, at least 97%, at least 98%, at least 99%, or up to 100% sequence identity to a sequence set forth in SEQ ID NO: 125. In some embodiments, the donor nucleic acid sequence comprises a nucleic acid sequence set forth in SEQ ID NO: 125.

In some embodiments, the donor nucleic acid sequence comprises one or more of introns 2, 3, and 4 of a SERPINA1 gene, which are appropriately positioned adjacent to and downstream of their respective exons. In some embodiments, the donor nucleic acid sequence comprises introns 2, 3, and 4 of a SERPINA1 gene, which are appropriately positioned adjacent to and downstream of their respective exons. In some embodiments, the donor nucleic acid sequence comprises a nucleic acid sequence having at least 80%, at least 85%, at least 90%, at least 95%, at least 96%, at least 97%, at least 98%, at least 99%, or up to 100% sequence identity to a sequence set forth in SEQ ID NO: 126. In some embodiments, the donor nucleic acid sequence comprises a nucleic acid sequence set forth in SEQ ID NO: 126.

Bidirectional Template Nucleic Acids

In some embodiments, the template nucleic acid is a bidirectional template nucleic acid. A bidirectional template nucleic acid refers to a template nucleic acid comprising a first nucleic acid sequence and a second nucleic sequence that is downstream of the first nucleic acid sequence, wherein the first nucleic acid sequence comprises one or more elements in 5' to 3' order, and the second nucleic acid sequence comprises reverse complements of the one or more elements of the first nucleic acid sequence (or variants thereof), wherein the reverse complements are arranged in reverse order relative to their arrangement in the first nucleic acid sequence. For example, in a bidirectional template nucleic acid comprising a first nucleic acid sequence comprising, in 5' to 3' order: an A element, a B element, and a C element, the second nucleic acid sequence comprises, in 5' to 3' order: a reverse complement of a C element, a reverse complement of a B element, and a reverse complement of an A element. Thus, regardless of the orientation in which the bidirectional template nucleic acid is introduced into the genome, the modified SERPINA1 gene produced by homologous recombination will contain, in 5' to 3' order: (a) a splice acceptor sequence capable of pairing with an endogenous splice donor sequence that is positioned 3' downstream and adjacent to exon 1c; (b) a sequence encoding an AAT protein encoded by exons 2, 3, 4, and 5 of a SERPINA1 gene; and (c) a termination sequence.

An element in a bidirectional template nucleic acid may refer to a class of sequences, such as termination sequences (stop codons and/or poly A tails), or to a specific nucleic acid sequence (a stop codon having the nucleic acid sequence TAA, or a poly A tail consisting of exactly 50 adenosine monophosphate nucleotides). In some embodiments, the first nucleic acid sequence (forward segment) and second nucleic acid sequence (reverse segment) comprise identical elements arranged in reverse order, with the reverse element being a reverse complement of the forward element. In some embodiments, the forward segment and reverse segment are separated by one or more intervening nucleotides. In some embodiments, the forward segment and reverse segment are flanked by nucleic acid sequences that do not have a corresponding reverse complement in the donor polynucleotide.

In particular embodiments, the donor nucleic acid sequence further comprises a reverse segment that is 3' downstream of the termination sequence, wherein the reverse segment comprises, from 5' to 3': (a) a reverse complement of a second termination sequence; (b) a reverse complement of a second donor nucleic acid sequence encoding an AAT protein that is encoded by exons 2, 3, 4, and 5 of a SERPINA1 gene; and (c) a reverse complement of a second splicing sequence comprising a splice acceptor sequence capable of pairing with an endogenous splice donor sequence that is positioned 3' downstream and adjacent to exon 1c in a SERPINA1 gene.

In some embodiments, the reverse segment comprises reverse complements of one or more elements of the forward segment that are not identical to their corresponding elements on the forward segment. For example, a bidirectional template nucleic acid may comprise identical SERPINA1 coding sequences, but the forward segment may comprise a CMV intron, while the reverse segment comprises a reverse complement of an SV40 intron. In some embodiments, the second termination sequence is identical to the first termination sequence. In some embodiments, the second termination sequence differs from the first termination sequence. Non-limiting examples of manners in which the second termination sequence may differ from the termination sequence include comprising a different stop codon, comprising multiple stop codons in sequence, comprising a poly A tail of a different length, presence of a poly A tail, and absence of a poly A tail.

In some embodiments, the second donor nucleic acid sequence is identical to the first donor nucleic acid sequence. In some embodiments, the second donor nucleic acid sequence differs from the first donor nucleic acid sequence, but encodes the same AAT protein. The first and second nucleic acid sequences encoding the AAT protein may be identical, or differ by one or more nucleotide substitutions, such as for codon modification, codon optimization, or the introduction of a barcode sequence that allows a primer or probe having a complementary sequence to bind specifically to the barcode sequence.

In some embodiments, the second splicing sequence is identical to the first splicing sequence. In some embodiments, the second splicing sequence differs from the first splicing sequence, but is still capable of pairing with the same endogenous splice donor sequence in a SERPINA1 gene.

2.5 Methods for Producing Modified SERPINA/Genes and/or Treating AAT Deficiency In another aspect, the disclosure provides methods of editing one or more SERPINA1 genes in a cell by providing (i) an engineered meganuclease described herein, or a polynucleotide comprising a nucleic acid sequence encoding an engineered meganuclease described herein; and (ii) a donor polynucleotide comprising a template nucleic acid described herein, comprising (a) a splicing sequence comprising a splice acceptor sequence capable of pairing with an endogenous splice donor sequence that is positioned 3' downstream and adjacent to exon 1c in a SERPINA1 gene; (b) a donor nucleic acid sequence encoding an AAT protein encoded by exons 2, 3, 4, and 5 of a SERPINA1 gene; and (c) a termination sequence.

In other aspects, disclosed herein is a method for modifying a SERPINA1 gene in a target cell in a subject, the method comprising delivering to the target cell: (a) a polynucleotide (i.e., a donor polypeptide) comprising a template nucleic acid described herein; and (b) an engineered meganuclease described herein, or a second polynucleotide comprising a nucleic acid sequence encoding an engineered meganuclease described herein that is expressed in the target cell, wherein the engineered meganuclease binds and cleaves a recognition sequence (i.e., SEQ ID NO: 9, 11, 13, or 15) within an endogenous SERPINA1 gene in the target cell to generate a cleavage site, and wherein the template nucleic acid is inserted into the cleavage site to generate the modified SERPINA1 gene.

In other aspects, disclosed herein is a method for treating AAT deficiency in a subject in need thereof, the method comprising administering to the subject: (a) a pharmaceutical composition comprising an effective amount of the polynucleotide comprising a template nucleic described herein, and (b) a pharmaceutical composition comprising an effective amount of an engineered meganuclease described herein, or a second polynucleotide comprising a nucleic acid sequence encoding an engineered meganuclease described herein, wherein the polynucleotide comprising the template nucleic acid, and the engineered meganuclease or the second polynucleotide, are delivered to a target cell in the subject, wherein the engineered meganuclease is expressed in the target cell if encoded by the second polynucleotide, wherein the engineered meganuclease binds and cleaves a recognition sequence (i.e., SEQ ID NO: 9, 11, 13, or 15) within an endogenous SERPINA1 gene in the target cell to generate a cleavage site, and wherein the template nucleic acid is inserted into the cleavage site to generate the modified SERPINA1 gene.

In some embodiments of the methods described herein, the polynucleotide comprising the template nucleic acid sequence further comprises a 5' homology and a 3' homology arm that flank the template nucleic acid, with one homology arm comprising a nucleic acid sequence with homology to a sequence 5' upstream of the recognition sequence, and the other homology arm comprising a nucleic acid sequence with homology to a sequence 3' downstream of the recognition sequence (i.e., wherein the recognition sequence is an AAT 35-36, 37-38, 41-42, or 43-44 recognition sequence of SEQ ID NO: 9, 11, 13, or 15, respectively). The double-stranded break created by meganuclease-mediated cleavage can stimulate a cell's endogenous DNA-repair pathways (e.g., homology-dependent repair (HDR)). HDR, which is also known as homologous recombination (HR), can occur when a homologous repair template (e.g., a donor polynucleotide) is available. In the absence of a donor polynucleotide, the sister chromatid is generally used by the cell as the repair template. However, for the purposes of genome editing, the repair template is often supplied as an exogenous nucleic acid, such as a plasmid, duplex oligonucleotide, single strand oligonucleotide, double-stranded oligonucleotide, or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. Thus, in some embodiments, homologous recombination is used to insert an exogenous polynucleotide sequence into the target nucleic acid cleavage site.

As an alternative to homologous recombination, when an exogenous DNA molecule is supplied in sufficient concentration inside the nucleus of a cell in which the double-strand break occurs, the exogenous DNA can be inserted at the double-stranded break during the NHEJ repair process and thus become a permanent addition to the genome. If a template nucleic acid contains a coding sequence for a gene of interest such as an AAT gene, as well as a splice acceptor sequence and termination sequence, the gene of interest can be expressed from the integrated copy in the genome, resulting in permanent expression for the life of the cell. Moreover, the integrated copy of the template nucleic acid can be transmitted to the daughter cells when the cell divides.

In some embodiments of the methods described herein, the endogenous SERPINA1 gene comprises at least one mutation relative to a wild-type SERPINA1 gene and encodes a mutant AAT protein. In some embodiments, the endogenous SERPINA1 gene comprises a Z allele mutation in exon 5. The "Z allele" refers to an allele comprising a mutation that changes a glutamate-encoding codon to a lysine-encoding one at position 342 of the amino acid sequence of AAT. Thus, an AAT protein encoded by a SERPINA1 gene comprising a Z allele mutation has a lysine (K) in place of a glutamate (E) amino acid at position 342. In some embodiments, some embodiments, the endogenous SERPINA1 gene comprises an S allele mutation in exon 3. The "S allele" refers to an allele comprising a mutation that changes a glutamate-encoding codon to a valine-encoding one at position 264 of the amino acid sequence of AAT. Thus, an AAT protein encoded by a SERPINA1 gene comprising an S allele mutation has a valine (V) in place of a glutamate (E) amino acid at position 264. In some embodiments, the genetically-modified cell expresses less of the mutant AAT protein, relative to an unmodified cell.

In some embodiments, the template nucleic acid is inserted in-frame in the SERPINA1 gene. In some embodiments, the donor nucleic acid sequence of the template nucleic acid is operably linked to an endogenous SERPINA1 promoter following insertion of the template nucleic acid into the cleavage site. A promoter is said to be operably linked to a nucleic acid sequence if the promoter regulates transcription of the operably linked nucleic acid sequence. Thus, in such embodiments, the template nucleic acid does not comprise an exogenous promoter, and the endogenous SERPINA1 promoter governs transcription of the modified SERPINA1 gene encoding the functional AAT protein.

In some embodiments, the modified SERPINA1 gene encodes a full-length wild-type AAT protein that does not comprise a Z allele mutation or an S allele mutation. While the Z allele and/or S allele mutations may be present downstream of the inserted template nucleic acid, and possibly transcribed during transcription of the modified SERPINA1 gene, the termination sequence of the template nucleic acid prevents such mutant AAT proteins from being translated. In some embodiments, the modified SERPINA1 gene comprises a nucleic acid sequence of a wild-type SERPINA1 gene. In some embodiments, the modified SERPINA1 gene comprises one or more codon-modified exons and/or introns and encodes a wild-type AAT protein. In some embodiments, the modified SERPINA1 gene comprises a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a sequence set forth in SEQ ID NO: 127. In some embodiments, the modified SERPINA1 gene comprises a nucleic acid sequence set forth in SEQ ID NO: 127.

In some embodiments, the eukaryotic cell modified according to the disclosure is a mammalian cell. Non-limiting examples of mammals include mice, rats, rabbits, hamsters, guinea pigs, swine, cattle, alpacas, llamas, and humans. In some embodiments, the mammalian cell is a human cell. In some embodiments, the mammalian cell is a liver cell (e.g., a hepatocyte). In some embodiments, the mammalian cell is a liver progenitor cell or stem cell. In some embodiments, the eukaryotic cell is a pluripotent stem cell. In some embodiments, the eukaryotic cell is an induced pluripotent stem cell. In specific embodiments, the eukaryotic cell is a human liver cell (e.g., a human hepatocyte).

In some embodiments of the methods of treating AAT deficiency described herein, the subject is a human. In some embodiments, the target cell in the subject is a liver cell (e.g., a hepatocyte). In some embodiments, the target cell in the subject is a liver progenitor cell or stem cell.

2.6 Pharmaceutical Compositions

In some embodiments, the disclosure provides a pharmaceutical composition comprising a pharmaceutically acceptable carrier and an engineered meganuclease described herein, or a pharmaceutically acceptable carrier and a polynucleotide described herein that comprises a nucleic acid sequence encoding an engineered meganuclease described herein. Such polynucleotides can be, for example, mRNA or DNA as described herein.

In some embodiments, the disclosure provides a pharmaceutical composition comprising a pharmaceutically acceptable carrier and a donor polynucleotide described herein that comprises a template nucleic acid comprising (a) a splicing sequence comprising a splice acceptor sequence capable of pairing with an endogenous splice donor sequence that is positioned 3' downstream and adjacent to exon 1c in a SERPINA1 gene; (b) a donor nucleic acid sequence encoding an AAT protein encoded by exons 2, 3, 4, and 5 of a SERPINA1 gene; and (c) a termination sequence. In some such examples, the polynucleotide in the pharmaceutical composition can be comprised by a lipid nanoparticle or can be comprised by a recombinant virus (e.g., a recombinant AAV).

Such pharmaceutical compositions are formulated, for example, for systemic administration, or administration to target tissues.

Pharmaceutical compositions of the disclosure can be useful for treating a subject having AAT deficiency. In some instances, the subject undergoing treatment in accordance with the methods and compositions described herein can be characterized by having a mutation in a SERPINA1 gene, such as a Pi*Z mutation or a Pi*S mutation. A subject having AAT deficiency, or a subject who may be particularly receptive to treatment with the engineered meganucleases and donor polynucleotides described herein, may be identified by ascertaining the presence or absence of one or more such risk factors, diagnostic, or prognostic indicators. The determination may be based on clinical and sonographic findings, including enzymology analyses and/or DNA analyses known in the art.

For example, the subject undergoing treatment can be characterized by bloodstream levels of mutant AAT, e.g., mutant AAT levels of at least 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg of mutant AAT per mL of blood, or more. In certain embodiments, the mutant AAT level is associated with one or more symptoms or pathologies, such as pulmonary edema. Mutant AAT levels may be measured in a biological sample, such as a body fluid including blood, serum, plasma, or urine. In some embodiments, the claimed methods include administration of an engineered meganuclease (or nucleic acid encoding the same) and a donor polynucleotide described herein to reduce serum mutant AAT levels in a subject to undetectable levels, or to less than 1% 2%, 5%, 10%, 20%, 30%, 40%, 50%, 60%, 70%, or 80% of the subject's mutant AAT levels prior to treatment, within 1 day, 3 days, 5 days, 7 days, 9 days, 12 days, or 15 days.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the disclosure, engineered meganucleases described herein, polynucleotides encoding the same, or cells expressing the same, are typically admixed with a pharmaceutically acceptable carrier and the resulting composition is administered to a subject. The carrier must be acceptable in the sense of being compatible with any other ingredients in the formulation and must not be deleterious to the subject. The carrier can be a solid or a liquid, or both, and can be formulated with the compound as a unit-dose formulation.

In some embodiments, pharmaceutical compositions of the disclosure can further comprise one or more additional agents or biological molecules useful in the treatment of a disease in the subject. Likewise, the additional agent(s) and/or biological molecule(s) can be co-administered as a separate composition.

The pharmaceutical compositions described herein can include a therapeutically effective amount of any engineered meganuclease disclosed herein, a therapeutically effective amount of a polynucleotide described herein encoding an engineered meganuclease described herein, and/or a therapeutically effective amount of a donor polynucleotide described herein. For example, in some embodiments, the pharmaceutical composition can include polynucleotides described herein at any of the doses (e.g., gc/kg of an encoding nucleic acid sequence or mg/kg of mRNA) described herein.

In particular embodiments of the disclosure, the pharmaceutical composition can comprise one or more recombinant viruses (e.g., recombinant AAVs) described herein that comprise one or more polynucleotides described herein (i.e., packaged within the viral genome). In some embodiments, the pharmaceutical composition comprises two or more recombinant viruses described herein (e.g., recombinant AAVs), each comprising a polynucleotide described herein, wherein a first recombinant virus comprises a polynucleotide comprising a nucleic acid sequence encoding an engineered meganuclease described herein having specificity for the AAT 35-36, AAT 37-38, AAT 41-42, or AAT 43- 44 recognition sequence, and a second recombinant virus that comprises a donor polynucleotide.

A "therapeutically effective amount" refers to an amount effective, at dosages and for periods of time necessary, to achieve a desired therapeutic result. The therapeutically effective amount may vary according to factors such as the age, sex, and weight of the individual, and the ability of the polypeptide, nucleic acid, or vector to elicit a desired response in the individual. As used herein a therapeutically effective result can refer to a reduction mutant AAT concentration in serum, an increase in functional (e.g., wild-type) AAT concentration in serum, an increase in functional (e.g., wild-type) AAT concentration in serum, a decrease in protease activity in the lungs and/or liver, and/or a decrease in the risk of an AATD-related disease, such as lung disease or liver disease.

The pharmaceutical compositions described herein can include an effective amount of an engineered meganuclease described herein, or a polynucleotide comprising a nucleic acid sequence encoding an engineered meganuclease described herein. In some embodiments, the pharmaceutical composition comprises about $1 \times 10^{10}$ gc/kg to about $1 \times 10^{14}$ gc/kg (e.g., $1 \times 10^{10}$ gc/kg, $1 \times 10^{11}$ gc/kg, $1 \times 10^{12}$ gc/kg, $1 \times 10^{13}$ gc/kg, or $1 \times 10^{14}$ gc/kg) of the encoding nucleic acid sequence. In some embodiments, the pharmaceutical composition comprises at least about $1 \times 10^{10}$ gc/kg, at least about $1 \times 10^{11}$ gc/kg, at least about $1 \times 10^{12}$ gc/kg, at least about $1 \times 10^{13}$ gc/kg, or at least about $1 \times 10^{14}$ gc/kg of the encoding nucleic acid sequence. In some embodiments, the pharmaceutical composition comprises about $1 \times 10^{10}$ gc/kg to about $1 \times 10^{11}$ gc/kg, about $1 \times 10^{11}$ gc/kg to about $1 \times 10^{12}$ gc/kg, about $1 \times 10^{12}$ gc/kg to about $1 \times 10^{13}$ gc/kg, or about $1 \times 10^{13}$ gc/kg to about $1 \times 10^{14}$ gc/kg of the encoding nucleic acid sequence. In certain embodiments, the pharmaceutical composition comprises about $1 \times 10^{12}$ gc/kg to about $9 \times 10^{13}$ gc/kg (e.g., about $1 \times 10^{12}$ gc/kg, about $2 \times 10^{12}$ gc/kg, about $3 \times 10^{12}$ gc/kg, about $4 \times 10^{12}$ gc/kg, about $5 \times 10^{12}$ gc/kg, about $6 \times 10^{12}$ gc/kg, about $7 \times 10^{12}$ gc/kg, about $8 \times 10^{12}$ gc/kg, about $9 \times 10^{12}$ gc/kg, about $1 \times 10^{13}$ gc/kg, about $2 \times 10^{13}$ gc/kg, about $3 \times 10^{13}$ gc/kg, about $4 \times 10^{13}$ gc/kg, about $5 \times 10^{13}$ gc/kg, about $6 \times 10^{13}$ gc/kg, about $7 \times 10^{13}$ gc/kg, about $8 \times 10^{13}$ gc/kg, or about $9 \times 10^{13}$ gc/kg) of the encoding nucleic acid sequence.

The pharmaceutical compositions described herein can include an effective amount of a donor polynucleotide described herein, which comprises a template nucleic acid described herein. In some embodiments, the pharmaceutical composition comprises about $1 \times 10^{10}$ gc/kg to about $1 \times 10^{14}$ gc/kg (e.g., $1 \times 10^{10}$ gc/kg, $1 \times 10^{11}$ gc/kg, $1 \times 10^{12}$ gc/kg, $1 \times 10^{13}$ gc/kg, or $1 \times 10^{14}$ gc/kg) of a template nucleic acid described herein. In some embodiments, the pharmaceutical composition comprises at least about $1 \times 10^{10}$ gc/kg, at least about $1 \times 10^{11}$ gc/kg, at least about $1 \times 10^{12}$ gc/kg, at least about $1 \times 10^{13}$ gc/kg, or at least about $1 \times 10^{14}$ gc/kg of a template nucleic acid described herein. In some embodiments, the pharmaceutical composition comprises about $1 \times 10^{10}$ gc/kg to about $1 \times 10^{11}$ gc/kg, about $1 \times 10^{11}$ gc/kg to about $1 \times 10^{12}$ gc/kg, about $1 \times 10^{12}$ gc/kg to about $1 \times 10^{13}$ gc/kg, or about $1 \times 10^{13}$ gc/kg to about $1 \times 10^{14}$ gc/kg of a template nucleic acid described herein. In certain embodiments, the pharmaceutical composition comprises about $1 \times 10^{12}$ gc/kg to about $9 \times 10^{13}$ gc/kg (e.g., about $1 \times 10^{12}$ gc/kg, about $2 \times 10^{12}$ gc/kg, about $3 \times 10^{12}$ gc/kg, about $4 \times 10^{12}$ gc/kg, about $5 \times 10^{12}$ gc/kg, about $6 \times 10^{12}$ gc/kg, about $7 \times 10^{12}$ gc/kg, about $8 \times 10^{12}$ gc/kg, about $9 \times 10^{12}$ gc/kg, about $1 \times 10^{13}$ gc/kg, about $2 \times 10^{13}$ gc/kg, about $3 \times 10^{13}$ gc/kg, about $4 \times 10^{13}$ gc/kg, about $5 \times 10^{13}$ gc/kg, about $6 \times 10^{13}$ gc/kg, about $7 \times 10^{13}$ gc/kg, about $8 \times 10^{13}$ gc/kg, or about $9 \times 10^{13}$ gc/kg) of a template nucleic acid described herein.

In particular embodiments of the disclosure, the pharmaceutical composition can comprise one or more mRNAs described herein encapsulated within lipid nanoparticles.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino) butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino) acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.C1), 1,2-dilinoleoyl-3-trimethylaminopropane chloride salt (DLin-TAP.C1), 1,2-dilinoleyloxy-3-(N-methylpiperazino) propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino) ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-

(2,3-dioleyloxy) propyl)-N,N,N-trimethylammonium chloride (DOTMA), N,N-distearyl-N,N-dimethylammonium bromide (DDAB), N-(1-(2,3-dioleoyloxy) propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propan-aminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy) propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxyben-zylamine (DMOBA), 1,2-N,N'-dioleylcarbamyl-3-dimeth-ylaminopropane (DOcarbDAP), 1,2-N,N'-dilinoleylcar-bamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cho-lesteryl-2'-hydroxyethyl ether, cholesteryl-4'-hydroxybutyl ether, and mixtures thereof. The phospholipid may be a neutral lipid including, but not limited to, dipalmitoylphos-phatidylcholine (DPPC), distearoylphosphatidylcholine (DSPC), dioleoylphosphatidylethanolamine (DOPE), palmi-toyloleoyl-phosphatidylcholine (POPC), palmitoyloleoyl-phosphatidylethanolamine (POPE), palmitoyloleyol-phos-phatidylglycerol (POPG), dipalmitoyl-phosph-atidylethanolamine (DPPE), dimyristoyl-phosphatidyletha-nolamine (DMPE), distearoyl-phosphatidylethanolamine (DSPE), monomethyl-phosphatidylethanolamine, dimethyl-phosphatidylethanolamine, dielaidoyl-phosphatidyletha-nolamine (DEPE), stearoyloleoyl-phosphatidyletha-nolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cho-lesterol or a cholesterol derivative, the mixture may com-prise up to about 40, 50, or 60 mol % of the total lipid present in the particle.

The conjugated lipid that inhibits aggregation of particles may comprise, e.g., one or more of the following: a poly-ethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodi-ments, the PEG-lipid conjugate or ATTA-lipid conjugate is used together with a CPL. The conjugated lipid that inhibits aggregation of particles may comprise a PEG-lipid includ-ing, e.g., a PEG-diacylglycerol (DAG), a PEG dialkyloxy-propyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-disteary-loxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-di-oxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggrega-tion of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N', N', N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethylamonium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoy]-sn-glycero-3-succinyl-2-hydroxyethyl disulfide omithine), DDAB dimethyldioctadecylammonium bromide, DOGS ((C18) 2GlySper3+) N,N-dioctadecylamido-glycol-spermin (Transfectam®) (C18) 2Gly+N,N-dioctadecylamido-glycine, CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particular examples are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition that specifically enhances delivery and uptake in the liver, and specifically within hepatocytes.

In some embodiments, the pharmaceutical composition comprises an effective amount of a lipid nanoparticle formulation, wherein the lipid nanoparticle formulation comprises a polynucleotide (e.g., mRNA) comprising a nucleic acid sequence encoding an engineered meganuclease described herein. In some examples, the lipid nanoparticle formulation comprises about 0.1 mg/kg to about 3 mg/kg of the polynucleotide (e.g., mRNA). In some embodiments, the lipid nanoparticle formulation comprises about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg of the polynucleotide (e.g., mRNA). In some embodiments, the lipid nanoparticle formulation comprises about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg of the polynucleotide (e.g., mRNA).

In some embodiments, the pharmaceutical composition comprises an effective amount of a lipid nanoparticle formulation comprising a donor polynucleotide comprising a template nucleic acid described herein, wherein lipid nanoparticle formulation comprises about 0.1 mg/kg to about 3 mg/kg of the donor polynucleotide. In some embodiments, the lipid nanoparticle formulation comprises about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg of the donor poly-nucleotide. In some embodiments, the lipid nanoparticle formulation comprises about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg of the donor polynucle-otide.

In some embodiments, pharmaceutical compositions of the disclosure can further comprise one or more additional agents useful in the treatment of AAT deficiency in the subject.

The present disclosure also provides engineered mega-nucleases described herein, polynucleotides encoding engineered meganucleases described herein, or polynucleotides comprising template nucleic acids described herein, for use as a medicament. The present disclosure further provides the use of engineered meganucleases described herein, poly-nucleotides encoding engineered meganucleases described herein, or polynucleotides comprising template nucleic acids described herein, in the manufacture of a medicament for treating AAT deficiency, for increasing levels of a functional (e.g., wild-type) AAT protein, or reducing one or more symptoms associated with AAT deficiency.

2.7 Methods for Producing Recombinant Viruses

In some embodiments, the disclosure provides recombi-nant viruses, such as recombinant AAVs, for use in the methods of the disclosure. Recombinant AAVs are typically produced in mammalian cell lines such as HEK-293. Because the viral cap and rep genes are removed from the recombinant virus to prevent its self-replication to make room for the therapeutic gene(s) to be delivered (e.g., the meganuclease gene), it is necessary to provide these in trans in the packaging cell line. In addition, it is necessary to provide the "helper" (e.g., adenoviral) components neces-sary to support replication (Cots D et al., (2013) Curr. Gene Ther. 13 (5): 370-81). Frequently, recombinant AAVs are produced using a triple-transfection in which a cell line is transfected with a first plasmid encoding the "helper" com-ponents, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically pro-duced (manufactured) in cells, precautions must be taken in practicing the current invention to ensure that the engineered meganuclease is not expressed in the packaging cells. Because the recombinant viral genomes of the disclosure may comprise a recognition sequence for the meganuclease, any meganuclease expressed in the packaging cell line may be capable of cleaving the viral genome before it can be packaged into viral particles. This will result in reduced packaging efficiency and/or the packaging of fragmented genomes. Several approaches can be used to prevent mega-nuclease expression in the packaging cells.

The nuclease can be placed under the control of a tissue-specific promoter that is not active in the packaging cells. Any tissue specific promoter described herein for expression of the engineered meganuclease or for a nucleic acid sequence of interest can be used. For example, if a recom-binant virus is developed for delivery of genes encoding an engineered meganuclease to liver tissue, a liver-specific promoter can be used. Examples of liver-specific promoters include, without limitation, those liver-specific promoters described elsewhere herein.

Alternatively, the recombinant virus can be packaged in cells from a different species in which the meganuclease is not likely to be expressed. For example, viral particles can be produced in microbial, insect, or plant cells using mam-malian promoters, such as the well-known cytomegalovirus- or SV40 virus-early promoters, which are not active in the non-mammalian packaging cells. In a particular embodi-ment, viral particles are produced in insect cells using the baculovirus system as described by Gao, et al. (Gao et al. (2007), J. Biotechnol. 131 (2): 138-43). A meganuclease under the control of a mammalian promoter is unlikely to be expressed in these cells (Airenne et al. (2013), Mol. Ther. 21 (4): 739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA tran-scripts in insect cells, insect cells will not express a func-tional meganuclease and will package the full-length genome. In contrast, mammalian cells to which the resulting recombinant AAV particles are delivered will properly splice the pre-mRNA and will express functional meganuclease protein. Haifeng Chen has reported the use of the HGH and SV40 large T antigen introns to attenuate expression of the toxic proteins barnase and diphtheria toxin fragment A in insect packaging cells, enabling the production of recombi-nant AAV vectors carrying these toxin genes (Chen, H (2012) Mol Ther Nucleic Acids. 1 (11): e57).

The engineered meganuclease gene can be operably linked to an inducible promoter such that a small-molecule inducer is required for meganuclease expression. Examples of inducible promoters include the Tet-On system (Clontech; Chen et al. (2015), BMC Biotechnol. 15 (1): 4)) and the RheoSwitch system (Intrexon; Sowa et al. (2011), Spine, 36 (10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respec-tively). Practicing the embodiments described herein using such ligand-inducible transcription activators includes: 1) placing the engineered meganuclease gene under the control of a promoter that responds to the corresponding transcrip-tion factor, the meganuclease gene having (a) binding site(s) for the transcription factor; and 2) including the gene encoding the transcription factor in the packaged viral genome. The latter step is necessary because the engineered meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the embodiments described herein, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183: 137-42). The use of a non-human transcription repressor ensures that transcription of the meganuclease gene will be repressed only in the packaging cells expressing the repressor and not in target cells or tissues transduced with the resulting recombinant AAV.

2.8 Variants

Embodiments of the disclosure encompass the engineered meganucleases described herein, polynucleotides comprising a nucleic acid sequence encoding the engineered meganucleases described herein, donor polynucleotides comprising template nucleic acids described herein, and variants thereof.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., for a variant of an engineered meganuclease described herein, the ability to bind and cleave a SERPINA1 gene recognition sequence described herein (e.g., an AAT 35-36, 37-38, 41-42, or 43-44 recognition sequence), and for a variant of a donor polynucleotide and template nucleic acid, the ability to insert the template nucleic acid into the engineered meganuclease cleavage site to generate a modified SERPINA1 gene that encodes a full-length and functional (e.g., wild-type) AAT protein. Such variants may result, for example, from human manipulation. Biologically active variants of a native polypeptide of the embodiments described herein, or a portion, domain, or subunit of a polypeptide of the embodiments, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, as determined by sequence alignment programs and parameters described elsewhere herein. A biologically active variant of a polypeptide of the embodiments may differ from the native sequence by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In the context of variant polypeptides, "corresponding to" means that an amino acid residue in the variant polypeptide (e.g., a variant protein, engineered meganuclease, subunit, or HVR) is the same amino acid residue (i.e., a separate identical residue) present in the parental polypeptide sequence (e.g., the parental protein, engineered meganuclease, subunit, or HVR) in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In some embodiments, engineered meganucleases of the disclosure can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the disclosure, a variant HVR1 region or variant HVR2 region can comprise residues corresponding to the amino acid residues found at specific positions within the parental HVR.

In particular embodiments, engineered meganucleases of the disclosure comprise an HVR1 that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NOs: 17-22, 41-46, 65-71, or 93-100.

In certain embodiments, engineered meganucleases of the disclosure comprise an HVR2 that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 215-270 of any one of SEQ ID NOs: 17-22, 41-46, 65-71, or 93-100.

In some embodiments, engineered meganucleases of the disclosure can comprise variants of the first and second subunits disclosed herein. In certain embodiments, the first subunit of an engineered meganuclease comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 7-153 of any one of SEQ ID NOs: 17-22, 41~46, 65-71, or 93-100. In certain embodiments, the second subunit of an engineered meganuclease comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 198-344 of any one of SEQ ID NOs: 17-22, 41-46, 65-71, or 93-100.

In some embodiments, the disclosure provides variants of the full-length engineered meganucleases described herein. In certain embodiments, the engineered meganuclease comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to any one of SEQ ID NOs: 17-22, 41-46, 65-71, or 93-100.

A substantial number of amino acid modifications to the DNA recognition domain of the wild-type I-CreI meganuclease have previously been identified (e.g., U.S. Pat. No. 8,021,867), which singly or in combination, result in engineered meganucleases with specificities altered at individual bases within the DNA recognition sequence half-site, such that the resulting rationally-designed meganucleases have half-site specificities different from the wild-type enzyme. Table 5 provides potential substitutions that can be made in an engineered meganuclease monomer or subunit to enhance specificity based on the base present at each half-site position (−1 through −9) of a recognition half-site.

TABLE 5

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75 | R70\* | K70 | Q70* | | | | T46\* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44\* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24\* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26\* | | | |
| −5 | | E42 | R42 | | | | K28\* | C28* | | | M66 |
| | | | | | | | | Q42 | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30\* | E38 | K38 | I38 | | | | C38 | | | H38 |
| | Q38 | K30* | R38 | L38 | | | | | | | N38 |
| | | R30* | E30* | | | | | | | | Q30* |

TABLE 5-continued

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −8 | F33 Y33 | E33 D33 | F33 H33 | L33 V33 I33 F33 C33 | | R32* | R33 | | | | |
| −9 | | E32 | R32 K32 | L32 V32 A32 C32 | | | | D32 I32 | | | S32 N32 H32 Q32 T32 |

Bold entries are wild-type contact residues and do not constitute "modifications" as used herein. An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or any one of SEQ ID NOs: 17-22, 41-46, 65-71, or 93-100 (WO 2009/001159), a Y, R. K, or D at a residue corresponding to position 66 of I-CreI or any one of SEQ ID NOs: 17-22, 41-46, 65-71, or 93-100, and/or an E, Q, or K at a residue corresponding to position 80 of I-CreI or any one of SEQ ID NOs: 17-22, 41-46, 65-71, or 93-100 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode various polypeptides of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

In some embodiments, the disclosure provides variants of the donor polynucleotides, template nucleic acids, and components thereof, described herein. In certain embodiments, the donor polynucleotides, template nucleic acids, or components thereof, comprise a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to their native sequence.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its intended activity. For example, variants of an engineered meganuclease would be screened for their ability preferentially bind and cleave recognition sequences found within a SERPINA1 gene.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Editing of AAT Recognition Sequences in a Reporter Cell Line

1. Methods and Materials

The purpose of this experiment was to determine whether AAT meganucleases could bind and cleave their respective human recognition sequences in mammalian cells. Each engineered meganuclease was evaluated using the CHO cell reporter assay previously described (see, WO/2012/167192). To perform the assays, CHO cell reporter lines were produced, which carried a non-functional Green Fluorescent Protein (GFP) gene expression cassette integrated into the genome of the cells. The GFP gene in each cell line contains a direct sequence duplication separated by a pair of recognition sequences such that intracellular cleavage of either recognition sequence by a meganuclease would stimulate a homologous recombination event resulting in a functional GFP gene.

In CHO reporter cell lines developed for this study, several recognition sequences were inserted into the GFP gene including the human AAT 33-34 (SEQ ID NO: 7), AAT 35-36 (SEQ ID NO: 9), AAT 37-38 (SEQ ID NO: 11), AAT 41-42 (SEQ ID NO: 13), and AAT 43-44 (SEQ ID NO: 15) recognition sequences. The second recognition sequence inserted into the GFP gene for each reporter cell line was a CHO-23/24 recognition sequence, which is recognized and cleaved by a control meganuclease called "CHO-23/24." The CHO-23/24 recognition sequence is used as a positive control and standard measure of activity.

CHO reporter cells were transfected with mRNA encoding the indicated meganucleases shown in FIG. 5 and FIG. 6, which included an N-terminal SV40 nuclear localization sequence (SEQ ID NO: 128), which is included at the N-terminus of all the meganucleases described in the examples (unless otherwise noted). A control sample of CHO reporter cells were transfected with mRNA encoding the CHO-23/24 meganuclease. In each assay, 5e4 CHO reporter cells were transfected with 90 ng of mRNA in a 96-well plate using Lipofectamine® MessengerMax (ThermoFisher) according to the manufacturer's instructions. The transfected CHO cells were evaluated by flow cytometry at 2 days, 5 days, and 7 days post transfection to determine the percentage of GFP-positive cells compared to an untransfected negative control. Data obtained at each time point was normalized to the % GFP positive cells observed using the CHO-23/24 meganuclease to determine an "activity score," and the normalized data from the earliest time point was subtracted from that of the latest time point to determine a "toxicity score." The activity and toxicity scores were then added together to determine an "activity index." The activity index for the indicated meganucleases is provided in FIG. 5 and the % GFP positive cells is provided in FIG. 6.

2. Results

Figure 5A:
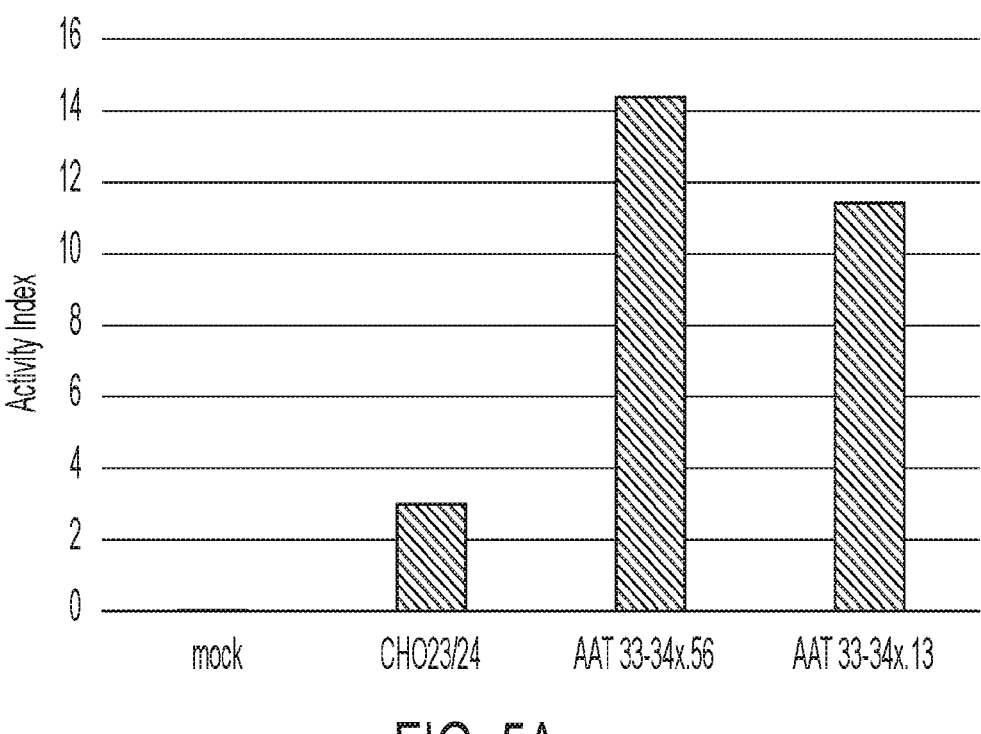
FIGS. 5A-5E provide data showing the efficiency of engineered AAT meganucleases described herein for recognizing and cleaving recognition sequences in a CHO cell reporter assay. The activity index represents % GFP positive cells for each cell line expressing the test meganucleases normalized to the cell line expressing the CHO-23/24 meganuclease accounting for the toxicity of the meganuclease.
Figure 5B:
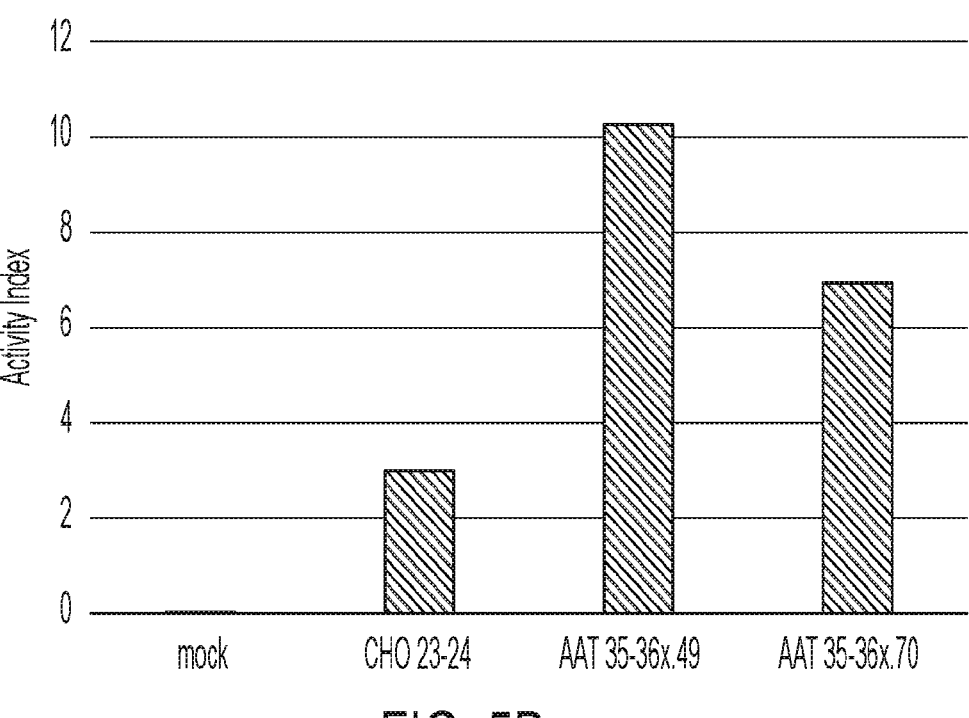
Figure 5C:
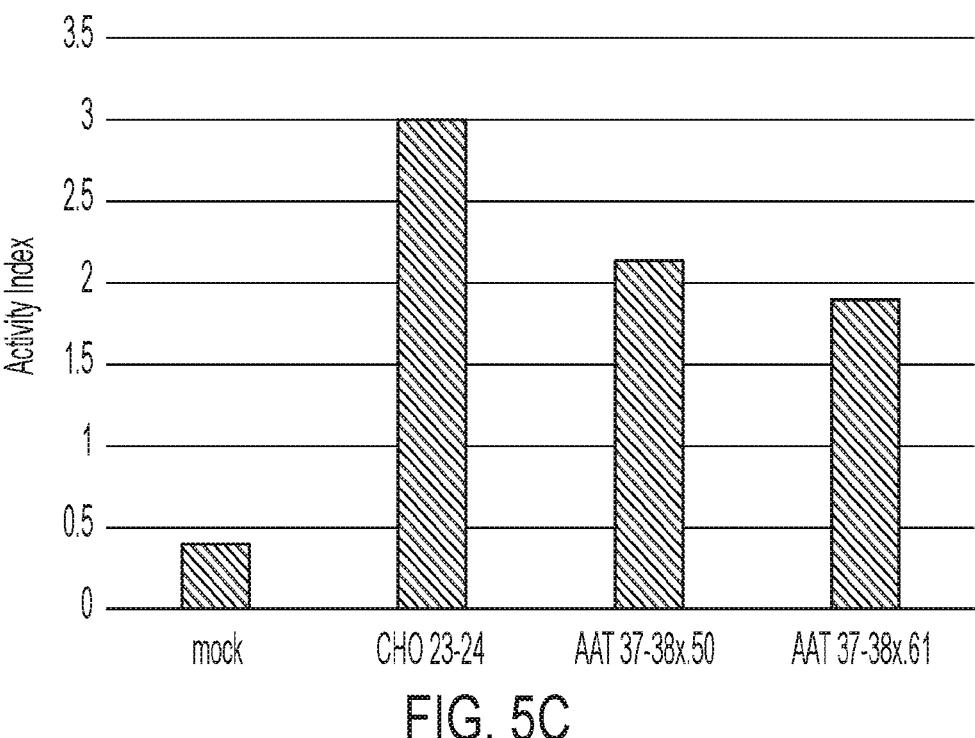
Figure 5D:
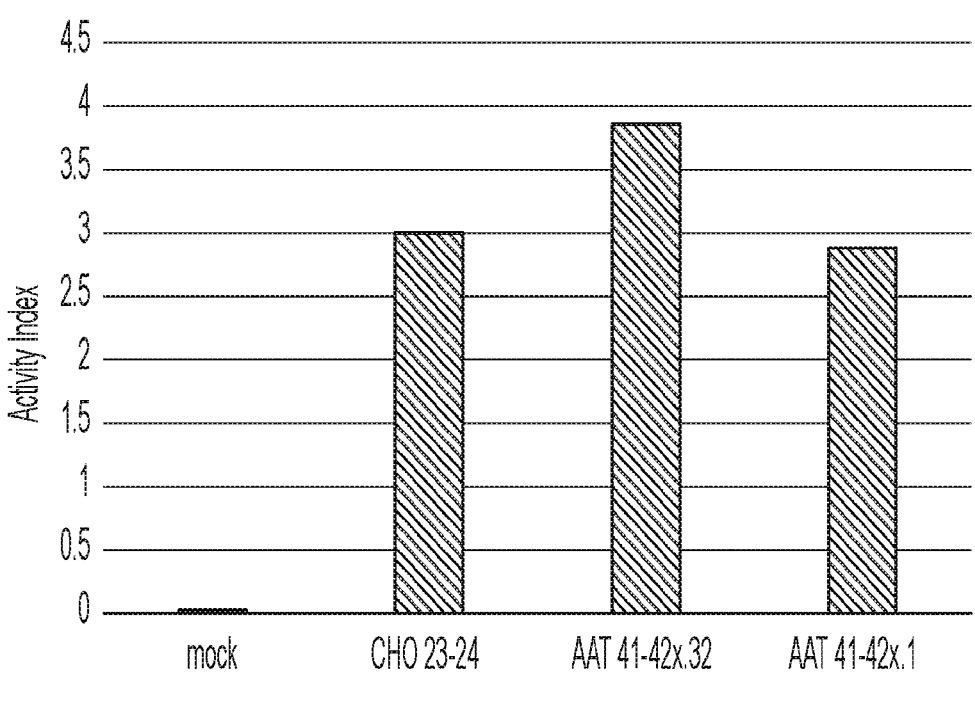
Figure 5E:
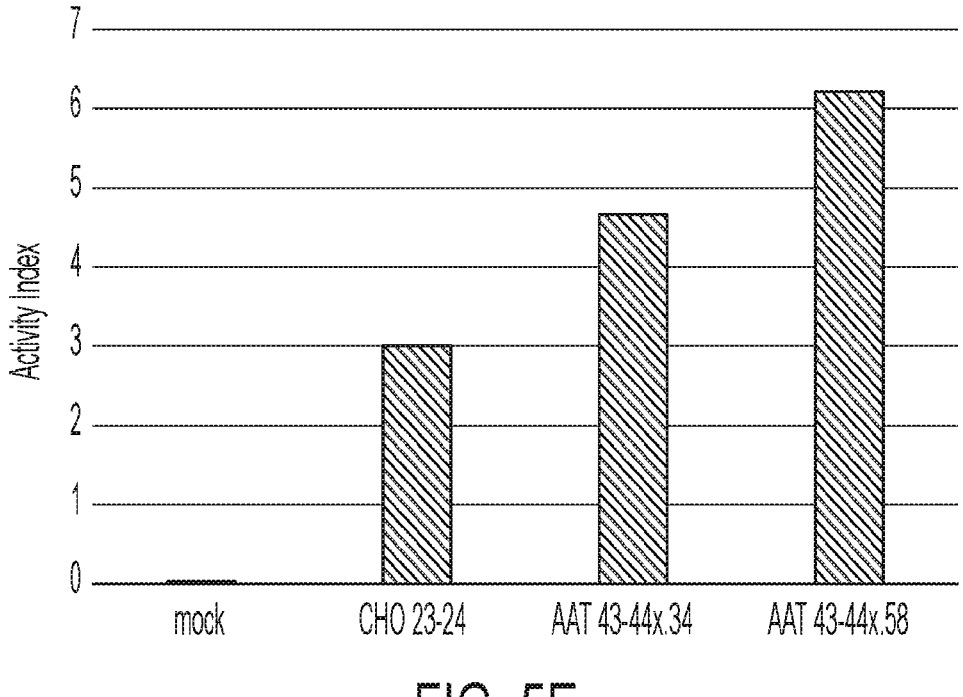
Figure 6A:
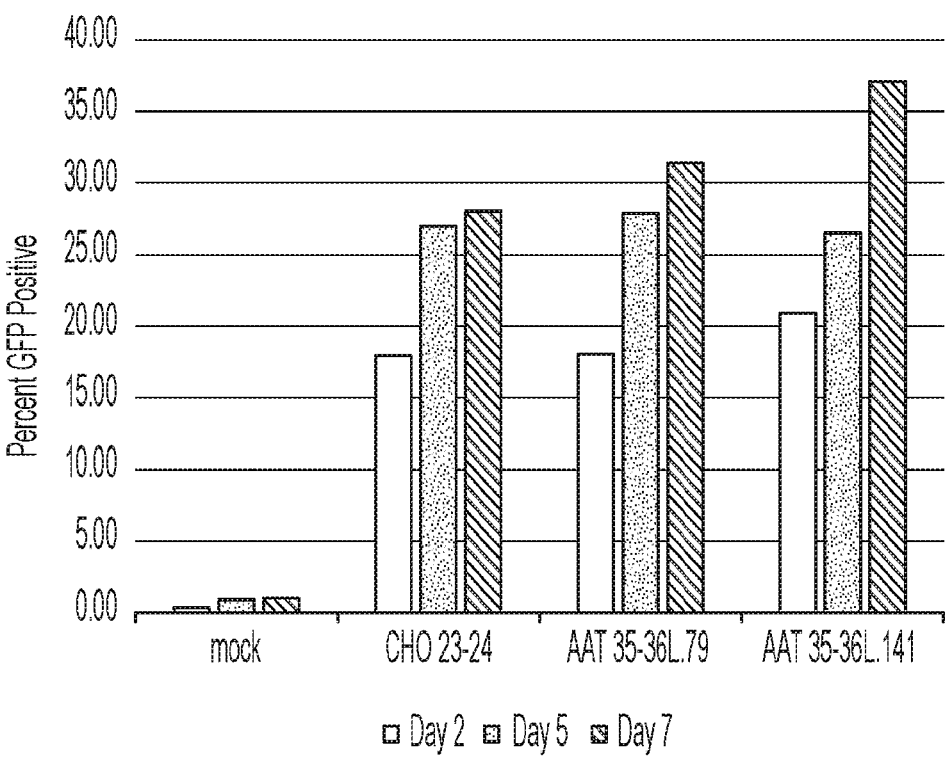
FIGS. 6A-6K provide data showing the efficiency of engineered AAT meganucleases described herein for recognizing and cleaving recognition sequences in a CHO cell reporter assay indicated as % GFP positive cells.
Figure 6B:
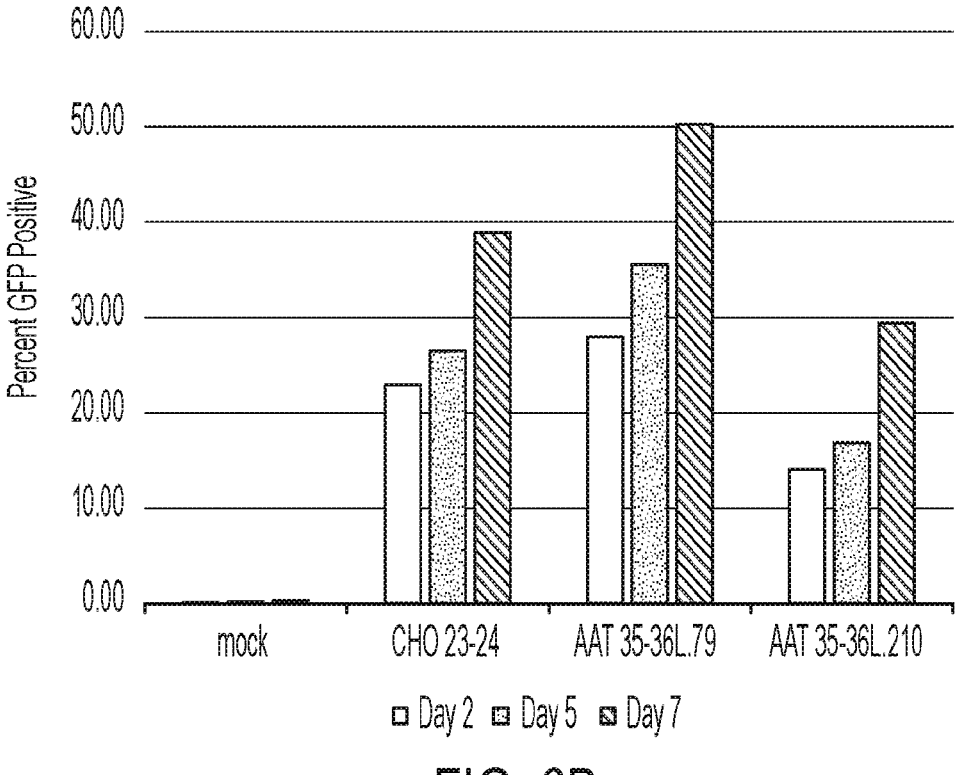
Figure 6C:
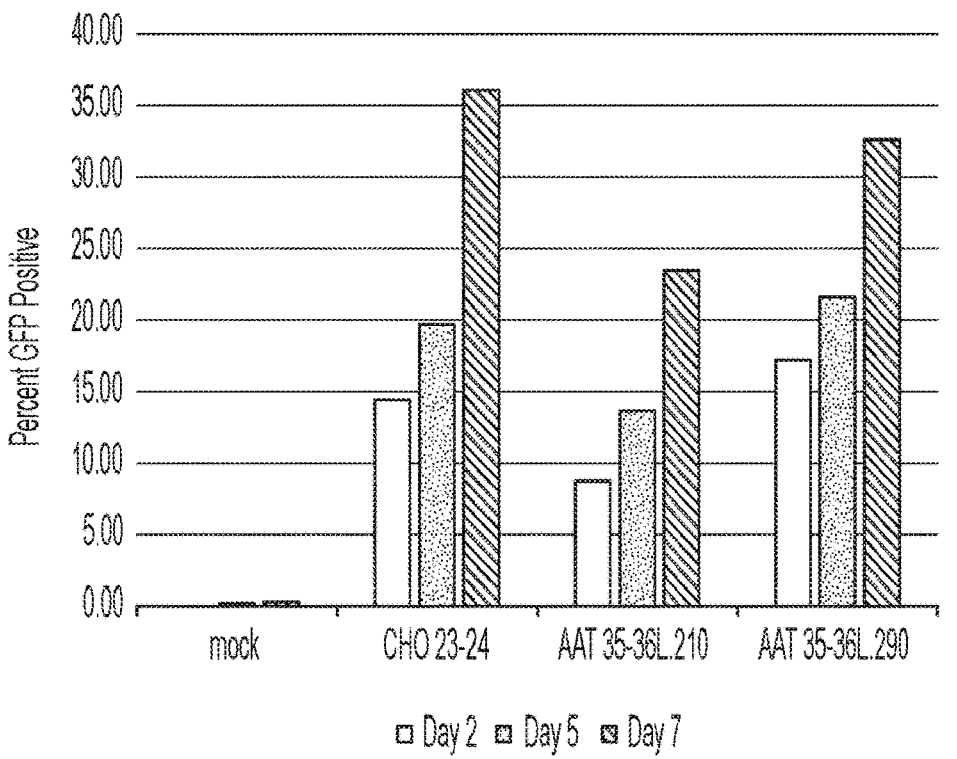
Figure 6D:
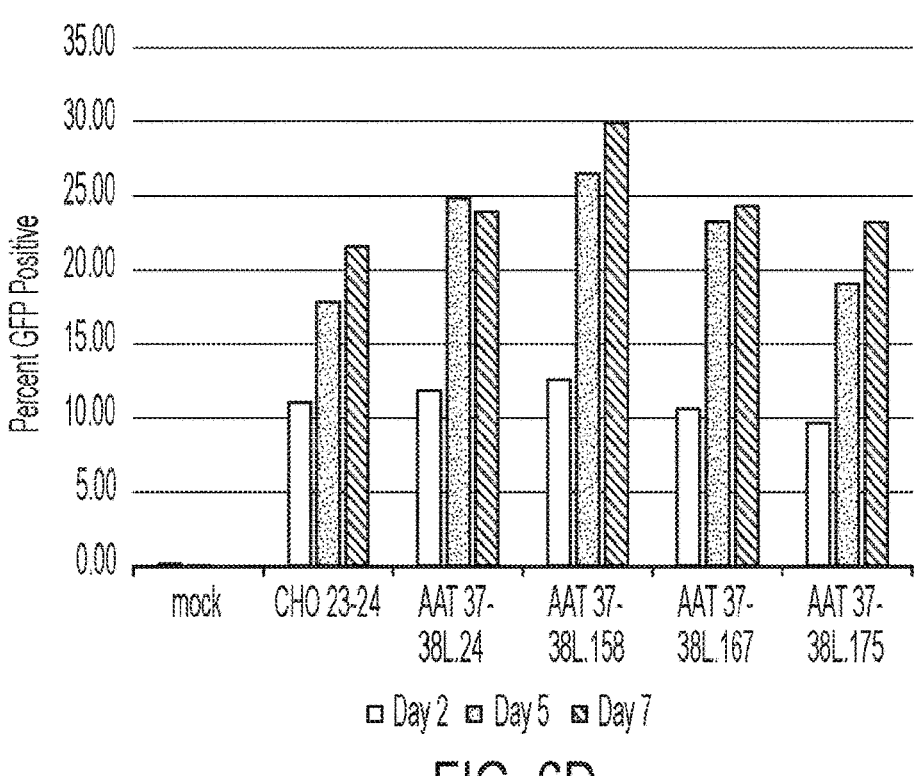
Figure 6E:
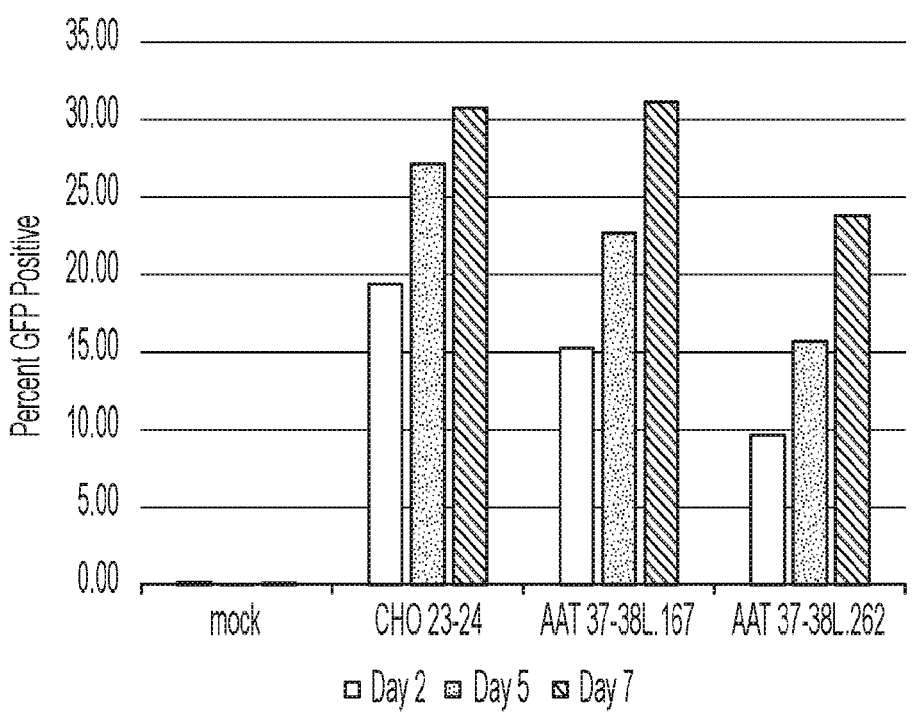
Figure 6F:
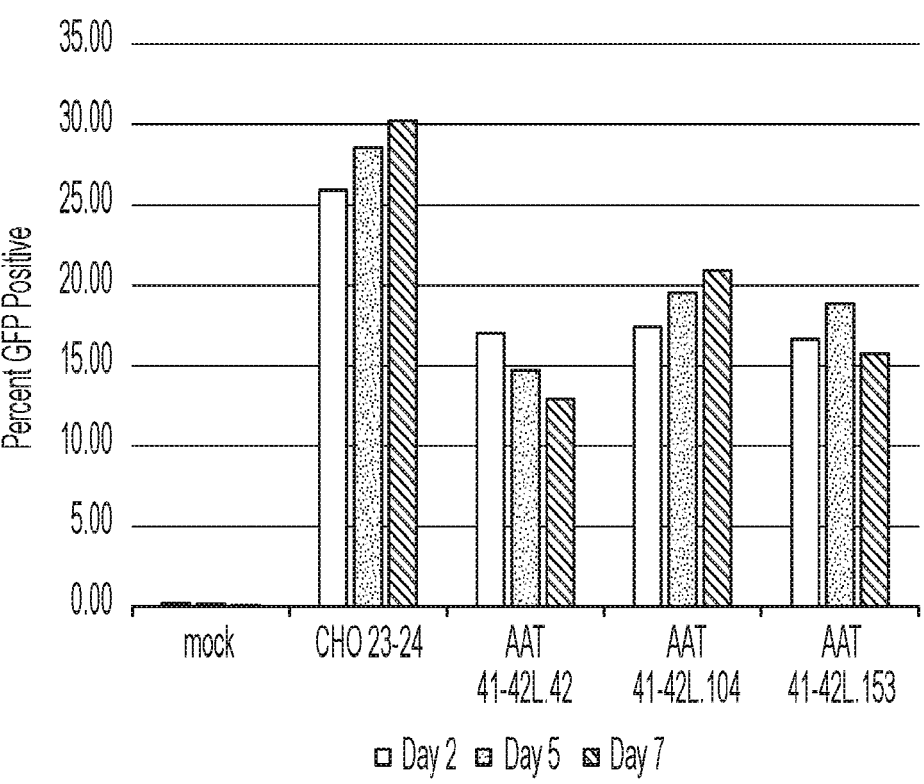
Figure 6G:
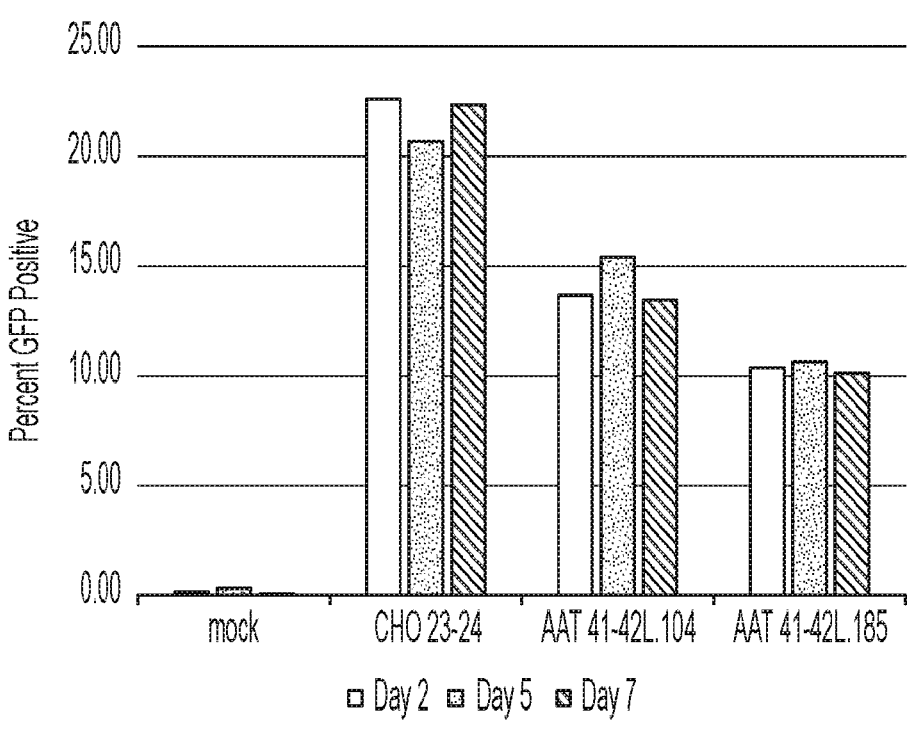
Figure 6H:
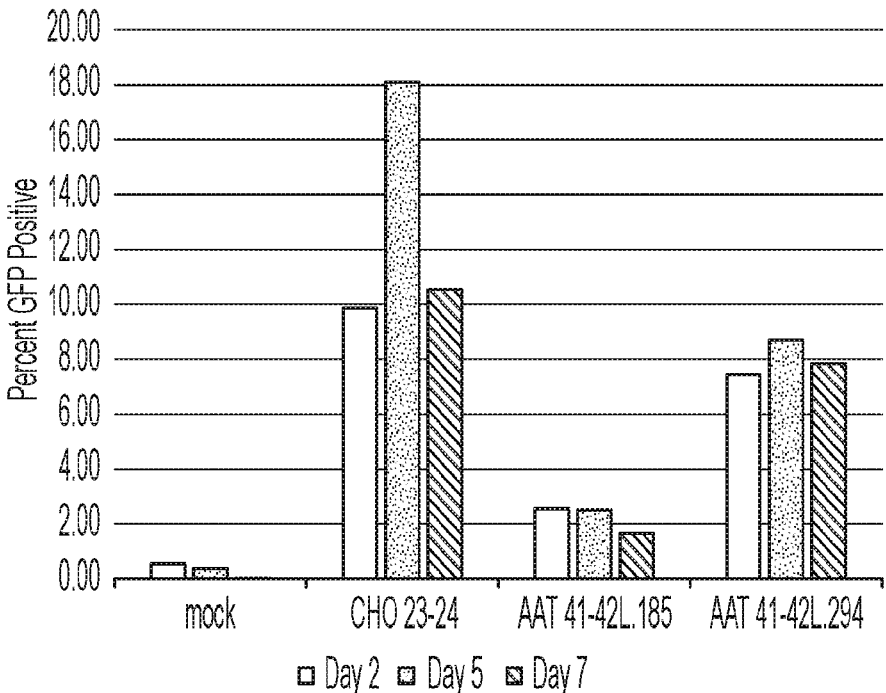
Figures 6I, 6J:
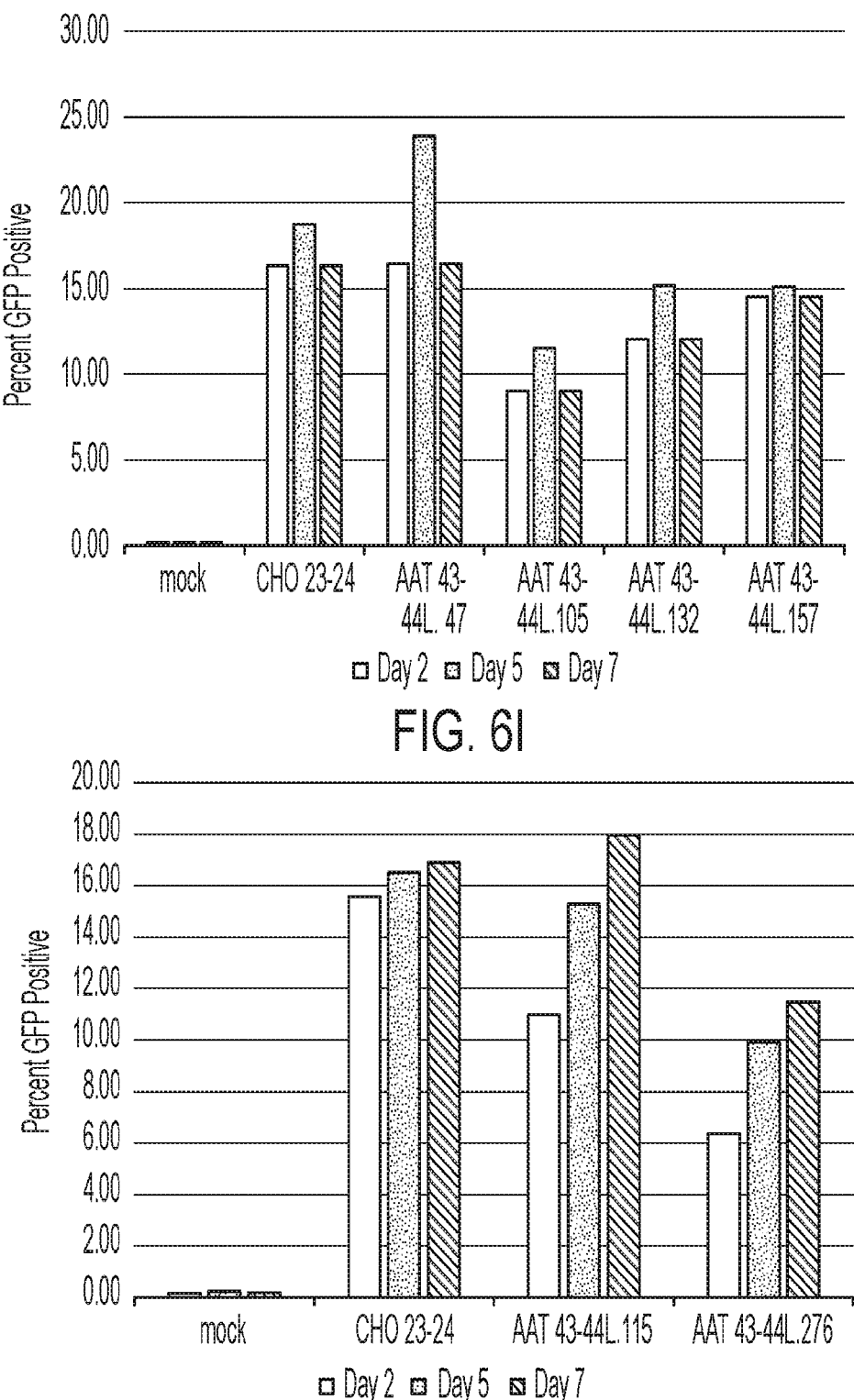
Figure 6K:
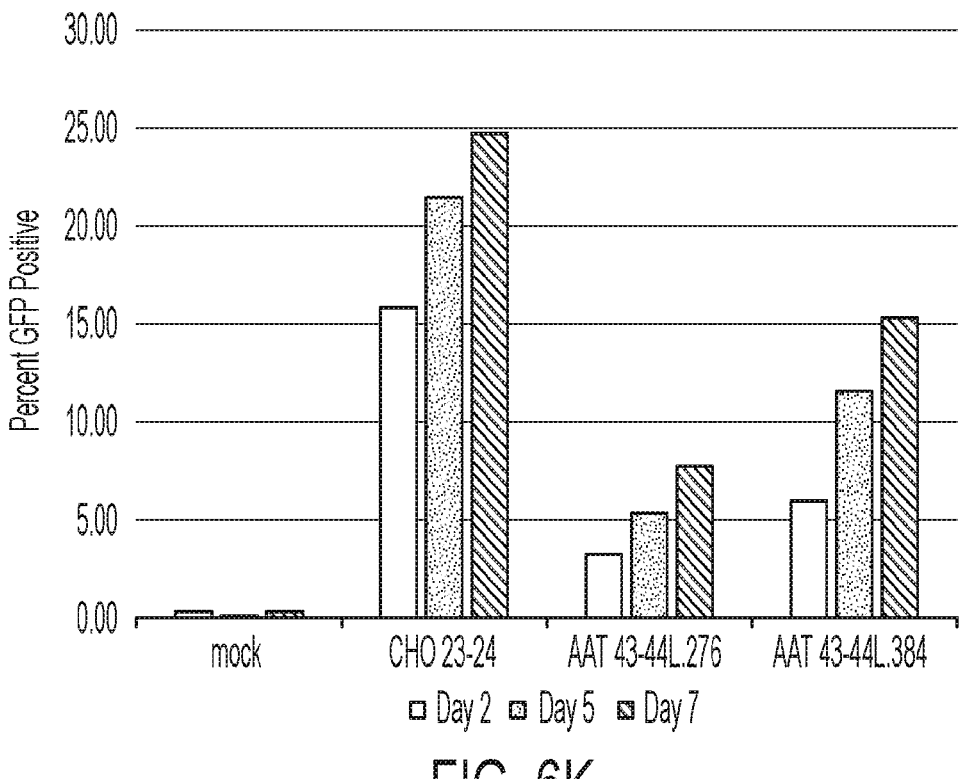

As shown, the positive control CHO-23/24 exhibited an activity index of 3. Each of the indicated AAT meganucleases that bound and cleaved the AAT 33-34, AAT 35-36, AAT 41-42, and AAT 43-44 recognition sequences showed as high, or higher, activity in this assay compared to the CHO-23/24 positive control (FIGS. 5A, 5B, 5D, and 5E). The AAT 37-38 meganucleases exhibited a slightly lower activity index relative (approximately 2) to the positive control (FIG. 5C).

Additionally developed generations of meganucleases targeting the AAT 33-34, AAT 35-36, AAT 41-42, and AAT 43-44 recognition sequences were tested in this assay and the results are shown in FIG. 6A-FIG. 6K. The results demonstrated that these further optimized meganucleases developed against these sites were all able to bind and cleave their recognition sequence.

3. Conclusions

This assay demonstrated that successive generations of engineered AAT meganucleases could bind and cleave five different recognition sequences present in the human SERPINA1 gene.

Example 2

Editing of AAT Recognition Sequences in Human Cell Lines

1. Methods and Materials

These studies were conducted using in vitro cell-based systems to evaluate editing efficiencies of different AAT meganucleases targeting the AAT 33-34, AAT 35-36, AAT 37-38, AAT 41-42, and AAT 43-44 recognition sequences by digital PCR using an indel detection assay.

In these experiments, mRNA encoding the AAT 33-34x.13, AAT 33-34x.56, AAT 35-36x.49, AAT 35-36x.70, AAT 37-38x.50, AAT 37-38x.61, AAT 41-42x.1, AAT 41-42x.32, AAT 43-44x.34, and AAT 43-44x.58 meganucleases were electroporated into cells (Hep3B 50 ng or 5 ng) using the Lonza Amaxa 4D system. All meganucleases included an N-terminal SV40 NLS as described in Example 1.

Cells were collected at two days and six days post electroporation for gDNA preparation and evaluated for transfection efficiency using a Beckman Coulter CytoFlex S cytometer. Transfection efficiency exceeded 90%. Two additional time points were collected at between 4 and 9-days post electroporation for gDNA extractions. gDNA was prepared using the Macherey Nagel NucleoSpin Blood QuickPure kit.

Next generation sequencing was used to determine the frequency of insertions and deletions (indel). Genomic DNA was first obtained from Hep3B cells electroporated with or without meganuclease mRNA, and the isolated genomic DNA was used in a polymerase chain reaction (PCR) using primers spanning between ~220-250 bp with the binding site located in the middle of the amplicon. The PCR 50 ul reaction consisted of repliQa Hifi Toughmix master mix (2×) (Hifi DNA polymerase, dNTPs, MgCl2) (QuantaBio), forward and reverse primers (10 uM) (see Table 6 below for barcoded primers) and genomic DNA (~200 ng). PCR cycling conditions were as follows: 1 cycle of 98° C. for 2 minutes, 45 cycles of 98° C. for 10 seconds, 60° C. for 1 second, 1 cycle of 72° C. for 30 seconds and a 4° C. hold. Some of the PCR product (5 ul) was run on a 1% agarose gel containing ethidium bromide for DNA visualization and analyzed via a UVP Gel Studio (Analytik jena). Some of the PCR product (1 ul) was used for DNA concentration determination using a Quant-iT PicoGreen dsDNA Assay Kit (ThermoFischer) according to the manufacturer's instructions. Each sample (200 ng) was pooled into one sample for NGS analysis.

TABLE 6

Barcoded primers used for NGS sequencing analysis

| Primer | Barcoded sequence* | SEQUENCE ID |
|---|---|---|
| AAT 31-32 Fwd | TATCCAGTccaagctgtatacggatcacactg | SEQ ID NO: 131 |
| AAT 31-32 Fwd | ATGCACCTccaagctgtatacggatcacactg | SEQ ID NO: 132 |
| AAT 31-32 Fwd | CAGTTCCAccaagctgtatacggatcacactg | SEQ ID NO: 133 |
| AAT 31-32 Fwd | TCTCGCCTccaagctgtatacggatcacactg | SEQ ID NO: 134 |
| AAT 31-32 Rvs | GTGGTTCCtgaaccaggaactgtttcacctgcatc | SEQ ID NO: 135 |

TABLE 6-continued

| Barcoded primers used for NGS sequencing analysis | | |
|---|---|---|
| Primer | Barcoded sequence* | SEQUENCE ID |
| AAT 31-32 Rvs | CGAACTTCtgaaccaggaactgtttcacctgcatc | SEQ ID NO: 136 |
| AAT 31-32 Rvs | AGGAATGGtgaaccaggaactgtttcacctgcatc | SEQ ID NO: 137 |
| AAT 31-32 Rvs | GTTAGGAAtgaaccaggaactgtttcacctgcatc | SEQ ID NO: 138 |
| AAT 31-32 Rvs | CGTTGAGGtgaaccaggaactgtttcacctgcatc | SEQ ID NO: 139 |
| AAT 31-32 Rvs | CTCCCAAAtgaaccaggaactgtttcacctgcatc | SEQ ID NO: 140 |
| AAT 31-32 Rvs | GACATTTCtgaaccaggaactgtttcacctgcatc | SEQ ID NO: 141 |
| AAT 31-32 Rvs | TGAGAGATtgaaccaggaactgtttcacctgcatc | SEQ ID NO: 142 |
| AAT 33-34 Fwd | TATCCAGTctcttgaacctggccctagtgtc | SEQ ID NO: 143 |
| AAT 33-34 Fwd | ATGCACCTctcttgaacctggccctagtgtc | SEQ ID NO: 144 |
| AAT 33-34 Fwd | CAGTTCCActcttgaacctggccctagtgtc | SEQ ID NO: 145 |
| AAT 33-34 Fwd | TCTCGCCTctcttgaacctggccctagtgtc | SEQ ID NO: 146 |
| AAT 33-34 Rvs | GTGGTTCCaaattaaatccttccaacacttcagagatcaaggtc | SEQ ID NO: 147 |
| AAT 33-34 Rvs | CGAACTTCaaattaaatccttccaacacttcagagatcaaggtc | SEQ ID NO: 148 |
| AAT 33-34 Rvs | AGGAATGGaaattaaatccttccaacacttcagagatcaaggtc | SEQ ID NO: 149 |
| AAT 33-34 Rvs | GTTAGGAAaaattaaatccttccaacacttcagagatcaaggtc | SEQ ID NO: 150 |
| AAT 33-34 Rvs | CGTTGAGGaaattaaatccttccaacacttcagagatcaaggtc | SEQ ID NO: 151 |
| AAT 33-34 Rvs | CTCCCAAAaaattaaatccttccaacacttcagagatcaaggtc | SEQ ID NO: 152 |
| AAT 33-34 Rvs | GACATTTCaaattaaatccttccaacacttcagagatcaaggtc | SEQ ID NO: 153 |
| AAT 33-34 Rvs | TGAGAGATaaattaaatccttccaacacttcagagatcaaggtc | SEQ ID NO: 154 |
| AAT 35-36 Fwd | TATCCAGTctccattgtacagctatgaagctagtg | SEQ ID NO: 155 |
| AAT 35-36 Fwd | ATGCACCTctccattgtacagctatgaagctagtg | SEQ ID NO: 156 |
| AAT 35-36 Fwd | CAGTTCCActccattgtacagctatgaagctagtg | SEQ ID NO: 157 |
| AAT 35-36 Fwd | TCTCGCCTctccattgtacagctatgaagctagtg | SEQ ID NO: 158 |
| AAT 35-36 Rvs | GTGGTTCCgggagcataaaataagggaccaagagc | SEQ ID NO: 159 |
| AAT 35-36 Rvs | CGAACTTCgggagcataaaataagggaccaagagc | SEQ ID NO: 160 |
| AAT 35-36 Rvs | AGGAATGGgggagcataaaataagggaccaagagc | SEQ ID NO: 161 |
| AAT 35-36 Rvs | GTTAGGAAgggagcataaaataagggaccaagagc | SEQ ID NO: 162 |
| AAT 35-36 Rvs | CGTTGAGGgggagcataaaataagggaccaagagc | SEQ ID NO: 163 |
| AAT 35-36 Rvs | CTCCCAAAgggagcataaaataagggaccaagagc | SEQ ID NO: 164 |
| AAT 35-36 RVS | GACATTTCgggagcataaaataagggaccaagagc | SEQ ID NO: 165 |
| AAT 35-36 Rvs | TGAGAGATgggagcataaaataagggaccaagagc | SEQ ID NO: 166 |
| AAT 37-38 Fwd | TATCCAGTtggcagataaagcgagactctgtc | SEQ ID NO: 167 |
| AAT 37-38 Fwd | ATGCACCTtggcagataaagcgagactctgtc | SEQ ID NO: 168 |
| AAT 37-38 Fwd | CAGTTCCAtggcagataaagcgagactctgtc | SEQ ID NO: 169 |
| AAT 37-38 Fwd | TCTCGCCTtggcagataaagcgagactctgtc | SEQ ID NO: 170 |
| AAT 37-38 Fwd | GCCGAATGtggcagataaagcgagactctgtc | SEQ ID NO: 171 |
| AAT 37-38 Fwd | TACTGCAGtggcagataaagcgagactctgtc | SEQ ID NO: 172 |
| AAT 37-38 Fwd | CATGTTGAtggcagataaagcgagactctgtc | SEQ ID NO: 173 |

TABLE 6-continued

| Barcoded primers used for NGS sequencing analysis | | |
|---|---|---|
| Primer | Barcoded sequence* | SEQUENCE ID |
| AAT 37-38 Fwd | ATAGAGTCtggcagataaagcgagactctgtc | SEQ ID NO: 174 |
| AAT 37-38 Fwd | TCACGCTCtggcagataaagcgagactctgtc | SEQ ID NO: 175 |
| AAT 37-38 Rvs | GTGGTTCCgggccagaggttgtggcttctag | SEQ ID NO: 176 |
| AAT 37-38 Rvs | CGAACTTCgggccagaggttgtggcttctag | SEQ ID NO: 177 |
| AAT 37-38 Rvs | AGGAATGGgggccagaggttgtggcttctag | SEQ ID NO: 178 |
| AAT 37-38 Rvs | GTTAGGAAgggccagaggttgtggcttctag | SEQ ID NO: 179 |
| AAT 37-38 Rvs | CGTTGAGGgggccagaggttgtggcttctag | SEQ ID NO: 180 |
| AAT 37-38 Rvs | CTCCCAAAgggccagaggttgtggcttctag | SEQ ID NO: 181 |
| AAT 37-38 Rvs | GACATTTCgggccagaggttgtggcttctag | SEQ ID NO: 182 |
| AAT 37-38 Rvs | TGAGAGATgggccagaggttgtggcttctag | SEQ ID NO: 183 |
| AAT 41-42 Fwd | TATCCAGTgctgactgcaggagcatcagc | SEQ ID NO: 184 |
| AAT 41-42 Rvs | GTGGTTCCacagaagggaaatgcatcttgcac | SEQ ID NO: 185 |
| AAT 41-42 Rvs | CGAACTTacagaagggaaatgcatcttgcac | SEQ ID NO: 186 |
| AAT 41-42 Rvs | AGGAATGGacagaagggaaatgcatcttgcac | SEQ ID NO: 187 |
| AAT 41-42 Rvs | GTTAGGAAacagaagggaaatgcatcttgcac | SEQ ID NO: 188 |
| AAT 41-42 Rvs | CGTTGAGGacagaagggaaatgcatcttgcac | SEQ ID NO: 189 |
| AAT 41-42 Rvs | CTCCCAAAacagaagggaaatgcatcttgcac | SEQ ID NO: 190 |
| AAT 41-42 Rvs | GACATTTCacagaagggaaatgcatcttgcac | SEQ ID NO: 191 |
| AAT 41-42 Rvs | TGAGAGATacagaagggaaatgcatcttgcac | SEQ ID NO: 192 |
| AAT 43-44 Fwd | TATCCAGTaggcccattcctcttcttgtgc | SEQ ID NO: 193 |
| AAT 43-44 Fwd | ATGCACCTaggcccattcctcttcttgtgc | SEQ ID NO: 194 |
| AAT 43-44 Fwd | CAGTTCCAaggcccattcctcttctigtgc | SEQ ID NO: 195 |
| AAT 43-44 Fwd | TCTCGCCTaggcccattcctcttcttgtgc | SEQ ID NO: 196 |
| AAT 43-44 Rvs | GTGGTTCCcaatcccgtgaggtgctaatgc | SEQ ID NO: 197 |
| AAT 43-44 Rvs | CGAACTTcaatcccgtgaggtgctaatgc | SEQ ID NO: 198 |
| AAT 43-44 Rvs | AGGAATGGcaatcccgtgaggtgctaatgc | SEQ ID NO: 199 |
| AAT 43-44 Rvs | GTTAGGAAcaatcccgtgaggtgctaatgc | SEQ ID NO: 200 |
| AAT 43-44 Rvs | CGTTGAGGcaatcccgtgaggtgctaatgc | SEQ ID NO: 201 |
| AAT 43-44 Rvs | CTCCCAAAcaatcccgtgaggtgctaatgc | SEQ ID NO: 202 |
| AAT 43-44 Rvs | GACATTTCcaatcccgtgaggtgctaatgc | SEQ ID NO: 203 |
| AAT 43-44 Rvs | TGAGAGATcaatcccgtgaggtgctaatgc | SEQ ID NO: 204 |

*the uppercase portion of primer indicates the 5' barcode sequence for each primer.

2. Results

Figure 7:
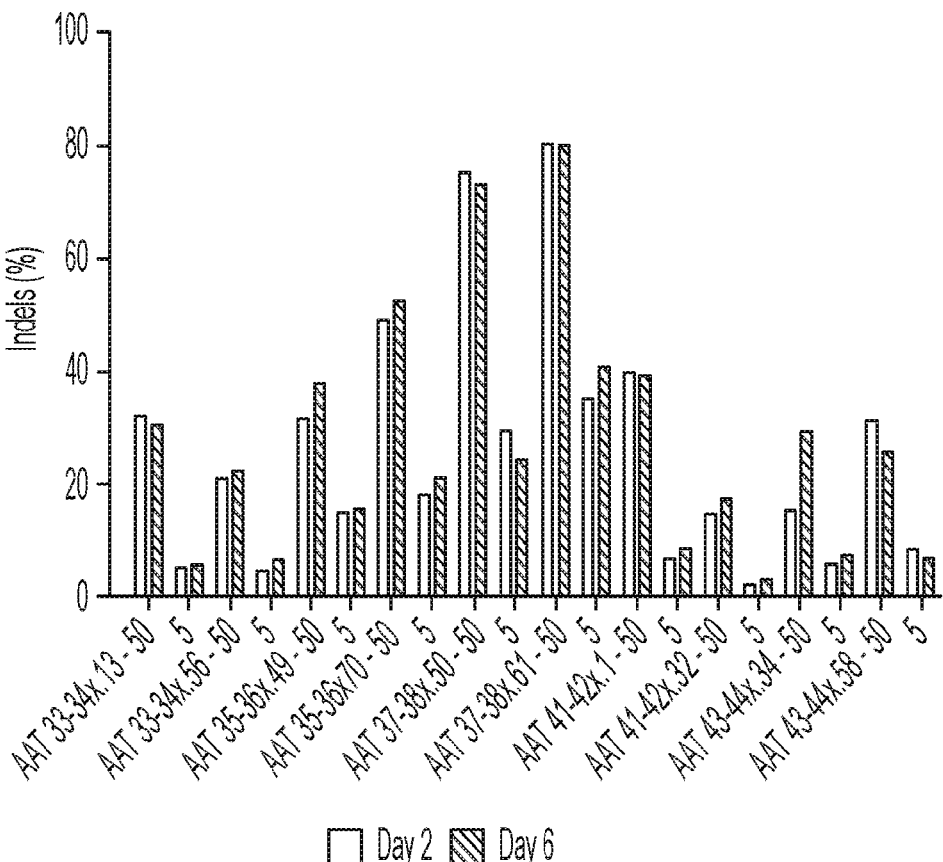
FIG. 7 provides a bar graph indicating the percentage (%) of insertions and deletions (indels) for each of the indicated engineered meganucleases in Hep3B cells at Day 2 (black bars) and Day 6 (gray bars) post transfection. A total of 50 ng or 5 ng of each meganuclease was transfected.

Indel frequencies varied between the AAT meganucleases tested in this study. The AAT 35-36 and AAT 37-38 meganucleases demonstrated the highest indel potency at days 2 and 6 at both the 5 ng and 50 ng doses. AAT 37-38x.61 exhibited the highest indel frequency with 80% indels by day 6 at the 50 ng dose. The AAT 41-42x.32 meganuclease gave the lowest indel frequency at 17% indels by day 6 at the 50 ng dose (FIG. 7).

3. Conclusions

The AAT meganucleases evaluated in this study demonstrated indel frequencies between 3% and 40% at the 5 ng dose, and between 15% and 80% at the 50 ng dose. The meganuclease with the highest indel percentage for each binding site was chosen to be further engineered for increased activity and target specificity, while maintaining or improving indel potency. The following meganucleases were chosen for further development: AAT 33-34x.13 and AAT 33-34x.56, AAT 35-36x.70, AAT 37-38x.50, AAT 41-42x.1 and AAT 43-44x.58.

Example 3

In Vivo AAT Gene Editing in a PiZ AAT Mouse Model

1. Methods and Materials

Figure 8:
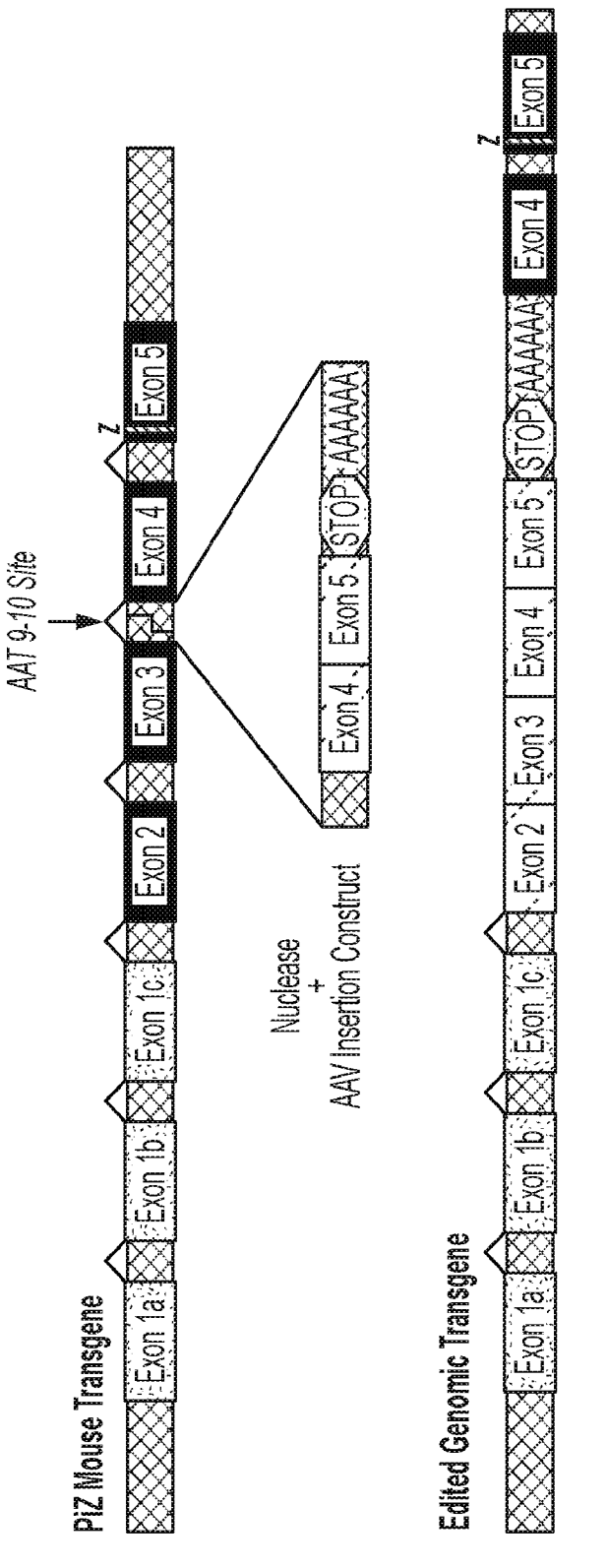
FIG. 8 provides a schematic of the gene editing approach used in the PIZ AAT murine model of Example 3. As shown, the AAT gene comprises seven exons (exons 1a, 1b, 1c and exons 2, 3, 4, and 5). The gene contains the 'Z' mutation in exon 5. The strategy used in this mouse model utilizes an engineered nuclease that cleaves an AAT recognition sequence in the intron between exon 3 and 4 (AAT 9-10). The repair WT AAT sequence shown in the middle of the figure contains exons 4 and 5, a stop codon, and poly A signal preventing the endogenous Z-AAT allele from being expressed. In addition, a flag tag was added for histological detection of WT AAT expressed off of the repair construct. The schematic at the bottom of the figure shows the edited and repaired AAT gene containing the exogenously inserted WT exons 4 and 5 with the stop codon and poly A signal to terminate translation and transcription of the allele prior to expression of the Z-AAT portion of the endogenous exon 5.

The NSG-Tg (SERPINA*E342K) Z11.03Slcw transgenic mice, abbreviated PiZ, were obtained from The Jackson Laboratory. This transgenic model contains the Z mutant allele of the human alpha1-antitrypsin (AAT) transgene, SERPINA1, which allows for human Z-AAT protein expression. PiZ mice contain numerous Z-AAT transgenes (>10), and this number is variable with age. This mouse model was utilized to determine if it was possible to cut within intron 3 of the endogenous mutant Z-AAT allele and insert exons 4 and 5 of the WT SERPINA1 CDS off of a promoterless AAV8 vector, thereby expressing a WT AAT protein in place of the mutant Z-AAT protein. A schematic of the gene editing approach is provided in FIG. 8. The repair WT AAT sequence contains both a stop codon and poly A signal at the N-terminus, preventing the endogenous Z-AAT allele from being expressed. In addition, a flag tag was added for histological detection of WT AAT expressed by the inserted donor polynucleotide.

A proof-of-concept meganuclease was designed to bind and cleave a recognition sequence, referred to as AAT 9-10 (SEQ ID NO: 3), located within intron 3 of the SERPINA1 gene. This engineered meganuclease is referred to as AAT 9-10x.311. The coding sequence of the AAT 9-10x.311 meganuclease was packaged as a single stranded transgene in an AAV8 capsid and was operably linked to the liver-specific promoter human thyroxine-binding globulin (TBG). The AAV8 serotype was chosen due to extensive data showing liver tropism in monkeys and humans, along with many current liver-directed gene therapy clinical trials using AAV8 showing its safety and tolerability.

Figure 9:
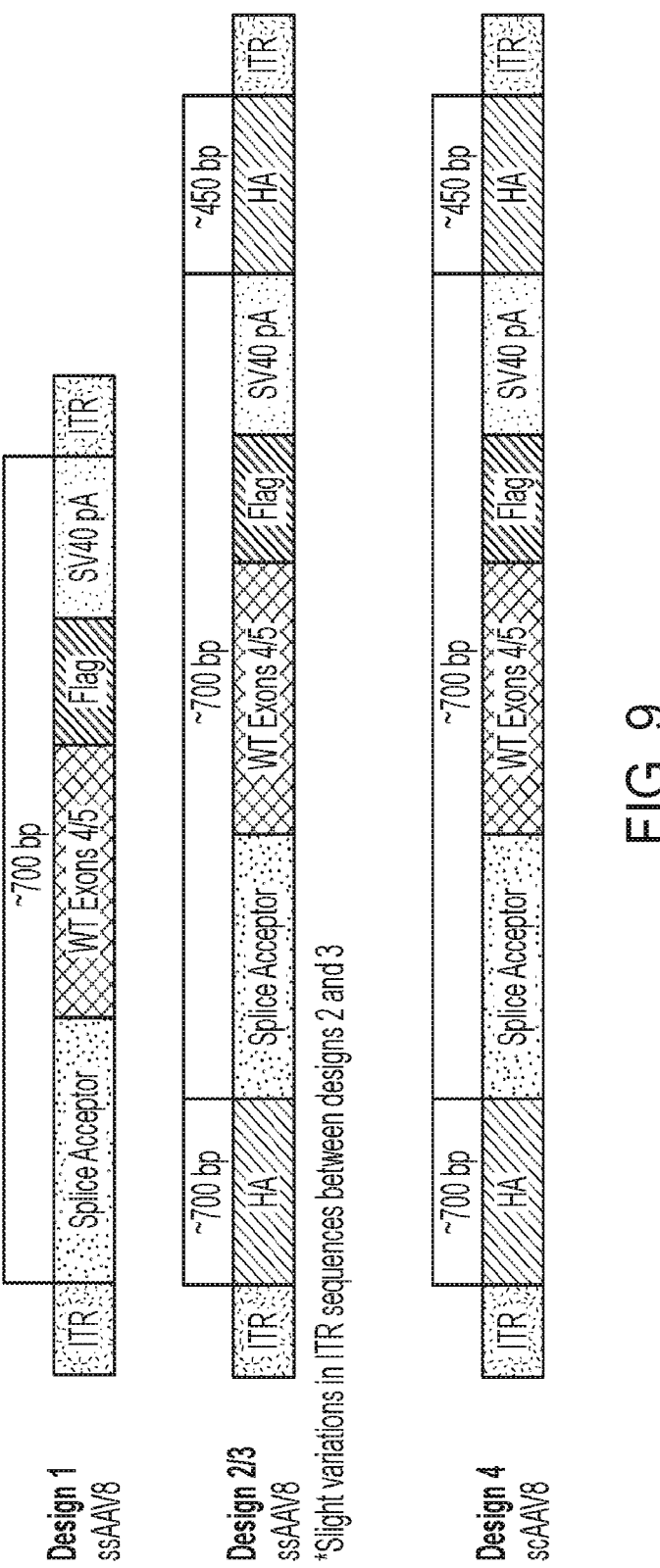
FIG. 9 provides schematics of AAT donor polynucleotide constructs used in the PiZ AAT murine model of Example 3.

A second AAV8 vector utilized in this study comprised one of four wild-type AAT (WT AAT) donor polynucleotides in its viral genome. As shown in FIG. 9, each WT AAV donor polynucleotide comprised a template nucleic acid that included, from 5' to 3', (i) a transferrin intron sequence (i.e., a splicing sequence), which comprises a splice acceptor sequence that can pair with the endogenous splice donor sequence that is downstream and adjacent to exon 3 of the SERPINA1 gene, (iii) exons 4 and 5 of the wild-type human SERPINA1 gene, (iii) a flag tag, and (iv) a termination sequence that included a stop codon and an SV40 poly A sequence. Three of the tested constructs included homology arms flanking the template nucleic acid (~700 bp 5' homology arm and ~450 bp 3' homology arm; designs 2-4), while and one construct was designed without homology arms to be used as a control for NHEJ-driven insertion frequencies (design 1). The included homology arms had homology to sequences upstream and downstream of the expected cleavage site in the AAT 9-10 recognition sequence. Two of the constructs that included homology arms were packaged as single-stranded genomes (rather than self-complimentary)

and varied in the 5' and 3' ITR sequences flanking the homology arms (designs 2 and 3). One of the constructs that included homology arms was packaged as a self-complimentary genome (design 4).

PiZ mice were either administered PBS and one of the WT AAT repair AAV8 vectors, or they were co-administered two AAV8 vectors, one encoding the engineered AAT 9-10 meganuclease and one comprising one of the four designed WT AAT repair sequences, via retro-orbital (RO) injections at doses 5e12 VG/kg and 2.5e13 VG/kg, respectively (Table 7). Blood was collected in EDTA tubes from mice at weekly intervals starting at study day-14 and continuing through necropsy at study day 42. The blood was centrifuged at 15,000×g for 5 minutes to isolate plasma, which was placed at −80° C. for mass spectrometry analysis. Livers were harvested at necropsy for genomic analysis. Briefly, animals were perfused with PBS, and a piece of the left median lobe of the liver was placed in RNAlater. A piece was also flash frozen and placed in a freezer set to maintain between −70° C. and −80° C. Liver tissue placed into RNAlater were held overnight at 4° C. and then transferred to a freezer set to maintain a temperature between −70° C. and −80° C. Genomic DNA was extracted from liver samples using the NucleoSpin Tissue kit (Macherey-Nagel) and used for AAT copy number, indel and insertion frequency analysis (ddPCR).

For analysis of human Z-AAT transgene copy number in PiZ mice livers at study day 40, primers P1, F1, and R1 were used to generate a reference amplicon in the human Z-AAT transgene at a recognition site referred to as AAT 13-14 (SEQ ID NO: 5), as well as P2, F2, and R2 to generate a reference amplicon at a meganuclease recognition sequence in the mouse transthyretin gene referred to as TTR 5-6 (SEQ ID NO: 129). Amplifications were multiplexed in a 20 uL reaction containing 1× ddPCR Supermix for Probes (no dUTP, BioRad), 250 nM of each probe, 900 nM of each primer, 5 U of HindIII-HF, and about 10 ng cellular gDNA. Droplets were generated using a QX100 droplet generator (BioRad). Cycling conditions for this assay were as follows: 1 cycle of 95° C. (2° C./s ramp) for 10 minutes, 44 cycles of 94° C. (2° C./s ramp) for 10 seconds, 56° C. (2° C./s ramp) for 30 seconds, 72° C. (2° C./s ramp) for 1 minute, 1 cycle of 98° C. for 10 minutes, 4° C. hold.

For ddPCR analysis of functional human WT AAT insertions at the AAT 9-10 site, per copy of human Z-AAT allele, the primers, P3, F3, and R3 at the junction of AAT 9-10 insertion and chromosomal PiZ mouse DNA and primers P1, F1, and R1 were used at the AAT 13-14 site. Amplifications were multiplexed in a 20 uL reaction containing 1× ddPCR Supermix for Probes (no dUTP, BioRad), 250 nM of each probe, 900 nM of each primer, 5 U of HindIII-HF, and about 20 ng cellular gDNA. Droplets were generated using a QX100 droplet generator (BioRad). Cycling conditions for this assay were as follows: 1 cycle of 95° C. (2° C./s ramp) for 10 minutes, 44 cycles of 94° C. (2° C./s ramp) for 10 seconds, 59.2° C. (2° C./s ramp) for 30 seconds, 72° C. (0.22° C./s ramp) for 1 minute, 1 cycle of 98° C. for 10 minutes, 4° C. hold.

For ddPCR analysis of human WT AAT insertions per diploid cell, primers, P3, F3, and R3 were used at the AAT9-10 site and primers P2, F2, and R2 at the mouse 5-6 TTR site (Table 8). To determine the total insertion (functional and non-functional) and deletion frequency at the AAT 9-10 site, primers P4, F4, and R4 at the AAT 9-10 recognition site. Amplifications were multiplexed in a 20 uL reaction containing 1× ddPCR Supermix for Probes (no dUTP, BioRad), 250 nM of each probe, 900 nM of each primer, 5 U of HindIII-HF, and about 10 ng cellular gDNA. Droplets were generated using a QX100 droplet generator (BioRad). Cycling conditions for this assay were as follows: 1 cycle of 95° C. (2° C./s ramp) for 10 minutes, 44 cycles of 94° C. (2° C./s ramp) for 10 seconds, 56° C. (2° C./s ramp) for 30 seconds, 72° C. (2° C./s ramp) for 1 minute, 1 cycle of 98° C. for 10 minutes, 4° C. hold.

Primer sequences referred to above are provide in Table 8 below. Droplets were analyzed using a QX200 droplet reader (BioRad) and QuantaSoft analysis software (BioRad) was used to acquire and analyze data. Isolated plasma was analyzed by mass spectrometry analysis for mutant and total AAT protein expression.

TABLE 7

PiZ Mouse Study #1 Design

| Group # | N | AAVS Gene Insertion Construct | PBS/AAV8 Meganuclease |
|---|---|---|---|
| 1 | 2* | Design 1 | PBS |
|  | 3 |  | ssAAV8 AAT9-10x.311 |
| 2 | 2 | Design 2 | PBS |
|  | 3 |  | ssAAV8 AAT9-10x.311 |
| 3 | 2 | Design 3 | PBS |
|  | 3 |  | ssAAV8 AAT9-10x.311 |
| 4 | 2 | Design 4 | PBS |
|  | 3** |  | scAAV8 AAT9-10x.311 |

*One mouse in the PBS treated Group 1 was euthanized 3 weeks post-AAV treatment (not test-article related)

**One mouse in the meganuclease treated Group 4 was euthanized 1 week post-AAV treatment (not test article related).

TABLE 8

Primers used for ddPCR analysis

| Primer Name | Primer Sequence | SEQ ID NO: |
|---|---|---|
| P1 | CTGCTCAGGCATCTGCATTTCCC | SEQ ID NO: 205 |
| F1 | ATGCCTCGATGGTGAAG | SEQ ID NO: 206 |
| R1 | GGCAAACATTCTGCTTACTATT | SEQ ID NO: 207 |
| P2 | CCTCGCTGGACTGGTATTTGTGTCT | SEQ ID NO: 208 |
| F2 | GACAGGATGGCTTCCCTTC | SEQ ID NO: 209 |
| R2 | GTCTAACTGCCATGTCTGGAT | SEQ ID NO: 210 |
| P3 | ACCTTAGTGATGCCCAGTTGACCC | SEQ ID NO: 211 |
| F3 | CCACAACTAGAATGCAGTGAA | SEQ ID NO: 212 |
| R3 | GAATCACGGGCATCTTCAG | SEQ ID NO: 213 |
| P4 | CTGCCCGCTCACACCAGAC | SEQ ID NO: 214 |
| F4 | AGCACCTCCTGAGGTC | SEQ ID NO: 215 |
| R4 | CACACCAGGCTGAGTG | SEQ ID NO: 216 |

2. Results

Figure 10A:
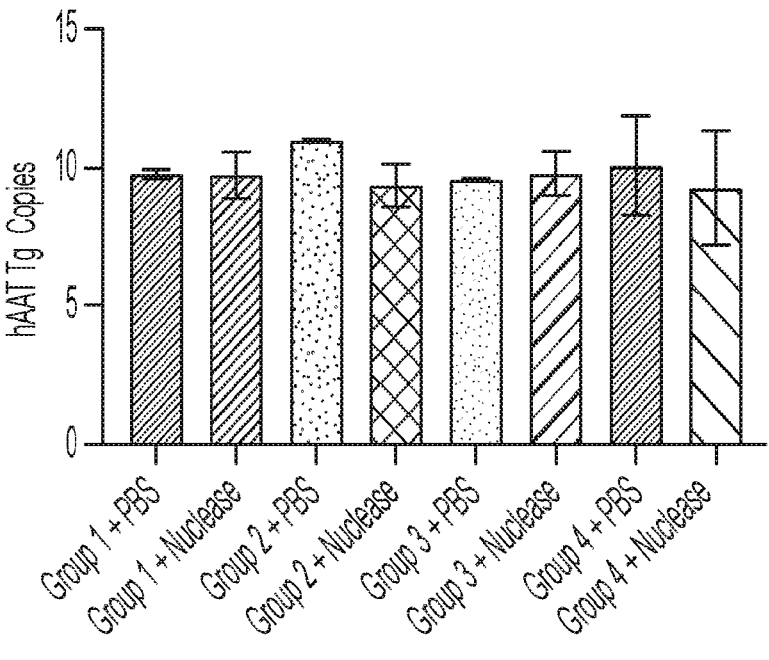
FIG. 10A provides a bar graph showing the number of hAAT transgene copies inserted for each group of mice corresponding to the PiZ AAT murine model of Example 3.
Figure 10B:
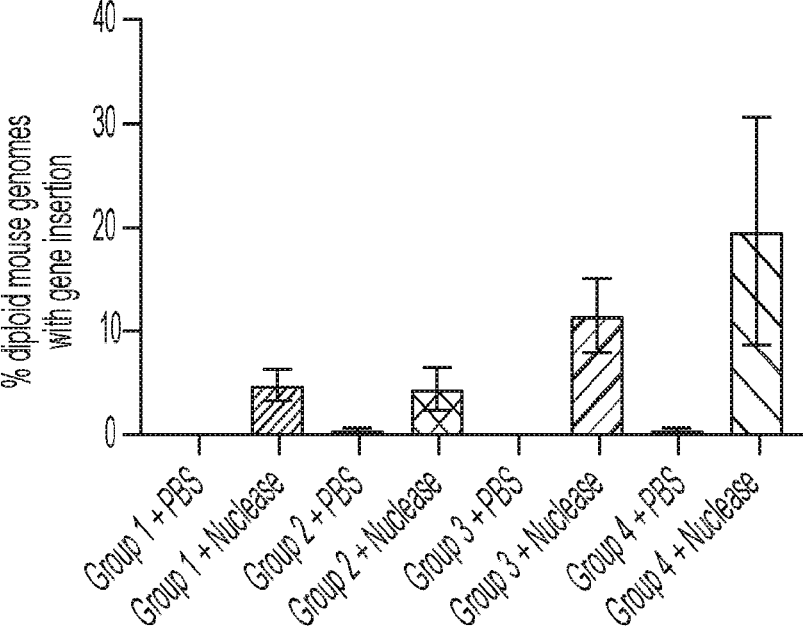
FIG. 10B provides a bar graph showing the percentage (%) of diploid mouse genomes with gene insertion for each group of mice corresponding to the PIZ AAT murine model of Example 3.
Figures 10C, 10D:
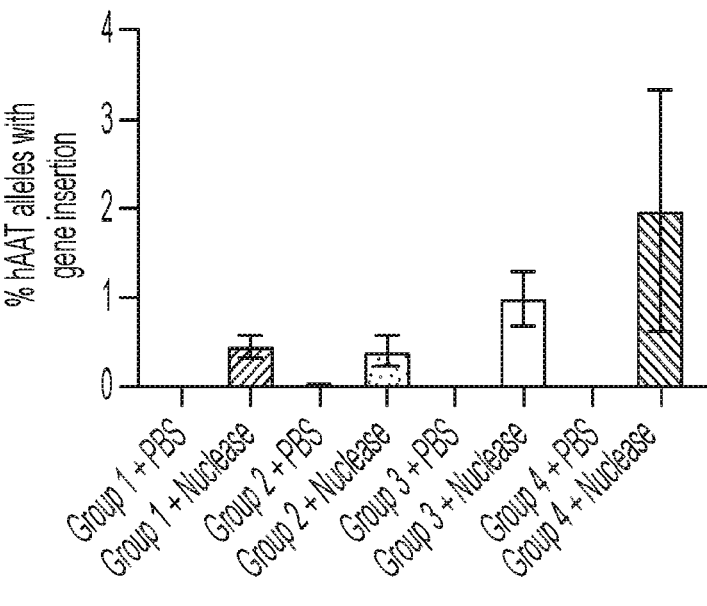
FIG. 10C provides a bar graph showing the percentage (%) of hAAT alleles with gene insertion for each group of mice corresponding to the PiZ AAT murine model of Example 3.
FIG. 10D provides a bar graph showing the percentage (%) of indels for each group of mice corresponding to the PiZ AAT murine model of Example 3.

The ddPCR analysis of genomic DNA from mouse liver determined that the hAAT copy number was the same regardless of treatment group at approximately 10 transgene copies per cell at 6 weeks post AAV injections (FIG. 10A). Insertion frequencies of the WT AAT repair sequence were highest in group 4 treated with the scAAV vector with an average insertion rate of 2% of all human AAT transgenes and ~20% per diploid cell (FIG. 10B and FIG. 10C). The single stranded AAV with ITR sequence B (ITRB) (design 3) had the second highest insertion frequency at ~1% and ~10% average insertion rate per transgene copy and diploid cell, respectively. The single stranded AAV construct without homology arms and ITR sequence A (ITRA) (design 1) and with homology arms and ITRA (design 2) had the lowest insertion frequencies at ~0.5% and 5% per transgene copy and diploid cell, respectively (FIG. 10B and FIG. 10C). Indel analysis showed that groups 1, 3, and 4 all had similar indel levels at 6 weeks post administration of the AAT 9-10 meganuclease with ~20% indels, while group 2 demonstrated only ~10% indels (FIG. 10D). Both insertions of the WT AAT genomic sequence and indels would have been picked up by this assay.

Figure 11A:
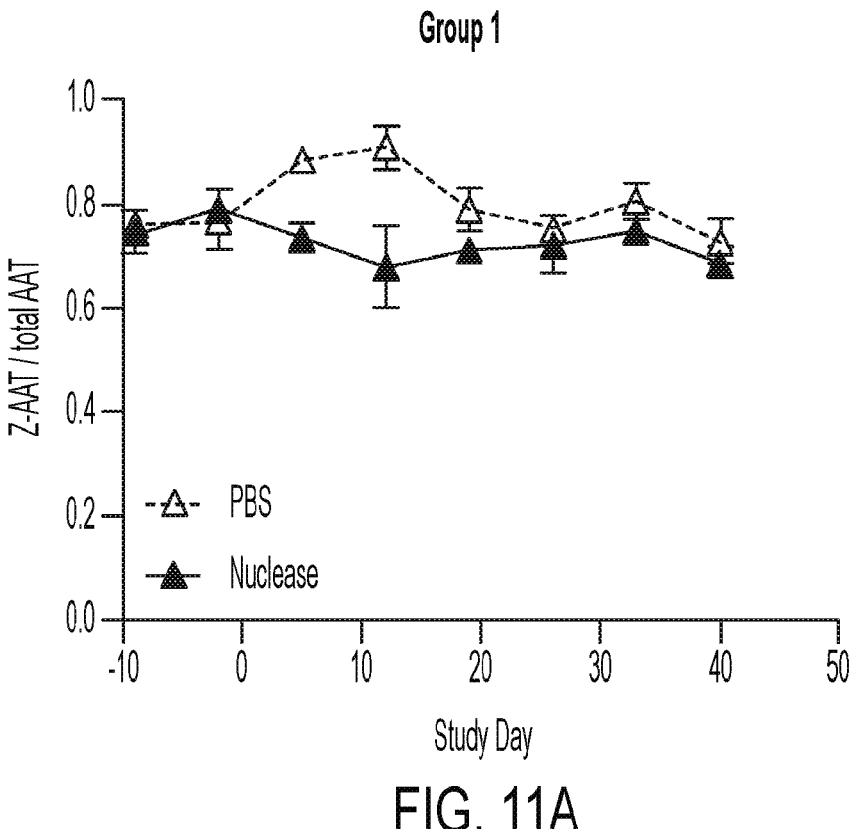
FIG. 11A-FIG. 11D provide line graphs showing ratios of mutant Z-AAT to total AAT until day 40 of the study of Example 3 for study groups 1, 2, 3, and 4, respectively (solid symbols represent animals treated with a nuclease and hollow symbols represent animals treated with mock PBS).
Figure 11B:
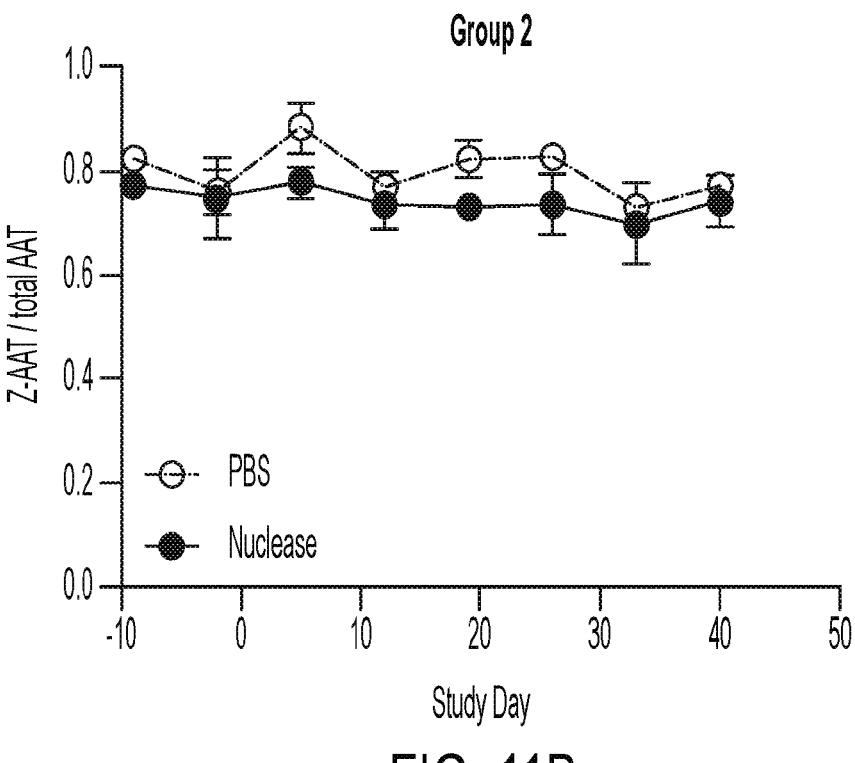
Figure 11C:
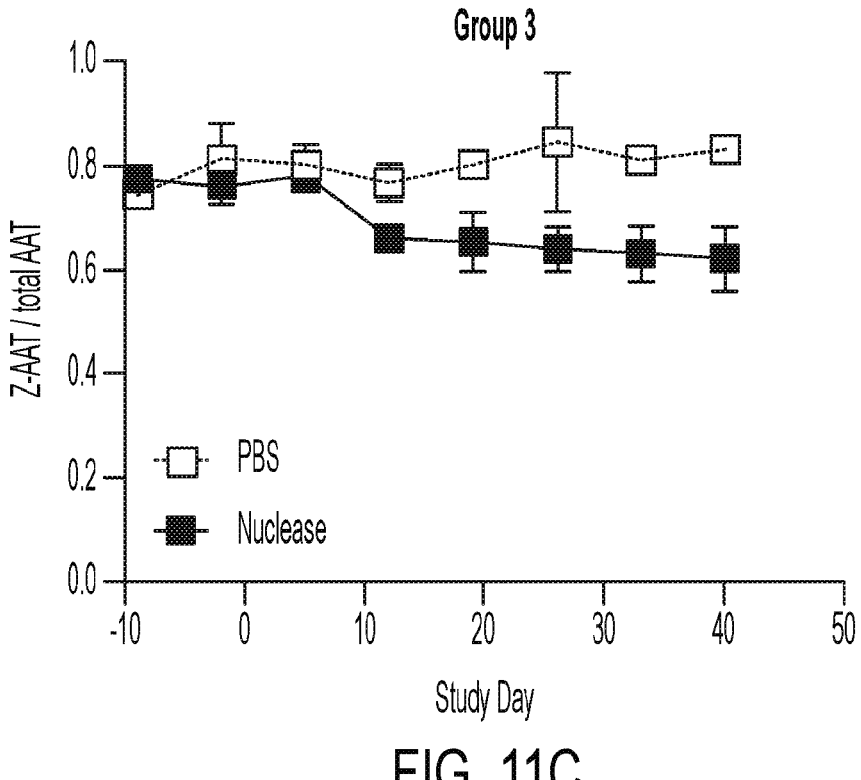
Figure 11D:
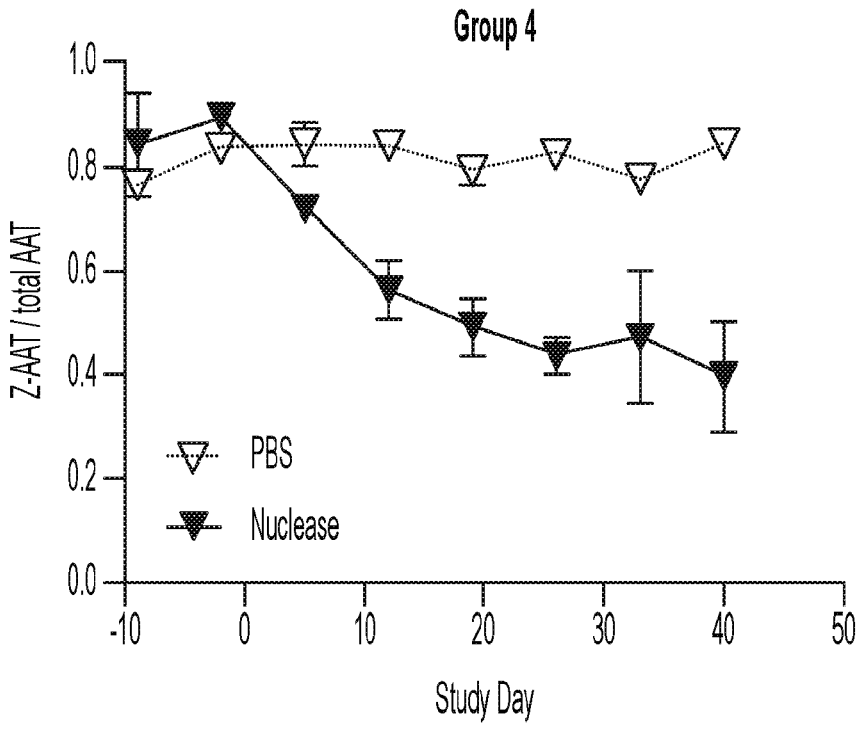

Mass spectrometry was used to determine the level of WT AAT protein circulating in the blood at weekly intervals post AAV injection. WT AAT protein levels were calculated by measuring the loss of the Z allele. Because the meganuclease cuts in an intron, interruption of the Z protein should only occur if a sequence is inserted into the endogenous AAT Z locus and the total protein being made should stay the same. The Z-AAT protein divided by the AAT total protein was calculated for each mouse sample and expressed as a ratio to normalize for the natural decrease of Z-AAT overtime in this model. Therefore, a decrease in this ratio likely indicates an increase in WT protein in the blood. Groups 1 and 2 did not show a significant decrease in Z-AAT through each time point in the study (FIG. 11A and FIG. 11B). Group 4 demonstrated the largest decrease in this ratio at ~50% by study day 40 of the PBS and pre-dose groups. Group 3 had the second largest decrease in the mutant over total ratio with an average of 20% decrease in Z-AAT protein at study day 40 (FIG. 11C and FIG. 11D). These data are consistent with the insertion data with group 4 having the best insertion of the WT AAT sequence, followed by group 3, and groups 1 and 2 showed similar trends with minimal insertion of the WT AAT sequence.

Figure 12:
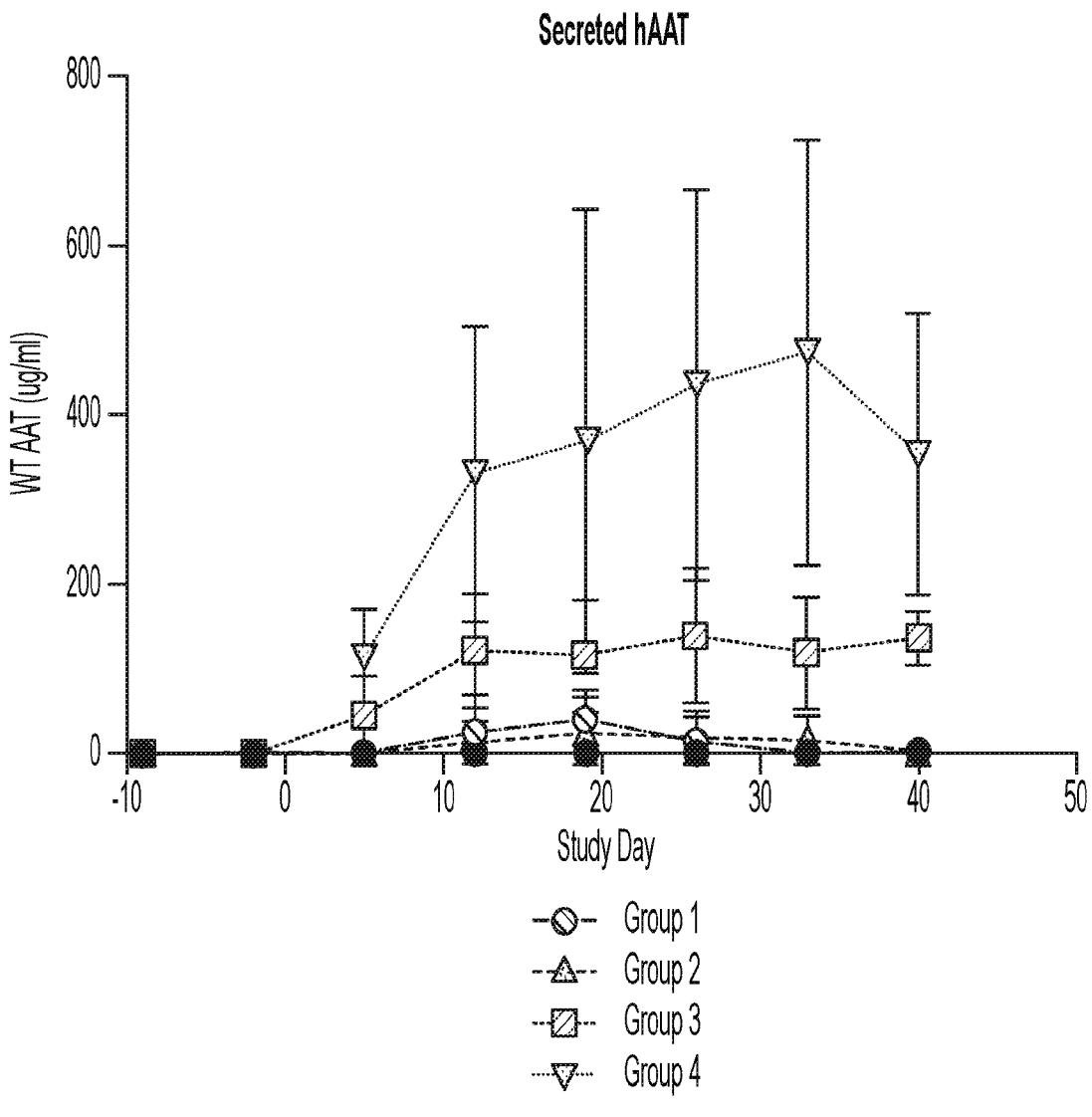
FIG. 12 provides a line graph showing the total amount of WT AAT in µM secreted into the plasma of tested animals of the study of Example 3 for groups 1, 2, 3, and 4.
Figure 13:
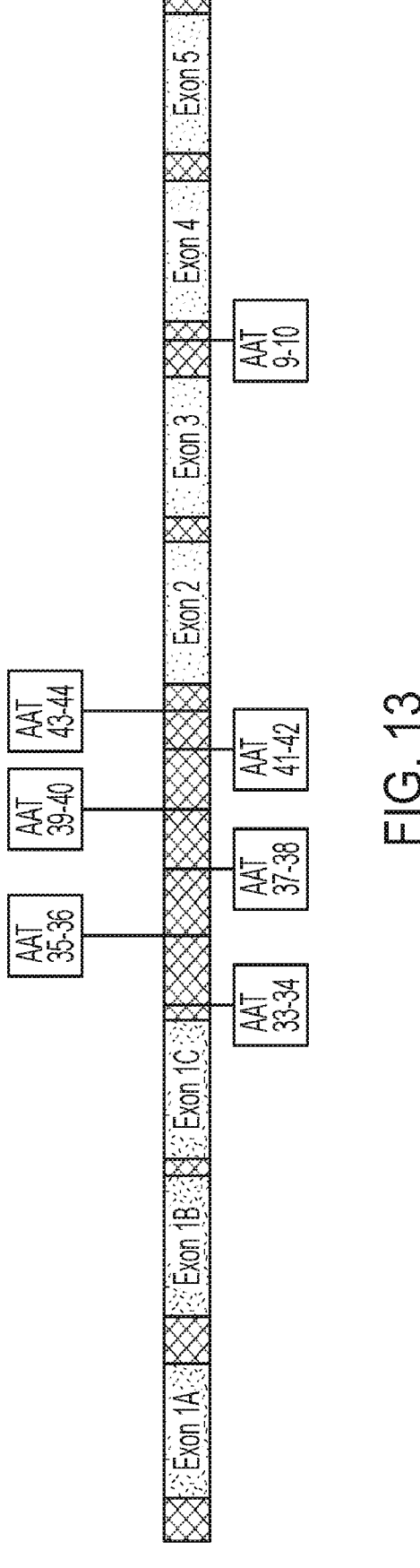
FIG. 13 provides a gene schematic of the hAAT gene indicating approximately where in the genome each of the engineered meganuclease recognition sequences are located for engineered meganucleases being tested in the study of Example 4.

Next, the WT AAT protein was measured directly to determine if the WT AAT protein was indeed being expressed in the blood. The mice in group 4 showed the highest circulating WT AAT protein from week 1 through week 6 with a maximum average of 474 µg/ml of WT AAT protein at study day 33 (FIG. 12). WT AAT was also circulating in group 3 mice throughout the study, but to a lesser extent than group 4, with a maximum average of 129 µg/ml of WT AAT protein at study day 26 (FIG. 12). Groups 1 and 2 had only one animal show circulating WT AAT protein with a maximum average expression of 58 µg/ml on study days 12 and 19, respectively. This data confirmed that WT AAT protein is circulating in PiZ mice after treatment with an AAT gene targeting meganuclease and WT AAT repair template.

3. Conclusions

The results from this study demonstrated the ability to insert a portion of the WT AAT coding sequence into an endogenous mutant Z-AAT locus by co-administering two AAVs separately expressing an engineered meganuclease and a WT AAT repair template, such that the WT AAT repair template is inserted into the endogenous SERPINA1 gene and is operably linked to the endogenous SERPINA1 promoter, and that a full-length WT AAT protein is expressed in the PiZ mice.

Example 4

Additional In Vivo AAT Gene Editing in a PiZ
AAT Mouse Model

1. Methods and Materials

Figure 14:
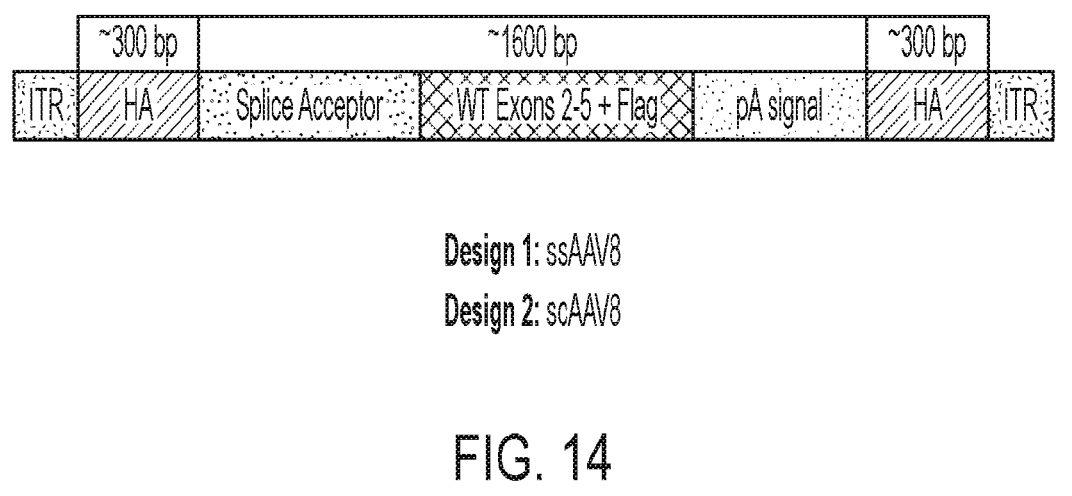

The engineered meganuclease AAT binding site of
Example 3 (AAT 9-10) was found to be highly methylated,
and therefore, potentially creating epigenetic interference
with meganuclease binding and cutting. Thus, additional
engineered meganucleases were designed to target new sites
within the SERPNA1 gene. All of the new engineered
meganucleases target intron 3, which is adjacent to and 3'
downstream of exon 1c, which contains the hepatocyte
specific promoter. Furthermore, AAT donor polynucleotides
were developed that comprise AAT coding exons 2-5, along
with a flag tag, stop codon, and poly-A tail. In this study, PiZ
mice were administered PBS or an AAV8 vector encoding
the following engineered meganucleases, which were pre-
viously described in Example 1: AAT 33-34x.13, AAT
35-36x.70, AAT 37-38x.50, or AAT 43-44x.58. Each mega-
nuclease AAV was administered with PBS or with a second
AAV8 vector comprising an AAT donor polynucleotide. PiZ
mice were either administered PBS and one of the WT AAT
repair AAV8 vectors, or they were co-administered two
AAV8 vectors, one encoding the engineered AAT mega-
nuclease and one comprising one of the four designed WT
AAT repair sequences, via retro-orbital (RO) injections at
doses 2.5e12 VG/kg and 1.25e13 VG/kg, respectively. In
one arm of the study, the AAT donor polynucleotide was
packaged as either an scAAV8 or a ssAAV8, and will include
~300 bp homology arms on either end of the transgene (FIG.
14, Table 9). The scAAV8 and ssAAV8 repair constructs
were chosen due to their superior insertion frequency and
production of WT AAT protein in PiZ mice as described in
Example 3. The repair constructs were designed with homol-
ogy arms for their corresponding binding sites (i.e., AAT
33-34, AAT 35-36, AAT 37-38, or AAT 43-44) with a size of
~300 bp due to the packaging limitations of scAAV (~2.4
kb), which allowed for the WT AAT coding repair construct
to be within these limitations. Blood was taken from mice at
weekly intervals from day-14 through day 42 and plasma
was isolated and analyzed via mass spectrometry as previ-
ously described in Example 3. Liver tissue was harvested
from the mice at day 42 and DNA was isolated from tissue
as described in Example 3. Insertion analysis was performed
by ddPCR with the following ddPCR parameters: 1 cycle of
95° C. for 10 minutes, 44 cycles of 94° C. for 10 seconds,
57° C. for 30 seconds and 72° C. for 4 minutes, 1 cycle of
98° C. for 10 minutes and a 4° C. hold using the primers and
probes in Table 10, assays 1, 2, 3 and 5. AAT transgene copy
number analysis was performed as described in Example 3.
In addition, immunohistochemistry was performed on liver
tissue. Briefly, liver tissue was placed in 10% neutral buffer
formalin (NBF) for at least 24 hours and subsequently
transferred into 70% ethanol for at least 24 hours and then
processed to paraffin blocks for analysis. The following
histological analyses was performed: PAS-D staining for
Z-globules and flag staining for detection of WT AAT
expression from the inserted donor polynucleotide.

TABLE 9

| PiZ Mouse Study #2 Design | | | |
|---|---|---|---|
| Group# | N | AAV8 Gene Insert Construct Design | PBS/AAV8 meganuclease |
| 1 | 2 | Design 1 (single stranded), | PBS |
| 2 | 3 | BS 33-34 | AAT 33-34x.13 |
| 3 | 3 | BS 35-36 | AAT 35-36x.70 |
| 4 | 3 | BS 37-38 | AAT 37-38x.50 |
| 5 | 3 | BS 43-44 | AAT 43-44x.58 |
| 6 | 2 | Design 2 (self-complementary), | PBS |
| 7 | 3 | BS 33-34 | AAT 33-34x.13 |
| 8 | 3 | BS 35-36 | AAT 35-36x.70 |
| 9 | 3 | BS 37-38 | AAT 37-38x.50 |
| 10 | 3 | BS 43-44 | AAT 43-44x.58 |
| 11 | 2 | PBS | PBS |

The AAV repair template with homology arms used in this
study can be inserted into a cut site via homologous directed
repair (HDR) or non-homologous end joining (NHEJ). HDR
results in correct gene orientation insertion that produces
protein or a productive insertion. NHEJ can result in the
repair construct being inserted in the forward or reverse
orientation and only the forward orientation will result in a
productive insertion. The ddPCR assay we used to detect
HDR and forward NHEJ measures total productive inser-
tions (Table 10, Assays 1-5). In order to determine the repair
mechanism, HDR or NHEJ, of the productive insertions we
used the NHEJ reverse (non-productive insertion) assay
(Table 10, Assays 6-10). Based on the hypothesis that NHEJ
insertion results in 50% forward and 50% reverse gene
orientation, we used the NHEJ reverse assay to estimate the
ratio of NHEJ forward and HDR insertions from the pro-
ductive insertions assay.

TABLE 10

| Primer and Probe Sequences for Productive and non-Productive Insertion Assays | | | |
|---|---|---|---|
| Assay No. | Primer/Probe | Sequence | SEQ ID NO: |
| ddPCR HDR/NHEF Forward (Productive) Insertions | | | |
| 1 | AAT33-34 Fwd | TGGACAAACCACAACTAGAA | 217 |
| 1 | AAT33-34 Rvs | AGCCTGGCTAAATGAAGAG | 218 |
| 1 | AAT33-34 Probe | AGCAAGTTGACGTGGAGCAATCTG | 219 |
| 2 | AAT35-36 Fwd | TGGACAAACCACAACTAGAA | 220 |
| 2 | AAT35-36 Rvs | CTCCCAAGCTGTTCCTTAT | 221 |
| 2 | AAT35-36 Probe | AGGGTGCTGCCTCTGATAGAAGG | 222 |
| 3 | AAT37-38 Fwd | TGGACAAACCACAACTAGAA | 223 |
| 3 | AAT37-38 Rvs | CCACAGTGATCCTTCTACTC | 224 |
| 3 | AAT37-38 Probe | TCTGTGAAGACGGCAGGTTCTACC | 225 |
| 4 | AAT41-42 Fwd | TGGACAAACCACAACTAGAA | 226 |
| 4 | AAT41-42 Rvs | CGTGAGGTGCTAATGCTAATA | 227 |
| 4 | AAT41-42 Probe | AGCTGACCTAATCTCTCTGGCTTTGG | 228 |
| 5 | AAT43-44 Fwd | TGGACAAACCACAACTAGAA | 229 |
| 5 | AAT43-44 Rvs | CTGCAAGACAGAGATGGG | 230 |
| 5 | AAT43-44 Probe | AGTCATCATGTGCCTTGACTCGG | 231 |

TABLE 10-continued

Primer and Probe Sequences for Productive and
non-Productive Insertion Assays

| Assay No. | Primer/Probe | Sequence | SEQ ID NO: |
|---|---|---|---|
| ddPCR NHEJ Reverse (non-Productive) Insertions | | | |
| 6 | AAT33-34 Fwd | GAGAGAACGCACCACTTTAC | 232 |
| 6 | AAT33-34 Rvs | AGCCTGGCTAAATGAAGAG | 233 |
| 6 | AAT33-34 Probe | AGCAAGTTGACGTGGAGCAATCTG | 234 |
| 7 | AAT35-36 Fwd | GAGAGAACGCACCACTTTAC | 235 |
| 7 | AAT35-36 Rvs | CTCCCAAGCTGTTCCTTAT | 236 |
| 7 | AAT35-36 Probe | AGGGTGCTGCCTCTGATAGAAGG | 237 |
| 8 | AAT37-38 Fwd | GAGAGAACGCACCACTTTAC | 238 |
| 8 | AAT37-38 Rvs | CCACAGTGATCCTTCTACTC | 239 |
| 8 | AAT37-38 Probe | TCTGTGAAGACGGCAGGTTCTACC | 240 |
| 9 | AAT41-42 Fwd | GAGAGAACGCACCACTTTAC | 241 |
| 9 | AAT41-42 Rvs | CGTGAGGTGCTAATGCTAATA | 242 |
| 9 | AAT41-42 Probe | AGCTGACCTAATCTCTCTGGCTTTGG | 243 |
| 10 | AAT43-44 Fwd | GAGAGAACGCACCACTTTAC | 244 |
| 10 | AAT43-44 Rvs | CTGCAAGACAGAGATGGG | 245 |
| 10 | AAT43-44 Probe | AGTCATCATGTGCCTTGACTCGG | 246 |

2. Results

Figure 15A:
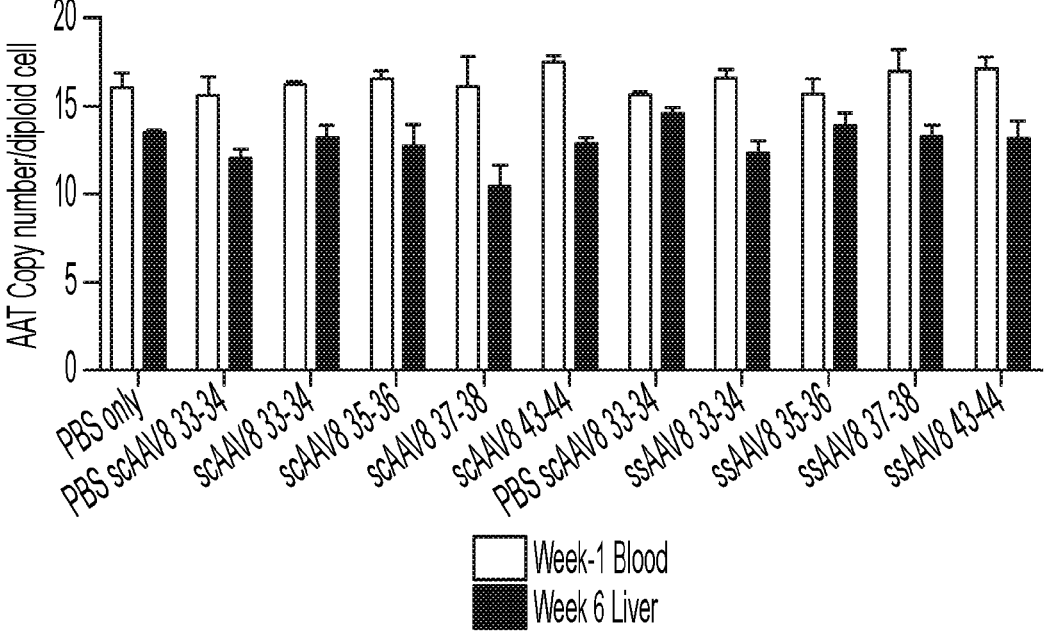
FIG. 15A and FIG. 15B provide bar graphs indicating the total human AAT Tg copy number in the blood at week 1 and week 6 and in the blood and liver at week 6 of PiZ mice treated with the indicated meganucleases, respectively.
Figure 15B:
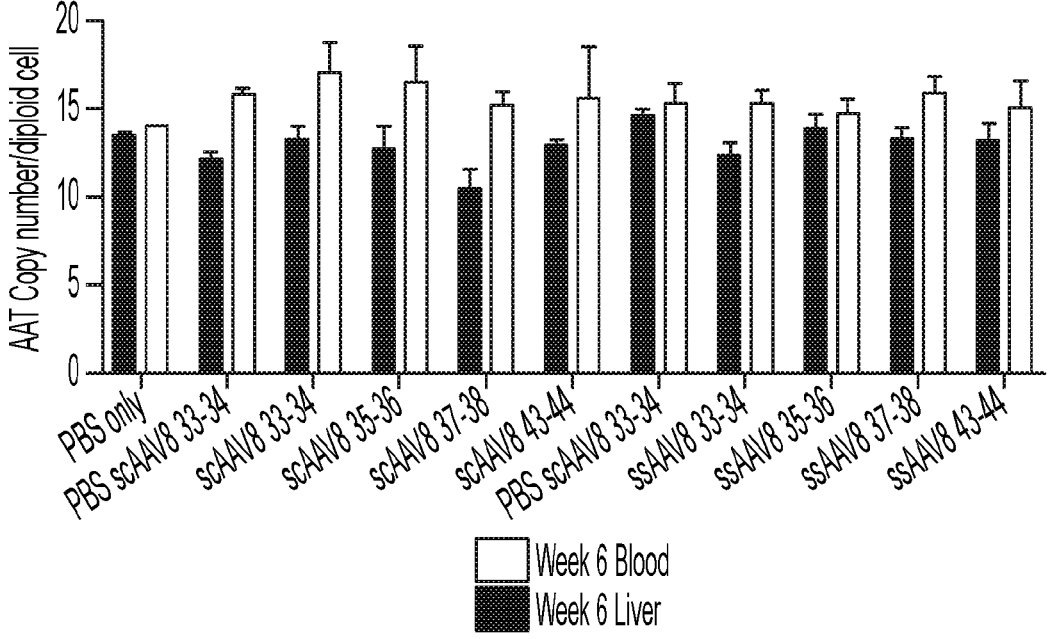

The SERPINA1 transgene copy number was analyzed in PiZ mouse blood from pre-treatment and terminal blood samples and terminal PiZ liver samples (week 6) via ddPCR to see if there was variation in copy number between groups and over time. There were no significant changes in SERPINA1 transgene copy number between groups of PiZ mice between pre and post test article administration in PiZ blood (FIG. 15A). When comparing SERPINA1 transgene copy number between terminal blood and terminal liver samples there is no significant difference in SERPINA1 transgene copy number except for in the group treated with meganuclease AAT 37-38x.50 and the scAAV repair construct (FIG. 15B).

Figure 16A:
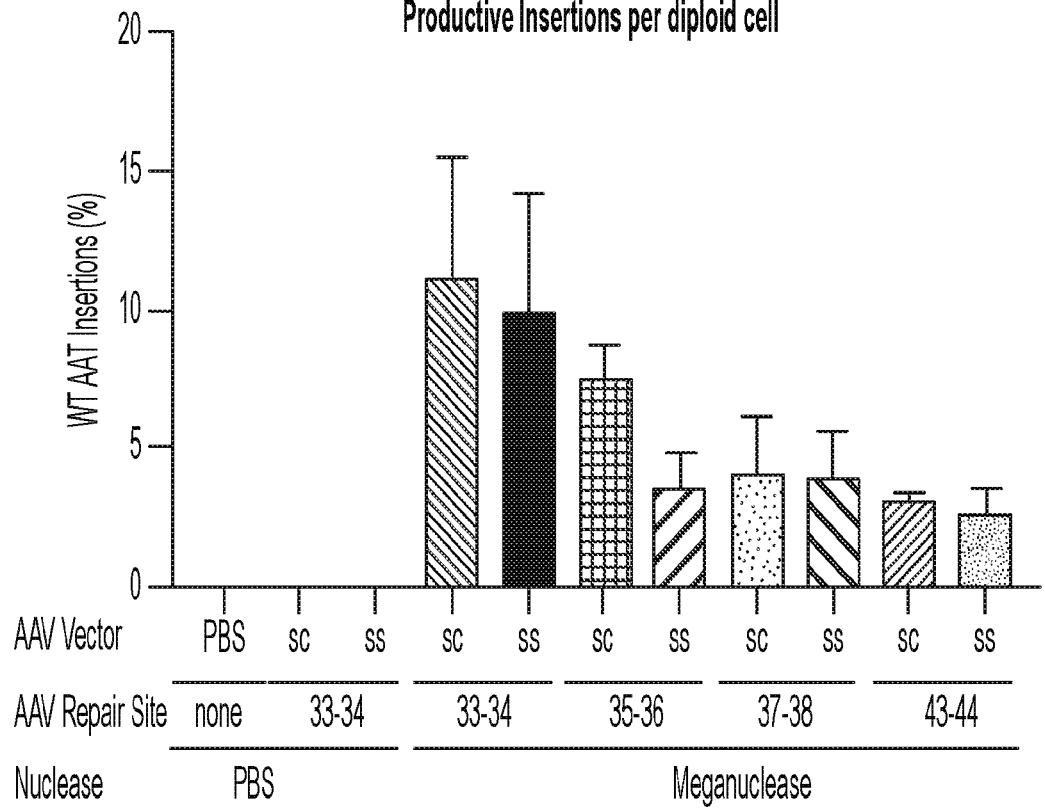
FIG. 16A and FIG. 16B provide bar graphs showing the percentage of insertions at each recognition sequence after treatment with the AAT 33-34x.13, AAT 35-36x.70, AAT 37-38x.50, and AAT 43-44x.58 meganucleases in either a self-complementary (sc) AAV vector or single stranded (ss) AAV vector.
Figure 16B:
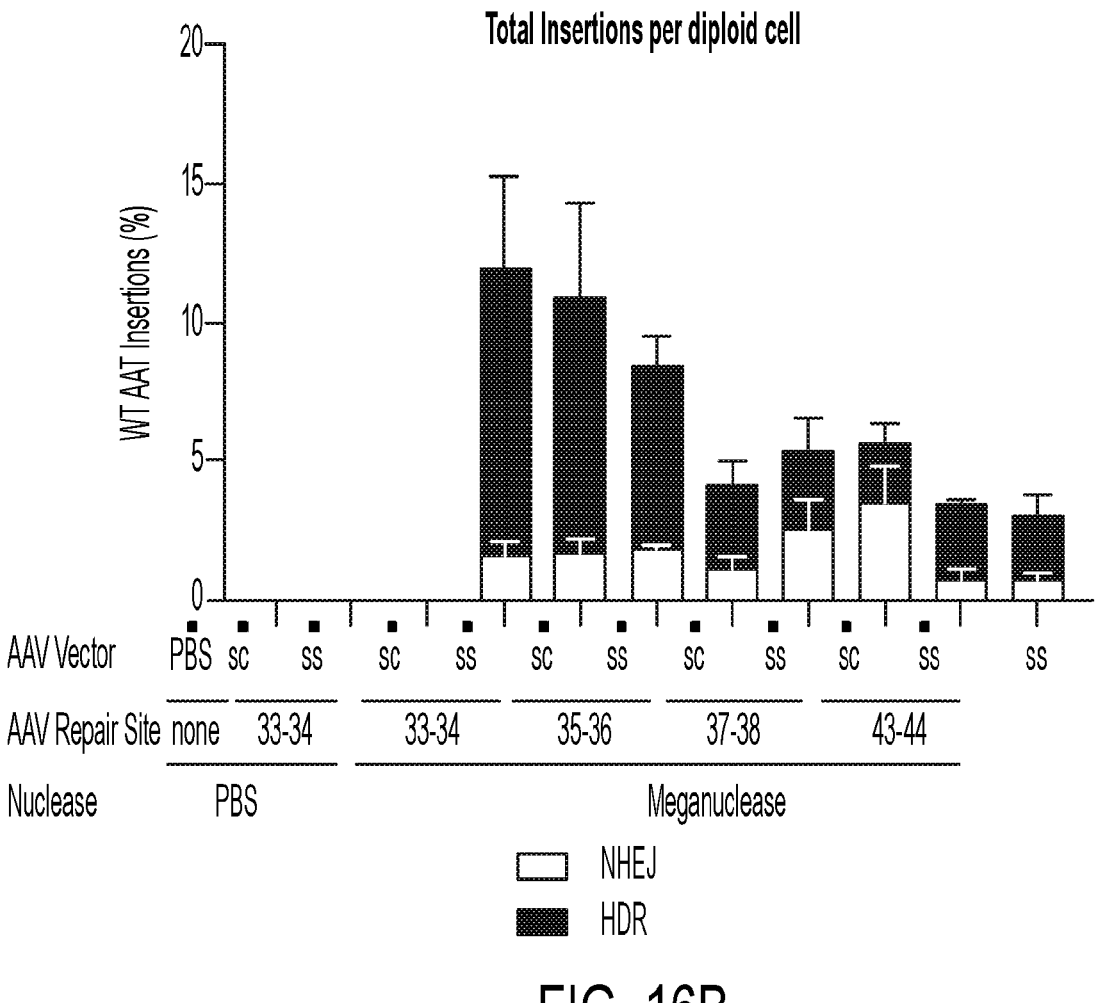

For total productive insertion analysis, we used assays 1, 2, 3 and 5 from Table 10. Insertion analysis determined that productive insertions were highest at the 33-34 site with an average of 10% and 11% insertions for ssAAV and scAAV, respectively. Only the 35-36 site showed a significant difference of insertions between ssAAV and scAAV repair at 3.5% and 7.5% insertions, respectively. An average of 4% insertions was seen for both ssAAV and scAAV for the AAT37-38 site. An average of 3% insertions was observed for both ssAAV and scAAV for the AAT43-44 site (FIG. 16A). We further analyzed if insertions were repaired via NHEJ or HDR using assays 1, 2, 3 and 5 from Table 10 and assays 6, 7, 8 and 10 from Table 10. The data shows that for sites 33-34, 35-36 and 43-44, the majority of repair is orchestrated by HDR mechanisms. Somewhat surprisingly, the 37-38 site shows repair is split between HDR and NHEJ or NHEJ is slightly favored (FIG. 16B).

Figure 18:
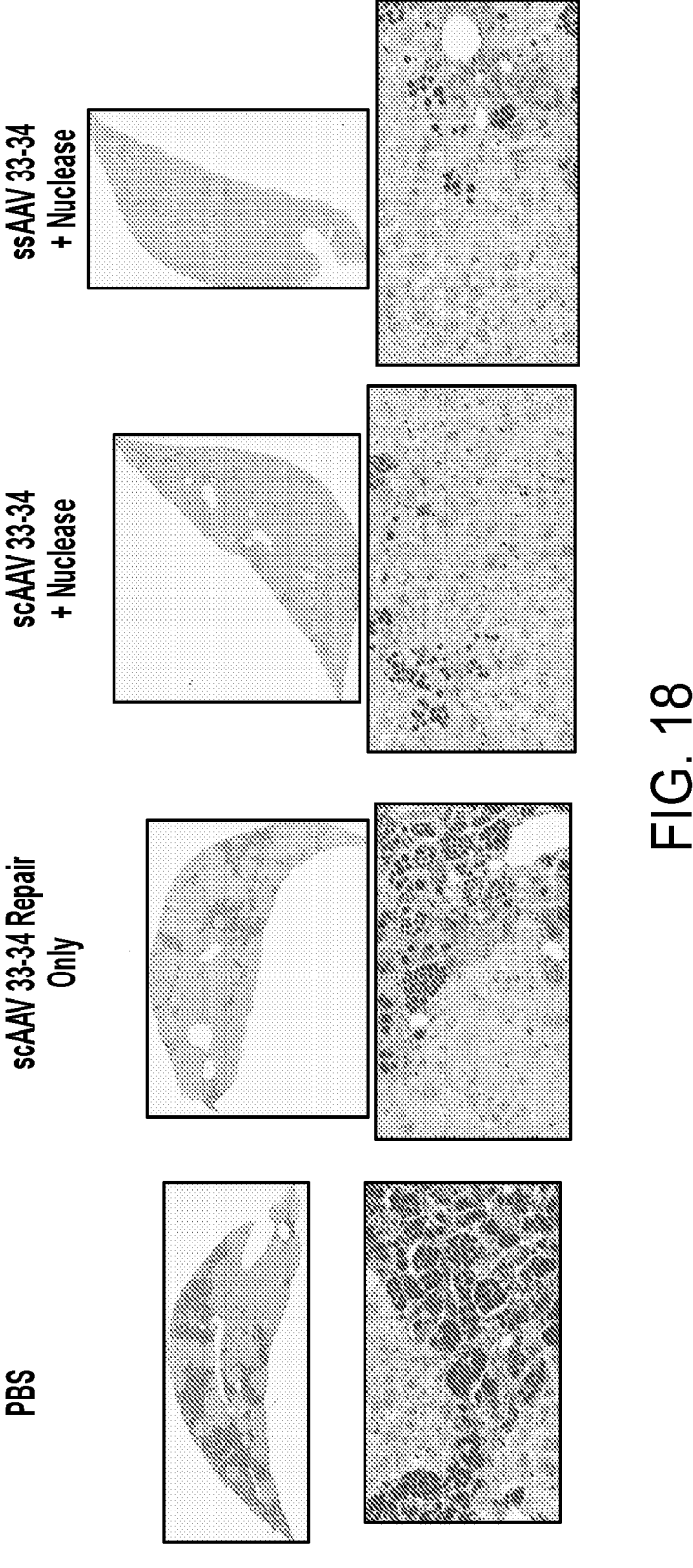
FIG. 18. Provides representative a representative histological image of PAS-D stained liver sections from PiZ mouse from Example 4.

PAS-D staining was used to analyze Z globules within the liver and there is significant reduction of PAS-D positive area in meganuclease treated animals compared to PBS treated animals (FIGS. 17 and 18). There is a slight decrease of PAS-D positive cells in the repair only groups and this may just be variability seen in PiZ mice.

Figure 19A:
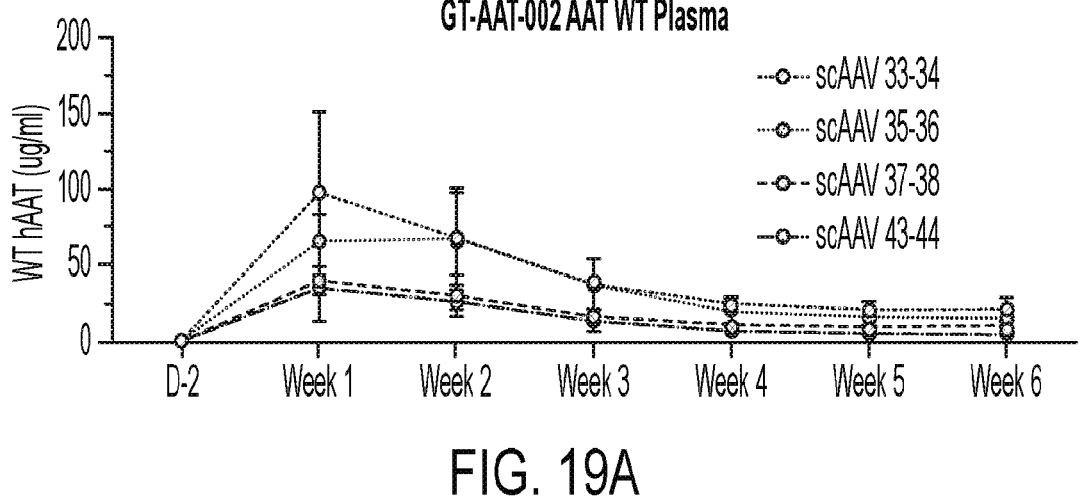
FIG. 19A and FIG. 19B. Provide graphs indicating the amount of WT AAT protein in PiZ mice treated with the AAT 33-34x.13, AAT 35-36x.70, AAT 37-38x.50, and AAT 43-44x.58 meganucleases in either an SC AAV or SS AAV from the study of Example 4.
Figure 19B:
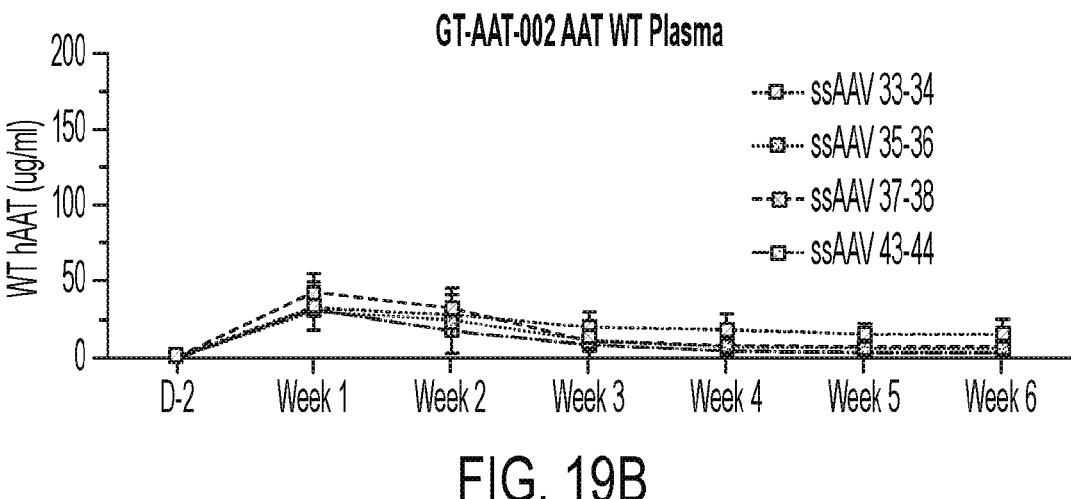

Both WT and Z plasma protein was measured via mass spectrometry. Groups treated with scAAV repair show higher plasma WT AAT protein for sites 33-34 and 35-36 at weeks 1-3 and less so for sites 37-38 and 43-44 (FIG. 19A, 19B). Plasma WT AAT protein peaks at week 1 with the maximum average protein expression of 100 µg/ml in the mice administered the scAAV 33-34 repair template (FIG. 19A).

The repair template contains a flag tag so we performed flag immunohistochemistry (IHC) on terminal PiZ mouse liver samples to observe distribution and quantification of our inserted WT AAT repair construct. Flag staining was observed heterogeneously throughout the liver (FIG. 20).

3. Conclusions

The AAT-002 study found that the highest level of insertions was around 11% at the 33-34 site with the scAAV repair construct. This group also had the highest plasma WT-AAT protein expression at week 1 post AAV administration at 100 µg/ml. However, AAT-WT plasma protein levels for all groups decreased after week 1 and plateaued below 30 µg/ml after week 4. The high variability of PAS-D staining in the PiZ mice receiving PBS only or repair AAV only made it difficult to conclude that there was a meganuclease-mediated effect on z globules in the liver.

Example 5

In Vivo AAT LNP Delivery of Engineered Meganucleases in a PiZ AAT Mouse Model

1. Methods and Materials

PiZ mice were dosed with 0.5-0.9 mg/kg LNP-M formulated with a first-generation 37-38x.50 meganuclease in order to analyze whether an AAV delivered AAT template could be inserted using an LNP to deliver the meganuclease. The study outline is provided in Table 11. The quantifications of human AAT transgene copy number and AAT protein was conducted as described in Example 3. The quantifications of insertions was conducted as described in Example 4 using primers and probes from Table 10, assay 3.

TABLE 11

Example 5 Study Design

| Group | | Dose #1 | Dose #2 |
|---|---|---|---|
| 1 | PBS | PBS | PBS |
| 2 | AAV Repair | LNP-Meganuclease | PBS |
| 3 | | PBS | LNP-Meganuclease |
| 4 | | LNP-Meganuclease | LNP-Meganuclease |
| 5 | | LNP-Meganuclease | PBS |
| 6 | | LNP-Meganuclease | LNP-Meganuclease |
| 7 | PBS | LNP-Meganuclease | PBS |

2. Results

Figure 21:
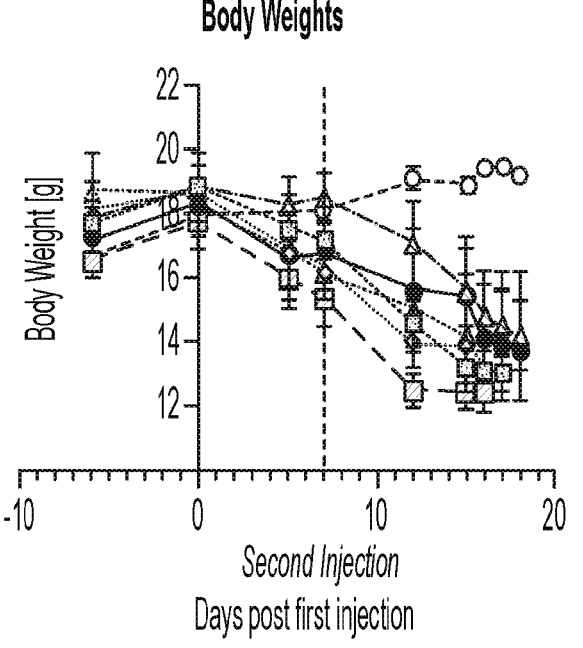
FIG. 21. Provides a graph indicating the body weight in grams of PiZ mice from the indicated treatment groups corresponding to Example 5.

The PiZ mouse study was intended to have three LNP-M doses, at day 0, day 7 and day 14. However, at day 15, the mice in all LNP/meganuclease treated groups showed clinical signs of distress and weight loss. Due to the tolerability issues, all remaining mice were euthanized at day 19. Body weight analysis shows that mice treated with the LNP/meganuclease had a steady decline in body weight post dose in contrast to the PBS and AAV repair alone groups (FIG. 21).

Figure 22:
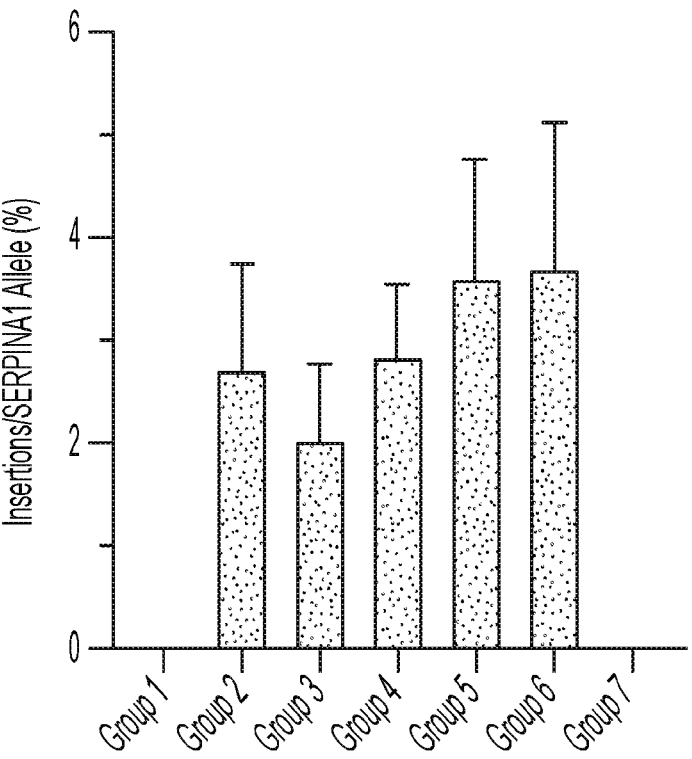
FIG. 22. Provides a bar graph showing the percentage of insertions of AAT (indicated as SERPINA1) template after 1 and 2 doses for each of the indicated treatment groups of Example 5.
Figure 23:
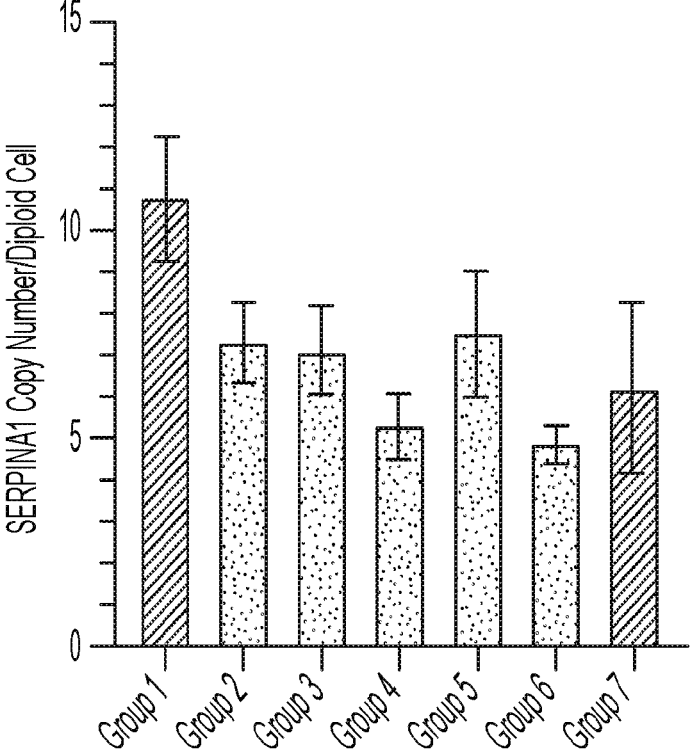
FIG. 23. Provides a bar graph showing the copy number of AAT (indicated as SERPINA1) after 1 and 2 doses for each of the indicated treatment groups of Example 5.

Insertion analysis shows the highest average insertions were around 4% insertions per SERPINA1 allele (FIG. 22). An additional LNP dose did not increase insertion frequency in this study. SERPINA1 copy number demonstrated a significant loss in copy number compared to PBS and LNP only control groups (FIG. 23). An additional LNP dose resulted in an additional loss in SERPINA1 copies.

Figure 24:
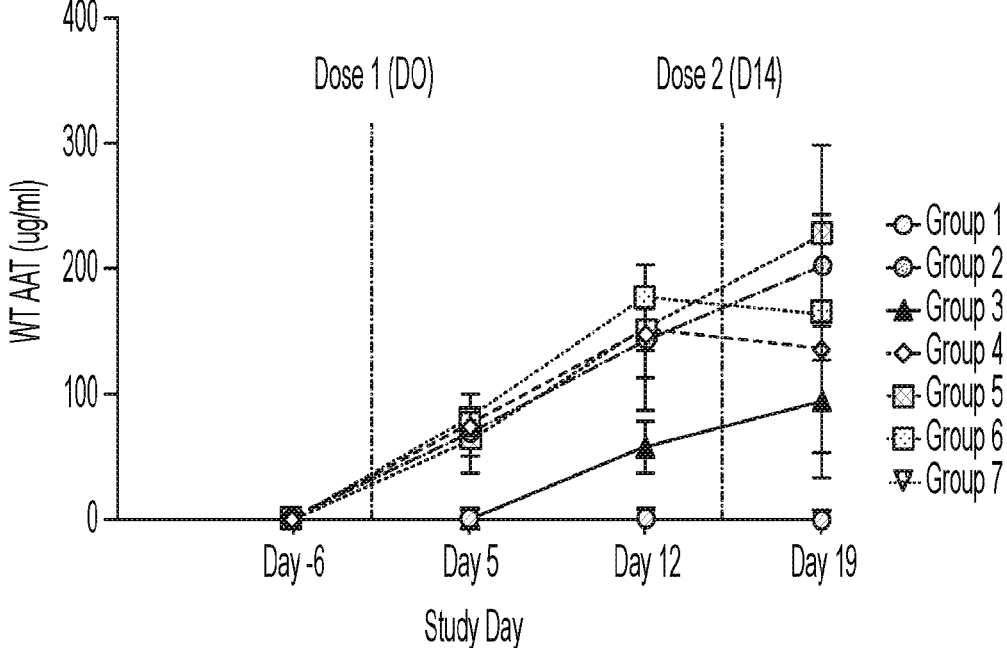
FIG. 24. Provides a graph of the amount of WT AAT after one and two doses of the indicated treatment in the treatment groups of Example 5.

WT protein analysis demonstrated a gradual increase in secreted AAT-WT protein through day 19 for all animals treated with a single dose of LNP-A/meganuclease and reached an average peak protein level of 228 µg/ml (FIG. 24). Animals dosed with two LNP-M/meganuclease doses saw a slight decline in AAT-WT protein the week following the second LNP dose.

3. Conclusions

In conclusion, using LNP-M to deliver the generation 1 AAT37-38x.50 meganuclease we demonstrated up to 4% insertions which resulted in a peak secreted WT-AAT protein expression of 228 µg/ml. Tolerability issues were observed in all mice treated with the LNP-M/meganuclease. Due to the timing of clinical observations in these mice, we can infer that the toxicity was likely due to a first-generation meganuclease with likely off target effects.

Example 6

Editing of AAT Recognition Sequences in Human Cell Lines with Additional Engineered Meganucleases with Off Target Analysis

1. Methods and Materials

These studies were conducted to determine the ability of successive iterations of optimized engineered meganucleases to generate indels at the genomic target site, insertions of a target plasmid into the genomic target site, and the off targeting profile of each meganuclease. The meganucleases in this study were re-engineered from each of the indicated first generation meganucleases. In this study, the engineered meganucleases provided in Table 12 were tested.

TABLE 12

Generations of Engineered Meganucleases

| Generation | Meganuclease |
| --- | --- |
| 1 | AAT 35-36x.70 |
| 2 | AAT 35-36L.79 |
| 3 | AAT 35-36L.141 |
| 4 | AAT 35-36L.210 |
| 5 | AAT 35-36L.290 |
| 1 | AAT 37-38x.50 |
| 2 | AAT 37-38L.24 |
| 3 | AAT 37-38L.158 |
| 3 | AAT 37-38L.167 |
| 3 | AAT 37-38L.175 |
| 4 | AAT 37-38L.262 |
| 1 | AAT 41-42x.1 |
| 2 | AAT 41-42L.42 |
| 3 | AAT 41-42L.104 |

TABLE 12-continued

Generations of Engineered Meganucleases

| Generation | Meganuclease |
| --- | --- |
| 3 | AAT 41-42L.153 |
| 4 | AAT 41-42L.185 |
| 5 | AAT 41-42L.294 |
| 1 | AAT 43-44x.58 |
| 2 | AAT 43-44L.47 |
| 3 | AAT 43-44L.105 |
| 3 | AAT 43-44L.132 |
| 3 | AAT 43-44L.157 |
| 4 | AAT 43-44L.276 |
| 5 | AAT 43-44L.384 |

Indel and Insertion Analysis

Quantification of indels and AAT template insertion was carried out by electroporating Hek293 cells with 25 ng of meganuclease RNA and 167 ng of DNA repair template and gDNA was collected at times indicated in the figures. DNA was extracted from cells as described in Example 2. The primer and probes used for insertion analysis are provided in Example 4. The primers and probes used for indel analysis are provided in Table 13. The insertion and indel ddPCR cycling conditions were carried out as in Example 4.

TABLE 13

Primers and Probes used in Indel Assay of Example 6 ddPCR AAT Indel Assays

| Assay # | Primer/Probe | Sequence | SEQ ID |
| --- | --- | --- | --- |
| 11 | AAT33-34 Fwd | CTGTTTCTCTTGGGTCTCAG | 247 |
| 11 | AAT33-34 Rev | GGGACAGAAGTCAAAGGTTAT | 248 |
| 11 | AAT33-34 Probe | AACAGAGAGGTTGAGCAACTGT | 249 |
| 12 | AAT35-36 Fwd | TGAAGTCATTTACCCCAGGC | 250 |
| 12 | AAT35-36 Rev | CTCACACCATTTCTACCCGG | 251 |
| 12 | AAT35-36 Probe | AATAAACCCAAGTGTGACCAGGCC | 252 |
| 13 | AAT37-38 Fwd | GCGAGACTCTGTCTCAAA | 253 |
| 13 | AAT37-38 Rev | GGCCATCACTATCCACTT | 254 |
| 13 | AAT37-38 Probe | TCCCCAGTTGTGCAAAG | 255 |
| 14 | AAT41-42 Fwd | CAGGAGCATCAGCCTAT | 256 |
| 14 | AAT41-42 Rev | ATGGCAACAGCTAGAGAG | 257 |
| 14 | AAT41-42 Probe | ATCCTTGTGAGTGTTGGGTGGGAA | 258 |
| 15 | AAT43-44 Fwd | GGCCCGATTCCTGGATAATC | 259 |
| 15 | AAT43-44 Rev | GCCAGAGAGATTAGGTCAGC | 260 |

TABLE 13-continued

Primers and Probes used in Indel Assay
of Example 6
ddPCR AAT Indel Assays

| Assay # | Primer/Probe | Sequence | SEQ ID |
|---|---|---|---|
| 15 | AAT43-44 Probe | CCAGAATCCTACATCT AGGTCCTGCAC | 261 |

Off Target Analysis

Figure 25:
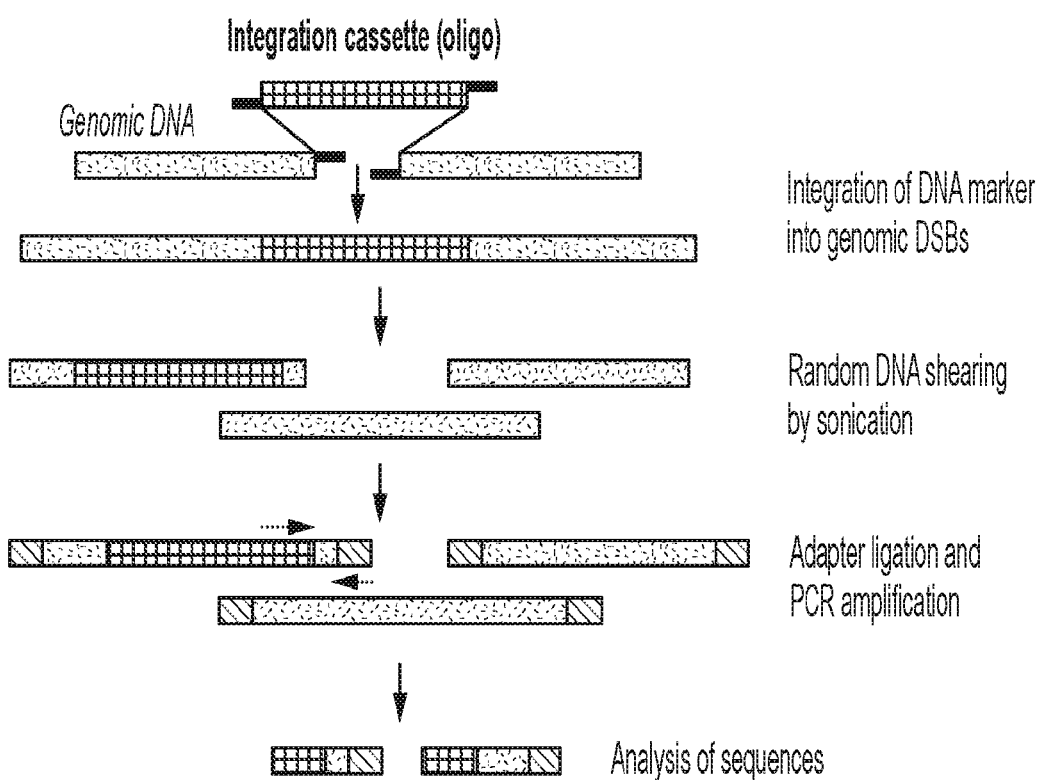
FIG. 25. Provides a schematic of the oligocapture assay utilized to determine off-target effects of an engineered nuclease (e.g., an engineered meganuclease described herein). As shown, the integration cassette or oligo anneals with a double stranded break in the genome that may be due to engineered nuclease cleavage. The DNA is then sheared by sonication, adapters are ligated and PCR amplified followed by sequence analysis to determine location of the double strand break.

Meganuclease specificity was measured using the oligo-capture assay. This is a cell-based, in vitro assay that relies on the integration of a synthetic oligonucleotide (oligo) cassette at DSBs within the genome. Using the oligo as an anchor, genomic DNA to either side of the integration site can be amplified, sequenced, and mapped (FIG. 25). This allows for a minimally biased assessment of potential off-target editing sites of the meganuclease. This technique was adapted from GuideSeq (Tsai et al. (2015) *Nat. Biotech.* 33:187-97) with specific modification to increase sensitivity and accommodate the 3' complementary overhangs induced by the meganucleases. The OligoCapture analysis software is sequence agnostic. That is, no a priori assumptions are made regarding which DNA sequences the meganuclease is capable of cutting. In the OligoCapture assay, cells are transfected with meganuclease mRNA and double-stranded DNA oligonucleotides. After 2 days, the cellular genomic DNA was isolated and sheared into smaller sizes. An oligonucleotide adapter was ligated to the sheared DNA and polymerase chain reaction was used to amplify any DNA pieces that contain an adapter at one end and the captured oligonucleotide at the other end. The amplified DNA was purified, and sequencing libraries were prepared and sequenced. The data were filtered and analyzed for valid sites that captured an oligonucleotide to identify potential off-target sites. The sequence reads were aligned to a reference genome, and grouped sequences within thousand-base pair windows scanned for a potential meganuclease cleavage site. HEK293 cells were transfected with mRNA for multiple of the AAT meganucleases at each round of optimization (rounds 1-4 or 5) gDNA was isolated and processed as written above in the assay description.

2. Results

Indels at the 33-34, 35-36, 37-38, 41-42 and 43-43 recognition site for the first generation meganucleases are shown in FIG. 7 as described in Example 2.

Figure 26A:
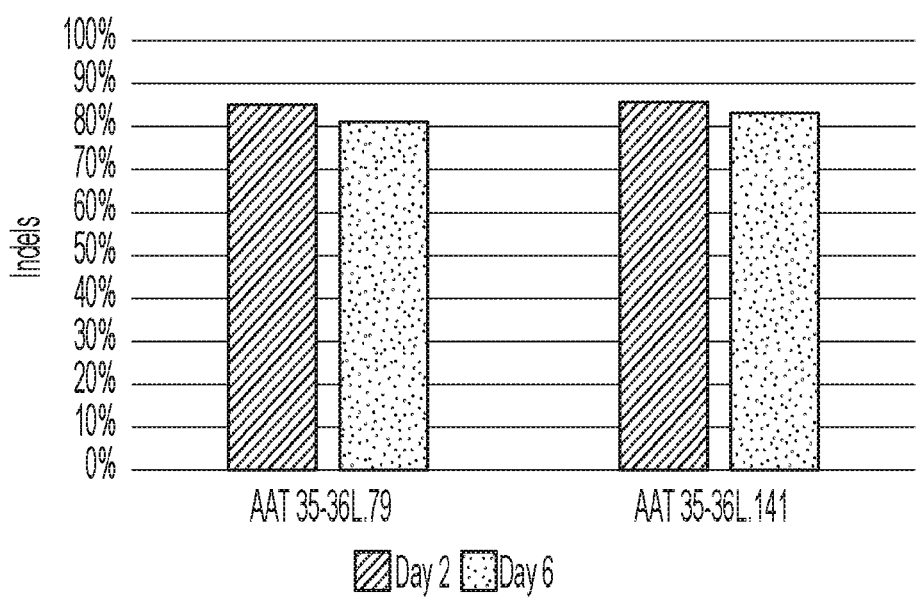
FIG. 26A-FIG. 26H. Provides a bar graph indicating the percentage (%) of insertions and deletions (indels) for each of the indicated engineered meganucleases in Hep3B cells at Day 2 (dark gray bars) and Day 6 (light gray bars) post transfection, respectively.
Figure 26B:
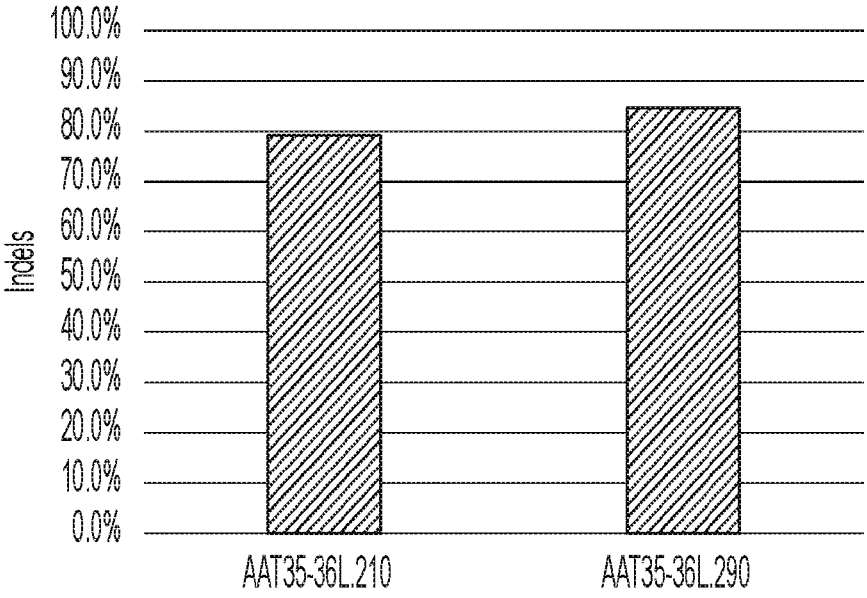

Indels at the 35-36 site for meganuclease generations 2-5 are shown in FIG. 26A and FIG. 26B. These four generations demonstrate indels around 80-85%. The indel activity does not change significantly from generation 2-5.

Figure 26C:
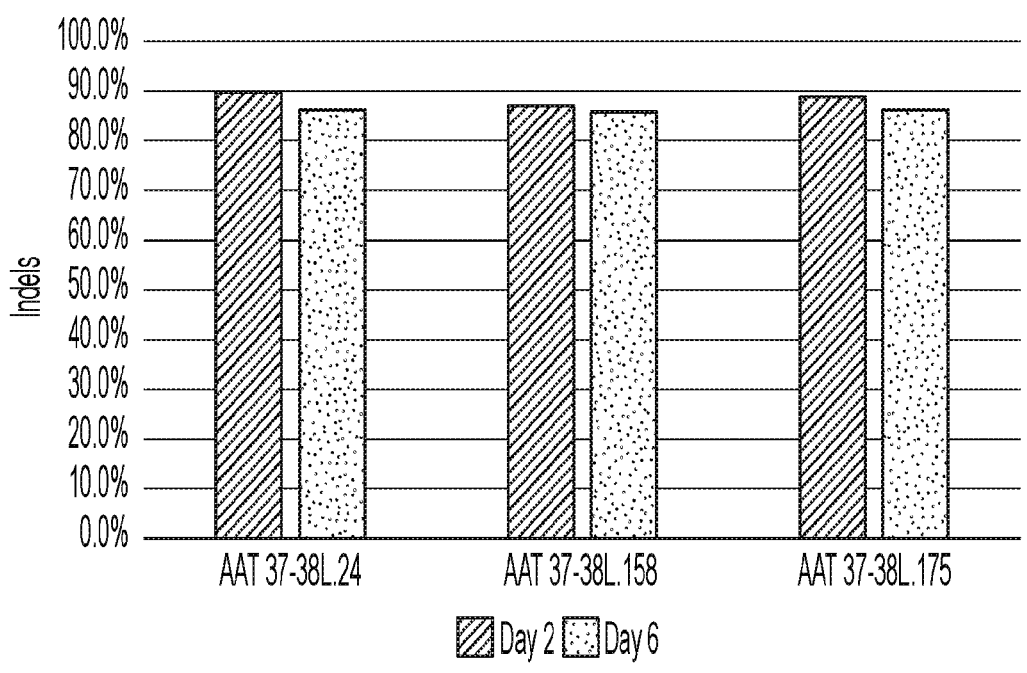
Figure 26D:
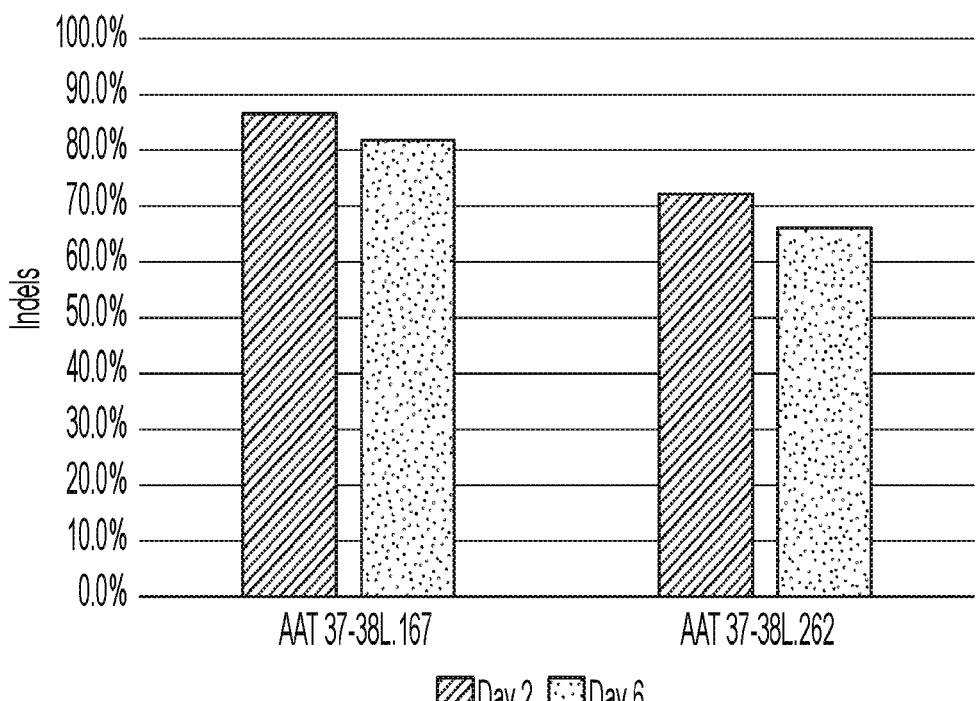

Indels at the 37-38 recognition site for generations 2-5 are shown in FIG. 26C and FIG. 26D. The AAT37-38 gen 2 meganuclease, AAT37-38L.24 and generation 3 nucleases, AAT37-38L.158 and AAT37-38L.175 all demonstrated 90% indels, Gen 4 meganuclease AAT37-38L.167 demonstrated 86% indels and the generation 5 nucleases show a slight decrease indels at ~70% indels.

Figures 26E, 26F:
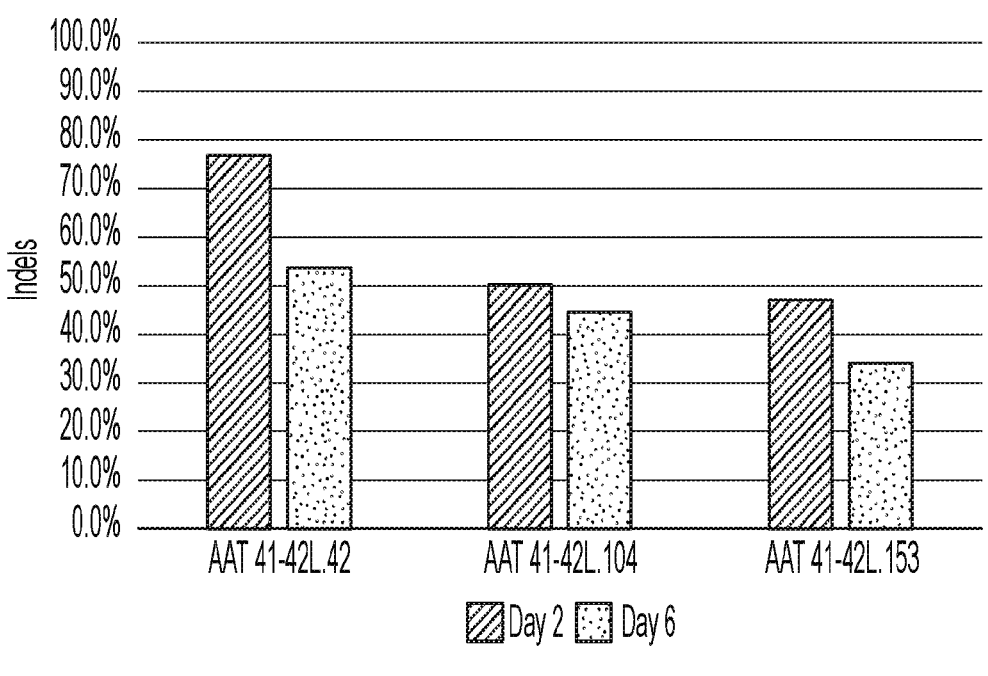

Indels at the AAT41-42 recognition site for generations 2-5 are shown in FIG. 26E and FIG. 26F. The generation 2 AAT41-42L.42 meganuclease demonstrated around 77% indels. Generation 3 nucleases AAT41-42L.104 and AAT41-42L.153 show a decrease in indels from generation 2 at ~50% indels. The generation 4 AAT41-42L.185 meganuclease demonstrated 20% indels and the generation 5 AAT41-42L.294 meganuclease demonstrated an increase at 40% indels.

Figure 26G:
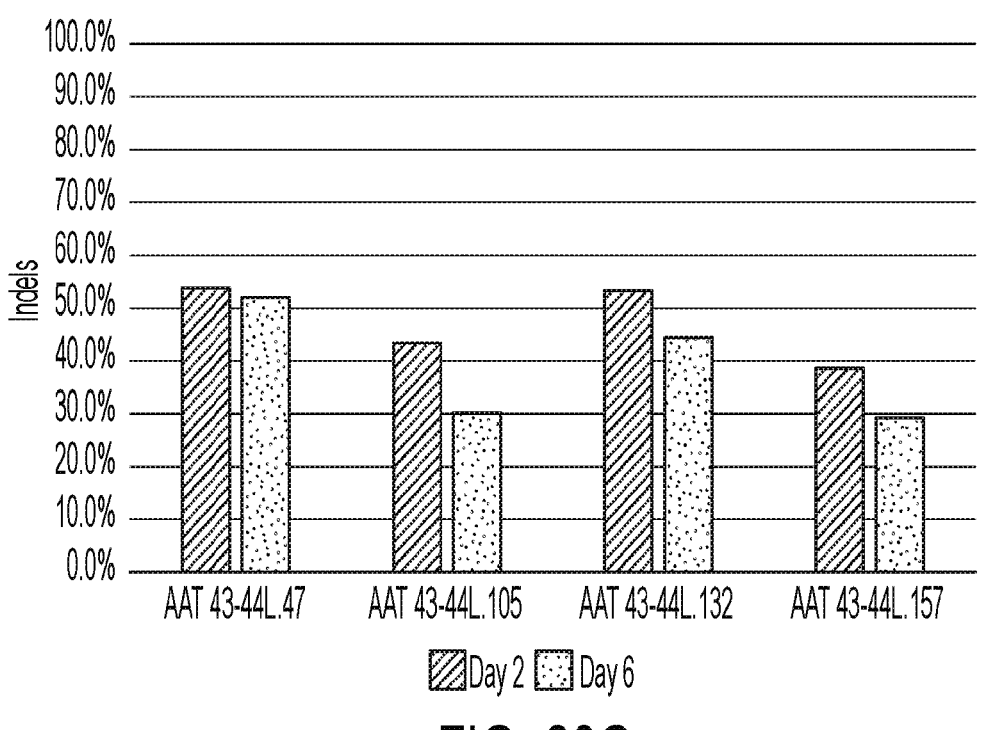
Figure 26H:
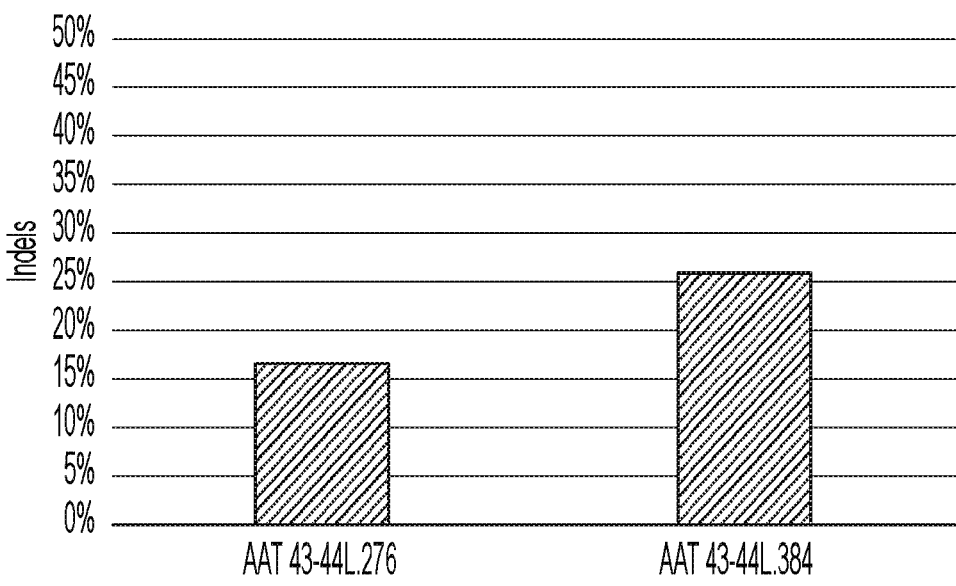

Indels at the AAT43-44 recognition site for generations 2-5 are shown in FIG. 26G and FIG. 26H. The generation 2 AAT43-44L.47 meganuclease demonstrated 52% indels. The generation 3 AAT43-44L.132 also showed 52% indels. The generation 4 meganuclease AAT43-44L.276 demonstrated 16% indels and the generation 5 AAT43-44L.384 meganuclease showed an increase in indels at 26%.

Figure 27A:
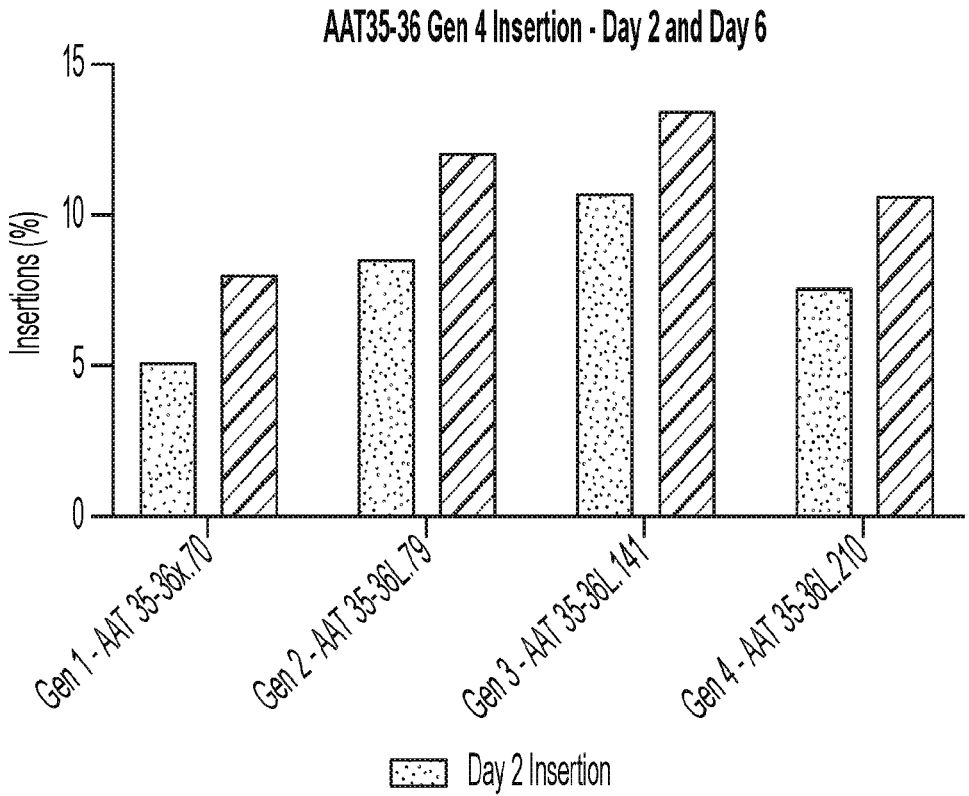
FIG. 27A and FIG. 27B. Provide bar graphs indicating the percentage of insertions for each of the indicated AAT 35-36 meganucleases, FIG. 28. Provides a graph depicting results from an oligo capture assay to identify off-target cutting induced by the indicated AAT 35-36 meganucleases transfected in HEK. 293 cells. The circled dots indicate the on-target site and the non-circled dots indicate off-target sites with the X axis representing the number of sequencing reads for each detected off-target site. The shade of the dot indicates the number of base-pair mismatches between the on target site and each of the detected off-target sites.
Figure 27B:
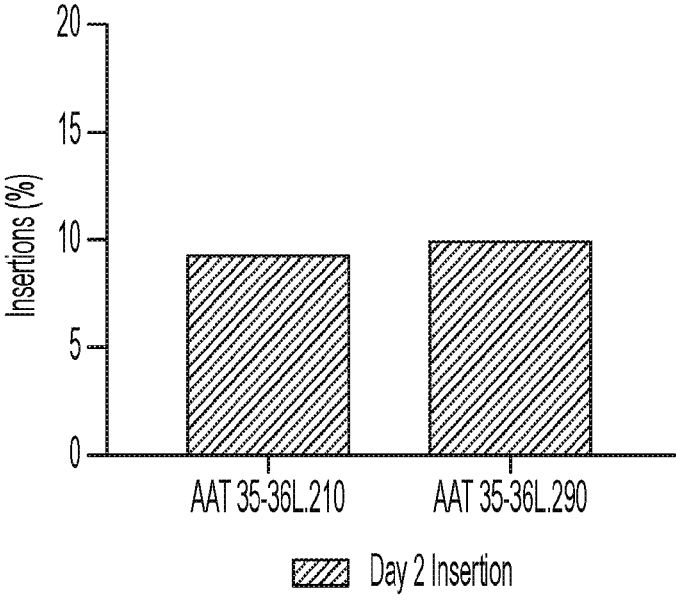

Insertions at the AAT 35-36 recognition site for the first four generations of tested meganucleases are shown in FIG. 27A. FIG. 27B provides the insertion data for a fourth generation meganuclease (AAT 35-36L.210) compared to a fifth generation meganuclease (AAT 35-36L.290). Overall, the insertions for the first-generation AAT 35-36x.70 meganuclease were lower than the later developed second generation to fourth generation meganucleases indicating an improvement in insertion capability in the later generation meganucleases (FIG. 27A). The fifth generation AAT35-36L.290 meganuclease demonstrated similar or higher insertional activity compared to the AAT 35-36L.210 meganuclease (FIG. 27B). While the exact percentage of insertions cannot be compared between independent experiments (e.g., the results of FIG. 27A cannot be directly compared to that of FIG. 27B), it can be inferred that the fifth generation AAT 35-36L.290 meganuclease would have higher insertional activity than the first-generation AAT 35-36x.70 meganuclease because the AAT 35-36L.290 meganuclease had higher activity than the AAT 35-36L.210 meganuclease when run in the same experiment.

Figure 28:
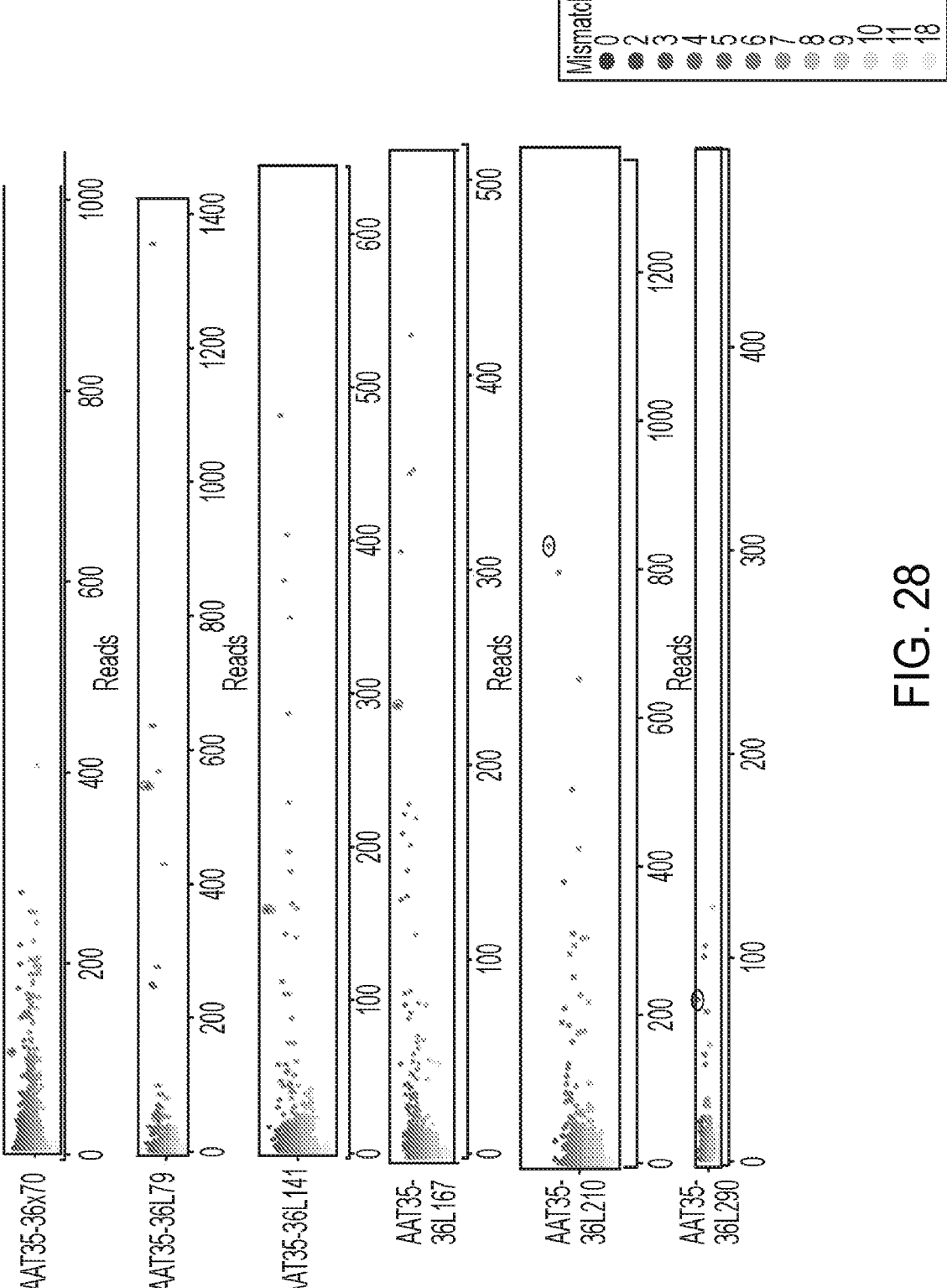

The oligocapture off targeting assay data for the tested AAT 35-36 meganucleases is provided in FIG. 28. The circled dot in each of these plots indicates the on-target site, which had progressively higher read count in the later developed meganucleases compared to the first-generation AAT 35-36x.70 meganucleases with less overall detected off target sites for all the later developed meganucleases.

Figure 29A:
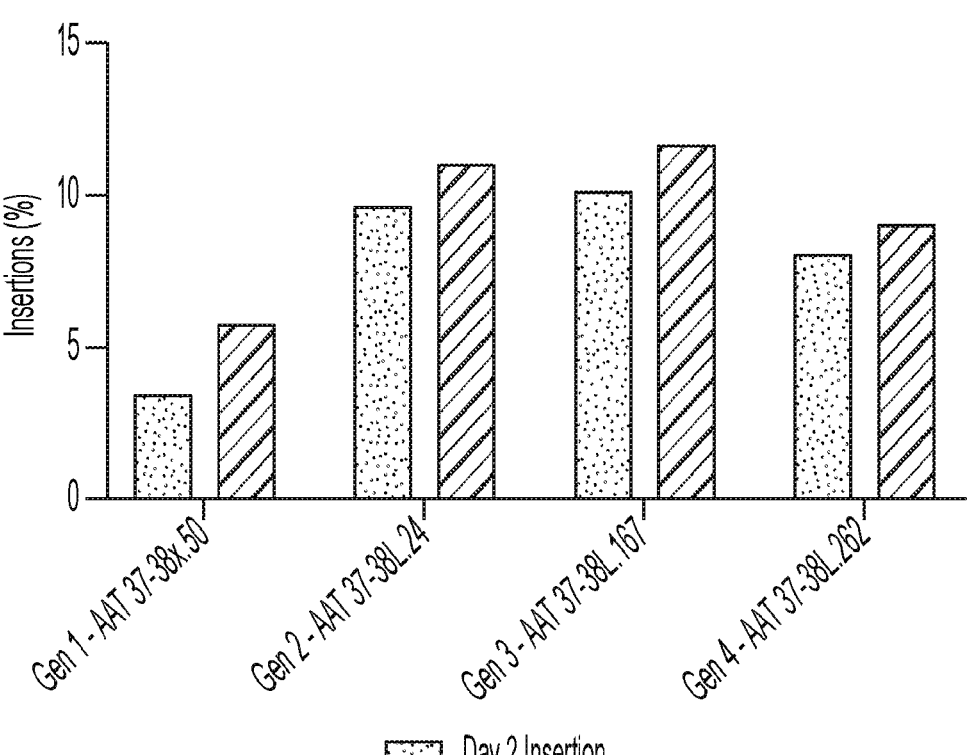
FIG. 29A and FIG. 29B. Provide bar graphs indicating the percentage of insertions for each of the indicated AAT 37-38 meganucleases.
Figure 29B:
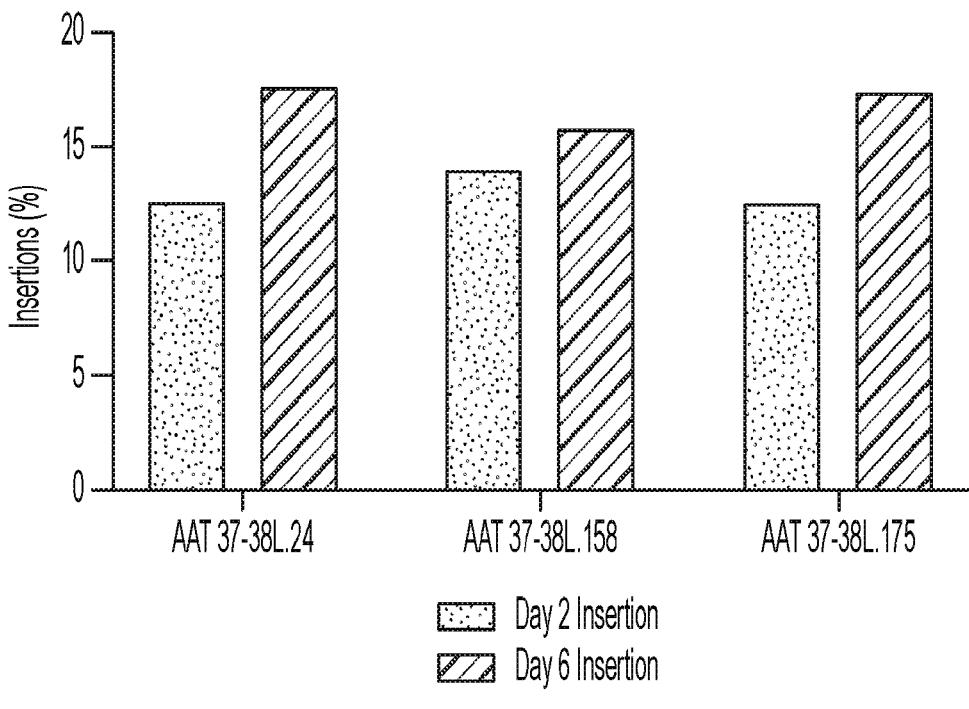

Insertions at the AAT 37-38 recognition site for the first four generations of tested meganucleases are shown in FIG. 29A and one generation 2 and two generation 3 tested meganucleases are shown in FIG. 29B. Consistent with the results observed for the meganucleases developed for the AAT 35-36 site, insertions for the first-generation AAT 37-38x.50 meganuclease was lower than the later developed second generation to fourth generation AAT 37-38 meganucleases again indicating an improvement in insertion capability in the later generation meganucleases (FIG. 29A).

Figure 30:
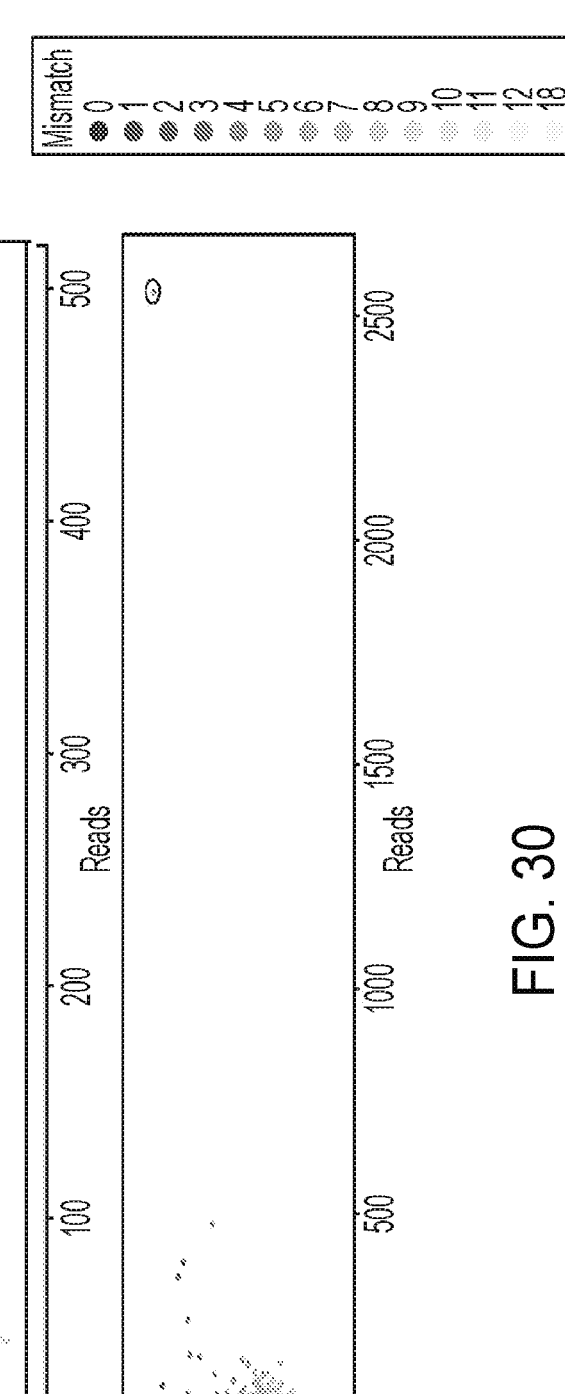
FIG. 30. Provides a graph depicting results from an oligo capture assay to identify off-target cutting induced by the indicated AAT 37-38 meganucleases transfected in HEK 293 cells. The circled dots indicate the on-target site and the non-circled dots indicate off-target sites with the X axis representing the number of sequencing reads for each detected off-target site. The shade of the dot indicates the number of base-pair mismatches between the on target site and each of the detected off-target sites.

The oligocapture off targeting assay data for the tested AAT 37-38 meganucleases is provided in FIG. 30. The on-target site had a progressively higher read count in the later developed meganucleases compared to the first-generation AAT 37-38x.50 meganuclease with less overall detected off target sites for all of the later developed meganucleases. The AAT 37-38L.262 meganuclease had the lowest number of off target reads and a high on target read count indicating that this meganuclease was the most specific of the tested meganucleases, which also had better optimized insertional activity compared to the first generation meganuclease.

Figure 31A:
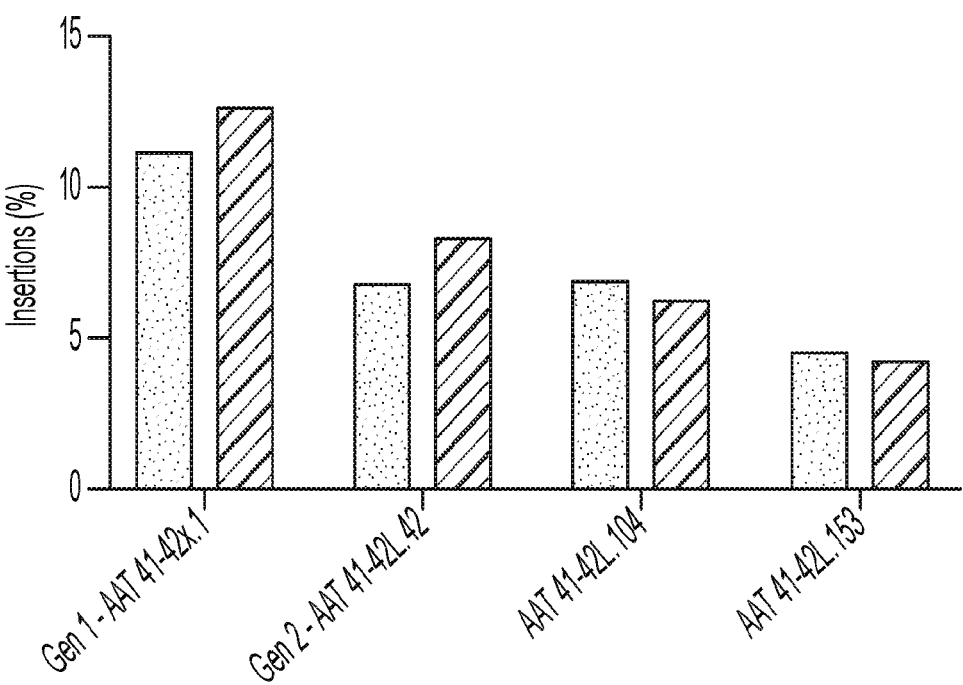
FIG. 31A and FIG. 31B. Provide bar graphs indicating the percentage of insertions for each of the indicated AAT 41-42 meganucleases.
Figure 31B:
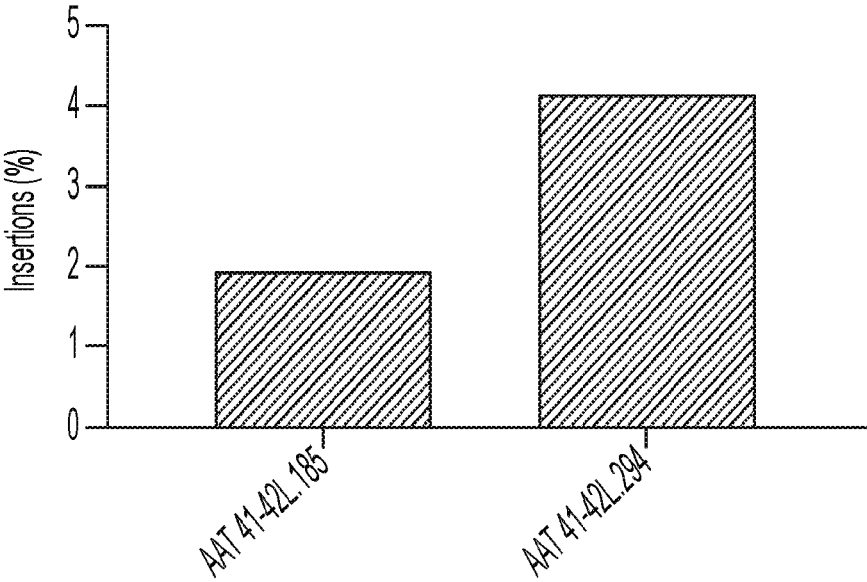

Insertions at the AAT 41-42 recognition site for the first three generations of tested meganucleases are shown in FIG. 31A. These results differ somewhat from the prior findings in that the first-generation AAT 41-42x.1 meganuclease demonstrated higher insertion activity compared to the later developed second and third generation meganucleases. FIG.

31B provides the insertion data of the fifth generation AAT 41-42L.294 meganuclease compared to the fourth generation AAT 41-42L.185 meganuclease, which shows that the fifth generation meganuclease has improved insertion capability compared to the fourth generation meganuclease.

Figure 32A:
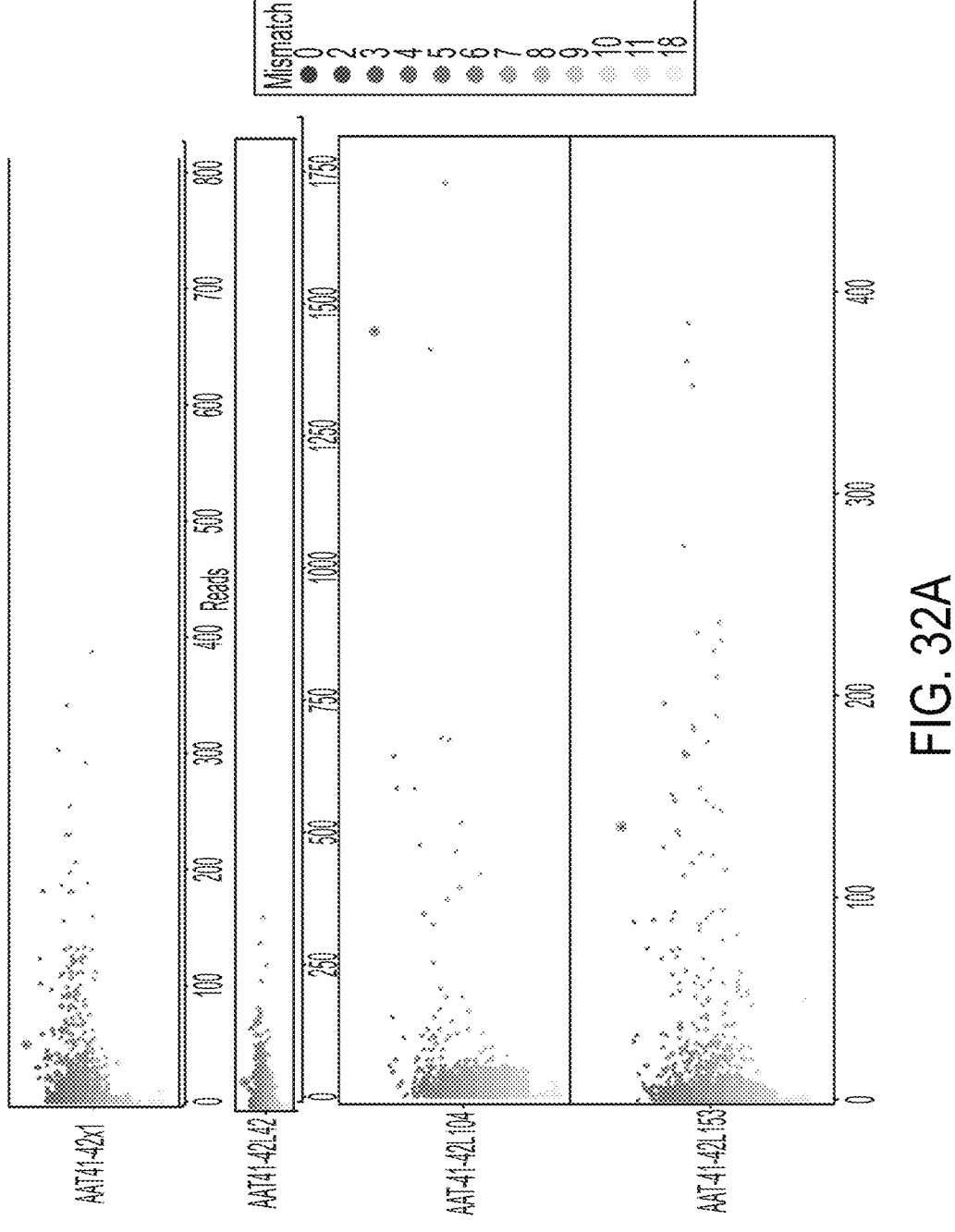
FIG. 32A and FIG. 32B. Provides a graph depicting results from an oligo capture assay to identify off-target cutting induced by the indicated AAT 41-42 meganucleases transfected in HEK 293 cells. The circled dots indicate the on-target site and the non-circled dots indicate off-target sites with the X axis representing the number of sequencing reads for each detected off-target site. The shade of the dot indicates the number of base-pair mismatches between the on target site and each of the detected off-target sites.
Figure 32B:
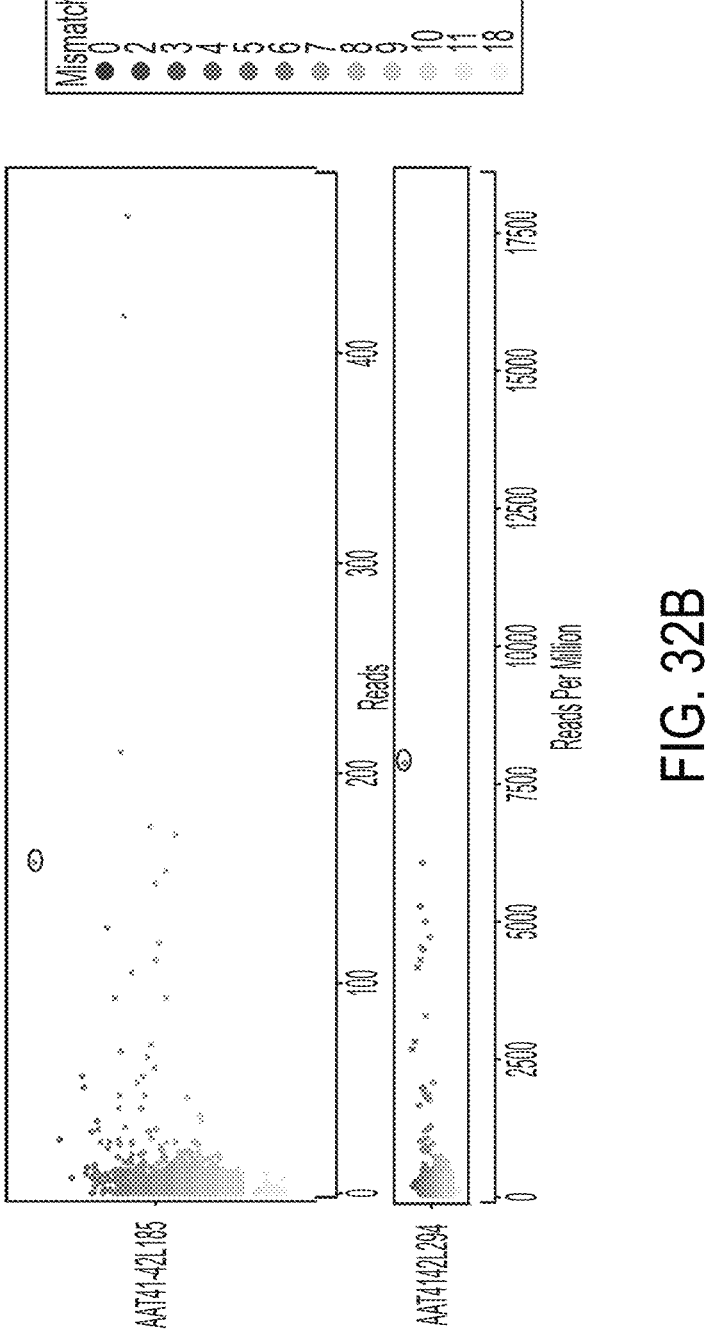

The oligocapture off targeting assay data for the tested AAT 41-42 meganucleases is provided in FIG. 32. The on-target site had a progressively higher read count in the later developed third to fifth generation meganucleases compared to the first-generation AAT 41-42x.1 meganuclease with less overall detected off target sites for all of the later developed meganucleases. The AAT 41-42L.294 meganuclease had the lowest number of off target reads and a very high on target read count indicating that this meganuclease was the most specific of the tested meganucleases. Thus, although the insertion percentage was higher in the first generation AAT 41-42x.1 meganuclease (FIG. 31A), the later developed third to fifth generation meganucleases had significantly lower off target sites, and therefore, would be expected to have a better safety profile in vivo.

Figure 33A:
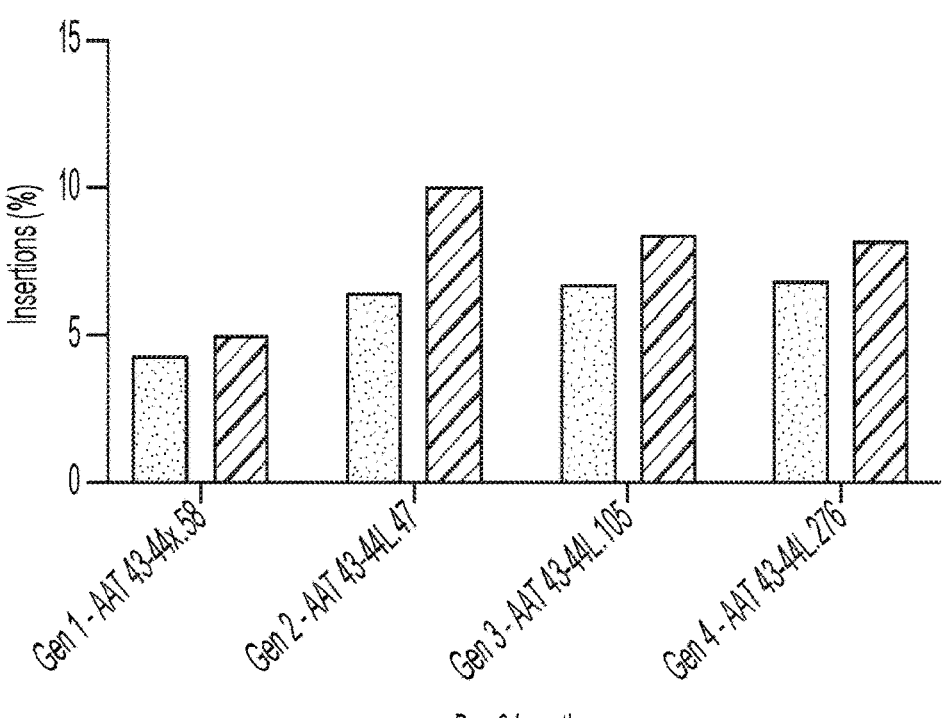
FIG. 33A-FIG. 33C. Provide bar graphs indicating the percentage of insertions for each of the indicated AAT 43-44 meganucleases.
Figure 33B:
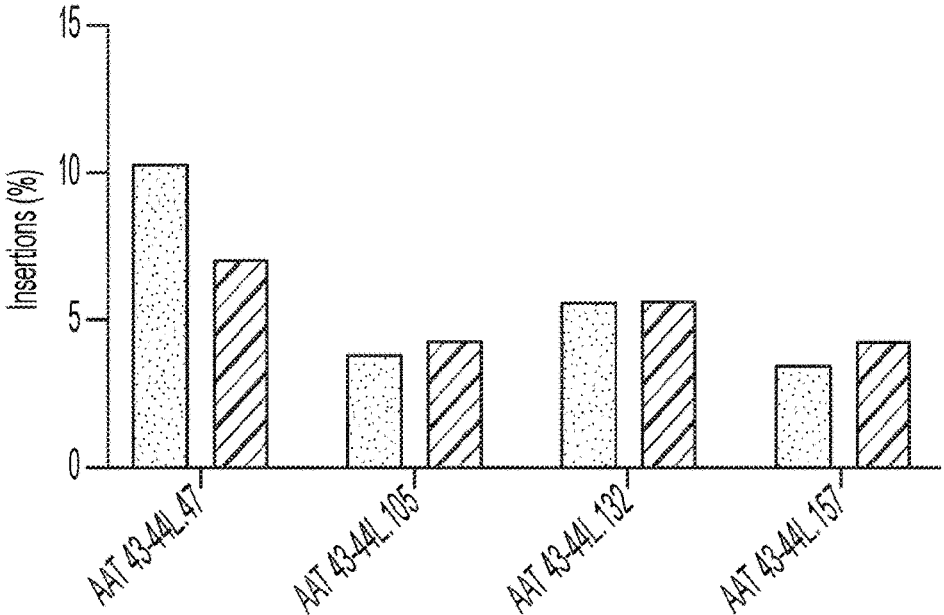
Figure 33C:
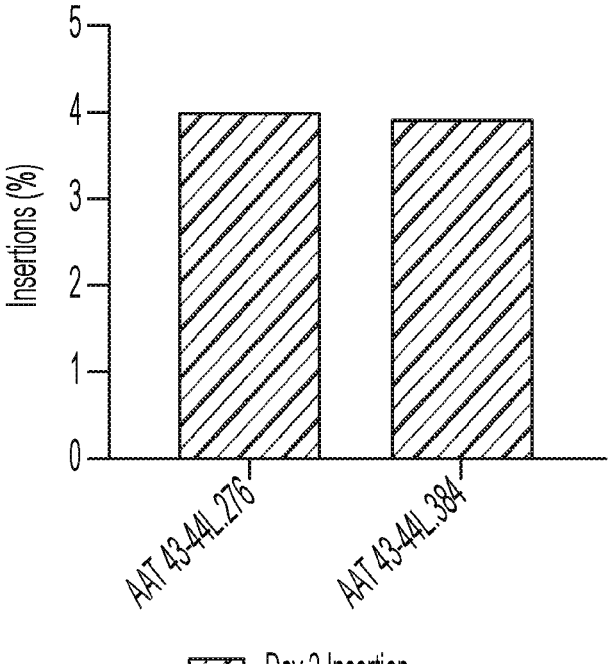

Insertions at the AAT 43-44 recognition site for the first four generations of tested meganucleases are shown in FIG. 33A and the second and third generation of tested meganucleases is shown in FIG. 33B. A comparison of insertional activity between the fourth generation AAT 43-44L.376 and fifth generation AAT 43-44L.384 meganuclease is provided in FIG. 33C. Consistent with the results observed for the meganucleases developed for the AAT 35-36 and AAT 37-38 sites, insertions for the first-generation AAT 43-44x.58 meganuclease was lower than the later developed second generation to fifth generation AAT 37-38 meganucleases again indicating an improvement in insertion capability in the later generation meganucleases (FIG. 33A).

Figure 34:
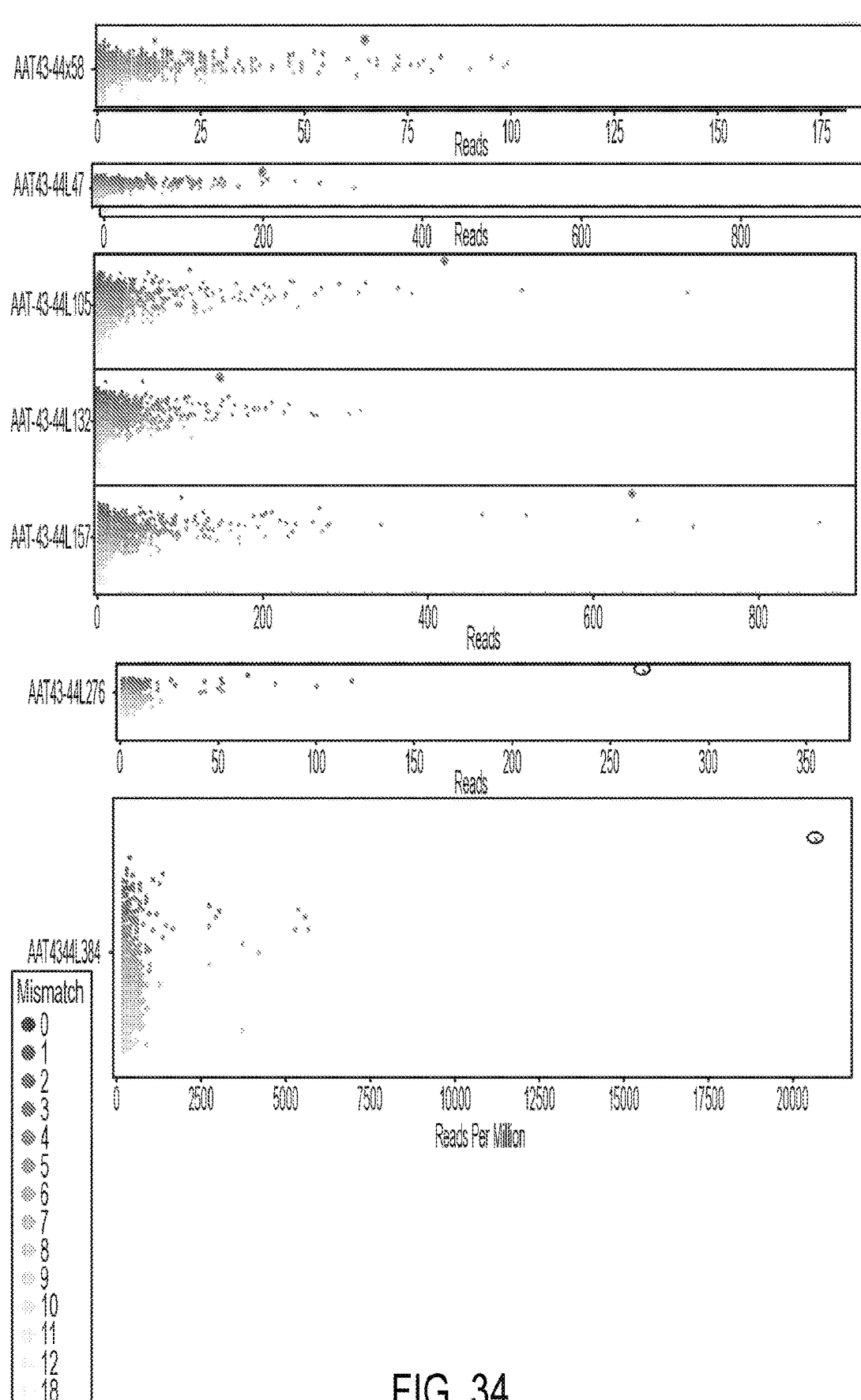
FIG. 34. Provides a graph depicting results from an oligo capture assay to identify off-target cutting induced by the indicated AAT 43-44 meganucleases transfected in HEK 293 cells. The circled dots indicate the on-target site and the non-circled dots indicate off-target sites with the X axis representing the number of sequencing reads for each detected off-target site. The shade of the dot indicates the number of base-pair mismatches between the on target site and each of the detected off-target sites.

The oligocapture off targeting assay data for the tested AAT 43-44 meganucleases is provided in FIG. 34. Consistent with the oligocapture data for the AAT 35-36, AAT 37-38, and AAT 41-42 sites, the detection of the on-target site had a progressively higher read count in the later developed meganucleases compared to the first-generation AAT 43-44x.58 meganuclease with less overall detected off target sites for the later developed meganucleases. The AAT 43-44L.384 meganuclease had a low number of off target reads and a very high on target read count. In addition, this fifth generation meganuclease retained the same amount of insertional activity as the fourth generation AAT 43-44L.276 meganuclease indicating that it is a significantly more active and specific meganuclease compared to the first generation AAT 43-44x.58 meganuclease.

3. Conclusions

The frequency of indels for optimized meganucleases at the 35-36 and 37-38 sites are consistently high and do not vary significantly across the successive generations. In contrast, for both the 41-42 and 43-44 sites, the frequency of indels varies more and tends to decrease from generation 2-4. However, the latest fifth generation meganuclease for both of these sites demonstrated improved indel activity indicating that these meganucleases were more active.

The insertion frequency of a template nucleic acid was improved at the AAT 35-36, AAT 37-38, and AAT 43-44 target sites using optimized meganucleases. In addition, for all sites, the later developed meganucleases were more specific. There was one caveat to this trend with the insertional activity at the AAT 41-42 site. With this site, the earlier generation of meganuclease demonstrated the highest insertional activity. However, that increased activity came at a significant cost in terms of specificity as shown in the oligocapture results. Accordingly, all later generation 3-4 or 3-5 meganucleases for all of the tested recognition sites demonstrated significantly reduced off-target profile as demonstrated in the oligocapture data. These meganucleases were able to balance adequate cleavage and insertional activity as assessed by indel and template insertion frequency with much lower off target cutting indicating the protein engineering to optimize these meganucleases resulted in significant clinically relevant improvements.

Example 7

In Vivo AAT Gene Editing in a PiZ AAT Mouse Model

1. Methods and Materials

Figure 39:
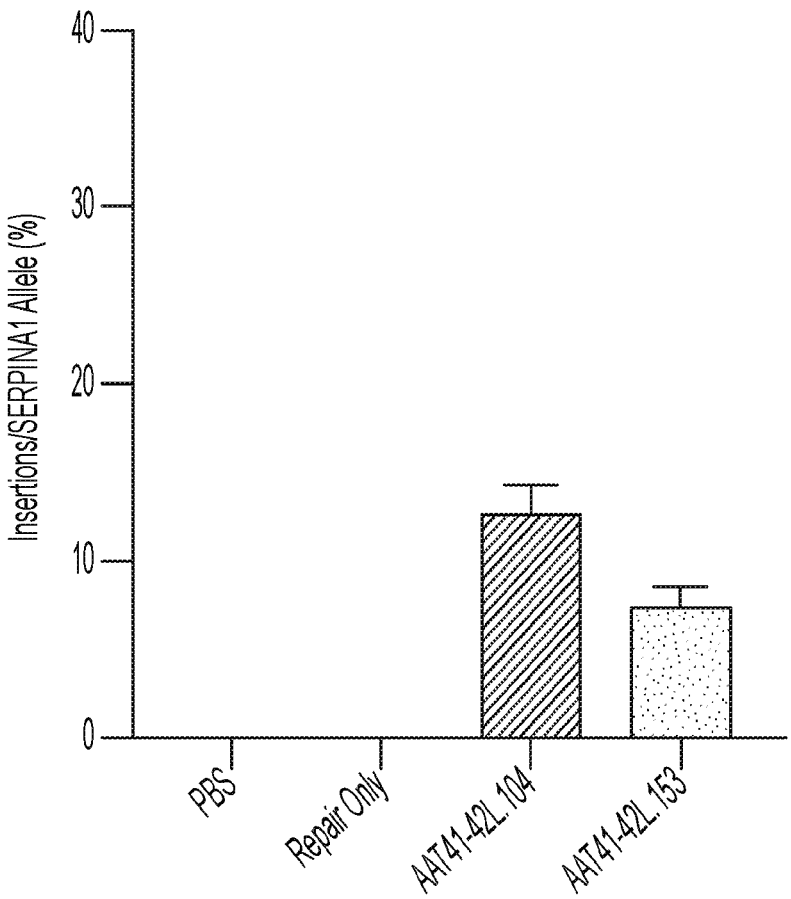
FIG. 39. Provides a bar graph showing percentage of repair construct insertion after administration of PBS, an AAV8 containing repair construct, or the AAV8 repair construct and the indicated AAT 41-42 meganucleases.

To understand any differences between meganuclease binding sites in the PiZ model, we delivered third generation nucleases at sites 37-38, 41-42 and 43-44 via a single stranded AAV and concurrently delivered the repair template as a self-complimentary AAV (FIG. 39). PiZ mice were either administered PBS and one of the WT AAT repair AAV8 vectors, or they were co-administered two AAV8 vectors, one encoding the engineered AAT meganuclease and one comprising one of the four designed WT AAT repair sequences, via retro-orbital (RO) injections at doses $5e^{12}$ VG/kg and $2.5e^{13}$ VG/kg, respectively. The study design is provided in Table 14 below.

TABLE 14

| | | | |
|---|---|---|---|
| | Study Design for Example 7. | | |
| Group # | PBS/AAV8 Repair | PBS/AAV8 Generation 3 Meganuclease | N = |
| 1A | PBS | PBS | 5 |
| 2 | scAAV 37-38 | PBS | 3 |
| 3 | | AAT 37-38L.167 | 5 |
| 4 | | AAT 37-38L.158 | 5 |
| 5 | | AAT 37-38L.175 | 5 |
| 1B | | PBS | 5 |
| 6 | scAAV 41-42 | PBS | 3 |
| 7 | | AAT 41-42L.104 | 5 |
| 8 | | AAT 41-42L.153 | 5 |
| 1C | | PBS | 5 |
| 9 | scAAV 43-44 | PBS | 3 |
| 10 | | AAT 43-44L.105 | 5 |
| 11 | | AAT 43-44L.132 | 5 |
| 12 | | AAT 43-44L.157 | 5 |
| Total | | | 64 |

The repair constructs were designed with homology arms for their corresponding binding sites (i.e. AAT 37-38, AAT41-42 or AAT 43-44) with a size of ~300 bp due to the packaging limitations of scAAV (~2.4 kb), which allowed for the WT AAT coding repair construct to be within these limitations. The third generation nucleases used in this study were chosen based on their in vitro insertion and specificity data (FIGS. 27-34).

Blood was collected from mice at weekly intervals from day-7 through day 28 and plasma was isolated and analyzed as previously described in Example 3. Liver tissue was harvested from the mice at day 28. DNA was isolated from tissues as described in Example 3. Insertion analysis was performed as described in Example 4 using the dPCR primers and probes provided in Table 10 utilizing assays 3, 4 and 5. Indel analysis was performed as described in Example 6, Table 13, utilizing assays 13, 14 and 15. The insertion and indel ddPCR cycling conditions were carried out as in Example 4. AAT WT and Z transcript quantification was performed using the ddPCR primers and probes from Table 15 using the following cycling conditions: 1 cycle of 95° C. for 10 minutes, 44 cycles of 94° C. for 10 seconds, 63° C. for 30 seconds and 72° C. for 1 minute, 1 cycle of 98° C. for 10 minutes and a 4° C. hold. The insertion and indel ddPCR cycling conditions were carried out as in Example 4. Liver immunohistochemistry was performed as described in Example 4.

TABLE 15

Primers and Probes used in AAT Transcript
ddPCR Assays of Example 7
AAT Transcript ddPCR Assays

| Assay # | Primer/Probe | Sequence | SEQ ID |
|---|---|---|---|
| 18 | AAT Transcript fwd | CTCCAAGGCCGTGCAT AA | 262 |
| 18 | AAT Transcript rev | AGACATGGGTATGGCC TCTA | 263 |
| 18 | WT AAT Transcript Probe | CTGACCATCGACGAGA AAGG | 264 |
| 19 | AAT Transcript fwd | CTCCAAGGCCGTGCAT AA | 262 |
| 19 | AAT Transcript rev | AGACATGGGTATGGCC TCTA | 263 |
| 19 | Z AAT Transcript Probe | CTGACCATCGACAAGA AAGG | 265 |
| 20 | Mouse GAPDH Thermo Fischer Assay - VIC mm99999915 g1 | | |

2. Results

All groups tolerated the meganuclease treatment well except for two groups that were treated with the AAT 41-42L.153 and AAT 43-44L.132 meganucleases, which saw tolerability issues and were euthanized 1 and 2 weeks early, respectively.

Figure 35:
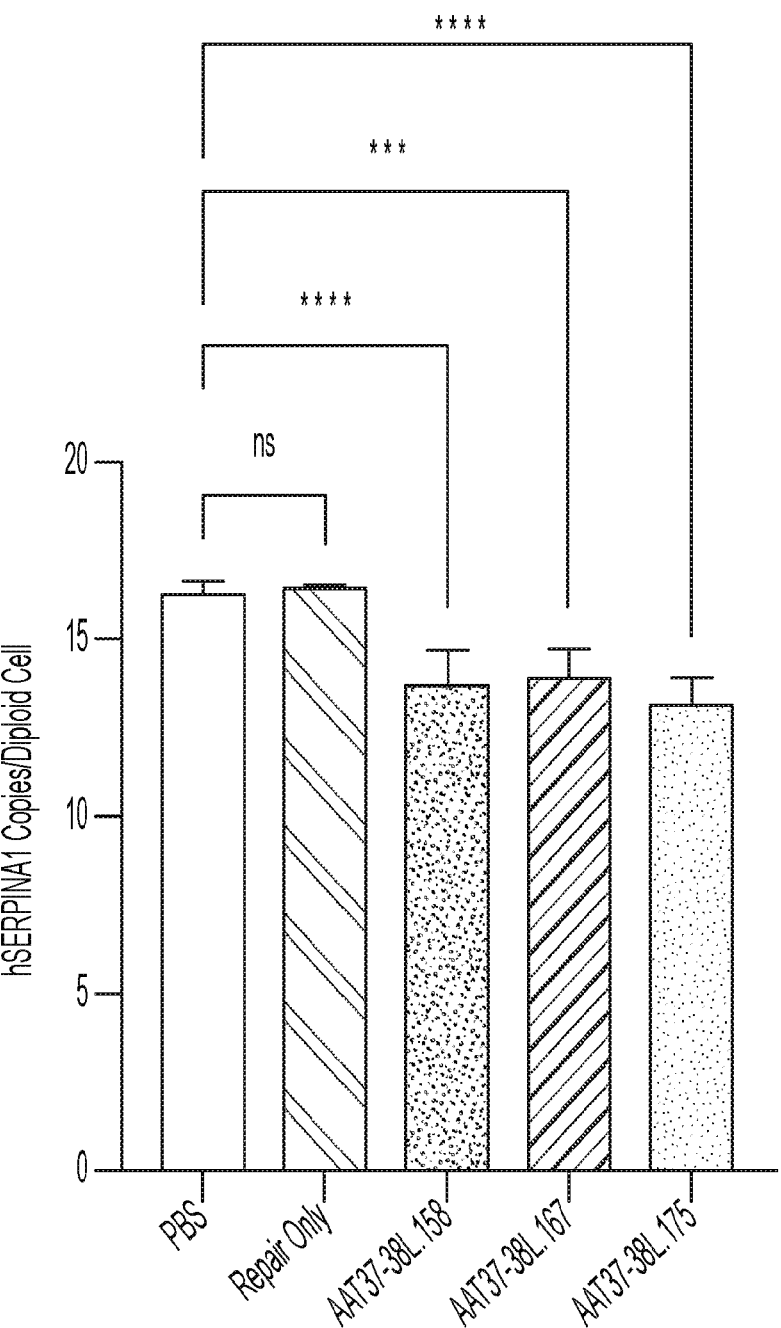
FIG. 35. Provides a bar graph showing the copy number/ diploid cell of AAT (indicated as hSERPINA1) after administration of PBS, an AAV8 containing repair construct, or the AAV8 repair construct and the indicated AAT 37-38 meganucleases. Asterisks indicate statistically significant difference between the treatment groups.
Figure 36:
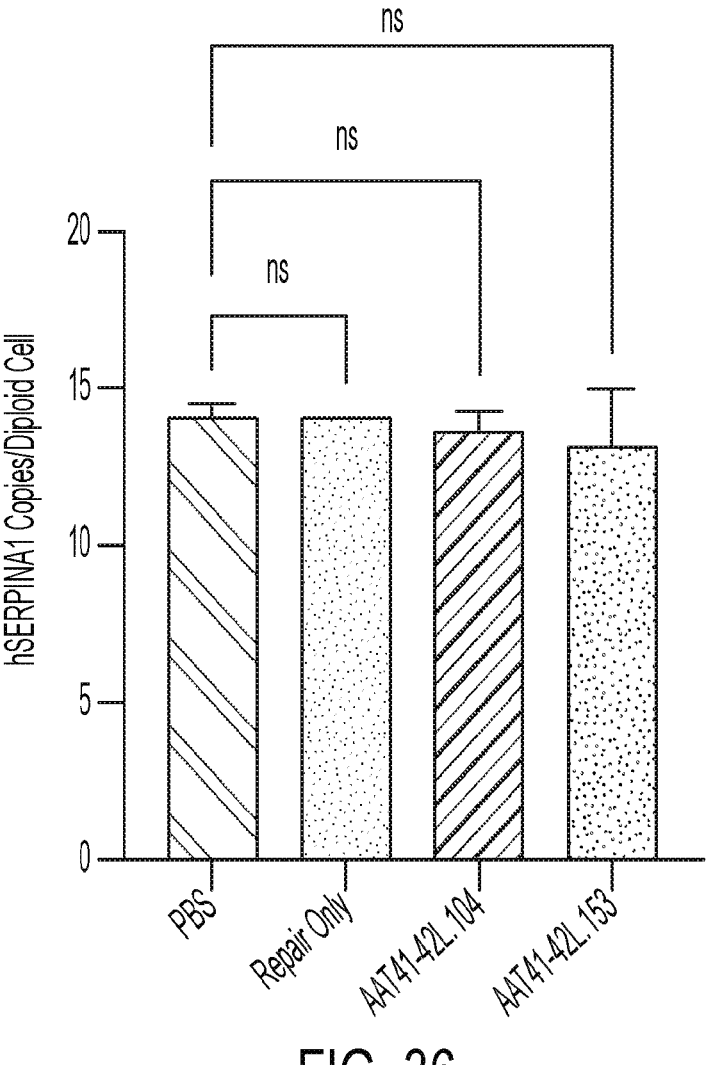
FIG. 36. Provides a bar graph showing the copy number/ diploid cell of AAT (indicated as hSERPINA1) after administration of PBS, an AAV8 containing repair construct, or the AAV8 repair construct and the indicated AAT 41-42 mega-nucleases (ns indicates no statistical significance).
Figure 37:
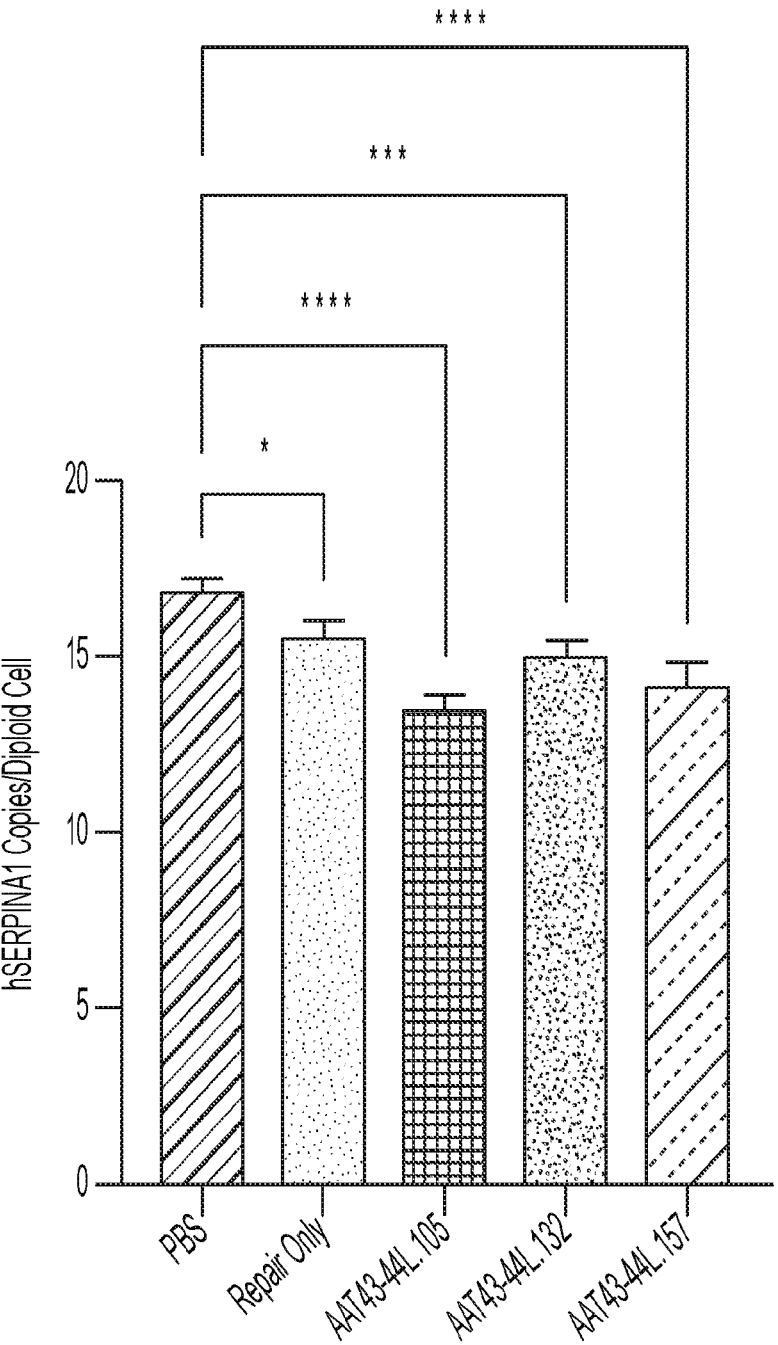
FIG. 37. Provides a bar graph showing the copy number/diploid cell of AAT (indicated as hSERPINA1) after administration of PBS, an AAV8 containing repair construct, or the AAV8 repair construct and the indicated AAT 43-44 mega-nucleases. Asterisks indicate a statistically significant difference between the treatment groups.

The SERPINA1 transgene copy number was analyzed in PiZ liver samples 4 weeks post AAV administration via ddPCR to see if there was variation in copy number between PiZ mouse cohorts A, B and C. There was a significant difference in SERPINA1 transgene copy number between meganuclease treated groups and the PBS or repair only groups for each 37-38 meganuclease and also for each 43-44 meganuclease with a drop in ~1-4 transgene copies (FIGS. 35 and 37). There was not a significant difference in SER-PINA1 transgene copy number in the 41-42 meganuclease treated PiZ mice compared to PBS or repair only groups (FIG. 36).

Figure 38:
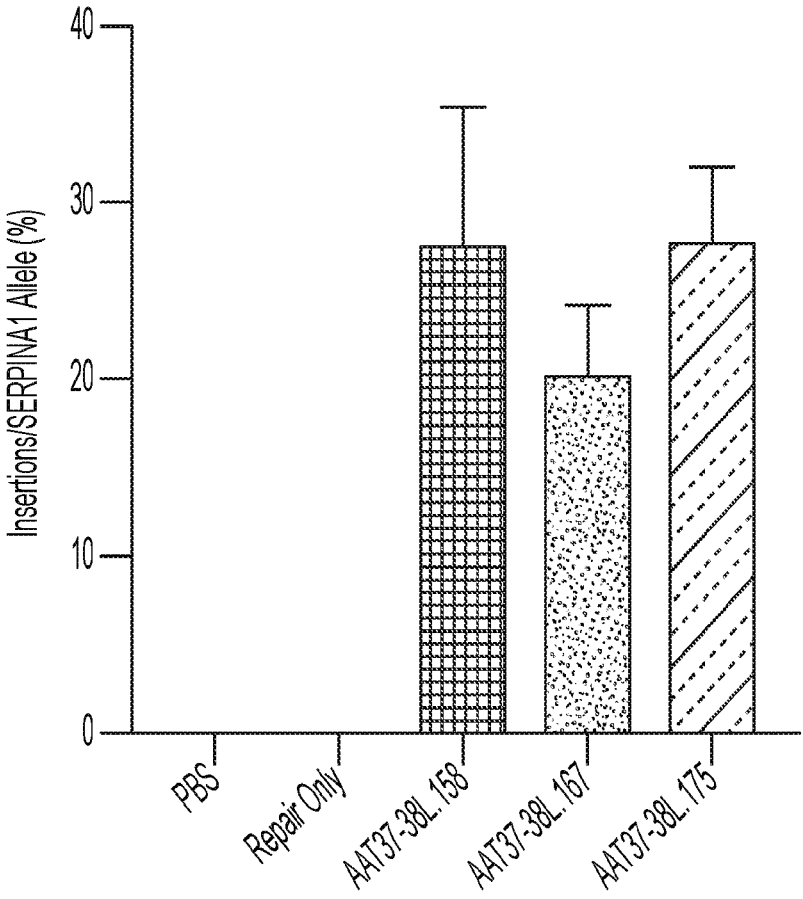
FIG. 38. Provides a bar graph showing percentage of repair construct insertion after administration of PBS, an AAV8 containing repair construct, or the AAV8 repair construct and the indicated AAT 37-38 meganucleases.
Figure 40:
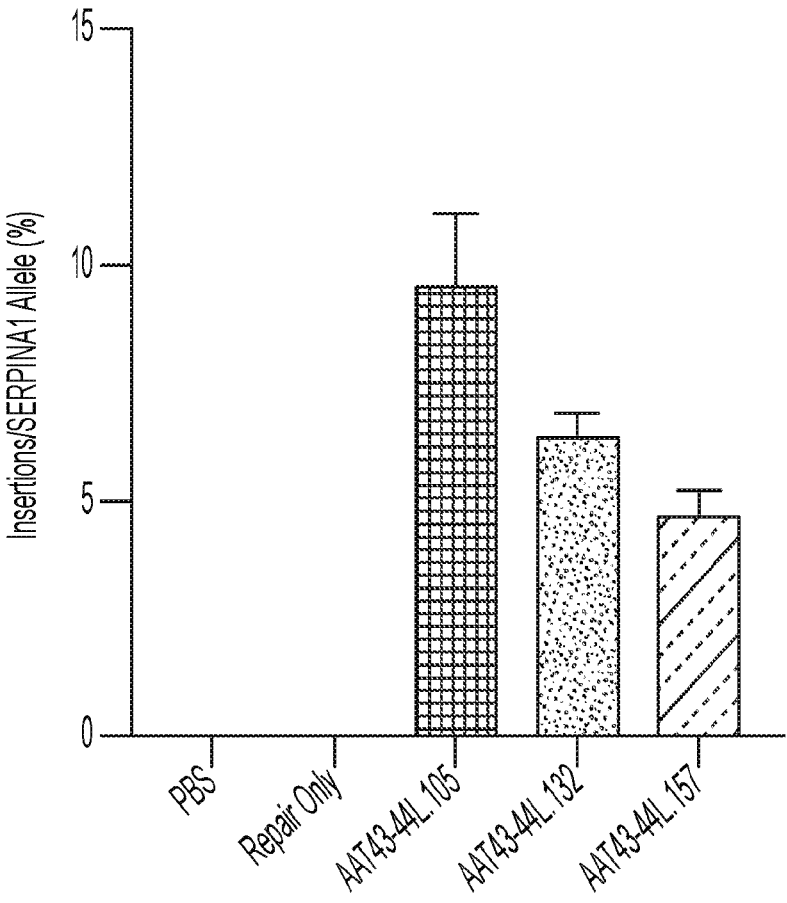
FIG. 40. Provides a bar graph showing percentage of repair construct insertion after administration of PBS, an AAV8 containing repair construct, or the AAV8 repair construct and the indicated AAT 43-44 meganucleases.

Insertion analysis determined that the AAT 37-38 site showed the highest levels of insertions with an average of up to 28% insertions per SERPINA1 allele for PiZ mice treated with the third generation AAT37-38L.158 meganuclease (FIG. 38). The AAT 41-42L.104 meganuclease treated PiZ mice saw an average of 13% insertions (FIG. 39) and the AAT43-44L.105 meganuclease demonstrated an average of 14% insertions (FIG. 40).

Figure 41:
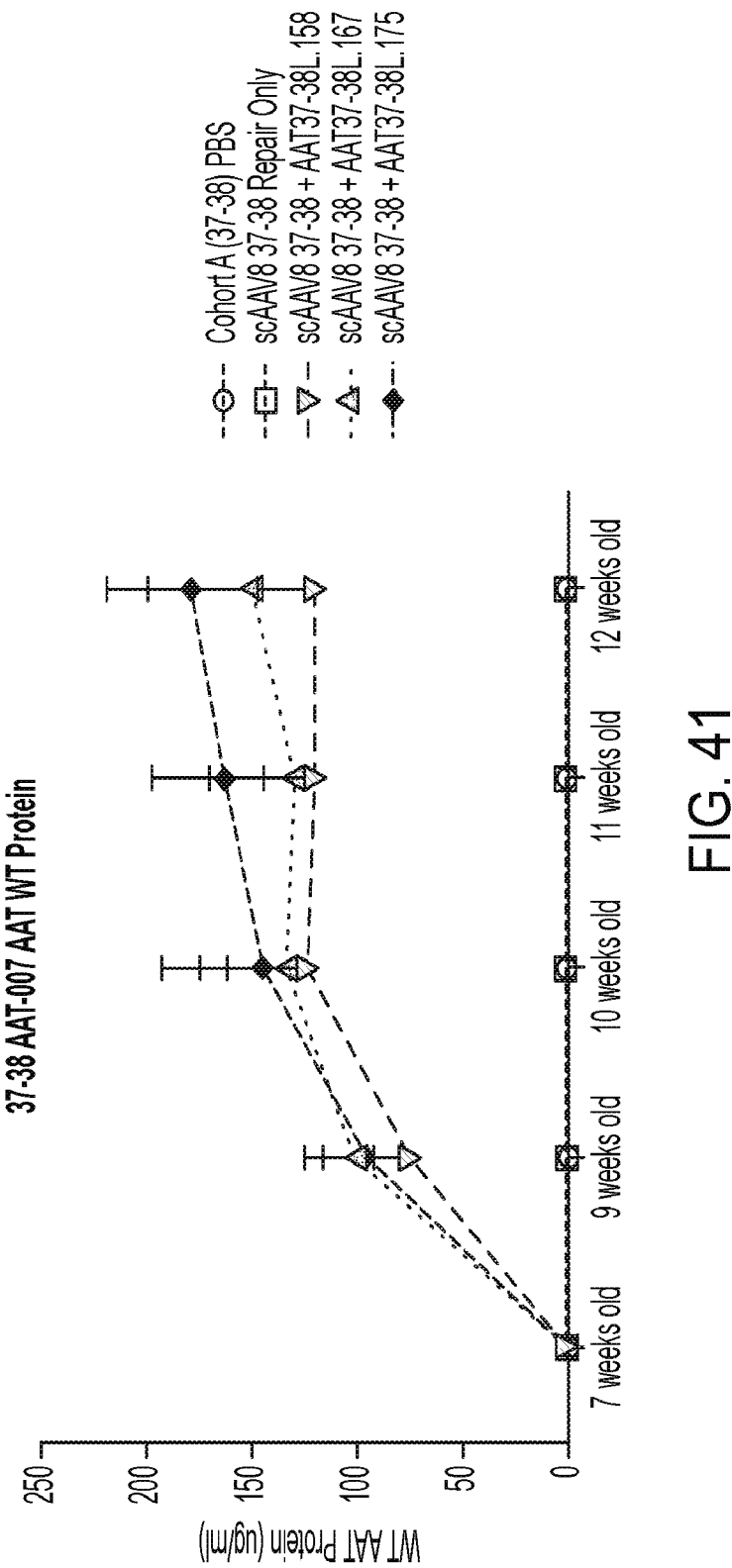
FIG. 41. Provides a graph showing concentration of WT AAT protein (µg/mL) in the plasma from PiZ mice after administration of PBS, an AAV8 containing repair construct, or the AAV8 repair construct and the indicated AAT 37-38 meganucleases at 7, 9, 10, 11, and 12 weeks.
Figure 42:
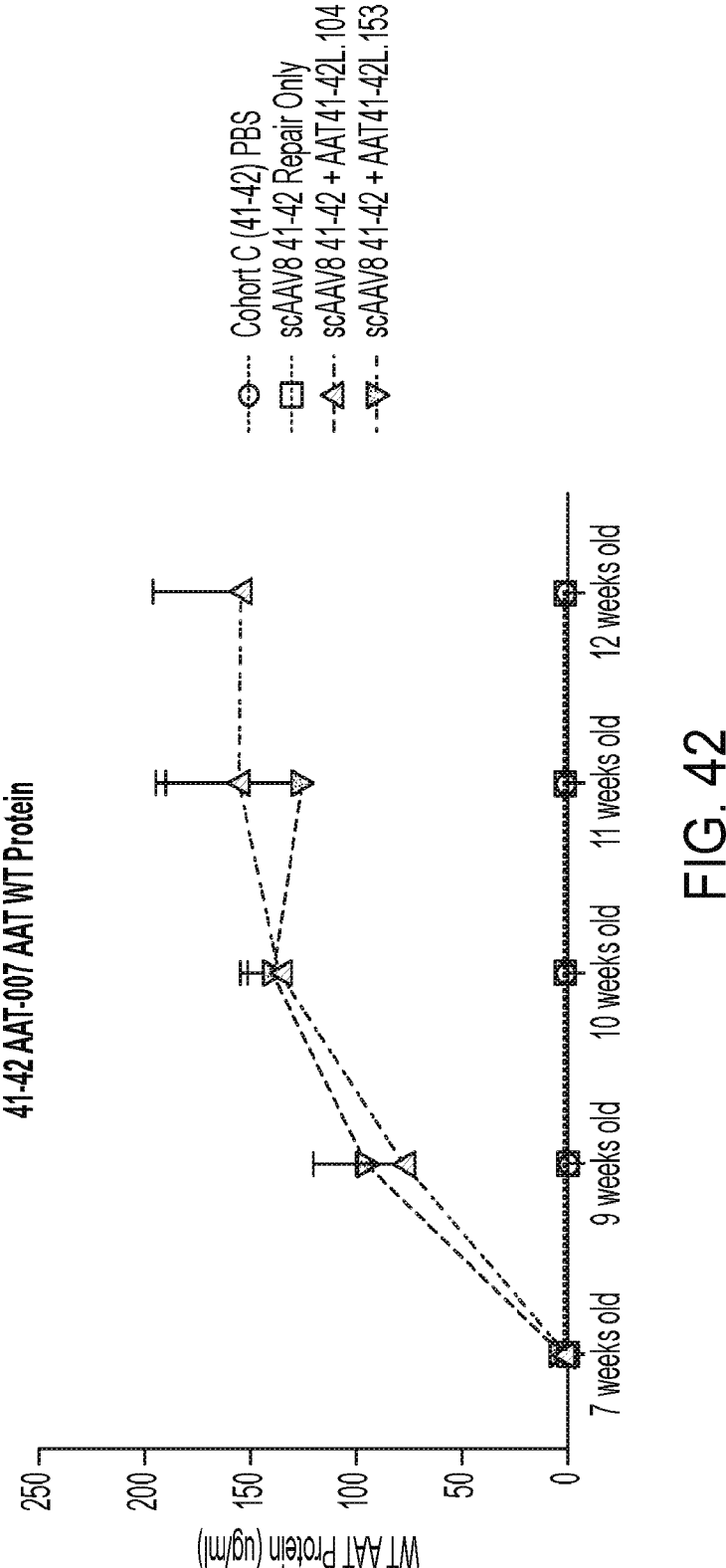
FIG. 42. Provides a graph showing concentration of WT AAT protein (µg/mL) in the plasma from PiZ mice after administration of PBS, an AAV8 containing repair construct, or the AAV8 repair construct and the indicated AAT 41-42 meganucleases at 7, 9, 10, 11, and 12 weeks.
Figure 43:
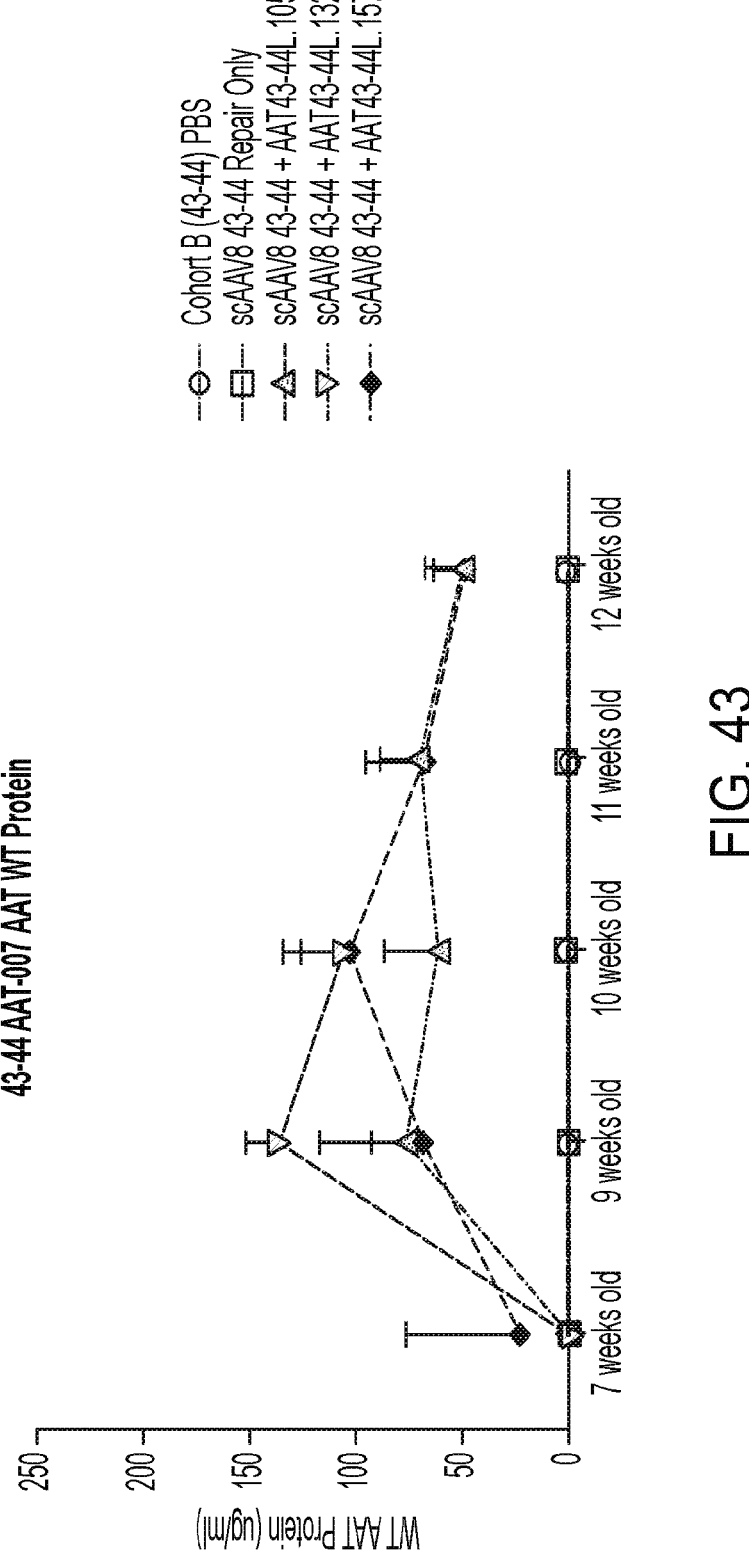
FIG. 43. Provides a graph showing concentration of WT AAT protein (µg/mL) in the plasma from PiZ mice after administration of PBS, an AAV8 containing repair construct, or the AAV8 repair construct and the indicated AAT 43-44 meganucleases at 7, 9, 10, 11, and 12 weeks.

Both WT and Z plasma protein was measured via mass spectrometry. All sites showed an increase in WT AAT protein 1 week after AAV administration. For the AAT37-38 and AAT41-42 nucleases the WT AAT protein peaked at around 3 or 4 weeks post administration with the highest average levels being reaching around 179 ng/ml of protein in the AAT37-38L.175 treated animals (FIG. 41). The AAT41-42L.104 treated animals saw a plateau of secreted WT AAT protein expression at around 150 µg/ml (FIG. 42). The 43-44 meganuclease treated animals saw a gradual decline in secreted WT AAT protein after an initial peak at 1 week with the highest level of WT-AAT expression reaching 137 µg/ml (FIG. 43).

Figure 44:
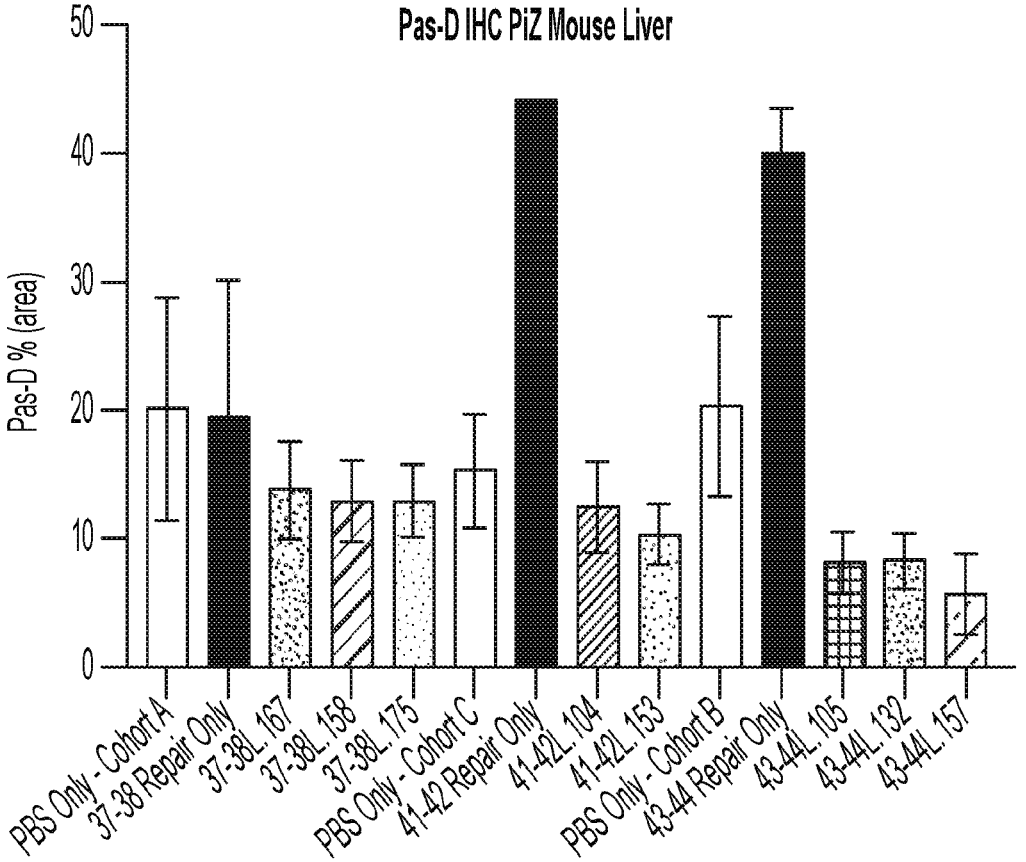
FIG. 44. Provides a bar graph showing the percentage of PAS-D positive staining in the livers of PiZ mice after administration of PBS, an AAV8 containing repair construct, or the AAV8 repair construct and the indicated AAT 37-38, AAT 41-42, and AAT 43-44 meganucleases.
Figure 45:
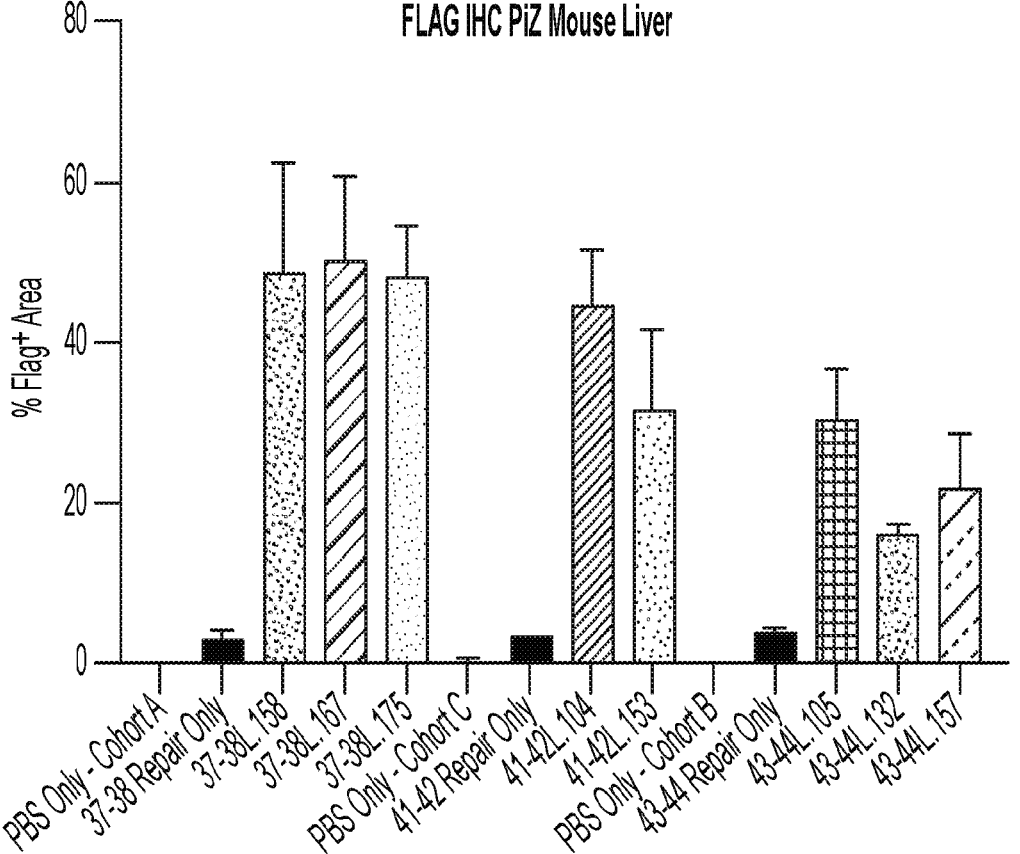
FIG. 45. Provides a bar graph showing the percentage of Flag positive staining for detection of Flag tagged WT-AAT insert in the livers of PiZ mice after administration of PBS, an AAV8 containing repair construct, or the AAV8 repair construct and the indicated AAT 37-38, AAT 41-42, and AAT 43-44 meganucleases.

PAS-D and flag immunohistochemistry was performed to identify z-globules and WT-AAT protein in terminal PiZ mouse liver samples. PAS-D staining shows there is a slight decrease in PAS-D staining in all meganuclease treated animals compare to PBS and repair only groups (FIG. 44). The WT-AAT insert contains a flag tag so we can identify the WT AAT protein in the liver without the concern of human and mouse AAT-antibody cross reaction. The flag immuno-histochemistry shows an average of approximately 50%, 30-50% and 20-30% of liver cells are positive for flag for sites AAT37-38, AAT41-42 and AAT43-44, respectively (FIG. 45).

Figure 46:
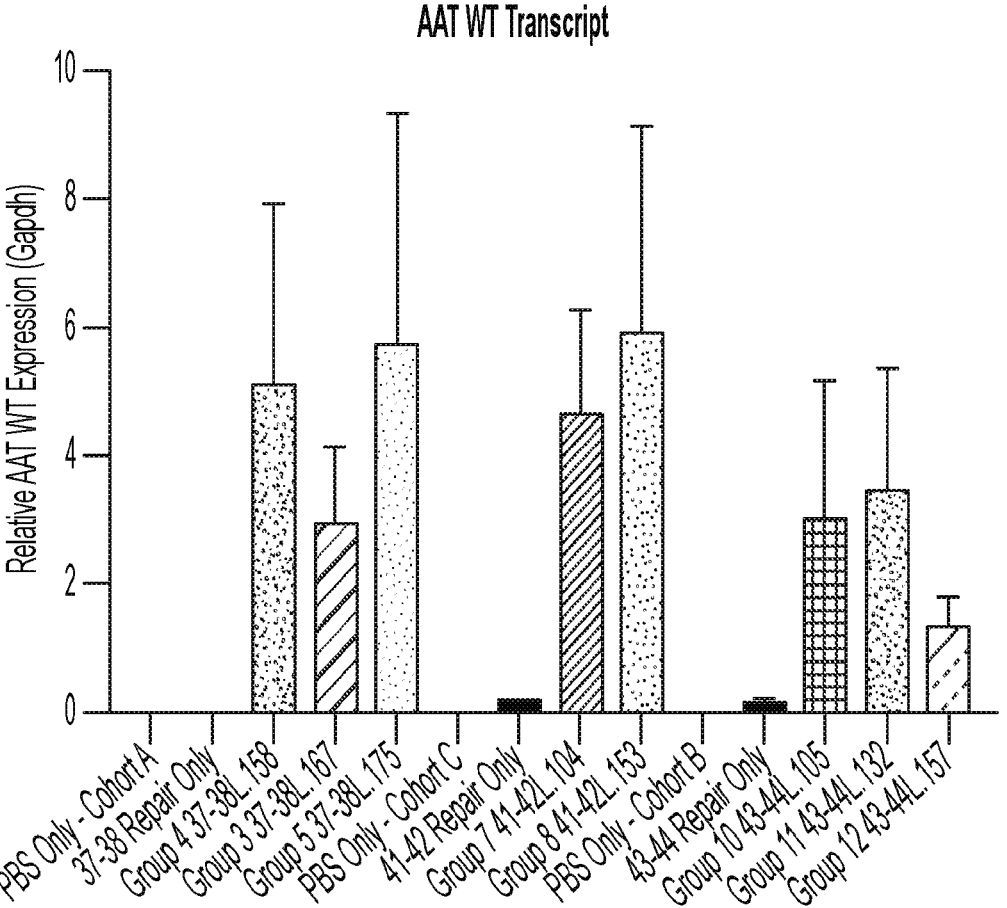
FIG. 46. Provides a bar graph showing the detection of WT AAT RNA transcript in the livers of PiZ mice after administration of PBS, an AAV8 containing repair construct, or the AAV8 repair construct and the indicated AAT 37-38. AAT 41-42, and AAT 43-44 meganucleases.
Figure 47:
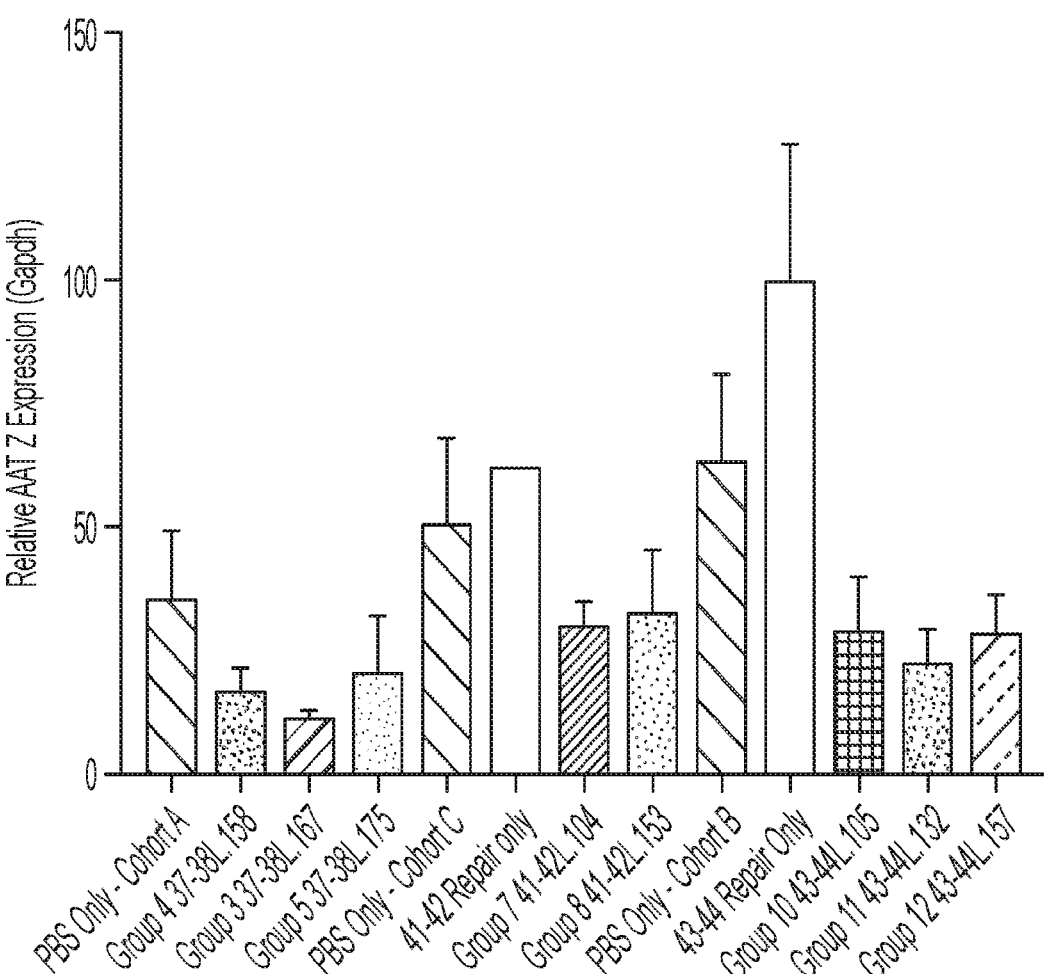
FIG. 47. Provides a bar graph showing the detection of AAT Z RNA transcript in the livers of PiZ mice after administration of PBS, an AAV8 containing repair construct, or the AAV8 repair construct and the indicated AAT 37-38, AAT 41-42, and AAT 43-44 meganucleases.

RNA transcript analysis was performed for both AAT-WT and AAT-Z transcript in terminal PiZ mouse livers. WT-AAT transcript shows there is an increase in WT transcript for all meganuclease sites and this trends closely with the insertion and AAT-WT protein data (FIG. 46). The AAT-Z transcript data suggest there may be a meganuclease-mediated decrease in Z-AAT protein, however, similarly to the PAS-D staining, the loss of SERPINA1 Z transgenes cannot be ruled out as a reason for this (FIG. 47). Interestingly, the AAT41-42 site does not see a loss of SERPINA1 Z transgenes yet there is a decrease in AAT-Z transcript, suggesting the loss is meganuclease mediated.

3. Conclusions

Overall, AAT-007 demonstrated up to an average of 28% insertions can be achieved by delivering an meganuclease via AAV8 in conjunction with an AAV8 repair template in PiZ mice. The insertions led to up to 179 µg/ml of circulating WT-AAT protein and correlated well with the WT transcript, decrease in PAS-D and decrease in Z transcript.

Example 8

In Vivo AAT Gene Editing in a PiZ AAT Mouse Model

1. Methods and Materials

The PiZ mouse model, as described in Example 3, was used for this study to determine the frequency of insertions after LNP delivery of ARCUS over multiple doses with the AAT WT ssAAV8 repair template. The generation 4 AAT37-38L.262 meganuclease was delivered as mRNA and formu-lated into an MC3 based LNP formulation (LNP-A). LNP-A was dosed at 0.5, 0.3, 0.1 or 0.05 mg/kg with the AAV repair template dosed at 3e13 vg/kg for all four groups. PBS and repair template only control groups were also included in this study. The study design is provided in Table 16 below. LNP and AAV were delivered together via retro-orbital (RO) injections in PiZ mice.

TABLE 16

Study Design for Example 8.

| | Treatment | AAV Repair Dose (vg/kg) | LNP Dose (mg/kg) | N = |
|---|---|---|---|---|
| 1 | PBS | X | X | 5 |
| 2 | ssAAV8_37-38 Alone | 3e13 | X | 5 |
| 3 | LNP-A_AAT37-38L.262/ | 3e13 | 0.5 | 5 |
| 4 | ssAAV8 37-38 | 3e13 | 0.3 | 5 |
| 5 | | 3e13 | 0.1 | 5 |
| 6 | | 3e13 | 0.05 | 5 |
| Total | | | | 30 |

Blood was collected from mice at weekly intervals from day-7 through day 28. Serum was collected at days-7, 2, 9 and 28 for serum chemistry (ALT, AST, ALP, Tbil) analysis. Plasma was isolated on study days 16, 23 and 28 and analyzed as previously described in Example 3. Liver tissue was harvested from the mice at day 28. DNA was isolated from liver tissue as described in Example 3. AAT Transgene copy number quantification was performed as described in Example 3. Insertion quantification was performed as described in Example 4 using primers and probes provided in Table 10, assay 3. Indel quantification was performed as described in Example 6, using primers and probes from Table 13, assay 13. Liver immunohistochemistry was performed as described in Example 4.

2. Results

Figure 48:
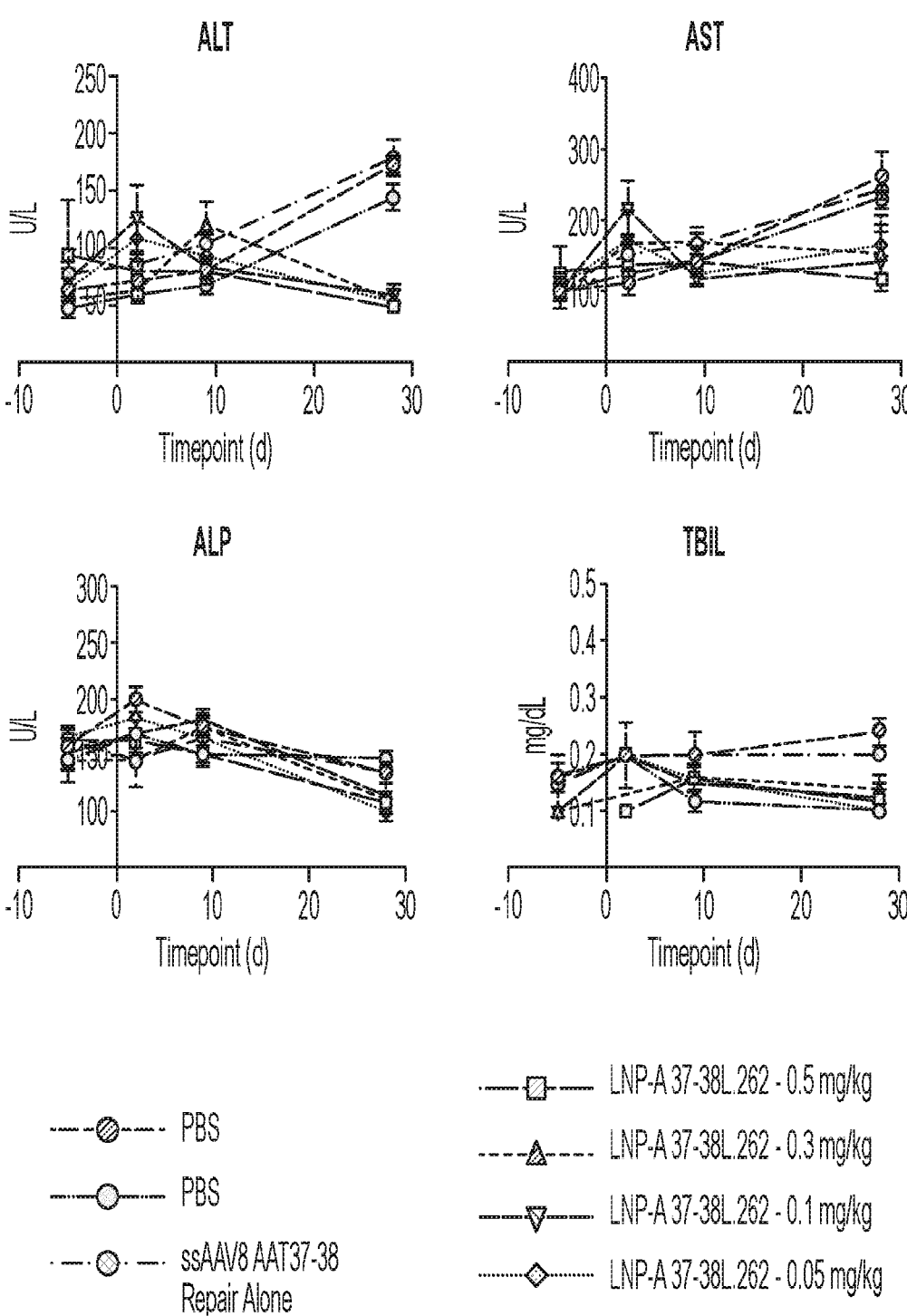
FIG. 48. Provides graphs showing the levels of liver enzymes ALT, AST, ALP, and TBIL for PiZ mice treated with PBS, an AAV8 repair template alone (3e13 vg/kg), or an AAV8 repair template (3e13 vg/kg) and an LNP-A containing the AAT 37-38L.262 meganuclease at 0.5 mg/kg, 0.3 mg/kg, 0.1 mg/kg, or 0.05 mg/kg.
Figure 49:
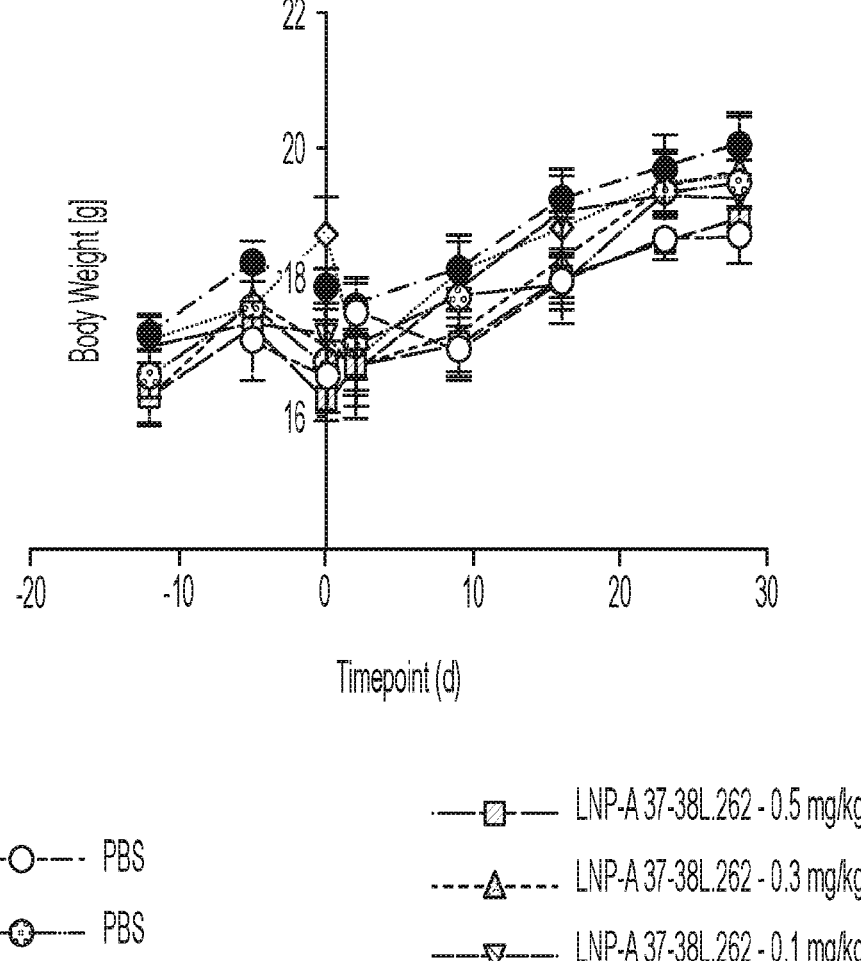
FIG. 49. Provides a graph showing the body weight of PiZ mice treated with PBS, an AAV8 repair template alone (3e13 vg/kg), or an AAV8 repair template (3e13 vg/kg) and an LNP-A containing the AAT 37-38L.262 meganuclease at 0.5 mg/kg, 0.3 mg/kg, 0.1 mg/kg, or 0.05 mg/kg.

Serum chemistry analysis shows a decrease in ALT, AST, ALP and Tbil in meganuclease treated mice at all LNP doses at day 28 compared to PBS and repair template alone treated mice (FIG. 48). A slight increase in ALT, AST and ALP was observed at 2 days or 1 week post LNP and AAV administration but all meganuclease treated groups serum chemistry levels were back to baseline by day 28. LNP-A formulated with the generation 4 AAT 37-38L.262 meganuclease was well tolerated across all doses and there was no test article related toxicities observed in these mice, which were observed in Example 6 utilizing the earlier developed first generation 37-38 meganuclease. PiZ mouse body weights continued to rise after test article administration indicating the animals were healthy throughout the study (FIG. 49). This indicates that the later developed AAT 37-38L.262 engineered meganuclease was better tolerated likely due to the greatly reduced off targeting profile established using the oligocapture assay (FIG. 34) in comparison to the first generation AAT 37-38x.50 meganuclease (FIG. 21).

Figure 50:
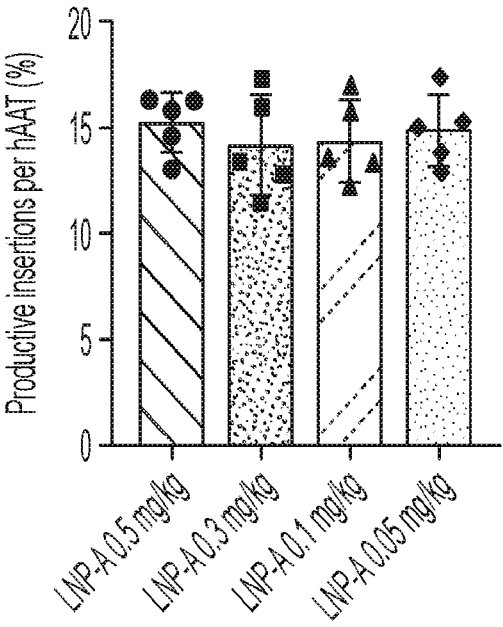
FIG. 50. Provides a bar graph showing the percentage of productive insertions (insert oriented in the functional orientation) per hAAT from the livers of PiZ mice treated with an AAV8 repair template (3e13 vg/kg) and an LNP-A containing the AAT 37-38L.262 meganuclease at 0.5 mg/kg, 0.3 mg/kg, 0.1 mg/kg, or 0.05 mg/kg.
Figure 51:
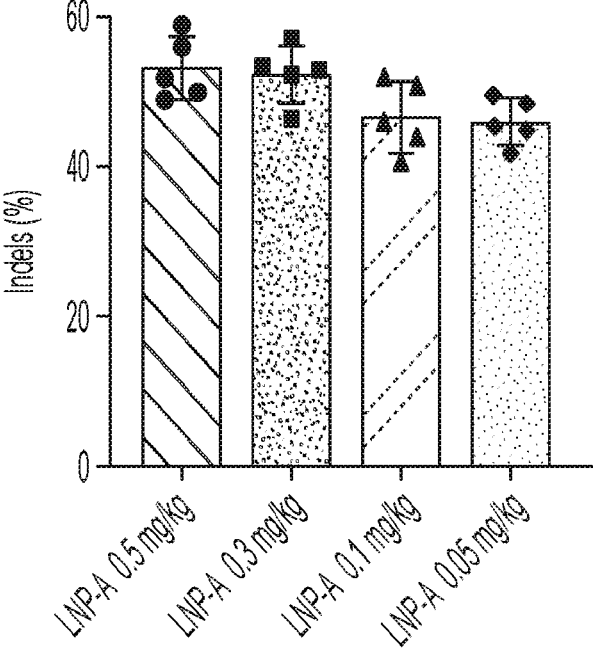
FIG. 51. Provides a bar graph showing the percentage of indels at the AAT 37-38 recognition sequence from the livers of PiZ mice treated with an AAV8 repair template (3e13 vg/kg) and an LNP-A containing the AAT 37-38L.262 meganuclease at 0.5 mg/kg, 0.3 mg/kg, 0.1 mg/kg, or 0.05 mg/kg.

Insertion analysis demonstrated that there is no significant difference between any of the LNP-A doses for insertion of the WT AAT repair with an average insertion frequency of ~14-15% (FIG. 50). However, indel analysis shows a slight dose mediated response across groups. The high dose (0.5 mg/kg) group shows an average of 53% indels and the low dose group shows an average of 45% indels (FIG. 51).

Figure 52:
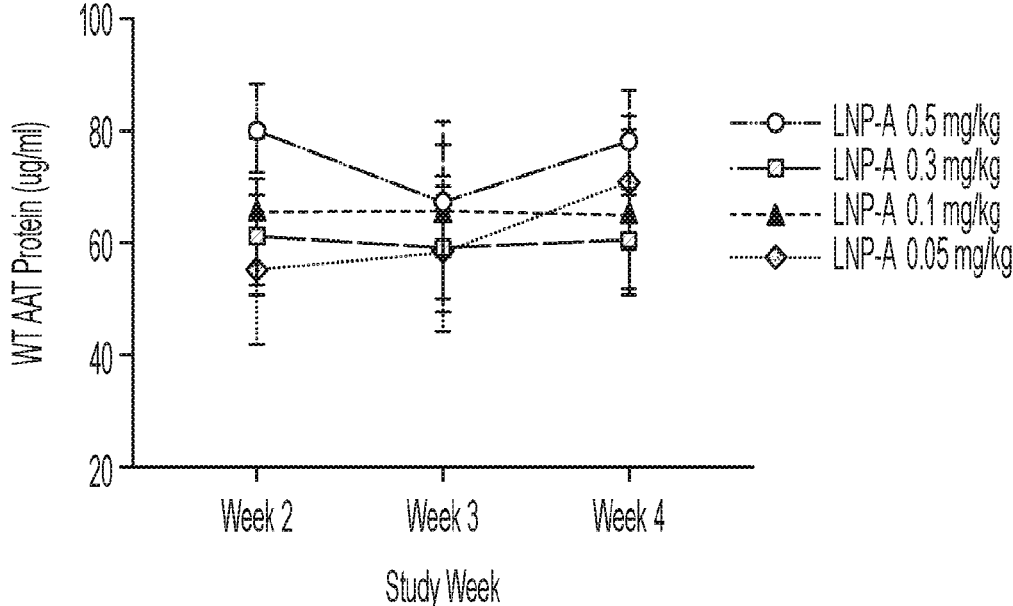
FIG. 52. Provides a graph showing the WT AAT protein concentration in µg/mL from the livers of PiZ mice at two weeks, three weeks, and four weeks after treatment with an AAV8 repair template (3e13 vg/kg) and an LNP-A containing the AAT 37-38L.262 meganuclease at 0.5 mg/kg, 0.3 mg/kg, 0.1 mg/kg, or 0.05 mg/kg.
Figure 53:
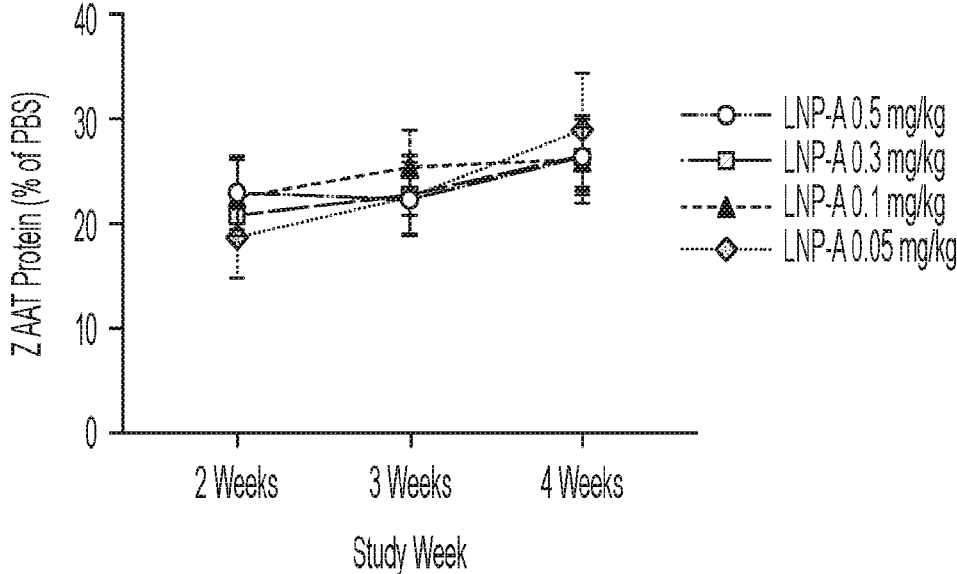
FIG. 53. Provides a graph showing the Z AAT protein concentration in µg/mL from the livers of PiZ mice at two weeks, three weeks, and four weeks after treatment with an AAV8 repair template (3e13 vg/kg) and an LNP-A containing the AAT 37-38L.262 meganuclease at 0.5 mg/kg, 0.3 mg/kg, 0.1 mg/kg, or 0.05 mg/kg.

WT AAT protein analysis demonstrated an average of 50-80 µg/ml WT protein for all dose groups (FIG. 52). There was no dose response in WT protein-similar to the insertion data. The 0.5 mg/kg LNP-A treated groups had slightly higher AAT-WT protein levels than the other doses at weeks 2 and 4 (FIG. 52). The decrease in AAT-Z protein also showed no dose response between groups and there was a 20-30% decrease in AAT-Z protein for all groups (FIG. 53).

3. Conclusions

In conclusion, we demonstrated up to 15% insertions with LNP-A formulated with the generation 4 AAT37-38L.262 meganuclease and ssAAV8 repair template which resulted in up to 80 µg/ml of AAT-WT secreted protein and a 30% decrease in AAT-Z secreted protein in the PiZ mouse model. In addition, the later developed fourth generation AAT 37-38L.262 was well tolerated with no toxicity issues, which were observed in LNP delivery of the first generation AAT 37-38x.50 meganuclease of Example 4.

Example 9

In Vivo AAT Gene Editing in a PiZ AAT Mouse Model

1. Methods and Materials

The PiZ mouse model, as described in Example 3, was used for this study to determine how the repair backbone and dose affect insertions when the meganuclease delivery method is via either ssAAV or LNP. The generation 4 AAT37-38L.262 meganuclease will be used in combination with the 37-38 repair template, as describe in example 3, as with ssAAV or scAAV. The study design is provided in Table 17 below.

TABLE 17

Study Design for Example 9

| Group | Treatment | LNP Dose (mg/kg) | N = |
|---|---|---|---|
| 1 | PBS | X | 4 |
| 2 | | 3.5 | 4 |
| 3 | LNP-A AAT 37- | 3 | 4 |
| 4 | 38L.262 | 1 | 4 |

Blood will be collected from mice at weekly intervals from day-7 through day 56. Serum will be collected at days-7, 2, 9, 29 and day 56 for serum chemistry (ALT, AST, ALP, Tbil) analysis. Plasma will be isolated on study days 16, 23, 36, 43, 51 and 56 and analyzed as previously described in Example 3. Liver tissue will be harvested from the mice at day 56. Liver tissue will be harvested at day 56. DNA will be isolated from liver tissue as described in Example 3. AAT Transgene copy number quantification will be performed as described in Example 3. Insertion quantification will be performed as described in Example 4 using primers and probes provided in Table 10, assay 3. Indel quantification will be performed as described in Example 6, using primers and probes from Table 13, assay 13. Liver immunohisto-chemistry will be performed as described in Example 4

Example 10

In Vivo Tolerability Study of an LNP Containing an Engineered Meganuclease

1. Methods and Materials

Sprague Dawley rats were used to assess tolerability of LNP-A formulated with the AAT 37-38L.262 meganuclease at various doses to choose a dose for the NHP study described in Example 11. Blood was collected from rats prior to dosing and post dose at 4 hr, 48 hr and day 7 and analyzed for serum chemistry: ALT, AST, ALP and Tbil and cytokines: MCP-1, IFN-y, IL-1β, TNF-α, IL-10 and KC/GRO. Livers were harvested at day 7, placed in 10% neutral buffer formalin (NBF) for at least 24 hours and subsequently transferred into 70% ethanol for at least 24 hours and then processed to paraffin blocks. Livers were stained with hematoxylin and eosin for histopathology analysis.

2. Results

All LNP-A-AAT37-38L.262 doses were well tolerated and the rats survived through the 7-day study. Serum chemistry results show there was a dose response for ALT and AST levels, with the 3.5 mg/kg LNP-A dose reaching an average maximum level of 272 U/L and 1212 U/L of ALT and AST at 4 hours post injection, which returns to baseline by day 7 FIG. 54. The ALP and Tbil levels are not significantly different compared to PBS treated animals FIG. 54.

Figure 55:
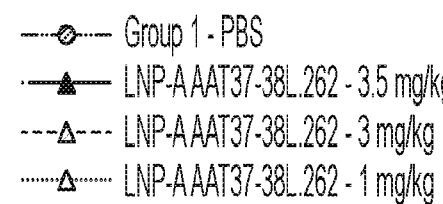
FIG. 55. Provides graphs showing the concentration of various cytokines (pg/mL) IFN-y, TNF-a, IL-6, IL-1β, IL-10 and KC/GRO from the livers of rats treated with an LNP-A containing the AAT 37-38L.262 meganuclease at 3.5 mg/kg, 3 mg/kg, and 1 mg/kg.

Cytokine analysis showed dose mediated increases for IFN-y, IL-1β, IL-10 and KC/GRO at the 4-hour timepoint, which returned to baseline by 48 hours (FIG. 55). Interestingly, IL-10 at the 3.5 mg/kg LNP-A dose elevated slightly from 48 hours to day 7. There was no significant difference in TNF-α and IL-6 for all groups with the exception of TNF-α being slightly elevated in the 3 mg/kg group at 48 hours, which returns to baseline by day 7 (FIG. 55). Histopathology analysis found minimal to mild oval cell proliferation in the 3.5 mg/kg and 3 mg/kg LNP-A dosed rats and no lesions were observed in any rats from the 1 mg/kg dose group.

3. Conclusions

Overall, the LNP-A AAT37-38L.262 was well-tolerated at doses 3.5 mg/kg, 3 mg/kg and 1 mg/kg. Due to the transient elevation of ALT, AST, IFN-y, IL-1β, IL-10 and KC/GRO, at 3.5 mg/kg and 3 mg/kg we decided to dose the NHPs at a lower dose of 1.75 mg/kg.

Example 11

In Vivo Gene Editing of Non-Human Primates with Engineered AAT Meganucleases

1. Methods and Materials

To analyze the insertion approach described herein in a large animal model, we will dose cynomolgus macaques with PBS, ssAAV8 repair alone (3e13 vg/kg) and the AAT37-38L.262 meganuclease delivered via ssAAV8 (5e12 vg/kg) or LNP-A (1.75 mg/kg) with the ssAAV8 repair (2.5e13 vg/kg and 3e13 vg/kg for AAV and LNP, respectively). The LNP dose was chosen based on the data of Example 9 and the AAV doses were chosen based on previous NHP studies showing a total of 3e13 vg/kg was well tolerated. Animals will receive prednisolone throughout the study in order to prevent the immune system from clearing secreted human W-AAT protein from the inserted repair. There will be a day 30 biopsy to understand how the insertion approach described herein is working at an earlier timepoint in a large animal model. All animals will be humanely euthanized at 3 months post dose. Blood will be collected throughout the study for serum chemistry and human WT-AAT protein analysis. Livers will be analyzed for insertions and indels via ddPCR similarly to the assays described in Example 4 and Example 6, respectively.

In addition, immunohistochemistry will be performed on liver tissue. Briefly, liver tissue will be placed in 10% neutral buffer formalin (NBF) for at least 24 hours and subsequently transferred into 70% ethanol for at least 24 hours and then processed to paraffin blocks for analysis. Hematoxylin and Eosin (H&E) and flag immunohistochemistry will be performed on the liver section for histopathology analysis and WT AAT expression from the inserted donor polynucleotide, respectively.

The study design for Example 11 is provided in Table 18 below.

TABLE 18

Study Design of Example 11.

| Group | Treatment | Repair Dose (vg/kg) | Meganuclease Dose (vg/kg) | LNP Meganuclease Dose (mg/kg) | N = |
|-------|-----------|---------------------|---------------------------|-------------------------------|-----|
| 1 | PBS | X | X | X | 1 |
| 2 | ssAAV8 AAT37-38 Repair Only | 3e13 | X | X | 2 |
| 3 | ssAAV8AAT37-38L.262/ssAAV8 37-38 | 2.5e13 | 5e12 | X | 3 |
| 4 | LNP-A 37-38L.262/ssAAV8 37-38 | 3e13 | X | 1.75 | 3 |

---

Sequence Listing

SEQ ID NO: 1
MNTKYNKEFLLYLAGFVDGDGSIIAQIKPNQSYKFKHQLSLAFQVTQKTQRRWFLD
KLVDEIGVGYVRDRGSVSDYILSEIKPLHNFLTQLQPFLKLKQKQANLVLKIIWRLPS
AKESPDKFLEVCTWVDQIAALNDSKTRKTTSETVRAVLDSLSEKKKSSP

SEQ ID NO: 2
LAGLIDADG

SEQ ID NO: 3
TGCCCGCTCACACCAGACCCTG

SEQ ID NO: 4
ACGGGCGAGTGTGGTCTGGGAC

SEQ ID NO: 5
GCTGCTCAGGCATCTGCATTTC

SEQ ID NO: 6
CGACGAGTCCGTAGACGTAAAG

SEQ ID NO: 7
TTCAGACAGTTGCTCAACCTCT

-continued

Sequence Listing

SEQ ID NO: 8
AAGTCTGTCAACGAGTTGGAGA

SEQ ID NO: 9
GGCCTGGTCACACTTGGGTTTA

SEQ ID NO: 10
CCGGACCAGTGTGAACCCAAAT

SEQ ID NO: 11
CCCCACTTTGCACAACTGGGGA

SEQ ID NO: 12
GGGGTGAAACGTGTTGACCCCT

SEQ ID NO: 13
TGAGGATCCTTGTGAGTGTTGG

SEQ ID NO: 14
ACTCCTAGGAACACTCACAACC

SEQ ID NO: 15
AGGACCTAGATGTAGGATTCTG

SEQ ID NO: 16
TCCTGGATCTACATCCTAAGAC

SEQ ID NO: 17
MNTKYNKEFLLYLAGFVDADGSIYACIRPRQSSKFKHTLELGFQVSQKTCRRWFLDK
LVDEIGVGYVRDRGRASDYRLSQIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIYAKITPHQKYKFKHQL
TLRFAVSQKTQRRWFLDKLVDEIGVGYVSDNGSVSSYTLSQIKPLHNFLTQLQPFLK
LKQKQANLVLKIIEQLPSAKESPDKFLEVCTWVDQIAALNDSHTRKTTSETVRAVLD
SLSEKKKSSP

SEQ ID NO: 18
MNTKYNKEFLLYLAGFVDSDGSIYACIRPRQARKFKHTLELGFQVTQATCRRWFLD
KLVDEIGVGYVRDRGRASDYRLSEIKPLHNFLTQLQPFLKLKQKQANLVLKIIBQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYAMIKPNQRYKFKH
QLNLRFNVSQKTQRRWFLDKLVDEIGVGYVSDNGSVSSYTLSQIKPLHNFLTQLQPF
LKLKQKQANLVLKIIEQLPSAKESPDKFLEVCTWVDQIAALNDSRTRKTTSETVRAV
LDSLSEKKKSSP

SEQ ID NO: 19
MNTKYNKEFLLYLAGFVDADGSIYACIRPRQRRKFKHMLELGFQVSQKTCRRWFLD
KLVDEIGVGYVRDRGRASDYRLSEIKPLHNFLTQLQPFLKLKQKQANLVLKHIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYAKITPHQKYKFKHQ
LTLRFVVSQKTQRRWFLDKLVDEIGVGYVSDNGSVSSYTLSEIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 20
MNTKYNKEFLLYLAGFVDADGSIYASIRPRQRRKFKHMLILGFQVSQKTCRRWFLD
KLVDEIGVGYVRDRGRASDYRLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYAKITPHQKYKFKHQ
LVLRFVVSQKTQRRWFLDKLVDEIGVGYVSDNGSVSSYTLSQIKPLHNFLTQLQPFL
KLKQKQANLVLKIIEQLPSAKESPDKFLEVCTWVDQIAALNDSHTRKTTSETVRAVL
DSLSEKKKSSP

SEQ ID NO: 21
MNTKYNKEFLLYLAGFVDSDGSIYATIRPRQRRKFKHMLELFFQVSQKTCRRWFLD
KLVDEIGVGYVRDRGRASDYRLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYAKITPHQKYKFKHQ
LHLRFVVSQKTQRRWFLDKLVDEIGVGYVSDNGSMSAYTLSEIKPLHNFLTQLQPFL
KLKQKQANLVLKIIEQLPSAKESPDKFLEVCTWVDQIAALNDSHTRKTTSETVRAVL
DSLSEKKKSSP

SEQ ID NO: 22
MNTKYNKEFLLYLAGFVDADGSIYARIRPRQRRKFKHMLEFGFQVSQKTRRRWFLD
KLVDEIGVGYVRDRGRASDYRLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA

---

Sequence Listing

---

```
SSASSSPGSGISEALRAGAGSGTGYNKEFLLYLAGFVDGDGSIYAKITPHQKYKFKHQ
LHLRFVVSQKTQRRWFLDKLVDEIGVGYVSDNGSMSAYTLSQIKPLHNFLTQLQPFL
KLKQKQANLVLKIIEQLPSAKESPDKFLEVCTWVDQIAALNDSHTRKTTSETVRAVL
DSLSEKKKSSP

SEQ ID NO: 23
KEFLLYLAGFVDADGSIYACIRPRQSSKFKHTLELGFQVSQKTCRRWFLDKLVDEIG
VGYVRDRGRASDYRLSQIKPLHNFLTQLQPFLKLKQKQANLVLKIIEQLPSAKESPDK
FLEVCTWVDQIAALNDSKTRKTTSETVRAVLD

SEQ ID NO: 24
KEFLLYLAGFVDSDGSIYACIRPRQARKFKHTLELGFQVTQATCRRWFLDKLVDEIG
VGYVRDRGRASDYRLSEIKPLHNFLTQLQPFLKLKQKQANLVLKIIEQLPSAKESPDK
FLEVCTWVDQIAALNDSKTRKTTSETVRAVLD

SEQ ID NO: 25
KEFLLYLAGFVDADGSIYACIRPRQRRKFKHMLELGFQVSQKTCRRWFLDKLVDEIG
VGYVRDRGRASDYRLSEIKPLHNFLTQLQPFLKLKQKQANLVLKIIEQLPSAKESPDK
FLEVCTWVDQIAALNDSKTRKTTSETVRAVLD

SEQ ID NO: 26
KEFLLYLAGFVDADGSIYASIRPRQRRKFKHMLILGFQVSQKTCRRWFLDKLVDEIG
VGYVRDRGRASDYRLSEIKPLHNFLTQLQPFLKLKQKQANLVLKIIEQLPSAKESPDK
FLEVCTWVDQIAALNDSKTRKTTSETVRAVLD

SEQ ID NO: 27
KEFLLYLAGFVDSDGSIYATIRPRQRRKFKHMLELFFQVSQKTCRRWFLDKLVDEIG
VGYVRDRGRASDYRLSEIKPLHNFLTQLQPFLKLKQKQANLVLKIIEQLPSAKESPDK
FLEVCTWVDQIAALNDSKTRKTTSETVRAVLD

SEQ ID NO: 28
KEFLLYLAGFVDADGSIYARIRPRQRRKFKHMLEFGFQVSQKTRRRWFLDKLVDEIG
VGYVRDRGRASDYRLSEIKPLHNFLTQLQPFLKLKQKQANLVLKIIEQLPSAKESPDK
FLEVCTWVDQIAALNDSKTRKTTSETVRAVLD

SEQ ID NO: 29
KEFLLYLAGFVDGDGSIYAKITPHQKYKFKHQLTLRFAVSQKTQRRWELDKLVDEIG
VGYVSDNGSVSSYTLSQIKPLHNFLTQLQPFLKLKQKQANLVLKIIEQLPSAKESPDK
FLEVCTWVDQIAALNDSHTRKTTSETVRAVLD

SEQ ID NO: 30
KEFLLYLAGFVDGDGSIYAMIKPNQRYKFKHQLNLRFNVSQKTQRRWFLDKLVDEI
GVGYVSDNGSVSSYTLSQIKPLHNFLTQLQPFLKLKQKQANLVLKIIEQLPSAKESPD
KFLEVCTWVDQIAALNDSRTRKTTSETVRAVLD

SEQ ID NO: 31
KEFLLYLAGFVDGDGSIYAKITPHQKYKFKHQLTLRFVVSQKTQRRWFLDKLVDEIG
VGYVSDNGSVSSYTLSEIKPLHNFLTQLQPFLKLKQKQANLVLKIIEQLPSAKESPDKF
LEVCTWVDQIAALNDSKTRKTTSETVRAVLD

SEQ ID NO: 32
KEFLLYLAGFVDGDGSIYAKITPHQKYKFKHQLVLRFVVSQKTQRRWFLDKLVDEIG
VGYVSDNGSVSSYTLSQIKPLHNFLTQLQPFLKLKQKQANLVLKIIEQLPSAKESPDK
FLEVCTWVDQIAALNDSHTRKTTSETVRAVLD

SEQ ID NO: 33
KEFLLYLAGFVDGDGSIYAKITPHQKYKFKHQLHLRFVVSQKTQRRWFLDKLVDEIG
VGYVSDNGSMSAYTLSEIKPLHNFLTQLQPFLKLKQANLVLKIIEQLPSAKESPDK
FLEVCTWVDQIAALNDSHTRKTTSETVRAVLD

SEQ ID NO: 34
KEFLLYLAGFVDGDGSIYAKITPHQKYKFKHQLHLRFVVSQKTQRRWFLDKLVDEIG
VGYVSDNGSMSAYTLSQIKPLHNFLTQLQPFLKLKQKQANLVLKIIEQLPSAKESPDK
FLEVCTWVDQIAALNDSHTRKTTSETVRAVLD

SEQ ID NO: 35
ATGAATACAAAATATAATAAAGAGTTCTTACTCTACTTAGCAGGGTTTGTAGACT
CTGACGGTTCCATCTATGCCTGTATCAGGCCGAGGCAGGCGCGGAAGTTCAAGC
ACACGCTGGAGCTCGGGTTCCAGGTCACCCAGGCTACATGCCGCCGTTGGTTCCT
CGACAAGCTGGTGGACGAGATCGGTGTGGGTTACGTGAGGGACCGGGGCCGCGC
GTCCGACTACCGGCTGTCCGAGATCAAGCCTTTGCATAATTTTTTAACACAGCTA
CAACCTTTTCTAAAACTAAAACAAAAACAAGCAAATTTAGTTTTAAAAATTATTG
AACAACTTCCGTCAGCAAAAGAATCCCCGGACAAATTCTTAGAAGTTTGTACATG
GGTGGATCAAATTGCAGCTCTGAATGATTCGAAGACGCGTAAAACAACTTCTGA
AACCGTTCGTGCTGTGCTAGACAGTTTACCAGGATCCGTGGGAGGTCTATCGCCA
TCTCAGGCATCCAGCGCCGCATCCTCGGCTTCCTCAAGCCCGGGTTCAGGGATCT
CCGAAGCACTCAGAGCTGGAGCAGGTTCCGGCACTGGATACAACAAGGAATTCC
```

Sequence Listing

TGCTCTACCTGGCGGGCTTCGTCGACGGGGACGGCTCCATCTATGCCATGATCAA
GCCTAATCAAAGGTATAAGTTCAAGCACCAGCTGAATCTCAGGTTCAATGTCAGT
CAGAAGACACAGCGCCGTTGGTTCCTCGACAAGCTGGTGGACGAGATCGGTGTG
GGTTACGTGTCGGACAATGGCAGCGTCTCCTCGTACACGCTGTCCCAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCAGGACCCGCAAGACCACTTCCGAAACCGTCCGCGCCGTTCTAGACAGTCTC
TCCGAGAAGAAGAAGTCGTCCCCC

SEQ ID NO: 36
ATGAATACAAAATATAATAAAGAGTTCTTACTCTACTTAGCAGGGTTTGTAGACG
CTGACGGTTCCATCTATGCCTGTATCCGGCCGCGGCAGAGTAGTAAGTTCAAGCA
CACGCTGGAGCTCGGGTTCCAGGTCAGCCAGAAGACATGCCGCCGTTGGTTCCTC
GACAAGCTGGTGGACGAGATCGGTGTGGGTTACGTGAGGGACCGGGGCCGCGCG
TCCGACTACCGGCTGTCCCAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTAGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTATGCCAAGATCACG
CCTCATCAAAAGTATAAGTTCAAGCACCAGCTGACGCTCCGTTTCGCGGTCTCTC
AGAAGACACAGCGCCGTTGGTTCCTCGACAAGCTGGTGGACGAGATCGGTGTGG
GTTACGTGAGTGACAATGGCAGCGTCTCCTCGTACACTCTGTCCCAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCCACACCCGCAAGACCACTTCCGAAACCGTCCGCGCCGTTCTAGACAGTCTCT
CCGAGAAGAAGAAGTCGTCCCCC

SEQ ID NO: 37
ATGAATACAAAATATAATAAAGAGTTCTTACTCTACTTAGCAGGGTTTGTAGACG
CTGACGGTTCCATCTATGCCTGTATCCGGCCGCGGCAGAGGCGGAAGTTCAAGC
ACATGCTGGAGCTCGGTTTCCAGGTCAGCCAGAAGACATGCCGCCGTTGGTTCCT
CGACAAGCTGGTGGACGAGATCGGTGTGGGTTACGTGAGGGACCGGGGCCGCGC
GTCCGACTACCGGCTGTCCGAGATCAAGCCTTTGCATAATTTTTTAACACAACTA
CAACCTTTTCTAAAACTAAAACAAAAACAAGCAAATTTAGTTTTAAAAATTATTG
AACAACTTCCGTCAGCAAAAGAATCCCCGGACAAATTCTTAGAAGTTTGTACATG
GGTGGATCAAATTGCAGCTCTGAATGATTCGAAGACGCGTAAAACAACTTCTGA
AACCGTTCGTGCTGTGCTAGACAGTTTACCAGGATCCGTGGGAGGTCTATCGCCA
TCTCAGGCATCCAGCGCCGCATCCTCGGCTTCCTCAAGCCCGGGTTCAGGGATCT
CCGAAGCACTCAGAGCTGGAGCAGGTTCCGGCACTGGATACAACAAGGAATTCC
TGCTCTACCTGGCGGGCTTCGTCGACGGGGACGGCTCCATCTATGCCAAGATCAC
GCCTCATCAAAAGTATAAGTTCAAGCACCAGCTGACGCTCCGTTTCGTTGTCTCT
CAGAAGACACAGCGCCGTTGGTTCCTCGACAAGCTGGTGGACGAGATCGGTGTG
GGTTACGTGAGTGACAATGGCAGCGTCTCCTCGTACACTCTGTCCGAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCAAGACCCGCAAGACCACTTCCGAAACCGTCCGCGCCGTTCTAGACAGTCTC
TCCGAGAAGAAGAAGTCGTCCCCC

SEQ ID NO: 38
ATGAATACAAAATATAATAAAGAGTTCTTACTCTACTTAGCAGGGTTTGTAGACG
CTGACGGTTCCATCTATGCCTCTATCCGGCCGCGGCAGAGGCGGAAGTTCAAGCA
CATGCTGATTCTCGGTTTCCAGGTCAGCCAGAAGACATGCCGCCGTTGGTTCCTC
GACAAGCTGGTGGACGAGATCGGTGTGGGTTACGTGAGGGACCGGGGCCGCGCG
TCCGACTACCGGCTGTCCGAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTAGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTATGCCAAGATCACG
CCTCATCAAAAGTATAAGTTCAAGCACCAGCTGGTTCTCCGTTTCGTTGTCTCTCA
GAAGACACAGCGCCGTTGGTTCCTCGACAAGCTGGTGGACGAGATCGGTGTGGG
TTACGTGAGTGACAATGGCAGCGTCTCCAGTTACACTCTGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCCACACCCGCAAGACCACTTCCGAAACCGTCCGCGCCGTTCTAGACAGTCTCTC
CGAGAAGAAGAAGTCGTCCCCC

-continued

Sequence Listing

SEQ ID NO: 39
ATGAATACAAAATATAATAAAGAGTTCTTACTCTACTTAGCAGGGTTTGTAGACT
CTGACGGTTCCATCTATGCCACCATCCGGCCGCGGCAGAGGCGGAAGTTCAAGC
ACATGCTGGAGCTCTTTTTCCAGGTCAGCCAGAAGACATGCCGCCGTTGGTTCCT
CGACAAGCTGGTGGACGAGATCGGTGTGGGTTACGTGAGGGACCGGGGCCGCGC
GTCCGACTACCGGCTGTCCGAGATCAAGCCTTTGCATAATTTTTTAACACAACTA
CAACCTTTTCTAAAACTAAAACAAAAACAAGCAAATTTAGTTTTAAAAATTATTG
AACAACTTCCGTCAGCAAAAGAATCCCCGGACAAATTCTTAGAAGTTTGTACATG
GGTGGATCAAATTGCAGCTCTGAATGATTCGAAGACGCGTAAAACAACTTCTGA
AACCGTTCGTGCTGTGCTAGACAGTTTACCAGGATCCGTGGGAGGTCTATCGCCA
TCTCAGGCATCCAGCGCCGCATCCTCGGCTTCCTCAAGCCCGGGTTCAGGGATCT
CCGAAGCACTCAGAGCTGGAGCAGGTTCCGGCACTGGATACAACAAGGAATTCC
TGCTCTACCTGGCGGGCTTCGTCGACGGGGACGGCTCCATCTATGCCAAGATCAC
GCCTCATCAGAAGTACAAGTTCAAGCACCAGCTGCATCTCCGTTTCGTTGTCAGT
CAGAAGACACAGCGCCGTTGGTTCCTCGACAAGCTGGTGGACGAGATCGGTGTG
GGTTACGTGAGTGACAATGGCAGCATGTCCGCTTACACTCTGTCCGAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCCACACCCGCAAGACCACTTCCGAAACCGTCCGCGCCGTTCTAGACAGTCTC
TCCGAGAAGAAGAAGTCGTCCCCC

SEQ ID NO: 40
ATGAATACAAAATATAATAAAGAGTTCTTACTCTACTTAGCAGGGTTTGTAGACG
CTGACGGTTCCATCTATGCGAGGATTCGGCCGCGGCAGAGGCGGAAGTTCAAGC
ACATGCTGGAGTTTGGGTTTCAGGTCAGCCAGAAGACCCGCCGCCGTTGGTTCCT
CGACAAGCTGGTGGACGAGATCGGTGTGGGTTACGTGAGGGACCGGGGCCGCGC
GTCCGACTACCGGCTGTCCGAGATCAAGCCTTTGCATAATTTTTTAACACAACTA
CAACCTTTTCTAAAACTAAAACAAAAACAAGCAAATTTAGTTTTAAAAATTATTG
AACAACTTCCGTCAGCAAAAGAATCCCCGGACAAATTCTTAGAAGTTTGTACATG
GGTGGATCAAATTGCAGCTCTGAATGATTCGAAGACGCGTAAAACAACTTCTGA
AACCGTTCGTGCTGTGCTAGACAGTTTACCAGGATCCGTGGGAGGTCTATCGCCA
TCTCAGGCATCCAGCGCCGCATCCTCGGCTTCCTCAAGCCCGGGTTCAGGGATCT
CCGAAGCACTCAGAGCCGGAGCAGGTTCCGGCACTGGATACAACAAGGAATTCC
TGCTCTACCTGGCGGGCTTCGTCGACGGGGACGGCTCCATCTATGCCAAGATCAC
GCCTCATCAGAAGTACAAGTTCAAGCACCAGCTGCATCTCCGTTTCGTTGTCAGT
CAGAAGACACAGCGCCGTTGGTTCCTCGACAAGCTGGTGGACGAGATCGGTGTG
GGTTACGTGAGTGACAATGGCAGCATGTCCGCTTACACTCTGTCCCAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCCACACCCGCAAGACCACTTCCGAAACCGTCCGCGCCGTTCTAGACAGTCTC
TCCGAGAAGAAGAAGTCGTCCCCC

SEQ ID NO: 41
MNTKYNKEFLLYLAGFVDADGSIHAIIRPKQSYKFKHELMLRFTVTQKTKRRWFLD
KLVDEIGVGYVFDAGMTSHYCLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIFAAIHPCQRSKFKHE
LRLLFTVTQKTQRRWFLDKLVDEIGVGYVRDTGSVSEYTLSQIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 42
MNTKYNKEFLLYLAGFVDSDGSIFACIRPSQASKFKHRLELRFTVTQKTRRRWFLDK
LVDEIGVGYVFDGGSVSHYCLSEIKPLHNFLTQLQPFLKLKQKQANLVLKIIEQLPSA
KESPDKFLEVCTWADQIAALNDSKTRKTTSETVRAVLDSLPGSVGGLSPSQASSAAS
SASSSPGSGISEALRAGAGSGTGYNKEFLLYLAGFVDGDGSIFAAIHPCQRSKFKHEL
RLLFTVTQKTQRRWFLDKLVDEIGVGYVRDTGSVSEYTLSQIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 43
MNTKYNKEFLLYLAGFVDADGSIHAIIRPKQDYKFKHELMLRFVVSQKTKRRWFLD
KLVDEIGVGYVFDAGMTSHYCLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIFAAIHPCQRSKFKHE
LRLLFTVTQKTQRRWFLDKLVDEIGVGYVRDTGSVSHYTLSQIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 44
MNTKYNKEFLLYLAGFVDSDGSIHAIIRPKQDYKFKHELMLRFVVSQKTKRRWFLD
KLVDEIGVGYVFDGGMTSHYCLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIFAAIHPCQRSKFKHE

-continued

---

Sequence Listing

---

LRLLFTVTQKTQRRWFLDKLVDEIGVGYVRDAGSVSHYTLSQIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 45
MNTKYNKEFLLYLAGFVDADGSIHAIIRPKQDYKFKHELMLRFIVSQKTKRRWFLDK
LVDEIGVGYVFDGGMTSHYCLSEIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFAAIHPCQRSKFKHEL
RLLFTVTQKTQRRWFLDKLVDEIGVGYVRDAGSVSHYTLSQIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 46
MNTKYNKEFLLYLAGFVDADGSIHAIIRPKQDYKFKHELMLRFVVSQKTKRRWFLD
KLVDEIGVGYVFDGRGTSHYCLSEIKPLHNFLTQLQPFLKLKQKQANLVLKIIEQLPS
AKESPDKFLEVCTWVDQIAALNDSKARKTTSETVRAVLDSLPGSVGGLSPSQASSAA
SSASSSPGSGISEALRAGAGSGTGYNKEFLLYLAGFVDGDGSIFAAIHPCQRSKFKHE
LRLLFTVTQKTQRRWFLDKLVDEIGVGYVRDAGSVSHYTLSEIKPLHNFLTQLQPFL
KLKQKQANLVLKIIEQLPSAKESPDKFLEVCTWVDQIAALNDSRTRKTTSETVRAVL
DSLSEKKKSSP

SEQ ID NO: 47
KEFLLYLAGFVDADGSIHAIIRPKQSYKFKHELMLRFTVTQKTKRRWFLDKLVDEIG
VGYVFDAGMTSHYCLSQIKPLHNFLTQLQPFLKLKQKQANLVLKIIEQLPSAKESPDK
FLEVCTWVDQIAALNDSKTRKTTSETVRAVLD

SEQ ID NO: 48
KEFLLYLAGFVDSDGSIFACIRPSQASKFKHRLELRFTVTQKTRRRWFLDKLVDEIGV
GYVFDGGSVSHYCLSEIKPLHNFLTQLQPFLKLKQKQANLVLKIIEQLPSAKESPDKF
LEVCTWADQIAALNDSKTRKTTSETVRAVLD

SEQ ID NO: 49
KEFLLYLAGFVDADGSIHAIRPKQDYKFKHELMLRFVVSQKTKRRWFLDKLVDEIG
VGYVFDAGMTSHYCLSEIKPLHNFLTQLQPFLKLKQKQANLVLKIIEQLPSAKESPDK
FLEVCTWVDQIAALNDSKTRKTTSETVRAVLD

SEQ ID NO: 50
KEFLLYLAGFVDSDGSIHAIIRPKQDYKFKHELMLRFVVSQKTKRRWFLDKLVDEIG
VGYVFDGGMTSHYCLSEIKPLHNFLTQLQPFLKLKQKQANLVLKIIEQLPSAKESPDK
FLEVCTWVDQIAALNDSKTRKTTSETVRAVLD

SEQ ID NO: 51
KEFLLYLAGFVDADGSIHAIIRPKQDYKFKHELMLRFIVSQKTKRRWFLDKLVDEIGV
GYVFDGGMTSHYCLSEIKPLHNFLTQLQPFLKLKQKQANLVLKIIEQLPSAKESPDKF
LEVCTWVDQIAALNDSKTRKTTSETVRAVLD

SEQ ID NO: 52
KEFLLYLAGFVDADGSIHAIIRPKQDYKFKHELMLRFVVSQKTKRRWFLDKLVDEIG
VGYVFDGRGTSHYCLSEIKPLHNFLTQLQPFLKLKQKQANLVLKIIEQLPSAKESPDK
FLEVCTWVDQIAALNDSKARKTTSETVRAVLD

SEQ ID NO: 53
KEFLLYLAGFVDGDGSIFAAIHPCQRSKFKHELRLLFTVTQKTQRRWFLDKLVDEIG
VGYVRDTGSVSEYTLSQIKPLHNFLTQLQPFLKLKQKQANLVLKIIEQLPSAKESPDK
FLEVCTWVDQIAALNDSKTRKTTSETVRAVLD

SEQ ID NO: 54
KEFLLYLAGFVDGDGSIFAAIHPCQRSKFKHELRLLFTVTQKTQRRWFLDKLVDEIG
VGYVRDTGSVSEYTLSQIKPLHNFLTQLQPFLKLKQKQANLVLKIIEQLPSAKESPDK
FLEVCTWVDQIAALNDSKTRKTTSETVRAVLD

SEQ ID NO: 55
KEFLLYLAGFVDGDGSIFAAIHPCQRSKFKHELRLLFTVTQKTQRRWFLDKLVDEIG
VGYVRDTGSVSHYTLSQIKPLHNFLTQLQPFLKLKQKQANLVLKIIEQLPSAKESPDK
FLEVCTWVDQIAALNDSKTRKTTSETVRAVLD

SEQ ID NO: 56
KEFLLYLAGFVDGDGSIFAAIHPCQRSKFKHELRLLFTVTQKTQRRWFLDKLVDEIG
VGYVRDAGSVSHYTLSQIKPLHNFLTQLQPFLKLKQKQANLVLKHIEQLPSAKESPDK
FLEVCTWVDQIAALNDSKTRKTTSETVRAVLD

SEQ ID NO: 57
KEFLLYLAGFVDGDGSIFAAIHPCQRSKFKHELRLLFTVTQKTQRRWFLDKLVDEIG
VGYVRDAGSVSHYTLSQIKPLHNFLTQLQPFLKLKQKQANLVLKIIEQLPSAKESPDK
FLEVCTWVDQIAALNDSKTRKTTSETVRAVLD

Sequence Listing

SEQ ID NO: 58
KEFLLYLAGFVDGDGSIFAAIHPCQRSKFKHELRLLFTVTQKTQRRWFLDKLVDEIG
VGYVRDAGSVSHYTLSEIKPLHNFLTQLQPFLKLKQKQANLVLKIIEQLPSAKESPDK
FLEVCTWVDQIAALNDSRTRKTTSETVRAVLD

SEQ ID NO: 59
ATGAATACAAAATATAATAAAGAGTTCTTACTCTACTTAGCAGGGTTTGTAGACG
CTGACGGTTCCATCCATGCCATTATCCGGCCTAAGCAAAGTTATAAGTTCAAGCA
CGAGCTGATGCTCCGTTTCACCGTCACCCAGAAGACAAAGCGCCGTTGGTTCCTC
GACAAGCTGGTGGACGAGATCGGTGTGGGTTACGTGTTCGACGCGGGCATGACC
TCCCACTACTGCCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCCATC
CTTGTCAACGTAGTAAGTTCAAGCACGAGCTGCGTCTCTTGTTCACTGTCACGCA
GAAGACACAGCGCCGTTGGTTCCTCGACAAGCTGGTGGACGAGATCGGTGTGGG
TTACGTGCGGGACACTGGCAGCGTCTCCGAGTACACGCTGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCC

SEQ ID NO: 60
ATGAATACAAAATATAATAAAGAGTTCTTACTCTACTTAGCAGGGTTTGTAGACT
CTGACGGTTCCATCTTTGCCTGTATCCGTCCTTCGCAAGCTAGTAAGTTCAAGCA
CCGGCTGGAGCTCCGGTTCACGGTCACCCAGAAGACAAGGCGCCGTTGGTTCCTC
GACAAGCTGGTGGACGAGATCGGTGTGGGTTACGTGTTTGACGGTGGCAGCGTC
TCCCATTACTGCCTGTCCGAGATCAAGCCTTTGCATAATTTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
CGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCCTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCCATC
CTTGTCAACGTAGTAAGTTCAAGCACGAGCTGCGTCTCTTGTTCACTGTCACGCA
GAAGACACAGCGCCGTTGGTTCCTCGACAAGCTGGTGGACGAGATCGGTGTGGG
TTACGTGCGGGACACTGGCAGCGTCTCCGAGTACACGCTGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCC

SEQ ID NO: 61
ATGAATACAAAATATAATAAAGAGTTCTTACTCTACTTAGCAGGGTTTGTAGACG
CTGACGGTTCCATCCATGCCATTATCCGGCCTAAGCAGGACTACAAGTTCAAGCA
CGAGCTGATGCTCCGTTTCGTTGTCTCTCAGAAGACAAAGCGCCGTTGGTTCCTC
GACAAGCTGGTGGACGAGATCGGTGTGGGTTACGTGTTCGACGCTGGCATGACC
TCCCATTACTGCCTGTCCGAGATCAAGCCTTTGCATAATTTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCCATC
CTTGTCAACGTAGTAAGTTCAAGCACGAGCTGCGTCTTTTGTTCACTGTCACGCA
GAAGACACAGCGCCGTTGGTTCCTCGACAAGCTGGTGGACGAGATCGGTGTGGG
TTACGTGCGGGACACTGGCAGCGTCTCCCATTACACGCTGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCC

SEQ ID NO: 62
ATGAATACAAAATATAATAAAGAGTTCTTACTCTACTTAGCAGGGTTTGTAGACT
CTGACGGTTCCATCCATGCCATTATCCGGCCTAAGCAGGACTACAAGTTCAAGCA
CGAGCTGATGCTCCGTTTCGTTGTCAGTCAGAAGACAAAGCGCCGTTGGTTCCTC
GACAAGCTGGTGGACGAGATCGGTGTGGGTTACGTGTTCGACGGGGGCATGACC
TCCCATTACTGCCTGTCCGAGATCAAGCCTTTGCATAATTTTTTTAACACAACTACA

Sequence Listing

```
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCCATC
CTTGTCAACGTAGTAAGTTCAAGCACGAGCTGCGTCTCTTGTTCACGGTCACGCA
GAAGACACAGCGCCGTTGGTTCCTCGACAAGCTGGTGGACGAGATCGGTGTGGG
TTACGTGCGGGACGCTGGCAGCGTCTCCCATTACACGCTGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCC

SEQ ID NO: 63
ATGAATACAAAATATAATAAAGAGTTCTTACTCTACTTAGCAGGGTTTGTAGACG
CTGACGGTTCCATCCATGCCATTATCCGGCCTAAGCAGGACTACAAGTTCAAGCA
CGAGCTGATGCTCCGTTTCATTGTCTCTCAGAAGACAAAGCGCCGTTGGTTCCTC
GACAAGCTGGTGGACGAGATCGGTGTGGGTTACGTGTTCGACGGGGGCATGACC
TCCCATTACTGCCTGTCCGAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCCATC
CTTGTCAACGTAGTAAGTTCAAGCACGAGCTGCGTCTCTTGTTCACGGTCACGCA
GAAGACACAGCGCCGTTGGTTCCTCGACAAGCTGGTGGACGAGATCGGTGTGGG
TTACGTGCGGGACGCTGGCAGCGTCTCCCATTACACGCTGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCC

SEQ ID NO: 64
ATGAATACAAAATATAATAAAGAGTTCTTACTCTACTTAGCAGGGTTTGTAGACG
CTGACGGTTCCATCCATGCCATTATCCGGCCTAAGCAGGACTATAAGTTCAAGCA
CGAGCTGATGCTCCGTTTCGTGGTCAGTCAGAAGACAAAGCGCCGTTGGTTCCTC
GACAAGCTGGTGGACGAGATCGGTGTGGGTTACGTGTTCGACGGGAGGGGGACG
TCCCATTACTGCCTGTCCGAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGGCGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGGGGGCTTCGTCGACGGGGACGGCTCCATCTTTGCCGCTATCCATC
CTTGTCAACGTAGTAAGTTCAAGCACGAGCTGCGTCTCTTGTTCACGGTCACGCA
GAAGACACAGCGCCGTTGGTTCCTCGACAAGCTGGTGGACGAGATCGGTGTGGG
TTACGTGCGGGACGCTGGCAGCGTCTCCCATTACACGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAGGACCCGCAAGACCACTTCCGAAACCGTCCGCGCCGTTCTAGACAGTCTCTC
CGAGAAGAAGAAGTCGTCCCCC

SEQ ID NO: 65
MNTKYNKEFLLYLAGFVDADGSIYASITPDQARKFKHQLRLYFNVRQATKRRWFLD
KLVDEIGVGYVTDGGTVSTYILSQIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFAAITPDQTCKFKHTL
RLRFQVTQHTCRRWFLDKLVDEIGVGYVSDRGRASDYTLSQIKPLHNFLTQLQPFLK
LKQKQANLVLKIIEQLPSAKESPDKFLEVCTWVDQIAALNDSRTRKTTSETVRAVLD
SLSEKKKSSP

SEQ ID NO: 66
MNTKYNKEFLLYLAGFVDADGSIYASITPSQGRKFKHQLRLYFNVRQSTKRRWFLD
KLVDEIGVGYVTDKGSVSTYLLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSSASSSPGSGISEALRAGAGSGTGYNKEFLLYLAGFVDGDGSIFAAITPDQTCKFKHT
LRLRFQVTQKTCRRWFLDKLVDEIGVGYVSDRGRASDYTLSQIKPLHNFLTQLQPFL
KLKQKQANLVLKIIEQLPSAKESPDKFLEVCTWVDQIAALNDSRTRKTTSETVRAVL
DSLSEKKKSSP
```

Sequence Listing

SEQ ID NO: 67
MNTKYNKEFLLYLAGFVDADGSIYASIEPSQARKFKHQLRLRFNVRQATKRRWFLD
KLVDEIGVGYVIDEGTVSTYILSQIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFAAITPDQTCKFKHTL
RLRFQVTQHTCRRWFLDKLVDEIGVGYVSDRGRASDYTLSQIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 68
MNTKYNKEFLLYLAGFVDADGSIYASIEPSQARKFKHQLRLRFNVRQATKRRWFLD
KLVDEIGVGYVDDGTVSTYLLSQIKPLHNFLTQLQPFLKLKQKQANLVLKIIEQLPS
AKESPDKFLEVCTWVDQIAALNDSKTRKTTSETVRAVLDSLPGSVGGLSPSQAPSAA
SSASSSPGSGISEALRAGAGSGTGYNKEFLLYLAGFVDGDGSIFAAITPDQTCKFKHW
LRLRFQVTQHTCRRWFLDKLVDEIGVGYVTDRGRASDYTLSEIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 69
MNTKYNKEFLLYLAGFVDSDGSIYASIEPSQARKFKHQLRLRFNVRQATKRRWFLD
KLVDEIGVGYVDDGTVSTYMLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIFAAITPDQTCKFKHT
LRLRFRVTQHTCRRWFLDKLVDEIGVGYVSDRGRASDYTLSQIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 70
MNTKYNKEFLLYLAGFVDADGSIYASIEPSQARKFKHQLRLRFNVRQATKRRWFLD
KLVDEIGVGYVDDGTVSTYMLSQIKPLHNFLTQLQPFLKLKQKQANLVLKIIEQLPS
AKESPDKFLEVCTWVDQIAALNDSKTRKTTSETVRAVLDSLPGSVGGLSPSQAPSAA
SSASSSPGSGISEALRAGAGSGTGYNKEFLLYLAGFVDGDGSIFAAITPDQTCKFKHW
LRLRFRVTQHTCRRWFLDKLVDEIGVGYVSDRGRASDYTLSQIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 71
MNTKYNKEFLLYLAGFVDADGSIYASIEPSQARKFKHQLRLRFNVRQATKRRWFLD
KLVDEIGVGYVATGTVSTYMLSQIKPLHNFLTQLQPFLKLKQKQANLVLKIIEQLPS
AKESPDKFLEVCTWVDQIAALNDSKTRKTTSETVRAVLDSLPGSVGGLSPSQAFSAA
SSASSSPGSGISEALRAGAGSGTGYNKEFLLYLAGFVDGDGSIFAAIRPDQTCKFKHW
LQLYFRVTQHTCRRWFLDKLVDEIGVGYVSDRGRASDYTLSQIKPLHNFLTQLQPFL
KLKQKQANLVLKIIEQLPSAKESPDKFLEVCTWVDQIAALNDSHTRKTTSETVRAVL
DSLSEKKKSSP

SEQ ID NO: 72
KEFLLYLAGFVDADGSIYASITPDQARKFKHQLRLYFNVRQATKRRWFLDKLVDEIG
VGYVTDGGTVSTYILSQIKPLHNFLTQLQPFLKLKQKQANLVLKITEQLPSAKESPDKF
LEVCTWVDQIAALNDSKTRKTTSETVRAVLD

SEQ ID NO: 73
KEFLLYLAGFVDADGSIYASITPSQGRKFKHQLRLYFNVRQSTKRRWFLDKLVDEIG
VGYVTDKGSVSTYLLSQIKPLHNFLTQLQPFLKLKQKQANLVLKIIEQLPSAKESPDK
FLEVCTWVDQIAALNDSKTRKTTSETVRAVLD

SEQ ID NO: 74
KEFLLYLAGFVDADGSIYASIEPSQARKFKHQLRLRFNVRQATKRRWFLDKLVDEIG
VGYVIDEGTVSTYILSQIKPLHNFLTQLQPFLKLKQKQANLVLKIIEQLPSAKESPDKF
LEVCTWVDQIAALNDSKTRKTTSETVRAVLD

SEQ ID NO: 75
KEFLLYLAGFVDADGSIYASIEPSQARKFKHQLRLRFNVRQATKRRWFLDKLVDEIG
VGYVVDDGTVSTYLLSQIKPLHNFLTQLQPFLKLKQKQANLVLKIIEQLPSAKESPDK
FLEVCTWVDQIAALNDSKTRKTTSETVRAVLD

SEQ ID NO: 76
KEFLLYLAGFVDSDGSIYASIEPSQARKFKHQLRLRFNVRQATKRRWFLDKLVDEIG
VGYVVDDGTVSTYMLSQIKPLHNFLTQLQPFLKLKQKQANLVLKIIEQLPSAKESPD
KFLEVCTWVDQIAALNDSKTRKTTSETVRAVLD

SEQ ID NO: 77
KEFLLYLAGFVDADGSIYASIEPSQARKFKHQLRLRFNVRQATKRRWFLDKLVDEIG
VGYVVDDGTVSTYMLSQIKPLHNFLTQLQPFLKLKQKQANLVLKIIEQLPSAKESPD
KFLEVCTWVDQIAALNDSKTRKTTSETVRAVLD

Sequence Listing

```
SEQ ID NO: 78
KEFLLYLAGFVDADGSIYASIEPSQARKFKHQLRLRFNVRQATKRRWFLDKLVDEIG
VGYVVATGTVSTYMLSQIKPLHNFLTQLQPFLKLKQKQANLVLKIIEQLPSAKESPDK
FLEVCTWVDQIAALNDSKTRKTTSETVRAVLD

SEQ ID NO: 79
KEFLLYLAGFVDGDGSIFAAITPDQTCKFKHTLRLRFQVTQHTCRRWFLDKLVDEIG
VGYVSDRGRASDYTLSQIKPLHNFLTQLQPFLKLKQKQANLVLKIIEQLPSAKESPDK
FLEVCTWVDQIAALNDSRTRKTTSETVRAVLD

SEQ ID NO: 80
KEFLLYLAGFVDGDGSIFAAITPDQTCKFKHTLRLRFQVTQKTCRRWFLDKLVDEIG
VGYVSDRGRASDYTLSQIKPLHNFLTQLQPFLKLKQKQANLVLKIIEQLPSAKESPDK
FLEVCTWVDQIAALNDSRTRKTTSETVRAVLD

SEQ ID NO: 81
KEFLLYLAGFVDGDGSIFAAITPDQTCKFKHTLRLRFQVTQHTCRRWFLDKLVDEIG
VGYVSDRGRASDYTLSQIKPLHNFLTQLQPFLKLKQKQANLVLKIIBQLPSAKESPDK
FLEVCTWVDQIAALNDSKTRKTTSETVRAVLD

SEQ ID NO: 82
KEFLLYLAGFVDGDGSIFAAITPDQTCKFKHWLRLRFQVTQHTCRRWFLDKLVDEIG
VGYVTDRGRASDYTLSEIKPLHNFLTQLQPFLKLKQKQANLVLKIIEQLPSAKESPDK
FLEVCTWVDQIAALNDSKTRKTTSETVRAVLD

SEQ ID NO: 83
KEFLLYLAGFVDGDGSIFAAITPDQTCKFKHTLRLRFRVTQHTCRRWFLDKLVDEIG
VGYVSDRGRASDYTLSQIKPLHNFLTQLQPFLKLKQKQANLVLKIIEQLPSAKESPDK
FLEVCTWVDQIAALNDSKTRKTTSETVRAVLD

SEQ ID NO: 84
KEFLLYLAGFVDGDGSIFAAITPDQTCKFKHWLRLRFRVTQHTCRRWFLDKLVDEIG
VGYVSDRGRASDYTLSQIKPLHNFLTQLQPFLKLKQKQANLVLKIIEQLPSAKESPDK
FLEVCTWVDQIAALNDSKTRKTTSETVRAVLD

SEQ ID NO: 85
KEFLLYLAGFVDGDGSIFAAIRPDQTCKFKHWLQLYFRVTQHTCRRWFLDKLVDEIG
VGYVSDRGRASDYTLSQIKPLHNFLTQLQPFLKLKQKQANLVLKIIEQLPSAKESPDK
FLEVCTWVDQIAALNDSHTRKTTSETVRAVLD

SEQ ID NO: 86
ATGAATACAAAATATAATAAAGAGTTCTTACTCTACTTAGCAGGGTTTGTAGACG
CTGACGGTTCCATCTATGCCAGTATCACTCCTGATCAAGCGCGGAAGTTCAAGCA
CCAGCTGCGTCTCTATTTCAACGTCAGGCAGGCGACAAAGCGCCGTTGGTTCCTC
GACAAGCTGGTGGACGAGATCGGTGTGGGTTACGTGACGGACGGCGGCACCGTC
TCCACCTACATCCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTGGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCACGC
CGGATCAGACGTGTAAGTTCAAGCACACGCTGAGGCTCCGGTTCCAGGTCACGC
AGCACACATGCCGCCGTTGGTTCCTCGACAAGCTGGTGGACGAGATCGGTGTGG
GTTACGTGTCCGACAGGGGCCGCGCGTCCGACTACACCCTGTCCCAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAGGACCCGCAAGACCACTTCCGAAACCGTCCGCGCCGTTCTAGACAGTCTCT
CCGAGAAGAAGAAGTCGTCCCCC

SEQ ID NO: 87
ATGAATACAAAATATAATAAAGAGTTCTTACTCTACTTAGCAGGGTTTGTAGACG
CTGACGGTTCCATCTATGCCAGTATCACGCCTTCTCAAGGGCGTAAGTTCAAGCA
CCAGCTGCGGCTCTATTTCAACGTCAGGCAGTCGACAAAGCGCCGTTGGTTCCTC
GACAAGCTGGTGGACGAGATCGGTGTGGGTTACGTGACGGACAAGGGCAGCGTC
TCCACCTACCTCCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCACGC
CGGATCAGACGTGTAAGTTCAAGCACACGCTGAGGCTCCGGTTCCAGGTCACTC
AGAAGACATGTCGCCGTTGGTTCCTCGACAAGCTGGTGGACGAGATCGGTGTGG
```

-continued

Sequence Listing

```
GTTACGTGTCCGACAGGGGCCGCGCGTCCGACTACACCCTGTCCCAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAGGACCCGCAAGACCACTTCCGAAACCGTCCGCGCCGTTCTAGACAGTCTCT
CCGAGAAGAAGAAGTCGTCCCCC

SEQ ID NO: 88
ATGAATACAAAATATAATAAAGAGTTCTTACTCTACTTAGCAGGGTTTGTAGACG
CTGACGGTTCCATCTATGCCAGTATCGAGCCTTCCCAAGCGCGGAAGTTCAAGCA
CCAGCTGCGTCTCCGTTTCAACGTCAGGCAGGCGACAAAGCGCCGTTGGTTCCTC
GACAAGCTGGTGGACGAGATCGGTGTGGGTTACGTGATTGACGAGGGCACCGTC
TCCACCTACATCCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTGGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGGGGGCTTCGTCGACGGGGACGGCTCCATCTTTGCCGCTATCACGC
CGGATCAGACGTGTAAGTTCAAGCACACGCTGAGGCTCCGGTTCCAGGTCACGC
AGCACACATGCCGCCGTTGGTTCCTCGACAAGCTGGTGGACGAGATCGGTGTGG
GTTACGTGTCGGACAGGGGCCGCGCGTCCGACTACACCCTGTCCCAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCAAGACCCGCAAGACCACTTCCGAAACCGTCCGCGCCGTTCTAGACAGTCTC
TCCGAGAAGAAGAAGTCGTCCCCC

SEQ ID NO: 89
ATGAATACAAAATATAATAAAGAGTTCTTACTCTACTTAGCAGGGTTTGTAGACG
CTGACGGTTCCATCTATGCCAGTATCGAGCCTTCGCAAGCGCGGAAGTTCAAGCA
CCAGCTGCGTCTCCGTTTCAACGTCAGGCAGGCGACAAAGCGCCGTTGGTTCCTC
GACAAGCTGGTGGACGAGATCGGTGTGGGTTACGTGGTTGACGATGGCACCGTC
TCCACCTACTTGCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTGGACAGTTTACCAGGATCCGTGGGAGGTCTATCGCCATC
TCAGGCACCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCGCTATCACGC
CGGATCAGACGTGTAAGTTCAAGCACTGGCTGAGGCTCCGGTTCCAGGTCACGC
AGCACACATGCCGCCGTTGGTTCCTCGACAAGCTGGTGGACGAGATCGGTGTGG
GTTACGTGACGGACAGGGGCCGCGCGTCCGACTACACCCTGTCCCAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCAAGACCCGCAAGACCACTTCCGAAACCGTCCGCGCCGTTCTAGACAGTCTC
TCCGAGAAGAAGAAGTCGTCCCCC

SEQ ID NO: 90
ATGAATACAAAATATAATAAAGAGTTCTTACTCTACTTAGCAGGGTTTGTAGACT
CTGACGGTTCCATCTATGCCAGTATCGAGCCTTCGCAAGCGCGGAAGTTCAAGCA
CCAGCTGCGTCTCCGTTTCAACGTCAGGCAGGCGACAAAGCGCCGTTGGTTCCTC
GACAAGCTGGTGGACGAGATCGGTGTGGGTTACGTGGTGGACGATGGCACCGTC
TCCACCTACATGCTGTCCCAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTGGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTTTGCCGCTATCACG
CCGGATCAGACGTGTAAGTTCAAGCACACGCTGAGGCTCCGGTTCCGGGTCACG
CAGCACACATGCCGCCGTTGGTTCCTCGACAAGCTGGTGGACGAGATCGGTGTG
GGTTACGTGTCGGACAGGGGCCGCGCGTCCGACTACACCCTGTCCCAGATCAAG
CCTCTGCACAACTTCCTGACCCAGCTCCAGCCCTTCCTGAAGCTCAAGCAGAAGC
AGGCCAACCTCGTGCTGAAGATCATCGAGCAGCTGCCCTCCGCCAAGGAATCCC
CGGACAAGTTCCTGGAGGTGTGCACCTGGGTGGACCAGATCGCCGCTCTGAACG
ACTCCAAGACCCGCAAGACCACTTCCGAAACCGTCCGCGCCGTTCTAGACAGTCT
CTCCGAGAAGAAGAAGTCGTCCCCC

SEQ ID NO: 91
ATGAATACAAAATATAATAAAGAGTTCTTACTCTACTTAGCAGGGTTTGTAGACG
CTGACGGTTCCATCTATGCCAGTATCGAGCCTTCGCAAGCGCGGAAGTTCAAGCA
CCAGCTGCGTCTCCGTTTCAATGTCCGTCAGGCGACAAAGCGCCGTTGGTTCCTC
```

-continued

---
Sequence Listing
---

```
GACAAGCTGGTGGACGAGATCGGTGTGGGTTACGTGGTTGACGATGGCACCGTC
TCCACCTACATGCTGTCCCAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTGGACAGTTTACCAGGATCCGTGGGAGGTCTATCGCCAT
CTCAGGCACCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTTTGCCGCTATCACG
CCGGATCAGACGTGTAAGTTCAAGCACTGGCTGAGGCTCCGGTTCCGCGTCACGC
AGCACACATGCCGCCGTTGGTTCCTCGACAAGCTGGTGGACGAGATCGGTGTGG
GTTACGTGAGCGACAGGGGCCGCGCGTCCGACTACACCCTGTCCCAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCAAGACCCGCAAGACCACTTCCGAAACCGTCCGCGCCGTTCTAGACAGTCTC
TCCGAGAAGAAGAAGTCGTCCCCC

SEQ ID NO: 92
ATGAATACAAAATATAATAAAGAGTTCTTACTCTACTTAGCAGGGTTTGTAGACG
CTGACGGTTCCATCTATGCCAGTATCGAGCCTTCGCAAGCGCGGAAGTTCAAGCA
CCAGCTGCGTCTCCGTTTCAATGTCCGTCAGGCGACAAAGCGCCGTTGGTTCCTC
GACAAGCTGGTGGACGAGATCGGTGTGGGTTACGTGGTTGCGACTGGCACCGTC
TCCACCTACATGCTGTCCCAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTGGACAGTTTACCAGGATCCGTGGGAGGTCTATCGCCAT
CTCAGGCATTCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTTTGCCGCTATCAGG
CCGGATCAGACGTGTAAGTTCAAGCACTGGCTGCAGCTCTATTTCCGGGTCACGC
AGCACACATGCCGCCGTTGGTTCCTCGACAAGCTGGTGGACGAGATCGGTGTGG
GTTACGTGAGCGACAGGGGCCGCGCGTCCGACTACACCCTGTCCCAGATCAAGC
CTCTGCACAACTTCCTGACCCAGCTCCAGCCCTTCCTGAAGCTCAAGCAGAAGCA
GGCCAACCTCGTGCTGAAGATCATCGAGCAGCTGCCCTCCGCCAAGGAATCCCC
GGACAAGTTCCTGGAGGTGTGCACCTGGGTGGACCAGATCGCCGCTCTGAACGA
CTCCCACACCCGCAAGACCACTTCCGAAACCGTCCGCGCCGTTCTAGACAGTCTC
TCCGAGAAGAAGAAGTCGTCCCCC

SEQ ID NO: 93
MNTKYNKEFLLYLAGFVDSDGSIYARIVPSQTSKFKHKLRLVFAVAQSTCRRWFLDK
LVDEIGVGYVRDHGRASYYTLSEIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFATIVPQQDRKFKHAL
RLQFRVHQKTCRRWFLDKLVDEIGVGYVYDFGRASHYCLSEIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 94
MNTKYNKEFLLYLAGFVDSDGSIYARIVPSQTSKFKHKLRLTFAVTQKTCRRWFLDK
LVDEIGVGYVTDNGRASNYFLSQIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFATIVPQQDRKFKHAL
RLQFRVHQHTRRRWFLDKLVDEIGMGYVSDRGRASFYSLSQIKPLHNFLTQLQPFLK
LKQKQANLVLKIIEQLPSAKESPDKFLEVCTWVDQIAALNDSRTRKTTSETVRAVLD
SLSEKKKSSP

SEQ ID NO: 95
MNTKYNKEFLLYLAGFVDSDGSIYARIVPSQGSKFKHKLRLTFAVTQKTCRRWFLD
KLVDEIGVGYVIDNGRASNYFLSEIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFATIVPQQDRKFKHAL
RLNFRVHQHTRRRWFLDKLVDEIGMGYVSDRGRASFYHLSEIKPLHNFLTQLQPFLK
LKQKQANLVLKIIEQLPSAKESPDKFLEVCTWVDQIAALNDSRTRKTTSETVRAVLD
SLSEKKKSSP

SEQ ID NO: 96
MNTKYNKEFLLYLAGFVDADGSIFARIVPSQTRKFKHKLNLTFAVTQKTCRRWFLD
KLVDEIGVGYVIDNGRASNYFLSEIKPLHNFLTQLQPFLKLKQKQANLVLKIIEQLPSA
KESPDKFLEVCTWVDQIAALNDSKTRKTTSETVRAVLDSLPGSVGGLSPSQASGAAS
SASSSPGSGISEALRAGAGSGTGYNKEFLLYLAGFVDGDGSIFATIVPQQDRKFKHAL
RLNFRVHQHTRRRWFLDKLVDEIGVGYVSDGGRASFYHLSEIKPLHNFLTQLQPFLK
LKQKQANLVLKHIEQLPSAKESPDKFLEVCTWVDQIAALNDSKTRKTTSETVRAVLD
SLSEKKKSSP
```

-continued

Sequence Listing

SEQ ID NO: 97
MNTKYNKEFLLYLAGFVDSDGSIYARIVPSQHRKFKHKLQLTFAVTQKTCRRWFLD
KLVDEIGVGYVIDNGRASNYFLSEIKPLHNFLTQLQPFLKLKQKQADLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFATIVPQQDRKFKHAL
RLNFRVHQHTRRRWFLDKLVDEIGVGYVSDTGRASFYHLSQIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 98
MNTKYNKEFLLYLAGFVDADGSIFARIVPSQSRKFKHKLNLTFAVTQKTCRRWELD
KLVDEIGVGYVIDNGRASNYFLSQIKPLHNFLTQLQPFLKLKQKQANLVLKHIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIFATIVPQQDRKFKHA
LRLNFRVHQHTRRRWFLDKLVDEIGVGYVSDKGRASFYHLSQIKPLHNFLTQLQPFL
KLKQKQANLVLKIIEQLPSAKESPDKFLEVCTWVDQIAALNDSRTRKTTSETVRAVL
DSLSEKKKSSP

SEQ ID NO: 99
MNTKYNKEFLLYLAGFVDADGSIFARIVPEQGRKFKHKLQLTFAVTQKTCRRWFLD
KLVDEIGVGYVIDGGRASNYWLSEIKPLHNFLTQLQPFLKLKQKQANLVLKIIEQLPS
AKESPDKFLEVCTWVDQIAALNDSKTRKTTSETVRAVLDSLPGSVGGLSPSQASGAA
SSASSSPGSGISEALRAGAGSGTGYNKEFLLYLAGFVDGDGSIFATIVPQQDRKFKHA
LRLNFRLHQHTRRRWFLDKLVDEIGVGYVSDGGRASFYHLSEIKPLHNFLTQLQPFL
KLKQKQANLVLKIIEQLPSAKESPDKFLEVCTWVDQIAALNDSRTRKTTSETVRAVL
DSLSEKKKSSP

SEQ ID NO: 100
MNTKYNKEFLLYLAGFVDADGSIFARIVPEQGRKFKHKLQLTFAVTQKTCRRWFLD
KLVDEIGVGYVIDNGRASNYVLSQIKPLHNFLTQLQPFLKLKQKQANLVLKIIEQLPS
AKESPDKFLEVCTWVDQIAALNDSNTRKTTSETVRAVLDSLPGSVGGLSPSQASGAA
SSASSSPGSGTSEALRAGAGSGTGYNKEFLLYLAGFVDGDGSIFAQIVPQQDRKFKH
ALRLKFRLHQHTRRRWFLDKLVDEIGVGYVSDGGRASFYNLSQIKPLHNFLTQLQPF
LKLKQKQANLVLKIIEQLPSAKESPDKFLEVCTWVDQIAALNDSKTRKTTSETVRAV
LDSLSEKKKSSP

SEQ ID NO: 101
KEFLLYLAGFVDSDGSIYARIVPSQTSKFKHKLRLVFAVAQSTCRRWFLDKLVDEIG
VGYVRDHGRASYYTLSEIKPLHNFLTQLQPFLKLKQKQANLVLKIIEQLPSAKESPDK
FLEVCTWVDQIAALNDSKTRKTTSETVRAVLD

SEQ ID NO: 102
KEFLLYLAGFVDSDGSIYARIVPSQTSKFKHKLRLTFAVTQKTCRRWFLDKLVDEIGV
GYVTDNGRASNYFLSQIKPLHNFLTQLQPFLKLKQKQANLVLKIIEQLPSAKESPDKF
LEVCTWVDQIAALNDSKTRKTTSETVRAVLD

SEQ ID NO: 103
KEFLLYLAGFVDSDGSIYARIVPSQGSKFKHKLRLTFAVTQKTCRRWFLDKLVDEIG
VGYVIDNGRASNYFLSEIKPLHNFLTQLQPFLKLKQKQANLVLKIIEQLPSAKESPDKF
LEVCTWVDQIAALNDSKTRKTTSETVRAVLD

SEQ ID NO: 104
KEFLLYLAGFVDADGSIFARIVPSQTRKFKHKLNLTFAVTQKTCRRWFLDKLVDEIG
VGYVIDNGRASNYFLSEIKPLHNFLTQLQPFLKLKQKQANLVLKIIEQLPSAKESPDKF
LEVCTWVDQIAALNDSKTRKTTSETVRAVLD

SEQ ID NO: 105
KEFLLYLAGFVDSDGSIYARIVPSQHRKFKHKLQLTFAVTQKTCRRWFLDKLVDEIG
VGYVIDNGRASNYFLSEIKPLHNFLTQLQPFLKLKQKQADLVLKIIEQLPSAKESPDKF
LEVCTWVDQIAALNDSKTRKTTSETVRAVLD

SEQ ID NO: 106
KEFLLYLAGFVDADGSIFARIVPSQSRKFKHKLNLTFAVTQKTCRRWFLDKLVDEIG
VGYVIDNGRASNYFLSQIKPLHNFLTQLQPFLKLKQKQANLVLKIIEQLPSAKESPDK
FLEVCTWVDQIAALNDSKTRKTTSETVRAVLD

SEQ ID NO: 107
KEFLLYLAGFVDADGSIFARIVPEQGRKFKHKLQLTFAVTQKTCRRWFLDKLVDEIG
VGYVIDGGRASNYWLSEIKPLHNFLTQLQPFLKLKQKQANLVLKIIEQLPSAKESPDK
FLEVCTWVDQIAALNDSKTRKTTSETVRAVLD

SEQ ID NO: 108
KEFLLYLAGFVDADGSIFARIVPEQGRKFKHKLQLTFAVTQKTCRRWFLDKLVDEIG
VGYVIDNGRASNYVLSQIKPLHNFLTQLQPFLKLKQKQANLVLKIIEQLPSAKESPDK
FLEVCTWVDQIAALNDSNTRKTTSETVRAVLD

Sequence Listing

SEQ ID NO: 109
KEFLLYLAGFVDGDGSIFATIVPQQDRKFKHALRLQFRVHQKTCRRWFLDKLVDEIG
VGYVYDFGRASHYCLSEIKPLHNFLTQLQPFLKLKQKQANLVLKIIEQLPSAKESPDK
FLEVCTWVDQIAALNDSKTRKTTSETVRAVLD

SEQ ID NO: 110
KEFLLYLAGFVDGDGSIFATIVPQQDRKFKHALRLQFRVHQTRRRWFLDKLVDEIG
MGYVSDRGRASFYSLSQIKPLHNFLTQLQPFLKLKQKQANLVLKIIEQLPSAKESPDK
FLEVCTWVDQIAALNDSRTRKTTSETVRAVLD

SEQ ID NO: 111
KEFLLYLAGFVDGDGSIFATIVPQQDRKFKHALRLNFRVHQTRRRWFLDKLVDEIG
MGYVSDRGRASFYHLSEIKPLHNFLTQLQPFLKLKQKQANLVLKIIEQLPSAKESPDK
FLEVCTWVDQIAALNDSRTRKTTSETVRAVLD

SEQ ID NO: 112
KEFLLYLAGFVDGDGSIFATIVPQQDRKFKHALRLNFRVHQTRRRWFLDKLVDEIG
VGYVSDGGRASFYHLSEIKPLHNFLTQLQPFLKLKQKQANLVLKIIEQLPSAKESPDK
FLEVCTWVDQIAALNDSKTRKTTSETVRAVLD

SEQ ID NO: 113
KEFLLYLAGFVDGDGSIFATIVPQQDRKFKHALRLNFRVHQTRRRWFLDKLVDEIG
VGYVSDTGRASFYHLSQIKPLHNFLTQLQPFLKLKQKQANLVLKIIEQLPSAKESPDK
FLEVCTWVDQIAALNDSKTRKTTSETVRAVLD

SEQ ID NO: 114
KEFLLYLAGFVDGDGSIFATIVPQQDRKFKHALRLNFRVHQTRRRWFLDKLVDEIG
VGYVSDKGRASFYHLSQIKPLHNFLTQLQPFLKLKQKQANLVLKIIEQLPSAKESPDK
FLEVCTWVDQIAALNDSRTRKTTSETVRAVLD

SEQ ID NO: 115
KEFLLYLAGFVDGDGSIFATIVPQQDRKFKHALRLNFRLHQTRRRWFLDKLVDEIG
VGYVSDGGRASFYHLSEIKPLHNFLTQLQPFLKLKQKQANLVLKIIEQLPSAKESPDK
FLEVCTWVDQIAALNDSRTRKTTSETVRAVLD

SEQ ID NO: 116
KEFLLYLAGFVDGDGSIFAQIVPQQDRKFKHALRLKFRLHQTRRRWFLDKLVDEIG
VGYVSDGGRASFYNLSQIKPLHNFLTQLQPFLKLKQKQANLVLKIIEQLPSAKESPDK
FLEVCTWVDQIAALNDSKTRKTTSETVRAVLD

SEQ ID NO: 117
ATGAATACAAAATATAATAAAGAGTTCTTACTCTACTTAGCAGGGTTTGTAGACT
CTGACGGTTCCATCTATGCCCGGATCGTTCCGTCGCAGACTAGTAAGTTCAAGCA
CAAGCTGAGGCTCGTGTTCGCCGTCGCCCAGTCTACATGTCGCCGTTGGTTCCTC
GACAAGCTGGTGGACGAGATCGGTGTGGGTTACGTGCGGGACCACGGCCGCGCG
TCCTACTACACCCTGTCCGAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTAGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGGGCTGGAGCAGGTTCCGGCACTGGATACAACAAGGAATTCCT
GCTCTACCTGGCGGGCTTCGTCGACGGGGACGGCTCCATCTTTGCCACTATCGTT
CCGCAGCAGGATCGGAAGTTCAAGCACGCTCTGCGTCTCCAGTTCAGGGTCCACC
AGAAGACATGCCGCCGTTGGTTCCTCGACAAGCTGGTGGACGAGATCGGTGTGG
GTTACGTGTACGACTTCGGCCGCGCGTCCCACTACTGCCTGTCCGAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAAGACCCGCAAGACCACTTCCGAAACCGTCCGCGCCGTTCTAGACAGTCTCT
CCGAGAAGAAGAAGTCGTCCCCC

SEQ ID NO: 118
ATGAATACAAAATATAATAAAGAGTTCTTACTCTACTTAGCAGGGTTTGTAGACT
CTGACGGTTCCATCTATGCCCGGATCGTTCCGTCGCAGACTAGTAAGTTCAAGCA
CAAGCTGCGCCTCACCTTCGCCGTCACCCAGAAGACATGCCGCCGTTGGTTCCTC
GACAAGCTGGTGGACGAGATCGGTGTGGGTTACGTGACCGACAACGGCCGCGCG
TCCAACTACTTCCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCACTATCGTTC
CGCAGCAGGATCGGAAGTTCAAGCACGCTCTGCGTCTCCAGTTCAGGGTCCACC
AGCACACAAGGCGCCGTTGGTTCCTCGACAAGCTGGTGGACGAGATCGGTATGG

-continued

Sequence Listing

```
GTTACGTGTCCGACCGCGGCCGCGCGTCCTTCTACAGCCTGTCCCAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAGGACCCGCAAGACCACTTCCGAAACCGTCCGCGCCGTTCTAGACAGTCTCT
CCGAGAAGAAGAAGTCGTCCCCC
```

SEQ ID NO: 119
```
ATGAATACAAAATATAATAAAGAGTTCTTACTCTACTTAGCAGGGTTTGTAGACT
CTGACGGTTCCATCTATGCCCGGATCGTTCCGTCGCAGGGTAGTAAGTTCAAGCA
CAAGCTGCGTCTCACCTTCGCCGTCACCCAGAAGACATGCCGCCGTTGGTTCCTC
GACAAGCTGGTGGACGAGATCGGTGTGGGTTACGTGATTGACAACGGCCGCGCG
TCCAACTACTTTCTGTCCGAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCACTATCGTTC
CGCAGCAGGATCGGAAGTTCAAGCACGCTCTGCGTCTCAATTTCAGGGTCCACCA
GCACACAAGGCGCCGTTGGTTCCTCGACAAGCTGGTGGACGAGATCGGTATGGG
TTACGTGTCCGACCGCGGCCGCGCGTCCTTCTACCATCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAGGACCCGCAAGACCACTTCCGAAACCGTCCGCGCCGTTCTAGACAGTCTCTC
CGAGAAGAAGAAGTCGTCCCCC
```

SEQ ID NO: 120
```
ATGAATACAAAATATAATAAAGAGTTCTTACTCTACTTAGCAGGGTTTGTAGACG
CTGACGGTTCCATCTTTGCCCGGATCGTTCCGTCGCAGACTCGGAAGTTCAAGCA
CAAGCTGAATCTCACCTTCGCCGTCACCCAGAAGACATGCCGCCGTTGGTTCCTC
GACAAGCTGGTGGACGAGATCGGTGTGGGTTACGTGATTGACAACGGCCGCGCG
TCCAACTACTTTCTGTCCGAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCGGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGGGGGCTTCGTCGACGGGGACGGCTCCATCTTTGCCACTATCGTTC
CGCAGCAGGATCGGAAGTTCAAGCACGCTCTGCGTCTCAATTTCAGGGTCCACCA
GCACACAAGGCGCCGTTGGTTCCTCGACAAGCTGGTGGACGAGATCGGTGTGGG
TTACGTGTCCGACGGTGGCCGCGCGTCCTTTTACCATCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCC
```

SEQ ID NO: 121
```
ATGAATACAAAATATAATAAAGAGTTCTTACTCTACTTAGCAGGGTTTGTAGACT
CTGACGGTTCCATCTATGCCCGGATCGTTCCGTCGCAGCATCGGAAGTTCAAGCA
CAAGCTGCAGCTCACCTTCGCCGTCACCCAGAAGACATGCCGCCGTTGGTTCCTC
GACAAGCTGGTGGACGAGATCGGTGTGGGTTACGTGATTGACAACGGCCGCGCG
TCCAACTACTTTCTGTCCGAGATCAAGCCTTTGCATAATTTTTTAACACAACTACA
ACCTTTTCTAAAACTAAAACAAAAACAAGCAGATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCACTATCGTTC
CGCAGCAGGATCGGAAGTTCAAGCACGCTCTGCGTCTCAATTTCAGGGTCCACCA
GCACACAAGGCGCCGTTGGTTCCTCGACAAGCTGGTGGACGAGATCGGTGTGGG
TTACGTGTCCGACACTGGCCGCGCGTCCTTTTACCATCTGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCC
```

SEQ ID NO: 122
```
ATGAATACAAAATATAATAAAGAGTTCTTACTCTACTTAGCAGGGTTTGTAGACG
CTGACGGTTCCATCTTTGCCCGGATCGTTCCGTCGCAGAGTCGGAAGTTCAAGCA
CAAGCTGAATCTCACCTTCGCCGTCACCCAGAAGACATGCCGCCGTTGGTTCCTC
```

---

Sequence Listing

---

GACAAGCTGGTGGACGAGATCGGTGTGGGTTACGTGATTGACAACGGCCGCGCG
TCCAACTACTTTCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCCACTATCGTTC
CGCAGCAGGATCGGAAGTTCAAGCACGCTCTGCGTCTCAATTTCAGGGTCCACCA
GCACACAAGGCGCCGTTGGTTCCTCGACAAGCTGGTGGACGAGATCGGTGTGGG
TTACGTGTCCGACAAGGGCCGCGCGTCCTTTTACCATCGTCCCAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAGGACCCGCAAGACCACTTCCGAAACCGTCCGCGCCGTTCTAGACAGTCTCTC
CGAGAAGAAGAAGTCGTCCCCC

SEQ ID NO: 123
ATGAATACAAAATATAATAAAGAGTTCTTACTCTACTTAGCAGGGTTTGTAGACG
CTGACGGTTCCATCTTTGCCCGGATCGTTCCGGAGCAGGGTAGGAAGTTCAAGCA
CAAGCTGCAGCTCACCTTCGCCGTCACCCAGAAGACATGCCGCCGTTGGTTCCTC
GACAAGCTGGTGGACGAGATCGGTGTGGGTTACGTGATTGACGGGGGCCGCGCG
TCCAACTACTGGCTGTCCGAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTAGACAGTTTACCAGGATCCGTGGGAGGTCTATCGCCAT
CTCAGGCATCCGGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTTTGCCACTATCGTT
CCGCAGCAGGATCGGAAGTTCAAGCACGCTCTGCGTCTCAATTTCAGGCTCCACC
AGCACACAAGGCGCCGTTGGTTCCTCGACAAGCTGGTGGACGAGATCGGTGTGG
GTTACGTGTCCGACGGTGGCCGCGCGTCCTTTTACCATCGTCCGAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAGGACCCGCAAGACCACTTCCGAAACCGTCCGCGCCGTTCTAGACAGTCTCT
CCGAGAAGAAGAAGTCGTCCCCC

SEQ ID NO: 124
ATGAATACAAAATATAATAAAGAGTTCTTACTCTACTTAGCAGGGTTTGTAGACG
CTGACGGTTCCATCTTTGCCCGGATCGTTCCGGAGCAGGGTAGGAAGTTCAAGCA
CAAGCTGCAGCTCACCTTCGCCGTCACCCAGAAGACATGCCGCCGTTGGTTCCTC
GACAAGCTGGTGGACGAGATCGGTGTGGGTTACGTGATTGACAATGGCCGCGCG
TCCAACTACGTGCTGTCCCAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAATACGCGTAAAACAACTTCTGAA
ACCGTTCGTGCTGTGCTAGACAGTTTACCAGGATCCGTGGGAGGTCTATCGCCAT
CTCAGGCATCCGGCGCCGCATCCTCGGCTTCCTCAAGCCCGGGTTCAGGGACCTC
CGAAGCACTCAGAGCTGGAGCAGGTTCCGGCACTGGATACAACAAGGAATTCCT
GCTCTACCTGGGGGCTTCGTCGACGGGGACGGCTCCATCTTTGCCCAGATCGTT
CCGCAGCAGGATCGGAAGTTCAAGCACGCTCTGCGTCTCAAGTTCAGGCTCCACC
AGCACACAAGGCGCCGTTGGTTCCTCGACAAGCTGGTGGACGAGATCGGTGTGG
GTTACGTGTCCGACGGTGGCCGCGCGTCCTTTTACAATCGTCCCAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAAGACCCGCAAGACCACTTCCGAAACCGTCCGCGCCGTTCTAGACAGTCTCT
CCGAGAAGAAGAAGTCGTCCCCC

SEQ ID NO: 125
ATGCCGTCTTCTGTCTCGTGGGGCATCCTCCTGCTGGCAGGCCTGTGCTGCCTGGT
CCCTGTCTCCCTGGCTGAGGATCCCCAGGGAGATGCTGCCCAGAAGACAGATAC
ATCCCACCATGATCAGGATCACCCAACCTTCAACAAGATCACCCCCAACCTGGCT
GAGTTCGCCTTCAGCCTATACCGCCAGCTGGCACACCAGTCCAACAGCACCAATA
TCTTCTTCTCCCCAGTGAGCATCGCTACAGCCTTTGCAATGCTCTCCCTGGGGACC
AAGGCTGACACTCACGATGAAATCCTGGAGGGCCTGAATTTCAACCTCACGGAG
ATTCCGGAGGCTCAGATCCATGAAGGCTTCCAGGAACTCCTCCGTACCCTCAACC
AGCCAGACAGCCAGCTCCAGCTGACCACCGGCAATGGCCTGTTCCTCAGCGAGG
GCCTGAAGCTAGTGGATAAGTTTTTGGAGGATGTTAAAAAGTTGTACCACTCAGA
AGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGA
CAGAGACACAGTTTTTGCTCTGGTGAATTACATCTTCTTTAAAGGCAAATGGGAG
AGACCCTTTGAAGTCAAGGACACCGAGGAAGAGGACTTCCACGTGGACCAGGTG
ACCACCGTGAAGGTGCCTATGATGAAGCGTTTAGGCATGTTTAACATCCAGCACT

```
GTAAGAAGCTGTCCAGCTGGGTGCTGCTGATGAAATACCTGGGCAATGCCACCG
CCATCTTCTTCCTGCCTGATGAGGGGAAACTACAGCACCTGGAAAATGAACTCAC
CCACGATATCATCACCAAGTTCCTGGAAAATGAAGACAGAAGGTCTGCCAGCTT
ACATTTACCCAAACTGTCCATTACTGGAACCTATGATCTGAAGAGCGTCCTGGGT
CAACTGGGCATCACTAAGGTCTTCAGCAATGGGGCTGACCTCTCCGGGGTCACA
GAGGAGGCACCCCTGAAGCTCTCCAAGGCCGTGCATAAGGCTGTGCTGACCATC
GACGAGAAAGGGACTGAAGCTGCTGGGGCCATGTTTTTAGAGGCCATACCCATG
TCTATCCCCCCCGAGGTCAAGTTCAACAAACCCTTTGTCTTCTTAATGATTGAAC
AAAATACCAAGTCTCCCCTCTTCATGGGAAAGTGGTGAATCCCACCCAAAAT
AA

SEQ ID NO: 126
ATGCCGTCTTCTGTCTCGTGGGGCATCCTCCTGCTGGCAGGCCTGTGCTGCCTGGT
CCCTGTCTCCCTGGCTGAGGATCCCCAGGGAGATGCTGCCCAGAAGACAGATAC
ATCCCACCATGATCAGGATCACCCAACCTTCAACAAGATCACCCCCAACCTGGCT
GAGTTCGCCTTCAGCCTATACCGCCAGCTGGCACACCAGTCCAACAGCACCAATA
TCTTCTTCTCCCCAGTGAGCATCGCTACAGCCTTTGCAATGCTCTCCCTGGGGACC
AAGGCTGACACTCACGATGAAATCCTGGAGGGCCTGAATTTCAACCTCACGGAG
ATTCCGGAGGCTCAGATCCATGAAGGCTTCCAGGAACTCCTCCGTACCCTCAACC
AGCCAGACAGCCAGCTCCAGCTGACCACCGGCAATGGCCTGTTCCTCAGCGAGG
GCCTGAAGCTAGTGGATAAGTTTTTGGAGGATGTTAAAAAGTTGTACCACTCAGA
AGCCTTCACTGTCAACTTCGGGGCACCGAAGAGGCCAAGAAACAGATCAACGA
TTACGTGGAGAAGGGTACTCAAGGGAAATTGTGGATTTGGTCAAGGAGCTTGA
CAGAGACACAGTTTTTGCTCTGGTGAATTACATCTTCTTTAAAGGTAAGGTTGCT
CAACCAGCCTGAGCTGTTCCCATAGAAACAAGCAAAAATATTCTCAAACCATCA
GTTCTTGAACTCTCCTTGGCAATGCATTATGGGCCATAGCAATGCTTTTCAGCGT
GGATTCTTCAGTTTTCTACACACAAACACTAAAATGTTTTCCATCATTGAGTAATT
TGAGGAAATAATAGATTAAACTGTCAAAACTACTGACAGCTCTGCAGAACTTTTC
AGAGCCTTTAATGTCCTTGTGTATACTGTATATGTAGAATATATAATGCTTAGAA
CTATAGAACAAATTGTAATACACTGCATAAAGGGATAGTTTCATGGAACATACTT
TACACGACTCTAGTGTCCCAGAATCAGTATCAGTTTTGCAATCTGAAAGACCTGG
GTTCAAATCCTGCCTCTAACACAATTAGCTTTTGACAAAAACAATGCATTCTACC
TCTTTGAGGTGCTAATTTCTCATCTTAGCATGGACAAAATACCATTCTTGCTGTCA
GGTTTTTTTAGGATTAAACAAATGACAAAGACTGTGGGGATGGTGTGTGGCATAC
AGCAGGTGATGGACTCTTCTGTATCTCAGGCTGCCTTCCTGCCCCTGAGGGGTTA
AAATGCCAGGGTCCTGGGGGCCCCAGGGCATTCTAAGCCAGCTCCCACTGTCCC
AGGAAAACAGCATAGGGGAGGGGAGGTGGGAGGCAAGGCCAGGGGCTGCTTCC
TCCACTCTGAGGCTCCCTTGCTCTTGAGGCAAAGGAGGGCAGTGGAGAGCAGCC
AGGCTGCAGTCAGCACAGCTAAAGTCCTGGCTCTGCTGTGGCCTTAGTGGGGGCC
CAGGTCCCTCTCCAGCCCCAGTCTCCTCCTTCTGTCCAATGAGAAAGCTGGGATC
AGGGGTCCCTGAGGCCCCTGTCCACTCTGCATGCCTCGATGGTGAAGCTCTGTTG
GTATGGCAGAGGGGAGGCTGCTCAGGCATCTGCATTTCCCCTGCCAATCTAGAG
GATGAGGAAAGCTCTCAGGAATAGTAAGCAGAATGTTTGCCCTGGATGAATAAC
TGAGCTGCCAATTAACAAGGGGCAGGGAGCCTTAGACAGAAGGTACCAAATATG
CCTGATGCTCCAACATTTTATTTGTAATATCCAAGCACCCTCAAATAAACATAT
GATTCCAATAAAAATGCACAGCCACGATGGCATCTCTTAGCCTGACATCGCCACG
ATGTAGAAATTCTGCATCTTCCTCTAGTTTTGAATTATCCCCACACAATCTTTTTC
GGCAGCTTGGATGGTCAGTTTCAGCACCTTTTACAGATGATGAAGCTGAGCCTCG
AGGGATGTGTGTCGTCAAGGGGGCTCAGGGCTTCTCAGGGAGGGGACTCATGGT
TTCTTTATTCTGCTACACTCTTCCAAACCTTCACTCACCCCTGGTGATGCCCACCT
TCCCCTCTCTCCAGGCAAATGGGAGAGACCCTTTGAAGTCAAGGACACCGAGGA
AGAGGACTTCCACGTGGACCAGGTGACCACCGTGAAGGTGCCTATGATGAAGCG
TTTAGGCATGTTTAACATCCAGCACTGTAAGAAGCTGTCCAGCTGGGTGCTGCTG
ATGAAATACCTGGGCAATGCCACCGCCATCTTCTTCCTGCCTGATGAGGGGAAAC
TACAGCACCTGGAAAATGAACTCACCCACGATATCATCACCAAGTTCCTGGAAA
ATGAAGACAGAAGGTGATTCCCCAACCTGAGGGTGACCAAGAAGCTGCCCACAC
CTCTTAGCCATGTTGGGACTGAGGCCCATCAGGACTGGCCAGAGGGCTGAGGAG
GGTGAACCCACATCCCTGGGTCACTGCTACTCTGTATAAACTTGGCTTCCAGAA
TGAGGCCACCACTGAGTTCAGGCAGCGCCATCCATGCTCATGAGGAGGACAGT
ACCCAGGGGTGAGGAGGTAAAGGTCTCGTCCCTGGGGACTTCCCACTCCAGTGT
GGACACTGTCCCTTCCCAATATCCAGTGCCCAGGGCAGGGACAGCAGCACCACC
ACACGTTCTGGCAGAACCAAAAAGGAACAGATGGGCTTCCTGGCAAAGGCAGCA
GTGGAGTGTGGAGTTCAAGGGTAGAATGTCCCTGGGGGGACGGGGGAAGAGCCT
GTGTGGCAAGGCCCAGAAAAGCAAGGTTCGGAATTGGAACAGCCAGGCCATGTT
CGCAGAAGGCTTGCGTTTCTCTGTCACTTTATCGGTGCTGTTAGATTGGGTGTCCT
GTAGTAAGTGATACTTAAACATGAGCCACACATTAGTGTATGTGTGTGCATTCGT
GATTATGCCCATGCCCTGCTGATCTAGTTCGTTTTGTACACTGTAAAACCAAGAT
GAAAATACAAAAGGTGTCGGGTTCATAATAGGAATCGAGGCTGGAATTTCTCTG
TTCCATGCCAGCACCTCCTGAGGTCTCTGCTCCAGGGGTTGAGAAAGAACAAAG
AGGCTGAGAGGGTAACGGATCAGAGAGCCCAGAGCCAAGCTGCCCGCTCACACC
AGACCCTGCTCAGGGTGGCATTGTCTCCCCATGGAAAACCAGAGAGGGAGCACTC
AGCCTGGTGTGGTCACTCTTCTCTTATCCACTAAACGGTTGTCACTGGGCACTGC
CACCAGCCCCGTGTTTCTCTGGGTGTAGGGCCCTGGGGATGTTACAGGCTGGGGG
CCAGGTGACCCAACACTACAGGGCAAGATGAGACAGGCTTCCAGGACACCTAGA
ATATCAGAGGAGGTGGCATTTCAAGCTTTTGTGATTCATTCGATGTTAACATTCTT
TGACTCAATGTAGAAGAGCTAAAAGTAGAACAAACCAAAGCCGAGTTCCCATCT
TAGTGTGGGTGGAGGACACAGGAGTAAGTGGCAGAAATAATCAGAAAAGAAAA
```

Sequence Listing

```
CACTTGCACTGTGGTGGGTCCCAGAAGAACAAGAGGAATGCTGTGCCATGCCTT
GAATTTCTTTTCTGCACGACAGGTCTGCCAGCTTACATTTACCCAAACTGTCCATT
ACTGGAACCTATGATCTGAAGAGCGTCCTGGGTCAACTGGGCATCACTAAGGTCT
TCAGCAATGGGGCTGACCTCTCCGGGGTCACAGAGGAGGCACCCCTGAAGCTCT
CCAAGGTGAGATCACCCTGACGACCTTGTTGCACCCTGGTATCTGTAGGGAAGA
ATGTGTGGGGGCTGCAGCTCTGTCCTGAGGCTGAGGAAGGGGCCGAGGGAAACA
AATGAAGACCCAGGCTGAGCTCCTGAAGATGCCCGTGATTCACTGACACGGGAC
GTGGTCAAACAGCAAAGCCAGGCAGGGGACTGCTGTGCAGCTGGCACTTTCGGG
GCCTCCCTTGAGGTTGTGTCACTGACCCTGAATTTCAACTTTGCCCAAGACCTTCT
AGACATTGGGCCTTGATTTATCCATACTGACACAGAAAGGTTTGGGCTAAGTTGT
TTCAAAGGAATTTCTGACTCCTTCGATCTGTGAGATTTGGTGTCTGAATTAATGA
ATGATTTCAGCTAAAGATGACACTTATTTTGGAAAACTAAAGGCGACCAATGAA
CAACTGCAGTTCCATGAATGGCTGCATTATCTTGGGGTCTGGGCACTGTGAAGGT
CACTGCCAGGGTCCGTGTCCTCAAGGAGCTTCAAGCCGTGTACTAGAAAGGAGA
GAGCCCTGGAGGCAGACGTGGAGTGACGATGCTCTTCCCTGTTCTGAGTTGTGGG
TGCACCTGAGCAGGGGGAGAGGCGCTTGTCAGGAAGATGGACAGAGGGGAGCC
AGCCCCATCAGCCAAAGCCTTGAGGAGGAGCAAGGCCTATGTGACAGGGAGGG
AGAGGATGTGCAGGGCCAGGGCCGTCCAGGGGGAGTGAGCGCTTCCTGGGAGGT
GTCCACGTGAGCCTTGCTCGAGGCCTGGGATCAGCCTTACAACGTGTCTCTGCTT
CTCTCCCCTCCAGGCCGTGCATAAGGCTGTGCTGACCATCGACGAGAAAGGGAC
TGAAGCTGCTGGGGCCATGTTTTTAGAGGCCATACCCATGTCTATCCCCCCCGAG
GTCAAGTTCAACAAACCCTTTGTCTTCTTAATGATTGAACAAAATACCAAGTCTC
CCCTCTTCATGGGAAAAGTGGTGAATCCCACCCAAAAATAA

SEQ ID NO: 127
TGGGCAGGAACTGGGCACTGTGCCCAGGGCATGCACTGCCTCCACGCAGCAACC
CTCAGAGTCCTGAGCTGAACCAAGAAGGAGGAGGGGGTCGGGCCTCCGAGGAA
GGCCTAGCCGCTGCTGCTGCCAGGAATTCCAGGTTGGAGGGGCGGCAACCTCCT
GCCAGCCTTCAGGCCACTCTCCTGTGCCTGCCAGAAGAGACAGAGCTTGAGGAG
AGCTTGAGGAGAGCAGGAAAGGTGGGACATTGCTGCTGCTGCTCACTCAGTTCC
ACAGGTGGGAGGGACAGCAGGGCTTAGAGTGGGGGTCATTGTGCAGATGGGAA
AACAAAGGCCCAGAGAGGGGAAGAAATGCCCAGGAGCTACCGAGGGCAGGCGA
CCTCAACCACAGCCCAGTGCTGGAGCTGTGAGTGGATGTAGAGCAGCGGAATAT
CCATTCAGCCAGCTCAGGGGAAGGACAGGGGCCCTGAAGCCAGGGGATGGAGCT
GCAGGGAAGGGAGCTCAGAGAGAAGGGGAGGGGAGTCTGAGCTCAGTTTCCCG
CTGCCTGAAAGGAGGGTGGTACCTACTCCCTTCACAGGGTAACTGAATGAGAGA
CTGCCTGGAGGAAAGCTCTTCAAGTGTGGCCCACCCCACCCCAGTGACACCAGC
CCCTGACACGGGGGAGGGAGGGCAGCATCAGGAGGGGCTTTCTGGGCACACCCA
GTACCCGTCTCTGAGCTTTCCTTGAACTGTTGCATTTTAATCCTCACAGCAGCTCA
ACAAGGTACATACCGTCACCATCCCCATTTTACAGATAGGGAAATTGAGGCTCG
GAGCGGTTAAACAACTCACCTGAGGCCTCACAGCCAGTAAGTGGGTTCCCTGGT
CTGAATGTGTGTGCTGGAGGATCCTGTGGGTCACTCGCCTGGTAGAGCCCCAAGG
TGGAGGCATAAATGGGACTGGTGAATGACAGAAGGGGCAAAAATGCACTCATCC
ATTCACTCTGCAAGTATCTACGGCACGTACGCCAGCTCCCAAGCAGGTTTGCGGG
TTGCACAGCGGGCGATGCAATCTGATTTAGGCTTTTAAAGGGATTGCAATCAAGT
GGGGCCCCACTAGCCTCAACCCTGTACCTCCCCTCCCCTCCACCCCCAGCAGTCT
CCAAAGGCCTCCAACAACCCCAGAGTGGGGGCCATGTATCCAAAGAAACTCCAA
GCTGTATACGGATCACACTGGTTTTCCAGGAGCAAAAACAGAAACAGGCCTGAG
GCTGGTCAAAATTGAACCTCCTCCTGCTCTGAGCAGCCTGGGGGGCAGACTAAG
CAGAGGGCTGTGCAGACCCACATAAAGAGCCTACTGTGTGCCAGGCACTTCACC
CGAGGCACTTCACAAGCATGCTTGGGAATGAAACTTCCAACTCTTTGGGATGCAG
GTGAAACAGTTCCTGGTTCAGAGAGGTGAAGCGGCCTGCCTGAGGCAGCACAGC
TCTTCTTTACAGATGTGCTTCCCCACCTCTACCCTGTCTCACGGCCCCCCATGCCA
GCCTGACGGTTGTGTCTGCCTCAGTCATGCTCCATTTTTCCATCGGGACCATCAA
GAGGGTGTTTGTGTCTAAGGCTGACTGGGTAACTTTGGATGAGCGGTCTCTCCGC
TCTGAGCCTGTTTCCTCATCTGTCAAATGGGCTCTAACCCACTCTGATCTCCCAGG
GCGGCAGTAAGTCTTCAGCATCAGGCATTTTGGGGTGACTCAGTAAATGGTAGAT
CTTGCTACCAGTGGAACAGCCACTAAGGATTCTGCAGTGAGAGCAGAGGGCCAG
CTAAGTGGTACTCTCCCAGAGACTGTCTGACTCACGCCACCCCCTCCACCTTGGA
CACAGGACGCTGTGGTTTCTGAGCCAGGTACAATGACTCCTTTCGGTAAGTGCAG
TGGAAGCTGTACACTGCCCAGGCAAAGCGTCCGGGCAGCGTAGGCGGGCGACTC
AGATCCCAGCCAGTGGACTTAGCCCCTGTTTGCTCCTCCGATAACTGGGGTGACC
TTGGTTAATATTCACCAGCAGCCTCCCCCGTTGCCCCTCTGGATCCACTGCTTAAA
TACGGACGAGGACAGGGCCCTGTCTCCTCAGCTTCAGGCACCACCACTGACCTG
GGACAGTGAATCGTAAGTATGCCTTTCACTGCGAGAGGTTCTGGAGAGGCTTCTG
AGCTCCCCATGGCCCAGGCAGGCAGCAGGTCTGGGGCAGGAGGGGGGTTGTGGA
GTGGGTATCCGCCTGCTGAGGTGCAGGGCAGATGGAGAGGCTGCAGCTGAGCTC
CTATTTTCATAATAACAGCAGCCATGAGGGTTGTGTCCTGTTTCCCAGTCCTGCCC
GGTCCCCCCTCGGTACCTCCTGGTGGATACACTGGTTCCTGTAAGCAGAAGTGGA
TGAGGGTGTCTAGGTCTGCAGTCCTGGCACCCCAGGATGGGGGACACCAGCCAA
GATACAGCAACAGCAACAAAGCGCAGCCATTTCTTTCTGTTTTGCACAGCTCCTCT
GTCTGTCGGGGGCTCCTGTCTGTTGTCTCCTATAAGCCTCACCACCTCTCCTACTG
CTTGGGCATGCATCTTTCTCCCCTTCTATAGATGAGGAGGTTAAGGTCCAGAGAG
GGGTGGGGAGGAACGCCGGCTCACATTCTCCATCCCCTCCAGATATGACCAGGA
ACAGACCTGTGCCAGGCCTCAGCCTTACATCAAAATGGGCCTCCCCATGCACCGT
GGACCTCTGGGCCTCCTGTCCCAGTGGAGGACAGGAAGCTGTGAGGGGCACTG
TCACCCAGGGCTCAAGCTGGCATTCCTGAATAATCGCTCTGCACCAGGCCACGGC
```

-continued

Sequence Listing

```
TAAGCTCAGTGCGTGATTAAGCCTCATAACCCTCCAAGGCAGTTACTAGTGTGAT
TCCCATTTTACAGATGAGGAAGATGGGGACAGAGAGGTGAATAACTGGCCCCAA
ATCACACACCATCCATAATTCGGGCTCAGGCACCTGGCTCCAGTCCCCAAACTCT
TGAACCTGGCCCTAGTGTCACTGTTTCTCTTGGGTCTCAGGCGCTGGATGGGGAA
CAGGAAACCTGGGCTGGACTTGAGGCCTCTCTGATGCTCGGTGACTTCAGACAGT
TGCTCAACCTCTCTGTTCTCTTGGGCAAAACATGATAACCTTTGACTTCTGTCCCC
TCCCCTCACCCCACCCGACCTTGATCTCTGAAGTGTTGGAAGGATTTAATTTTTCC
TGCACTGAGTTTTGGAGACAGGTCAAAAAGATGACCAAGGCCAAGGTGGCCAGT
TTCCTATAGAACGCCTCTAAAAGACCTGCAGCAATAGCAGCAAGAACTGGTATT
CTCGAGAACTTGCTGCGCAGCAGGCACTTCTTGGCATTTTATGTGTATTTAATTTC
ACAATAGCTCTATGACAAAGTCCACCTTTCTCATCTCCAGGAAACTGAGGTTCAG
AGAGGTTAAGTAACTTGTCCAAGGTCACACAGCTAATAGCAAGTTGACGTGGAG
CAATCTGGCCTCAGAGCCTTTAATTTTAGCCACAGACTGATGCTCCCCTCTTCATT
TAGCCAGGCTGCCTCTGAAGTTTTCTGATTCAAGACTTCTGGCTTCAGCTTTGTAC
ACAGAGATGATTCAATGTCAGGTTTTGGAGTGAAATCTGTTTAATCCCAGACAAA
ACATTTAGGATTACATCTCAGTTTTGTAAGCAAGTAGCTCTGTGATTTTTAGTGAG
TTATTTAATGCTCTTTGGGGCTCAATTTTTCTATCTATAAAATAGGGCTAATAATT
TGCACCTTATAGGGTAAGCTTTGAGGACAGATTAGATGATACGGTGCCTGTAAAA
CACCAGGTGTTAGTAAGTGTGGCAATGATGGTGACGCTGAGGCTGATGTTTGCTT
AGCATAGGGTTAGGCAGCTGGCAGGCAGTAAACAGTTGGATAATTTAATGGAAA
ATTTGCCAAACTCAGATGCTGTTCACTGCTGAGCAGGAGCCCCTTCCTGCTGAAA
TGGTCCTGGGGAGTGCAGCAGGCTCTCCGGGAAGAAATCTACCATCTCTCGGGC
AGGAGCTCAACCTGTGTGCAGGTACAGGGAGGGCTTCCTCACCTGGTGCCCACTC
ATGCATTACGTCAGTTATTCCTCATCCCTGTCCAAAGGATTCTTTTCTCCATTGTA
CAGCTATGAAGCTAGTGCTCAAAGAAGTGAAGTCATTTACCCCAGGCCCCTGCC
AGTAAGTGACAGGGCCTGGTCACACTTGGGTTTATTTATTGCCCAGTTCAACAGG
TTGTTTGACCATAGGCGAGATTCTCTTCCCTGCACCCTGCCGGGTTGCTCTTGGTC
CCTTATTTTATGCTCCCGGGTAGAAATGGTGTGAGATTAGGCAGGGAGTGGCTCG
CTTCCCTGTCCCTGGCCCCGCAAAGAGTGCTCCCACCTGCCCCGATCCCAGAAAT
GTCACCATGAAGCCTTCATTCTTTTGGTTTAAAGCTTGGCCTCAGTGTCCGTACAC
CATGGGGTACTTGGCCAGATGGCGACTTTCTCCTCTCCAGTCGCCCTCCCAGGCA
CTAGCTTTTAGGAGTGCAGGGTGCTGCCTCTGATAGAAGGGCCAGGAGAGGAGCA
GGTTTTGGAGTCCTGATGTTATAAGGAACAGCTTGGGAGGCATAATGAACCCAA
CATGATGCTTGAGACCAATGTCACAGCCCAATTCTGACATTCATCATCTGAGATC
TGAGGACACAGCTGTCTCAGTTCATGATCTGAGTGCTGGGAAAGCCAAGACTTGT
TCCAGCTTTGTCACTGACTTGCTGTATAGCCTCAACAAGGCCCTGACCCTCTCTG
GGCTTCAAACTCTTCACTGTGAAAGGAGGAAACCAGAGTAGGTGATGTGACACC
AGGAAAGATGGATGGGTGTGGGGGAATGTGCTCCTCCCAGCTGTCACCCCCTCG
CCACCCTCCCTGCACCAGCCTCTCCACCTCCTTTGAGCCCAGAATTCCCCTGTCTA
GGAGGGCACCTGTCTCATGCCTAGCCATGGGAATTCTCCATCTGTTTTGCTACAT
TGAACCCAGATGCCATTCTAACCAAGAATCCTGGCTGGGTGCAGGGGCTCTCGCC
TGTAACCCCAGCACTTTGGGAGGCCAAGGCAGGCGGATCAAGAGGTCAGGAGTT
CAAGACCTGCCTGGCCAACACGGTGAAACCTCAGCTCTACTAAAAATACAAAAA
TTAGCCAGGCGTGGTGGCACACGCCTGTAATCCCAGCTATTTGGGAAGCTGAGA
CAGAAGAATTTCTTGAACCCGGGAGGTGGAGGTTTCAGTGAGCCGAGATCACGC
CACTGCACTCCACCCTGGCAGATAAAGCGAGACTCTGTCTCAAAAAAAAACCCAA
AAACCTATGTTAGTGTACAGAGGGCCCCAGTGAAGTCTTCTCCCAGCCCCACTTT
GCACAACTGGGGAGAGTGAGGCCCCAGGACCAGAGGATTCTTGCTAAAGGCCAA
GTGGATAGTGATGGCCCTGCCAGGGCTAGAAGCCACAACCTCTGGCCCTGAGGC
CACTCAGCATATTTAGTGTCCCCACCCTGCAGAGGCCCAACTCCCTCCTGACCAC
TGAGCCCTGTAATGATGGGGGAATTTCCATAAGCCATGAAGGACTGCACAAAGT
TCAGTTGGGAAGTGAAAGAGAAATTAAAGGGAGATGGAAATATACAGCACTAAT
TTTAGCACCGTCTTTAGTTCTAACAACACTAGCTAGCTGAAGAAAAATACAAACA
TGTATTATGTAATGTGTGGTCTGTTCCATTTGGATTACTTAGAGGCACGAGGGCC
AGGAGAAAGGTGGTGGAGAGAAACCAGCTTTGCACTTCATTTGTTGCTTTATTGG
AAGGAAACTTTTAAAAGTCCAAGGGGGTTGAAGAATCTCAATATTTGTTATTTCC
AGCTTTTTTTCTCCAGTTTTTCATTTCCCAAATTCAAGGACACCTTTTTTCTTTGTAT
TTTGTTAAGATGATGGTTTTGGTTTTGTGACTAGTAGTTAACAATGTGGCTGCCGG
GCATATTCTCCTCAGCTAGGACCTCAGTTTTCCCATCTGTGAAGACGGCAGGTTC
TACCTAGGGGGCTGCAGGCTGGTGGTCCGAAGCCTGGGCATATCTGGAGTAGAA
GGATCACTGTGGGGCAGGGCAGGTTCTGTGTTGCTGTGGATGACGTTGACTTTGA
CCATTGCTCGGCAGAGCCTGCTCTCGCTGGTTCAGCCACAGGCCCCACCACTCCC
TATTGTCTCAGCCCCGGGTATGAAACATGTATTCCTCACTGGCCTATCACCTGAA
GCCTTTGAATTTGCAACACCTGCCAACCCCTCCCTCAAAAGAGTTGCCCTCTCAG
ATCCTTTTGATGTAAGGTTTGGTGTTGAGACTTATTTCACTAAATTCTCATACATA
AACATCACTTTATGTATGAGGCAAAATGAGGACCAGGGAGATGAATGACTTGTC
CTGGCTCATACACCTGGAAAGTGACAGAGTCAGATTAGATCCCAGGTCTATCTGA
AGTTAAAAGAGGTGTCTTTTCACTTCCCACCTCCTCCATCTACTTTAAAGCAGCA
CAAACCCCTGCTTTCAAGGAGAGATGAGCGTCTCTAAAGCCCCTGACAGCAAGA
GCCCAGAACTGGGACACCATTAGTGACCCAGACGGCAGGTAAGCTGACTGCAGG
AGCATCAGCCTATTCTTGTGTCTGGGACCACAGAGCATTGTGGGGACAGCCCCGT
CTCTTGGGAAAAAAACCCTAAGGGCTGAGGATCCTTGTGAGTGTTGGGTGGGAA
CAGCTCCCAGGAGGTTTAATCACAGCCCCTCCATGCTCTCTAGCTGTTGCCATTG
TGCAAGATGCATTTCCCTTCTGTGCAGCAGTTTCCCTGGCCACTAAATAGTGGGA
TTAGATAGAAGCCCTCCAAGGGCTTCCAGCTTGACATGATTCTTGATTCTGATCT
GGCCCGATTCCTGGATAATCGTGGGCAGGCCCATTCCTCTTCTTGTGCCTCATTTT
CTTCTTTTGTAAAACAATGGCTGTACCATTTGCATCTTAGGGTCATTGCAGATGTA
```

```
AGTGTTGCTGTCCAGAGCCTGGGTGCAGGACCTAGATGTAGGATTCTGGTTCTGC
TACTTCCTCAGTGACATTGAATAGCTGACCTAATCTCTCTGGCTTTGGTTTCTTCA
TCTGTAAAAGAAGGATATTAGCATTAGCACCTCACGGGATTGTTACAAGAAAGC
AATGAATTAACACATGTGAGCACGGAGAACAGTGCTTGGCATATGGTAAGCACT
ACGTACATTTTGCTATTCTTCTGATTCTTTCAGTGTTACTGATGTCGGCAAGTACT
TGGCACAGGCTGGTTTAATAATCCCTAGGCACTTCCACGTGGTGTCAATCCCTGA
TCACTGGGAGTCATCATGTGCCTTGACTCGGGGCCTGGCCCCCCCCATCTCTGTCTT
GCAGGACAATGCCGTCTTCTGTCTCGTGGGGCATCCTCCTGCTGGCAGGCCTGTG
CTGCCTGGTCCCTGTCTCCCTGGCTGAGGATCCCCAGGGAGATGCTGCCCAGAAG
ACAGATACATCCCACCATGATCAGGATCACCCAACCTTCAACAAGATCACCCCC
AACCTGGCTGAGTTCGCCTTCAGCCTATACCGCCAGCTGGCACACCAGTCCAACA
GCACCAATATCTTCTTCTCCCCAGTGAGCATCGCTACAGCCTTTGCAATGCTCTCC
CTGGGGACCAAGGCTGACACTCACGATGAAATCCTGGAGGGCCTGAATTTCAAC
CTCACGGAGATTCCGGAGGCTCAGATCCATGAAGGCTTCCAGGAACTCCTCCGTA
CCCTCAACCAGCCAGACAGCCAGCTCCAGCTGACCACCGGCAATGGCCTGTTCCT
CAGCGAGGGCCTGAAGCTAGTGGATAAGTTTTTGGAGGATGTTAAAAAGTTGTA
CCACTCAGAAGCCTTCACTGTCAACTTCGGGGGACACCGAAGAGGCCAAGAAACA
GATCAACGATTACGTGGAGAAGGGTACTCAAGGGAAAATTGTGGATTTGGTCAA
GGAGCTTGACAGAGACACAGTTTTTGCTCTGGTGAATTACATCTTCTTTAAAGGC
AAATGGGAGAGACCCTTTGAAGTCAAGGACACCGAGGAAGAGGACTTCCACGTG
GACCAGGTGACCACCGTGAAGGTGCCTATGATGAAGCGTTTAGGCATGTTTAAC
ATCCAGCACTGTAAGAAGCTGTCCAGCTGGGTGCTGCTGATGAAATACCTGGGC
AATGCCACCGCCATCTTCTTCCTGCCTGATGAGGGGAAACTACAGCACCTGGAAA
ATGAACTCACCCACGATATCATCACCAAGTTCCTGGAAAATGAAGACAGAAGGT
CTGCCAGCTTACATTTACCCAAACTGTCCATTACTGGAACCTATGATCTGAAGAG
CGTCCTGGGTCAACTGGGCATCACTAAGGTCTTCAGCAATGGGGCTGACCTCTCC
GGGGTCACAGAGGAGGCACCCCTGAAGCTCTCCAAGGCCGTGCATAAGGCTGTG
CTGACCATCGACGAGAAAGGGACTGAAGCTGCTGGGGCCATGTTTTTAGAGGCC
ATACCCATGTCTATCCCCCCCGAGGTCAAGTTCAACAAACCCTTTGTCTTCTTAAT
GATTGAACAAAATACCAAGTCTCCCCTCTTCATGGGAAAAGTGGTGAATCCCACC
CAAAAATAA
```

SEQ ID NO: 128
MAPKKKRKVH

SEQ ID NO: 129
GCTGGACTGGTATTTGTGTCTG

SEQ ID NO: 130
CGACCTGACCATAAACACAGAC

SEQ ID NO: 131
TATCCAGTCCAAGCTGTATACGGATCACACTG

SEQ ID NO: 132
ATGCACCTCCAAGCTGTATACGGATCACACTG

SEQ ID NO: 133
CAGTTCCACCAAGCTGTATACGGATCACACTG

SEQ ID NO: 134
TCTCGCCTCCAAGCTGTATACGGATCACACTG

SEQ ID NO: 135
GTGGTTCCTGAACCAGGAACTGTTTCACCTGCATC

SEQ ID NO: 136
CGAACTTCTGAACCAGGAACTGTTTCACCTGCATC

SEQ ID NO: 137
AGGAATGGTGAACCAGGAACTGTTTCACCTGCATC

SEQ ID NO: 138
GTTAGGAATGAACCAGGAACTGTTTCACCTGCATC

SEQ ID NO: 139
CGTTGAGGTGAACCAGGAACTGTTTCACCTGCATC

SEQ ID NO: 140
CTCCCAAATGAACCAGGAACTGTTTCACCTGCATC

SEQ ID NO: 141
GACATTTCTGAACCAGGAACTGTTTCACCTGCATC

SEQ ID NO: 142
TGAGAGATTGAACCAGGAACTGITTCACCTGCATC

-continued

| Sequence Listing |
| --- |

SEQ ID NO: 143
TATCCAGTCTCTTGAACCTGGCCCTAGTGTC

SEQ ID NO: 144
ATGCACCTCTCTTGAACCTGGCCCTAGTGTC

SEQ ID NO: 145
CAGTTCCACTCTTGAACCTGGCCCTAGTGTC

SEQ ID NO: 146
TCTCGCCTCTCTTGAACCTGGCCCTAGTGTC

SEQ ID NO: 147
GTGGTTCCAAATTAAATCCTTCCAACACTTCAGAGATCAAGGTC

SEQ ID NO: 148
CGAACTTCAAATTAAATCCTTCCAACACTTCAGAGATCAAGGTC

SEQ ID NO: 149
AGGAATGGAAATTAAATCCTTCCAACACTTCAGAGATCAAGGTC

SEQ ID NO: 150
GTTAGGAAAAATTAAATCCTTCCAACACTTCAGAGATCAAGGTC

SEQ ID NO: 151
CGTTGAGGAAATTAAATCCTTCCAACACTTCAGAGATCAAGGTC

SEQ ID NO: 152
CTCCCAAAAAATTAAATCCTTCCAACACTTCAGAGATCAAGGTC

SEQ ID NO: 153
GACATTTCAAATTAAATCCTTCCAACACTTCAGAGATCAAGGTC

SEQ ID NO: 154
TGAGAGATAAATTAAATCCTTCCAACACTTCAGAGATCAAGGTC

SEQ ID NO: 155
TATCCAGTCTCCATTGTACAGCTATGAAGCTAGTG

SEQ ID NO: 156
ATGCACCTCTCCATTGTACAGCTATGAAGCTAGTG

SEQ ID NO: 157
CAGTTCCACTCCATTGTACAGCTATGAAGCTAGTG

SEQ ID NO: 158
TCTCGCCTCTCCATTGTACAGCTATGAAGCTAGTG

SEQ ID NO: 159
GTGGTTCCGGGAGCATAAAATAAGGGACCAAGAGC

SEQ ID NO: 160
CGAACTTCGGGAGCATAAAATAAGGGACCAAGAGC

SEQ ID NO: 161
AGGAATGGGGGAGCATAAAATAAGGGACCAAGAGC

SEQ ID NO: 162
GTTAGGAAGGGAGCATAAAATAAGGGACCAAGAGC

SEQ ID NO: 163
CGTTGAGGGGGAGCATAAAATAAGGGACCAAGAGC

SEQ ID NO: 164
CTCCCAAAGGGAGCATAAAATAAGGGACCAAGAGC

SEQ ID NO: 165
GACATTTCGGGAGCATAAAATAAGGGACCAAGAGC

SEQ ID NO: 166
TGAGAGATGGGAGCATAAAATAAGGGACCAAGAGC

SEQ ID NO: 167
TATCCAGTTGGCAGATAAAGCGAGACTCTGTC

SEQ ID NO: 168
ATGCACCTTGGCAGATAAAGCGAGACTCTGTC

-continued

Sequence Listing

SEQ ID NO: 169
CAGTTCCATGGCAGATAAAGCGAGACTCTGTC

SEQ ID NO: 170
TCTCGCCTTGGCAGATAAAGCGAGACTCTGTC

SEQ ID NO: 171
GCCGAATGTGGCAGATAAAGCGAGACTCTGTC

SEQ ID NO: 172
TACTGCAGTGGCAGATAAAGCGAGACTCTGTC

SEQ ID NO: 173
CATGTTGATGGCAGATAAAGCGAGACTCTGTC

SEQ ID NO: 174
ATAGAGTCTGGCAGATAAAGCGAGACTCTGTC

SEQ ID NO: 175
TCACGCTCTGGCAGATAAAGCGAGACTCTGTC

SEQ ID NO: 176
GTGGTTCCGGGCCAGAGGTTGTGGCTTCTAG

SEQ ID NO: 177
CGAACTTCGGGCCAGAGGTTGTGGCTTCTAG

SEQ ID NO: 178
AGGAATGGGGGCCAGAGGTTGTGGCTTCTAG

SEQ ID NO: 179
GTTAGGAAGGGCCAGAGGTTGTGGCTTCTAG

SEQ ID NO: 180
CGTTGAGGGGGCCAGAGGTTGTGGCTTCTAG

SEQ ID NO: 181
CTCCCAAAGGGCCAGAGGTTGTGGCTTCTAG

SEQ ID NO: 182
GACATTTCGGGCCAGAGGTTGTGGCTTCTAG

SEQ ID NO: 183
TGAGAGATGGGCCAGAGGTTGTGGCTTCTAG

SEQ ID NO: 184
TATCCAGTGCTGACTGCAGGAGCATCAGC

SEQ ID NO: 185
GTGGTTCCACAGAAGGGAAATGCATCTTGCAC

SEQ ID NO: 186
CGAACTTACAGAAGGGAAATGCATCTTGCAC

SEQ ID NO: 187
AGGAATGGACAGAAGGGAAATGCATCTTGCAC

SEQ ID NO: 188
GTTAGGAAACAGAAGGGAAATGCATCTTGCAC

SEQ ID NO: 189
CGTTGAGGACAGAAGGGAAATGCATCTTGCAC

SEQ ID NO: 190
CTCCCAAAACAGAAGGGAAATGCATCTTGCAC

SEQ ID NO: 191
GACATTTCACAGAAGGGAAATGCATCTTGCAC

SEQ ID NO: 192
TGAGAGATACAGAAGGGAAATGCATCTTGCAC

SEQ ID NO: 193
TATCCAGTAGGCCCATTCCTCTTCTTGTGC

-continued

| Sequence Listing |
| --- |

SEQ ID NO: 194
ATGCACCTAGGCCCATTCCTCTTCTTGTGC

SEQ ID NO: 195
CAGTTCCAAGGCCCATTCCTCTTCTTGTGC

SEQ ID NO: 196
TCTCGCCTAGGCCCATTCCTCTTCTTGTGC

SEQ ID NO: 197
GTGGTTCCCAATCCCGTGAGGTGCTAATGC

SEQ ID NO: 198
CGAACTTCAATCCCGTGAGGTGCTAATGC

SEQ ID NO: 199
AGGAATGGCAATCCCGTGAGGTGCTAATGC

SEQ ID NO: 200
GTTAGGAACAATCCCGTGAGGTGCTAATGC

SEQ ID NO: 201
CGTTGAGGCAATCCCGTGAGGTGCTAATGC

SEQ ID NO: 202
CTCCCAAACAATCCCGTGAGGTGCTAATGC

SEQ ID NO: 203
GACATTTCCAATCCCGTGAGGTGCTAATGC

SEQ ID NO: 204
TGAGAGATCAATCCCGTGAGGTGCTAATGC

SEQ ID NO: 205
CTGCTCAGGCATCTGCATTTCCC

SEQ ID NO: 206
ATGCCTCGATGGTGAAG

SEQ ID NO: 207
GGCAAACATTCTGCTTACTATT

SEQ ID NO: 208
CCTCGCTGGACTGGTATTTGTGTCT

SBQ ID NO: 209
GACAGGATGGCTTCCCTTC

SEQ ID NO: 210
GTCTAACTGCCATGTCTGGAT

SEQ ID NO: 211
ACCTTAGTGATGCCCAGTTGACCC

SEQ ID NO: 212
CCACAACTAGAATGCAGTGAA

SEQ ID NO: 213
GAATCACGGGCATCTTCAG

SEQ ID NO: 214
CTGCCCGCTCACACCAGAC

SEQ ID NO: 215
AGCACCTCCTGAGGTC

SEQ ID NO: 216
CACACCAGGCTGAGTG

SEQ ID NO: 217
TGGACAAACCACAACTAGAA

SEQ ID NO: 218
AGCCTGGCTAAATGAAGAG

SEQ ID NO: 219
AGCAAGTTGACGTGGAGCAATCTG

-continued

| Sequence Listing |
| --- |

SEQ ID NO: 220
TGGACAAACCACAACTAGAA

SEQ ID NO: 221
CTCCCAAGCTGTTCCTTAT

SEQ ID NO: 222
AGGGTGCTGCCTCTGATAGAAGG

SEQ ID NO: 223
TGGACAAACCACAACTAGAA

SEQ ID NO: 224
CCACAGTGATCCTTCTACTC

SEQ ID NO: 225
TCTGTGAAGACGGCAGGTTCTACC

SEQ ID NO: 226
TGGACAAACCACAACTAGAA

SEQ ID NO: 227
CGTGAGGTGCTAATGCTAATA

SEQ ID NO: 228
AGCTGACCTAATCTCTCTGGCTTTGG

SEQ ID NO: 229
TGGACAAACCACAACTAGAA

SEQ ID NO: 230
CTGCAAGACAGAGATGGG

SEQ ID NO: 231
AGTCATCATGTGCCTTGACTCGG

SEQ ID NO: 232
GAGAGAACGCACCACTTTAC

SEQ ID NO: 233
AGCCTGGCTAAATGAAGAG

SEQ ID NO: 234
AGCAAGTTGACGTGGAGCAATCTG

SEQ ID NO: 235
GAGAGAACGCACCACTTTAC

SEQ ID NO: 236
CTCCCAAGCTGTTCCTTAT

SEQ ID NO: 237
AGGGTGCTGCCTCTGATAGAAGG

SEQ ID NO: 238
GAGAGAACGCACCACTTTAC

SEQ ID NO: 239
CCACAGTGATCCTTCTACTC

SEQ ID NO: 240
TCTGTGAAGACGGCAGGTTCTACC

SEQ ID NO: 241
GAGAGAACGCACCACTTTAC

SEQ ID NO: 242
CGTGAGGTGCTAATGCTAATA

SEQ ID NO: 243
AGCTGACCTAATCTCTCTGGCTTTGG

SEQ ID NO: 244
GAGAGAACGCACCACTTTAC

-continued

---
Sequence Listing
---

SEQ ID NO: 245
CTGCAAGACAGAGATGGG

SEQ ID NO: 246
AGTCATCATGTGCCTTGACTCGG

SEQ ID NO: 247
CTGTTTCTCTTGGGTCTCAG

SEQ ID NO: 248
GGGACAGAAGTCAAAGGTTAT

SEQ ID NO: 249
AACAGAGAGGTTGAGCAACTGT

SEQ ID NO: 250
TGAAGTCATTTACCCCAGGC

SEQ ID NO: 251
CTCACACCATTTCTACCCGG

SEQ ID NO: 252
AATAAACCCAAGTGTGACCAGGCC

SEQ ID NO: 253
GCGAGACTCTGTCTCAAA

SEQ ID NO: 254
GGCCATCACTATCCACTT

SEQ ID NO: 255
TCCCCAGITGTGCAAAG

SEQ ID NO: 256
CAGGAGCATCAGCCTAT

SEQ ID NO: 257
ATGGCAACAGCTAGAGAG

SEQ ID NO: 258
ATCCTTGTGAGTGTTGGGTGGGAA

SEQ ID NO: 259
GGCCCGATTCCTGGATAATC

SEQ ID NO: 260
GCCAGAGAGATTAGGTCAGC

SEQ ID NO: 261
CCAGAATCCTACATCTAGGTCCTGCAC

SEQ ID NO: 262
CTCCAAGGCCGTGCATAA

SEQ ID NO: 263
AGACATGGGTATGGCCTCTA

SEQ ID NO: 264
CTGACCATCGACGAGAAAGG

SEQ ID NO: 265
CTGACCATCGACAAGAAAGG

---

The invention claimed is:

1. An engineered meganuclease that binds and cleaves a recognition sequence comprising SEQ ID NO: 9 within a SERPINA1 gene, wherein said engineered meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region, wherein said engineered meganuclease comprises the amino acid sequence of any one of SEQ ID NOs: 17-22.

2. An engineered meganuclease that binds and cleaves a recognition sequence comprising SEQ ID NO: 11 within a SERPINA1 gene, wherein said engineered meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region, wherein said engineered meganuclease comprises the amino acid sequence of any one of SEQ ID NOs: 41-46.

3. An engineered meganuclease that binds and cleaves a recognition sequence comprising SEQ ID NO: 13 within a SERPINA1 gene, wherein said engineered meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region, wherein said engineered meganuclease comprises the amino acid sequence of any one of SEQ ID NOs: 65-71.

4. An engineered meganuclease that binds and cleaves a recognition sequence comprising SEQ ID NO: 15 within a SERPINA1 gene, wherein said engineered meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region, wherein said engineered meganuclease comprises the amino acid sequence of any one of SEQ ID NOs: 93-100.

\* \* \* \* \*